US008598333B2

(12) United States Patent
MacLachlan et al.

(10) Patent No.: US 8,598,333 B2
(45) Date of Patent: Dec. 3, 2013

(54) SIRNA SILENCING OF GENES EXPRESSED IN CANCER

(75) Inventors: Ian MacLachlan, Mission (CA); Adam Judge, Vancouver (CA); Vandana Sood, Vancouver (CA); James Heyes, Vancouver (CA); Lloyd B. Jeffs, Delta (CA); Lorne Palmer, Vancouver (CA)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 1422 days.

(21) Appl. No.: 11/807,872

(22) Filed: May 29, 2007

(65) Prior Publication Data
US 2009/0149403 A1 Jun. 11, 2009

Related U.S. Application Data

(60) Provisional application No. 60/808,859, filed on May 26, 2006, provisional application No. 60/817,556, filed on Jun. 28, 2006.

(51) Int. Cl.
C07H 21/04 (2006.01)

(52) U.S. Cl.
USPC ......................................................... 536/24.5

(58) Field of Classification Search
USPC ......................................................... 536/24.5
See application file for complete search history.

(56) References Cited

U.S. PATENT DOCUMENTS

| | | | |
|---|---|---|---|
| 4,426,330 A | 1/1984 | Sears | |
| 4,534,899 A | 8/1985 | Sears | |
| 4,837,028 A | 6/1989 | Allen | |
| 4,868,116 A | 9/1989 | Morgan et al. | |
| 4,980,286 A | 12/1990 | Morgan et al. | |
| 5,013,556 A | 5/1991 | Woodle et al. | |
| 5,139,941 A | 8/1992 | Muzyczka et al. | |
| 5,213,804 A | 5/1993 | Martin et al. | |
| 5,225,212 A | 7/1993 | Martin et al. | |
| 5,252,479 A | 10/1993 | Srivastava | |
| 5,264,221 A | 11/1993 | Tagawa et al. | |
| 5,328,470 A | 7/1994 | Nabel et al. | |
| 5,334,711 A | 8/1994 | Sproat et al. | |
| 5,356,633 A | 10/1994 | Woodle et al. | |
| 5,540,935 A | 7/1996 | Miyazaki et al. | |
| 5,543,152 A | 8/1996 | Webb et al. | |
| 5,556,948 A | 9/1996 | Tagawa et al. | |
| 5,595,760 A | 1/1997 | Cherif-Cheikh | |
| 5,627,053 A | 5/1997 | Usman et al. | |
| 5,665,710 A | 9/1997 | Rahman et al. | |
| 5,672,659 A | 9/1997 | Shalaby et al. | |
| 5,705,188 A | 1/1998 | Junichi et al. | |
| 5,716,824 A | 2/1998 | Beigelman et al. | |
| 5,854,038 A | 12/1998 | Sullenger et al. | |
| 5,902,880 A | 5/1999 | Thompson | |
| 5,976,567 A | 11/1999 | Wheeler et al. | |
| 5,981,501 A | 11/1999 | Wheeler et al. | |
| 6,054,299 A | 4/2000 | Conrad | |
| 6,110,745 A * | 8/2000 | Zhang et al. | 435/458 |
| 6,146,886 A | 11/2000 | Thompson | |
| 6,150,092 A | 11/2000 | Uchida et al. | |
| 6,395,713 B1 | 5/2002 | Beigelman et al. | |
| 6,534,484 B1 | 3/2003 | Wheeler et al. | |
| 6,586,410 B1 | 7/2003 | Wheeler et al. | |
| 6,680,068 B2 | 1/2004 | Campbell et al. | |
| 6,815,432 B2 | 11/2004 | Wheeler et al. | |
| 7,427,605 B2 | 9/2008 | Davis et al. | |
| 7,718,629 B2 | 5/2010 | Bumcrot et al. | |
| 7,919,473 B2 | 4/2011 | De Fougerolles et al. | |
| 7,947,659 B2 | 5/2011 | De Fougerolles et al. | |
| 2003/0143732 A1 | 7/2003 | Fosnaugh et al. | |
| 2003/0170891 A1 | 9/2003 | McSwiggen | |
| 2003/0203844 A1 | 10/2003 | Delfani et al. | |
| 2003/0229037 A1 | 12/2003 | Massing et al. | |
| 2004/0018176 A1 | 1/2004 | Tolentino et al. | |
| 2004/0115201 A1 | 6/2004 | Einat et al. | |
| 2004/0180847 A1 | 9/2004 | Dobie et al. | |
| 2004/0209832 A1 | 10/2004 | McSwiggen et al. | |
| 2004/0259247 A1 | 12/2004 | Tuschl et al. | |
| 2005/0064595 A1 | 3/2005 | MacLachlan et al. | |
| 2005/0112141 A1 | 5/2005 | Terman | |
| 2005/0175682 A1 | 8/2005 | Heyes et al. | |
| 2005/0244858 A1 | 11/2005 | Rossi et al. | |
| 2005/0255487 A1 | 11/2005 | Khvorova et al. | |
| 2005/0282188 A1 | 12/2005 | Haeberli et al. | |
| 2006/0008910 A1 | 1/2006 | MacLachlan et al. | |
| 2006/0063751 A1 | 3/2006 | Aquila et al. | |
| 2006/0083780 A1 | 4/2006 | Heyes et al. | |

(Continued)

FOREIGN PATENT DOCUMENTS

DE 101 00 586 4/2002
EP 0445131 10/1989

(Continued)

OTHER PUBLICATIONS

Elbashir et al. "Analysis of gene function in somatic mammalian cells using small interfering RNAs," Methods, 2002, vol. 26, pp. 199-213.
Elbashir et al. "Functional anatomy of siRNAs for mediating efficient RNAi in *Drosphila melanogaster* embryo lysate," The EMBO Journal, 2001, vol. 20, No. 23, pp. 6877-6888.
Judge et al. "Design of Noninflammatory Synthetic siRNA Mediating Potent Gene Silencing in Vivo," Molecular Therapy, 2006, vol. 13, No. 3, pp. 494-505.
Reynolds et al. "Rational siRNA design for RNA interference," Nature Biotechnology, 2004, vol. 22, No. 3, pp. 326-330.
Weil et al. "Targeting the Kinesin Eg5 to Monitor siRNA Transfection in Mammalian Cells," Biotechniques, 2002, vol. 33, No. 6, pp. 1244-1248.
Akhtar et al. "Cellular uptake and intracellular fate of antisense oligonucleotides" Trends Cell Bio. 2:139-144 (1992).
Aldrian-Herrada et al., "A peptide nucleic acid (PNA) is more rapidly internalized in cultured neurons when coupled to a retro-inverse delivery peptide. The antisense activity depresses the target mRNA and protein in magnocellular oxytocin neurons" Nucleic Acids Res. 26:4910-4916 (1998).

(Continued)

*Primary Examiner* — Brian Whiteman
(74) *Attorney, Agent, or Firm* — Fenwick & West LLP

(57) ABSTRACT

The present invention provides nucleic acid-lipid particles comprising siRNA molecules that silence genes expressed in cancer (e.g., Eg5, EGFR or XIAP) and methods of using such nucleic acid-lipid particles to silence Eg5, EGFR or XIAP gene expression.

8 Claims, 378 Drawing Sheets

(56) References Cited

U.S. PATENT DOCUMENTS

| | | | |
|---|---|---|---|
| 2006/0094032 A1 | 5/2006 | De Fougerolles |
| 2006/0223770 A1 | 10/2006 | De Fougerolles |
| 2006/0240093 A1 | 10/2006 | MacLachlan et al. |
| 2006/0263435 A1 | 11/2006 | Davis et al. |
| 2007/0004664 A1 | 1/2007 | McSwiggen et al. |
| 2007/0031844 A1 | 2/2007 | Khvorova et al. |
| 2007/0135372 A1 | 6/2007 | MacLachlan et al. |
| 2007/0281899 A1 | 12/2007 | Bumcrot et al. |
| 2008/0188675 A1 | 8/2008 | Chen et al. |
| 2008/0213350 A1 | 9/2008 | Ko et al. |
| 2009/0023215 A1 | 1/2009 | Jessee et al. |
| 2009/0023673 A1 | 1/2009 | Manoharan |
| 2009/0099109 A1 | 4/2009 | Shames et al. |
| 2009/0149403 A1 | 6/2009 | MacLachlan et al. |
| 2009/0291131 A1 | 11/2009 | MacLachlan et al. |
| 2010/0087508 A1 | 4/2010 | Bumcrot et al. |
| 2010/0130588 A1 | 5/2010 | Yaworski |
| 2010/0267806 A1 | 10/2010 | Bumcrot et al. |
| 2010/0324120 A1 | 12/2010 | Chen et al. |
| 2011/0015250 A1 | 1/2011 | Bumcrot et al. |
| 2011/0224282 A1 | 9/2011 | De Fougerolles et al. |
| 2012/0136145 A1 | 5/2012 | Bumcrot et al. |

FOREIGN PATENT DOCUMENTS

| | | |
|---|---|---|
| EP | 0496813 | 10/1990 |
| WO | WO 88/04924 | 7/1988 |
| WO | WO 89/02468 | 3/1989 |
| WO | WO 89/05345 | 6/1989 |
| WO | WO 89/07136 | 8/1989 |
| WO | WO 90/04384 | 5/1990 |
| WO | WO 91/05545 | 5/1991 |
| WO | WO 92/07065 | 4/1992 |
| WO | WO 92/07573 | 5/1992 |
| WO | WO 93/15187 | 5/1993 |
| WO | WO 93/23569 | 11/1993 |
| WO | WO 93/24641 | 12/1993 |
| WO | WO 94/02595 | 2/1994 |
| WO | WO 94/13788 | 6/1994 |
| WO | WO 94/20073 | 9/1994 |
| WO | WO 96/10390 | 4/1996 |
| WO | WO 96/10391 | 4/1996 |
| WO | WO 96/10392 | 4/1996 |
| WO | WO 96/23065 | 8/1996 |
| WO | WO 96/40062 | 12/1996 |
| WO | WO 96/40964 | 12/1996 |
| WO | WO 97/04787 | 2/1997 |
| WO | WO 97/13499 | 4/1997 |
| WO | WO 97/26270 | 7/1997 |
| WO | WO 97/30731 | 8/1997 |
| WO | WO 98/13526 | 4/1998 |
| WO | WO 98/35978 | 8/1998 |
| WO | WO 99/32619 | 7/1999 |
| WO | WO 99/53050 | 10/1999 |
| WO | WO 99/61631 | 12/1999 |
| WO | WO 00/03683 | 1/2000 |
| WO | WO 00/22113 | 4/2000 |
| WO | WO 00/22114 | 4/2000 |
| WO | WO 00/44895 | 8/2000 |
| WO | WO 00/53722 | 9/2000 |
| WO | WO 03/070910 | 8/2003 |
| WO | WO 03/070917 | 8/2003 |
| WO | WO/03/070918 | 8/2003 |
| WO | WO 03/074654 | 9/2003 |
| WO | WO 2004/001193 | 12/2003 |
| WO | WO 2004/007070 | 1/2004 |
| WO | WO 2004/009769 | 1/2004 |
| WO | WO 2004/011822 | 2/2004 |
| WO | WO 2004/011829 | 2/2004 |
| WO | WO 2004/013310 | 2/2004 |
| WO | WO 2004/064737 | 8/2004 |
| WO | WO 2004/065601 | 8/2004 |
| WO | WO 2004/080406 | 9/2004 |
| WO | WO 2004/090108 | 10/2004 |
| WO | WO 2004/094345 | 11/2004 |
| WO | WO 2004/094595 | 11/2004 |
| WO | WO 2004/099410 A2 | 11/2004 |
| WO | WO 2005/007196 A2 | 1/2005 |
| WO | WO 2005/014782 | 2/2005 |
| WO | WO 2005/026372 A1 | 3/2005 |
| WO | WO 2005/031002 A2 | 4/2005 |
| WO | WO 2005/089224 | 9/2005 |
| WO | WO 2005/120152 | 12/2005 |
| WO | WO 2007/002191 | 1/2007 |
| WO | WO 2007/012191 | 2/2007 |
| WO | WO 2007/051303 A1 | 5/2007 |
| WO | WO 2007/115168 | 10/2007 |
| WO | WO 2008/042973 | 4/2008 |
| WO | WO 2009/111658 | 9/2009 |
| WO | WO 2009/127060 | 10/2009 |
| WO | WO 2009/134487 | 11/2009 |
| WO | WO 2010/054406 | 5/2010 |
| WO | WO 2010/088537 | 8/2010 |
| WO | WO 2010/105209 | 9/2010 |
| WO | WO 2010/129709 | 11/2010 |
| WO | WO 2010/144740 | 12/2010 |
| WO | WO 2011/017548 | 2/2011 |
| WO | WO 2011/034798 | 3/2011 |

OTHER PUBLICATIONS

Allen et al., "Large Unilamellar Liposomes with Low Uptake into the Reticuloendothelial System," Feb. 23:42-46 (1987).

Anderson et al., "Human Gene Therapy," Nature, 392 (Suppl): 25-30 (1998).

Armentano et al., "Expression of Human Facot IX in Rabbit Hepatocytes by Retrovirus-Mediated Gene Transfer: Potential for Gene Therapy of hemophilia B" Proc. Natl. Acad. Sci. USA 87: 6141-6145 (1990).

Bass, B., "The short answer," Nature, May 24, 2001, pp. 428-429, vol. 411.

Berkner, K., "Development of Adenovirus Vectors for the Expression of Heterologous Genes," Biotechniques, 6(7): 616-629 (1988).

Beigelman et al., "Chemical Modification of Hammerhead Ribozymes" Journal of Biological Chemistry, Oct. 27, 1995, p. 25702-25708, vol. 270, No. 43.

Bernstein et al., "Role for a bidentate ribonuclease in the initiation step of RNA interference" Nature, Jan. 18, 2000, p. 363-366, vol. 409.

Blume et al., "Liposomes for the Sustained Drug Release in Vivo," Biochimica et Biophysica Acta, 1029:91-97 (1990).

Boado, "Antisense drug delivery through the blood-brain barrier" Adv. Drug. Delivery Reviews, 1995, 15:73-107.

Boado et al., "Drug Delivery of Antisense Molecules to the Brain for Treatment of Alzheimer's Disease and Cerebral AIDS" J. Pharm. Sciences, Nov. 1998, p. 1308-1315, vol. 87, No. 11.

Boese et al., "Mechanical Insights Aid Computational Short Interfering RNA Design," Methods in Enzymology 392:73-96, 2005.

Bucchini et al., "Pancreatic Expression in Human Insulin Gene in Transgenic Mice" Proc. Natl. Acad. Sci. USA, 83: 2511-2515 (1986).

Burgin, Jr. et al., "Chemically Modified Hammerhead Ribozymes with Improved Catalytic Rates" Biochemistry, 1996, p. 14090-14097, vol. 35.

Burlina et al, "Chemical Engineering of RNase Resistant and Catalytically Active Hammerhead Ribozymes" Bioorg. Med. Chem. 5(11):1999-2010 (1997).

Chen et al., "Gene Therapy for Brain Tumors: Regression of Experimental Gliomas by Adenovirus-Mediated Gene Transfer in vivo", Proc. Natl. Acad. Sci. USA, 91: 3054-3057 (1994).

Chen et al., "Multitarget-ribozyme directed to cleave at up to nine highly conserved HIV-1 env RNA regions inhibits HIV-1 replication—potential effectiveness against most presently sequenced HIV-1 isolates" Nucleic Acids Research, Sep. 11, 1992, p. 4581-4589, vol. 20, No. 17.

Chowrira et al., "In Vitro and in Vivo Comparison of Hammerhead, Hairpin, and Hepatitis Delta Virus Self-processing Ribozyme Cassettes" J. Biol. Chem., Oct. 1994, p. 25856-25864, vol. 269, No. 41.

(56) References Cited

OTHER PUBLICATIONS

Chowdhury et al., "Long-Term Improvements of Hypercholesterolemia After ex Vivo Gene Therapy in LDLR-Deficient Rabbits," Science, 254(5039): 1802-1805 (1991).
Cone, R. and Mulligan, R., "High-Efficiency Gene Transfer into Mammalian Cells: Generation of Helper-Free Recombinant Retrovirus with Broad Mammalian Host Range," Proceedings of the National Academy of Sciences of the United States of America, 81(20): 6349-6353 (1984).
Cornetta et al., "Safety Issues Related to Retroviral-Mediated Gene Transfer in Humans," Human Gene Therapy 2:5-14 (1991).
Couture et al., "Anti-Gene Therapy: The Use of Ribozymes to Inhibit Gene Function" TGI 12(12): 510-515 (1996).
Crooke et al., "Pharmacokinetic Properties of Several Novel Oligonucleotide Analogs in Mice" The Journal of Pharmacology and Experimental Therapeutics, 277(2): 923-937 (1996).
Dai et al., "Gene Therapy Via Primary Myoblasts: Long-Term Expression of Factor IX Protein Following Transplantation in vivo" Proc. Natl. Acad. Sci. USA, 89: 10892-10895 (1992).
Danos, O. and Mulligan, R., "Safe and Efficient Generation of Recombinant Retroviruses with Amphotropic and Ecotropic Host Ranges" Proc. Natl. Acad. Sci. USA, 85: 6460-6464 (1988).
Docherty, K. and Clark, A., "Nutrient Regulation of Insulin Gene Expression," The FASEB Journal 8: 20-27 (1994).
Dornburg, R., "Reticuloendotheliosis Viruses and Derived Vectors," Gene Therapy, 2:301-310 (1995).
du Plessis et al., "Topical Delivery of Liposomally Encapsulated Gamma-Interferon," Antiviral Research, 18:259-265 (1992).
Dunn, K.C., et al., "A Human Retinal Pigment Epithelial Cell Line with Differentiated Properties," Exp. Eye Res., 1996, pp. 155-169, vol. 62.
Dropulic et al., "Functional Characterization of a U5 Ribozyme: Intracellular Suppression of Human Immunodeficiency Virus Type I Expression" Journal of Virology, Mar. 1992, p. 1432-1441, vol. 66, No. 3.
Earnshaw et al., "Modified Oligoribonucleotides as Site-Specific Probes of RNA Structure and Function" Biopolymers (Nucleic Acid Sciences), 1998, p. 39-55, vol. 48.
Eglitis et al., "Gene Expression in Mice After High Efficiency Retroviral-Mediated Gene Transfer," Science 230(4732): 1395-1398 (1995).
Eglitis et al., "Retroviral Vectors for Introductions of Genes into Mammalian Cells," Biotechniques 6:608-614 (1988).
Elbashir, S., et al., "Duplexes of 21-nucleotide RNAs mediate RNA interference in mammalian cell culture," Nature, May 24, 2001, p. 494-498, vol. 411.
Elbashir, S., et al., "RNA Interference is Mediated by 21-and 22 Nucleotide RNAs," Genes & Development, 2001, pp. 188-200, vol. 15.
El-Hariri et al., "The Mitigating Effects of Phosphatidylcholines on Bile Salt- and Lysophosphatidylcholine-Induced Membrane Damage," J. Pharm. Pharmacol., 44:651-654 (1992).
Fattal et al., "Ocular delivery of nucleic acids: antisense oligonucleotides aptamers and siRNA," (2006) Advanced Drug Delivery Reviews 58:1203-1223.
Filleur et al., "SiRNA-mediated Inhibition of Vascular-Endothelial Growth Factor Severely Limits Tumor Resistance to Antiangiogenic Thrombospondin-1 and Slows Tumor Vascularization and Growth" Cancer Res. 63:3919-3922 (2003).
Fire, A., et al., "Potent and Specific Genetic Interference by Double Stranded RNA in *Caenorhabditis elegans*," Nature, Feb. 19, 1998, pp. 806-811, vol. 391.
Ferry et al., "Retroviral-Mediated Gene Transfer into Hepatocytes in vivo" Proc. Natl. Acad. Sci. USA, 88: 8377-8381 (1991).
Fisher et al., "Transduction with Recombinant Adeno-Associated Virus for Gene Therapy is Limited by Leading-Strand Synthesis," Journal of Virology, 70:520-532 (1996).
Gabizon et al., "Liposome Formulations with Prolonged Circulation Time in Blood and Enhanced Uptake by Tumors," Proc. Natl. Acad. Sci. USA 85:3949-3953 (1988).

Gassmann et al., "Maintenance of an Extrachromosomal Plasmid Vecot in Mouse Embryonic Stem Cells" Proc. Natl. Acad. Sci. USA, 92: 1292-1296 (1995).
Genbank Accession No. AF214570, "*Homo sapiens* vascular endothelial growth factor isoform 121 precursor, mRNA, complete cds," Dec. 23, 1999.
Good et al., "Expression of small, therapeutic RNAs in human cell nuclei" Gene Therapy 4:45-54, 1997.
Gonzalez, H., et al., "New Class of Polymers for the Delivery of Macromolecular Therapeutics," Bioconjugate Chem., 1999, p. 1068-1074, vol. 10.
Harborth, J., et al., "Sequence, chemical, and structural variation of small interfering RNAs and short hairpin RNAs and the effect on mammalian gene silencing," Antisense & Nucleic Acid Drug Development, Apr. 1, 2003, pp. 83-105, vol. 13, No. 2.
Hofland, H.E.J. et al., "Formulation and Delivery of Nucleic Acids," Novel Therapeutics from Modern Biotechnology, 1999, p. 166-192.
Nolen et al. "Positional effects of short interfering RNAs targeting the human coagulation trigger Tissue Factor," Nucleic Acid Res. 2002, 30:1757-1766.
Hsu et al., "Immunogenicity of Recombinant Adenovirus-Respiratory Syncytial Virus Vaccines with Adenovirus Types 4, 5, and 7 Vecotrs in Dogs and Chimpanzee," The Journal of Infectious Diseases 166:769-775 (1992).
Hu et al., "Topical Delivery of Cyclosporin a from Non-Ionic Liposomal Systems: An In Vovo/In Vitro Correlation Study Using Hairless Mouse Skin," S.T.P. Pharma Sciences, 4: 377-379 (1994).
Huber et al., "Retroviral-Mediated Gene Therapy for the Treatment of Hepatocellular Carcinoma: An Innovative Approach for Cancer Therapy" Proc. Natl. Acad. Sci. USA, 88: 8039-8043 (1991).
Hwu et al., "Functional and Molecular Characterization of Tumor-Infiltrating Lymphocytes Transduced with Tumor Necrosis Factor-.alpha. cDNA for the Gene Therapy of Cancer in Humans," The Journal of Immunology 150: 4104-4115 (1993).
Ilium et al., "The Organ Uptake of Intravenously Administered Collodial Particles can be Altered Using a Non-Ionic Surfactant (Poloxamer 338)," FEBS 167:79-82 (1984).
Ishiwata, H., et al., "Physical-Chemistry Characteristics and Biodistribution of Poly(ethylene glycol)-Coated Liposomes Using Poly(oxyethylene) Cholesteryl Ether," Pharmaceutical Society of Japan, Jun. 1995, p. 1005-1011, vol. 43.
Izant J., et al., "Constitutive and Conditional Suppression of Exogenous and Endogenous Genes by Anti-Sense RNA" Science 229:345-352 (1985).
Jolliet-Riant, P., et al., "Drug transfer across the blood-brain barrier and improvement of brain delivery," Fundam. Clin, Pharmacol., 1996, p. 16-26, vol. 13.
Kabanov et al., "A New Class of Antivirals: Antisense Oligonucleotides Combined with a Hydrophobic Substituent Effitively Inhibit Influenza Virus Reproduction and Synthesis of Virus-Specific Proteins in MDCK Cells" FEB 259(2): 327-330 (1990).
Kapoor et al., "Probing Spindle Assembly Mechanisms with Monastrol, A Small Molecule Inhibitor of the Mototic Kinesin, Eg5," The Journal of Cell Biology, 150:975-988 (2000).
Karpeisky et al., "Highly Efficient Synthesis of 2'-O-Amino Nucleosides and Their Incorporation in Hammerhead Ribozymes" Tetrahedron Lett. 39:1131-1134 (1998).
Kashani-Sabet et al., "Reversal of the Malignant Phenotype by an Anti-ras Ribozyme" Antisense Res. Dev. 2:3-15 (1992).
Kay et al., "Hepatic Gene Therapy: Persistent Expression of Human .alpha.I-Antitypsin in Mice after Direct Gene Delivery in Vivo," Human Gene Therapy 3: 641-647 (1992).
Kawaski et al., "Uniformly Modified 2'-Deoxy-2'-fluoro Phosphorothioate Oligonucleotides as Nuclease-Resistant Antisense Compounds with High Affinity and Specificity for RNA Targets" J. Med. Chem. 36:831-841 (1993).
Klibanov et al., "Amphipathic Polyethyleneglycols Effectively Prolong the Circulation Time of Liposomes," FEBS 268:235-237 (1990).
Kumar et al., "Express Protocol for Functionalization of Polymer Supports for Oligonucleotide Synthesis" Nucleosides & Nucleotides 15(4):879-888 (1996).

(56) References Cited

OTHER PUBLICATIONS

Lasic, D., et al., "Liposomes Revisited," Science, Mar. 3, 1995, 1275-1276, vol. 267.
Lasic, D., et al., "The "Stealth" Liposome: A Prototypical Biomaterial," Chemical Reviews, Dec. 1995, p. 2601-2628, vol. 95, No. 8.
Lee et al., "Mucosal Penetration Enhancers for Facilitation of Peptide and Protein Drug Absorption," Critical Reviews in Therapeutic Drug Carrier Systems, 8:91-192 (1991).
Lee, K., et al., "Modified Liposome Formulations for Cytosolic Delivery for Macromolecules," Controlled Drug Delivery, Designing Technologies for the Future, 2000, p. 184-192.
Letsinger et al., "Cholesteryl-Conjugated Oligonucleotides: Synthesis, Properties, and Activity as Inhibitors of replication of Human Immunodeficiency Virus in Cell Culture" Proc. Natl. Acad. Sci. USA 86: 6533-6556 (1989).
Liu, Y., et al., "Cationic Liposome-mediated Intravenous Gene Delivery," The Journal of Biological Chemistry, Jun. 30, 1995, p. 24864-24870, vol. 270, No. 42.
Manoharan et al., "Chemical Modifications to Improve Uptake and Bioavailability of Anisense Oligonucleotides", Annals of the New York Academy of Sciences, 660: 306-308 (1992).
Manoharan et al., "Cholic Acid-Oligonucleotide Conjugates for Antisense Applications" Bioorganic & Medicinal Chemistry Letters 4(8): 1053-1060 (1994).
Manoharan et al., "Introduction of a Lipophilic Thioehter Tether in the Minor Groove of Nucleic Acids for Antisense Applications" Bioorganic & Medicinal Chemistry Letters 13(12):2765-2770 (1993).
Manoharan et al., "Lipidic Nucleic Acids" Tetrahedron Letters 36(21): 3651-3654 (1995).
Manoharan et al., "Oligonucleotide Conjugates: Alteration of the Pharmacokinetic Properties of Antisense Agents" Nucleosides & Nucleotides 14(3-5): 969-973 (1995).
Martin, Pierre, "Streoselektive Sytheses von 2'-o-(2-Methoxyethyl)ribonucleosiden: Nachbargruppenbeteiligung der Methoxyethoxy-Gruppe bei der Ribosylierung von Heterocyclen," Helvetica Chimica Acta 79: 1930-1938 (1996).
Maurer et al., "Lipid-based systems for the intracellular delivery of genetics Drugs," Molecular Membrane Biology, 16:129-140, 1999.
Mayer, T. U. et. al. "Small Molecule Inhibitor of Mitotic Spindle Bipolarity Identified in a Phenotype-Based Screen," Science, Oct. 1999, pp. 971-974, vol. 286, No. 5441.
McGarry T., et al., "Inhibition of heat shock protein synthesis by heat-inducible antisense RNA" Proc. Nat. Acad. Sci. USA 83:399-403, Jan. 1986.
Miller, Dusty A., "Retrovirus Packaging Cells," Human Gene Therapy, 1:5-14 (1990).
Mishra et al., "Improved Leislunanicidal Effect of Phosphorotioate Antisense Oligonucleotides by LDL-Mediated Delivery" Biochimica et Biophysica Acta 1264: 229-237 (1995).
Miyao et al., "Stability and Pharmacokinetic Characteristics of Oligonucleotides Modified at Terminal Linkages in Mice," Antisense Research and Development, 5:115-121 (1995).
Muranishi, S., "Absorption Enhancers," Critical Reviews in Therapeutic Drug Carrier Systems, 7(1): 1-33 (1990).
Muzyczka, N., "Use of Adeno-Associated Virus as a General Transduction Vector for Mammalian Cells," Current Topics in Microbiology and Immunology, 158: 97-129 (1992).
Nykanen et al., "ATP Requirements and Small Interfering RNA Structure in the RNA Interference Pathway" Cell, Nov. 2, 2001, p. 309-321, vol. 107.
Oberhauser et al., "Effectve Incorporation of 2'-O-Methly-Oligoribonucleotides Into Liposomes and Enhanced Cell Association Through Modification with Thiocholesterol" Nucleic Acids Research, 20(3): 533-538 (1992).
Ohkawa et al., "Activities of HIV-RNA targeted ribozymes transcribed from a 'shot-gun' type ribozyme-trimming plasmid" Nucleic Acids Symp. Ser. No. 27, 1992, p. 15-16.

Ojwang at al., "Inhibition of human immunodeficiency virus type I expression by a hairpin ribozyme," Proc. Natl. Acad. Sci. USA, Nov. 1992, p. 10802-10806, vol. 89.
Oku et al., "Real-time analysis of liposomal trafficking in tumor-bearing mice by use of positron emission tomography" Biochimica et Biophysics Acta 1238, 1995, p. 86-90.
Papahadjopoulos et al., "Targeting Liposomes to Tumor Cells in Vivo," Annals of the New York Academy of Sciences, 507: 64-74 (1987).
Pardridge et al., "Vector-mediated delivery of a polyamide ('peptide') nucleic acid analogue through the blood-brain barrier in vivo" Proc. Natl. Acad. Sci. USA, Jun. 1995, p. 5592-5596, vol. 92.
Perreault et al., "Mixed deoxyribo- and ribo-oligonucleotides with catalytic activity" Nature, Apr. 5, 1990, p. 565-567, col. 344.
Pieken et al., "Kinetic Characterization of Ribonuclease-Resistant 2'-Modified Hammerhead Ribozymes," Science, Jul. 19, 1991, p. 314-317, vol. 253.
Prakash et al., "Synthesis of 2'-O[2-[(N,M'Dimethylamino)oxy]ethyl] Modified Nucleosides and Olionucleotides" J. Org. Chem., 2002, p. 357-369, vol. 67.
Rabinowitz et al., "Cross-Packaging of a Single Adeno-Associated Virus (AAV) Type 2 Vector Genome into Muliple AAV Serotypes Enables Transduction with Broad Specificity," Journal of Virology, 76:791-701 (2002).
Reich et al., "Small interfering RNA (siRNA) targeting VEGF effectively inhibits ocular neovascularization in a mouse model" Molecular Vision, May 30, 2003, p. 210-216, vol. 9.
Rosenfeld et al., "In Vivo Transfer of the Human Cystic Fibrosis Transmembrane Conductance Regulator Gene to the Airway Epithelium," Cell 68:143-155 (1992).
Rubinson et al., "A Lentivirus-Based System to Functionally Silence Genes in Primary Mammalian Cells,. Stem Cells and Transgenic Mice by RNA Interference," Nature Genetics, 33: 401-406 (2003).
Saison-Behmoaras et al., "Short Modified Antisense Oligonucleotides Directed Against Ha-ras Point Mutation Induce Selective Cleavage of the mRNA and Inhibit T24 Cells Proliferation" EMBO J., 10: 1111-1118 (1991).
Samulski et al., "A Recombinant Plasmid from Which an Infectious Adeno-Associated Virus Genome Can be Excised in Vitro and Its Use to Study Viral Replication," Journal of Virology, 61:3096-3101 (1987).
Samulski et al., "Helper-Free Stocks of Recombinant Adeno-Associated Viruses: Normal Integration Does Not Require Viral Gene Expression," Journal of Virology 63:3822-3828 (1989).
Sarver et al., "Ribozymes as Potential Anti-HIV-1 Therapeutic Agents" Science, Mar. 9, 1990, p. 1222-1225, vol. 247.
Scanlon et al., "Ribozyme-mediated cleavage of c-fos mRNA reduces gene expression of DNA synthesis enzymes and metallothionein" Proc. Natl. Acad. Sci. USA, Dec. 1991, p. 10591-10595, vol. 88.
Shea et al., "Synthesis, Hybridization Properties and Antiviral Activity of Lipid-Oligodeoxynucleotide Conjugates" Nucleic Acids Research 18(13): 3777-3783 (1990).
Sunamoto et al., "Liposomeal Membranes. V. Interaction of Zinc (II) Ion with Egg Phosphatidylcholine Liposomes," Bull. Chem. Soc. Jpn., 53: 2778-2781 (1980).
Svinarchuk et al., "Inhibition of HIV Proloferation in MT-4 Cells by Antisense Oligonucleotide Conjugated to Lipophilic Groups" Biochimie 75: 49-54 (1993).
Taira et al., "Construction of a novel RNA-transcript-trimming plasmid which can be used both in vitro in place of run-off and (G)-free transcriptions and in vivo as multi-sequences transcription vectors" Nucleic Acids Research, 1991, p. 5125-5130, vol. 19, No. 19.
Takahashi et al., "The Use of a Perfluorochemical Emulsion as a Vascular Perfusate in Drug Absorption," J. Pharm. Phramacol. 40:252-257 (1988).
Takakura et al., "Uptake Characteristics of Oligonucleotides in the Isolated Rat Liver Perfusion System," Antisense & Nucleic Acid Drug Development 6:177-183 (1996).

(56) References Cited

OTHER PUBLICATIONS

Takimoto, C., et al., "Safety and anti-tumor activity of sorafenib (Nexavar .RTM.) in combination with other anti-cancer agents: a review of clinical trials," Cancer Chemotherapy and Pharmacology, Apr. 2008, pp. 535-548, vol. 61, No. 4.
Thompson et al., "Improved accumulation and activity of ribozymes expressed from a tRNA-based RNA of erase III promoter" Nucleic Acids Research, 1995, p. 2259-2268, vol. 23, No. 12.
Tyler et al., "Peptide nucleic acids targeted to the neurotensin receptor and administered i.p. cross the blood-brain barrier and specifically reduce gene expression" Proc. Natl. Acad. Sci. USA, Jun. 1999, vol. 96, p. 7053-7058.
Tyler et al., "Specific gene blockade shows that peptide nucleic acids readily enter neuronal cells in vivo," FEBS Letters, 1998, p. 280-284, vol. 421.
Usman et al., "Chemical modification of hammerhead ribozymes: activity and nuclease resistance," Nucleic Acids Symposium Series, 1994, No. 31, p. 163-164.
Usman et al., "Exploiting the chemical synthesis of RNA" Trends Biochem. Sci. 17:334-339 (1992).
Van Beusechem et al., "Long-Term Expression of Human Adenosine Deaminase in Rhesus Monkeys Transplanted With Retrovirus-Infected Bone-Marrow Cells" Proc. Natl. Acad. Sci. USA, 89: 7640-7644 (1992).
Ventura et al., "Activation of HIV-specific ribozyme activity by self-cleavage" Nucleic Acids Research, 1993, p. 3249-3255, vol. 21, No. 14.
Verma et al., "Modified Oligonucleotides: Synthesis and Strategy for Users" Annu. Rev. Biochem. 1998, p. 99-134, vol. 67, No. 99.
Vickers, T., et al., "Efficient Reduction of Target RNAs by Small Interfering RNA and RNase H-dependent Antisense Agents," The Journal of Biological Chemistry, Feb. 28, 2003, pp. 7108-7118, vol. 278, No. 9.
Wang et al., "Plasmid DNA Absorbed to pH-Sensitive Liposomes Efficiently Transforms the Target Cells," Biochemical and Biophysical Research Communications, 147:980-985 (1987).
Weiner et al., "Liposomes: A Novel Topical Delivery System for Pharmaceutical and Cosmetic Applications," Journal of Drug Targeting 2:405-410 (1994).
Weerasinghe et al., "Resistance to Human Immunodeficiency Virus Type I (HIV-1) Infection in Human CD4+ Lymphocyte-Derived Cell Lines Conferred by Using Retroviral Vectors Expressing an HIV-1 RNA-Specific Ribozyme" Journal of Virology, 1991, p. 5531-5534, vol. 65, No. 10.
Wincott et al., "Synthesis, deprotection, analysis and purification of RNA and ribozymes" Nucleic Acids Research, 1995, p. 2677-2684, vol. 23, No. 14.
Wilson et al., "Retrovirus-Mediated Transduction of Adult Hepatocytes" Proc. Natl. Acad. Sci. USA, 85: 3014-3018 (1988).
Xia et al., "siRNA-Mediated Gene Silencing in Vitro and in Vivo," Nature Biotechnology, 20:1006-1010 (2002).
Yang et al., "Evidence That Processed Small dsRNAs May Mediate Sequence-Specific mRNA Degradation during RNAi in *Drosophila* embryos" Current Biology 10: 1191-1200 (2000).
Zhou et al., "Targeted Delivery of DNA by Liposomes and Polymers, "Journal of Controlled Release 19:269-274 (1992).
Zimmerman, et al., "RNAi-mediated gene silencing in non-human primates," Nature, May 4, 2006, pp. 111-114, With supplementary information, vol. 441.
Agrawal, S., et al., "Antisense oligonucleotides: towards clinical trials." Trends in Biotechnology. Oct. 1996, vol. 14, pp. 376-387.
Byrom, M., et al., "Inducing RNAi with siRNA Cocktails Generated by RNase III," Ambiom, TechNotes 10(1), 2004, 8 Pages [online] [Archived on web.archive.org on Jan. 1, 2004] [Retrieved on Jun. 13, 2013] Retrieved from the internet <URL:http://web.archive.org/web/20040101035700/http://www.ambion.com/techlib/tn/101/4.html>.
Cui, W., et al., "OptiRNAi, an RNAi design tool," Computer Methods and Programs Biomedicine, 2004, vol. 75, p. 67-73.
De Fougerolles, A.R., et al., Discovery and development of RNAi Therapeutics, in "Antisense Drug Technologies: Principles, Strategies and Applications, second edition", edited by Crooke, S., Taylor and Francis, 2007, pp. 465-484.
Fire, A., "RNA-triggered Gene Silencing," Trends in Genetics, Sep. 1999, pp. 358-363, vol. 15, No. 9.
Harborth, J., et al., "Identification of essiential genes in cultured mammalian cells using small interfering RNAs," Journal of Cell Science, Oct. 2001, pp. 4557-4565, vol. 114.
Haque, S., et al., "Monastrol, a Prototype Anti-Cancer Drug That Inhibits Mitotic Kinesin, Induces Rapid Bursts of Axonal Outgrowth From Cultured Postmitotic Neurons," Cell Motility and the Cytoskeleton, 2004, vol. 58, p. 10-16.
Hornung, V., et al., "Sequence-specific potent induction of IFN-α by short interfering RNA in plasmacytoid dendritic cells through TLR7," Nature Medicine, Mar. 2005, pp. 263-270, vol. 11, No. 3.
Kim, D.H., et al., "Synthetic dsRNA Dicer substrates enhance RNAi potency and efficacy," Nature Biotechnology, Feb. 2005, pp. 222-226, vol. 23, No. 2.
Li, L., et al., "Overcoming obstacles to develop effective and safe siRNA therapeutics," Expert Opinion on Biological Therapym <ay 2009, pp. 609-619, vol. 9, No. 5.
Love, K., et al., "Lipid-like materials for low-dose, in vivo gene silencing," PNAS, Feb. 2, 2010, pp. 1864-69, vol. 107, No. 5.
Luo, L., et al., "Mechanism of Inhibition of Human KSP by Monastrol: Insights from Kinetic Analysis and the Effect of Ionic Strength on KSP Inhibition," Biochemistry, 2004, vol. 43, p. 15258-15266.
Robbins, M., et al., "Stable expression of shRNAs in human CD34+progenitor cells can avoid induction of interferon responses to siRNAs in vitro," Nature Biotechnology, May 2006, pp. 566-571, vol. 24, No. 5.
Rose, S., et al., "Functional polarity is introduced by Dicer processing of short substrate RNAs," Nucleic Acids Research, 2005, pp. 4140-4156, vol. 33, No. 13.
Sunder-Plassmann, N., et al., "Systhesis and biological evaluation of new tetrahydro-β-cardonlines as inhibitors of the mitotic kinesin Eg5," Bioorganic & Medicinal Chemistry, 2005, vol. 13, p. 6094-6111.
Tolentino, M., et al., "Intravitreal Injection of Vascular Endothelial Growth Factor Small Interfering RNA Inhibits Growth and Leakage in a Nonhuman Primate, Laser-Induced Model of Choroidal Neovascularization," The Journal of Retinal and Vitreous Diseases, 2004, pp. 132-138, vol. 24, No. 1.
Tuschl, T., "Functional genomics: RNA sets the standard," Nature, Jan. 16, 2003, vol. 421, No. 6920, pp. 220-221.
Tuschl T., "RNA Interference and Small Interfering RNAs" Chembiochem, 2001, pp. 239-245, vol. 2.
Tuschl, T., et al., "Small Interfering RNAs: A Revolutionary Tool for the Analysis of Gene Function and Gene Therapy," Molecular Interventions, 2002, pgs. 158-167, vol. 2, No. 3.
Tuschl, T., "Mammalian RNA Interference," RNAi, A Guide to Gene Silencing, Chapter 13, G.J. Hannon (ed,), 2003, pp. 265-295.
Tuschl, T., et al., "Targeted mRNA Degradation by Double-Stranded RNA In Vitro," Genes & Development, 1999, pp. 3191-3197, vol. 13.
Tuschl, T., "Expanding small RNA interference," Nature Biotechnology, May 2002, pp. 446-448, vol. 20.
Zhu, A., et al., "Development of sofafenib and other molecularly targeted agents in hepatocellular carcinoma," Cancer, Jan. 2008, pp. 250-259, vol. 112, No. 2.
Patent Interference No. 105,792: Bumcrot v. Maclachlan v. Bumcrot, U.S. Appl. No. 11/694,215 v. U.S. Appl. No. 11/807,872 v. U.S. Appl. No. 13/165,568; Declaration date Feb. 28, 2011; Judgment Date Nov. 30, 2012; Distribution Date Nov. 30, 2013.

\* cited by examiner

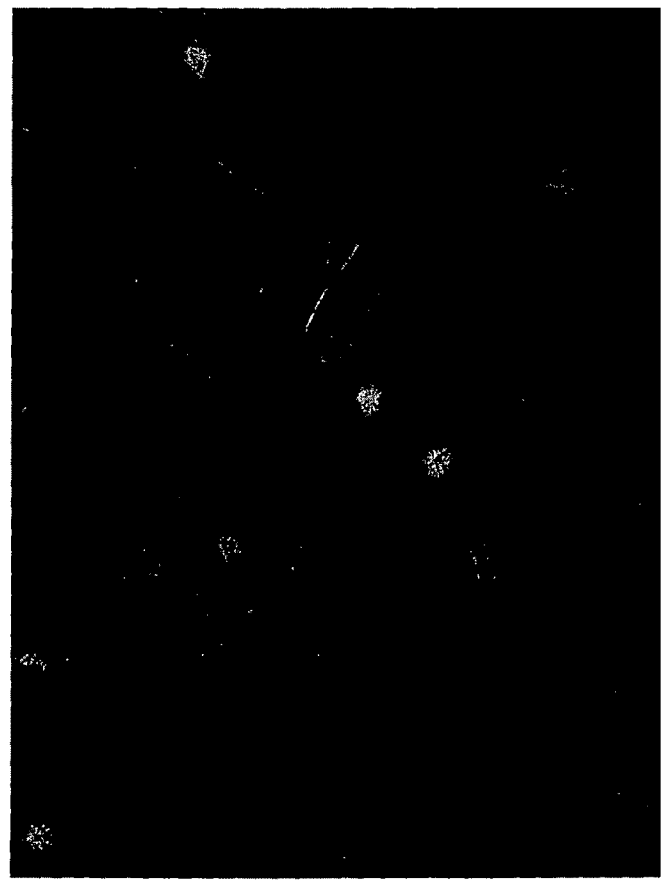
Figure 5

| | Sense/AS |
|---|---|
| 1 | 0/0 |
| 2 | U/0 |
| 3 | G/0 |
| 4 | 0/U |
| 5 | 0/G |
| 6 | U/U |
| 7 | U/G |
| 8 | G/G |
| 9 | G/U |

5' C U G A A G A C C U G A A G A C A A U dT dT sense
3' dT dT G A C U U C U G G A C U U C U G U U A   antisense 5' C [U] G A A G A C C U G A A G A C A A [U] dT dT sense
3' dT dT G A C U U C U G G A C U U C U G U U A   antisense 5' C U [G] A A G A C C U G A A G A C A A U dT dT sense
3' dT dT G A C U U C U G G A C U U C U G U U A   antisense 5' C U G A A G A C C U G A A G A C A A U dT dT sense
3' dT dT G A C [U] [U] C [U] G G A C [U] [U] C [U] G [U] [U] A   antisense 5' C U G A A G A C C U G A A G A C A A U dT dT sense
3' dT dT [G] A C U U C U [G] [G] A C U U C U [G] U U A   antisense 5' C [U] G A A G A C C U G A A G A C A A [U] dT dT sense
3' dT dT G A C [U] [U] C [U] G G A C [U] [U] C [U] G [U] [U] A   antisense 5' C [U] G A A G A C C U G A A G A C A A [U] dT dT sense
3' dT dT [G] A C U U C U [G] [G] A C U U C U [G] U U A   antisense 5' C U [G] A A [G] A C C U [G] A A [G] A C A A U dT dT sense
3' dT dT [G] A C U U C U [G] [G] A C U U C U [G] U U A   antisense 5' C U [G] A A [G] A C C U [G] A A [G] A C A A U dT dT sense
3' dT dT G A C [U] [U] C [U] G G A C [U] [U] C [U] G [U] [U] A   antisense

Figure 6

TABLE 1: Eg5 (Kif11) siRNA Sequences

| Start site | Sense strand 5p-3p – 19bp core | Sense leader-trailer | Reynolds score | %GC | Thermo (AS-S) | mRNA secondary structure |
|---|---|---|---|---|---|---|
| 196 | UCCAGGUGGUGGUGAGAUG | CA-CA | 5 | 57.9% | 1.7 | Y |
| 200 | GGUGGUGGUGAGAUGCAGA | CA-CC | 3 | 57.9% | 2.0 | M |
| 347 | UAUGGUGUUUGGAGCAUCU | GA-AC | 2 | 42.1% | 0.6 | Y |
| 349 | UGGUGUUUGGAGCAUCUAC | UA-UA | 3 | 47.4% | 0.6 | Y |
| 380 | UGUUUACCGAAGUGUUGUU | GA-UG | 6 | 36.8% | 0.5 | M |
| 390 | AGUGUUGUUUGUCCAAUUC | GA-UG | 5 | 36.8% | 1.7 | M |
| 391 | GUGUUGUUUGUCCAAUUCU | AA-GG | 5 | 36.8% | 2.5 | M |
| 413 | TGAAGUUAUUAUGGGCUAU | GA-AA | 5 | 31.6% | 0.1 | M |
| 416 | AGUUAUUAUGGGCUAUAAU | GA-UG | 3 | 26.3% | 2.1 | N |
| 417 | GUUAUUAUGGGCUAUAAUU | AA-GC | 3 | 26.3% | 2.9 | N |
| 488 | AGGUGAAAGGUCACCUAAU | GA-GA | 2 | 42.1% | 4.3 | M |
| 489 | GGUGAAAGGUCACCUAAUG | AA-AA | 3 | 47.4% | 5.2 | Y |
| 893 | UGGAGAAGAGCUUGUGUAA | GA-AT | 5 | 36.8% | 5.9 | Y |
| 1073 | UCGAGAAUCUAAACUAACU | UA-AG | 3 | 31.6% | 3.3 | M |
| 1077 | GAAUCUAAACUAACUAGAA | GA-TC | 3 | 26.3% | 1.2 | Y |
| 1172 | GGAAACUCUGAGUACAUUG | GA-GA | 2 | 42.1% | 1.9 | M |
| 1176 | ACUCUGAGUACAUUGGAAU | AA-AU | 2 | 36.8% | 1.1 | M |
| 1177 | CUCUGAGUACAUUGGAAUA | AA-UG | 3 | 36.8% | 3.5 | N |
| 1256 | AGCUCUUAUUAAGGAGUAU | AA-AC | 0 | 31.6% | 3.3 | Y |
| 1257 | GCUCUUAUUAAGGAGUAUA | AA-CG | 1 | 31.6% | 5.2 | M |
| 1478 | ACUUGACCAGUGUAAAUCU | GA-GA | 6 | 36.8% | 0.8 | Y |
| 1487 | GUGUAAAUCUGACCUGCAA | CA-AA | 5 | 42.1% | 0.4 | Y |
| 2262 | ACUGAAGACCUGAAGACAA | UA-UA | 8 | 42.1% | 0.7 | M |
| 2263 | CUGAAGACCUGAAGACAAU | AA-AA | 8 | 42.1% | 2.2 | M |
| 2267 | AGACCUGAAGACAAUAAAG | GA-CA | 8 | 36.8% | 3.8 | M |
| 2331 | GAGAGAUUCUGUGCUUUGG | CA-AG | 5 | 47.4% | 2.4 | M |

Figure 21

TABLE 2: Eg5 (Kif11) siRNA Sequences

| HEg5 21bp Start Pos | 19bp core hEg5 start bp | Sense | Antisense |
|---|---|---|---|
| 389 | 391 | GUGUUGUUUGUCCAAUUCUdTdT | AGAAUUGGACAAACAACACdTdT |
| 415 | 417 | GUUAUUAUGGGCUAUAAUUdTdT | AAUUAUAGCCCAUAAUAACdTdT |
| 486 | 488 | AGGUGAAAGGUCACCUAAUdTdT | AUUAGGUGACCUUUCACCUdTdT |
| 487 | 489 | GGUGAAAGGUCACCUAAUGdTdT | CAUUAGGUGACCUUUCACCdTdT |
| 891 | 893 | UGGAGAAGAGCUUGUUAAAdTdT | UUUAACAAGCUCUUCUCCAdTdT |
| 1071 | 1073 | UCGAGAAUCUAAACUAACUdTdT | AGUUAGUUUAGAUUCUCGAdTdT |
| 1170 | 1172 | GGAAACUCUGAGUACAUUGdTdT | CAAUGUACUCAGAGUUUCCdTdT |
| 1175 | 1177 | CUCUGAGUACAUUGGAAUAdTdT | UAUUCCAAUGUACUCAGAGdTdT |
| 1254 | 1256 | AGCUCUUAUUAAGGAGUAUdTdT | AUACUCCUUAAUAAGAGCUdTdT |
| 1255 | 1257 | GCUCUUAUUAAGGAGUAUAdTdT | UAUACUCCUUAAUAAGAGCdTdT |
| 1476 | 1478 | ACUUGACCAGUGUAAAUCUdTdT | AGAUUUACACUGGUCAAGUdTdT |
| 2260 | 2262 | ACUGAAGACCUGAAGACAAdTdT | UUGUCUUCAGGUCUUCAGUdTdT |
| 2261 | 2263 | CUGAAGACCUGAAGACAAUdTdT | AUUGUCUUCAGGUCUUCAGdTdT |
| 2265 | 2267 | AGACCUGAAGACAAUAAAGdTdT | CUUUAUUGUCUUCAGGUCUdTdT |
| 2329 | 2331 | GAGAGAUUCUGUGCUUUGGdTdT | CCAAAGCACAGAAUCUCUCdTdT |

Figure 22

TABLE 3: EGFR siRNA Sequences

| bp start (human) | Sense strand target 5p-3p – 19bp + TT |
|---|---|
| 510 | UGUCCUCAUUGCCCUCAACUTT |
| 511 | GUCCUCAUUGCCCUCAACAUU |
| 512 | UCCUCAUUGCCCUCAACACUU |
| 816 | UGAUCCAAGCUGUCCCAAUUU |
| 817 | GAUCCAAGCUGUCCCAAUGUU |
| 854 | GAGAGGAGAACUGCCAGAAUU |
| 855 | AGAGGAGAACUGCCAGAAAUU |
| 928 | CCCAGUGACUGCUGCCACAUU |
| 929 | CCAGUGACUGCUGCCACAAUU |
| 1252 | GUGUGUAACGGAAUAGGUAUU |
| 1986 | CCAGUGCCACUACACAUUUU |
| 1987 | CAGUGCCACUACACAUUGUU |
| 1988 | AGUGCCCACUACACAUUGAUU |
| 2438 | GGAUCCCAGAAGGUGAGAAUU |
| 2439 | GAUCCCAGAAGGUGAGAAAUU |
| 2440 | AUCCCAGAAGGUGAGAAAGUU |
| 2441 | UCCCAGAAGGUGAGAAAGUUU |
| 2793 | GCAUGUCAAGAUCACAGAUUU |
| 2794 | CAUGUCAAGAUCACAGAUUUU |
| 2795 | AUGUCAAGAUCACAGAUUUUU |
| 2872 | GUGCCUAUCAAGUGGAUGGUU |
| 3068 | UCGAUGUCUACAUGGAUCAUU |
| 3086 | UGGUCAAGUGCUGGAUGAUUU |
| 3087 | GGUCAAGUGCUGGAUGAUAUU |
| 3088 | GUCAAGUGCUGGAUGAUAGUU |
| 3194 | GGGAUGAAAGAAUGCAUUUUU |
| 3195 | GGAUGAAAGAAUGCAUUUGUU |
| 3755 | CUGACUACCAGGACUUUUU |
| 3757 | GACUACCAGGACUUUUUU |
| 3758 | ACUACCAGGACUUUUUUU |

Figure 23

TABLE 4: EGFR siRNA Sequences

| bp start (human) | Sense 5p-3p – 19bp + TT | AntiSense 5p-3p – 19bp + TT |
|---|---|---|
| 511 | GUCCUCAUUGCCCUCAACAUTT | UGUUGAGGGCAAUGAGGACTT |
| 512 | UCCUCAUUGCCCUCAACACTT | GUGUUGAGGGCAAUGAGGATT |
| 816 | UGAUCCAAGCUGUCCCAAUTT | AUUGGGACAGCUUGGAUCATT |
| 817 | GAUCCAAGCUGUCCCAAUGTT | CAUUGGGACAGCUUGGAUCTT |
| 1252 | GUGUGUAACGGAAUAGGUATT | UACCUAUUCCGUUACACACTT |
| 1986 | CCAGUGUGCCACUACAUUTT | AAUGUAGUGGGCACACUGGTT |
| 2440 | AUCCCAGAAGGUGAGAAAGTT | CUUUCUCACCUUCUGGGAUTT |
| 2795 | AUGUCAAGAUCACAGAUUUTT | AAAUCUGUGAUCUUGACAUTT |
| 3068 | UCGAUGUCUACAUGAUCAUTT | AUGAUCAUGUAGACAUCGATT |
| 3088 | GUCAAGUGCUGGAUGAUAGTT | CUAUCAUCCAGCACUUGACTT |
| 3755 | CUGACUACCAGCAGGACUUTT | AAGUCCUGCUGGUAGUCAGTT |
| 3757 | GACUACCAGCAGGACUUCUTT | AGAAGUCCUGCUGGUAGUCTT |
| 3758 | ACUACCAGCAGGACUUCUUTT | AAGAAGUCCUGCUGGUAGUTT |

Figure 24

TABLE 5: XIAP siRNA Sequences

| bp start (human) | Sense strand target (5p-3p – 19bp + TT) |
|---|---|
| 5'UTR1 | AAGGUGGACAAGUCCUAUUTT |
| 5'UTR2 | AGGUGGACAAGUCCUAUUUTT |
| 64 | GAAUUGUAGAAGAGAGUUUAUTT |
| 67 | UUUGUAGAAGAGUUUAAAUATT |
| 70 | GUAGAAGAGUUUAAUAGAUTT |
| 72 | AGAAGAGUUUAAUAGAUUATT |
| 73 | GAAGAGUUUAAUAGAUUAATT |
| 74 | AAGAGUUUAAUAGAUUAAUTT |
| 113 | GUGGUAGUCCUGUUUCAGCTT |
| 118 | AGUCCUGUUUCAGCAUCAATT |
| 119 | GUCCUGUUUCAGCAUCAACTT |
| 120 | UCCUGUUUCAGCAUCAACATT |
| 261 | CCCAAAUUGCAGAUUUAUCTT |
| 300 | UAGUGCCAGCAGUCUACATT |
| 732 | GAGUUCAGUAGGAAUUUCTT |
| 738 | UGAUAGGAAUUUCCCAAAUTT |
| 739 | GAUAGGAAUUUCCCAAAUUTT |
| 741 | UAGGAAUUUCCCAAAUUCATT |
| 742 | AGGAAUUUCCCAAAUUCAATT |
| 849 | GCUUGCAAGAGCUGGAUUUTT |
| 1307 | GUACUGAAGAGCAGCUAAGTT |
| 1353 | AAUCUGUAUGGAUAGAAAUTT |
| 1354 | AUCUGUAUGGAUAGAAAUATT |
| 1355 | UCUGUAUGGAUAGAAAUAUTT |
| 1356 | CUGUAUGGAUAGAAAUAUUTT |
| 1361 | UGGAUAGAAAUAUUGCUAUTT |
| 1362 | GGAUAGAAAUAUUGCUAUCTT |

Figure 25

TABLE 6: XIAP siRNA Sequences

| bp start (human) | Sense 5p-3p – 19bp + TT | AntiSense 5p-3p – 19bp + TT |
| --- | --- | --- |
| 64 | GAAUUGUAGAAGAGAGUUUATT | UAAACUCUCUCUACAAAUUCTT |
| 73 | GAAGAGUUUAAUAGAUUAATT | UUAAUCUAUUAAACUCUUCTT |
| 74 | AAGAGUUUAAUAGAUUAAAATT | UUUAAUCUAUUAAACUCUUTT |
| 113 | GUGGUAGUCCUGUUUCAGCTT | GCUGAAACAGGACUACCACTT |
| 120 | UCCUGUUUCAGCAUCAACATT | UGUUGAUGCUGAAACAGGATT |
| 261 | CCCAAAUUGCAGAUUUAUCTT | GAUAAAUCUGCAAUUUGGGTT |
| 300 | UAGUGCCACGCAGUCUACATT | UGUAGACUGCGUGGCACUATT |
| 732 | GAGUUCUGAUAGGAAUUUCTT | GAAAUUCCUAUCAGAACUCTT |
| 741 | UAGGAAUUUCCCAAAUUCATT | UGAAUUUGGGAAAUUCCUATT |
| 742 | AGGAAUUUCCCAAAUUCAATT | UUGAAUUUGGGAAAUUCCUTT |
| 849 | GCUUGCAAGAGCUGGAUUUTT | AAAUCCAGCUCUUGCAAGCTT |
| 1307 | GUACUGAGAGCAGCUAAGTT | CUUAGCUGCUCUCUCAGUACTT |
| 1361 | UGGAUAGAAAUAUUGCUAUTT | AUAGCAAUAUUUCUAUCCATT |
| 1362 | GGAUAGAAAUAUUGCUAUCTT | GAUAGCAAUAUUUCUAUCCTT |

Figure 26

TABLE 7

| ID | SEQUENCE |
|---|---|
| 1 | ACCTGCGTGCAGTCGGTCCTCCA |
| 2 | CCTGCGTGCAGTCGGTCCTCCAG |
| 3 | CTGCGTGCAGTCGGTCCTCCAGG |
| 4 | TGCGTGCAGTCGGTCCTCCAGGC |
| 5 | GCGTGCAGTCGGTCCTCCAGGCC |
| 6 | CGTGCAGTCGGTCCTCCAGGCCA |
| 7 | GTGCAGTCGGTCCTCCAGGCCAC |
| 8 | TGCAGTCGGTCCTCCAGGCCACG |
| 9 | GCAGTCGGTCCTCCAGGCCACGC |
| 10 | CAGTCGGTCCTCCAGGCCACGCA |
| 11 | AGTCGGTCCTCCAGGCCACGCAG |
| 12 | GTCGGTCCTCCAGGCCACGCAGC |
| 13 | TCGGTCCTCCAGGCCACGCAGCG |
| 14 | CGGTCCTCCAGGCCACGCAGCGC |
| 15 | GGTCCTCCAGGCCACGCAGCGCC |
| 16 | GTCCTCCAGGCCACGCAGCGCCC |
| 17 | TCCTCCAGGCCACGCAGCGCCCG |
| 18 | CCTCCAGGCCACGCAGCGCCCGA |
| 19 | CTCCAGGCCACGCAGCGCCCGAG |
| 20 | TCCAGGCCACGCAGCGCCCGAGA |
| 21 | CCAGGCCACGCAGCGCCCGAGAG |
| 22 | CAGGCCACGCAGCGCCCGAGAGT |
| 23 | AGGCCACGCAGCGCCCGAGAGTA |
| 24 | GGCCACGCAGCGCCCGAGAGTAC |
| 25 | GCCACGCAGCGCCCGAGAGTACC |
| 26 | CCACGCAGCGCCCGAGAGTACCA |
| 27 | CACGCAGCGCCCGAGAGTACCAG |
| 28 | ACGCAGCGCCCGAGAGTACCAGG |
| 29 | CGCAGCGCCCGAGAGTACCAGGG |
| 30 | GCAGCGCCCGAGAGTACCAGGGA |
| 31 | CAGCGCCCGAGAGTACCAGGGAG |
| 32 | AGCGCCCGAGAGTACCAGGGAGA |
| 33 | GCGCCCGAGAGTACCAGGGAGAC |
| 34 | CGCCCGAGAGTACCAGGGAGACT |
| 35 | GCCCGAGAGTACCAGGGAGACTC |
| 36 | CCCGAGAGTACCAGGGAGACTCC |
| 37 | CCGAGAGTACCAGGGAGACTCCG |
| 38 | CGAGAGTACCAGGGAGACTCCGG |
| 39 | GAGAGTACCAGGGAGACTCCGGC |
| 40 | AGAGTACCAGGGAGACTCCGGCC |
| 41 | GAGTACCAGGGAGACTCCGGCCC |
| 42 | AGTACCAGGGAGACTCCGGCCCC |
| 43 | GTACCAGGGAGACTCCGGCCCCT |
| 44 | TACCAGGGAGACTCCGGCCCCTG |
| 45 | ACCAGGGAGACTCCGGCCCCTGT |
| 46 | CCAGGGAGACTCCGGCCCCTGTC |
| 47 | CAGGGAGACTCCGGCCCCTGTCG |
| 48 | AGGGAGACTCCGGCCCCTGTCGG |
| 49 | GGGAGACTCCGGCCCCTGTCGGC |
| 50 | GGAGACTCCGGCCCCTGTCGGCG |
| 51 | GAGACTCCGGCCCCTGTCGGCGC |
| 52 | AGACTCCGGCCCCTGTCGGCGCC |
| 53 | GACTCCGGCCCCTGTCGGCGCCA |
| 54 | ACTCCGGCCCCTGTCGGCGCCAA |
| 55 | CTCCGGCCCCTGTCGGCGCCAAG |

| ID | SEQUENCE |
|---|---|
| 56 | TCCGGCCCCTGTCGGCGCCAAGC |
| 57 | CCGGCCCCTGTCGGCGCCAAGCC |
| 58 | CGGCCCCTGTCGGCGCCAAGCCC |
| 59 | GGCCCCTGTCGGCGCCAAGCCCC |
| 60 | GCCCCTGTCGGCGCCAAGCCCCT |
| 61 | CCCCTGTCGGCGCCAAGCCCCTC |
| 62 | CCCTGTCGGCGCCAAGCCCCTCC |
| 63 | CCTGTCGGCGCCAAGCCCCTCCG |
| 64 | CTGTCGGCGCCAAGCCCCTCCGC |
| 65 | TGTCGGCGCCAAGCCCCTCCGCC |
| 66 | GTCGGCGCCAAGCCCCTCCGCCC |
| 67 | TCGGCGCCAAGCCCCTCCGCCCC |
| 68 | CGGCGCCAAGCCCCTCCGCCCCT |
| 69 | GGCGCCAAGCCCCTCCGCCCCTC |
| 70 | GCGCCAAGCCCCTCCGCCCCTCA |
| 71 | CGCCAAGCCCCTCCGCCCCTCAC |
| 72 | GCCAAGCCCCTCCGCCCCTCACA |
| 73 | CCAAGCCCCTCCGCCCCTCACAG |
| 74 | CAAGCCCCTCCGCCCCTCACAGC |
| 75 | AAGCCCCTCCGCCCCTCACAGCG |
| 76 | AGCCCCTCCGCCCCTCACAGCGC |
| 77 | GCCCCTCCGCCCCTCACAGCGCC |
| 78 | CCCCTCCGCCCCTCACAGCGCCC |
| 79 | CCCTCCGCCCCTCACAGCGCCCA |
| 80 | CCTCCGCCCCTCACAGCGCCCAG |
| 81 | CTCCGCCCCTCACAGCGCCCAGG |
| 82 | TCCGCCCCTCACAGCGCCCAGGT |
| 83 | CCGCCCCTCACAGCGCCCAGGTC |
| 84 | CGCCCCTCACAGCGCCCAGGTCC |
| 85 | GCCCCTCACAGCGCCCAGGTCCG |
| 86 | CCCCTCACAGCGCCCAGGTCCGC |
| 87 | CCCTCACAGCGCCCAGGTCCGCG |
| 88 | CCTCACAGCGCCCAGGTCCGCGG |
| 89 | CTCACAGCGCCCAGGTCCGCGGC |
| 90 | TCACAGCGCCCAGGTCCGCGGCC |
| 91 | GCCGGGCCTTGATTTTTTGGCGG |
| 92 | CCGGGCCTTGATTTTTTGGCGGG |
| 93 | CGGGCCTTGATTTTTTGGCGGGG |
| 94 | GGGCCTTGATTTTTTGGCGGGGA |
| 95 | GGCCTTGATTTTTTGGCGGGGAC |
| 96 | GCCTTGATTTTTTGGCGGGGACC |
| 97 | CCTTGATTTTTTGGCGGGGACCG |
| 98 | CTTGATTTTTTGGCGGGGACCGT |
| 99 | ATGGCGTCGCAGCCAAATTCGTC |
| 100 | TGGCGTCGCAGCCAAATTCGTCT |
| 101 | GGCGTCGCAGCCAAATTCGTCTG |
| 102 | GCGTCGCAGCCAAATTCGTCTGC |
| 103 | CGTCGCAGCCAAATTCGTCTGCG |
| 104 | GTCGCAGCCAAATTCGTCTGCGA |
| 105 | TCGCAGCCAAATTCGTCTGCGAA |
| 106 | CGCAGCCAAATTCGTCTGCGAAG |
| 107 | GCAGCCAAATTCGTCTGCGAAGA |
| 108 | CAGCCAAATTCGTCTGCGAAGAA |
| 109 | AGCCAAATTCGTCTGCGAAGAAG |
| 110 | GCCAAATTCGTCTGCGAAGAAGA |
| 111 | CCAAATTCGTCTGCGAAGAAGAA |
| 112 | CAAATTCGTCTGCGAAGAAGAAA |
| 113 | AAATTCGTCTGCGAAGAAGAAAG |

| ID | SEQUENCE |
|---|---|
| 114 | AATTCGTCTGCGAAGAAGAAAGA |
| 115 | ATTCGTCTGCGAAGAAGAAAGAG |
| 116 | TTCGTCTGCGAAGAAGAAAGAGG |
| 117 | TCGTCTGCGAAGAAGAAAGAGGA |
| 118 | CGTCTGCGAAGAAGAAAGAGGAG |
| 119 | GTCTGCGAAGAAGAAAGAGGAGA |
| 120 | TCTGCGAAGAAGAAAGAGGAGAA |
| 121 | CTGCGAAGAAGAAAGAGGAGAAG |
| 122 | TGCGAAGAAGAAAGAGGAGAAGG |
| 123 | GCGAAGAAGAAAGAGGAGAAGGG |
| 124 | CGAAGAAGAAAGAGGAGAAGGGG |
| 125 | GAAGAAGAAAGAGGAGAAGGGGA |
| 126 | AAGAAGAAAGAGGAGAAGGGGAA |
| 127 | AGAAGAAAGAGGAGAAGGGGAAG |
| 128 | GAAGAAAGAGGAGAAGGGGAAGA |
| 129 | AAGAAAGAGGAGAAGGGGAAGAA |
| 130 | AGAAAGAGGAGAAGGGGAAGAAC |
| 131 | GAAAGAGGAGAAGGGGAAGAACA |
| 132 | AAAGAGGAGAAGGGGAAGAACAT |
| 133 | AAGAGGAGAAGGGGAAGAACATC |
| 134 | AGAGGAGAAGGGGAAGAACATCC |
| 135 | GAGGAGAAGGGGAAGAACATCCA |
| 136 | AGGAGAAGGGGAAGAACATCCAG |
| 137 | GGAGAAGGGGAAGAACATCCAGG |
| 138 | GAGAAGGGGAAGAACATCCAGGT |
| 139 | AGAAGGGGAAGAACATCCAGGTG |
| 140 | GAAGGGGAAGAACATCCAGGTGG |
| 141 | AAGGGGAAGAACATCCAGGTGGT |
| 142 | AGGGGAAGAACATCCAGGTGGTG |
| 143 | GGGGAAGAACATCCAGGTGGTGG |
| 144 | GGGAAGAACATCCAGGTGGTGGT |
| 145 | GGAAGAACATCCAGGTGGTGGTG |
| 146 | GAAGAACATCCAGGTGGTGGTGA |
| 147 | AAGAACATCCAGGTGGTGGTGAG |
| 148 | AGAACATCCAGGTGGTGGTGAGA |
| 149 | GAACATCCAGGTGGTGGTGAGAT |
| 150 | AACATCCAGGTGGTGGTGAGATG |
| 151 | ACATCCAGGTGGTGGTGAGATGC |
| 152 | CATCCAGGTGGTGGTGAGATGCA |
| 153 | ATCCAGGTGGTGGTGAGATGCAG |
| 154 | TCCAGGTGGTGGTGAGATGCAGA |
| 155 | CCAGGTGGTGGTGAGATGCAGAC |
| 156 | CAGGTGGTGGTGAGATGCAGACC |
| 157 | AGGTGGTGGTGAGATGCAGACCA |
| 158 | GGTGGTGGTGAGATGCAGACCAT |
| 159 | GTGGTGGTGAGATGCAGACCATT |
| 160 | TGGTGGTGAGATGCAGACCATTT |
| 161 | GGTGGTGAGATGCAGACCATTTA |
| 162 | GTGGTGAGATGCAGACCATTTAA |
| 163 | TGGTGAGATGCAGACCATTTAAT |
| 164 | GGTGAGATGCAGACCATTTAATT |
| 165 | GTGAGATGCAGACCATTTAATTT |
| 166 | TGAGATGCAGACCATTTAATTTG |
| 167 | GAGATGCAGACCATTTAATTTGG |
| 168 | AGATGCAGACCATTTAATTTGGC |
| 169 | GATGCAGACCATTTAATTTGGCA |
| 170 | ATGCAGACCATTTAATTTGGCAG |
| 171 | TGCAGACCATTTAATTTGGCAGA |

| ID | SEQUENCE |
|---|---|
| 172 | GCAGACCATTTAATTTGGCAGAG |
| 173 | CAGACCATTTAATTTGGCAGAGC |
| 174 | AGACCATTTAATTTGGCAGAGCG |
| 175 | GACCATTTAATTTGGCAGAGCGG |
| 176 | ACCATTTAATTTGGCAGAGCGGA |
| 177 | CCATTTAATTTGGCAGAGCGGAA |
| 178 | CATTTAATTTGGCAGAGCGGAAA |
| 179 | ATTTAATTTGGCAGAGCGGAAAG |
| 180 | TTTAATTTGGCAGAGCGGAAAGC |
| 181 | TTAATTTGGCAGAGCGGAAAGCT |
| 182 | TAATTTGGCAGAGCGGAAAGCTA |
| 183 | AATTTGGCAGAGCGGAAAGCTAG |
| 184 | ATTTGGCAGAGCGGAAAGCTAGC |
| 185 | TTTGGCAGAGCGGAAAGCTAGCG |
| 186 | TTGGCAGAGCGGAAAGCTAGCGC |
| 187 | TGGCAGAGCGGAAAGCTAGCGCC |
| 188 | GGCAGAGCGGAAAGCTAGCGCCC |
| 189 | GCAGAGCGGAAAGCTAGCGCCCA |
| 190 | CAGAGCGGAAAGCTAGCGCCCAT |
| 191 | AGAGCGGAAAGCTAGCGCCCATT |
| 192 | GAGCGGAAAGCTAGCGCCCATTC |
| 193 | AGCGGAAAGCTAGCGCCCATTCA |
| 194 | GCGGAAAGCTAGCGCCCATTCAA |
| 195 | CGGAAAGCTAGCGCCCATTCAAT |
| 196 | GGAAAGCTAGCGCCCATTCAATA |
| 197 | GAAAGCTAGCGCCCATTCAATAG |
| 198 | AAAGCTAGCGCCCATTCAATAGT |
| 199 | AAGCTAGCGCCCATTCAATAGTA |
| 200 | AGCTAGCGCCCATTCAATAGTAG |
| 201 | GCTAGCGCCCATTCAATAGTAGA |
| 202 | CTAGCGCCCATTCAATAGTAGAA |
| 203 | TAGCGCCCATTCAATAGTAGAAT |
| 204 | AGCGCCCATTCAATAGTAGAATG |
| 205 | GCGCCCATTCAATAGTAGAATGT |
| 206 | CGCCCATTCAATAGTAGAATGTG |
| 207 | GCCCATTCAATAGTAGAATGTGA |
| 208 | CCCATTCAATAGTAGAATGTGAT |
| 209 | CCATTCAATAGTAGAATGTGATC |
| 210 | CATTCAATAGTAGAATGTGATCC |
| 211 | ATTCAATAGTAGAATGTGATCCT |
| 212 | TTCAATAGTAGAATGTGATCCTG |
| 213 | TCAATAGTAGAATGTGATCCTGT |
| 214 | CAATAGTAGAATGTGATCCTGTA |
| 215 | AATAGTAGAATGTGATCCTGTAC |
| 216 | ATAGTAGAATGTGATCCTGTACG |
| 217 | TAGTAGAATGTGATCCTGTACGA |
| 218 | AGTAGAATGTGATCCTGTACGAA |
| 219 | GTAGAATGTGATCCTGTACGAAA |
| 220 | TAGAATGTGATCCTGTACGAAAA |
| 221 | AGAATGTGATCCTGTACGAAAAG |
| 222 | GAATGTGATCCTGTACGAAAAGA |
| 223 | AATGTGATCCTGTACGAAAAGAA |
| 224 | ATGTGATCCTGTACGAAAAGAAG |
| 225 | TGTGATCCTGTACGAAAAGAAGT |
| 226 | GTGATCCTGTACGAAAAGAAGTT |
| 227 | TGATCCTGTACGAAAAGAAGTTA |
| 228 | GATCCTGTACGAAAAGAAGTTAG |
| 229 | ATCCTGTACGAAAAGAAGTTAGT |

| ID | SEQUENCE |
|---|---|
| 230 | TCCTGTACGAAAAGAAGTTAGTG |
| 231 | CCTGTACGAAAAGAAGTTAGTGT |
| 232 | CTGTACGAAAAGAAGTTAGTGTA |
| 233 | TGTACGAAAAGAAGTTAGTGTAC |
| 234 | GTACGAAAAGAAGTTAGTGTACG |
| 235 | TACGAAAAGAAGTTAGTGTACGA |
| 236 | ACGAAAAGAAGTTAGTGTACGAA |
| 237 | CGAAAAGAAGTTAGTGTACGAAC |
| 238 | GAAAAGAAGTTAGTGTACGAACT |
| 239 | AAAAGAAGTTAGTGTACGAACTG |
| 240 | AAAGAAGTTAGTGTACGAACTGG |
| 241 | AAGAAGTTAGTGTACGAACTGGA |
| 242 | AGAAGTTAGTGTACGAACTGGAG |
| 243 | GAAGTTAGTGTACGAACTGGAGG |
| 244 | AAGTTAGTGTACGAACTGGAGGA |
| 245 | AGTTAGTGTACGAACTGGAGGAT |
| 246 | GTTAGTGTACGAACTGGAGGATT |
| 247 | TTAGTGTACGAACTGGAGGATTG |
| 248 | TAGTGTACGAACTGGAGGATTGG |
| 249 | AGTGTACGAACTGGAGGATTGGC |
| 250 | GTGTACGAACTGGAGGATTGGCT |
| 251 | TGTACGAACTGGAGGATTGGCTG |
| 252 | GTACGAACTGGAGGATTGGCTGA |
| 253 | TACGAACTGGAGGATTGGCTGAC |
| 254 | ACGAACTGGAGGATTGGCTGACA |
| 255 | CGAACTGGAGGATTGGCTGACAA |
| 256 | GAACTGGAGGATTGGCTGACAAG |
| 257 | AACTGGAGGATTGGCTGACAAGA |
| 258 | ACTGGAGGATTGGCTGACAAGAG |
| 259 | CTGGAGGATTGGCTGACAAGAGC |
| 260 | TGGAGGATTGGCTGACAAGAGCT |
| 261 | GGAGGATTGGCTGACAAGAGCTC |
| 262 | GAGGATTGGCTGACAAGAGCTCA |
| 263 | AGGATTGGCTGACAAGAGCTCAA |
| 264 | GGATTGGCTGACAAGAGCTCAAG |
| 265 | GATTGGCTGACAAGAGCTCAAGG |
| 266 | ATTGGCTGACAAGAGCTCAAGGA |
| 267 | TTGGCTGACAAGAGCTCAAGGAA |
| 268 | TGGCTGACAAGAGCTCAAGGAAA |
| 269 | GGCTGACAAGAGCTCAAGGAAAA |
| 270 | GCTGACAAGAGCTCAAGGAAAAC |
| 271 | CTGACAAGAGCTCAAGGAAAACA |
| 272 | TGACAAGAGCTCAAGGAAAACAT |
| 273 | GACAAGAGCTCAAGGAAAACATA |
| 274 | ACAAGAGCTCAAGGAAAACATAC |
| 275 | CAAGAGCTCAAGGAAAACATACA |
| 276 | AAGAGCTCAAGGAAAACATACAC |
| 277 | AGAGCTCAAGGAAAACATACACT |
| 278 | GAGCTCAAGGAAAACATACACTT |
| 279 | AGCTCAAGGAAAACATACACTTT |
| 280 | GCTCAAGGAAAACATACACTTTT |
| 281 | CTCAAGGAAAACATACACTTTTG |
| 282 | TCAAGGAAAACATACACTTTTGA |
| 283 | CAAGGAAAACATACACTTTTGAT |
| 284 | AAGGAAAACATACACTTTTGATA |
| 285 | AGGAAAACATACACTTTTGATAT |
| 286 | GGAAAACATACACTTTTGATATG |
| 287 | GAAAACATACACTTTTGATATGG |

| ID | SEQUENCE |
|---|---|
| 288 | AAAACATACACTTTTGATATGGT |
| 289 | AAACATACACTTTTGATATGGTG |
| 290 | AACATACACTTTTGATATGGTGT |
| 291 | ACATACACTTTTGATATGGTGTT |
| 292 | CATACACTTTTGATATGGTGTTT |
| 293 | ATACACTTTTGATATGGTGTTTG |
| 294 | TACACTTTTGATATGGTGTTTGG |
| 295 | ACACTTTTGATATGGTGTTTGGA |
| 296 | CACTTTTGATATGGTGTTTGGAG |
| 297 | ACTTTTGATATGGTGTTTGGAGC |
| 298 | CTTTTGATATGGTGTTTGGAGCA |
| 299 | TTTTGATATGGTGTTTGGAGCAT |
| 300 | TTTGATATGGTGTTTGGAGCATC |
| 301 | TTGATATGGTGTTTGGAGCATCT |
| 302 | TGATATGGTGTTTGGAGCATCTA |
| 303 | GATATGGTGTTTGGAGCATCTAC |
| 304 | ATATGGTGTTTGGAGCATCTACT |
| 305 | TATGGTGTTTGGAGCATCTACTA |
| 306 | ATGGTGTTTGGAGCATCTACTAA |
| 307 | TGGTGTTTGGAGCATCTACTAAA |
| 308 | GGTGTTTGGAGCATCTACTAAAC |
| 309 | GTGTTTGGAGCATCTACTAAACA |
| 310 | TGTTTGGAGCATCTACTAAACAG |
| 311 | GTTTGGAGCATCTACTAAACAGA |
| 312 | TTTGGAGCATCTACTAAACAGAT |
| 313 | TTGGAGCATCTACTAAACAGATT |
| 314 | TGGAGCATCTACTAAACAGATTG |
| 315 | GGAGCATCTACTAAACAGATTGA |
| 316 | GAGCATCTACTAAACAGATTGAT |
| 317 | AGCATCTACTAAACAGATTGATG |
| 318 | GCATCTACTAAACAGATTGATGT |
| 319 | CATCTACTAAACAGATTGATGTT |
| 320 | ATCTACTAAACAGATTGATGTTT |
| 321 | TCTACTAAACAGATTGATGTTTA |
| 322 | CTACTAAACAGATTGATGTTTAC |
| 323 | TACTAAACAGATTGATGTTTACC |
| 324 | ACTAAACAGATTGATGTTTACCG |
| 325 | CTAAACAGATTGATGTTTACCGA |
| 326 | TAAACAGATTGATGTTTACCGAA |
| 327 | AAACAGATTGATGTTTACCGAAG |
| 328 | AACAGATTGATGTTTACCGAAGT |
| 329 | ACAGATTGATGTTTACCGAAGTG |
| 330 | CAGATTGATGTTTACCGAAGTGT |
| 331 | AGATTGATGTTTACCGAAGTGTT |
| 332 | GATTGATGTTTACCGAAGTGTTG |
| 333 | ATTGATGTTTACCGAAGTGTTGT |
| 334 | TTGATGTTTACCGAAGTGTTGTT |
| 335 | TGATGTTTACCGAAGTGTTGTTT |
| 336 | GATGTTTACCGAAGTGTTGTTTG |
| 337 | ATGTTTACCGAAGTGTTGTTTGT |
| 338 | TGTTTACCGAAGTGTTGTTTGTC |
| 339 | GTTTACCGAAGTGTTGTTTGTCC |
| 340 | TTTACCGAAGTGTTGTTTGTCCA |
| 341 | TTACCGAAGTGTTGTTTGTCCAA |
| 342 | TACCGAAGTGTTGTTTGTCCAAT |
| 343 | ACCGAAGTGTTGTTTGTCCAATT |
| 344 | CCGAAGTGTTGTTTGTCCAATTC |
| 345 | CGAAGTGTTGTTTGTCCAATTCT |

| ID | SEQUENCE |
|---|---|
| 346 | GAAGTGTTGTTTGTCCAATTCTG |
| 347 | AAGTGTTGTTTGTCCAATTCTGG |
| 348 | AGTGTTGTTTGTCCAATTCTGGA |
| 349 | GTGTTGTTTGTCCAATTCTGGAT |
| 350 | TGTTGTTTGTCCAATTCTGGATG |
| 351 | GTTGTTTGTCCAATTCTGGATGA |
| 352 | TTGTTTGTCCAATTCTGGATGAA |
| 353 | TGTTTGTCCAATTCTGGATGAAG |
| 354 | GTTTGTCCAATTCTGGATGAAGT |
| 355 | TTTGTCCAATTCTGGATGAAGTT |
| 356 | TTGTCCAATTCTGGATGAAGTTA |
| 357 | TGTCCAATTCTGGATGAAGTTAT |
| 358 | GTCCAATTCTGGATGAAGTTATT |
| 359 | TCCAATTCTGGATGAAGTTATTA |
| 360 | CCAATTCTGGATGAAGTTATTAT |
| 361 | CAATTCTGGATGAAGTTATTATG |
| 362 | AATTCTGGATGAAGTTATTATGG |
| 363 | ATTCTGGATGAAGTTATTATGGG |
| 364 | TTCTGGATGAAGTTATTATGGGC |
| 365 | TCTGGATGAAGTTATTATGGGCT |
| 366 | CTGGATGAAGTTATTATGGGCTA |
| 367 | TGGATGAAGTTATTATGGGCTAT |
| 368 | GGATGAAGTTATTATGGGCTATA |
| 369 | GATGAAGTTATTATGGGCTATAA |
| 370 | ATGAAGTTATTATGGGCTATAAT |
| 371 | TGAAGTTATTATGGGCTATAATT |
| 372 | GAAGTTATTATGGGCTATAATTG |
| 373 | AAGTTATTATGGGCTATAATTGC |
| 374 | AGTTATTATGGGCTATAATTGCA |
| 375 | GTTATTATGGGCTATAATTGCAC |
| 376 | TTATTATGGGCTATAATTGCACT |
| 377 | TATTATGGGCTATAATTGCACTA |
| 378 | ATTATGGGCTATAATTGCACTAT |
| 379 | TTATGGGCTATAATTGCACTATC |
| 380 | TATGGGCTATAATTGCACTATCT |
| 381 | ATGGGCTATAATTGCACTATCTT |
| 382 | TGGGCTATAATTGCACTATCTTT |
| 383 | GGGCTATAATTGCACTATCTTTG |
| 384 | GGCTATAATTGCACTATCTTTGC |
| 385 | GCTATAATTGCACTATCTTTGCG |
| 386 | CTATAATTGCACTATCTTTGCGT |
| 387 | TATAATTGCACTATCTTTGCGTA |
| 388 | ATAATTGCACTATCTTTGCGTAT |
| 389 | TAATTGCACTATCTTTGCGTATG |
| 390 | AATTGCACTATCTTTGCGTATGG |
| 391 | ATTGCACTATCTTTGCGTATGGC |
| 392 | TTGCACTATCTTTGCGTATGGCC |
| 393 | TGCACTATCTTTGCGTATGGCCA |
| 394 | GCACTATCTTTGCGTATGGCCAA |
| 395 | CACTATCTTTGCGTATGGCCAAA |
| 396 | ACTATCTTTGCGTATGGCCAAAC |
| 397 | CTATCTTTGCGTATGGCCAAACT |
| 398 | TATCTTTGCGTATGGCCAAACTG |
| 399 | ATCTTTGCGTATGGCCAAACTGG |
| 400 | TCTTTGCGTATGGCCAAACTGGC |
| 401 | CTTTGCGTATGGCCAAACTGGCA |
| 402 | TTTGCGTATGGCCAAACTGGCAC |
| 403 | TTGCGTATGGCCAAACTGGCACT |

| ID | SEQUENCE |
|---|---|
| 404 | TGCGTATGGCCAAACTGGCACTG |
| 405 | GCGTATGGCCAAACTGGCACTGG |
| 406 | CGTATGGCCAAACTGGCACTGGA |
| 407 | GTATGGCCAAACTGGCACTGGAA |
| 408 | TATGGCCAAACTGGCACTGGAAA |
| 409 | ATGGCCAAACTGGCACTGGAAAA |
| 410 | TGGCCAAACTGGCACTGGAAAAA |
| 411 | GGCCAAACTGGCACTGGAAAAAC |
| 412 | GCCAAACTGGCACTGGAAAAACT |
| 413 | CCAAACTGGCACTGGAAAAACTT |
| 414 | CAAACTGGCACTGGAAAAACTTT |
| 415 | AAACTGGCACTGGAAAAACTTTT |
| 416 | AACTGGCACTGGAAAAACTTTTA |
| 417 | ACTGGCACTGGAAAAACTTTTAC |
| 418 | CTGGCACTGGAAAAACTTTTACA |
| 419 | TGGCACTGGAAAAACTTTTACAA |
| 420 | GGCACTGGAAAAACTTTTACAAT |
| 421 | GCACTGGAAAAACTTTTACAATG |
| 422 | CACTGGAAAAACTTTTACAATGG |
| 423 | ACTGGAAAAACTTTTACAATGGA |
| 424 | CTGGAAAAACTTTTACAATGGAA |
| 425 | TGGAAAAACTTTTACAATGGAAG |
| 426 | GGAAAAACTTTTACAATGGAAGG |
| 427 | GAAAAACTTTTACAATGGAAGGT |
| 428 | AAAAACTTTTACAATGGAAGGTG |
| 429 | AAAACTTTTACAATGGAAGGTGA |
| 430 | AAACTTTTACAATGGAAGGTGAA |
| 431 | AACTTTTACAATGGAAGGTGAAA |
| 432 | ACTTTTACAATGGAAGGTGAAAG |
| 433 | CTTTTACAATGGAAGGTGAAAGG |
| 434 | TTTTACAATGGAAGGTGAAAGGT |
| 435 | TTTACAATGGAAGGTGAAAGGTC |
| 436 | TTACAATGGAAGGTGAAAGGTCA |
| 437 | TACAATGGAAGGTGAAAGGTCAC |
| 438 | ACAATGGAAGGTGAAAGGTCACC |
| 439 | CAATGGAAGGTGAAAGGTCACCT |
| 440 | AATGGAAGGTGAAAGGTCACCTA |
| 441 | ATGGAAGGTGAAAGGTCACCTAA |
| 442 | TGGAAGGTGAAAGGTCACCTAAT |
| 443 | GGAAGGTGAAAGGTCACCTAATG |
| 444 | GAAGGTGAAAGGTCACCTAATGA |
| 445 | AAGGTGAAAGGTCACCTAATGAA |
| 446 | AGGTGAAAGGTCACCTAATGAAG |
| 447 | GGTGAAAGGTCACCTAATGAAGA |
| 448 | GTGAAAGGTCACCTAATGAAGAG |
| 449 | TGAAAGGTCACCTAATGAAGAGT |
| 450 | GAAAGGTCACCTAATGAAGAGTA |
| 451 | AAAGGTCACCTAATGAAGAGTAT |
| 452 | AAGGTCACCTAATGAAGAGTATA |
| 453 | AGGTCACCTAATGAAGAGTATAC |
| 454 | GGTCACCTAATGAAGAGTATACC |
| 455 | GTCACCTAATGAAGAGTATACCT |
| 456 | TCACCTAATGAAGAGTATACCTG |
| 457 | CACCTAATGAAGAGTATACCTGG |
| 458 | ACCTAATGAAGAGTATACCTGGG |
| 459 | CCTAATGAAGAGTATACCTGGGA |
| 460 | CTAATGAAGAGTATACCTGGGAA |
| 461 | TAATGAAGAGTATACCTGGGAAG |

| ID | SEQUENCE |
|---|---|
| 462 | AATGAAGAGTATACCTGGGAAGA |
| 463 | ATGAAGAGTATACCTGGGAAGAG |
| 464 | TGAAGAGTATACCTGGGAAGAGG |
| 465 | TTCAAATCTTAACCCTTAGGACT |
| 466 | TCAAATCTTAACCCTTAGGACTC |
| 467 | AGAGTATACCTGGGAAGAGGATC |
| 468 | GAGTATACCTGGGAAGAGGATCC |
| 469 | AGTATACCTGGGAAGAGGATCCC |
| 470 | GTATACCTGGGAAGAGGATCCCT |
| 471 | TATACCTGGGAAGAGGATCCCTT |
| 472 | ATACCTGGGAAGAGGATCCCTTG |
| 473 | TACCTGGGAAGAGGATCCCTTGG |
| 474 | ACCTGGGAAGAGGATCCCTTGGC |
| 475 | CCTGGGAAGAGGATCCCTTGGCT |
| 476 | CTGGGAAGAGGATCCCTTGGCTG |
| 477 | TGGGAAGAGGATCCCTTGGCTGG |
| 478 | GGGAAGAGGATCCCTTGGCTGGT |
| 479 | GGAAGAGGATCCCTTGGCTGGTA |
| 480 | GAAGAGGATCCCTTGGCTGGTAT |
| 481 | AAGAGGATCCCTTGGCTGGTATA |
| 482 | AGAGGATCCCTTGGCTGGTATAA |
| 483 | GAGGATCCCTTGGCTGGTATAAT |
| 484 | AGGATCCCTTGGCTGGTATAATT |
| 485 | GGATCCCTTGGCTGGTATAATTC |
| 486 | GATCCCTTGGCTGGTATAATTCC |
| 487 | ATCCCTTGGCTGGTATAATTCCA |
| 488 | TCCCTTGGCTGGTATAATTCCAC |
| 489 | CCCTTGGCTGGTATAATTCCACG |
| 490 | CCTTGGCTGGTATAATTCCACGT |
| 491 | CTTGGCTGGTATAATTCCACGTA |
| 492 | TTGGCTGGTATAATTCCACGTAC |
| 493 | TGGCTGGTATAATTCCACGTACC |
| 494 | GGCTGGTATAATTCCACGTACCC |
| 495 | GCTGGTATAATTCCACGTACCCT |
| 496 | CTGGTATAATTCCACGTACCCTT |
| 497 | TGGTATAATTCCACGTACCCTTC |
| 498 | GGTATAATTCCACGTACCCTTCA |
| 499 | GTATAATTCCACGTACCCTTCAT |
| 500 | TATAATTCCACGTACCCTTCATC |
| 501 | ATAATTCCACGTACCCTTCATCA |
| 502 | TAATTCCACGTACCCTTCATCAA |
| 503 | AATTCCACGTACCCTTCATCAAA |
| 504 | ATTCCACGTACCCTTCATCAAAT |
| 505 | TTCCACGTACCCTTCATCAAATT |
| 506 | TCCACGTACCCTTCATCAAATTT |
| 507 | CCACGTACCCTTCATCAAATTTT |
| 508 | CACGTACCCTTCATCAAATTTTT |
| 509 | ACGTACCCTTCATCAAATTTTTG |
| 510 | CGTACCCTTCATCAAATTTTTGA |
| 511 | GTACCCTTCATCAAATTTTTGAG |
| 512 | TACCCTTCATCAAATTTTTGAGA |
| 513 | ACCCTTCATCAAATTTTTGAGAA |
| 514 | CCCTTCATCAAATTTTTGAGAAA |
| 515 | CCTTCATCAAATTTTTGAGAAAC |
| 516 | CTTCATCAAATTTTTGAGAAACT |
| 517 | TTCATCAAATTTTTGAGAAACTT |
| 518 | TCATCAAATTTTTGAGAAACTTA |
| 519 | CATCAAATTTTTGAGAAACTTAC |

| ID | SEQUENCE |
|---|---|
| 520 | ATCAAATTTTTGAGAAACTTACT |
| 521 | TCAAATTTTTGAGAAACTTACTG |
| 522 | CAAATTTTTGAGAAACTTACTGA |
| 523 | AAATTTTTGAGAAACTTACTGAT |
| 524 | AATTTTTGAGAAACTTACTGATA |
| 525 | ATTTTTGAGAAACTTACTGATAA |
| 526 | TTTTTGAGAAACTTACTGATAAT |
| 527 | TTTTGAGAAACTTACTGATAATG |
| 528 | TTTGAGAAACTTACTGATAATGG |
| 529 | TTGAGAAACTTACTGATAATGGT |
| 530 | TGAGAAACTTACTGATAATGGTA |
| 531 | GAGAAACTTACTGATAATGGTAC |
| 532 | AGAAACTTACTGATAATGGTACT |
| 533 | GAAACTTACTGATAATGGTACTG |
| 534 | AAACTTACTGATAATGGTACTGA |
| 535 | AACTTACTGATAATGGTACTGAA |
| 536 | ACTTACTGATAATGGTACTGAAT |
| 537 | CTTACTGATAATGGTACTGAATT |
| 538 | TTACTGATAATGGTACTGAATTT |
| 539 | TACTGATAATGGTACTGAATTTT |
| 540 | ACTGATAATGGTACTGAATTTTC |
| 541 | CTGATAATGGTACTGAATTTTCA |
| 542 | TGATAATGGTACTGAATTTTCAG |
| 543 | GATAATGGTACTGAATTTTCAGT |
| 544 | ATAATGGTACTGAATTTTCAGTC |
| 545 | TAATGGTACTGAATTTTCAGTCA |
| 546 | AATGGTACTGAATTTTCAGTCAA |
| 547 | ATGGTACTGAATTTTCAGTCAAA |
| 548 | TGGTACTGAATTTTCAGTCAAAG |
| 549 | GGTACTGAATTTTCAGTCAAAGT |
| 550 | GTACTGAATTTTCAGTCAAAGTG |
| 551 | TACTGAATTTTCAGTCAAAGTGT |
| 552 | ACTGAATTTTCAGTCAAAGTGTC |
| 553 | CTGAATTTTCAGTCAAAGTGTCT |
| 554 | TGAATTTTCAGTCAAAGTGTCTC |
| 555 | GAATTTTCAGTCAAAGTGTCTCT |
| 556 | AATTTTCAGTCAAAGTGTCTCTG |
| 557 | ATTTTCAGTCAAAGTGTCTCTGT |
| 558 | TTTTCAGTCAAAGTGTCTCTGTT |
| 559 | TTTCAGTCAAAGTGTCTCTGTTG |
| 560 | TTCAGTCAAAGTGTCTCTGTTGG |
| 561 | TCAGTCAAAGTGTCTCTGTTGGA |
| 562 | CAGTCAAAGTGTCTCTGTTGGAG |
| 563 | AGTCAAAGTGTCTCTGTTGGAGA |
| 564 | GTCAAAGTGTCTCTGTTGGAGAT |
| 565 | TCAAAGTGTCTCTGTTGGAGATC |
| 566 | CAAAGTGTCTCTGTTGGAGATCT |
| 567 | AAAGTGTCTCTGTTGGAGATCTA |
| 568 | AAGTGTCTCTGTTGGAGATCTAT |
| 569 | AGTGTCTCTGTTGGAGATCTATA |
| 570 | GTGTCTCTGTTGGAGATCTATAA |
| 571 | TGTCTCTGTTGGAGATCTATAAT |
| 572 | GTCTCTGTTGGAGATCTATAATG |
| 573 | TCTCTGTTGGAGATCTATAATGA |
| 574 | CTCTGTTGGAGATCTATAATGAA |
| 575 | TCTGTTGGAGATCTATAATGAAG |
| 576 | CTGTTGGAGATCTATAATGAAGA |
| 577 | TGTTGGAGATCTATAATGAAGAG |

| ID | SEQUENCE |
|---|---|
| 578 | GTTGGAGATCTATAATGAAGAGC |
| 579 | TTGGAGATCTATAATGAAGAGCT |
| 580 | TGGAGATCTATAATGAAGAGCTT |
| 581 | GGAGATCTATAATGAAGAGCTTT |
| 582 | GAGATCTATAATGAAGAGCTTTT |
| 583 | AGATCTATAATGAAGAGCTTTTT |
| 584 | GATCTATAATGAAGAGCTTTTTG |
| 585 | ATCTATAATGAAGAGCTTTTTGA |
| 586 | TCTATAATGAAGAGCTTTTTGAT |
| 587 | CTATAATGAAGAGCTTTTTGATC |
| 588 | TATAATGAAGAGCTTTTTGATCT |
| 589 | ATAATGAAGAGCTTTTTGATCTT |
| 590 | TAATGAAGAGCTTTTTGATCTTC |
| 591 | AATGAAGAGCTTTTTGATCTTCT |
| 592 | ATGAAGAGCTTTTTGATCTTCTT |
| 593 | TGAAGAGCTTTTTGATCTTCTTA |
| 594 | GAAGAGCTTTTTGATCTTCTTAA |
| 595 | AAGAGCTTTTTGATCTTCTTAAT |
| 596 | AGAGCTTTTTGATCTTCTTAATC |
| 597 | GAGCTTTTTGATCTTCTTAATCC |
| 598 | AGCTTTTTGATCTTCTTAATCCA |
| 599 | GCTTTTTGATCTTCTTAATCCAT |
| 600 | CTTTTTGATCTTCTTAATCCATC |
| 601 | TTTTTGATCTTCTTAATCCATCA |
| 602 | TTTTGATCTTCTTAATCCATCAT |
| 603 | TTTGATCTTCTTAATCCATCATC |
| 604 | TTGATCTTCTTAATCCATCATCT |
| 605 | TGATCTTCTTAATCCATCATCTG |
| 606 | GATCTTCTTAATCCATCATCTGA |
| 607 | ATCTTCTTAATCCATCATCTGAT |
| 608 | TCTTCTTAATCCATCATCTGATG |
| 609 | CTTCTTAATCCATCATCTGATGT |
| 610 | TTCTTAATCCATCATCTGATGTT |
| 611 | TCTTAATCCATCATCTGATGTTT |
| 612 | CTTAATCCATCATCTGATGTTTC |
| 613 | TTAATCCATCATCTGATGTTTCT |
| 614 | TAATCCATCATCTGATGTTTCTG |
| 615 | AATCCATCATCTGATGTTTCTGA |
| 616 | ATCCATCATCTGATGTTTCTGAG |
| 617 | TCCATCATCTGATGTTTCTGAGA |
| 618 | CCATCATCTGATGTTTCTGAGAG |
| 619 | CATCATCTGATGTTTCTGAGAGA |
| 620 | ATCATCTGATGTTTCTGAGAGAC |
| 621 | TCATCTGATGTTTCTGAGAGACT |
| 622 | CATCTGATGTTTCTGAGAGACTA |
| 623 | ATCTGATGTTTCTGAGAGACTAC |
| 624 | TCTGATGTTTCTGAGAGACTACA |
| 625 | CTGATGTTTCTGAGAGACTACAG |
| 626 | TGATGTTTCTGAGAGACTACAGA |
| 627 | GATGTTTCTGAGAGACTACAGAT |
| 628 | ATGTTTCTGAGAGACTACAGATG |
| 629 | TGTTTCTGAGAGACTACAGATGT |
| 630 | GTTTCTGAGAGACTACAGATGTT |
| 631 | TTTCTGAGAGACTACAGATGTTT |
| 632 | TTCTGAGAGACTACAGATGTTTG |
| 633 | TCTGAGAGACTACAGATGTTTGA |
| 634 | CTGAGAGACTACAGATGTTTGAT |
| 635 | TGAGAGACTACAGATGTTTGATG |

| ID | SEQUENCE |
|---|---|
| 636 | GAGAGACTACAGATGTTTGATGA |
| 637 | AGAGACTACAGATGTTTGATGAT |
| 638 | GAGACTACAGATGTTTGATGATC |
| 639 | AGACTACAGATGTTTGATGATCC |
| 640 | GACTACAGATGTTTGATGATCCC |
| 641 | ACTACAGATGTTTGATGATCCCC |
| 642 | CTACAGATGTTTGATGATCCCCG |
| 643 | TACAGATGTTTGATGATCCCCGT |
| 644 | ACAGATGTTTGATGATCCCCGTA |
| 645 | CAGATGTTTGATGATCCCCGTAA |
| 646 | AGATGTTTGATGATCCCCGTAAC |
| 647 | GATGTTTGATGATCCCCGTAACA |
| 648 | ATGTTTGATGATCCCCGTAACAA |
| 649 | TGTTTGATGATCCCCGTAACAAG |
| 650 | GTTTGATGATCCCCGTAACAAGA |
| 651 | TTTGATGATCCCCGTAACAAGAG |
| 652 | TTGATGATCCCCGTAACAAGAGA |
| 653 | TGATGATCCCCGTAACAAGAGAG |
| 654 | GATGATCCCCGTAACAAGAGAGG |
| 655 | ATGATCCCCGTAACAAGAGAGGA |
| 656 | TGATCCCCGTAACAAGAGAGGAG |
| 657 | GATCCCCGTAACAAGAGAGGAGT |
| 658 | ATCCCCGTAACAAGAGAGGAGTG |
| 659 | TCCCCGTAACAAGAGAGGAGTGA |
| 660 | CCCCGTAACAAGAGAGGAGTGAT |
| 661 | CCCGTAACAAGAGAGGAGTGATA |
| 662 | CCGTAACAAGAGAGGAGTGATAA |
| 663 | CGTAACAAGAGAGGAGTGATAAT |
| 664 | GTAACAAGAGAGGAGTGATAATT |
| 665 | TAACAAGAGAGGAGTGATAATTA |
| 666 | AACAAGAGAGGAGTGATAATTAA |
| 667 | ACAAGAGAGGAGTGATAATTAAA |
| 668 | CAAGAGAGGAGTGATAATTAAAG |
| 669 | AAGAGAGGAGTGATAATTAAAGG |
| 670 | AGAGAGGAGTGATAATTAAAGGT |
| 671 | GAGAGGAGTGATAATTAAAGGTT |
| 672 | AGAGGAGTGATAATTAAAGGTTT |
| 673 | GAGGAGTGATAATTAAAGGTTTA |
| 674 | AGGAGTGATAATTAAAGGTTTAG |
| 675 | GGAGTGATAATTAAAGGTTTAGA |
| 676 | GAGTGATAATTAAAGGTTTAGAA |
| 677 | AGTGATAATTAAAGGTTTAGAAG |
| 678 | GTGATAATTAAAGGTTTAGAAGA |
| 679 | TGATAATTAAAGGTTTAGAAGAA |
| 680 | GATAATTAAAGGTTTAGAAGAAA |
| 681 | ATAATTAAAGGTTTAGAAGAAAT |
| 682 | TAATTAAAGGTTTAGAAGAAATT |
| 683 | AATTAAAGGTTTAGAAGAAATTA |
| 684 | ATTAAAGGTTTAGAAGAAATTAC |
| 685 | TTAAAGGTTTAGAAGAAATTACA |
| 686 | TAAAGGTTTAGAAGAAATTACAG |
| 687 | AAAGGTTTAGAAGAAATTACAGT |
| 688 | AAGGTTTAGAAGAAATTACAGTA |
| 689 | AGGTTTAGAAGAAATTACAGTAC |
| 690 | GGTTTAGAAGAAATTACAGTACA |
| 691 | GTTTAGAAGAAATTACAGTACAC |
| 692 | TTTAGAAGAAATTACAGTACACA |
| 693 | TTAGAAGAAATTACAGTACACAA |

| ID | SEQUENCE |
|---|---|
| 694 | TAGAAGAAATTACAGTACACAAC |
| 695 | AGAAGAAATTACAGTACACAACA |
| 696 | GAAGAAATTACAGTACACAACAA |
| 697 | AAGAAATTACAGTACACAACAAG |
| 698 | AGAAATTACAGTACACAACAAGG |
| 699 | GAAATTACAGTACACAACAAGGA |
| 700 | AAATTACAGTACACAACAAGGAT |
| 701 | AATTACAGTACACAACAAGGATG |
| 702 | ATTACAGTACACAACAAGGATGA |
| 703 | TTACAGTACACAACAAGGATGAA |
| 704 | TACAGTACACAACAAGGATGAAG |
| 705 | ACAGTACACAACAAGGATGAAGT |
| 706 | CAGTACACAACAAGGATGAAGTC |
| 707 | AGTACACAACAAGGATGAAGTCT |
| 708 | GTACACAACAAGGATGAAGTCTA |
| 709 | TACACAACAAGGATGAAGTCTAT |
| 710 | ACACAACAAGGATGAAGTCTATC |
| 711 | CACAACAAGGATGAAGTCTATCA |
| 712 | ACAACAAGGATGAAGTCTATCAA |
| 713 | CAACAAGGATGAAGTCTATCAAA |
| 714 | AACAAGGATGAAGTCTATCAAAT |
| 715 | ACAAGGATGAAGTCTATCAAATT |
| 716 | CAAGGATGAAGTCTATCAAATTT |
| 717 | AAGGATGAAGTCTATCAAATTTT |
| 718 | AGGATGAAGTCTATCAAATTTTA |
| 719 | GGATGAAGTCTATCAAATTTTAG |
| 720 | GATGAAGTCTATCAAATTTTAGA |
| 721 | ATGAAGTCTATCAAATTTTAGAA |
| 722 | TGAAGTCTATCAAATTTTAGAAA |
| 723 | GAAGTCTATCAAATTTTAGAAAA |
| 724 | AAGTCTATCAAATTTTAGAAAAG |
| 725 | AGTCTATCAAATTTTAGAAAAGG |
| 726 | GTCTATCAAATTTTAGAAAAGGG |
| 727 | TCTATCAAATTTTAGAAAAGGGG |
| 728 | CTATCAAATTTTAGAAAAGGGGG |
| 729 | TATCAAATTTTAGAAAAGGGGGC |
| 730 | ATCAAATTTTAGAAAAGGGGGCA |
| 731 | TCAAATTTTAGAAAAGGGGGCAG |
| 732 | CAAATTTTAGAAAAGGGGGCAGC |
| 733 | AAATTTTAGAAAAGGGGGCAGCA |
| 734 | AATTTTAGAAAAGGGGGCAGCAA |
| 735 | ATTTTAGAAAAGGGGGCAGCAAA |
| 736 | TTTTAGAAAAGGGGGCAGCAAAA |
| 737 | TTTAGAAAAGGGGGCAGCAAAAA |
| 738 | TTAGAAAAGGGGGCAGCAAAAAG |
| 739 | TAGAAAAGGGGGCAGCAAAAAGG |
| 740 | AGAAAAGGGGGCAGCAAAAAGGA |
| 741 | GAAAAGGGGGCAGCAAAAAGGAC |
| 742 | AAAAGGGGGCAGCAAAAAGGACA |
| 743 | AAAGGGGGCAGCAAAAAGGACAA |
| 744 | AAGGGGGCAGCAAAAAGGACAAC |
| 745 | AGGGGGCAGCAAAAAGGACAACT |
| 746 | GGGGGCAGCAAAAAGGACAACTG |
| 747 | GGGGCAGCAAAAAGGACAACTGC |
| 748 | GGGCAGCAAAAAGGACAACTGCA |
| 749 | GGCAGCAAAAAGGACAACTGCAG |
| 750 | GCAGCAAAAAGGACAACTGCAGC |
| 751 | CAGCAAAAAGGACAACTGCAGCT |

| ID | SEQUENCE |
|---|---|
| 752 | AGCAAAAAGGACAACTGCAGCTA |
| 753 | GCAAAAAGGACAACTGCAGCTAC |
| 754 | CAAAAAGGACAACTGCAGCTACT |
| 755 | AAAAAGGACAACTGCAGCTACTC |
| 756 | AAAAGGACAACTGCAGCTACTCT |
| 757 | AAAGGACAACTGCAGCTACTCTG |
| 758 | AAGGACAACTGCAGCTACTCTGA |
| 759 | AGGACAACTGCAGCTACTCTGAT |
| 760 | GGACAACTGCAGCTACTCTGATG |
| 761 | GACAACTGCAGCTACTCTGATGA |
| 762 | ACAACTGCAGCTACTCTGATGAA |
| 763 | CAACTGCAGCTACTCTGATGAAT |
| 764 | AACTGCAGCTACTCTGATGAATG |
| 765 | ACTGCAGCTACTCTGATGAATGC |
| 766 | CTGCAGCTACTCTGATGAATGCA |
| 767 | TGCAGCTACTCTGATGAATGCAT |
| 768 | GCAGCTACTCTGATGAATGCATA |
| 769 | CAGCTACTCTGATGAATGCATAC |
| 770 | AGCTACTCTGATGAATGCATACT |
| 771 | GCTACTCTGATGAATGCATACTC |
| 772 | CTACTCTGATGAATGCATACTCT |
| 773 | TACTCTGATGAATGCATACTCTA |
| 774 | ACTCTGATGAATGCATACTCTAG |
| 775 | CTCTGATGAATGCATACTCTAGT |
| 776 | TCTGATGAATGCATACTCTAGTC |
| 777 | CTGATGAATGCATACTCTAGTCG |
| 778 | TGATGAATGCATACTCTAGTCGT |
| 779 | GATGAATGCATACTCTAGTCGTT |
| 780 | ATGAATGCATACTCTAGTCGTTC |
| 781 | TGAATGCATACTCTAGTCGTTCC |
| 782 | GAATGCATACTCTAGTCGTTCCC |
| 783 | AATGCATACTCTAGTCGTTCCCA |
| 784 | ATGCATACTCTAGTCGTTCCCAC |
| 785 | TGCATACTCTAGTCGTTCCCACT |
| 786 | GCATACTCTAGTCGTTCCCACTC |
| 787 | CATACTCTAGTCGTTCCCACTCA |
| 788 | ATACTCTAGTCGTTCCCACTCAG |
| 789 | TACTCTAGTCGTTCCCACTCAGT |
| 790 | ACTCTAGTCGTTCCCACTCAGTT |
| 791 | CTCTAGTCGTTCCCACTCAGTTT |
| 792 | TCTAGTCGTTCCCACTCAGTTTT |
| 793 | CTAGTCGTTCCCACTCAGTTTTC |
| 794 | TAGTCGTTCCCACTCAGTTTTCT |
| 795 | AGTCGTTCCCACTCAGTTTTCTC |
| 796 | GTCGTTCCCACTCAGTTTTCTCT |
| 797 | TCGTTCCCACTCAGTTTTCTCTG |
| 798 | CGTTCCCACTCAGTTTTCTCTGT |
| 799 | GTTCCCACTCAGTTTTCTCTGTT |
| 800 | TTCCCACTCAGTTTTCTCTGTTA |
| 801 | TCCCACTCAGTTTTCTCTGTTAC |
| 802 | CCCACTCAGTTTTCTCTGTTACA |
| 803 | CCACTCAGTTTTCTCTGTTACAA |
| 804 | CACTCAGTTTTCTCTGTTACAAT |
| 805 | ACTCAGTTTTCTCTGTTACAATA |
| 806 | CTCAGTTTTCTCTGTTACAATAC |
| 807 | TCAGTTTTCTCTGTTACAATACA |
| 808 | CAGTTTTCTCTGTTACAATACAT |
| 809 | AGTTTTCTCTGTTACAATACATA |

| ID | SEQUENCE |
|---|---|
| 810 | GTTTTCTCTGTTACAATACATAT |
| 811 | TTTTCTCTGTTACAATACATATG |
| 812 | TTTCTCTGTTACAATACATATGA |
| 813 | TTCTCTGTTACAATACATATGAA |
| 814 | TCTCTGTTACAATACATATGAAA |
| 815 | CTCTGTTACAATACATATGAAAG |
| 816 | TCTGTTACAATACATATGAAAGA |
| 817 | CTGTTACAATACATATGAAAGAA |
| 818 | TGTTACAATACATATGAAAGAAA |
| 819 | GTTACAATACATATGAAAGAAAC |
| 820 | TTACAATACATATGAAAGAAACT |
| 821 | TACAATACATATGAAAGAAACTA |
| 822 | ACAATACATATGAAAGAAACTAC |
| 823 | CAATACATATGAAAGAAACTACG |
| 824 | AATACATATGAAAGAAACTACGA |
| 825 | ATACATATGAAAGAAACTACGAT |
| 826 | TACATATGAAAGAAACTACGATT |
| 827 | ACATATGAAAGAAACTACGATTG |
| 828 | CATATGAAAGAAACTACGATTGA |
| 829 | ATATGAAAGAAACTACGATTGAT |
| 830 | TATGAAAGAAACTACGATTGATG |
| 831 | ATGAAAGAAACTACGATTGATGG |
| 832 | TGAAAGAAACTACGATTGATGGA |
| 833 | GAAAGAAACTACGATTGATGGAG |
| 834 | AAAGAAACTACGATTGATGGAGA |
| 835 | AAGAAACTACGATTGATGGAGAA |
| 836 | AGAAACTACGATTGATGGAGAAG |
| 837 | GAAACTACGATTGATGGAGAAGA |
| 838 | AAACTACGATTGATGGAGAAGAG |
| 839 | AACTACGATTGATGGAGAAGAGC |
| 840 | ACTACGATTGATGGAGAAGAGCT |
| 841 | CTACGATTGATGGAGAAGAGCTT |
| 842 | TACGATTGATGGAGAAGAGCTTG |
| 843 | ACGATTGATGGAGAAGAGCTTGT |
| 844 | CGATTGATGGAGAAGAGCTTGTT |
| 845 | GATTGATGGAGAAGAGCTTGTTA |
| 846 | ATTGATGGAGAAGAGCTTGTTAA |
| 847 | TTGATGGAGAAGAGCTTGTTAAA |
| 848 | TGATGGAGAAGAGCTTGTTAAAA |
| 849 | GATGGAGAAGAGCTTGTTAAAAT |
| 850 | ATGGAGAAGAGCTTGTTAAAATC |
| 851 | TGGAGAAGAGCTTGTTAAAATCG |
| 852 | GGAGAAGAGCTTGTTAAAATCGG |
| 853 | GAGAAGAGCTTGTTAAAATCGGA |
| 854 | AGAAGAGCTTGTTAAAATCGGAA |
| 855 | GAAGAGCTTGTTAAAATCGGAAA |
| 856 | AAGAGCTTGTTAAAATCGGAAAG |
| 857 | AGAGCTTGTTAAAATCGGAAAGT |
| 858 | GAGCTTGTTAAAATCGGAAAGTT |
| 859 | AGCTTGTTAAAATCGGAAAGTTG |
| 860 | GCTTGTTAAAATCGGAAAGTTGA |
| 861 | CTTGTTAAAATCGGAAAGTTGAA |
| 862 | TTGTTAAAATCGGAAAGTTGAAC |
| 863 | TGTTAAAATCGGAAAGTTGAACT |
| 864 | GTTAAAATCGGAAAGTTGAACTT |
| 865 | TTAAAATCGGAAAGTTGAACTTG |
| 866 | TAAAATCGGAAAGTTGAACTTGG |
| 867 | AAAATCGGAAAGTTGAACTTGGT |

| ID | SEQUENCE |
|---|---|
| 868 | AAATCGGAAAGTTGAACTTGGTT |
| 869 | AATCGGAAAGTTGAACTTGGTTG |
| 870 | ATCGGAAAGTTGAACTTGGTTGA |
| 871 | TCGGAAAGTTGAACTTGGTTGAT |
| 872 | CGGAAAGTTGAACTTGGTTGATC |
| 873 | GGAAAGTTGAACTTGGTTGATCT |
| 874 | GAAAGTTGAACTTGGTTGATCTT |
| 875 | AAAGTTGAACTTGGTTGATCTTG |
| 876 | AAGTTGAACTTGGTTGATCTTGC |
| 877 | AGTTGAACTTGGTTGATCTTGCA |
| 878 | GTTGAACTTGGTTGATCTTGCAG |
| 879 | TTGAACTTGGTTGATCTTGCAGG |
| 880 | TGAACTTGGTTGATCTTGCAGGA |
| 881 | GAACTTGGTTGATCTTGCAGGAA |
| 882 | AACTTGGTTGATCTTGCAGGAAG |
| 883 | ACTTGGTTGATCTTGCAGGAAGT |
| 884 | CTTGGTTGATCTTGCAGGAAGTG |
| 885 | TTGGTTGATCTTGCAGGAAGTGA |
| 886 | TGGTTGATCTTGCAGGAAGTGAA |
| 887 | GGTTGATCTTGCAGGAAGTGAAA |
| 888 | GTTGATCTTGCAGGAAGTGAAAA |
| 889 | TTGATCTTGCAGGAAGTGAAAAC |
| 890 | TGATCTTGCAGGAAGTGAAAACA |
| 891 | GATCTTGCAGGAAGTGAAAACAT |
| 892 | ATCTTGCAGGAAGTGAAAACATT |
| 893 | TCTTGCAGGAAGTGAAAACATTG |
| 894 | CTTGCAGGAAGTGAAAACATTGG |
| 895 | TTGCAGGAAGTGAAAACATTGGC |
| 896 | TGCAGGAAGTGAAAACATTGGCC |
| 897 | GCAGGAAGTGAAAACATTGGCCG |
| 898 | CAGGAAGTGAAAACATTGGCCGT |
| 899 | AGGAAGTGAAAACATTGGCCGTT |
| 900 | GGAAGTGAAAACATTGGCCGTTC |
| 901 | GAAGTGAAAACATTGGCCGTTCT |
| 902 | AAGTGAAAACATTGGCCGTTCTG |
| 903 | AGTGAAAACATTGGCCGTTCTGG |
| 904 | GTGAAAACATTGGCCGTTCTGGA |
| 905 | TGAAAACATTGGCCGTTCTGGAG |
| 906 | GAAAACATTGGCCGTTCTGGAGC |
| 907 | AAAACATTGGCCGTTCTGGAGCT |
| 908 | AAACATTGGCCGTTCTGGAGCTG |
| 909 | AACATTGGCCGTTCTGGAGCTGT |
| 910 | ACATTGGCCGTTCTGGAGCTGTT |
| 911 | CATTGGCCGTTCTGGAGCTGTTG |
| 912 | ATTGGCCGTTCTGGAGCTGTTGA |
| 913 | TTGGCCGTTCTGGAGCTGTTGAT |
| 914 | TGGCCGTTCTGGAGCTGTTGATA |
| 915 | GGCCGTTCTGGAGCTGTTGATAA |
| 916 | GCCGTTCTGGAGCTGTTGATAAG |
| 917 | CCGTTCTGGAGCTGTTGATAAGA |
| 918 | CGTTCTGGAGCTGTTGATAAGAG |
| 919 | GTTCTGGAGCTGTTGATAAGAGA |
| 920 | TTCTGGAGCTGTTGATAAGAGAG |
| 921 | TCTGGAGCTGTTGATAAGAGAGC |
| 922 | CTGGAGCTGTTGATAAGAGAGCT |
| 923 | TGGAGCTGTTGATAAGAGAGCTC |
| 924 | GGAGCTGTTGATAAGAGAGCTCG |
| 925 | GAGCTGTTGATAAGAGAGCTCGG |

| ID | SEQUENCE |
|---|---|
| 926 | AGCTGTTGATAAGAGAGCTCGGG |
| 927 | GCTGTTGATAAGAGAGCTCGGGA |
| 928 | CTGTTGATAAGAGAGCTCGGGAA |
| 929 | TGTTGATAAGAGAGCTCGGGAAG |
| 930 | GTTGATAAGAGAGCTCGGGAAGC |
| 931 | TTGATAAGAGAGCTCGGGAAGCT |
| 932 | TGATAAGAGAGCTCGGGAAGCTG |
| 933 | GATAAGAGAGCTCGGGAAGCTGG |
| 934 | ATAAGAGAGCTCGGGAAGCTGGA |
| 935 | TAAGAGAGCTCGGGAAGCTGGAA |
| 936 | AAGAGAGCTCGGGAAGCTGGAAA |
| 937 | AGAGAGCTCGGGAAGCTGGAAAT |
| 938 | GAGAGCTCGGGAAGCTGGAAATA |
| 939 | AGAGCTCGGGAAGCTGGAAATAT |
| 940 | GAGCTCGGGAAGCTGGAAATATA |
| 941 | AGCTCGGGAAGCTGGAAATATAA |
| 942 | GCTCGGGAAGCTGGAAATATAAA |
| 943 | CTCGGGAAGCTGGAAATATAAAT |
| 944 | TCGGGAAGCTGGAAATATAAATC |
| 945 | CGGGAAGCTGGAAATATAAATCA |
| 946 | GGGAAGCTGGAAATATAAATCAA |
| 947 | GGAAGCTGGAAATATAAATCAAT |
| 948 | GAAGCTGGAAATATAAATCAATC |
| 949 | AAGCTGGAAATATAAATCAATCC |
| 950 | AGCTGGAAATATAAATCAATCCC |
| 951 | GCTGGAAATATAAATCAATCCCT |
| 952 | CTGGAAATATAAATCAATCCCTG |
| 953 | TGGAAATATAAATCAATCCCTGT |
| 954 | GGAAATATAAATCAATCCCTGTT |
| 955 | GAAATATAAATCAATCCCTGTTG |
| 956 | AAATATAAATCAATCCCTGTTGA |
| 957 | AATATAAATCAATCCCTGTTGAC |
| 958 | ATATAAATCAATCCCTGTTGACT |
| 959 | TATAAATCAATCCCTGTTGACTT |
| 960 | ATAAATCAATCCCTGTTGACTTT |
| 961 | TAAATCAATCCCTGTTGACTTTG |
| 962 | AAATCAATCCCTGTTGACTTTGG |
| 963 | AATCAATCCCTGTTGACTTTGGG |
| 964 | ATCAATCCCTGTTGACTTTGGGA |
| 965 | TCAATCCCTGTTGACTTTGGGAA |
| 966 | CAATCCCTGTTGACTTTGGGAAG |
| 967 | AATCCCTGTTGACTTTGGGAAGG |
| 968 | ATCCCTGTTGACTTTGGGAAGGG |
| 969 | TCCCTGTTGACTTTGGGAAGGGT |
| 970 | CCCTGTTGACTTTGGGAAGGGTC |
| 971 | CCTGTTGACTTTGGGAAGGGTCA |
| 972 | CTGTTGACTTTGGGAAGGGTCAT |
| 973 | TGTTGACTTTGGGAAGGGTCATT |
| 974 | GTTGACTTTGGGAAGGGTCATTA |
| 975 | TTGACTTTGGGAAGGGTCATTAC |
| 976 | TGACTTTGGGAAGGGTCATTACT |
| 977 | GACTTTGGGAAGGGTCATTACTG |
| 978 | ACTTTGGGAAGGGTCATTACTGC |
| 979 | CTTTGGGAAGGGTCATTACTGCC |
| 980 | TTTGGGAAGGGTCATTACTGCCC |
| 981 | TTGGGAAGGGTCATTACTGCCCT |
| 982 | TGGGAAGGGTCATTACTGCCCTT |
| 983 | GGGAAGGGTCATTACTGCCCTTG |

| ID | SEQUENCE |
|---|---|
| 984 | GGAAGGGTCATTACTGCCCTTGT |
| 985 | GAAGGGTCATTACTGCCCTTGTA |
| 986 | AAGGGTCATTACTGCCCTTGTAG |
| 987 | AGGGTCATTACTGCCCTTGTAGA |
| 988 | GGGTCATTACTGCCCTTGTAGAA |
| 989 | GGTCATTACTGCCCTTGTAGAAA |
| 990 | GTCATTACTGCCCTTGTAGAAAG |
| 991 | TCATTACTGCCCTTGTAGAAAGA |
| 992 | CATTACTGCCCTTGTAGAAAGAA |
| 993 | ATTACTGCCCTTGTAGAAAGAAC |
| 994 | TTACTGCCCTTGTAGAAAGAACA |
| 995 | TACTGCCCTTGTAGAAAGAACAC |
| 996 | ACTGCCCTTGTAGAAAGAACACC |
| 997 | CTGCCCTTGTAGAAAGAACACCT |
| 998 | TGCCCTTGTAGAAAGAACACCTC |
| 999 | GCCCTTGTAGAAAGAACACCTCA |
| 1000 | CCCTTGTAGAAAGAACACCTCAT |
| 1001 | CCTTGTAGAAAGAACACCTCATG |
| 1002 | CTTGTAGAAAGAACACCTCATGT |
| 1003 | TTGTAGAAAGAACACCTCATGTT |
| 1004 | TGTAGAAAGAACACCTCATGTTC |
| 1005 | GTAGAAAGAACACCTCATGTTCC |
| 1006 | TAGAAAGAACACCTCATGTTCCT |
| 1007 | AGAAAGAACACCTCATGTTCCTT |
| 1008 | GAAAGAACACCTCATGTTCCTTA |
| 1009 | AAAGAACACCTCATGTTCCTTAT |
| 1010 | AAGAACACCTCATGTTCCTTATC |
| 1011 | AGAACACCTCATGTTCCTTATCG |
| 1012 | GAACACCTCATGTTCCTTATCGA |
| 1013 | AACACCTCATGTTCCTTATCGAG |
| 1014 | ACACCTCATGTTCCTTATCGAGA |
| 1015 | CACCTCATGTTCCTTATCGAGAA |
| 1016 | ACCTCATGTTCCTTATCGAGAAT |
| 1017 | CCTCATGTTCCTTATCGAGAATC |
| 1018 | CTCATGTTCCTTATCGAGAATCT |
| 1019 | TCATGTTCCTTATCGAGAATCTA |
| 1020 | CATGTTCCTTATCGAGAATCTAA |
| 1021 | ATGTTCCTTATCGAGAATCTAAA |
| 1022 | TGTTCCTTATCGAGAATCTAAAC |
| 1023 | GTTCCTTATCGAGAATCTAAACT |
| 1024 | TTCCTTATCGAGAATCTAAACTA |
| 1025 | TCCTTATCGAGAATCTAAACTAA |
| 1026 | CCTTATCGAGAATCTAAACTAAC |
| 1027 | CTTATCGAGAATCTAAACTAACT |
| 1028 | TTATCGAGAATCTAAACTAACTA |
| 1029 | TATCGAGAATCTAAACTAACTAG |
| 1030 | ATCGAGAATCTAAACTAACTAGA |
| 1031 | TCGAGAATCTAAACTAACTAGAA |
| 1032 | CGAGAATCTAAACTAACTAGAAT |
| 1033 | GAGAATCTAAACTAACTAGAATC |
| 1034 | AGAATCTAAACTAACTAGAATCC |
| 1035 | GAATCTAAACTAACTAGAATCCT |
| 1036 | AATCTAAACTAACTAGAATCCTC |
| 1037 | ATCTAAACTAACTAGAATCCTCC |
| 1038 | TCTAAACTAACTAGAATCCTCCA |
| 1039 | CTAAACTAACTAGAATCCTCCAG |
| 1040 | TAAACTAACTAGAATCCTCCAGG |
| 1041 | AAACTAACTAGAATCCTCCAGGA |

| ID | SEQUENCE |
|---|---|
| 1042 | AACTAACTAGAATCCTCCAGGAT |
| 1043 | ACTAACTAGAATCCTCCAGGATT |
| 1044 | CTAACTAGAATCCTCCAGGATTC |
| 1045 | TAACTAGAATCCTCCAGGATTCT |
| 1046 | AACTAGAATCCTCCAGGATTCTC |
| 1047 | ACTAGAATCCTCCAGGATTCTCT |
| 1048 | CTAGAATCCTCCAGGATTCTCTT |
| 1049 | TAGAATCCTCCAGGATTCTCTTG |
| 1050 | AGAATCCTCCAGGATTCTCTTGG |
| 1051 | GAATCCTCCAGGATTCTCTTGGA |
| 1052 | AATCCTCCAGGATTCTCTTGGAG |
| 1053 | ATCCTCCAGGATTCTCTTGGAGG |
| 1054 | TCCTCCAGGATTCTCTTGGAGGG |
| 1055 | CCTCCAGGATTCTCTTGGAGGGC |
| 1056 | CTCCAGGATTCTCTTGGAGGGCG |
| 1057 | TCCAGGATTCTCTTGGAGGGCGT |
| 1058 | CCAGGATTCTCTTGGAGGGCGTA |
| 1059 | CAGGATTCTCTTGGAGGGCGTAC |
| 1060 | AGGATTCTCTTGGAGGGCGTACA |
| 1061 | GGATTCTCTTGGAGGGCGTACAA |
| 1062 | GATTCTCTTGGAGGGCGTACAAG |
| 1063 | ATTCTCTTGGAGGGCGTACAAGA |
| 1064 | TTCTCTTGGAGGGCGTACAAGAA |
| 1065 | TCTCTTGGAGGGCGTACAAGAAC |
| 1066 | CTCTTGGAGGGCGTACAAGAACA |
| 1067 | TCTTGGAGGGCGTACAAGAACAT |
| 1068 | CTTGGAGGGCGTACAAGAACATC |
| 1069 | TTGGAGGGCGTACAAGAACATCT |
| 1070 | TGGAGGGCGTACAAGAACATCTA |
| 1071 | GGAGGGCGTACAAGAACATCTAT |
| 1072 | GAGGGCGTACAAGAACATCTATA |
| 1073 | AGGGCGTACAAGAACATCTATAA |
| 1074 | GGGCGTACAAGAACATCTATAAT |
| 1075 | GGCGTACAAGAACATCTATAATT |
| 1076 | GCGTACAAGAACATCTATAATTG |
| 1077 | CGTACAAGAACATCTATAATTGC |
| 1078 | GTACAAGAACATCTATAATTGCA |
| 1079 | TACAAGAACATCTATAATTGCAA |
| 1080 | ACAAGAACATCTATAATTGCAAC |
| 1081 | CAAGAACATCTATAATTGCAACA |
| 1082 | AAGAACATCTATAATTGCAACAA |
| 1083 | AGAACATCTATAATTGCAACAAT |
| 1084 | GAACATCTATAATTGCAACAATT |
| 1085 | AACATCTATAATTGCAACAATTT |
| 1086 | ACATCTATAATTGCAACAATTTC |
| 1087 | CATCTATAATTGCAACAATTTCT |
| 1088 | ATCTATAATTGCAACAATTTCTC |
| 1089 | TCTATAATTGCAACAATTTCTCC |
| 1090 | CTATAATTGCAACAATTTCTCCT |
| 1091 | TATAATTGCAACAATTTCTCCTG |
| 1092 | ATAATTGCAACAATTTCTCCTGC |
| 1093 | TAATTGCAACAATTTCTCCTGCA |
| 1094 | AATTGCAACAATTTCTCCTGCAT |
| 1095 | ATTGCAACAATTTCTCCTGCATC |
| 1096 | TTGCAACAATTTCTCCTGCATCT |
| 1097 | TGCAACAATTTCTCCTGCATCTC |
| 1098 | GCAACAATTTCTCCTGCATCTCT |
| 1099 | CAACAATTTCTCCTGCATCTCTC |

| ID | SEQUENCE |
|---|---|
| 1100 | AACAATTTCTCCTGCATCTCTCA |
| 1101 | ACAATTTCTCCTGCATCTCTCAA |
| 1102 | CAATTTCTCCTGCATCTCTCAAT |
| 1103 | AATTTCTCCTGCATCTCTCAATC |
| 1104 | ATTTCTCCTGCATCTCTCAATCT |
| 1105 | TTTCTCCTGCATCTCTCAATCTT |
| 1106 | TTCTCCTGCATCTCTCAATCTTG |
| 1107 | TCTCCTGCATCTCTCAATCTTGA |
| 1108 | CTCCTGCATCTCTCAATCTTGAG |
| 1109 | TCCTGCATCTCTCAATCTTGAGG |
| 1110 | CCTGCATCTCTCAATCTTGAGGA |
| 1111 | CTGCATCTCTCAATCTTGAGGAA |
| 1112 | TGCATCTCTCAATCTTGAGGAAA |
| 1113 | GCATCTCTCAATCTTGAGGAAAC |
| 1114 | CATCTCTCAATCTTGAGGAAACT |
| 1115 | ATCTCTCAATCTTGAGGAAACTC |
| 1116 | TCTCTCAATCTTGAGGAAACTCT |
| 1117 | CTCTCAATCTTGAGGAAACTCTG |
| 1118 | TCTCAATCTTGAGGAAACTCTGA |
| 1119 | CTCAATCTTGAGGAAACTCTGAG |
| 1120 | TCAATCTTGAGGAAACTCTGAGT |
| 1121 | CAATCTTGAGGAAACTCTGAGTA |
| 1122 | AATCTTGAGGAAACTCTGAGTAC |
| 1123 | ATCTTGAGGAAACTCTGAGTACA |
| 1124 | TCTTGAGGAAACTCTGAGTACAT |
| 1125 | CTTGAGGAAACTCTGAGTACATT |
| 1126 | TTGAGGAAACTCTGAGTACATTG |
| 1127 | TGAGGAAACTCTGAGTACATTGG |
| 1128 | GAGGAAACTCTGAGTACATTGGA |
| 1129 | AGGAAACTCTGAGTACATTGGAA |
| 1130 | GGAAACTCTGAGTACATTGGAAT |
| 1131 | GAAACTCTGAGTACATTGGAATA |
| 1132 | AAACTCTGAGTACATTGGAATAT |
| 1133 | AACTCTGAGTACATTGGAATATG |
| 1134 | ACTCTGAGTACATTGGAATATGC |
| 1135 | CTCTGAGTACATTGGAATATGCT |
| 1136 | TCTGAGTACATTGGAATATGCTC |
| 1137 | CTGAGTACATTGGAATATGCTCA |
| 1138 | TGAGTACATTGGAATATGCTCAT |
| 1139 | GAGTACATTGGAATATGCTCATA |
| 1140 | AGTACATTGGAATATGCTCATAG |
| 1141 | GTACATTGGAATATGCTCATAGA |
| 1142 | TACATTGGAATATGCTCATAGAG |
| 1143 | ACATTGGAATATGCTCATAGAGC |
| 1144 | CATTGGAATATGCTCATAGAGCA |
| 1145 | ATTGGAATATGCTCATAGAGCAA |
| 1146 | TTGGAATATGCTCATAGAGCAAA |
| 1147 | TGGAATATGCTCATAGAGCAAAG |
| 1148 | GGAATATGCTCATAGAGCAAAGA |
| 1149 | GAATATGCTCATAGAGCAAAGAA |
| 1150 | AATATGCTCATAGAGCAAAGAAC |
| 1151 | ATATGCTCATAGAGCAAAGAACA |
| 1152 | TATGCTCATAGAGCAAAGAACAT |
| 1153 | ATGCTCATAGAGCAAAGAACATA |
| 1154 | TGCTCATAGAGCAAAGAACATAT |
| 1155 | GCTCATAGAGCAAAGAACATATT |
| 1156 | CTCATAGAGCAAAGAACATATTG |
| 1157 | TCATAGAGCAAAGAACATATTGA |

| ID | SEQUENCE |
|---|---|
| 1158 | CATAGAGCAAAGAACATATTGAA |
| 1159 | ATAGAGCAAAGAACATATTGAAT |
| 1160 | TAGAGCAAAGAACATATTGAATA |
| 1161 | AGAGCAAAGAACATATTGAATAA |
| 1162 | GAGCAAAGAACATATTGAATAAG |
| 1163 | AGCAAAGAACATATTGAATAAGC |
| 1164 | GCAAAGAACATATTGAATAAGCC |
| 1165 | CAAAGAACATATTGAATAAGCCT |
| 1166 | AAAGAACATATTGAATAAGCCTG |
| 1167 | AAGAACATATTGAATAAGCCTGA |
| 1168 | AGAACATATTGAATAAGCCTGAA |
| 1169 | GAACATATTGAATAAGCCTGAAG |
| 1170 | AACATATTGAATAAGCCTGAAGT |
| 1171 | ACATATTGAATAAGCCTGAAGTG |
| 1172 | CATATTGAATAAGCCTGAAGTGA |
| 1173 | ATATTGAATAAGCCTGAAGTGAA |
| 1174 | TATTGAATAAGCCTGAAGTGAAT |
| 1175 | ATTGAATAAGCCTGAAGTGAATC |
| 1176 | TTGAATAAGCCTGAAGTGAATCA |
| 1177 | TGAATAAGCCTGAAGTGAATCAG |
| 1178 | GAATAAGCCTGAAGTGAATCAGA |
| 1179 | AATAAGCCTGAAGTGAATCAGAA |
| 1180 | ATAAGCCTGAAGTGAATCAGAAA |
| 1181 | TAAGCCTGAAGTGAATCAGAAAC |
| 1182 | AAGCCTGAAGTGAATCAGAAACT |
| 1183 | AGCCTGAAGTGAATCAGAAACTC |
| 1184 | GCCTGAAGTGAATCAGAAACTCA |
| 1185 | CCTGAAGTGAATCAGAAACTCAC |
| 1186 | CTGAAGTGAATCAGAAACTCACC |
| 1187 | TGAAGTGAATCAGAAACTCACCA |
| 1188 | GAAGTGAATCAGAAACTCACCAA |
| 1189 | AAGTGAATCAGAAACTCACCAAA |
| 1190 | AGTGAATCAGAAACTCACCAAAA |
| 1191 | GTGAATCAGAAACTCACCAAAAA |
| 1192 | TGAATCAGAAACTCACCAAAAAA |
| 1193 | GAATCAGAAACTCACCAAAAAAG |
| 1194 | AATCAGAAACTCACCAAAAAAGC |
| 1195 | ATCAGAAACTCACCAAAAAAGCT |
| 1196 | TCAGAAACTCACCAAAAAAGCTC |
| 1197 | CAGAAACTCACCAAAAAAGCTCT |
| 1198 | AGAAACTCACCAAAAAAGCTCTT |
| 1199 | GAAACTCACCAAAAAAGCTCTTA |
| 1200 | AAACTCACCAAAAAAGCTCTTAT |
| 1201 | AACTCACCAAAAAAGCTCTTATT |
| 1202 | ACTCACCAAAAAAGCTCTTATTA |
| 1203 | CTCACCAAAAAAGCTCTTATTAA |
| 1204 | TCACCAAAAAAGCTCTTATTAAG |
| 1205 | CACCAAAAAAGCTCTTATTAAGG |
| 1206 | ACCAAAAAAGCTCTTATTAAGGA |
| 1207 | CCAAAAAAGCTCTTATTAAGGAG |
| 1208 | CAAAAAAGCTCTTATTAAGGAGT |
| 1209 | AAAAAAGCTCTTATTAAGGAGTA |
| 1210 | AAAAAGCTCTTATTAAGGAGTAT |
| 1211 | AAAAGCTCTTATTAAGGAGTATA |
| 1212 | AAAGCTCTTATTAAGGAGTATAC |
| 1213 | AAGCTCTTATTAAGGAGTATACG |
| 1214 | AGCTCTTATTAAGGAGTATACGG |
| 1215 | GCTCTTATTAAGGAGTATACGGA |

| ID | SEQUENCE |
|---|---|
| 1216 | CTCTTATTAAGGAGTATACGGAG |
| 1217 | TCTTATTAAGGAGTATACGGAGG |
| 1218 | CTTATTAAGGAGTATACGGAGGA |
| 1219 | TTATTAAGGAGTATACGGAGGAG |
| 1220 | TATTAAGGAGTATACGGAGGAGA |
| 1221 | ATTAAGGAGTATACGGAGGAGAT |
| 1222 | TTAAGGAGTATACGGAGGAGATA |
| 1223 | TAAGGAGTATACGGAGGAGATAG |
| 1224 | AAGGAGTATACGGAGGAGATAGA |
| 1225 | AGGAGTATACGGAGGAGATAGAA |
| 1226 | GGAGTATACGGAGGAGATAGAAC |
| 1227 | GAGTATACGGAGGAGATAGAACG |
| 1228 | AGTATACGGAGGAGATAGAACGT |
| 1229 | GTATACGGAGGAGATAGAACGTT |
| 1230 | TATACGGAGGAGATAGAACGTTT |
| 1231 | ATACGGAGGAGATAGAACGTTTA |
| 1232 | TACGGAGGAGATAGAACGTTTAA |
| 1233 | ACGGAGGAGATAGAACGTTTAAA |
| 1234 | CGGAGGAGATAGAACGTTTAAAA |
| 1235 | GGAGGAGATAGAACGTTTAAAAC |
| 1236 | GAGGAGATAGAACGTTTAAAACG |
| 1237 | AGGAGATAGAACGTTTAAAACGA |
| 1238 | GGAGATAGAACGTTTAAAACGAG |
| 1239 | GAGATAGAACGTTTAAAACGAGA |
| 1240 | AGATAGAACGTTTAAAACGAGAT |
| 1241 | GATAGAACGTTTAAAACGAGATC |
| 1242 | ATAGAACGTTTAAAACGAGATCT |
| 1243 | TAGAACGTTTAAAACGAGATCTT |
| 1244 | AGAACGTTTAAAACGAGATCTTG |
| 1245 | GAACGTTTAAAACGAGATCTTGC |
| 1246 | AACGTTTAAAACGAGATCTTGCT |
| 1247 | ACGTTTAAAACGAGATCTTGCTG |
| 1248 | CGTTTAAAACGAGATCTTGCTGC |
| 1249 | GTTTAAAACGAGATCTTGCTGCA |
| 1250 | TTTAAAACGAGATCTTGCTGCAG |
| 1251 | TTAAAACGAGATCTTGCTGCAGC |
| 1252 | TAAAACGAGATCTTGCTGCAGCC |
| 1253 | AAAACGAGATCTTGCTGCAGCCC |
| 1254 | AAACGAGATCTTGCTGCAGCCCG |
| 1255 | AACGAGATCTTGCTGCAGCCCGT |
| 1256 | ACGAGATCTTGCTGCAGCCCGTG |
| 1257 | CGAGATCTTGCTGCAGCCCGTGA |
| 1258 | GAGATCTTGCTGCAGCCCGTGAG |
| 1259 | AGATCTTGCTGCAGCCCGTGAGA |
| 1260 | GATCTTGCTGCAGCCCGTGAGAA |
| 1261 | ATCTTGCTGCAGCCCGTGAGAAA |
| 1262 | TCTTGCTGCAGCCCGTGAGAAAA |
| 1263 | CTTGCTGCAGCCCGTGAGAAAAA |
| 1264 | TTGCTGCAGCCCGTGAGAAAAAT |
| 1265 | TGCTGCAGCCCGTGAGAAAAATG |
| 1266 | GCTGCAGCCCGTGAGAAAAATGG |
| 1267 | CTGCAGCCCGTGAGAAAAATGGA |
| 1268 | TGCAGCCCGTGAGAAAAATGGAG |
| 1269 | GCAGCCCGTGAGAAAAATGGAGT |
| 1270 | CAGCCCGTGAGAAAAATGGAGTG |
| 1271 | AGCCCGTGAGAAAAATGGAGTGT |
| 1272 | GCCCGTGAGAAAAATGGAGTGTA |
| 1273 | CCCGTGAGAAAAATGGAGTGTAT |

| ID | SEQUENCE |
|---|---|
| 1274 | CCGTGAGAAAAATGGAGTGTATA |
| 1275 | CGTGAGAAAAATGGAGTGTATAT |
| 1276 | GTGAGAAAAATGGAGTGTATATT |
| 1277 | TGAGAAAAATGGAGTGTATATTT |
| 1278 | GAGAAAAATGGAGTGTATATTTC |
| 1279 | AGAAAAATGGAGTGTATATTTCT |
| 1280 | GAAAAATGGAGTGTATATTTCTG |
| 1281 | AAAAATGGAGTGTATATTTCTGA |
| 1282 | AAAATGGAGTGTATATTTCTGAA |
| 1283 | AAATGGAGTGTATATTTCTGAAG |
| 1284 | AATGGAGTGTATATTTCTGAAGA |
| 1285 | ATGGAGTGTATATTTCTGAAGAA |
| 1286 | TGGAGTGTATATTTCTGAAGAAA |
| 1287 | GGAGTGTATATTTCTGAAGAAAA |
| 1288 | GAGTGTATATTTCTGAAGAAAAT |
| 1289 | AGTGTATATTTCTGAAGAAAATT |
| 1290 | GTGTATATTTCTGAAGAAAATTT |
| 1291 | TGTATATTTCTGAAGAAAATTTT |
| 1292 | GTATATTTCTGAAGAAAATTTTA |
| 1293 | TATATTTCTGAAGAAAATTTTAG |
| 1294 | ATATTTCTGAAGAAAATTTTAGA |
| 1295 | TATTTCTGAAGAAAATTTTAGAG |
| 1296 | ATTTCTGAAGAAAATTTTAGAGT |
| 1297 | TTTCTGAAGAAAATTTTAGAGTC |
| 1298 | TTCTGAAGAAAATTTTAGAGTCA |
| 1299 | TCTGAAGAAAATTTTAGAGTCAT |
| 1300 | CTGAAGAAAATTTTAGAGTCATG |
| 1301 | TGAAGAAAATTTTAGAGTCATGA |
| 1302 | GAAGAAAATTTTAGAGTCATGAG |
| 1303 | AAGAAAATTTTAGAGTCATGAGT |
| 1304 | AGAAAATTTTAGAGTCATGAGTG |
| 1305 | GAAAATTTTAGAGTCATGAGTGG |
| 1306 | AAAATTTTAGAGTCATGAGTGGA |
| 1307 | AAATTTTAGAGTCATGAGTGGAA |
| 1308 | AATTTTAGAGTCATGAGTGGAAA |
| 1309 | ATTTTAGAGTCATGAGTGGAAAA |
| 1310 | TTTTAGAGTCATGAGTGGAAAAT |
| 1311 | TTTAGAGTCATGAGTGGAAAATT |
| 1312 | TTAGAGTCATGAGTGGAAAATTA |
| 1313 | TAGAGTCATGAGTGGAAAATTAA |
| 1314 | AGAGTCATGAGTGGAAAATTAAC |
| 1315 | GAGTCATGAGTGGAAAATTAACT |
| 1316 | AGTCATGAGTGGAAAATTAACTG |
| 1317 | GTCATGAGTGGAAAATTAACTGT |
| 1318 | TCATGAGTGGAAAATTAACTGTT |
| 1319 | CATGAGTGGAAAATTAACTGTTC |
| 1320 | ATGAGTGGAAAATTAACTGTTCA |
| 1321 | TGAGTGGAAAATTAACTGTTCAA |
| 1322 | GAGTGGAAAATTAACTGTTCAAG |
| 1323 | AGTGGAAAATTAACTGTTCAAGA |
| 1324 | GTGGAAAATTAACTGTTCAAGAA |
| 1325 | TGGAAAATTAACTGTTCAAGAAG |
| 1326 | GGAAAATTAACTGTTCAAGAAGA |
| 1327 | GAAAATTAACTGTTCAAGAAGAG |
| 1328 | AAAATTAACTGTTCAAGAAGAGC |
| 1329 | AAATTAACTGTTCAAGAAGAGCA |
| 1330 | AATTAACTGTTCAAGAAGAGCAG |
| 1331 | ATTAACTGTTCAAGAAGAGCAGA |

| ID | SEQUENCE |
|---|---|
| 1332 | TTAACTGTTCAAGAAGAGCAGAT |
| 1333 | TAACTGTTCAAGAAGAGCAGATT |
| 1334 | AACTGTTCAAGAAGAGCAGATTG |
| 1335 | ACTGTTCAAGAAGAGCAGATTGT |
| 1336 | CTGTTCAAGAAGAGCAGATTGTA |
| 1337 | TGTTCAAGAAGAGCAGATTGTAG |
| 1338 | GTTCAAGAAGAGCAGATTGTAGA |
| 1339 | TTCAAGAAGAGCAGATTGTAGAA |
| 1340 | TCAAGAAGAGCAGATTGTAGAAT |
| 1341 | CAAGAAGAGCAGATTGTAGAATT |
| 1342 | AAGAAGAGCAGATTGTAGAATTG |
| 1343 | AGAAGAGCAGATTGTAGAATTGA |
| 1344 | GAAGAGCAGATTGTAGAATTGAT |
| 1345 | AAGAGCAGATTGTAGAATTGATT |
| 1346 | AGAGCAGATTGTAGAATTGATTG |
| 1347 | GAGCAGATTGTAGAATTGATTGA |
| 1348 | AGCAGATTGTAGAATTGATTGAA |
| 1349 | GCAGATTGTAGAATTGATTGAAA |
| 1350 | CAGATTGTAGAATTGATTGAAAA |
| 1351 | AGATTGTAGAATTGATTGAAAAA |
| 1352 | GATTGTAGAATTGATTGAAAAAA |
| 1353 | ATTGTAGAATTGATTGAAAAAAT |
| 1354 | TTGTAGAATTGATTGAAAAAATT |
| 1355 | TGTAGAATTGATTGAAAAAATTG |
| 1356 | GTAGAATTGATTGAAAAAATTGG |
| 1357 | TAGAATTGATTGAAAAAATTGGT |
| 1358 | AGAATTGATTGAAAAAATTGGTG |
| 1359 | GAATTGATTGAAAAAATTGGTGC |
| 1360 | AATTGATTGAAAAAATTGGTGCT |
| 1361 | ATTGATTGAAAAAATTGGTGCTG |
| 1362 | TTGATTGAAAAAATTGGTGCTGT |
| 1363 | TGATTGAAAAAATTGGTGCTGTT |
| 1364 | GATTGAAAAAATTGGTGCTGTTG |
| 1365 | ATTGAAAAAATTGGTGCTGTTGA |
| 1366 | TTGAAAAAATTGGTGCTGTTGAG |
| 1367 | TGAAAAAATTGGTGCTGTTGAGG |
| 1368 | GAAAAAATTGGTGCTGTTGAGGA |
| 1369 | AAAAAATTGGTGCTGTTGAGGAG |
| 1370 | AAAAATTGGTGCTGTTGAGGAGG |
| 1371 | AAAATTGGTGCTGTTGAGGAGGA |
| 1372 | AAATTGGTGCTGTTGAGGAGGAG |
| 1373 | AATTGGTGCTGTTGAGGAGGAGC |
| 1374 | ATTGGTGCTGTTGAGGAGGAGCT |
| 1375 | TTGGTGCTGTTGAGGAGGAGCTG |
| 1376 | TGGTGCTGTTGAGGAGGAGCTGA |
| 1377 | GGTGCTGTTGAGGAGGAGCTGAA |
| 1378 | GTGCTGTTGAGGAGGAGCTGAAT |
| 1379 | TGCTGTTGAGGAGGAGCTGAATA |
| 1380 | GCTGTTGAGGAGGAGCTGAATAG |
| 1381 | CTGTTGAGGAGGAGCTGAATAGG |
| 1382 | TGTTGAGGAGGAGCTGAATAGGG |
| 1383 | GTTGAGGAGGAGCTGAATAGGGT |
| 1384 | TTGAGGAGGAGCTGAATAGGGTT |
| 1385 | TGAGGAGGAGCTGAATAGGGTTA |
| 1386 | GAGGAGGAGCTGAATAGGGTTAC |
| 1387 | AGGAGGAGCTGAATAGGGTTACA |
| 1388 | GGAGGAGCTGAATAGGGTTACAG |
| 1389 | GAGGAGCTGAATAGGGTTACAGA |

| ID | SEQUENCE |
|---|---|
| 1390 | AGGAGCTGAATAGGGTTACAGAG |
| 1391 | GGAGCTGAATAGGGTTACAGAGT |
| 1392 | GAGCTGAATAGGGTTACAGAGTT |
| 1393 | AGCTGAATAGGGTTACAGAGTTG |
| 1394 | GCTGAATAGGGTTACAGAGTTGT |
| 1395 | CTGAATAGGGTTACAGAGTTGTT |
| 1396 | TGAATAGGGTTACAGAGTTGTTT |
| 1397 | GAATAGGGTTACAGAGTTGTTTA |
| 1398 | AATAGGGTTACAGAGTTGTTTAT |
| 1399 | ATAGGGTTACAGAGTTGTTTATG |
| 1400 | TAGGGTTACAGAGTTGTTTATGG |
| 1401 | AGGGTTACAGAGTTGTTTATGGA |
| 1402 | GGGTTACAGAGTTGTTTATGGAT |
| 1403 | GGTTACAGAGTTGTTTATGGATA |
| 1404 | GTTACAGAGTTGTTTATGGATAA |
| 1405 | TTACAGAGTTGTTTATGGATAAT |
| 1406 | TACAGAGTTGTTTATGGATAATA |
| 1407 | ACAGAGTTGTTTATGGATAATAA |
| 1408 | CAGAGTTGTTTATGGATAATAAA |
| 1409 | AGAGTTGTTTATGGATAATAAAA |
| 1410 | GAGTTGTTTATGGATAATAAAAA |
| 1411 | AGTTGTTTATGGATAATAAAAAT |
| 1412 | GTTGTTTATGGATAATAAAAATG |
| 1413 | TTGTTTATGGATAATAAAAATGA |
| 1414 | TGTTTATGGATAATAAAAATGAA |
| 1415 | GTTTATGGATAATAAAAATGAAC |
| 1416 | TTTATGGATAATAAAAATGAACT |
| 1417 | TTATGGATAATAAAAATGAACTT |
| 1418 | TATGGATAATAAAAATGAACTTG |
| 1419 | ATGGATAATAAAAATGAACTTGA |
| 1420 | TGGATAATAAAAATGAACTTGAC |
| 1421 | GGATAATAAAAATGAACTTGACC |
| 1422 | GATAATAAAAATGAACTTGACCA |
| 1423 | ATAATAAAAATGAACTTGACCAG |
| 1424 | TAATAAAAATGAACTTGACCAGT |
| 1425 | AATAAAAATGAACTTGACCAGTG |
| 1426 | ATAAAAATGAACTTGACCAGTGT |
| 1427 | TAAAAATGAACTTGACCAGTGTA |
| 1428 | AAAAATGAACTTGACCAGTGTAA |
| 1429 | AAAATGAACTTGACCAGTGTAAA |
| 1430 | AAATGAACTTGACCAGTGTAAAT |
| 1431 | AATGAACTTGACCAGTGTAAATC |
| 1432 | ATGAACTTGACCAGTGTAAATCT |
| 1433 | TGAACTTGACCAGTGTAAATCTG |
| 1434 | GAACTTGACCAGTGTAAATCTGA |
| 1435 | AACTTGACCAGTGTAAATCTGAC |
| 1436 | ACTTGACCAGTGTAAATCTGACC |
| 1437 | CTTGACCAGTGTAAATCTGACCT |
| 1438 | TTGACCAGTGTAAATCTGACCTG |
| 1439 | TGACCAGTGTAAATCTGACCTGC |
| 1440 | GACCAGTGTAAATCTGACCTGCA |
| 1441 | ACCAGTGTAAATCTGACCTGCAA |
| 1442 | CCAGTGTAAATCTGACCTGCAAA |
| 1443 | CAGTGTAAATCTGACCTGCAAAA |
| 1444 | AGTGTAAATCTGACCTGCAAAAT |
| 1445 | GTGTAAATCTGACCTGCAAAATA |
| 1446 | TGTAAATCTGACCTGCAAAATAA |
| 1447 | GTAAATCTGACCTGCAAAATAAA |

| ID | SEQUENCE |
|---|---|
| 1448 | TAAATCTGACCTGCAAAATAAAA |
| 1449 | AAATCTGACCTGCAAAATAAAAC |
| 1450 | AATCTGACCTGCAAAATAAAACA |
| 1451 | ATCTGACCTGCAAAATAAAACAC |
| 1452 | TCTGACCTGCAAAATAAAACACA |
| 1453 | CTGACCTGCAAAATAAAACACAA |
| 1454 | TGACCTGCAAAATAAAACACAAG |
| 1455 | GACCTGCAAAATAAAACACAAGA |
| 1456 | ACCTGCAAAATAAAACACAAGAA |
| 1457 | CCTGCAAAATAAAACACAAGAAC |
| 1458 | CTGCAAAATAAAACACAAGAACT |
| 1459 | TGCAAAATAAAACACAAGAACTT |
| 1460 | GCAAAATAAAACACAAGAACTTG |
| 1461 | CAAAATAAAACACAAGAACTTGA |
| 1462 | AAAATAAAACACAAGAACTTGAA |
| 1463 | AAATAAAACACAAGAACTTGAAA |
| 1464 | AATAAAACACAAGAACTTGAAAC |
| 1465 | ATAAAACACAAGAACTTGAAACC |
| 1466 | TAAAACACAAGAACTTGAAACCA |
| 1467 | AAAACACAAGAACTTGAAACCAC |
| 1468 | AAACACAAGAACTTGAAACCACT |
| 1469 | AACACAAGAACTTGAAACCACTC |
| 1470 | ACACAAGAACTTGAAACCACTCA |
| 1471 | CACAAGAACTTGAAACCACTCAA |
| 1472 | ACAAGAACTTGAAACCACTCAAA |
| 1473 | CAAGAACTTGAAACCACTCAAAA |
| 1474 | AAGAACTTGAAACCACTCAAAAA |
| 1475 | AGAACTTGAAACCACTCAAAAAC |
| 1476 | GAACTTGAAACCACTCAAAAACA |
| 1477 | AACTTGAAACCACTCAAAAACAT |
| 1478 | ACTTGAAACCACTCAAAAACATT |
| 1479 | CTTGAAACCACTCAAAAACATTT |
| 1480 | TTGAAACCACTCAAAAACATTTG |
| 1481 | TGAAACCACTCAAAAACATTTGC |
| 1482 | GAAACCACTCAAAAACATTTGCA |
| 1483 | AAACCACTCAAAAACATTTGCAA |
| 1484 | AACCACTCAAAAACATTTGCAAG |
| 1485 | ACCACTCAAAAACATTTGCAAGA |
| 1486 | CCACTCAAAAACATTTGCAAGAA |
| 1487 | CACTCAAAAACATTTGCAAGAAA |
| 1488 | ACTCAAAAACATTTGCAAGAAAC |
| 1489 | CTCAAAAACATTTGCAAGAAACT |
| 1490 | TCAAAAACATTTGCAAGAAACTA |
| 1491 | CAAAAACATTTGCAAGAAACTAA |
| 1492 | AAAAACATTTGCAAGAAACTAAA |
| 1493 | AAAACATTTGCAAGAAACTAAAT |
| 1494 | AAACATTTGCAAGAAACTAAATT |
| 1495 | AACATTTGCAAGAAACTAAATTA |
| 1496 | ACATTTGCAAGAAACTAAATTAC |
| 1497 | CATTTGCAAGAAACTAAATTACA |
| 1498 | ATTTGCAAGAAACTAAATTACAA |
| 1499 | TTTGCAAGAAACTAAATTACAAC |
| 1500 | TTGCAAGAAACTAAATTACAACT |
| 1501 | TGCAAGAAACTAAATTACAACTT |
| 1502 | GCAAGAAACTAAATTACAACTTG |
| 1503 | CAAGAAACTAAATTACAACTTGT |
| 1504 | AAGAAACTAAATTACAACTTGTT |
| 1505 | AGAAACTAAATTACAACTTGTTA |

| ID | SEQUENCE |
|---|---|
| 1506 | GAAACTAAATTACAACTTGTTAA |
| 1507 | AAACTAAATTACAACTTGTTAAA |
| 1508 | AACTAAATTACAACTTGTTAAAG |
| 1509 | ACTAAATTACAACTTGTTAAAGA |
| 1510 | CTAAATTACAACTTGTTAAAGAA |
| 1511 | TAAATTACAACTTGTTAAAGAAG |
| 1512 | AAATTACAACTTGTTAAAGAAGA |
| 1513 | AATTACAACTTGTTAAAGAAGAA |
| 1514 | ATTACAACTTGTTAAAGAAGAAT |
| 1515 | TTACAACTTGTTAAAGAAGAATA |
| 1516 | TACAACTTGTTAAAGAAGAATAT |
| 1517 | ACAACTTGTTAAAGAAGAATATA |
| 1518 | CAACTTGTTAAAGAAGAATATAT |
| 1519 | AACTTGTTAAAGAAGAATATATC |
| 1520 | ACTTGTTAAAGAAGAATATATCA |
| 1521 | CTTGTTAAAGAAGAATATATCAC |
| 1522 | TTGTTAAAGAAGAATATATCACA |
| 1523 | TGTTAAAGAAGAATATATCACAT |
| 1524 | GTTAAAGAAGAATATATCACATC |
| 1525 | TTAAAGAAGAATATATCACATCA |
| 1526 | TAAAGAAGAATATATCACATCAG |
| 1527 | AAAGAAGAATATATCACATCAGC |
| 1528 | AAGAAGAATATATCACATCAGCT |
| 1529 | AGAAGAATATATCACATCAGCTT |
| 1530 | GAAGAATATATCACATCAGCTTT |
| 1531 | AAGAATATATCACATCAGCTTTG |
| 1532 | AGAATATATCACATCAGCTTTGG |
| 1533 | GAATATATCACATCAGCTTTGGA |
| 1534 | AATATATCACATCAGCTTTGGAA |
| 1535 | ATATATCACATCAGCTTTGGAAA |
| 1536 | TATATCACATCAGCTTTGGAAAG |
| 1537 | ATATCACATCAGCTTTGGAAAGT |
| 1538 | TATCACATCAGCTTTGGAAAGTA |
| 1539 | ATCACATCAGCTTTGGAAAGTAC |
| 1540 | TCACATCAGCTTTGGAAAGTACT |
| 1541 | CACATCAGCTTTGGAAAGTACTG |
| 1542 | ACATCAGCTTTGGAAAGTACTGA |
| 1543 | CATCAGCTTTGGAAAGTACTGAG |
| 1544 | ATCAGCTTTGGAAAGTACTGAGG |
| 1545 | TCAGCTTTGGAAAGTACTGAGGA |
| 1546 | CAGCTTTGGAAAGTACTGAGGAG |
| 1547 | AGCTTTGGAAAGTACTGAGGAGA |
| 1548 | GCTTTGGAAAGTACTGAGGAGAA |
| 1549 | CTTTGGAAAGTACTGAGGAGAAA |
| 1550 | TTTGGAAAGTACTGAGGAGAAAC |
| 1551 | TTGGAAAGTACTGAGGAGAAACT |
| 1552 | TGGAAAGTACTGAGGAGAAACTT |
| 1553 | GGAAAGTACTGAGGAGAAACTTC |
| 1554 | GAAAGTACTGAGGAGAAACTTCA |
| 1555 | AAAGTACTGAGGAGAAACTTCAT |
| 1556 | AAGTACTGAGGAGAAACTTCATG |
| 1557 | AGTACTGAGGAGAAACTTCATGA |
| 1558 | GTACTGAGGAGAAACTTCATGAT |
| 1559 | TACTGAGGAGAAACTTCATGATG |
| 1560 | ACTGAGGAGAAACTTCATGATGC |
| 1561 | CTGAGGAGAAACTTCATGATGCT |
| 1562 | TGAGGAGAAACTTCATGATGCTG |
| 1563 | GAGGAGAAACTTCATGATGCTGC |

| ID | SEQUENCE |
|---|---|
| 1564 | AGGAGAAACTTCATGATGCTGCC |
| 1565 | GGAGAAACTTCATGATGCTGCCA |
| 1566 | GAGAAACTTCATGATGCTGCCAG |
| 1567 | AGAAACTTCATGATGCTGCCAGC |
| 1568 | GAAACTTCATGATGCTGCCAGCA |
| 1569 | AAACTTCATGATGCTGCCAGCAA |
| 1570 | AACTTCATGATGCTGCCAGCAAG |
| 1571 | ACTTCATGATGCTGCCAGCAAGC |
| 1572 | CTTCATGATGCTGCCAGCAAGCT |
| 1573 | TTCATGATGCTGCCAGCAAGCTG |
| 1574 | TCATGATGCTGCCAGCAAGCTGC |
| 1575 | CATGATGCTGCCAGCAAGCTGCT |
| 1576 | ATGATGCTGCCAGCAAGCTGCTT |
| 1577 | TGATGCTGCCAGCAAGCTGCTTA |
| 1578 | GATGCTGCCAGCAAGCTGCTTAA |
| 1579 | ATGCTGCCAGCAAGCTGCTTAAC |
| 1580 | TGCTGCCAGCAAGCTGCTTAACA |
| 1581 | GCTGCCAGCAAGCTGCTTAACAC |
| 1582 | CTGCCAGCAAGCTGCTTAACACA |
| 1583 | TGCCAGCAAGCTGCTTAACACAG |
| 1584 | GCCAGCAAGCTGCTTAACACAGT |
| 1585 | CCAGCAAGCTGCTTAACACAGTT |
| 1586 | CAGCAAGCTGCTTAACACAGTTG |
| 1587 | AGCAAGCTGCTTAACACAGTTGA |
| 1588 | GCAAGCTGCTTAACACAGTTGAA |
| 1589 | CAAGCTGCTTAACACAGTTGAAG |
| 1590 | AAGCTGCTTAACACAGTTGAAGA |
| 1591 | AGCTGCTTAACACAGTTGAAGAA |
| 1592 | GCTGCTTAACACAGTTGAAGAAA |
| 1593 | CTGCTTAACACAGTTGAAGAAAC |
| 1594 | TGCTTAACACAGTTGAAGAAACT |
| 1595 | GCTTAACACAGTTGAAGAAACTA |
| 1596 | CTTAACACAGTTGAAGAAACTAC |
| 1597 | TTAACACAGTTGAAGAAACTACA |
| 1598 | TAACACAGTTGAAGAAACTACAA |
| 1599 | AACACAGTTGAAGAAACTACAAA |
| 1600 | ACACAGTTGAAGAAACTACAAAA |
| 1601 | CACAGTTGAAGAAACTACAAAAG |
| 1602 | ACAGTTGAAGAAACTACAAAAGA |
| 1603 | CAGTTGAAGAAACTACAAAAGAT |
| 1604 | AGTTGAAGAAACTACAAAAGATG |
| 1605 | GTTGAAGAAACTACAAAAGATGT |
| 1606 | TTGAAGAAACTACAAAAGATGTA |
| 1607 | TGAAGAAACTACAAAAGATGTAT |
| 1608 | GAAGAAACTACAAAAGATGTATC |
| 1609 | AAGAAACTACAAAAGATGTATCT |
| 1610 | AGAAACTACAAAAGATGTATCTG |
| 1611 | GAAACTACAAAAGATGTATCTGG |
| 1612 | AAACTACAAAAGATGTATCTGGT |
| 1613 | AACTACAAAAGATGTATCTGGTC |
| 1614 | ACTACAAAAGATGTATCTGGTCT |
| 1615 | CTACAAAAGATGTATCTGGTCTC |
| 1616 | TACAAAAGATGTATCTGGTCTCC |
| 1617 | ACAAAAGATGTATCTGGTCTCCA |
| 1618 | CAAAAGATGTATCTGGTCTCCAT |
| 1619 | AAAAGATGTATCTGGTCTCCATT |
| 1620 | AAAGATGTATCTGGTCTCCATTC |
| 1621 | AAGATGTATCTGGTCTCCATTCC |

| ID | SEQUENCE |
|---|---|
| 1622 | AGATGTATCTGGTCTCCATTCCA |
| 1623 | GATGTATCTGGTCTCCATTCCAA |
| 1624 | ATGTATCTGGTCTCCATTCCAAA |
| 1625 | TGTATCTGGTCTCCATTCCAAAC |
| 1626 | GTATCTGGTCTCCATTCCAAACT |
| 1627 | TATCTGGTCTCCATTCCAAACTG |
| 1628 | ATCTGGTCTCCATTCCAAACTGG |
| 1629 | TCTGGTCTCCATTCCAAACTGGA |
| 1630 | CTGGTCTCCATTCCAAACTGGAT |
| 1631 | TGGTCTCCATTCCAAACTGGATC |
| 1632 | GGTCTCCATTCCAAACTGGATCG |
| 1633 | GTCTCCATTCCAAACTGGATCGT |
| 1634 | TCTCCATTCCAAACTGGATCGTA |
| 1635 | CTCCATTCCAAACTGGATCGTAA |
| 1636 | TCCATTCCAAACTGGATCGTAAG |
| 1637 | CCATTCCAAACTGGATCGTAAGA |
| 1638 | CATTCCAAACTGGATCGTAAGAA |
| 1639 | ATTCCAAACTGGATCGTAAGAAG |
| 1640 | TTCCAAACTGGATCGTAAGAAGG |
| 1641 | TCCAAACTGGATCGTAAGAAGGC |
| 1642 | CCAAACTGGATCGTAAGAAGGCA |
| 1643 | CAAACTGGATCGTAAGAAGGCAG |
| 1644 | AAACTGGATCGTAAGAAGGCAGT |
| 1645 | AACTGGATCGTAAGAAGGCAGTT |
| 1646 | ACTGGATCGTAAGAAGGCAGTTG |
| 1647 | CTGGATCGTAAGAAGGCAGTTGA |
| 1648 | TGGATCGTAAGAAGGCAGTTGAC |
| 1649 | GGATCGTAAGAAGGCAGTTGACC |
| 1650 | GATCGTAAGAAGGCAGTTGACCA |
| 1651 | ATCGTAAGAAGGCAGTTGACCAA |
| 1652 | TCGTAAGAAGGCAGTTGACCAAC |
| 1653 | CGTAAGAAGGCAGTTGACCAACA |
| 1654 | GTAAGAAGGCAGTTGACCAACAC |
| 1655 | TAAGAAGGCAGTTGACCAACACA |
| 1656 | AAGAAGGCAGTTGACCAACACAA |
| 1657 | AGAAGGCAGTTGACCAACACAAT |
| 1658 | GAAGGCAGTTGACCAACACAATG |
| 1659 | AAGGCAGTTGACCAACACAATGC |
| 1660 | AGGCAGTTGACCAACACAATGCA |
| 1661 | GGCAGTTGACCAACACAATGCAG |
| 1662 | GCAGTTGACCAACACAATGCAGA |
| 1663 | CAGTTGACCAACACAATGCAGAA |
| 1664 | AGTTGACCAACACAATGCAGAAG |
| 1665 | GTTGACCAACACAATGCAGAAGC |
| 1666 | TTGACCAACACAATGCAGAAGCT |
| 1667 | TGACCAACACAATGCAGAAGCTC |
| 1668 | GACCAACACAATGCAGAAGCTCA |
| 1669 | ACCAACACAATGCAGAAGCTCAG |
| 1670 | CCAACACAATGCAGAAGCTCAGG |
| 1671 | CAACACAATGCAGAAGCTCAGGA |
| 1672 | AACACAATGCAGAAGCTCAGGAT |
| 1673 | ACACAATGCAGAAGCTCAGGATA |
| 1674 | CACAATGCAGAAGCTCAGGATAT |
| 1675 | ACAATGCAGAAGCTCAGGATATT |
| 1676 | CAATGCAGAAGCTCAGGATATTT |
| 1677 | AATGCAGAAGCTCAGGATATTTT |
| 1678 | ATGCAGAAGCTCAGGATATTTTT |
| 1679 | TGCAGAAGCTCAGGATATTTTTG |

| ID | SEQUENCE |
|---|---|
| 1680 | GCAGAAGCTCAGGATATTTTTGG |
| 1681 | CAGAAGCTCAGGATATTTTTGGC |
| 1682 | AGAAGCTCAGGATATTTTTGGCA |
| 1683 | GAAGCTCAGGATATTTTTGGCAA |
| 1684 | AAGCTCAGGATATTTTTGGCAAA |
| 1685 | AGCTCAGGATATTTTTGGCAAAA |
| 1686 | GCTCAGGATATTTTTGGCAAAAA |
| 1687 | CTCAGGATATTTTTGGCAAAAAC |
| 1688 | TCAGGATATTTTTGGCAAAAACC |
| 1689 | CAGGATATTTTTGGCAAAAACCT |
| 1690 | AGGATATTTTTGGCAAAAACCTG |
| 1691 | GGATATTTTTGGCAAAAACCTGA |
| 1692 | GATATTTTTGGCAAAAACCTGAA |
| 1693 | ATATTTTTGGCAAAAACCTGAAT |
| 1694 | TATTTTTGGCAAAAACCTGAATA |
| 1695 | ATTTTTGGCAAAAACCTGAATAG |
| 1696 | TTTTTGGCAAAAACCTGAATAGT |
| 1697 | TTTTGGCAAAAACCTGAATAGTC |
| 1698 | TTTGGCAAAAACCTGAATAGTCT |
| 1699 | TTGGCAAAAACCTGAATAGTCTG |
| 1700 | TGGCAAAAACCTGAATAGTCTGT |
| 1701 | GGCAAAAACCTGAATAGTCTGTT |
| 1702 | GCAAAAACCTGAATAGTCTGTTT |
| 1703 | CAAAAACCTGAATAGTCTGTTTA |
| 1704 | AAAAACCTGAATAGTCTGTTTAA |
| 1705 | AAAACCTGAATAGTCTGTTTAAT |
| 1706 | AAACCTGAATAGTCTGTTTAATA |
| 1707 | AACCTGAATAGTCTGTTTAATAA |
| 1708 | ACCTGAATAGTCTGTTTAATAAT |
| 1709 | CCTGAATAGTCTGTTTAATAATA |
| 1710 | CTGAATAGTCTGTTTAATAATAT |
| 1711 | TGAATAGTCTGTTTAATAATATG |
| 1712 | GAATAGTCTGTTTAATAATATGG |
| 1713 | AATAGTCTGTTTAATAATATGGA |
| 1714 | ATAGTCTGTTTAATAATATGGAA |
| 1715 | TAGTCTGTTTAATAATATGGAAG |
| 1716 | AGTCTGTTTAATAATATGGAAGA |
| 1717 | GTCTGTTTAATAATATGGAAGAA |
| 1718 | TCTGTTTAATAATATGGAAGAAT |
| 1719 | CTGTTTAATAATATGGAAGAATT |
| 1720 | TGTTTAATAATATGGAAGAATTA |
| 1721 | GTTTAATAATATGGAAGAATTAA |
| 1722 | TTTAATAATATGGAAGAATTAAT |
| 1723 | TTAATAATATGGAAGAATTAATT |
| 1724 | TAATAATATGGAAGAATTAATTA |
| 1725 | AATAATATGGAAGAATTAATTAA |
| 1726 | ATAATATGGAAGAATTAATTAAG |
| 1727 | TAATATGGAAGAATTAATTAAGG |
| 1728 | AATATGGAAGAATTAATTAAGGA |
| 1729 | ATATGGAAGAATTAATTAAGGAT |
| 1730 | TATGGAAGAATTAATTAAGGATG |
| 1731 | ATGGAAGAATTAATTAAGGATGG |
| 1732 | TGGAAGAATTAATTAAGGATGGC |
| 1733 | GGAAGAATTAATTAAGGATGGCA |
| 1734 | GAAGAATTAATTAAGGATGGCAG |
| 1735 | AAGAATTAATTAAGGATGGCAGC |
| 1736 | AGAATTAATTAAGGATGGCAGCT |
| 1737 | GAATTAATTAAGGATGGCAGCTC |

| ID | SEQUENCE |
|---|---|
| 1738 | AATTAATTAAGGATGGCAGCTCA |
| 1739 | ATTAATTAAGGATGGCAGCTCAA |
| 1740 | TTAATTAAGGATGGCAGCTCAAA |
| 1741 | TAATTAAGGATGGCAGCTCAAAG |
| 1742 | AATTAAGGATGGCAGCTCAAAGC |
| 1743 | ATTAAGGATGGCAGCTCAAAGCA |
| 1744 | TTAAGGATGGCAGCTCAAAGCAA |
| 1745 | TAAGGATGGCAGCTCAAAGCAAA |
| 1746 | AAGGATGGCAGCTCAAAGCAAAA |
| 1747 | AGGATGGCAGCTCAAAGCAAAAG |
| 1748 | GGATGGCAGCTCAAAGCAAAAGG |
| 1749 | GATGGCAGCTCAAAGCAAAAGGC |
| 1750 | ATGGCAGCTCAAAGCAAAAGGCC |
| 1751 | TGGCAGCTCAAAGCAAAAGGCCA |
| 1752 | GGCAGCTCAAAGCAAAAGGCCAT |
| 1753 | GCAGCTCAAAGCAAAAGGCCATG |
| 1754 | CAGCTCAAAGCAAAAGGCCATGC |
| 1755 | AGCTCAAAGCAAAAGGCCATGCT |
| 1756 | GCTCAAAGCAAAAGGCCATGCTA |
| 1757 | CTCAAAGCAAAAGGCCATGCTAG |
| 1758 | TCAAAGCAAAAGGCCATGCTAGA |
| 1759 | CAAAGCAAAAGGCCATGCTAGAA |
| 1760 | AAAGCAAAAGGCCATGCTAGAAG |
| 1761 | AAGCAAAAGGCCATGCTAGAAGT |
| 1762 | AGCAAAAGGCCATGCTAGAAGTA |
| 1763 | GCAAAAGGCCATGCTAGAAGTAC |
| 1764 | CAAAAGGCCATGCTAGAAGTACA |
| 1765 | AAAAGGCCATGCTAGAAGTACAT |
| 1766 | AAAGGCCATGCTAGAAGTACATA |
| 1767 | AAGGCCATGCTAGAAGTACATAA |
| 1768 | AGGCCATGCTAGAAGTACATAAG |
| 1769 | GGCCATGCTAGAAGTACATAAGA |
| 1770 | GCCATGCTAGAAGTACATAAGAC |
| 1771 | CCATGCTAGAAGTACATAAGACC |
| 1772 | CATGCTAGAAGTACATAAGACCT |
| 1773 | ATGCTAGAAGTACATAAGACCTT |
| 1774 | TGCTAGAAGTACATAAGACCTTA |
| 1775 | GCTAGAAGTACATAAGACCTTAT |
| 1776 | CTAGAAGTACATAAGACCTTATT |
| 1777 | TAGAAGTACATAAGACCTTATTT |
| 1778 | AGAAGTACATAAGACCTTATTTG |
| 1779 | GAAGTACATAAGACCTTATTTGG |
| 1780 | AAGTACATAAGACCTTATTTGGT |
| 1781 | AGTACATAAGACCTTATTTGGTA |
| 1782 | GTACATAAGACCTTATTTGGTAA |
| 1783 | TACATAAGACCTTATTTGGTAAT |
| 1784 | ACATAAGACCTTATTTGGTAATC |
| 1785 | CATAAGACCTTATTTGGTAATCT |
| 1786 | ATAAGACCTTATTTGGTAATCTG |
| 1787 | TAAGACCTTATTTGGTAATCTGC |
| 1788 | AAGACCTTATTTGGTAATCTGCT |
| 1789 | AGACCTTATTTGGTAATCTGCTG |
| 1790 | GACCTTATTTGGTAATCTGCTGT |
| 1791 | ACCTTATTTGGTAATCTGCTGTC |
| 1792 | CCTTATTTGGTAATCTGCTGTCT |
| 1793 | CTTATTTGGTAATCTGCTGTCTT |
| 1794 | TTATTTGGTAATCTGCTGTCTTC |
| 1795 | TATTTGGTAATCTGCTGTCTTCC |

| ID | SEQUENCE |
|---|---|
| 1796 | ATTTGGTAATCTGCTGTCTTCCA |
| 1797 | TTTGGTAATCTGCTGTCTTCCAG |
| 1798 | TTGGTAATCTGCTGTCTTCCAGT |
| 1799 | TGGTAATCTGCTGTCTTCCAGTG |
| 1800 | GGTAATCTGCTGTCTTCCAGTGT |
| 1801 | GTAATCTGCTGTCTTCCAGTGTC |
| 1802 | TAATCTGCTGTCTTCCAGTGTCT |
| 1803 | AATCTGCTGTCTTCCAGTGTCTC |
| 1804 | ATCTGCTGTCTTCCAGTGTCTCT |
| 1805 | TCTGCTGTCTTCCAGTGTCTCTG |
| 1806 | CTGCTGTCTTCCAGTGTCTCTGC |
| 1807 | TGCTGTCTTCCAGTGTCTCTGCA |
| 1808 | GCTGTCTTCCAGTGTCTCTGCAT |
| 1809 | CTGTCTTCCAGTGTCTCTGCATT |
| 1810 | TGTCTTCCAGTGTCTCTGCATTA |
| 1811 | GTCTTCCAGTGTCTCTGCATTAG |
| 1812 | TCTTCCAGTGTCTCTGCATTAGA |
| 1813 | CTTCCAGTGTCTCTGCATTAGAT |
| 1814 | TTCCAGTGTCTCTGCATTAGATA |
| 1815 | TCCAGTGTCTCTGCATTAGATAC |
| 1816 | CCAGTGTCTCTGCATTAGATACC |
| 1817 | CAGTGTCTCTGCATTAGATACCA |
| 1818 | AGTGTCTCTGCATTAGATACCAT |
| 1819 | GTGTCTCTGCATTAGATACCATT |
| 1820 | TGTCTCTGCATTAGATACCATTA |
| 1821 | GTCTCTGCATTAGATACCATTAC |
| 1822 | TCTCTGCATTAGATACCATTACT |
| 1823 | CTCTGCATTAGATACCATTACTA |
| 1824 | TCTGCATTAGATACCATTACTAC |
| 1825 | CTGCATTAGATACCATTACTACA |
| 1826 | TGCATTAGATACCATTACTACAG |
| 1827 | GCATTAGATACCATTACTACAGT |
| 1828 | CATTAGATACCATTACTACAGTA |
| 1829 | ATTAGATACCATTACTACAGTAG |
| 1830 | TTAGATACCATTACTACAGTAGC |
| 1831 | TAGATACCATTACTACAGTAGCA |
| 1832 | AGATACCATTACTACAGTAGCAC |
| 1833 | GATACCATTACTACAGTAGCACT |
| 1834 | ATACCATTACTACAGTAGCACTT |
| 1835 | TACCATTACTACAGTAGCACTTG |
| 1836 | ACCATTACTACAGTAGCACTTGG |
| 1837 | CCATTACTACAGTAGCACTTGGA |
| 1838 | CATTACTACAGTAGCACTTGGAT |
| 1839 | ATTACTACAGTAGCACTTGGATC |
| 1840 | TTACTACAGTAGCACTTGGATCT |
| 1841 | TACTACAGTAGCACTTGGATCTC |
| 1842 | ACTACAGTAGCACTTGGATCTCT |
| 1843 | CTACAGTAGCACTTGGATCTCTC |
| 1844 | TACAGTAGCACTTGGATCTCTCA |
| 1845 | ACAGTAGCACTTGGATCTCTCAC |
| 1846 | CAGTAGCACTTGGATCTCTCACA |
| 1847 | AGTAGCACTTGGATCTCTCACAT |
| 1848 | GTAGCACTTGGATCTCTCACATC |
| 1849 | TAGCACTTGGATCTCTCACATCT |
| 1850 | AGCACTTGGATCTCTCACATCTA |
| 1851 | GCACTTGGATCTCTCACATCTAT |
| 1852 | CACTTGGATCTCTCACATCTATT |
| 1853 | ACTTGGATCTCTCACATCTATTC |

| ID | SEQUENCE |
|---|---|
| 1854 | CTTGGATCTCTCACATCTATTCC |
| 1855 | TTGGATCTCTCACATCTATTCCA |
| 1856 | TGGATCTCTCACATCTATTCCAG |
| 1857 | GGATCTCTCACATCTATTCCAGA |
| 1858 | GATCTCTCACATCTATTCCAGAA |
| 1859 | ATCTCTCACATCTATTCCAGAAA |
| 1860 | TCTCTCACATCTATTCCAGAAAA |
| 1861 | CTCTCACATCTATTCCAGAAAAT |
| 1862 | TCTCACATCTATTCCAGAAAATG |
| 1863 | CTCACATCTATTCCAGAAAATGT |
| 1864 | TCACATCTATTCCAGAAAATGTG |
| 1865 | CACATCTATTCCAGAAAATGTGT |
| 1866 | ACATCTATTCCAGAAAATGTGTC |
| 1867 | CATCTATTCCAGAAAATGTGTCT |
| 1868 | ATCTATTCCAGAAAATGTGTCTA |
| 1869 | TCTATTCCAGAAAATGTGTCTAC |
| 1870 | CTATTCCAGAAAATGTGTCTACT |
| 1871 | TATTCCAGAAAATGTGTCTACTC |
| 1872 | ATTCCAGAAAATGTGTCTACTCA |
| 1873 | TTCCAGAAAATGTGTCTACTCAT |
| 1874 | TCCAGAAAATGTGTCTACTCATG |
| 1875 | CCAGAAAATGTGTCTACTCATGT |
| 1876 | CAGAAAATGTGTCTACTCATGTT |
| 1877 | AGAAAATGTGTCTACTCATGTTT |
| 1878 | GAAAATGTGTCTACTCATGTTTC |
| 1879 | AAAATGTGTCTACTCATGTTTCT |
| 1880 | AAATGTGTCTACTCATGTTTCTC |
| 1881 | AATGTGTCTACTCATGTTTCTCA |
| 1882 | ATGTGTCTACTCATGTTTCTCAG |
| 1883 | TGTGTCTACTCATGTTTCTCAGA |
| 1884 | GTGTCTACTCATGTTTCTCAGAT |
| 1885 | TGTCTACTCATGTTTCTCAGATT |
| 1886 | GTCTACTCATGTTTCTCAGATTT |
| 1887 | TCTACTCATGTTTCTCAGATTTT |
| 1888 | CTACTCATGTTTCTCAGATTTTT |
| 1889 | TACTCATGTTTCTCAGATTTTTA |
| 1890 | ACTCATGTTTCTCAGATTTTTAA |
| 1891 | CTCATGTTTCTCAGATTTTTAAT |
| 1892 | TCATGTTTCTCAGATTTTTAATA |
| 1893 | CATGTTTCTCAGATTTTTAATAT |
| 1894 | ATGTTTCTCAGATTTTTAATATG |
| 1895 | TGTTTCTCAGATTTTTAATATGA |
| 1896 | GTTTCTCAGATTTTTAATATGAT |
| 1897 | TTTCTCAGATTTTTAATATGATA |
| 1898 | TTCTCAGATTTTTAATATGATAC |
| 1899 | TCTCAGATTTTTAATATGATACT |
| 1900 | CTCAGATTTTTAATATGATACTA |
| 1901 | TCAGATTTTTAATATGATACTAA |
| 1902 | CAGATTTTTAATATGATACTAAA |
| 1903 | AGATTTTTAATATGATACTAAAA |
| 1904 | GATTTTTAATATGATACTAAAAG |
| 1905 | ATTTTTAATATGATACTAAAAGA |
| 1906 | TTTTTAATATGATACTAAAAGAA |
| 1907 | TTTTAATATGATACTAAAAGAAC |
| 1908 | TTTAATATGATACTAAAAGAACA |
| 1909 | TTAATATGATACTAAAAGAACAA |
| 1910 | TAATATGATACTAAAAGAACAAT |
| 1911 | AATATGATACTAAAAGAACAATC |

| ID | SEQUENCE |
|---|---|
| 1912 | ATATGATACTAAAAGAACAATCA |
| 1913 | TATGATACTAAAAGAACAATCAT |
| 1914 | ATGATACTAAAAGAACAATCATT |
| 1915 | TGATACTAAAAGAACAATCATTA |
| 1916 | GATACTAAAAGAACAATCATTAG |
| 1917 | ATACTAAAAGAACAATCATTAGC |
| 1918 | TACTAAAAGAACAATCATTAGCA |
| 1919 | ACTAAAAGAACAATCATTAGCAG |
| 1920 | CTAAAAGAACAATCATTAGCAGC |
| 1921 | TAAAAGAACAATCATTAGCAGCA |
| 1922 | AAAAGAACAATCATTAGCAGCAG |
| 1923 | AAAGAACAATCATTAGCAGCAGA |
| 1924 | AAGAACAATCATTAGCAGCAGAA |
| 1925 | AGAACAATCATTAGCAGCAGAAA |
| 1926 | GAACAATCATTAGCAGCAGAAAG |
| 1927 | AACAATCATTAGCAGCAGAAAGT |
| 1928 | ACAATCATTAGCAGCAGAAAGTA |
| 1929 | CAATCATTAGCAGCAGAAAGTAA |
| 1930 | AATCATTAGCAGCAGAAAGTAAA |
| 1931 | ATCATTAGCAGCAGAAAGTAAAA |
| 1932 | TCATTAGCAGCAGAAAGTAAAAC |
| 1933 | CATTAGCAGCAGAAAGTAAAACT |
| 1934 | ATTAGCAGCAGAAAGTAAAACTG |
| 1935 | TTAGCAGCAGAAAGTAAAACTGT |
| 1936 | TAGCAGCAGAAAGTAAAACTGTA |
| 1937 | AGCAGCAGAAAGTAAAACTGTAC |
| 1938 | GCAGCAGAAAGTAAAACTGTACT |
| 1939 | CAGCAGAAAGTAAAACTGTACTA |
| 1940 | AGCAGAAAGTAAAACTGTACTAC |
| 1941 | GCAGAAAGTAAAACTGTACTACA |
| 1942 | CAGAAAGTAAAACTGTACTACAG |
| 1943 | AGAAAGTAAAACTGTACTACAGG |
| 1944 | GAAAGTAAAACTGTACTACAGGA |
| 1945 | AAAGTAAAACTGTACTACAGGAA |
| 1946 | AAGTAAAACTGTACTACAGGAAT |
| 1947 | AGTAAAACTGTACTACAGGAATT |
| 1948 | GTAAAACTGTACTACAGGAATTG |
| 1949 | TAAAACTGTACTACAGGAATTGA |
| 1950 | AAAACTGTACTACAGGAATTGAT |
| 1951 | AAACTGTACTACAGGAATTGATT |
| 1952 | AACTGTACTACAGGAATTGATTA |
| 1953 | ACTGTACTACAGGAATTGATTAA |
| 1954 | CTGTACTACAGGAATTGATTAAT |
| 1955 | TGTACTACAGGAATTGATTAATG |
| 1956 | GTACTACAGGAATTGATTAATGT |
| 1957 | TACTACAGGAATTGATTAATGTA |
| 1958 | ACTACAGGAATTGATTAATGTAC |
| 1959 | CTACAGGAATTGATTAATGTACT |
| 1960 | TACAGGAATTGATTAATGTACTC |
| 1961 | ACAGGAATTGATTAATGTACTCA |
| 1962 | CAGGAATTGATTAATGTACTCAA |
| 1963 | AGGAATTGATTAATGTACTCAAG |
| 1964 | GGAATTGATTAATGTACTCAAGA |
| 1965 | GAATTGATTAATGTACTCAAGAC |
| 1966 | AATTGATTAATGTACTCAAGACT |
| 1967 | ATTGATTAATGTACTCAAGACTG |
| 1968 | TTGATTAATGTACTCAAGACTGA |
| 1969 | TGATTAATGTACTCAAGACTGAT |

| ID | SEQUENCE |
|---|---|
| 1970 | GATTAATGTACTCAAGACTGATC |
| 1971 | ATTAATGTACTCAAGACTGATCT |
| 1972 | TTAATGTACTCAAGACTGATCTT |
| 1973 | TAATGTACTCAAGACTGATCTTC |
| 1974 | AATGTACTCAAGACTGATCTTCT |
| 1975 | ATGTACTCAAGACTGATCTTCTA |
| 1976 | TGTACTCAAGACTGATCTTCTAA |
| 1977 | GTACTCAAGACTGATCTTCTAAG |
| 1978 | TACTCAAGACTGATCTTCTAAGT |
| 1979 | ACTCAAGACTGATCTTCTAAGTT |
| 1980 | CTCAAGACTGATCTTCTAAGTTC |
| 1981 | TCAAGACTGATCTTCTAAGTTCA |
| 1982 | CAAGACTGATCTTCTAAGTTCAC |
| 1983 | AAGACTGATCTTCTAAGTTCACT |
| 1984 | AGACTGATCTTCTAAGTTCACTG |
| 1985 | GACTGATCTTCTAAGTTCACTGG |
| 1986 | ACTGATCTTCTAAGTTCACTGGA |
| 1987 | CTGATCTTCTAAGTTCACTGGAA |
| 1988 | TGATCTTCTAAGTTCACTGGAAA |
| 1989 | GATCTTCTAAGTTCACTGGAAAT |
| 1990 | ATCTTCTAAGTTCACTGGAAATG |
| 1991 | TCTTCTAAGTTCACTGGAAATGA |
| 1992 | CTTCTAAGTTCACTGGAAATGAT |
| 1993 | TTCTAAGTTCACTGGAAATGATT |
| 1994 | TCTAAGTTCACTGGAAATGATTT |
| 1995 | CTAAGTTCACTGGAAATGATTTT |
| 1996 | TAAGTTCACTGGAAATGATTTTA |
| 1997 | AAGTTCACTGGAAATGATTTTAT |
| 1998 | AGTTCACTGGAAATGATTTTATC |
| 1999 | GTTCACTGGAAATGATTTTATCC |
| 2000 | TTCACTGGAAATGATTTTATCCC |
| 2001 | TCACTGGAAATGATTTTATCCCC |
| 2002 | CACTGGAAATGATTTTATCCCCA |
| 2003 | ACTGGAAATGATTTTATCCCCAA |
| 2004 | CTGGAAATGATTTTATCCCCAAC |
| 2005 | TGGAAATGATTTTATCCCCAACT |
| 2006 | GGAAATGATTTTATCCCCAACTG |
| 2007 | GAAATGATTTTATCCCCAACTGT |
| 2008 | AAATGATTTTATCCCCAACTGTG |
| 2009 | AATGATTTTATCCCCAACTGTGG |
| 2010 | ATGATTTTATCCCCAACTGTGGT |
| 2011 | TGATTTTATCCCCAACTGTGGTG |
| 2012 | GATTTTATCCCCAACTGTGGTGT |
| 2013 | ATTTTATCCCCAACTGTGGTGTC |
| 2014 | TTTTATCCCCAACTGTGGTGTCT |
| 2015 | TTTATCCCCAACTGTGGTGTCTA |
| 2016 | TTATCCCCAACTGTGGTGTCTAT |
| 2017 | TATCCCCAACTGTGGTGTCTATA |
| 2018 | ATCCCCAACTGTGGTGTCTATAC |
| 2019 | TCCCCAACTGTGGTGTCTATACT |
| 2020 | CCCCAACTGTGGTGTCTATACTG |
| 2021 | CCCAACTGTGGTGTCTATACTGA |
| 2022 | CCAACTGTGGTGTCTATACTGAA |
| 2023 | CAACTGTGGTGTCTATACTGAAA |
| 2024 | AACTGTGGTGTCTATACTGAAAA |
| 2025 | ACTGTGGTGTCTATACTGAAAAT |
| 2026 | CTGTGGTGTCTATACTGAAAATC |
| 2027 | TGTGGTGTCTATACTGAAAATCA |

| ID | SEQUENCE |
|---|---|
| 2028 | GTGGTGTCTATACTGAAAATCAA |
| 2029 | TGGTGTCTATACTGAAAATCAAT |
| 2030 | GGTGTCTATACTGAAAATCAATA |
| 2031 | GTGTCTATACTGAAAATCAATAG |
| 2032 | TGTCTATACTGAAAATCAATAGT |
| 2033 | GTCTATACTGAAAATCAATAGTC |
| 2034 | TCTATACTGAAAATCAATAGTCA |
| 2035 | CTATACTGAAAATCAATAGTCAA |
| 2036 | TATACTGAAAATCAATAGTCAAC |
| 2037 | ATACTGAAAATCAATAGTCAACT |
| 2038 | TACTGAAAATCAATAGTCAACTA |
| 2039 | ACTGAAAATCAATAGTCAACTAA |
| 2040 | CTGAAAATCAATAGTCAACTAAA |
| 2041 | TGAAAATCAATAGTCAACTAAAG |
| 2042 | GAAAATCAATAGTCAACTAAAGC |
| 2043 | AAAATCAATAGTCAACTAAAGCA |
| 2044 | AAATCAATAGTCAACTAAAGCAT |
| 2045 | AATCAATAGTCAACTAAAGCATA |
| 2046 | ATCAATAGTCAACTAAAGCATAT |
| 2047 | TCAATAGTCAACTAAAGCATATT |
| 2048 | CAATAGTCAACTAAAGCATATTT |
| 2049 | AATAGTCAACTAAAGCATATTTT |
| 2050 | ATAGTCAACTAAAGCATATTTTC |
| 2051 | TAGTCAACTAAAGCATATTTTCA |
| 2052 | AGTCAACTAAAGCATATTTTCAA |
| 2053 | GTCAACTAAAGCATATTTTCAAG |
| 2054 | TCAACTAAAGCATATTTTCAAGA |
| 2055 | CAACTAAAGCATATTTTCAAGAC |
| 2056 | AACTAAAGCATATTTTCAAGACT |
| 2057 | ACTAAAGCATATTTTCAAGACTT |
| 2058 | CTAAAGCATATTTTCAAGACTTC |
| 2059 | TAAAGCATATTTTCAAGACTTCA |
| 2060 | AAAGCATATTTTCAAGACTTCAT |
| 2061 | AAGCATATTTTCAAGACTTCATT |
| 2062 | AGCATATTTTCAAGACTTCATTG |
| 2063 | GCATATTTTCAAGACTTCATTGA |
| 2064 | CATATTTTCAAGACTTCATTGAC |
| 2065 | ATATTTTCAAGACTTCATTGACA |
| 2066 | TATTTTCAAGACTTCATTGACAG |
| 2067 | ATTTTCAAGACTTCATTGACAGT |
| 2068 | TTTTCAAGACTTCATTGACAGTG |
| 2069 | TTTCAAGACTTCATTGACAGTGG |
| 2070 | TTCAAGACTTCATTGACAGTGGC |
| 2071 | TCAAGACTTCATTGACAGTGGCC |
| 2072 | CAAGACTTCATTGACAGTGGCCG |
| 2073 | AAGACTTCATTGACAGTGGCCGA |
| 2074 | AGACTTCATTGACAGTGGCCGAT |
| 2075 | GACTTCATTGACAGTGGCCGATA |
| 2076 | ACTTCATTGACAGTGGCCGATAA |
| 2077 | CTTCATTGACAGTGGCCGATAAG |
| 2078 | TTCATTGACAGTGGCCGATAAGA |
| 2079 | TCATTGACAGTGGCCGATAAGAT |
| 2080 | CATTGACAGTGGCCGATAAGATA |
| 2081 | ATTGACAGTGGCCGATAAGATAG |
| 2082 | TTGACAGTGGCCGATAAGATAGA |
| 2083 | TGACAGTGGCCGATAAGATAGAA |
| 2084 | GACAGTGGCCGATAAGATAGAAG |
| 2085 | ACAGTGGCCGATAAGATAGAAGA |

| ID | SEQUENCE |
|---|---|
| 2086 | CAGTGGCCGATAAGATAGAAGAT |
| 2087 | AGTGGCCGATAAGATAGAAGATC |
| 2088 | GTGGCCGATAAGATAGAAGATCA |
| 2089 | TGGCCGATAAGATAGAAGATCAA |
| 2090 | GGCCGATAAGATAGAAGATCAAA |
| 2091 | GCCGATAAGATAGAAGATCAAAA |
| 2092 | CCGATAAGATAGAAGATCAAAAA |
| 2093 | CGATAAGATAGAAGATCAAAAAA |
| 2094 | GATAAGATAGAAGATCAAAAAAA |
| 2095 | ATAAGATAGAAGATCAAAAAAAG |
| 2096 | TAAGATAGAAGATCAAAAAAAGG |
| 2097 | AAGATAGAAGATCAAAAAAAGGA |
| 2098 | AGATAGAAGATCAAAAAAAGGAA |
| 2099 | GATAGAAGATCAAAAAAAGGAAC |
| 2100 | ATAGAAGATCAAAAAAAGGAACT |
| 2101 | TAGAAGATCAAAAAAAGGAACTA |
| 2102 | AGAAGATCAAAAAAAGGAACTAG |
| 2103 | GAAGATCAAAAAAAGGAACTAGA |
| 2104 | AAGATCAAAAAAAGGAACTAGAT |
| 2105 | AGATCAAAAAAAGGAACTAGATG |
| 2106 | GATCAAAAAAAGGAACTAGATGG |
| 2107 | ATCAAAAAAAGGAACTAGATGGC |
| 2108 | TCAAAAAAAGGAACTAGATGGCT |
| 2109 | CAAAAAAAGGAACTAGATGGCTT |
| 2110 | AAAAAAAGGAACTAGATGGCTTT |
| 2111 | AAAAAAGGAACTAGATGGCTTTC |
| 2112 | AAAAAGGAACTAGATGGCTTTCT |
| 2113 | AAAAGGAACTAGATGGCTTTCTC |
| 2114 | AAAGGAACTAGATGGCTTTCTCA |
| 2115 | AAGGAACTAGATGGCTTTCTCAG |
| 2116 | AGGAACTAGATGGCTTTCTCAGT |
| 2117 | GGAACTAGATGGCTTTCTCAGTA |
| 2118 | GAACTAGATGGCTTTCTCAGTAT |
| 2119 | AACTAGATGGCTTTCTCAGTATA |
| 2120 | ACTAGATGGCTTTCTCAGTATAC |
| 2121 | CTAGATGGCTTTCTCAGTATACT |
| 2122 | TAGATGGCTTTCTCAGTATACTG |
| 2123 | AGATGGCTTTCTCAGTATACTGT |
| 2124 | GATGGCTTTCTCAGTATACTGTG |
| 2125 | ATGGCTTTCTCAGTATACTGTGT |
| 2126 | TGGCTTTCTCAGTATACTGTGTA |
| 2127 | GGCTTTCTCAGTATACTGTGTAA |
| 2128 | GCTTTCTCAGTATACTGTGTAAC |
| 2129 | CTTTCTCAGTATACTGTGTAACA |
| 2130 | TTTCTCAGTATACTGTGTAACAA |
| 2131 | TTCTCAGTATACTGTGTAACAAT |
| 2132 | TCTCAGTATACTGTGTAACAATC |
| 2133 | CTCAGTATACTGTGTAACAATCT |
| 2134 | TCAGTATACTGTGTAACAATCTA |
| 2135 | CAGTATACTGTGTAACAATCTAC |
| 2136 | AGTATACTGTGTAACAATCTACA |
| 2137 | GTATACTGTGTAACAATCTACAT |
| 2138 | TATACTGTGTAACAATCTACATG |
| 2139 | ATACTGTGTAACAATCTACATGA |
| 2140 | TACTGTGTAACAATCTACATGAA |
| 2141 | ACTGTGTAACAATCTACATGAAC |
| 2142 | CTGTGTAACAATCTACATGAACT |
| 2143 | TGTGTAACAATCTACATGAACTA |

| ID | SEQUENCE |
|---|---|
| 2144 | GTGTAACAATCTACATGAACTAC |
| 2145 | TGTAACAATCTACATGAACTACA |
| 2146 | GTAACAATCTACATGAACTACAA |
| 2147 | TAACAATCTACATGAACTACAAG |
| 2148 | AACAATCTACATGAACTACAAGA |
| 2149 | ACAATCTACATGAACTACAAGAA |
| 2150 | CAATCTACATGAACTACAAGAAA |
| 2151 | AATCTACATGAACTACAAGAAAA |
| 2152 | ATCTACATGAACTACAAGAAAAT |
| 2153 | TCTACATGAACTACAAGAAAATA |
| 2154 | CTACATGAACTACAAGAAAATAC |
| 2155 | TACATGAACTACAAGAAAATACC |
| 2156 | ACATGAACTACAAGAAAATACCA |
| 2157 | CATGAACTACAAGAAAATACCAT |
| 2158 | ATGAACTACAAGAAAATACCATT |
| 2159 | TGAACTACAAGAAAATACCATTT |
| 2160 | GAACTACAAGAAAATACCATTTG |
| 2161 | AACTACAAGAAAATACCATTTGT |
| 2162 | ACTACAAGAAAATACCATTTGTT |
| 2163 | CTACAAGAAAATACCATTTGTTC |
| 2164 | TACAAGAAAATACCATTTGTTCC |
| 2165 | ACAAGAAAATACCATTTGTTCCT |
| 2166 | CAAGAAAATACCATTTGTTCCTT |
| 2167 | AAGAAAATACCATTTGTTCCTTG |
| 2168 | AGAAAATACCATTTGTTCCTTGG |
| 2169 | GAAAATACCATTTGTTCCTTGGT |
| 2170 | AAAATACCATTTGTTCCTTGGTT |
| 2171 | AAATACCATTTGTTCCTTGGTTG |
| 2172 | AATACCATTTGTTCCTTGGTTGA |
| 2173 | ATACCATTTGTTCCTTGGTTGAG |
| 2174 | TACCATTTGTTCCTTGGTTGAGT |
| 2175 | ACCATTTGTTCCTTGGTTGAGTC |
| 2176 | CCATTTGTTCCTTGGTTGAGTCA |
| 2177 | CATTTGTTCCTTGGTTGAGTCAC |
| 2178 | ATTTGTTCCTTGGTTGAGTCACA |
| 2179 | TTTGTTCCTTGGTTGAGTCACAA |
| 2180 | TTGTTCCTTGGTTGAGTCACAAA |
| 2181 | TGTTCCTTGGTTGAGTCACAAAA |
| 2182 | GTTCCTTGGTTGAGTCACAAAAG |
| 2183 | TTCCTTGGTTGAGTCACAAAAGC |
| 2184 | TCCTTGGTTGAGTCACAAAAGCA |
| 2185 | CCTTGGTTGAGTCACAAAAGCAA |
| 2186 | CTTGGTTGAGTCACAAAAGCAAT |
| 2187 | TTGGTTGAGTCACAAAAGCAATG |
| 2188 | TGGTTGAGTCACAAAAGCAATGT |
| 2189 | GGTTGAGTCACAAAAGCAATGTG |
| 2190 | GTTGAGTCACAAAAGCAATGTGG |
| 2191 | TTGAGTCACAAAAGCAATGTGGA |
| 2192 | TGAGTCACAAAAGCAATGTGGAA |
| 2193 | GAGTCACAAAAGCAATGTGGAAA |
| 2194 | AGTCACAAAAGCAATGTGGAAAC |
| 2195 | GTCACAAAAGCAATGTGGAAACC |
| 2196 | TCACAAAAGCAATGTGGAAACCT |
| 2197 | CACAAAAGCAATGTGGAAACCTA |
| 2198 | ACAAAAGCAATGTGGAAACCTAA |
| 2199 | CAAAAGCAATGTGGAAACCTAAC |
| 2200 | AAAAGCAATGTGGAAACCTAACT |
| 2201 | AAAGCAATGTGGAAACCTAACTG |

| ID | SEQUENCE |
|---|---|
| 2202 | AAGCAATGTGGAAACCTAACTGA |
| 2203 | AGCAATGTGGAAACCTAACTGAA |
| 2204 | GCAATGTGGAAACCTAACTGAAG |
| 2205 | CAATGTGGAAACCTAACTGAAGA |
| 2206 | AATGTGGAAACCTAACTGAAGAC |
| 2207 | ATGTGGAAACCTAACTGAAGACC |
| 2208 | TGTGGAAACCTAACTGAAGACCT |
| 2209 | GTGGAAACCTAACTGAAGACCTG |
| 2210 | TGGAAACCTAACTGAAGACCTGA |
| 2211 | GGAAACCTAACTGAAGACCTGAA |
| 2212 | GAAACCTAACTGAAGACCTGAAG |
| 2213 | AAACCTAACTGAAGACCTGAAGA |
| 2214 | AACCTAACTGAAGACCTGAAGAC |
| 2215 | ACCTAACTGAAGACCTGAAGACA |
| 2216 | CCTAACTGAAGACCTGAAGACAA |
| 2217 | CTAACTGAAGACCTGAAGACAAT |
| 2218 | TAACTGAAGACCTGAAGACAATA |
| 2219 | AACTGAAGACCTGAAGACAATAA |
| 2220 | ACTGAAGACCTGAAGACAATAAA |
| 2221 | CTGAAGACCTGAAGACAATAAAG |
| 2222 | TGAAGACCTGAAGACAATAAAGC |
| 2223 | GAAGACCTGAAGACAATAAAGCA |
| 2224 | AAGACCTGAAGACAATAAAGCAG |
| 2225 | AGACCTGAAGACAATAAAGCAGA |
| 2226 | GACCTGAAGACAATAAAGCAGAC |
| 2227 | ACCTGAAGACAATAAAGCAGACC |
| 2228 | CCTGAAGACAATAAAGCAGACCC |
| 2229 | CTGAAGACAATAAAGCAGACCCA |
| 2230 | TGAAGACAATAAAGCAGACCCAT |
| 2231 | GAAGACAATAAAGCAGACCCATT |
| 2232 | AAGACAATAAAGCAGACCCATTC |
| 2233 | AGACAATAAAGCAGACCCATTCC |
| 2234 | GACAATAAAGCAGACCCATTCCC |
| 2235 | ACAATAAAGCAGACCCATTCCCA |
| 2236 | CAATAAAGCAGACCCATTCCCAG |
| 2237 | AATAAAGCAGACCCATTCCCAGG |
| 2238 | ATAAAGCAGACCCATTCCCAGGA |
| 2239 | TAAAGCAGACCCATTCCCAGGAA |
| 2240 | AAAGCAGACCCATTCCCAGGAAC |
| 2241 | AAGCAGACCCATTCCCAGGAACT |
| 2242 | AGCAGACCCATTCCCAGGAACTT |
| 2243 | GCAGACCCATTCCCAGGAACTTT |
| 2244 | CAGACCCATTCCCAGGAACTTTG |
| 2245 | AGACCCATTCCCAGGAACTTTGC |
| 2246 | GACCCATTCCCAGGAACTTTGCA |
| 2247 | ACCCATTCCCAGGAACTTTGCAA |
| 2248 | CCCATTCCCAGGAACTTTGCAAG |
| 2249 | CCATTCCCAGGAACTTTGCAAGT |
| 2250 | CATTCCCAGGAACTTTGCAAGTT |
| 2251 | ATTCCCAGGAACTTTGCAAGTTA |
| 2252 | TTCCCAGGAACTTTGCAAGTTAA |
| 2253 | TCCCAGGAACTTTGCAAGTTAAT |
| 2254 | CCCAGGAACTTTGCAAGTTAATG |
| 2255 | CCAGGAACTTTGCAAGTTAATGA |
| 2256 | CAGGAACTTTGCAAGTTAATGAA |
| 2257 | AGGAACTTTGCAAGTTAATGAAT |
| 2258 | GGAACTTTGCAAGTTAATGAATC |
| 2259 | GAACTTTGCAAGTTAATGAATCT |

| ID | SEQUENCE |
|---|---|
| 2260 | AACTTTGCAAGTTAATGAATCTT |
| 2261 | ACTTTGCAAGTTAATGAATCTTT |
| 2262 | CTTTGCAAGTTAATGAATCTTTG |
| 2263 | TTTGCAAGTTAATGAATCTTTGG |
| 2264 | TTGCAAGTTAATGAATCTTTGGA |
| 2265 | TGCAAGTTAATGAATCTTTGGAC |
| 2266 | GCAAGTTAATGAATCTTTGGACA |
| 2267 | CAAGTTAATGAATCTTTGGACAG |
| 2268 | AAGTTAATGAATCTTTGGACAGA |
| 2269 | AGTTAATGAATCTTTGGACAGAG |
| 2270 | GTTAATGAATCTTTGGACAGAGA |
| 2271 | TTAATGAATCTTTGGACAGAGAG |
| 2272 | TAATGAATCTTTGGACAGAGAGA |
| 2273 | AATGAATCTTTGGACAGAGAGAT |
| 2274 | ATGAATCTTTGGACAGAGAGATT |
| 2275 | TGAATCTTTGGACAGAGAGATTC |
| 2276 | GAATCTTTGGACAGAGAGATTCT |
| 2277 | AATCTTTGGACAGAGAGATTCTG |
| 2278 | ATCTTTGGACAGAGAGATTCTGT |
| 2279 | TCTTTGGACAGAGAGATTCTGTG |
| 2280 | CTTTGGACAGAGAGATTCTGTGC |
| 2281 | TTTGGACAGAGAGATTCTGTGCT |
| 2282 | TTGGACAGAGAGATTCTGTGCTT |
| 2283 | TGGACAGAGAGATTCTGTGCTTT |
| 2284 | GGACAGAGAGATTCTGTGCTTTG |
| 2285 | GACAGAGAGATTCTGTGCTTTGG |
| 2286 | ACAGAGAGATTCTGTGCTTTGGA |
| 2287 | CAGAGAGATTCTGTGCTTTGGAG |
| 2288 | AGAGAGATTCTGTGCTTTGGAGG |
| 2289 | GAGAGATTCTGTGCTTTGGAGGA |
| 2290 | AGAGATTCTGTGCTTTGGAGGAA |
| 2291 | GAGATTCTGTGCTTTGGAGGAAA |
| 2292 | AGATTCTGTGCTTTGGAGGAAAA |
| 2293 | GATTCTGTGCTTTGGAGGAAAAG |
| 2294 | ATTCTGTGCTTTGGAGGAAAAGT |
| 2295 | TTCTGTGCTTTGGAGGAAAAGTG |
| 2296 | TCTGTGCTTTGGAGGAAAAGTGT |
| 2297 | CTGTGCTTTGGAGGAAAAGTGTG |
| 2298 | TGTGCTTTGGAGGAAAAGTGTGA |
| 2299 | GTGCTTTGGAGGAAAAGTGTGAA |
| 2300 | TGCTTTGGAGGAAAAGTGTGAAA |
| 2301 | GCTTTGGAGGAAAAGTGTGAAAA |
| 2302 | CTTTGGAGGAAAAGTGTGAAAAT |
| 2303 | TTTGGAGGAAAAGTGTGAAAATA |
| 2304 | TTGGAGGAAAAGTGTGAAAATAT |
| 2305 | TGGAGGAAAAGTGTGAAAATATA |
| 2306 | GGAGGAAAAGTGTGAAAATATAC |
| 2307 | GAGGAAAAGTGTGAAAATATACA |
| 2308 | AGGAAAAGTGTGAAAATATACAG |
| 2309 | GGAAAAGTGTGAAAATATACAGA |
| 2310 | GAAAAGTGTGAAAATATACAGAA |
| 2311 | AAAAGTGTGAAAATATACAGAAA |
| 2312 | AAAGTGTGAAAATATACAGAAAC |
| 2313 | AAGTGTGAAAATATACAGAAACC |
| 2314 | AGTGTGAAAATATACAGAAACCA |
| 2315 | GTGTGAAAATATACAGAAACCAC |
| 2316 | TGTGAAAATATACAGAAACCACT |
| 2317 | GTGAAAATATACAGAAACCACTT |

| ID | SEQUENCE |
|---|---|
| 2318 | TGAAAATATACAGAAACCACTTA |
| 2319 | GAAAATATACAGAAACCACTTAG |
| 2320 | AAAATATACAGAAACCACTTAGT |
| 2321 | AAATATACAGAAACCACTTAGTA |
| 2322 | AATATACAGAAACCACTTAGTAG |
| 2323 | ATATACAGAAACCACTTAGTAGT |
| 2324 | TATACAGAAACCACTTAGTAGTG |
| 2325 | ATACAGAAACCACTTAGTAGTGT |
| 2326 | TACAGAAACCACTTAGTAGTGTC |
| 2327 | ACAGAAACCACTTAGTAGTGTCC |
| 2328 | CAGAAACCACTTAGTAGTGTCCA |
| 2329 | AGAAACCACTTAGTAGTGTCCAG |
| 2330 | GAAACCACTTAGTAGTGTCCAGG |
| 2331 | AAACCACTTAGTAGTGTCCAGGA |
| 2332 | AACCACTTAGTAGTGTCCAGGAA |
| 2333 | ACCACTTAGTAGTGTCCAGGAAA |
| 2334 | CCACTTAGTAGTGTCCAGGAAAA |
| 2335 | CACTTAGTAGTGTCCAGGAAAAT |
| 2336 | ACTTAGTAGTGTCCAGGAAAATA |
| 2337 | CTTAGTAGTGTCCAGGAAAATAT |
| 2338 | TTAGTAGTGTCCAGGAAAATATA |
| 2339 | TAGTAGTGTCCAGGAAAATATAC |
| 2340 | AGTAGTGTCCAGGAAAATATACA |
| 2341 | GTAGTGTCCAGGAAAATATACAG |
| 2342 | TAGTGTCCAGGAAAATATACAGC |
| 2343 | AGTGTCCAGGAAAATATACAGCA |
| 2344 | GTGTCCAGGAAAATATACAGCAG |
| 2345 | TGTCCAGGAAAATATACAGCAGA |
| 2346 | GTCCAGGAAAATATACAGCAGAA |
| 2347 | TCCAGGAAAATATACAGCAGAAA |
| 2348 | CCAGGAAAATATACAGCAGAAAT |
| 2349 | CAGGAAAATATACAGCAGAAATC |
| 2350 | AGGAAAATATACAGCAGAAATCT |
| 2351 | GGAAAATATACAGCAGAAATCTA |
| 2352 | GAAAATATACAGCAGAAATCTAA |
| 2353 | AAAATATACAGCAGAAATCTAAG |
| 2354 | AAATATACAGCAGAAATCTAAGG |
| 2355 | AATATACAGCAGAAATCTAAGGA |
| 2356 | ATATACAGCAGAAATCTAAGGAT |
| 2357 | TATACAGCAGAAATCTAAGGATA |
| 2358 | ATACAGCAGAAATCTAAGGATAT |
| 2359 | TACAGCAGAAATCTAAGGATATA |
| 2360 | ACAGCAGAAATCTAAGGATATAG |
| 2361 | CAGCAGAAATCTAAGGATATAGT |
| 2362 | AGCAGAAATCTAAGGATATAGTC |
| 2363 | GCAGAAATCTAAGGATATAGTCA |
| 2364 | CAGAAATCTAAGGATATAGTCAA |
| 2365 | AGAAATCTAAGGATATAGTCAAC |
| 2366 | GAAATCTAAGGATATAGTCAACA |
| 2367 | AAATCTAAGGATATAGTCAACAA |
| 2368 | AATCTAAGGATATAGTCAACAAA |
| 2369 | ATCTAAGGATATAGTCAACAAAA |
| 2370 | TCTAAGGATATAGTCAACAAAAT |
| 2371 | CTAAGGATATAGTCAACAAAATG |
| 2372 | TAAGGATATAGTCAACAAAATGA |
| 2373 | AAGGATATAGTCAACAAAATGAC |
| 2374 | AGGATATAGTCAACAAAATGACT |
| 2375 | GGATATAGTCAACAAAATGACTT |

| ID | SEQUENCE |
|---|---|
| 2376 | GATATAGTCAACAAAATGACTTT |
| 2377 | ATATAGTCAACAAAATGACTTTT |
| 2378 | TATAGTCAACAAAATGACTTTTC |
| 2379 | ATAGTCAACAAAATGACTTTTCA |
| 2380 | TAGTCAACAAAATGACTTTTCAC |
| 2381 | AGTCAACAAAATGACTTTTCACA |
| 2382 | GTCAACAAAATGACTTTTCACAG |
| 2383 | TCAACAAAATGACTTTTCACAGT |
| 2384 | CAACAAAATGACTTTTCACAGTC |
| 2385 | AACAAAATGACTTTTCACAGTCA |
| 2386 | ACAAAATGACTTTTCACAGTCAA |
| 2387 | CAAAATGACTTTTCACAGTCAAA |
| 2388 | AAAATGACTTTTCACAGTCAAAA |
| 2389 | AAATGACTTTTCACAGTCAAAAA |
| 2390 | AATGACTTTTCACAGTCAAAAAT |
| 2391 | ATGACTTTTCACAGTCAAAAATT |
| 2392 | TGACTTTTCACAGTCAAAAATTT |
| 2393 | GACTTTTCACAGTCAAAAATTTT |
| 2394 | ACTTTTCACAGTCAAAAATTTTG |
| 2395 | CTTTTCACAGTCAAAAATTTTGT |
| 2396 | TTTTCACAGTCAAAAATTTTGTG |
| 2397 | TTTCACAGTCAAAAATTTTGTGC |
| 2398 | TTCACAGTCAAAAATTTTGTGCT |
| 2399 | TCACAGTCAAAAATTTTGTGCTG |
| 2400 | CACAGTCAAAAATTTTGTGCTGA |
| 2401 | ACAGTCAAAAATTTTGTGCTGAT |
| 2402 | CAGTCAAAAATTTTGTGCTGATT |
| 2403 | AGTCAAAAATTTTGTGCTGATTC |
| 2404 | GTCAAAAATTTTGTGCTGATTCT |
| 2405 | TCAAAAATTTTGTGCTGATTCTG |
| 2406 | CAAAAATTTTGTGCTGATTCTGA |
| 2407 | AAAAATTTTGTGCTGATTCTGAT |
| 2408 | AAAATTTTGTGCTGATTCTGATG |
| 2409 | AAATTTTGTGCTGATTCTGATGG |
| 2410 | AATTTTGTGCTGATTCTGATGGC |
| 2411 | ATTTTGTGCTGATTCTGATGGCT |
| 2412 | TTTTGTGCTGATTCTGATGGCTT |
| 2413 | TTTGTGCTGATTCTGATGGCTTC |
| 2414 | TTGTGCTGATTCTGATGGCTTCT |
| 2415 | TGTGCTGATTCTGATGGCTTCTC |
| 2416 | GTGCTGATTCTGATGGCTTCTCA |
| 2417 | TGCTGATTCTGATGGCTTCTCAC |
| 2418 | GCTGATTCTGATGGCTTCTCACA |
| 2419 | CTGATTCTGATGGCTTCTCACAG |
| 2420 | TGATTCTGATGGCTTCTCACAGG |
| 2421 | GATTCTGATGGCTTCTCACAGGA |
| 2422 | ATTCTGATGGCTTCTCACAGGAA |
| 2423 | TTCTGATGGCTTCTCACAGGAAC |
| 2424 | TCTGATGGCTTCTCACAGGAACT |
| 2425 | CTGATGGCTTCTCACAGGAACTC |
| 2426 | TGATGGCTTCTCACAGGAACTCA |
| 2427 | GATGGCTTCTCACAGGAACTCAG |
| 2428 | ATGGCTTCTCACAGGAACTCAGA |
| 2429 | TGGCTTCTCACAGGAACTCAGAA |
| 2430 | GGCTTCTCACAGGAACTCAGAAA |
| 2431 | GCTTCTCACAGGAACTCAGAAAT |
| 2432 | CTTCTCACAGGAACTCAGAAATT |
| 2433 | TTCTCACAGGAACTCAGAAATTT |

| ID | SEQUENCE |
|---|---|
| 2434 | TCTCACAGGAACTCAGAAATTTT |
| 2435 | CTCACAGGAACTCAGAAATTTTA |
| 2436 | TCACAGGAACTCAGAAATTTTAA |
| 2437 | CACAGGAACTCAGAAATTTTAAC |
| 2438 | ACAGGAACTCAGAAATTTTAACC |
| 2439 | CAGGAACTCAGAAATTTTAACCA |
| 2440 | AGGAACTCAGAAATTTTAACCAA |
| 2441 | GGAACTCAGAAATTTTAACCAAG |
| 2442 | GAACTCAGAAATTTTAACCAAGA |
| 2443 | AACTCAGAAATTTTAACCAAGAA |
| 2444 | ACTCAGAAATTTTAACCAAGAAG |
| 2445 | CTCAGAAATTTTAACCAAGAAGG |
| 2446 | TCAGAAATTTTAACCAAGAAGGT |
| 2447 | CAGAAATTTTAACCAAGAAGGTA |
| 2448 | AGAAATTTTAACCAAGAAGGTAC |
| 2449 | GAAATTTTAACCAAGAAGGTACA |
| 2450 | AAATTTTAACCAAGAAGGTACAA |
| 2451 | AATTTTAACCAAGAAGGTACAAA |
| 2452 | ATTTTAACCAAGAAGGTACAAAA |
| 2453 | TTTTAACCAAGAAGGTACAAAAT |
| 2454 | TTTAACCAAGAAGGTACAAAATT |
| 2455 | TTAACCAAGAAGGTACAAAATTG |
| 2456 | TAACCAAGAAGGTACAAAATTGG |
| 2457 | AACCAAGAAGGTACAAAATTGGT |
| 2458 | ACCAAGAAGGTACAAAATTGGTT |
| 2459 | CCAAGAAGGTACAAAATTGGTTG |
| 2460 | CAAGAAGGTACAAAATTGGTTGA |
| 2461 | AAGAAGGTACAAAATTGGTTGAA |
| 2462 | AGAAGGTACAAAATTGGTTGAAG |
| 2463 | GAAGGTACAAAATTGGTTGAAGA |
| 2464 | AAGGTACAAAATTGGTTGAAGAA |
| 2465 | AGGTACAAAATTGGTTGAAGAAT |
| 2466 | GGTACAAAATTGGTTGAAGAATC |
| 2467 | GTACAAAATTGGTTGAAGAATCT |
| 2468 | TACAAAATTGGTTGAAGAATCTG |
| 2469 | ACAAAATTGGTTGAAGAATCTGT |
| 2470 | CAAAATTGGTTGAAGAATCTGTG |
| 2471 | AAAATTGGTTGAAGAATCTGTGA |
| 2472 | AAATTGGTTGAAGAATCTGTGAA |
| 2473 | AATTGGTTGAAGAATCTGTGAAA |
| 2474 | ATTGGTTGAAGAATCTGTGAAAC |
| 2475 | TTGGTTGAAGAATCTGTGAAACA |
| 2476 | TGGTTGAAGAATCTGTGAAACAC |
| 2477 | GGTTGAAGAATCTGTGAAACACT |
| 2478 | GTTGAAGAATCTGTGAAACACTC |
| 2479 | TTGAAGAATCTGTGAAACACTCT |
| 2480 | TGAAGAATCTGTGAAACACTCTG |
| 2481 | GAAGAATCTGTGAAACACTCTGA |
| 2482 | AAGAATCTGTGAAACACTCTGAT |
| 2483 | AGAATCTGTGAAACACTCTGATA |
| 2484 | GAATCTGTGAAACACTCTGATAA |
| 2485 | AATCTGTGAAACACTCTGATAAA |
| 2486 | ATCTGTGAAACACTCTGATAAAC |
| 2487 | TCTGTGAAACACTCTGATAAACT |
| 2488 | CTGTGAAACACTCTGATAAACTC |
| 2489 | TGTGAAACACTCTGATAAACTCA |
| 2490 | GTGAAACACTCTGATAAACTCAA |
| 2491 | TGAAACACTCTGATAAACTCAAT |

| ID | SEQUENCE |
|---|---|
| 2492 | GAAACACTCTGATAAACTCAATG |
| 2493 | AAACACTCTGATAAACTCAATGG |
| 2494 | AACACTCTGATAAACTCAATGGC |
| 2495 | ACACTCTGATAAACTCAATGGCA |
| 2496 | CACTCTGATAAACTCAATGGCAA |
| 2497 | ACTCTGATAAACTCAATGGCAAC |
| 2498 | CTCTGATAAACTCAATGGCAACC |
| 2499 | TCTGATAAACTCAATGGCAACCT |
| 2500 | CTGATAAACTCAATGGCAACCTG |
| 2501 | TGATAAACTCAATGGCAACCTGG |
| 2502 | GATAAACTCAATGGCAACCTGGA |
| 2503 | ATAAACTCAATGGCAACCTGGAA |
| 2504 | TAAACTCAATGGCAACCTGGAAA |
| 2505 | AAACTCAATGGCAACCTGGAAAA |
| 2506 | AACTCAATGGCAACCTGGAAAAA |
| 2507 | ACTCAATGGCAACCTGGAAAAAA |
| 2508 | CTCAATGGCAACCTGGAAAAAAT |
| 2509 | TCAATGGCAACCTGGAAAAAATA |
| 2510 | CAATGGCAACCTGGAAAAAATAT |
| 2511 | AATGGCAACCTGGAAAAAATATC |
| 2512 | ATGGCAACCTGGAAAAAATATCT |
| 2513 | TGGCAACCTGGAAAAAATATCTC |
| 2514 | GGCAACCTGGAAAAAATATCTCA |
| 2515 | GCAACCTGGAAAAAATATCTCAA |
| 2516 | CAACCTGGAAAAAATATCTCAAG |
| 2517 | AACCTGGAAAAAATATCTCAAGA |
| 2518 | ACCTGGAAAAAATATCTCAAGAG |
| 2519 | CCTGGAAAAAATATCTCAAGAGA |
| 2520 | CTGGAAAAAATATCTCAAGAGAC |
| 2521 | TGGAAAAAATATCTCAAGAGACT |
| 2522 | GGAAAAAATATCTCAAGAGACTG |
| 2523 | GAAAAAATATCTCAAGAGACTGA |
| 2524 | AAAAAATATCTCAAGAGACTGAA |
| 2525 | AAAAATATCTCAAGAGACTGAAC |
| 2526 | AAAATATCTCAAGAGACTGAACA |
| 2527 | AAATATCTCAAGAGACTGAACAG |
| 2528 | AATATCTCAAGAGACTGAACAGA |
| 2529 | ATATCTCAAGAGACTGAACAGAG |
| 2530 | TATCTCAAGAGACTGAACAGAGA |
| 2531 | ATCTCAAGAGACTGAACAGAGAT |
| 2532 | TCTCAAGAGACTGAACAGAGATG |
| 2533 | CTCAAGAGACTGAACAGAGATGT |
| 2534 | TCAAGAGACTGAACAGAGATGTG |
| 2535 | CAAGAGACTGAACAGAGATGTGA |
| 2536 | AAGAGACTGAACAGAGATGTGAA |
| 2537 | AGAGACTGAACAGAGATGTGAAT |
| 2538 | GAGACTGAACAGAGATGTGAATC |
| 2539 | AGACTGAACAGAGATGTGAATCT |
| 2540 | GACTGAACAGAGATGTGAATCTC |
| 2541 | ACTGAACAGAGATGTGAATCTCT |
| 2542 | CTGAACAGAGATGTGAATCTCTG |
| 2543 | TGAACAGAGATGTGAATCTCTGA |
| 2544 | GAACAGAGATGTGAATCTCTGAA |
| 2545 | AACAGAGATGTGAATCTCTGAAC |
| 2546 | ACAGAGATGTGAATCTCTGAACA |
| 2547 | CAGAGATGTGAATCTCTGAACAC |
| 2548 | AGAGATGTGAATCTCTGAACACA |
| 2549 | GAGATGTGAATCTCTGAACACAA |

| ID | SEQUENCE |
|---|---|
| 2550 | AGATGTGAATCTCTGAACACAAG |
| 2551 | GATGTGAATCTCTGAACACAAGA |
| 2552 | ATGTGAATCTCTGAACACAAGAA |
| 2553 | TGTGAATCTCTGAACACAAGAAC |
| 2554 | GTGAATCTCTGAACACAAGAACA |
| 2555 | TGAATCTCTGAACACAAGAACAG |
| 2556 | GAATCTCTGAACACAAGAACAGT |
| 2557 | AATCTCTGAACACAAGAACAGTT |
| 2558 | ATCTCTGAACACAAGAACAGTTT |
| 2559 | TCTCTGAACACAAGAACAGTTTA |
| 2560 | CTCTGAACACAAGAACAGTTTAT |
| 2561 | TCTGAACACAAGAACAGTTTATT |
| 2562 | CTGAACACAAGAACAGTTTATTT |
| 2563 | TGAACACAAGAACAGTTTATTTT |
| 2564 | GAACACAAGAACAGTTTATTTTT |
| 2565 | AACACAAGAACAGTTTATTTTTC |
| 2566 | ACACAAGAACAGTTTATTTTTCT |
| 2567 | CACAAGAACAGTTTATTTTTCTG |
| 2568 | ACAAGAACAGTTTATTTTTCTGA |
| 2569 | CAAGAACAGTTTATTTTTCTGAA |
| 2570 | AAGAACAGTTTATTTTTCTGAAC |
| 2571 | AGAACAGTTTATTTTTCTGAACA |
| 2572 | GAACAGTTTATTTTTCTGAACAG |
| 2573 | AACAGTTTATTTTTCTGAACAGT |
| 2574 | ACAGTTTATTTTTCTGAACAGTG |
| 2575 | CAGTTTATTTTTCTGAACAGTGG |
| 2576 | AGTTTATTTTTCTGAACAGTGGG |
| 2577 | GTTTATTTTTCTGAACAGTGGGT |
| 2578 | TTTATTTTTCTGAACAGTGGGTA |
| 2579 | TTATTTTTCTGAACAGTGGGTAT |
| 2580 | TATTTTTCTGAACAGTGGGTATC |
| 2581 | ATTTTTCTGAACAGTGGGTATCT |
| 2582 | TTTTTCTGAACAGTGGGTATCTT |
| 2583 | TTTTCTGAACAGTGGGTATCTTC |
| 2584 | TTTCTGAACAGTGGGTATCTTCC |
| 2585 | TTCTGAACAGTGGGTATCTTCCT |
| 2586 | TCTGAACAGTGGGTATCTTCCTT |
| 2587 | CTGAACAGTGGGTATCTTCCTTA |
| 2588 | TGAACAGTGGGTATCTTCCTTAA |
| 2589 | GAACAGTGGGTATCTTCCTTAAA |
| 2590 | AACAGTGGGTATCTTCCTTAAAT |
| 2591 | ACAGTGGGTATCTTCCTTAAATG |
| 2592 | CAGTGGGTATCTTCCTTAAATGA |
| 2593 | AGTGGGTATCTTCCTTAAATGAA |
| 2594 | GTGGGTATCTTCCTTAAATGAAA |
| 2595 | TGGGTATCTTCCTTAAATGAAAG |
| 2596 | GGGTATCTTCCTTAAATGAAAGG |
| 2597 | GGTATCTTCCTTAAATGAAAGGG |
| 2598 | GTATCTTCCTTAAATGAAAGGGA |
| 2599 | TATCTTCCTTAAATGAAAGGGAA |
| 2600 | ATCTTCCTTAAATGAAAGGGAAC |
| 2601 | TCTTCCTTAAATGAAAGGGAACA |
| 2602 | CTTCCTTAAATGAAAGGGAACAG |
| 2603 | TTCCTTAAATGAAAGGGAACAGG |
| 2604 | TCCTTAAATGAAAGGGAACAGGA |
| 2605 | CCTTAAATGAAAGGGAACAGGAA |
| 2606 | CTTAAATGAAAGGGAACAGGAAC |
| 2607 | TTAAATGAAAGGGAACAGGAACT |

| ID | SEQUENCE |
|---|---|
| 2608 | TAAATGAAAGGGAACAGGAACTT |
| 2609 | AAATGAAAGGGAACAGGAACTTC |
| 2610 | AATGAAAGGGAACAGGAACTTCA |
| 2611 | ATGAAAGGGAACAGGAACTTCAC |
| 2612 | TGAAAGGGAACAGGAACTTCACA |
| 2613 | GAAAGGGAACAGGAACTTCACAA |
| 2614 | AAAGGGAACAGGAACTTCACAAC |
| 2615 | AAGGGAACAGGAACTTCACAACT |
| 2616 | AGGGAACAGGAACTTCACAACTT |
| 2617 | GGGAACAGGAACTTCACAACTTA |
| 2618 | GGAACAGGAACTTCACAACTTAT |
| 2619 | GAACAGGAACTTCACAACTTATT |
| 2620 | AACAGGAACTTCACAACTTATTG |
| 2621 | ACAGGAACTTCACAACTTATTGG |
| 2622 | CAGGAACTTCACAACTTATTGGA |
| 2623 | AGGAACTTCACAACTTATTGGAG |
| 2624 | GGAACTTCACAACTTATTGGAGG |
| 2625 | GAACTTCACAACTTATTGGAGGT |
| 2626 | AACTTCACAACTTATTGGAGGTT |
| 2627 | ACTTCACAACTTATTGGAGGTTG |
| 2628 | CTTCACAACTTATTGGAGGTTGT |
| 2629 | TTCACAACTTATTGGAGGTTGTA |
| 2630 | TCACAACTTATTGGAGGTTGTAA |
| 2631 | CACAACTTATTGGAGGTTGTAAG |
| 2632 | ACAACTTATTGGAGGTTGTAAGC |
| 2633 | CAACTTATTGGAGGTTGTAAGCC |
| 2634 | AACTTATTGGAGGTTGTAAGCCA |
| 2635 | ACTTATTGGAGGTTGTAAGCCAA |
| 2636 | CTTATTGGAGGTTGTAAGCCAAT |
| 2637 | TTATTGGAGGTTGTAAGCCAATG |
| 2638 | TATTGGAGGTTGTAAGCCAATGT |
| 2639 | ATTGGAGGTTGTAAGCCAATGTT |
| 2640 | TTGGAGGTTGTAAGCCAATGTTG |
| 2641 | TGGAGGTTGTAAGCCAATGTTGT |
| 2642 | GGAGGTTGTAAGCCAATGTTGTG |
| 2643 | GAGGTTGTAAGCCAATGTTGTGA |
| 2644 | AGGTTGTAAGCCAATGTTGTGAG |
| 2645 | GGTTGTAAGCCAATGTTGTGAGG |
| 2646 | GTTGTAAGCCAATGTTGTGAGGC |
| 2647 | TTGTAAGCCAATGTTGTGAGGCT |
| 2648 | TGTAAGCCAATGTTGTGAGGCTT |
| 2649 | GTAAGCCAATGTTGTGAGGCTTC |
| 2650 | TAAGCCAATGTTGTGAGGCTTCA |
| 2651 | AAGCCAATGTTGTGAGGCTTCAA |
| 2652 | AGCCAATGTTGTGAGGCTTCAAG |
| 2653 | GCCAATGTTGTGAGGCTTCAAGT |
| 2654 | CCAATGTTGTGAGGCTTCAAGTT |
| 2655 | CAATGTTGTGAGGCTTCAAGTTC |
| 2656 | AATGTTGTGAGGCTTCAAGTTCA |
| 2657 | ATGTTGTGAGGCTTCAAGTTCAG |
| 2658 | TGTTGTGAGGCTTCAAGTTCAGA |
| 2659 | GTTGTGAGGCTTCAAGTTCAGAC |
| 2660 | TTGTGAGGCTTCAAGTTCAGACA |
| 2661 | TGTGAGGCTTCAAGTTCAGACAT |
| 2662 | GTGAGGCTTCAAGTTCAGACATC |
| 2663 | TGAGGCTTCAAGTTCAGACATCA |
| 2664 | GAGGCTTCAAGTTCAGACATCAC |
| 2665 | AGGCTTCAAGTTCAGACATCACT |

| ID | SEQUENCE |
|---|---|
| 2666 | GGCTTCAAGTTCAGACATCACTG |
| 2667 | GCTTCAAGTTCAGACATCACTGA |
| 2668 | CTTCAAGTTCAGACATCACTGAG |
| 2669 | TTCAAGTTCAGACATCACTGAGA |
| 2670 | TCAAGTTCAGACATCACTGAGAA |
| 2671 | CAAGTTCAGACATCACTGAGAAA |
| 2672 | AAGTTCAGACATCACTGAGAAAT |
| 2673 | AGTTCAGACATCACTGAGAAATC |
| 2674 | GTTCAGACATCACTGAGAAATCA |
| 2675 | TTCAGACATCACTGAGAAATCAG |
| 2676 | TCAGACATCACTGAGAAATCAGA |
| 2677 | CAGACATCACTGAGAAATCAGAT |
| 2678 | AGACATCACTGAGAAATCAGATG |
| 2679 | GACATCACTGAGAAATCAGATGG |
| 2680 | ACATCACTGAGAAATCAGATGGA |
| 2681 | CATCACTGAGAAATCAGATGGAC |
| 2682 | ATCACTGAGAAATCAGATGGACG |
| 2683 | TCACTGAGAAATCAGATGGACGT |
| 2684 | CACTGAGAAATCAGATGGACGTA |
| 2685 | ACTGAGAAATCAGATGGACGTAA |
| 2686 | CTGAGAAATCAGATGGACGTAAG |
| 2687 | TGAGAAATCAGATGGACGTAAGG |
| 2688 | GAGAAATCAGATGGACGTAAGGC |
| 2689 | AGAAATCAGATGGACGTAAGGCA |
| 2690 | GAAATCAGATGGACGTAAGGCAG |
| 2691 | AAATCAGATGGACGTAAGGCAGC |
| 2692 | AATCAGATGGACGTAAGGCAGCT |
| 2693 | ATCAGATGGACGTAAGGCAGCTC |
| 2694 | TCAGATGGACGTAAGGCAGCTCA |
| 2695 | CAGATGGACGTAAGGCAGCTCAT |
| 2696 | AGATGGACGTAAGGCAGCTCATG |
| 2697 | GATGGACGTAAGGCAGCTCATGA |
| 2698 | ATGGACGTAAGGCAGCTCATGAG |
| 2699 | TGGACGTAAGGCAGCTCATGAGA |
| 2700 | GGACGTAAGGCAGCTCATGAGAA |
| 2701 | GACGTAAGGCAGCTCATGAGAAA |
| 2702 | ACGTAAGGCAGCTCATGAGAAAC |
| 2703 | CGTAAGGCAGCTCATGAGAAACA |
| 2704 | GTAAGGCAGCTCATGAGAAACAG |
| 2705 | TAAGGCAGCTCATGAGAAACAGC |
| 2706 | AAGGCAGCTCATGAGAAACAGCA |
| 2707 | AGGCAGCTCATGAGAAACAGCAT |
| 2708 | GGCAGCTCATGAGAAACAGCATA |
| 2709 | GCAGCTCATGAGAAACAGCATAA |
| 2710 | CAGCTCATGAGAAACAGCATAAC |
| 2711 | AGCTCATGAGAAACAGCATAACA |
| 2712 | GCTCATGAGAAACAGCATAACAT |
| 2713 | CTCATGAGAAACAGCATAACATT |
| 2714 | TCATGAGAAACAGCATAACATTT |
| 2715 | CATGAGAAACAGCATAACATTTT |
| 2716 | ATGAGAAACAGCATAACATTTTT |
| 2717 | TGAGAAACAGCATAACATTTTTC |
| 2718 | GAGAAACAGCATAACATTTTTCT |
| 2719 | AGAAACAGCATAACATTTTTCTT |
| 2720 | GAAACAGCATAACATTTTTCTTG |
| 2721 | AAACAGCATAACATTTTTCTTGA |
| 2722 | AACAGCATAACATTTTTCTTGAT |
| 2723 | ACAGCATAACATTTTTCTTGATC |

| ID | SEQUENCE |
|---|---|
| 2724 | CAGCATAACATTTTTCTTGATCA |
| 2725 | AGCATAACATTTTTCTTGATCAG |
| 2726 | GCATAACATTTTTCTTGATCAGA |
| 2727 | CATAACATTTTTCTTGATCAGAT |
| 2728 | ATAACATTTTTCTTGATCAGATG |
| 2729 | TAACATTTTTCTTGATCAGATGA |
| 2730 | AACATTTTTCTTGATCAGATGAC |
| 2731 | ACATTTTTCTTGATCAGATGACT |
| 2732 | CATTTTTCTTGATCAGATGACTA |
| 2733 | ATTTTTCTTGATCAGATGACTAT |
| 2734 | TTTTTCTTGATCAGATGACTATT |
| 2735 | TTTTCTTGATCAGATGACTATTG |
| 2736 | TTTCTTGATCAGATGACTATTGA |
| 2737 | TTCTTGATCAGATGACTATTGAT |
| 2738 | TCTTGATCAGATGACTATTGATG |
| 2739 | CTTGATCAGATGACTATTGATGA |
| 2740 | TTGATCAGATGACTATTGATGAA |
| 2741 | TGATCAGATGACTATTGATGAAG |
| 2742 | GATCAGATGACTATTGATGAAGA |
| 2743 | ATCAGATGACTATTGATGAAGAT |
| 2744 | TCAGATGACTATTGATGAAGATA |
| 2745 | CAGATGACTATTGATGAAGATAA |
| 2746 | AGATGACTATTGATGAAGATAAA |
| 2747 | GATGACTATTGATGAAGATAAAT |
| 2748 | ATGACTATTGATGAAGATAAATT |
| 2749 | TGACTATTGATGAAGATAAATTG |
| 2750 | GACTATTGATGAAGATAAATTGA |
| 2751 | ACTATTGATGAAGATAAATTGAT |
| 2752 | CTATTGATGAAGATAAATTGATA |
| 2753 | TATTGATGAAGATAAATTGATAG |
| 2754 | ATTGATGAAGATAAATTGATAGC |
| 2755 | TTGATGAAGATAAATTGATAGCA |
| 2756 | TGATGAAGATAAATTGATAGCAC |
| 2757 | GATGAAGATAAATTGATAGCACA |
| 2758 | ATGAAGATAAATTGATAGCACAA |
| 2759 | TGAAGATAAATTGATAGCACAAA |
| 2760 | GAAGATAAATTGATAGCACAAAA |
| 2761 | AAGATAAATTGATAGCACAAAAT |
| 2762 | AGATAAATTGATAGCACAAAATC |
| 2763 | GATAAATTGATAGCACAAAATCT |
| 2764 | ATAAATTGATAGCACAAAATCTA |
| 2765 | TAAATTGATAGCACAAAATCTAG |
| 2766 | AAATTGATAGCACAAAATCTAGA |
| 2767 | AATTGATAGCACAAAATCTAGAA |
| 2768 | ATTGATAGCACAAAATCTAGAAC |
| 2769 | TTGATAGCACAAAATCTAGAACT |
| 2770 | TGATAGCACAAAATCTAGAACTT |
| 2771 | GATAGCACAAAATCTAGAACTTA |
| 2772 | ATAGCACAAAATCTAGAACTTAA |
| 2773 | TAGCACAAAATCTAGAACTTAAT |
| 2774 | AGCACAAAATCTAGAACTTAATG |
| 2775 | GCACAAAATCTAGAACTTAATGA |
| 2776 | CACAAAATCTAGAACTTAATGAA |
| 2777 | ACAAAATCTAGAACTTAATGAAA |
| 2778 | CAAAATCTAGAACTTAATGAAAC |
| 2779 | AAAATCTAGAACTTAATGAAACC |
| 2780 | AAATCTAGAACTTAATGAAACCA |
| 2781 | AATCTAGAACTTAATGAAACCAT |

| ID | SEQUENCE |
|---|---|
| 2782 | ATCTAGAACTTAATGAAACCATA |
| 2783 | TCTAGAACTTAATGAAACCATAA |
| 2784 | CTAGAACTTAATGAAACCATAAA |
| 2785 | TAGAACTTAATGAAACCATAAAA |
| 2786 | AGAACTTAATGAAACCATAAAAA |
| 2787 | GAACTTAATGAAACCATAAAAAT |
| 2788 | AACTTAATGAAACCATAAAAATT |
| 2789 | ACTTAATGAAACCATAAAAATTG |
| 2790 | CTTAATGAAACCATAAAAATTGG |
| 2791 | TTAATGAAACCATAAAAATTGGT |
| 2792 | TAATGAAACCATAAAAATTGGTT |
| 2793 | AATGAAACCATAAAAATTGGTTT |
| 2794 | ATGAAACCATAAAAATTGGTTTG |
| 2795 | TGAAACCATAAAAATTGGTTTGA |
| 2796 | GAAACCATAAAAATTGGTTTGAC |
| 2797 | AAACCATAAAAATTGGTTTGACT |
| 2798 | AACCATAAAAATTGGTTTGACTA |
| 2799 | ACCATAAAAATTGGTTTGACTAA |
| 2800 | CCATAAAAATTGGTTTGACTAAG |
| 2801 | CATAAAAATTGGTTTGACTAAGC |
| 2802 | ATAAAAATTGGTTTGACTAAGCT |
| 2803 | TAAAAATTGGTTTGACTAAGCTT |
| 2804 | AAAAATTGGTTTGACTAAGCTTA |
| 2805 | AAAATTGGTTTGACTAAGCTTAA |
| 2806 | AAATTGGTTTGACTAAGCTTAAT |
| 2807 | AATTGGTTTGACTAAGCTTAATT |
| 2808 | ATTGGTTTGACTAAGCTTAATTG |
| 2809 | TTGGTTTGACTAAGCTTAATTGC |
| 2810 | TGGTTTGACTAAGCTTAATTGCT |
| 2811 | GGTTTGACTAAGCTTAATTGCTT |
| 2812 | GTTTGACTAAGCTTAATTGCTTT |
| 2813 | TTTGACTAAGCTTAATTGCTTTC |
| 2814 | TTGACTAAGCTTAATTGCTTTCT |
| 2815 | TGACTAAGCTTAATTGCTTTCTG |
| 2816 | GACTAAGCTTAATTGCTTTCTGG |
| 2817 | ACTAAGCTTAATTGCTTTCTGGA |
| 2818 | CTAAGCTTAATTGCTTTCTGGAA |
| 2819 | TAAGCTTAATTGCTTTCTGGAAC |
| 2820 | AAGCTTAATTGCTTTCTGGAACA |
| 2821 | AGCTTAATTGCTTTCTGGAACAG |
| 2822 | GCTTAATTGCTTTCTGGAACAGG |
| 2823 | CTTAATTGCTTTCTGGAACAGGA |
| 2824 | TTAATTGCTTTCTGGAACAGGAT |
| 2825 | TAATTGCTTTCTGGAACAGGATC |
| 2826 | AATTGCTTTCTGGAACAGGATCT |
| 2827 | ATTGCTTTCTGGAACAGGATCTG |
| 2828 | TTGCTTTCTGGAACAGGATCTGA |
| 2829 | TGCTTTCTGGAACAGGATCTGAA |
| 2830 | GCTTTCTGGAACAGGATCTGAAA |
| 2831 | CTTTCTGGAACAGGATCTGAAAC |
| 2832 | TTTCTGGAACAGGATCTGAAACT |
| 2833 | TTCTGGAACAGGATCTGAAACTG |
| 2834 | TCTGGAACAGGATCTGAAACTGG |
| 2835 | CTGGAACAGGATCTGAAACTGGA |
| 2836 | TGGAACAGGATCTGAAACTGGAT |
| 2837 | GGAACAGGATCTGAAACTGGATA |
| 2838 | GAACAGGATCTGAAACTGGATAT |
| 2839 | AACAGGATCTGAAACTGGATATC |

| ID | SEQUENCE |
|---|---|
| 2840 | ACAGGATCTGAAACTGGATATCC |
| 2841 | CAGGATCTGAAACTGGATATCCC |
| 2842 | AGGATCTGAAACTGGATATCCCA |
| 2843 | GGATCTGAAACTGGATATCCCAA |
| 2844 | GATCTGAAACTGGATATCCCAAC |
| 2845 | ATCTGAAACTGGATATCCCAACA |
| 2846 | TCTGAAACTGGATATCCCAACAG |
| 2847 | CTGAAACTGGATATCCCAACAGG |
| 2848 | TGAAACTGGATATCCCAACAGGT |
| 2849 | GAAACTGGATATCCCAACAGGTA |
| 2850 | AAACTGGATATCCCAACAGGTAC |
| 2851 | AACTGGATATCCCAACAGGTACG |
| 2852 | ACTGGATATCCCAACAGGTACGA |
| 2853 | CTGGATATCCCAACAGGTACGAC |
| 2854 | TGGATATCCCAACAGGTACGACA |
| 2855 | GGATATCCCAACAGGTACGACAC |
| 2856 | GATATCCCAACAGGTACGACACC |
| 2857 | ATATCCCAACAGGTACGACACCA |
| 2858 | TATCCCAACAGGTACGACACCAC |
| 2859 | ATCCCAACAGGTACGACACCACA |
| 2860 | TCCCAACAGGTACGACACCACAG |
| 2861 | CCCAACAGGTACGACACCACAGA |
| 2862 | CCAACAGGTACGACACCACAGAG |
| 2863 | CAACAGGTACGACACCACAGAGG |
| 2864 | AACAGGTACGACACCACAGAGGA |
| 2865 | ACAGGTACGACACCACAGAGGAA |
| 2866 | CAGGTACGACACCACAGAGGAAA |
| 2867 | AGGTACGACACCACAGAGGAAAA |
| 2868 | GGTACGACACCACAGAGGAAAAG |
| 2869 | GTACGACACCACAGAGGAAAAGT |
| 2870 | TACGACACCACAGAGGAAAAGTT |
| 2871 | ACGACACCACAGAGGAAAAGTTA |
| 2872 | CGACACCACAGAGGAAAAGTTAT |
| 2873 | GACACCACAGAGGAAAAGTTATT |
| 2874 | ACACCACAGAGGAAAAGTTATTT |
| 2875 | CACCACAGAGGAAAAGTTATTTA |
| 2876 | ACCACAGAGGAAAAGTTATTTAT |
| 2877 | CCACAGAGGAAAAGTTATTTATA |
| 2878 | CACAGAGGAAAAGTTATTTATAC |
| 2879 | ACAGAGGAAAAGTTATTTATACC |
| 2880 | CAGAGGAAAAGTTATTTATACCC |
| 2881 | AGAGGAAAAGTTATTTATACCCA |
| 2882 | GAGGAAAAGTTATTTATACCCAT |
| 2883 | AGGAAAAGTTATTTATACCCATC |
| 2884 | GGAAAAGTTATTTATACCCATCA |
| 2885 | GAAAAGTTATTTATACCCATCAA |
| 2886 | AAAAGTTATTTATACCCATCAAC |
| 2887 | AAAGTTATTTATACCCATCAACA |
| 2888 | AAGTTATTTATACCCATCAACAC |
| 2889 | AGTTATTTATACCCATCAACACT |
| 2890 | GTTATTTATACCCATCAACACTG |
| 2891 | TTATTTATACCCATCAACACTGG |
| 2892 | TATTTATACCCATCAACACTGGT |
| 2893 | ATTTATACCCATCAACACTGGTA |
| 2894 | TTTATACCCATCAACACTGGTAA |
| 2895 | TTATACCCATCAACACTGGTAAG |
| 2896 | TATACCCATCAACACTGGTAAGA |
| 2897 | ATACCCATCAACACTGGTAAGAA |

| ID | SEQUENCE |
|---|---|
| 2898 | TACCCATCAACACTGGTAAGAAC |
| 2899 | ACCCATCAACACTGGTAAGAACT |
| 2900 | CCCATCAACACTGGTAAGAACTG |
| 2901 | CCATCAACACTGGTAAGAACTGA |
| 2902 | CATCAACACTGGTAAGAACTGAA |
| 2903 | ATCAACACTGGTAAGAACTGAAC |
| 2904 | TCAACACTGGTAAGAACTGAACC |
| 2905 | CAACACTGGTAAGAACTGAACCA |
| 2906 | AACACTGGTAAGAACTGAACCAC |
| 2907 | ACACTGGTAAGAACTGAACCACG |
| 2908 | CACTGGTAAGAACTGAACCACGT |
| 2909 | ACTGGTAAGAACTGAACCACGTG |
| 2910 | CTGGTAAGAACTGAACCACGTGA |
| 2911 | TGGTAAGAACTGAACCACGTGAA |
| 2912 | GGTAAGAACTGAACCACGTGAAC |
| 2913 | GTAAGAACTGAACCACGTGAACA |
| 2914 | TAAGAACTGAACCACGTGAACAT |
| 2915 | AAGAACTGAACCACGTGAACATC |
| 2916 | AGAACTGAACCACGTGAACATCT |
| 2917 | GAACTGAACCACGTGAACATCTC |
| 2918 | AACTGAACCACGTGAACATCTCC |
| 2919 | ACTGAACCACGTGAACATCTCCT |
| 2920 | CTGAACCACGTGAACATCTCCTT |
| 2921 | TGAACCACGTGAACATCTCCTTG |
| 2922 | GAACCACGTGAACATCTCCTTGA |
| 2923 | AACCACGTGAACATCTCCTTGAT |
| 2924 | ACCACGTGAACATCTCCTTGATC |
| 2925 | CCACGTGAACATCTCCTTGATCA |
| 2926 | CACGTGAACATCTCCTTGATCAG |
| 2927 | ACGTGAACATCTCCTTGATCAGC |
| 2928 | CGTGAACATCTCCTTGATCAGCT |
| 2929 | GTGAACATCTCCTTGATCAGCTG |
| 2930 | TGAACATCTCCTTGATCAGCTGA |
| 2931 | GAACATCTCCTTGATCAGCTGAA |
| 2932 | AACATCTCCTTGATCAGCTGAAA |
| 2933 | ACATCTCCTTGATCAGCTGAAAA |
| 2934 | CATCTCCTTGATCAGCTGAAAAG |
| 2935 | ATCTCCTTGATCAGCTGAAAAGG |
| 2936 | TCTCCTTGATCAGCTGAAAAGGA |
| 2937 | CTCCTTGATCAGCTGAAAAGGAA |
| 2938 | TCCTTGATCAGCTGAAAAGGAAA |
| 2939 | CCTTGATCAGCTGAAAAGGAAAC |
| 2940 | CTTGATCAGCTGAAAAGGAAACA |
| 2941 | TTGATCAGCTGAAAAGGAAACAG |
| 2942 | TGATCAGCTGAAAAGGAAACAGC |
| 2943 | GATCAGCTGAAAAGGAAACAGCC |
| 2944 | ATCAGCTGAAAAGGAAACAGCCT |
| 2945 | TCAGCTGAAAAGGAAACAGCCTG |
| 2946 | CAGCTGAAAAGGAAACAGCCTGA |
| 2947 | AGCTGAAAAGGAAACAGCCTGAG |
| 2948 | GCTGAAAAGGAAACAGCCTGAGC |
| 2949 | CTGAAAAGGAAACAGCCTGAGCT |
| 2950 | TGAAAAGGAAACAGCCTGAGCTG |
| 2951 | GAAAAGGAAACAGCCTGAGCTGT |
| 2952 | AAAAGGAAACAGCCTGAGCTGTT |
| 2953 | AAAGGAAACAGCCTGAGCTGTTA |
| 2954 | AAGGAAACAGCCTGAGCTGTTAA |
| 2955 | AGGAAACAGCCTGAGCTGTTAAT |

| ID | SEQUENCE |
|---|---|
| 2956 | GGAAACAGCCTGAGCTGTTAATG |
| 2957 | GAAACAGCCTGAGCTGTTAATGA |
| 2958 | AAACAGCCTGAGCTGTTAATGAT |
| 2959 | AACAGCCTGAGCTGTTAATGATG |
| 2960 | ACAGCCTGAGCTGTTAATGATGC |
| 2961 | CAGCCTGAGCTGTTAATGATGCT |
| 2962 | AGCCTGAGCTGTTAATGATGCTA |
| 2963 | GCCTGAGCTGTTAATGATGCTAA |
| 2964 | CCTGAGCTGTTAATGATGCTAAA |
| 2965 | CTGAGCTGTTAATGATGCTAAAC |
| 2966 | TGAGCTGTTAATGATGCTAAACT |
| 2967 | GAGCTGTTAATGATGCTAAACTG |
| 2968 | AGCTGTTAATGATGCTAAACTGT |
| 2969 | GCTGTTAATGATGCTAAACTGTT |
| 2970 | CTGTTAATGATGCTAAACTGTTC |
| 2971 | TGTTAATGATGCTAAACTGTTCA |
| 2972 | GTTAATGATGCTAAACTGTTCAG |
| 2973 | TTAATGATGCTAAACTGTTCAGA |
| 2974 | TAATGATGCTAAACTGTTCAGAA |
| 2975 | AATGATGCTAAACTGTTCAGAAA |
| 2976 | ATGATGCTAAACTGTTCAGAAAA |
| 2977 | TGATGCTAAACTGTTCAGAAAAC |
| 2978 | GATGCTAAACTGTTCAGAAAACA |
| 2979 | ATGCTAAACTGTTCAGAAAACAA |
| 2980 | TGCTAAACTGTTCAGAAAACAAC |
| 2981 | GCTAAACTGTTCAGAAAACAACA |
| 2982 | CTAAACTGTTCAGAAAACAACAA |
| 2983 | TAAACTGTTCAGAAAACAACAAA |
| 2984 | AAACTGTTCAGAAAACAACAAAG |
| 2985 | AACTGTTCAGAAAACAACAAAGA |
| 2986 | ACTGTTCAGAAAACAACAAAGAA |
| 2987 | CTGTTCAGAAAACAACAAAGAAG |
| 2988 | TGTTCAGAAAACAACAAAGAAGA |
| 2989 | GTTCAGAAAACAACAAAGAAGAG |
| 2990 | TTCAGAAAACAACAAAGAAGAGA |
| 2991 | TCAGAAAACAACAAAGAAGAGAC |
| 2992 | CAGAAAACAACAAAGAAGAGACA |
| 2993 | AGAAAACAACAAAGAAGAGACAA |
| 2994 | GAAAACAACAAAGAAGAGACAAT |
| 2995 | AAAACAACAAAGAAGAGACAATT |
| 2996 | AAACAACAAAGAAGAGACAATTC |
| 2997 | AACAACAAAGAAGAGACAATTCC |
| 2998 | ACAACAAAGAAGAGACAATTCCG |
| 2999 | CAACAAAGAAGAGACAATTCCGG |
| 3000 | AACAAAGAAGAGACAATTCCGGA |
| 3001 | ACAAAGAAGAGACAATTCCGGAT |
| 3002 | CAAAGAAGAGACAATTCCGGATG |
| 3003 | AAAGAAGAGACAATTCCGGATGT |
| 3004 | AAGAAGAGACAATTCCGGATGTG |
| 3005 | AGAAGAGACAATTCCGGATGTGG |
| 3006 | GAAGAGACAATTCCGGATGTGGA |
| 3007 | AAGAGACAATTCCGGATGTGGAT |
| 3008 | AGAGACAATTCCGGATGTGGATG |
| 3009 | GAGACAATTCCGGATGTGGATGT |
| 3010 | AGACAATTCCGGATGTGGATGTA |
| 3011 | GACAATTCCGGATGTGGATGTAG |
| 3012 | ACAATTCCGGATGTGGATGTAGA |
| 3013 | CAATTCCGGATGTGGATGTAGAA |

| ID | SEQUENCE |
|---|---|
| 3014 | AATTCCGGATGTGGATGTAGAAG |
| 3015 | ATTCCGGATGTGGATGTAGAAGA |
| 3016 | TTCCGGATGTGGATGTAGAAGAG |
| 3017 | TCCGGATGTGGATGTAGAAGAGG |
| 3018 | CCGGATGTGGATGTAGAAGAGGC |
| 3019 | CGGATGTGGATGTAGAAGAGGCA |
| 3020 | GGATGTGGATGTAGAAGAGGCAG |
| 3021 | GATGTGGATGTAGAAGAGGCAGT |
| 3022 | ATGTGGATGTAGAAGAGGCAGTT |
| 3023 | TGTGGATGTAGAAGAGGCAGTTC |
| 3024 | GTGGATGTAGAAGAGGCAGTTCT |
| 3025 | TGGATGTAGAAGAGGCAGTTCTG |
| 3026 | GGATGTAGAAGAGGCAGTTCTGG |
| 3027 | GATGTAGAAGAGGCAGTTCTGGG |
| 3028 | ATGTAGAAGAGGCAGTTCTGGGG |
| 3029 | TGTAGAAGAGGCAGTTCTGGGGC |
| 3030 | GTAGAAGAGGCAGTTCTGGGGCA |
| 3031 | TAGAAGAGGCAGTTCTGGGGCAG |
| 3032 | AGAAGAGGCAGTTCTGGGGCAGT |
| 3033 | GAAGAGGCAGTTCTGGGGCAGTA |
| 3034 | AAGAGGCAGTTCTGGGGCAGTAT |
| 3035 | AGAGGCAGTTCTGGGGCAGTATA |
| 3036 | GAGGCAGTTCTGGGGCAGTATAC |
| 3037 | AGGCAGTTCTGGGGCAGTATACT |
| 3038 | GGCAGTTCTGGGGCAGTATACTG |
| 3039 | GCAGTTCTGGGGCAGTATACTGA |
| 3040 | CAGTTCTGGGGCAGTATACTGAA |
| 3041 | AGTTCTGGGGCAGTATACTGAAG |
| 3042 | GTTCTGGGGCAGTATACTGAAGA |
| 3043 | TTCTGGGGCAGTATACTGAAGAA |
| 3044 | TCTGGGGCAGTATACTGAAGAAC |
| 3045 | CTGGGGCAGTATACTGAAGAACC |
| 3046 | TGGGGCAGTATACTGAAGAACCT |
| 3047 | GGGGCAGTATACTGAAGAACCTC |
| 3048 | GGGCAGTATACTGAAGAACCTCT |
| 3049 | GGCAGTATACTGAAGAACCTCTA |
| 3050 | GCAGTATACTGAAGAACCTCTAA |
| 3051 | CAGTATACTGAAGAACCTCTAAG |
| 3052 | AGTATACTGAAGAACCTCTAAGT |
| 3053 | GTATACTGAAGAACCTCTAAGTC |
| 3054 | TATACTGAAGAACCTCTAAGTCA |
| 3055 | ATACTGAAGAACCTCTAAGTCAA |
| 3056 | TACTGAAGAACCTCTAAGTCAAG |
| 3057 | ACTGAAGAACCTCTAAGTCAAGA |
| 3058 | CTGAAGAACCTCTAAGTCAAGAG |
| 3059 | TGAAGAACCTCTAAGTCAAGAGC |
| 3060 | GAAGAACCTCTAAGTCAAGAGCC |
| 3061 | AAGAACCTCTAAGTCAAGAGCCA |
| 3062 | AGAACCTCTAAGTCAAGAGCCAT |
| 3063 | GAACCTCTAAGTCAAGAGCCATC |
| 3064 | AACCTCTAAGTCAAGAGCCATCT |
| 3065 | ACCTCTAAGTCAAGAGCCATCTG |
| 3066 | CCTCTAAGTCAAGAGCCATCTGT |
| 3067 | CTCTAAGTCAAGAGCCATCTGTA |
| 3068 | TCTAAGTCAAGAGCCATCTGTAG |
| 3069 | CTAAGTCAAGAGCCATCTGTAGA |
| 3070 | TAAGTCAAGAGCCATCTGTAGAT |
| 3071 | AAGTCAAGAGCCATCTGTAGATG |

| ID | SEQUENCE |
|---|---|
| 3072 | AGTCAAGAGCCATCTGTAGATGC |
| 3073 | GTCAAGAGCCATCTGTAGATGCT |
| 3074 | TCAAGAGCCATCTGTAGATGCTG |
| 3075 | CAAGAGCCATCTGTAGATGCTGG |
| 3076 | AAGAGCCATCTGTAGATGCTGGT |
| 3077 | AGAGCCATCTGTAGATGCTGGTG |
| 3078 | GAGCCATCTGTAGATGCTGGTGT |
| 3079 | AGCCATCTGTAGATGCTGGTGTG |
| 3080 | GCCATCTGTAGATGCTGGTGTGG |
| 3081 | CCATCTGTAGATGCTGGTGTGGA |
| 3082 | CATCTGTAGATGCTGGTGTGGAT |
| 3083 | ATCTGTAGATGCTGGTGTGGATT |
| 3084 | TCTGTAGATGCTGGTGTGGATTG |
| 3085 | CTGTAGATGCTGGTGTGGATTGT |
| 3086 | TGTAGATGCTGGTGTGGATTGTT |
| 3087 | GTAGATGCTGGTGTGGATTGTTC |
| 3088 | TAGATGCTGGTGTGGATTGTTCA |
| 3089 | AGATGCTGGTGTGGATTGTTCAT |
| 3090 | GATGCTGGTGTGGATTGTTCATC |
| 3091 | ATGCTGGTGTGGATTGTTCATCA |
| 3092 | TGCTGGTGTGGATTGTTCATCAA |
| 3093 | GCTGGTGTGGATTGTTCATCAAT |
| 3094 | CTGGTGTGGATTGTTCATCAATT |
| 3095 | TGGTGTGGATTGTTCATCAATTG |
| 3096 | GGTGTGGATTGTTCATCAATTGG |
| 3097 | GTGTGGATTGTTCATCAATTGGC |
| 3098 | TGTGGATTGTTCATCAATTGGCG |
| 3099 | GTGGATTGTTCATCAATTGGCGG |
| 3100 | TGGATTGTTCATCAATTGGCGGG |
| 3101 | GGATTGTTCATCAATTGGCGGGG |
| 3102 | GATTGTTCATCAATTGGCGGGGT |
| 3103 | ATTGTTCATCAATTGGCGGGGTT |
| 3104 | TTGTTCATCAATTGGCGGGGTTC |
| 3105 | TGTTCATCAATTGGCGGGGTTCC |
| 3106 | GTTCATCAATTGGCGGGGTTCCA |
| 3107 | TTCATCAATTGGCGGGGTTCCAT |
| 3108 | TCATCAATTGGCGGGGTTCCATT |
| 3109 | CATCAATTGGCGGGGTTCCATTT |
| 3110 | ATCAATTGGCGGGGTTCCATTTT |
| 3111 | TCAATTGGCGGGGTTCCATTTTT |
| 3112 | CAATTGGCGGGGTTCCATTTTTC |
| 3113 | AATTGGCGGGGTTCCATTTTTCC |
| 3114 | ATTGGCGGGGTTCCATTTTTCCA |
| 3115 | TTGGCGGGGTTCCATTTTTCCAG |
| 3116 | TGGCGGGGTTCCATTTTTCCAGC |
| 3117 | GGCGGGGTTCCATTTTTCCAGCA |
| 3118 | GCGGGGTTCCATTTTTCCAGCAT |
| 3119 | CGGGGTTCCATTTTTCCAGCATA |
| 3120 | GGGGTTCCATTTTTCCAGCATAA |
| 3121 | GGGTTCCATTTTTCCAGCATAAA |
| 3122 | GGTTCCATTTTTCCAGCATAAAA |
| 3123 | GTTCCATTTTTCCAGCATAAAAA |
| 3124 | TTCCATTTTTCCAGCATAAAAAA |
| 3125 | TCCATTTTTCCAGCATAAAAAAT |
| 3126 | CCATTTTTCCAGCATAAAAAATC |
| 3127 | CATTTTTCCAGCATAAAAAATCA |
| 3128 | ATTTTTCCAGCATAAAAAATCAC |
| 3129 | TTTTTCCAGCATAAAAAATCACA |

| ID | SEQUENCE |
|---|---|
| 3130 | TTTTCCAGCATAAAAAATCACAT |
| 3131 | TTTCCAGCATAAAAAATCACATG |
| 3132 | TTCCAGCATAAAAAATCACATGG |
| 3133 | TCCAGCATAAAAAATCACATGGA |
| 3134 | CCAGCATAAAAAATCACATGGAA |
| 3135 | CAGCATAAAAAATCACATGGAAA |
| 3136 | AGCATAAAAAATCACATGGAAAA |
| 3137 | GCATAAAAAATCACATGGAAAAG |
| 3138 | CATAAAAAATCACATGGAAAAGA |
| 3139 | ATAAAAAATCACATGGAAAAGAC |
| 3140 | TAAAAAATCACATGGAAAAGACA |
| 3141 | AAAAAATCACATGGAAAAGACAA |
| 3142 | AAAAATCACATGGAAAAGACAAA |
| 3143 | AAAATCACATGGAAAAGACAAAG |
| 3144 | AAATCACATGGAAAAGACAAAGA |
| 3145 | AATCACATGGAAAAGACAAAGAA |
| 3146 | ATCACATGGAAAAGACAAAGAAA |
| 3147 | TCACATGGAAAAGACAAAGAAAA |
| 3148 | CACATGGAAAAGACAAAGAAAAC |
| 3149 | ACATGGAAAAGACAAAGAAAACA |
| 3150 | CATGGAAAAGACAAAGAAAACAG |
| 3151 | ATGGAAAAGACAAAGAAAACAGA |
| 3152 | TGGAAAAGACAAAGAAAACAGAG |
| 3153 | GGAAAAGACAAAGAAAACAGAGG |
| 3154 | GAAAAGACAAAGAAAACAGAGGC |
| 3155 | AAAAGACAAAGAAAACAGAGGCA |
| 3156 | AAAGACAAAGAAAACAGAGGCAT |
| 3157 | AAGACAAAGAAAACAGAGGCATT |
| 3158 | AGACAAAGAAAACAGAGGCATTA |
| 3159 | GACAAAGAAAACAGAGGCATTAA |
| 3160 | ACAAAGAAAACAGAGGCATTAAC |
| 3161 | CAAAGAAAACAGAGGCATTAACA |
| 3162 | AAAGAAAACAGAGGCATTAACAC |
| 3163 | AAGAAAACAGAGGCATTAACACA |
| 3164 | AGAAAACAGAGGCATTAACACAC |
| 3165 | GAAAACAGAGGCATTAACACACT |
| 3166 | AAAACAGAGGCATTAACACACTG |
| 3167 | AAACAGAGGCATTAACACACTGG |
| 3168 | AACAGAGGCATTAACACACTGGA |
| 3169 | ACAGAGGCATTAACACACTGGAG |
| 3170 | CAGAGGCATTAACACACTGGAGA |
| 3171 | AGAGGCATTAACACACTGGAGAG |
| 3172 | GAGGCATTAACACACTGGAGAGG |
| 3173 | AGGCATTAACACACTGGAGAGGT |
| 3174 | GGCATTAACACACTGGAGAGGTC |
| 3175 | GCATTAACACACTGGAGAGGTCT |
| 3176 | CATTAACACACTGGAGAGGTCTA |
| 3177 | ATTAACACACTGGAGAGGTCTAA |
| 3178 | TTAACACACTGGAGAGGTCTAAA |
| 3179 | TAACACACTGGAGAGGTCTAAAG |
| 3180 | AACACACTGGAGAGGTCTAAAGT |
| 3181 | ACACACTGGAGAGGTCTAAAGTG |
| 3182 | CACACTGGAGAGGTCTAAAGTGG |
| 3183 | ACACTGGAGAGGTCTAAAGTGGA |
| 3184 | CACTGGAGAGGTCTAAAGTGGAA |
| 3185 | ACTGGAGAGGTCTAAAGTGGAAG |
| 3186 | CTGGAGAGGTCTAAAGTGGAAGA |
| 3187 | TGGAGAGGTCTAAAGTGGAAGAA |

| ID | SEQUENCE |
|---|---|
| 3188 | GGAGAGGTCTAAAGTGGAAGAAA |
| 3189 | GAGAGGTCTAAAGTGGAAGAAAC |
| 3190 | AGAGGTCTAAAGTGGAAGAAACT |
| 3191 | GAGGTCTAAAGTGGAAGAAACTA |
| 3192 | AGGTCTAAAGTGGAAGAAACTAC |
| 3193 | GGTCTAAAGTGGAAGAAACTACA |
| 3194 | GTCTAAAGTGGAAGAAACTACAG |
| 3195 | TCTAAAGTGGAAGAAACTACAGA |
| 3196 | CTAAAGTGGAAGAAACTACAGAG |
| 3197 | TAAAGTGGAAGAAACTACAGAGC |
| 3198 | AAAGTGGAAGAAACTACAGAGCA |
| 3199 | AAGTGGAAGAAACTACAGAGCAC |
| 3200 | AGTGGAAGAAACTACAGAGCACT |
| 3201 | GTGGAAGAAACTACAGAGCACTT |
| 3202 | TGGAAGAAACTACAGAGCACTTG |
| 3203 | GGAAGAAACTACAGAGCACTTGG |
| 3204 | GAAGAAACTACAGAGCACTTGGT |
| 3205 | AAGAAACTACAGAGCACTTGGTT |
| 3206 | AGAAACTACAGAGCACTTGGTTA |
| 3207 | GAAACTACAGAGCACTTGGTTAC |
| 3208 | AAACTACAGAGCACTTGGTTACA |
| 3209 | AACTACAGAGCACTTGGTTACAA |
| 3210 | ACTACAGAGCACTTGGTTACAAA |
| 3211 | CTACAGAGCACTTGGTTACAAAG |
| 3212 | TACAGAGCACTTGGTTACAAAGA |
| 3213 | ACAGAGCACTTGGTTACAAAGAG |
| 3214 | CAGAGCACTTGGTTACAAAGAGC |
| 3215 | AGAGCACTTGGTTACAAAGAGCA |
| 3216 | GAGCACTTGGTTACAAAGAGCAG |
| 3217 | AGCACTTGGTTACAAAGAGCAGA |
| 3218 | GCACTTGGTTACAAAGAGCAGAT |
| 3219 | CACTTGGTTACAAAGAGCAGATT |
| 3220 | ACTTGGTTACAAAGAGCAGATTA |
| 3221 | CTTGGTTACAAAGAGCAGATTAC |
| 3222 | TTGGTTACAAAGAGCAGATTACC |
| 3223 | TGGTTACAAAGAGCAGATTACCT |
| 3224 | GGTTACAAAGAGCAGATTACCTC |
| 3225 | GTTACAAAGAGCAGATTACCTCT |
| 3226 | TTACAAAGAGCAGATTACCTCTG |
| 3227 | TACAAAGAGCAGATTACCTCTGC |
| 3228 | ACAAAGAGCAGATTACCTCTGCG |
| 3229 | CAAAGAGCAGATTACCTCTGCGA |
| 3230 | AAAGAGCAGATTACCTCTGCGAG |
| 3231 | AAGAGCAGATTACCTCTGCGAGC |
| 3232 | AGAGCAGATTACCTCTGCGAGCC |
| 3233 | GAGCAGATTACCTCTGCGAGCCC |
| 3234 | AGCAGATTACCTCTGCGAGCCCA |
| 3235 | GCAGATTACCTCTGCGAGCCCAG |
| 3236 | CAGATTACCTCTGCGAGCCCAGA |
| 3237 | AGATTACCTCTGCGAGCCCAGAT |
| 3238 | GATTACCTCTGCGAGCCCAGATC |
| 3239 | ATTACCTCTGCGAGCCCAGATCA |
| 3240 | TTACCTCTGCGAGCCCAGATCAA |
| 3241 | TACCTCTGCGAGCCCAGATCAAC |
| 3242 | ACCTCTGCGAGCCCAGATCAACC |
| 3243 | CCTCTGCGAGCCCAGATCAACCT |
| 3244 | CTCTGCGAGCCCAGATCAACCTT |
| 3245 | TCTGCGAGCCCAGATCAACCTTT |

| ID | SEQUENCE |
|---|---|
| 3246 | CTGCGAGCCCAGATCAACCTTTA |
| 3247 | TTCACTTGGGGGTTGGCAATTTT |
| 3248 | TCACTTGGGGGTTGGCAATTTTA |
| 3249 | CACTTGGGGGTTGGCAATTTTAT |
| 3250 | ACTTGGGGGTTGGCAATTTTATT |
| 3251 | CTTGGGGGTTGGCAATTTTATTT |
| 3252 | TTGGGGGTTGGCAATTTTATTTT |
| 3253 | TGGGGGTTGGCAATTTTATTTTT |
| 3254 | GGGGGTTGGCAATTTTATTTTTA |
| 3255 | GGGGTTGGCAATTTTATTTTTAA |
| 3256 | GGGTTGGCAATTTTATTTTTAAA |
| 3257 | GGTTGGCAATTTTATTTTTAAAG |
| 3258 | GTTGGCAATTTTATTTTTAAAGA |
| 3259 | TTGGCAATTTTATTTTTAAAGAA |
| 3260 | TGGCAATTTTATTTTTAAAGAAA |
| 3261 | GGCAATTTTATTTTTAAAGAAAA |
| 3262 | GCAATTTTATTTTTAAAGAAAAC |
| 3263 | CAATTTTATTTTTAAAGAAAACT |
| 3264 | AATTTTATTTTTAAAGAAAACTT |
| 3265 | ATTTTATTTTTAAAGAAAACTTA |
| 3266 | TTTTATTTTTAAAGAAAACTTAA |
| 3267 | TTTATTTTTAAAGAAAACTTAAA |
| 3268 | TTATTTTTAAAGAAAACTTAAAA |
| 3269 | TATTTTTAAAGAAAACTTAAAAA |
| 3270 | ATTTTTAAAGAAAACTTAAAAAT |
| 3271 | TTTTTAAAGAAAACTTAAAAATA |
| 3272 | TTTTAAAGAAAACTTAAAAATAA |
| 3273 | TTTAAAGAAAACTTAAAAATAAA |
| 3274 | TTAAAGAAAACTTAAAAATAAAA |
| 3275 | TAAAGAAAACTTAAAAATAAAAC |
| 3276 | AAAGAAAACTTAAAAATAAAACC |
| 3277 | AAGAAAACTTAAAAATAAAACCT |
| 3278 | AGAAAACTTAAAAATAAAACCTG |
| 3279 | GAAAACTTAAAAATAAAACCTGA |
| 3280 | AAAACTTAAAAATAAAACCTGAA |
| 3281 | AAACTTAAAAATAAAACCTGAAA |
| 3282 | AACTTAAAAATAAAACCTGAAAC |
| 3283 | ACTTAAAAATAAAACCTGAAACC |
| 3284 | CTTAAAAATAAAACCTGAAACCC |
| 3285 | TTAAAAATAAAACCTGAAACCCC |
| 3286 | TAAAAATAAAACCTGAAACCCCA |
| 3287 | AAAAATAAAACCTGAAACCCCAG |
| 3288 | AAAATAAAACCTGAAACCCCAGA |
| 3289 | AAATAAAACCTGAAACCCCAGAA |
| 3290 | AATAAAACCTGAAACCCCAGAAC |
| 3291 | ATAAAACCTGAAACCCCAGAACT |
| 3292 | TAAAACCTGAAACCCCAGAACTT |
| 3293 | AAAACCTGAAACCCCAGAACTTG |
| 3294 | AAACCTGAAACCCCAGAACTTGA |
| 3295 | AACCTGAAACCCCAGAACTTGAG |
| 3296 | ACCTGAAACCCCAGAACTTGAGC |
| 3297 | CCTGAAACCCCAGAACTTGAGCC |
| 3298 | CTGAAACCCCAGAACTTGAGCCT |
| 3299 | TGAAACCCCAGAACTTGAGCCTT |
| 3300 | GAAACCCCAGAACTTGAGCCTTG |
| 3301 | AAACCCCAGAACTTGAGCCTTGT |
| 3302 | AACCCCAGAACTTGAGCCTTGTG |
| 3303 | ACCCCAGAACTTGAGCCTTGTGT |

| ID | SEQUENCE |
|---|---|
| 3304 | CCCCAGAACTTGAGCCTTGTGTA |
| 3305 | CCCAGAACTTGAGCCTTGTGTAT |
| 3306 | CCAGAACTTGAGCCTTGTGTATA |
| 3307 | CAGAACTTGAGCCTTGTGTATAG |
| 3308 | AGAACTTGAGCCTTGTGTATAGA |
| 3309 | GAACTTGAGCCTTGTGTATAGAT |
| 3310 | AACTTGAGCCTTGTGTATAGATT |
| 3311 | ACTTGAGCCTTGTGTATAGATTT |
| 3312 | CTTGAGCCTTGTGTATAGATTTT |
| 3313 | TTGAGCCTTGTGTATAGATTTTA |
| 3314 | TGAGCCTTGTGTATAGATTTTAA |
| 3315 | GAGCCTTGTGTATAGATTTTAAA |
| 3316 | AGCCTTGTGTATAGATTTTAAAA |
| 3317 | GCCTTGTGTATAGATTTTAAAAG |
| 3318 | CCTTGTGTATAGATTTTAAAAGA |
| 3319 | CTTGTGTATAGATTTTAAAAGAA |
| 3320 | TTGTGTATAGATTTTAAAAGAAT |
| 3321 | TGTGTATAGATTTTAAAAGAATA |
| 3322 | GTGTATAGATTTTAAAAGAATAT |
| 3323 | TGTATAGATTTTAAAAGAATATA |
| 3324 | GTATAGATTTTAAAAGAATATAT |
| 3325 | TATAGATTTTAAAAGAATATATA |
| 3326 | ATAGATTTTAAAAGAATATATAT |
| 3327 | TAGATTTTAAAAGAATATATATA |
| 3328 | AGATTTTAAAAGAATATATATAT |
| 3329 | GATTTTAAAAGAATATATATATC |
| 3330 | ATTTTAAAAGAATATATATATCA |
| 3331 | TTTTAAAAGAATATATATATCAG |
| 3332 | TTTAAAAGAATATATATATCAGC |
| 3333 | TTAAAAGAATATATATATCAGCC |
| 3334 | TAAAAGAATATATATATCAGCCG |
| 3335 | AAAAGAATATATATATCAGCCGG |
| 3336 | AAAGAATATATATATCAGCCGGG |
| 3337 | AAGAATATATATATCAGCCGGGC |
| 3338 | AGAATATATATATCAGCCGGGCG |
| 3339 | GGGCGCGGTGGCTCATGCCTGTA |
| 3340 | GGCGCGGTGGCTCATGCCTGTAA |
| 3341 | GCGCGGTGGCTCATGCCTGTAAT |
| 3342 | CGCGGTGGCTCATGCCTGTAATC |
| 3343 | GCGGTGGCTCATGCCTGTAATCC |
| 3344 | CGGTGGCTCATGCCTGTAATCCC |
| 3345 | GGTGGCTCATGCCTGTAATCCCA |
| 3346 | GTGGCTCATGCCTGTAATCCCAG |
| 3347 | TGGCTCATGCCTGTAATCCCAGC |
| 3348 | GGCTCATGCCTGTAATCCCAGCA |
| 3349 | GCTCATGCCTGTAATCCCAGCAC |
| 3350 | CTCATGCCTGTAATCCCAGCACT |
| 3351 | TCATGCCTGTAATCCCAGCACTT |
| 3352 | CATGCCTGTAATCCCAGCACTTT |
| 3353 | ATGCCTGTAATCCCAGCACTTTG |
| 3354 | TGCCTGTAATCCCAGCACTTTGG |
| 3355 | GCCTGTAATCCCAGCACTTTGGG |
| 3356 | CCTGTAATCCCAGCACTTTGGGA |
| 3357 | CTGTAATCCCAGCACTTTGGGAG |
| 3358 | TGTAATCCCAGCACTTTGGGAGG |
| 3359 | GTAATCCCAGCACTTTGGGAGGC |
| 3360 | TAATCCCAGCACTTTGGGAGGCT |
| 3361 | AATCCCAGCACTTTGGGAGGCTG |

| ID | SEQUENCE |
|---|---|
| 3362 | ATCCCAGCACTTTGGGAGGCTGA |
| 3363 | TCCCAGCACTTTGGGAGGCTGAG |
| 3364 | CCCAGCACTTTGGGAGGCTGAGG |
| 3365 | CCAGCACTTTGGGAGGCTGAGGC |
| 3366 | CAGCACTTTGGGAGGCTGAGGCG |
| 3367 | AGCACTTTGGGAGGCTGAGGCGG |
| 3368 | GCACTTTGGGAGGCTGAGGCGGG |
| 3369 | CACTTTGGGAGGCTGAGGCGGGT |
| 3370 | ACTTTGGGAGGCTGAGGCGGGTG |
| 3371 | CTTTGGGAGGCTGAGGCGGGTGG |
| 3372 | TTTGGGAGGCTGAGGCGGGTGGA |
| 3373 | TTGGGAGGCTGAGGCGGGTGGAT |
| 3374 | TGGGAGGCTGAGGCGGGTGGATT |
| 3375 | GGGAGGCTGAGGCGGGTGGATTG |
| 3376 | GGAGGCTGAGGCGGGTGGATTGC |
| 3377 | GAGGCTGAGGCGGGTGGATTGCT |
| 3378 | AGGCTGAGGCGGGTGGATTGCTT |
| 3379 | GGCTGAGGCGGGTGGATTGCTTG |
| 3380 | GCTGAGGCGGGTGGATTGCTTGA |
| 3381 | CTGAGGCGGGTGGATTGCTTGAG |
| 3382 | TGAGGCGGGTGGATTGCTTGAGC |
| 3383 | GAGGCGGGTGGATTGCTTGAGCC |
| 3384 | AGGCGGGTGGATTGCTTGAGCCC |
| 3385 | GGCGGGTGGATTGCTTGAGCCCA |
| 3386 | GCGGGTGGATTGCTTGAGCCCAG |
| 3387 | CGGGTGGATTGCTTGAGCCCAGG |
| 3388 | GGGTGGATTGCTTGAGCCCAGGA |
| 3389 | GGTGGATTGCTTGAGCCCAGGAG |
| 3390 | GTGGATTGCTTGAGCCCAGGAGT |
| 3391 | TGGATTGCTTGAGCCCAGGAGTT |
| 3392 | GGATTGCTTGAGCCCAGGAGTTT |
| 3393 | GATTGCTTGAGCCCAGGAGTTTG |
| 3394 | ATTGCTTGAGCCCAGGAGTTTGA |
| 3395 | TTGCTTGAGCCCAGGAGTTTGAG |
| 3396 | TGCTTGAGCCCAGGAGTTTGAGA |
| 3397 | GCTTGAGCCCAGGAGTTTGAGAC |
| 3398 | CTTGAGCCCAGGAGTTTGAGACC |
| 3399 | TTGAGCCCAGGAGTTTGAGACCA |
| 3400 | TGAGCCCAGGAGTTTGAGACCAG |
| 3401 | GAGCCCAGGAGTTTGAGACCAGC |
| 3402 | AGCCCAGGAGTTTGAGACCAGCC |
| 3403 | GCCCAGGAGTTTGAGACCAGCCT |
| 3404 | CCCAGGAGTTTGAGACCAGCCTG |
| 3405 | CCAGGAGTTTGAGACCAGCCTGG |
| 3406 | CAGGAGTTTGAGACCAGCCTGGC |
| 3407 | AGGAGTTTGAGACCAGCCTGGCC |
| 3408 | GGAGTTTGAGACCAGCCTGGCCA |
| 3409 | GAGTTTGAGACCAGCCTGGCCAA |
| 3410 | AGTTTGAGACCAGCCTGGCCAAC |
| 3411 | GTTTGAGACCAGCCTGGCCAACG |
| 3412 | TTTGAGACCAGCCTGGCCAACGT |
| 3413 | TTGAGACCAGCCTGGCCAACGTG |
| 3414 | TGAGACCAGCCTGGCCAACGTGG |
| 3415 | GAGACCAGCCTGGCCAACGTGGC |
| 3416 | AGACCAGCCTGGCCAACGTGGCA |
| 3417 | GACCAGCCTGGCCAACGTGGCAA |
| 3418 | ACCAGCCTGGCCAACGTGGCAAA |
| 3419 | CCAGCCTGGCCAACGTGGCAAAA |

| ID | SEQUENCE |
|---|---|
| 3420 | CAGCCTGGCCAACGTGGCAAAAC |
| 3421 | AGCCTGGCCAACGTGGCAAAACC |
| 3422 | GCCTGGCCAACGTGGCAAAACCT |
| 3423 | CCTGGCCAACGTGGCAAAACCTC |
| 3424 | CTGGCCAACGTGGCAAAACCTCG |
| 3425 | TGGCCAACGTGGCAAAACCTCGT |
| 3426 | GGCCAACGTGGCAAAACCTCGTC |
| 3427 | GCCAACGTGGCAAAACCTCGTCT |
| 3428 | CCAACGTGGCAAAACCTCGTCTC |
| 3429 | CAACGTGGCAAAACCTCGTCTCT |
| 3430 | AACGTGGCAAAACCTCGTCTCTG |
| 3431 | ACGTGGCAAAACCTCGTCTCTGT |
| 3432 | CGTGGCAAAACCTCGTCTCTGTT |
| 3433 | GTGGCAAAACCTCGTCTCTGTTA |
| 3434 | TGGCAAAACCTCGTCTCTGTTAA |
| 3435 | GGCAAAACCTCGTCTCTGTTAAA |
| 3436 | GCAAAACCTCGTCTCTGTTAAAA |
| 3437 | CAAAACCTCGTCTCTGTTAAAAA |
| 3438 | AAAACCTCGTCTCTGTTAAAAAT |
| 3439 | AAACCTCGTCTCTGTTAAAAATT |
| 3440 | AACCTCGTCTCTGTTAAAAATTA |
| 3441 | ACCTCGTCTCTGTTAAAAATTAG |
| 3442 | CCTCGTCTCTGTTAAAAATTAGC |
| 3443 | CTCGTCTCTGTTAAAAATTAGCC |
| 3444 | TCGTCTCTGTTAAAAATTAGCCG |
| 3445 | CGTCTCTGTTAAAAATTAGCCGG |
| 3446 | GTCTCTGTTAAAAATTAGCCGGG |
| 3447 | TCTCTGTTAAAAATTAGCCGGGC |
| 3448 | CTCTGTTAAAAATTAGCCGGGCG |
| 3449 | TCTGTTAAAAATTAGCCGGGCGT |
| 3450 | CTGTTAAAAATTAGCCGGGCGTG |
| 3451 | TGTTAAAAATTAGCCGGGCGTGG |
| 3452 | GTTAAAAATTAGCCGGGCGTGGT |
| 3453 | TTAAAAATTAGCCGGGCGTGGTG |
| 3454 | TAAAAATTAGCCGGGCGTGGTGG |
| 3455 | AAAAATTAGCCGGGCGTGGTGGC |
| 3456 | AAAATTAGCCGGGCGTGGTGGCA |
| 3457 | AAATTAGCCGGGCGTGGTGGCAC |
| 3458 | AATTAGCCGGGCGTGGTGGCACA |
| 3459 | ATTAGCCGGGCGTGGTGGCACAC |
| 3460 | TTAGCCGGGCGTGGTGGCACACT |
| 3461 | TAGCCGGGCGTGGTGGCACACTC |
| 3462 | AGCCGGGCGTGGTGGCACACTCC |
| 3463 | GCCGGGCGTGGTGGCACACTCCT |
| 3464 | CCGGGCGTGGTGGCACACTCCTG |
| 3465 | CGGGCGTGGTGGCACACTCCTGT |
| 3466 | GGGCGTGGTGGCACACTCCTGTA |
| 3467 | GGCGTGGTGGCACACTCCTGTAA |
| 3468 | GCGTGGTGGCACACTCCTGTAAT |
| 3469 | CGTGGTGGCACACTCCTGTAATC |
| 3470 | GTGGTGGCACACTCCTGTAATCC |
| 3471 | TGGTGGCACACTCCTGTAATCCC |
| 3472 | GGTGGCACACTCCTGTAATCCCA |
| 3473 | GTGGCACACTCCTGTAATCCCAG |
| 3474 | TGGCACACTCCTGTAATCCCAGC |
| 3475 | GGCACACTCCTGTAATCCCAGCT |
| 3476 | GCACACTCCTGTAATCCCAGCTA |
| 3477 | CACACTCCTGTAATCCCAGCTAC |

| ID | SEQUENCE |
|---|---|
| 3478 | ACACTCCTGTAATCCCAGCTACT |
| 3479 | CACTCCTGTAATCCCAGCTACTG |
| 3480 | ACTCCTGTAATCCCAGCTACTGG |
| 3481 | CTCCTGTAATCCCAGCTACTGGG |
| 3482 | TCCTGTAATCCCAGCTACTGGGG |
| 3483 | CCTGTAATCCCAGCTACTGGGGA |
| 3484 | CTGTAATCCCAGCTACTGGGGAG |
| 3485 | TGTAATCCCAGCTACTGGGGAGG |
| 3486 | GTAATCCCAGCTACTGGGGAGGC |
| 3487 | TAATCCCAGCTACTGGGGAGGCT |
| 3488 | AATCCCAGCTACTGGGGAGGCTG |
| 3489 | ATCCCAGCTACTGGGGAGGCTGA |
| 3490 | TCCCAGCTACTGGGGAGGCTGAG |
| 3491 | CCCAGCTACTGGGGAGGCTGAGG |
| 3492 | CCAGCTACTGGGGAGGCTGAGGC |
| 3493 | CAGCTACTGGGGAGGCTGAGGCA |
| 3494 | AGCTACTGGGGAGGCTGAGGCAC |
| 3495 | GCTACTGGGGAGGCTGAGGCACG |
| 3496 | CTACTGGGGAGGCTGAGGCACGA |
| 3497 | TACTGGGGAGGCTGAGGCACGAG |
| 3498 | ACTGGGGAGGCTGAGGCACGAGA |
| 3499 | CTGGGGAGGCTGAGGCACGAGAA |
| 3500 | TGGGGAGGCTGAGGCACGAGAAT |
| 3501 | GGGGAGGCTGAGGCACGAGAATC |
| 3502 | GGGAGGCTGAGGCACGAGAATCA |
| 3503 | GGAGGCTGAGGCACGAGAATCAC |
| 3504 | GAGGCTGAGGCACGAGAATCACT |
| 3505 | AGGCTGAGGCACGAGAATCACTT |
| 3506 | GGCTGAGGCACGAGAATCACTTG |
| 3507 | GCTGAGGCACGAGAATCACTTGA |
| 3508 | CTGAGGCACGAGAATCACTTGAA |
| 3509 | TGAGGCACGAGAATCACTTGAAC |
| 3510 | GAGGCACGAGAATCACTTGAACC |
| 3511 | AGGCACGAGAATCACTTGAACCC |
| 3512 | GGCACGAGAATCACTTGAACCCA |
| 3513 | GCACGAGAATCACTTGAACCCAG |
| 3514 | CACGAGAATCACTTGAACCCAGG |
| 3515 | ACGAGAATCACTTGAACCCAGGA |
| 3516 | CGAGAATCACTTGAACCCAGGAA |
| 3517 | GAGAATCACTTGAACCCAGGAAG |
| 3518 | AGAATCACTTGAACCCAGGAAGC |
| 3519 | GAATCACTTGAACCCAGGAAGCG |
| 3520 | AATCACTTGAACCCAGGAAGCGG |
| 3521 | ATCACTTGAACCCAGGAAGCGGG |
| 3522 | TCACTTGAACCCAGGAAGCGGGG |
| 3523 | CACTTGAACCCAGGAAGCGGGGT |
| 3524 | ACTTGAACCCAGGAAGCGGGGTT |
| 3525 | CTTGAACCCAGGAAGCGGGGTTG |
| 3526 | TTGAACCCAGGAAGCGGGGTTGC |
| 3527 | TGAACCCAGGAAGCGGGGTTGCA |
| 3528 | GAACCCAGGAAGCGGGGTTGCAG |
| 3529 | AACCCAGGAAGCGGGGTTGCAGT |
| 3530 | ACCCAGGAAGCGGGGTTGCAGTG |
| 3531 | CCCAGGAAGCGGGGTTGCAGTGA |
| 3532 | CCAGGAAGCGGGGTTGCAGTGAG |
| 3533 | CAGGAAGCGGGGTTGCAGTGAGC |
| 3534 | AGGAAGCGGGGTTGCAGTGAGCC |
| 3535 | GGAAGCGGGGTTGCAGTGAGCCA |

| ID | SEQUENCE |
|---|---|
| 3536 | GAAGCGGGGTTGCAGTGAGCCAA |
| 3537 | AAGCGGGGTTGCAGTGAGCCAAA |
| 3538 | AGCGGGGTTGCAGTGAGCCAAAG |
| 3539 | GCGGGGTTGCAGTGAGCCAAAGG |
| 3540 | CGGGGTTGCAGTGAGCCAAAGGT |
| 3541 | GGGGTTGCAGTGAGCCAAAGGTA |
| 3542 | GGGTTGCAGTGAGCCAAAGGTAC |
| 3543 | GGTTGCAGTGAGCCAAAGGTACA |
| 3544 | GTTGCAGTGAGCCAAAGGTACAC |
| 3545 | TTGCAGTGAGCCAAAGGTACACC |
| 3546 | TGCAGTGAGCCAAAGGTACACCA |
| 3547 | GCAGTGAGCCAAAGGTACACCAC |
| 3548 | CAGTGAGCCAAAGGTACACCACT |
| 3549 | AGTGAGCCAAAGGTACACCACTA |
| 3550 | GTGAGCCAAAGGTACACCACTAC |
| 3551 | TGAGCCAAAGGTACACCACTACA |
| 3552 | GAGCCAAAGGTACACCACTACAC |
| 3553 | AGCCAAAGGTACACCACTACACT |
| 3554 | GCCAAAGGTACACCACTACACTC |
| 3555 | CCAAAGGTACACCACTACACTCC |
| 3556 | CAAAGGTACACCACTACACTCCA |
| 3557 | AAAGGTACACCACTACACTCCAG |
| 3558 | AAGGTACACCACTACACTCCAGC |
| 3559 | AGGTACACCACTACACTCCAGCC |
| 3560 | GGTACACCACTACACTCCAGCCT |
| 3561 | GTACACCACTACACTCCAGCCTG |
| 3562 | TACACCACTACACTCCAGCCTGG |
| 3563 | ACACCACTACACTCCAGCCTGGG |
| 3564 | CACCACTACACTCCAGCCTGGGC |
| 3565 | ACCACTACACTCCAGCCTGGGCA |
| 3566 | CCACTACACTCCAGCCTGGGCAA |
| 3567 | CACTACACTCCAGCCTGGGCAAC |
| 3568 | ACTACACTCCAGCCTGGGCAACA |
| 3569 | CTACACTCCAGCCTGGGCAACAG |
| 3570 | TACACTCCAGCCTGGGCAACAGA |
| 3571 | ACACTCCAGCCTGGGCAACAGAG |
| 3572 | CACTCCAGCCTGGGCAACAGAGC |
| 3573 | ACTCCAGCCTGGGCAACAGAGCA |
| 3574 | CTCCAGCCTGGGCAACAGAGCAA |
| 3575 | TCCAGCCTGGGCAACAGAGCAAG |
| 3576 | CCAGCCTGGGCAACAGAGCAAGA |
| 3577 | CAGCCTGGGCAACAGAGCAAGAC |
| 3578 | AGCCTGGGCAACAGAGCAAGACT |
| 3579 | GCCTGGGCAACAGAGCAAGACTC |
| 3580 | CCTGGGCAACAGAGCAAGACTCG |
| 3581 | CTGGGCAACAGAGCAAGACTCGG |
| 3582 | TGGGCAACAGAGCAAGACTCGGT |
| 3583 | GGGCAACAGAGCAAGACTCGGTC |
| 3584 | GGCAACAGAGCAAGACTCGGTCT |
| 3585 | GCAACAGAGCAAGACTCGGTCTC |
| 3586 | CAACAGAGCAAGACTCGGTCTCA |
| 3587 | AACAGAGCAAGACTCGGTCTCAA |
| 3588 | ACAGAGCAAGACTCGGTCTCAAA |
| 3589 | CAGAGCAAGACTCGGTCTCAAAA |
| 3590 | AGAGCAAGACTCGGTCTCAAAAA |
| 3591 | GAGCAAGACTCGGTCTCAAAAAC |
| 3592 | AGCAAGACTCGGTCTCAAAAACA |
| 3593 | GCAAGACTCGGTCTCAAAAACAA |

| ID | SEQUENCE |
|---|---|
| 3594 | CAAGACTCGGTCTCAAAAACAAA |
| 3595 | AAGACTCGGTCTCAAAAACAAAA |
| 3596 | AGACTCGGTCTCAAAAACAAAAT |
| 3597 | GACTCGGTCTCAAAAACAAAATT |
| 3598 | ACTCGGTCTCAAAAACAAAATTT |
| 3599 | CTCGGTCTCAAAAACAAAATTTA |
| 3600 | TCGGTCTCAAAAACAAAATTTAA |
| 3601 | CGGTCTCAAAAACAAAATTTAAA |
| 3602 | GGTCTCAAAAACAAAATTTAAAA |
| 3603 | GTCTCAAAAACAAAATTTAAAAA |
| 3604 | TCTCAAAAACAAAATTTAAAAAA |
| 3605 | CTCAAAAACAAAATTTAAAAAAG |
| 3606 | TCAAAAACAAAATTTAAAAAAGA |
| 3607 | CAAAAACAAAATTTAAAAAAGAT |
| 3608 | AAAAACAAAATTTAAAAAAGATA |
| 3609 | AAAACAAAATTTAAAAAAGATAT |
| 3610 | AAACAAAATTTAAAAAAGATATA |
| 3611 | AACAAAATTTAAAAAAGATATAA |
| 3612 | ACAAAATTTAAAAAAGATATAAG |
| 3613 | CAAAATTTAAAAAAGATATAAGG |
| 3614 | AAAATTTAAAAAAGATATAAGGC |
| 3615 | AAATTTAAAAAAGATATAAGGCA |
| 3616 | AATTTAAAAAAGATATAAGGCAG |
| 3617 | ATTTAAAAAAGATATAAGGCAGT |
| 3618 | TTTAAAAAAGATATAAGGCAGTA |
| 3619 | TTAAAAAAGATATAAGGCAGTAC |
| 3620 | TAAAAAAGATATAAGGCAGTACT |
| 3621 | AAAAAAGATATAAGGCAGTACTG |
| 3622 | AAAAAGATATAAGGCAGTACTGT |
| 3623 | AAAAGATATAAGGCAGTACTGTA |
| 3624 | AAAGATATAAGGCAGTACTGTAA |
| 3625 | AAGATATAAGGCAGTACTGTAAA |
| 3626 | AGATATAAGGCAGTACTGTAAAT |
| 3627 | GATATAAGGCAGTACTGTAAATT |
| 3628 | ATATAAGGCAGTACTGTAAATTC |
| 3629 | TATAAGGCAGTACTGTAAATTCA |
| 3630 | ATAAGGCAGTACTGTAAATTCAG |
| 3631 | TAAGGCAGTACTGTAAATTCAGT |
| 3632 | AAGGCAGTACTGTAAATTCAGTT |
| 3633 | AGGCAGTACTGTAAATTCAGTTG |
| 3634 | GGCAGTACTGTAAATTCAGTTGA |
| 3635 | GCAGTACTGTAAATTCAGTTGAA |
| 3636 | CAGTACTGTAAATTCAGTTGAAT |
| 3637 | AGTACTGTAAATTCAGTTGAATT |
| 3638 | GTACTGTAAATTCAGTTGAATTT |
| 3639 | TACTGTAAATTCAGTTGAATTTT |
| 3640 | ACTGTAAATTCAGTTGAATTTTG |
| 3641 | CTGTAAATTCAGTTGAATTTTGA |
| 3642 | TGTAAATTCAGTTGAATTTTGAT |
| 3643 | GTAAATTCAGTTGAATTTTGATA |
| 3644 | TAAATTCAGTTGAATTTTGATAT |
| 3645 | AAATTCAGTTGAATTTTGATATC |
| 3646 | AATTCAGTTGAATTTTGATATCT |
| 3647 | ATTCAGTTGAATTTTGATATCTA |
| 3648 | TTCAGTTGAATTTTGATATCTAC |
| 3649 | TCAGTTGAATTTTGATATCTACC |
| 3650 | CAGTTGAATTTTGATATCTACCC |
| 3651 | AGTTGAATTTTGATATCTACCCA |

| ID | SEQUENCE |
|---|---|
| 3652 | GTTGAATTTTGATATCTACCCAT |
| 3653 | TTGAATTTTGATATCTACCCATT |
| 3654 | TGAATTTTGATATCTACCCATTT |
| 3655 | GAATTTTGATATCTACCCATTTT |
| 3656 | AATTTTGATATCTACCCATTTTT |
| 3657 | ATTTTGATATCTACCCATTTTTC |
| 3658 | TTTTGATATCTACCCATTTTTCT |
| 3659 | TTTGATATCTACCCATTTTTCTG |
| 3660 | TTGATATCTACCCATTTTTCTGT |
| 3661 | TGATATCTACCCATTTTTCTGTC |
| 3662 | GATATCTACCCATTTTTCTGTCA |
| 3663 | ATATCTACCCATTTTTCTGTCAT |
| 3664 | TATCTACCCATTTTTCTGTCATC |
| 3665 | ATCTACCCATTTTTCTGTCATCC |
| 3666 | TCTACCCATTTTTCTGTCATCCC |
| 3667 | CTACCCATTTTTCTGTCATCCCT |
| 3668 | TACCCATTTTTCTGTCATCCCTA |
| 3669 | ACCCATTTTTCTGTCATCCCTAT |
| 3670 | CCCATTTTTCTGTCATCCCTATA |
| 3671 | CCATTTTTCTGTCATCCCTATAG |
| 3672 | CATTTTTCTGTCATCCCTATAGT |
| 3673 | ATTTTTCTGTCATCCCTATAGTT |
| 3674 | TTTTTCTGTCATCCCTATAGTTC |
| 3675 | TTTTCTGTCATCCCTATAGTTCA |
| 3676 | TTTCTGTCATCCCTATAGTTCAC |
| 3677 | TTCTGTCATCCCTATAGTTCACT |
| 3678 | TCTGTCATCCCTATAGTTCACTT |
| 3679 | CTGTCATCCCTATAGTTCACTTT |
| 3680 | TGTCATCCCTATAGTTCACTTTG |
| 3681 | GTCATCCCTATAGTTCACTTTGT |
| 3682 | TCATCCCTATAGTTCACTTTGTA |
| 3683 | CATCCCTATAGTTCACTTTGTAT |
| 3684 | ATCCCTATAGTTCACTTTGTATT |
| 3685 | TCCCTATAGTTCACTTTGTATTA |
| 3686 | CCCTATAGTTCACTTTGTATTAA |
| 3687 | CCTATAGTTCACTTTGTATTAAA |
| 3688 | CTATAGTTCACTTTGTATTAAAT |
| 3689 | TATAGTTCACTTTGTATTAAATT |
| 3690 | ATAGTTCACTTTGTATTAAATTG |
| 3691 | TAGTTCACTTTGTATTAAATTGG |
| 3692 | AGTTCACTTTGTATTAAATTGGG |
| 3693 | GTTCACTTTGTATTAAATTGGGT |
| 3694 | TTCACTTTGTATTAAATTGGGTT |
| 3695 | TCACTTTGTATTAAATTGGGTTT |
| 3696 | CACTTTGTATTAAATTGGGTTTC |
| 3697 | ACTTTGTATTAAATTGGGTTTCA |
| 3698 | CTTTGTATTAAATTGGGTTTCAT |
| 3699 | TTTGTATTAAATTGGGTTTCATT |
| 3700 | TTGTATTAAATTGGGTTTCATTT |
| 3701 | TGTATTAAATTGGGTTTCATTTG |
| 3702 | GTATTAAATTGGGTTTCATTTGG |
| 3703 | TATTAAATTGGGTTTCATTTGGG |
| 3704 | ATTAAATTGGGTTTCATTTGGGA |
| 3705 | TTAAATTGGGTTTCATTTGGGAT |
| 3706 | TAAATTGGGTTTCATTTGGGATT |
| 3707 | AAATTGGGTTTCATTTGGGATTT |
| 3708 | AATTGGGTTTCATTTGGGATTTG |
| 3709 | ATTGGGTTTCATTTGGGATTTGC |

| ID | SEQUENCE |
|---|---|
| 3710 | TTGGGTTTCATTTGGGATTTGCA |
| 3711 | TGGGTTTCATTTGGGATTTGCAA |
| 3712 | GGGTTTCATTTGGGATTTGCAAT |
| 3713 | GGTTTCATTTGGGATTTGCAATG |
| 3714 | GTTTCATTTGGGATTTGCAATGT |
| 3715 | TTTCATTTGGGATTTGCAATGTA |
| 3716 | TTCATTTGGGATTTGCAATGTAA |
| 3717 | TCATTTGGGATTTGCAATGTAAA |
| 3718 | CATTTGGGATTTGCAATGTAAAT |
| 3719 | ATTTGGGATTTGCAATGTAAATA |
| 3720 | TTTGGGATTTGCAATGTAAATAC |
| 3721 | TTGGGATTTGCAATGTAAATACG |
| 3722 | TGGGATTTGCAATGTAAATACGT |
| 3723 | GGGATTTGCAATGTAAATACGTA |
| 3724 | GGATTTGCAATGTAAATACGTAT |
| 3725 | GATTTGCAATGTAAATACGTATT |
| 3726 | ATTTGCAATGTAAATACGTATTT |
| 3727 | TTTGCAATGTAAATACGTATTTC |
| 3728 | TTGCAATGTAAATACGTATTTCT |
| 3729 | TGCAATGTAAATACGTATTTCTA |
| 3730 | GCAATGTAAATACGTATTTCTAG |
| 3731 | CAATGTAAATACGTATTTCTAGT |
| 3732 | AATGTAAATACGTATTTCTAGTT |
| 3733 | ATGTAAATACGTATTTCTAGTTT |
| 3734 | TGTAAATACGTATTTCTAGTTTT |
| 3735 | GTAAATACGTATTTCTAGTTTTC |
| 3736 | TAAATACGTATTTCTAGTTTTCA |
| 3737 | AAATACGTATTTCTAGTTTTCAT |
| 3738 | AATACGTATTTCTAGTTTTCATA |
| 3739 | ATACGTATTTCTAGTTTTCATAT |
| 3740 | TACGTATTTCTAGTTTTCATATA |
| 3741 | ACGTATTTCTAGTTTTCATATAA |
| 3742 | CGTATTTCTAGTTTTCATATAAA |
| 3743 | GTATTTCTAGTTTTCATATAAAG |
| 3744 | TATTTCTAGTTTTCATATAAAGT |
| 3745 | ATTTCTAGTTTTCATATAAAGTA |
| 3746 | TTTCTAGTTTTCATATAAAGTAG |
| 3747 | TTCTAGTTTTCATATAAAGTAGT |
| 3748 | TCTAGTTTTCATATAAAGTAGTT |
| 3749 | CTAGTTTTCATATAAAGTAGTTC |
| 3750 | TAGTTTTCATATAAAGTAGTTCT |
| 3751 | AGTTTTCATATAAAGTAGTTCTT |
| 3752 | GTTTTCATATAAAGTAGTTCTTT |
| 3753 | TTTTCATATAAAGTAGTTCTTTT |
| 3754 | TTTCATATAAAGTAGTTCTTTTA |
| 3755 | TTCATATAAAGTAGTTCTTTTAT |
| 3756 | TCATATAAAGTAGTTCTTTTATA |
| 3757 | CATATAAAGTAGTTCTTTTATAA |
| 3758 | ATATAAAGTAGTTCTTTTATAAC |
| 3759 | TATAAAGTAGTTCTTTTATAACA |
| 3760 | ATAAAGTAGTTCTTTTATAACAA |
| 3761 | TAAAGTAGTTCTTTTATAACAAA |
| 3762 | AAAGTAGTTCTTTTATAACAAAT |
| 3763 | AAGTAGTTCTTTTATAACAAATG |
| 3764 | AGTAGTTCTTTTATAACAAATGA |
| 3765 | GTAGTTCTTTTATAACAAATGAA |
| 3766 | TAGTTCTTTTATAACAAATGAAA |
| 3767 | AGTTCTTTTATAACAAATGAAAA |

| ID | SEQUENCE |
|---|---|
| 3768 | GTTCTTTTATAACAAATGAAAAG |
| 3769 | TTCTTTTATAACAAATGAAAAGT |
| 3770 | TCTTTTATAACAAATGAAAAGTA |
| 3771 | CTTTTATAACAAATGAAAAGTAT |
| 3772 | TTTTATAACAAATGAAAAGTATT |
| 3773 | TTTATAACAAATGAAAAGTATTT |
| 3774 | TTATAACAAATGAAAAGTATTTT |
| 3775 | TATAACAAATGAAAAGTATTTTT |
| 3776 | ATAACAAATGAAAAGTATTTTTC |
| 3777 | TAACAAATGAAAAGTATTTTTCT |
| 3778 | AACAAATGAAAAGTATTTTTCTT |
| 3779 | ACAAATGAAAAGTATTTTTCTTG |
| 3780 | CAAATGAAAAGTATTTTTCTTGT |
| 3781 | AAATGAAAAGTATTTTTCTTGTA |
| 3782 | AATGAAAAGTATTTTTCTTGTAT |
| 3783 | ATGAAAAGTATTTTTCTTGTATA |
| 3784 | TGAAAAGTATTTTTCTTGTATAT |
| 3785 | GAAAAGTATTTTTCTTGTATATT |
| 3786 | AAAAGTATTTTTCTTGTATATTA |
| 3787 | AAAGTATTTTTCTTGTATATTAT |
| 3788 | AAGTATTTTTCTTGTATATTATT |
| 3789 | AGTATTTTTCTTGTATATTATTA |
| 3790 | GTATTTTTCTTGTATATTATTAA |
| 3791 | TATTTTTCTTGTATATTATTAAG |
| 3792 | ATTTTTCTTGTATATTATTAAGT |
| 3793 | TTTTTCTTGTATATTATTAAGTA |
| 3794 | TTTTCTTGTATATTATTAAGTAA |
| 3795 | TTTCTTGTATATTATTAAGTAAT |
| 3796 | TTCTTGTATATTATTAAGTAATG |
| 3797 | TCTTGTATATTATTAAGTAATGA |
| 3798 | CTTGTATATTATTAAGTAATGAA |
| 3799 | TTGTATATTATTAAGTAATGAAT |
| 3800 | TGTATATTATTAAGTAATGAATA |
| 3801 | GTATATTATTAAGTAATGAATAT |
| 3802 | TATATTATTAAGTAATGAATATA |
| 3803 | ATATTATTAAGTAATGAATATAT |
| 3804 | TATTATTAAGTAATGAATATATA |
| 3805 | ATTATTAAGTAATGAATATATAA |
| 3806 | TTATTAAGTAATGAATATATAAG |
| 3807 | TATTAAGTAATGAATATATAAGA |
| 3808 | ATTAAGTAATGAATATATAAGAA |
| 3809 | TTAAGTAATGAATATATAAGAAC |
| 3810 | TAAGTAATGAATATATAAGAACT |
| 3811 | AAGTAATGAATATATAAGAACTG |
| 3812 | AGTAATGAATATATAAGAACTGT |
| 3813 | GTAATGAATATATAAGAACTGTA |
| 3814 | TAATGAATATATAAGAACTGTAC |
| 3815 | AATGAATATATAAGAACTGTACT |
| 3816 | ATGAATATATAAGAACTGTACTC |
| 3817 | TGAATATATAAGAACTGTACTCT |
| 3818 | GAATATATAAGAACTGTACTCTT |
| 3819 | AATATATAAGAACTGTACTCTTC |
| 3820 | ATATATAAGAACTGTACTCTTCT |
| 3821 | TATATAAGAACTGTACTCTTCTC |
| 3822 | ATATAAGAACTGTACTCTTCTCA |
| 3823 | TATAAGAACTGTACTCTTCTCAG |
| 3824 | ATAAGAACTGTACTCTTCTCAGC |
| 3825 | TAAGAACTGTACTCTTCTCAGCT |

| ID | SEQUENCE |
|---|---|
| 3826 | AAGAACTGTACTCTTCTCAGCTT |
| 3827 | AGAACTGTACTCTTCTCAGCTTG |
| 3828 | GAACTGTACTCTTCTCAGCTTGA |
| 3829 | AACTGTACTCTTCTCAGCTTGAG |
| 3830 | ACTGTACTCTTCTCAGCTTGAGC |
| 3831 | CTGTACTCTTCTCAGCTTGAGCT |
| 3832 | TGTACTCTTCTCAGCTTGAGCTT |
| 3833 | GTACTCTTCTCAGCTTGAGCTTA |
| 3834 | TACTCTTCTCAGCTTGAGCTTAA |
| 3835 | ACTCTTCTCAGCTTGAGCTTAAC |
| 3836 | CTCTTCTCAGCTTGAGCTTAACA |
| 3837 | TCTTCTCAGCTTGAGCTTAACAT |
| 3838 | CTTCTCAGCTTGAGCTTAACATA |
| 3839 | TTCTCAGCTTGAGCTTAACATAG |
| 3840 | TCTCAGCTTGAGCTTAACATAGG |
| 3841 | CTCAGCTTGAGCTTAACATAGGT |
| 3842 | TCAGCTTGAGCTTAACATAGGTA |
| 3843 | CAGCTTGAGCTTAACATAGGTAA |
| 3844 | AGCTTGAGCTTAACATAGGTAAA |
| 3845 | GCTTGAGCTTAACATAGGTAAAT |
| 3846 | CTTGAGCTTAACATAGGTAAATA |
| 3847 | TTGAGCTTAACATAGGTAAATAT |
| 3848 | TGAGCTTAACATAGGTAAATATC |
| 3849 | GAGCTTAACATAGGTAAATATCA |
| 3850 | AGCTTAACATAGGTAAATATCAC |
| 3851 | GCTTAACATAGGTAAATATCACC |
| 3852 | CTTAACATAGGTAAATATCACCA |
| 3853 | TTAACATAGGTAAATATCACCAA |
| 3854 | TAACATAGGTAAATATCACCAAC |
| 3855 | AACATAGGTAAATATCACCAACA |
| 3856 | ACATAGGTAAATATCACCAACAT |
| 3857 | CATAGGTAAATATCACCAACATC |
| 3858 | ATAGGTAAATATCACCAACATCT |
| 3859 | TAGGTAAATATCACCAACATCTG |
| 3860 | AGGTAAATATCACCAACATCTGT |
| 3861 | GGTAAATATCACCAACATCTGTC |
| 3862 | GTAAATATCACCAACATCTGTCC |
| 3863 | TAAATATCACCAACATCTGTCCT |
| 3864 | AAATATCACCAACATCTGTCCTT |
| 3865 | AATATCACCAACATCTGTCCTTA |
| 3866 | ATATCACCAACATCTGTCCTTAG |
| 3867 | TATCACCAACATCTGTCCTTAGA |
| 3868 | ATCACCAACATCTGTCCTTAGAA |
| 3869 | TCACCAACATCTGTCCTTAGAAA |
| 3870 | CACCAACATCTGTCCTTAGAAAG |
| 3871 | ACCAACATCTGTCCTTAGAAAGG |
| 3872 | CCAACATCTGTCCTTAGAAAGGA |
| 3873 | CAACATCTGTCCTTAGAAAGGAC |
| 3874 | AACATCTGTCCTTAGAAAGGACC |
| 3875 | ACATCTGTCCTTAGAAAGGACCA |
| 3876 | CATCTGTCCTTAGAAAGGACCAT |
| 3877 | ATCTGTCCTTAGAAAGGACCATC |
| 3878 | TCTGTCCTTAGAAAGGACCATCT |
| 3879 | CTGTCCTTAGAAAGGACCATCTC |
| 3880 | TGTCCTTAGAAAGGACCATCTCA |
| 3881 | GTCCTTAGAAAGGACCATCTCAT |
| 3882 | TCCTTAGAAAGGACCATCTCATG |
| 3883 | CCTTAGAAAGGACCATCTCATGT |

| ID | SEQUENCE |
|---|---|
| 3884 | CTTAGAAAGGACCATCTCATGTT |
| 3885 | TTAGAAAGGACCATCTCATGTTT |
| 3886 | TAGAAAGGACCATCTCATGTTTT |
| 3887 | AGAAAGGACCATCTCATGTTTTT |
| 3888 | GAAAGGACCATCTCATGTTTTTT |
| 3889 | AAAGGACCATCTCATGTTTTTTT |
| 3890 | AAGGACCATCTCATGTTTTTTTT |
| 3891 | AGGACCATCTCATGTTTTTTTC |
| 3892 | GGACCATCTCATGTTTTTTTCT |
| 3893 | GACCATCTCATGTTTTTTTCTT |
| 3894 | ACCATCTCATGTTTTTTTCTTG |
| 3895 | CCATCTCATGTTTTTTTCTTGC |
| 3896 | CATCTCATGTTTTTTTCTTGCT |
| 3897 | ATCTCATGTTTTTTTCTTGCTA |
| 3898 | TCTCATGTTTTTTTCTTGCTAT |
| 3899 | CTCATGTTTTTTTCTTGCTATG |
| 3900 | TCATGTTTTTTTCTTGCTATGA |
| 3901 | CATGTTTTTTTCTTGCTATGAC |
| 3902 | ATGTTTTTTTCTTGCTATGACT |
| 3903 | TGTTTTTTTCTTGCTATGACTT |
| 3904 | GTTTTTTTCTTGCTATGACTTG |
| 3905 | TTTTTTTCTTGCTATGACTTGT |
| 3906 | TTTTTTCTTGCTATGACTTGTG |
| 3907 | TTTTTCTTGCTATGACTTGTGT |
| 3908 | TTTTCTTGCTATGACTTGTGTA |
| 3909 | TTTCTTGCTATGACTTGTGTAT |
| 3910 | TTCTTGCTATGACTTGTGTATT |
| 3911 | TCTTGCTATGACTTGTGTATTT |
| 3912 | CTTGCTATGACTTGTGTATTTT |
| 3913 | TTGCTATGACTTGTGTATTTTC |
| 3914 | TGCTATGACTTGTGTATTTTCT |
| 3915 | GCTATGACTTGTGTATTTTCTT |
| 3916 | CTATGACTTGTGTATTTTCTTG |
| 3917 | TATGACTTGTGTATTTTCTTGC |
| 3918 | ATGACTTGTGTATTTTCTTGCA |
| 3919 | TGACTTGTGTATTTTCTTGCAT |
| 3920 | GACTTGTGTATTTTCTTGCATC |
| 3921 | ACTTGTGTATTTTCTTGCATCC |
| 3922 | CTTGTGTATTTTCTTGCATCCT |
| 3923 | TTGTGTATTTTCTTGCATCCTC |
| 3924 | TGTGTATTTTCTTGCATCCTCC |
| 3925 | GTGTATTTTCTTGCATCCTCCC |
| 3926 | TGTATTTTCTTGCATCCTCCCT |
| 3927 | GTATTTTCTTGCATCCTCCCTA |
| 3928 | TATTTTCTTGCATCCTCCCTAG |
| 3929 | ATTTTCTTGCATCCTCCCTAGA |
| 3930 | TTTTCTTGCATCCTCCCTAGAC |
| 3931 | TTTCTTGCATCCTCCCTAGACT |
| 3932 | TTCTTGCATCCTCCCTAGACTT |
| 3933 | TCTTGCATCCTCCCTAGACTTC |
| 3934 | CTTGCATCCTCCCTAGACTTCC |
| 3935 | TTGCATCCTCCCTAGACTTCCC |
| 3936 | TGCATCCTCCCTAGACTTCCCT |
| 3937 | GCATCCTCCCTAGACTTCCCTA |
| 3938 | CATCCTCCCTAGACTTCCCTAT |
| 3939 | ATCCTCCCTAGACTTCCCTATT |
| 3940 | TCCTCCCTAGACTTCCCTATTT |
| 3941 | CCTCCCTAGACTTCCCTATTTC |

| ID | SEQUENCE |
|---|---|
| 3942 | CCTCCCTAGACTTCCCTATTTCG |
| 3943 | CTCCCTAGACTTCCCTATTTCGC |
| 3944 | TCCCTAGACTTCCCTATTTCGCT |
| 3945 | CCCTAGACTTCCCTATTTCGCTT |
| 3946 | CCTAGACTTCCCTATTTCGCTTT |
| 3947 | CTAGACTTCCCTATTTCGCTTTC |
| 3948 | TAGACTTCCCTATTTCGCTTTCT |
| 3949 | AGACTTCCCTATTTCGCTTTCTC |
| 3950 | GACTTCCCTATTTCGCTTTCTCC |
| 3951 | ACTTCCCTATTTCGCTTTCTCCT |
| 3952 | CTTCCCTATTTCGCTTTCTCCTC |
| 3953 | TTCCCTATTTCGCTTTCTCCTCG |
| 3954 | TCCCTATTTCGCTTTCTCCTCGG |
| 3955 | CCCTATTTCGCTTTCTCCTCGGC |
| 3956 | CCTATTTCGCTTTCTCCTCGGCT |
| 3957 | CTATTTCGCTTTCTCCTCGGCTC |
| 3958 | TATTTCGCTTTCTCCTCGGCTCA |
| 3959 | ATTTCGCTTTCTCCTCGGCTCAC |
| 3960 | TTTCGCTTTCTCCTCGGCTCACT |
| 3961 | TTCGCTTTCTCCTCGGCTCACTT |
| 3962 | TCGCTTTCTCCTCGGCTCACTTT |
| 3963 | CGCTTTCTCCTCGGCTCACTTTC |
| 3964 | GCTTTCTCCTCGGCTCACTTTCT |
| 3965 | CTTTCTCCTCGGCTCACTTTCTC |
| 3966 | TTTCTCCTCGGCTCACTTTCTCC |
| 3967 | TTCTCCTCGGCTCACTTTCTCCC |
| 3968 | TCTCCTCGGCTCACTTTCTCCCT |
| 3969 | CTCCTCGGCTCACTTTCTCCCTT |
| 3970 | TCCTCGGCTCACTTTCTCCCTTT |
| 3971 | CCTCGGCTCACTTTCTCCCTTTT |
| 3972 | CTCGGCTCACTTTCTCCCTTTTT |
| 3973 | TCGGCTCACTTTCTCCCTTTTTA |
| 3974 | CGGCTCACTTTCTCCCTTTTTAT |
| 3975 | GGCTCACTTTCTCCCTTTTTATT |
| 3976 | GCTCACTTTCTCCCTTTTTATTT |
| 3977 | CTCACTTTCTCCCTTTTTATTTT |
| 3978 | TCACTTTCTCCCTTTTTATTTTT |
| 3979 | CACTTTCTCCCTTTTTATTTTTC |
| 3980 | ACTTTCTCCCTTTTTATTTTTCA |
| 3981 | CTTTCTCCCTTTTTATTTTTCAC |
| 3982 | TTTCTCCCTTTTTATTTTTCACC |
| 3983 | TTCTCCCTTTTTATTTTTCACCA |
| 3984 | TCTCCCTTTTTATTTTTCACCAA |
| 3985 | CTCCCTTTTTATTTTTCACCAAA |
| 3986 | TCCCTTTTTATTTTTCACCAAAC |
| 3987 | CCCTTTTTATTTTTCACCAAACC |
| 3988 | CCTTTTTATTTTTCACCAAACCA |
| 3989 | CTTTTTATTTTTCACCAAACCAT |
| 3990 | TTTTTATTTTTCACCAAACCATT |
| 3991 | TTTTATTTTTCACCAAACCATTT |
| 3992 | TTTATTTTTCACCAAACCATTTG |
| 3993 | TTATTTTTCACCAAACCATTTGT |
| 3994 | TATTTTTCACCAAACCATTTGTA |
| 3995 | ATTTTTCACCAAACCATTTGTAG |
| 3996 | TTTTTCACCAAACCATTTGTAGA |
| 3997 | TTTTCACCAAACCATTTGTAGAG |
| 3998 | TTTCACCAAACCATTTGTAGAGC |
| 3999 | TTCACCAAACCATTTGTAGAGCT |

| ID | SEQUENCE |
|---|---|
| 4000 | TCACCAAACCATTTGTAGAGCTA |
| 4001 | CACCAAACCATTTGTAGAGCTAC |
| 4002 | ACCAAACCATTTGTAGAGCTACA |
| 4003 | CCAAACCATTTGTAGAGCTACAA |
| 4004 | CAAACCATTTGTAGAGCTACAAA |
| 4005 | AAACCATTTGTAGAGCTACAAAA |
| 4006 | AACCATTTGTAGAGCTACAAAAC |
| 4007 | ACCATTTGTAGAGCTACAAAACC |
| 4008 | CCATTTGTAGAGCTACAAAACCT |
| 4009 | CATTTGTAGAGCTACAAAACCTA |
| 4010 | ATTTGTAGAGCTACAAAACCTAT |
| 4011 | TTTGTAGAGCTACAAAACCTATC |
| 4012 | TTGTAGAGCTACAAAACCTATCC |
| 4013 | TGTAGAGCTACAAAACCTATCCT |
| 4014 | GTAGAGCTACAAAACCTATCCTT |
| 4015 | TAGAGCTACAAAACCTATCCTTT |
| 4016 | AGAGCTACAAAACCTATCCTTTC |
| 4017 | GAGCTACAAAACCTATCCTTTCT |
| 4018 | AGCTACAAAACCTATCCTTTCTT |
| 4019 | GCTACAAAACCTATCCTTTCTTA |
| 4020 | CTACAAAACCTATCCTTTCTTAT |
| 4021 | TACAAAACCTATCCTTTCTTATT |
| 4022 | ACAAAACCTATCCTTTCTTATTT |
| 4023 | CAAAACCTATCCTTTCTTATTTT |
| 4024 | AAAACCTATCCTTTCTTATTTTC |
| 4025 | AAACCTATCCTTTCTTATTTTCA |
| 4026 | AACCTATCCTTTCTTATTTTCAG |
| 4027 | ACCTATCCTTTCTTATTTTCAGT |
| 4028 | CCTATCCTTTCTTATTTTCAGTA |
| 4029 | CTATCCTTTCTTATTTTCAGTAG |
| 4030 | TATCCTTTCTTATTTTCAGTAGT |
| 4031 | ATCCTTTCTTATTTTCAGTAGTC |
| 4032 | TCCTTTCTTATTTTCAGTAGTCA |
| 4033 | CCTTTCTTATTTTCAGTAGTCAG |
| 4034 | CTTTCTTATTTTCAGTAGTCAGA |
| 4035 | TTTCTTATTTTCAGTAGTCAGAA |
| 4036 | TTCTTATTTTCAGTAGTCAGAAT |
| 4037 | TCTTATTTTCAGTAGTCAGAATT |
| 4038 | CTTATTTTCAGTAGTCAGAATTT |
| 4039 | TTATTTTCAGTAGTCAGAATTTT |
| 4040 | TATTTTCAGTAGTCAGAATTTTA |
| 4041 | ATTTTCAGTAGTCAGAATTTTAT |
| 4042 | TTTTCAGTAGTCAGAATTTTATC |
| 4043 | TTTCAGTAGTCAGAATTTTATCT |
| 4044 | TTCAGTAGTCAGAATTTTATCTA |
| 4045 | TCAGTAGTCAGAATTTTATCTAG |
| 4046 | CAGTAGTCAGAATTTTATCTAGA |
| 4047 | AGTAGTCAGAATTTTATCTAGAA |
| 4048 | GTAGTCAGAATTTTATCTAGAAA |
| 4049 | TAGTCAGAATTTTATCTAGAAAT |
| 4050 | AGTCAGAATTTTATCTAGAAATC |
| 4051 | GTCAGAATTTTATCTAGAAATCT |
| 4052 | TCAGAATTTTATCTAGAAATCTT |
| 4053 | CAGAATTTTATCTAGAAATCTTT |
| 4054 | AGAATTTTATCTAGAAATCTTTT |
| 4055 | GAATTTTATCTAGAAATCTTTTA |
| 4056 | AATTTTATCTAGAAATCTTTTAA |
| 4057 | ATTTTATCTAGAAATCTTTTAAC |

| ID | SEQUENCE |
|---|---|
| 4058 | TTTTATCTAGAAATCTTTTAACA |
| 4059 | TTTATCTAGAAATCTTTTAACAC |
| 4060 | TTATCTAGAAATCTTTTAACACC |
| 4061 | TATCTAGAAATCTTTTAACACCT |
| 4062 | ATCTAGAAATCTTTTAACACCTT |
| 4063 | TCTAGAAATCTTTTAACACCTTT |
| 4064 | CTAGAAATCTTTTAACACCTTTT |
| 4065 | TAGAAATCTTTTAACACCTTTTT |
| 4066 | AGAAATCTTTTAACACCTTTTTA |
| 4067 | GAAATCTTTTAACACCTTTTTAG |
| 4068 | AAATCTTTTAACACCTTTTTAGT |
| 4069 | AATCTTTTAACACCTTTTTAGTG |
| 4070 | ATCTTTTAACACCTTTTTAGTGG |
| 4071 | TCTTTTAACACCTTTTTAGTGGT |
| 4072 | CTTTTAACACCTTTTTAGTGGTT |
| 4073 | TTTTAACACCTTTTTAGTGGTTA |
| 4074 | TTTAACACCTTTTTAGTGGTTAT |
| 4075 | TTAACACCTTTTTAGTGGTTATT |
| 4076 | TAACACCTTTTTAGTGGTTATTT |
| 4077 | AACACCTTTTTAGTGGTTATTTC |
| 4078 | ACACCTTTTTAGTGGTTATTTCT |
| 4079 | CACCTTTTTAGTGGTTATTTCTA |
| 4080 | ACCTTTTTAGTGGTTATTTCTAA |
| 4081 | CCTTTTTAGTGGTTATTTCTAAA |
| 4082 | CTTTTTAGTGGTTATTTCTAAAA |
| 4083 | TTTTTAGTGGTTATTTCTAAAAT |
| 4084 | TTTTAGTGGTTATTTCTAAAATC |
| 4085 | TTTAGTGGTTATTTCTAAAATCA |
| 4086 | TTAGTGGTTATTTCTAAAATCAC |
| 4087 | TAGTGGTTATTTCTAAAATCACT |
| 4088 | AGTGGTTATTTCTAAAATCACTG |
| 4089 | GTGGTTATTTCTAAAATCACTGT |
| 4090 | TGGTTATTTCTAAAATCACTGTC |
| 4091 | GGTTATTTCTAAAATCACTGTCA |
| 4092 | GTTATTTCTAAAATCACTGTCAA |
| 4093 | TTATTTCTAAAATCACTGTCAAC |
| 4094 | TATTTCTAAAATCACTGTCAACA |
| 4095 | ATTTCTAAAATCACTGTCAACAA |
| 4096 | TTTCTAAAATCACTGTCAACAAT |
| 4097 | TTCTAAAATCACTGTCAACAATA |
| 4098 | TCTAAAATCACTGTCAACAATAA |
| 4099 | CTAAAATCACTGTCAACAATAAA |
| 4100 | TAAAATCACTGTCAACAATAAAT |
| 4101 | AAAATCACTGTCAACAATAAATC |
| 4102 | AAATCACTGTCAACAATAAATCT |
| 4103 | AATCACTGTCAACAATAAATCTA |
| 4104 | ATCACTGTCAACAATAAATCTAA |
| 4105 | TCACTGTCAACAATAAATCTAAC |
| 4106 | CACTGTCAACAATAAATCTAACC |
| 4107 | ACTGTCAACAATAAATCTAACCC |
| 4108 | CTGTCAACAATAAATCTAACCCT |
| 4109 | TGTCAACAATAAATCTAACCCTA |
| 4110 | GTCAACAATAAATCTAACCCTAG |
| 4111 | TCAACAATAAATCTAACCCTAGT |
| 4112 | CAACAATAAATCTAACCCTAGTT |
| 4113 | AACAATAAATCTAACCCTAGTTG |
| 4114 | ACAATAAATCTAACCCTAGTTGT |
| 4115 | CAATAAATCTAACCCTAGTTGTA |

| ID | SEQUENCE |
|---|---|
| 4116 | AATAAATCTAACCCTAGTTGTAT |
| 4117 | ATAAATCTAACCCTAGTTGTATC |
| 4118 | TAAATCTAACCCTAGTTGTATCC |
| 4119 | AAATCTAACCCTAGTTGTATCCC |
| 4120 | AATCTAACCCTAGTTGTATCCCT |
| 4121 | ATCTAACCCTAGTTGTATCCCTC |
| 4122 | TCTAACCCTAGTTGTATCCCTCC |
| 4123 | CTAACCCTAGTTGTATCCCTCCT |
| 4124 | TAACCCTAGTTGTATCCCTCCTT |
| 4125 | AACCCTAGTTGTATCCCTCCTTT |
| 4126 | ACCCTAGTTGTATCCCTCCTTTA |
| 4127 | CCCTAGTTGTATCCCTCCTTTAA |
| 4128 | CCTAGTTGTATCCCTCCTTTAAG |
| 4129 | CTAGTTGTATCCCTCCTTTAAGT |
| 4130 | TAGTTGTATCCCTCCTTTAAGTA |
| 4131 | AGTTGTATCCCTCCTTTAAGTAT |
| 4132 | GTTGTATCCCTCCTTTAAGTATT |
| 4133 | TTGTATCCCTCCTTTAAGTATTT |
| 4134 | TGTATCCCTCCTTTAAGTATTTA |
| 4135 | GTATCCCTCCTTTAAGTATTTAA |
| 4136 | TATCCCTCCTTTAAGTATTTAAA |
| 4137 | ATCCCTCCTTTAAGTATTTAAAA |
| 4138 | TCCCTCCTTTAAGTATTTAAAAC |
| 4139 | CCCTCCTTTAAGTATTTAAAACT |
| 4140 | CCTCCTTTAAGTATTTAAAACTT |
| 4141 | CTCCTTTAAGTATTTAAAACTTG |
| 4142 | TCCTTTAAGTATTTAAAACTTGT |
| 4143 | CCTTTAAGTATTTAAAACTTGTT |
| 4144 | CTTTAAGTATTTAAAACTTGTTG |
| 4145 | TTTAAGTATTTAAAACTTGTTGC |
| 4146 | TTAAGTATTTAAAACTTGTTGCC |
| 4147 | TAAGTATTTAAAACTTGTTGCCC |
| 4148 | AAGTATTTAAAACTTGTTGCCCC |
| 4149 | AGTATTTAAAACTTGTTGCCCCA |
| 4150 | GTATTTAAAACTTGTTGCCCCAA |
| 4151 | TATTTAAAACTTGTTGCCCCAAA |
| 4152 | ATTTAAAACTTGTTGCCCCAAAT |
| 4153 | TTTAAAACTTGTTGCCCCAAATG |
| 4154 | TTAAAACTTGTTGCCCCAAATGT |
| 4155 | TAAAACTTGTTGCCCCAAATGTG |
| 4156 | AAAACTTGTTGCCCCAAATGTGA |
| 4157 | AAACTTGTTGCCCCAAATGTGAA |
| 4158 | AACTTGTTGCCCCAAATGTGAAA |
| 4159 | ACTTGTTGCCCCAAATGTGAAAG |
| 4160 | CTTGTTGCCCCAAATGTGAAAGC |
| 4161 | TTGTTGCCCCAAATGTGAAAGCA |
| 4162 | TGTTGCCCCAAATGTGAAAGCAT |
| 4163 | GTTGCCCCAAATGTGAAAGCATT |
| 4164 | TTGCCCCAAATGTGAAAGCATTT |
| 4165 | TGCCCCAAATGTGAAAGCATTTA |
| 4166 | GCCCCAAATGTGAAAGCATTTAA |
| 4167 | CCCCAAATGTGAAAGCATTTAAT |
| 4168 | CCCAAATGTGAAAGCATTTAATT |
| 4169 | CCAAATGTGAAAGCATTTAATTC |
| 4170 | CAAATGTGAAAGCATTTAATTCC |
| 4171 | AAATGTGAAAGCATTTAATTCCT |
| 4172 | AATGTGAAAGCATTTAATTCCTT |
| 4173 | ATGTGAAAGCATTTAATTCCTTT |

| ID | SEQUENCE |
|---|---|
| 4174 | TGTGAAAGCATTTAATTCCTTTA |
| 4175 | GTGAAAGCATTTAATTCCTTTAA |
| 4176 | TGAAAGCATTTAATTCCTTTAAG |
| 4177 | GAAAGCATTTAATTCCTTTAAGA |
| 4178 | AAAGCATTTAATTCCTTTAAGAG |
| 4179 | AAGCATTTAATTCCTTTAAGAGG |
| 4180 | AGCATTTAATTCCTTTAAGAGGC |
| 4181 | GCATTTAATTCCTTTAAGAGGCC |
| 4182 | CATTTAATTCCTTTAAGAGGCCT |
| 4183 | ATTTAATTCCTTTAAGAGGCCTA |
| 4184 | TTTAATTCCTTTAAGAGGCCTAA |
| 4185 | TTAATTCCTTTAAGAGGCCTAAC |
| 4186 | TAATTCCTTTAAGAGGCCTAACT |
| 4187 | AATTCCTTTAAGAGGCCTAACTC |
| 4188 | ATTCCTTTAAGAGGCCTAACTCA |
| 4189 | TTCCTTTAAGAGGCCTAACTCAT |
| 4190 | TCCTTTAAGAGGCCTAACTCATT |
| 4191 | CCTTTAAGAGGCCTAACTCATTC |
| 4192 | CTTTAAGAGGCCTAACTCATTCA |
| 4193 | TTTAAGAGGCCTAACTCATTCAC |
| 4194 | TTAAGAGGCCTAACTCATTCACC |
| 4195 | TAAGAGGCCTAACTCATTCACCC |
| 4196 | AAGAGGCCTAACTCATTCACCCT |
| 4197 | AGAGGCCTAACTCATTCACCCTG |
| 4198 | GAGGCCTAACTCATTCACCCTGA |
| 4199 | AGGCCTAACTCATTCACCCTGAC |
| 4200 | GGCCTAACTCATTCACCCTGACA |
| 4201 | GCCTAACTCATTCACCCTGACAG |
| 4202 | CCTAACTCATTCACCCTGACAGA |
| 4203 | CTAACTCATTCACCCTGACAGAG |
| 4204 | TAACTCATTCACCCTGACAGAGT |
| 4205 | AACTCATTCACCCTGACAGAGTT |
| 4206 | ACTCATTCACCCTGACAGAGTTC |
| 4207 | CTCATTCACCCTGACAGAGTTCA |
| 4208 | TCATTCACCCTGACAGAGTTCAC |
| 4209 | CATTCACCCTGACAGAGTTCACA |
| 4210 | ATTCACCCTGACAGAGTTCACAA |
| 4211 | TTCACCCTGACAGAGTTCACAAA |
| 4212 | TCACCCTGACAGAGTTCACAAAA |
| 4213 | CACCCTGACAGAGTTCACAAAAA |
| 4214 | ACCCTGACAGAGTTCACAAAAAG |
| 4215 | CCCTGACAGAGTTCACAAAAAGC |
| 4216 | CCTGACAGAGTTCACAAAAAGCC |
| 4217 | CTGACAGAGTTCACAAAAAGCCC |
| 4218 | TGACAGAGTTCACAAAAAGCCCA |
| 4219 | GACAGAGTTCACAAAAAGCCCAC |
| 4220 | ACAGAGTTCACAAAAAGCCCACT |
| 4221 | CAGAGTTCACAAAAAGCCCACTT |
| 4222 | AGAGTTCACAAAAAGCCCACTTT |
| 4223 | GAGTTCACAAAAAGCCCACTTTA |
| 4224 | AGTTCACAAAAAGCCCACTTTAG |
| 4225 | GTTCACAAAAAGCCCACTTTAGA |
| 4226 | TTCACAAAAAGCCCACTTTAGAG |
| 4227 | TCACAAAAAGCCCACTTTAGAGT |
| 4228 | CACAAAAAGCCCACTTTAGAGTA |
| 4229 | ACAAAAAGCCCACTTTAGAGTAT |
| 4230 | CAAAAAGCCCACTTTAGAGTATA |
| 4231 | AAAAAGCCCACTTTAGAGTATAC |

| ID | SEQUENCE |
|---|---|
| 4232 | AAAAGCCCACTTTAGAGTATACA |
| 4233 | AAAGCCCACTTTAGAGTATACAT |
| 4234 | AAGCCCACTTTAGAGTATACATT |
| 4235 | AGCCCACTTTAGAGTATACATTG |
| 4236 | GCCCACTTTAGAGTATACATTGC |
| 4237 | CCCACTTTAGAGTATACATTGCT |
| 4238 | CCACTTTAGAGTATACATTGCTA |
| 4239 | CACTTTAGAGTATACATTGCTAT |
| 4240 | ACTTTAGAGTATACATTGCTATT |
| 4241 | CTTTAGAGTATACATTGCTATTA |
| 4242 | TTTAGAGTATACATTGCTATTAT |
| 4243 | TTAGAGTATACATTGCTATTATG |
| 4244 | TAGAGTATACATTGCTATTATGG |
| 4245 | AGAGTATACATTGCTATTATGGG |
| 4246 | GAGTATACATTGCTATTATGGGA |
| 4247 | AGTATACATTGCTATTATGGGAG |
| 4248 | GTATACATTGCTATTATGGGAGA |
| 4249 | TATACATTGCTATTATGGGAGAC |
| 4250 | ATACATTGCTATTATGGGAGACC |
| 4251 | TACATTGCTATTATGGGAGACCA |
| 4252 | ACATTGCTATTATGGGAGACCAC |
| 4253 | CATTGCTATTATGGGAGACCACC |
| 4254 | ATTGCTATTATGGGAGACCACCC |
| 4255 | TTGCTATTATGGGAGACCACCCA |
| 4256 | TGCTATTATGGGAGACCACCCAG |
| 4257 | GCTATTATGGGAGACCACCCAGA |
| 4258 | CTATTATGGGAGACCACCCAGAC |
| 4259 | TATTATGGGAGACCACCCAGACA |
| 4260 | ATTATGGGAGACCACCCAGACAT |
| 4261 | TTATGGGAGACCACCCAGACATC |
| 4262 | TATGGGAGACCACCCAGACATCT |
| 4263 | ATGGGAGACCACCCAGACATCTG |
| 4264 | TGGGAGACCACCCAGACATCTGA |
| 4265 | GGGAGACCACCCAGACATCTGAC |
| 4266 | GGAGACCACCCAGACATCTGACT |
| 4267 | GAGACCACCCAGACATCTGACTA |
| 4268 | AGACCACCCAGACATCTGACTAA |
| 4269 | GACCACCCAGACATCTGACTAAT |
| 4270 | ACCACCCAGACATCTGACTAATG |
| 4271 | CCACCCAGACATCTGACTAATGG |
| 4272 | CACCCAGACATCTGACTAATGGC |
| 4273 | ACCCAGACATCTGACTAATGGCT |
| 4274 | CCCAGACATCTGACTAATGGCTC |
| 4275 | CCAGACATCTGACTAATGGCTCT |
| 4276 | CAGACATCTGACTAATGGCTCTG |
| 4277 | AGACATCTGACTAATGGCTCTGT |
| 4278 | GACATCTGACTAATGGCTCTGTG |
| 4279 | ACATCTGACTAATGGCTCTGTGC |
| 4280 | CATCTGACTAATGGCTCTGTGCC |
| 4281 | ATCTGACTAATGGCTCTGTGCCA |
| 4282 | TCTGACTAATGGCTCTGTGCCAC |
| 4283 | CTGACTAATGGCTCTGTGCCACA |
| 4284 | TGACTAATGGCTCTGTGCCACAC |
| 4285 | GACTAATGGCTCTGTGCCACACT |
| 4286 | ACTAATGGCTCTGTGCCACACTC |
| 4287 | CTAATGGCTCTGTGCCACACTCC |
| 4288 | TAATGGCTCTGTGCCACACTCCA |
| 4289 | AATGGCTCTGTGCCACACTCCAA |

| ID | SEQUENCE |
|---|---|
| 4290 | ATGGCTCTGTGCCACACTCCAAG |
| 4291 | TGGCTCTGTGCCACACTCCAAGA |
| 4292 | GGCTCTGTGCCACACTCCAAGAC |
| 4293 | GCTCTGTGCCACACTCCAAGACC |
| 4294 | CTCTGTGCCACACTCCAAGACCT |
| 4295 | TCTGTGCCACACTCCAAGACCTG |
| 4296 | CTGTGCCACACTCCAAGACCTGT |
| 4297 | TGTGCCACACTCCAAGACCTGTG |
| 4298 | GTGCCACACTCCAAGACCTGTGC |
| 4299 | TGCCACACTCCAAGACCTGTGCC |
| 4300 | GCCACACTCCAAGACCTGTGCCT |
| 4301 | CCACACTCCAAGACCTGTGCCTT |
| 4302 | CACACTCCAAGACCTGTGCCTTT |
| 4303 | ACACTCCAAGACCTGTGCCTTTT |
| 4304 | CACTCCAAGACCTGTGCCTTTTA |
| 4305 | ACTCCAAGACCTGTGCCTTTTAG |
| 4306 | CTCCAAGACCTGTGCCTTTTAGA |
| 4307 | TCCAAGACCTGTGCCTTTTAGAG |
| 4308 | CCAAGACCTGTGCCTTTTAGAGA |
| 4309 | CAAGACCTGTGCCTTTTAGAGAA |
| 4310 | AAGACCTGTGCCTTTTAGAGAAG |
| 4311 | AGACCTGTGCCTTTTAGAGAAGC |
| 4312 | GACCTGTGCCTTTTAGAGAAGCT |
| 4313 | ACCTGTGCCTTTTAGAGAAGCTC |
| 4314 | CCTGTGCCTTTTAGAGAAGCTCA |
| 4315 | CTGTGCCTTTTAGAGAAGCTCAC |
| 4316 | TGTGCCTTTTAGAGAAGCTCACA |
| 4317 | GTGCCTTTTAGAGAAGCTCACAA |
| 4318 | TGCCTTTTAGAGAAGCTCACAAT |
| 4319 | GCCTTTTAGAGAAGCTCACAATG |
| 4320 | CCTTTTAGAGAAGCTCACAATGA |
| 4321 | CTTTTAGAGAAGCTCACAATGAT |
| 4322 | TTTTAGAGAAGCTCACAATGATT |
| 4323 | TTTAGAGAAGCTCACAATGATTT |
| 4324 | TTAGAGAAGCTCACAATGATTTA |
| 4325 | TAGAGAAGCTCACAATGATTTAA |
| 4326 | AGAGAAGCTCACAATGATTTAAG |
| 4327 | GAGAAGCTCACAATGATTTAAGG |
| 4328 | AGAAGCTCACAATGATTTAAGGA |
| 4329 | GAAGCTCACAATGATTTAAGGAC |
| 4330 | AAGCTCACAATGATTTAAGGACT |
| 4331 | AGCTCACAATGATTTAAGGACTG |
| 4332 | GCTCACAATGATTTAAGGACTGT |
| 4333 | CTCACAATGATTTAAGGACTGTT |
| 4334 | TCACAATGATTTAAGGACTGTTT |
| 4335 | CACAATGATTTAAGGACTGTTTG |
| 4336 | ACAATGATTTAAGGACTGTTTGA |
| 4337 | CAATGATTTAAGGACTGTTTGAA |
| 4338 | AATGATTTAAGGACTGTTTGAAA |
| 4339 | ATGATTTAAGGACTGTTTGAAAC |
| 4340 | TGATTTAAGGACTGTTTGAAACT |
| 4341 | GATTTAAGGACTGTTTGAAACTT |
| 4342 | ATTTAAGGACTGTTTGAAACTTC |
| 4343 | TTTAAGGACTGTTTGAAACTTCC |
| 4344 | TTAAGGACTGTTTGAAACTTCCA |
| 4345 | TAAGGACTGTTTGAAACTTCCAA |
| 4346 | AAGGACTGTTTGAAACTTCCAAT |
| 4347 | AGGACTGTTTGAAACTTCCAATT |

| ID | SEQUENCE |
|---|---|
| 4348 | GGACTGTTTGAAACTTCCAATTA |
| 4349 | GACTGTTTGAAACTTCCAATTAT |
| 4350 | ACTGTTTGAAACTTCCAATTATG |
| 4351 | CTGTTTGAAACTTCCAATTATGT |
| 4352 | TGTTTGAAACTTCCAATTATGTC |
| 4353 | GTTTGAAACTTCCAATTATGTCT |
| 4354 | TTTGAAACTTCCAATTATGTCTA |
| 4355 | TTGAAACTTCCAATTATGTCTAT |
| 4356 | TGAAACTTCCAATTATGTCTATA |
| 4357 | GAAACTTCCAATTATGTCTATAA |
| 4358 | AAACTTCCAATTATGTCTATAAT |
| 4359 | AACTTCCAATTATGTCTATAATT |
| 4360 | ACTTCCAATTATGTCTATAATTT |
| 4361 | CTTCCAATTATGTCTATAATTTA |
| 4362 | TTCCAATTATGTCTATAATTTAT |
| 4363 | TCCAATTATGTCTATAATTTATA |
| 4364 | CCAATTATGTCTATAATTTATAT |
| 4365 | CAATTATGTCTATAATTTATATT |
| 4366 | AATTATGTCTATAATTTATATTC |
| 4367 | ATTATGTCTATAATTTATATTCT |
| 4368 | TTATGTCTATAATTTATATTCTT |
| 4369 | TATGTCTATAATTTATATTCTTT |
| 4370 | ATGTCTATAATTTATATTCTTTT |
| 4371 | TGTCTATAATTTATATTCTTTTG |
| 4372 | GTCTATAATTTATATTCTTTTGT |
| 4373 | TCTATAATTTATATTCTTTTGTT |
| 4374 | CTATAATTTATATTCTTTTGTTT |
| 4375 | TATAATTTATATTCTTTTGTTTA |
| 4376 | ATAATTTATATTCTTTTGTTTAC |
| 4377 | TAATTTATATTCTTTTGTTTACA |
| 4378 | AATTTATATTCTTTTGTTTACAT |
| 4379 | ATTTATATTCTTTTGTTTACATG |
| 4380 | TTTATATTCTTTTGTTTACATGA |
| 4381 | TTATATTCTTTTGTTTACATGAT |
| 4382 | TATATTCTTTTGTTTACATGATG |
| 4383 | ATATTCTTTTGTTTACATGATGA |
| 4384 | TATTCTTTTGTTTACATGATGAA |
| 4385 | ATTCTTTTGTTTACATGATGAAA |
| 4386 | TTCTTTTGTTTACATGATGAAAC |
| 4387 | TCTTTTGTTTACATGATGAAACT |
| 4388 | CTTTTGTTTACATGATGAAACTT |
| 4389 | TTTTGTTTACATGATGAAACTTT |
| 4390 | TTTGTTTACATGATGAAACTTTT |
| 4391 | TTGTTTACATGATGAAACTTTTT |
| 4392 | TGTTTACATGATGAAACTTTTTG |
| 4393 | GTTTACATGATGAAACTTTTTGT |
| 4394 | TTTACATGATGAAACTTTTTGTT |
| 4395 | TTACATGATGAAACTTTTTGTTG |
| 4396 | TACATGATGAAACTTTTTGTTGT |
| 4397 | ACATGATGAAACTTTTTGTTGTT |
| 4398 | CATGATGAAACTTTTTGTTGTTG |
| 4399 | ATGATGAAACTTTTTGTTGTTGC |
| 4400 | TGATGAAACTTTTTGTTGTTGCT |
| 4401 | GATGAAACTTTTTGTTGTTGCTT |
| 4402 | ATGAAACTTTTTGTTGTTGCTTG |
| 4403 | TGAAACTTTTTGTTGTTGCTTGT |
| 4404 | GAAACTTTTTGTTGTTGCTTGTT |
| 4405 | AAACTTTTTGTTGTTGCTTGTTT |

| ID | SEQUENCE |
|---|---|
| 4406 | AACTTTTTGTTGTTGCTTGTTTG |
| 4407 | ACTTTTTGTTGTTGCTTGTTTGT |
| 4408 | CTTTTTGTTGTTGCTTGTTTGTA |
| 4409 | TTTTTGTTGTTGCTTGTTTGTAT |
| 4410 | TTTTGTTGTTGCTTGTTTGTATA |
| 4411 | TTTGTTGTTGCTTGTTTGTATAT |
| 4412 | TTGTTGTTGCTTGTTTGTATATA |
| 4413 | TGTTGTTGCTTGTTTGTATATAA |
| 4414 | GTTGTTGCTTGTTTGTATATAAT |
| 4415 | TTGTTGCTTGTTTGTATATAATA |
| 4416 | TGTTGCTTGTTTGTATATAATAC |
| 4417 | GTTGCTTGTTTGTATATAATACA |
| 4418 | TTGCTTGTTTGTATATAATACAA |
| 4419 | TGCTTGTTTGTATATAATACAAT |
| 4420 | GCTTGTTTGTATATAATACAATG |
| 4421 | CTTGTTTGTATATAATACAATGT |
| 4422 | TTGTTTGTATATAATACAATGTG |
| 4423 | TGTTTGTATATAATACAATGTGT |
| 4424 | GTTTGTATATAATACAATGTGTA |
| 4425 | TTTGTATATAATACAATGTGTAC |
| 4426 | TTGTATATAATACAATGTGTACA |
| 4427 | TGTATATAATACAATGTGTACAT |
| 4428 | GTATATAATACAATGTGTACATG |
| 4429 | TATATAATACAATGTGTACATGT |
| 4430 | ATATAATACAATGTGTACATGTA |
| 4431 | TATAATACAATGTGTACATGTAT |
| 4432 | ATAATACAATGTGTACATGTATC |
| 4433 | TAATACAATGTGTACATGTATCT |
| 4434 | AATACAATGTGTACATGTATCTT |
| 4435 | ATACAATGTGTACATGTATCTTT |
| 4436 | TACAATGTGTACATGTATCTTTT |
| 4437 | ACAATGTGTACATGTATCTTTTT |
| 4438 | CAATGTGTACATGTATCTTTTTC |
| 4439 | AATGTGTACATGTATCTTTTTCT |
| 4440 | ATGTGTACATGTATCTTTTTCTC |
| 4441 | TGTGTACATGTATCTTTTTCTCG |
| 4442 | GTGTACATGTATCTTTTTCTCGA |
| 4443 | TGTACATGTATCTTTTTCTCGAT |
| 4444 | GTACATGTATCTTTTTCTCGATT |
| 4445 | TACATGTATCTTTTTCTCGATTC |
| 4446 | ACATGTATCTTTTTCTCGATTCA |
| 4447 | CATGTATCTTTTTCTCGATTCAA |
| 4448 | ATGTATCTTTTTCTCGATTCAAA |
| 4449 | TGTATCTTTTTCTCGATTCAAAT |
| 4450 | GTATCTTTTTCTCGATTCAAATC |
| 4451 | TATCTTTTTCTCGATTCAAATCT |
| 4452 | ATCTTTTTCTCGATTCAAATCTT |
| 4453 | TCTTTTTCTCGATTCAAATCTTA |
| 4454 | CTTTTTCTCGATTCAAATCTTAA |
| 4455 | TTTTTCTCGATTCAAATCTTAAC |
| 4456 | TTTTCTCGATTCAAATCTTAACC |
| 4457 | TTTCTCGATTCAAATCTTAACCC |
| 4458 | TTCTCGATTCAAATCTTAACCCT |
| 4459 | TCTCGATTCAAATCTTAACCCTT |
| 4460 | CTCGATTCAAATCTTAACCCTTA |
| 4461 | TCGATTCAAATCTTAACCCTTAG |
| 4462 | CGATTCAAATCTTAACCCTTAGG |
| 4463 | GATTCAAATCTTAACCCTTAGGA |

| ID | SEQUENCE |
|---|---|
| 4464 | ATTCAAATCTTAACCCTTAGGAC |
| 4465 | TTCAAATCTTAACCCTTAGGACT |
| 4466 | TCAAATCTTAACCCTTAGGACTC |
| 4467 | CAAATCTTAACCCTTAGGACTCT |
| 4468 | AAATCTTAACCCTTAGGACTCTG |
| 4469 | AATCTTAACCCTTAGGACTCTGG |
| 4470 | ATCTTAACCCTTAGGACTCTGGT |
| 4471 | TCTTAACCCTTAGGACTCTGGTA |
| 4472 | CTTAACCCTTAGGACTCTGGTAT |
| 4473 | TTAACCCTTAGGACTCTGGTATT |
| 4474 | TAACCCTTAGGACTCTGGTATTT |
| 4475 | AACCCTTAGGACTCTGGTATTTT |
| 4476 | ACCCTTAGGACTCTGGTATTTTT |
| 4477 | CCCTTAGGACTCTGGTATTTTTG |
| 4478 | CCTTAGGACTCTGGTATTTTTGA |
| 4479 | CTTAGGACTCTGGTATTTTTGAT |
| 4480 | TTAGGACTCTGGTATTTTTGATC |
| 4481 | TAGGACTCTGGTATTTTTGATCT |
| 4482 | AGGACTCTGGTATTTTTGATCTG |
| 4483 | GGACTCTGGTATTTTTGATCTGG |
| 4484 | GACTCTGGTATTTTTGATCTGGC |
| 4485 | ACTCTGGTATTTTTGATCTGGCA |
| 4486 | CTCTGGTATTTTTGATCTGGCAA |
| 4487 | TCTGGTATTTTTGATCTGGCAAC |
| 4488 | CTGGTATTTTTGATCTGGCAACC |
| 4489 | TGGTATTTTTGATCTGGCAACCA |
| 4490 | GGTATTTTTGATCTGGCAACCAT |
| 4491 | GTATTTTTGATCTGGCAACCATA |
| 4492 | TATTTTTGATCTGGCAACCATAT |
| 4493 | ATTTTTGATCTGGCAACCATATT |
| 4494 | TTTTTGATCTGGCAACCATATTT |
| 4495 | TTTTGATCTGGCAACCATATTTC |
| 4496 | TTTGATCTGGCAACCATATTTCT |
| 4497 | TTGATCTGGCAACCATATTTCTG |
| 4498 | TGATCTGGCAACCATATTTCTGG |
| 4499 | GATCTGGCAACCATATTTCTGGA |
| 4500 | ATCTGGCAACCATATTTCTGGAA |
| 4501 | TCTGGCAACCATATTTCTGGAAG |
| 4502 | CTGGCAACCATATTTCTGGAAGT |
| 4503 | TGGCAACCATATTTCTGGAAGTT |
| 4504 | GGCAACCATATTTCTGGAAGTTG |
| 4505 | GCAACCATATTTCTGGAAGTTGA |
| 4506 | CAACCATATTTCTGGAAGTTGAG |
| 4507 | AACCATATTTCTGGAAGTTGAGA |
| 4508 | ACCATATTTCTGGAAGTTGAGAT |
| 4509 | CCATATTTCTGGAAGTTGAGATG |
| 4510 | CATATTTCTGGAAGTTGAGATGT |
| 4511 | ATATTTCTGGAAGTTGAGATGTT |
| 4512 | TATTTCTGGAAGTTGAGATGTTT |
| 4513 | ATTTCTGGAAGTTGAGATGTTTC |
| 4514 | TTTCTGGAAGTTGAGATGTTTCA |
| 4515 | TTCTGGAAGTTGAGATGTTTCAG |
| 4516 | TCTGGAAGTTGAGATGTTTCAGC |
| 4517 | CTGGAAGTTGAGATGTTTCAGCT |
| 4518 | TGGAAGTTGAGATGTTTCAGCTT |
| 4519 | GGAAGTTGAGATGTTTCAGCTTG |
| 4520 | GAAGTTGAGATGTTTCAGCTTGA |
| 4521 | AAGTTGAGATGTTTCAGCTTGAA |

| ID | SEQUENCE |
|---|---|
| 4522 | AGTTGAGATGTTTCAGCTTGAAG |
| 4523 | GTTGAGATGTTTCAGCTTGAAGA |
| 4524 | TTGAGATGTTTCAGCTTGAAGAA |
| 4525 | TGAGATGTTTCAGCTTGAAGAAC |
| 4526 | GAGATGTTTCAGCTTGAAGAACC |
| 4527 | AGATGTTTCAGCTTGAAGAACCA |
| 4528 | GATGTTTCAGCTTGAAGAACCAA |
| 4529 | ATGTTTCAGCTTGAAGAACCAAA |
| 4530 | TGTTTCAGCTTGAAGAACCAAAA |
| 4531 | GTTTCAGCTTGAAGAACCAAAAC |
| 4532 | TTTCAGCTTGAAGAACCAAAACA |
| 4533 | TTCAGCTTGAAGAACCAAAACAG |
| 4534 | TCAGCTTGAAGAACCAAAACAGA |
| 4535 | CAGCTTGAAGAACCAAAACAGAA |
| 4536 | AGCTTGAAGAACCAAAACAGAAG |
| 4537 | GCTTGAAGAACCAAAACAGAAGG |
| 4538 | CTTGAAGAACCAAAACAGAAGGA |
| 4539 | TTGAAGAACCAAAACAGAAGGAA |
| 4540 | TGAAGAACCAAAACAGAAGGAAT |
| 4541 | GAAGAACCAAAACAGAAGGAATA |
| 4542 | AAGAACCAAAACAGAAGGAATAT |
| 4543 | AGAACCAAAACAGAAGGAATATG |
| 4544 | GAACCAAAACAGAAGGAATATGT |
| 4545 | AACCAAAACAGAAGGAATATGTA |
| 4546 | ACCAAAACAGAAGGAATATGTAC |
| 4547 | CCAAAACAGAAGGAATATGTACA |
| 4548 | CAAAACAGAAGGAATATGTACAA |
| 4549 | AAAACAGAAGGAATATGTACAAA |
| 4550 | AAACAGAAGGAATATGTACAAAG |
| 4551 | AACAGAAGGAATATGTACAAAGA |
| 4552 | ACAGAAGGAATATGTACAAAGAA |
| 4553 | CAGAAGGAATATGTACAAAGAAT |
| 4554 | AGAAGGAATATGTACAAAGAATA |
| 4555 | GAAGGAATATGTACAAAGAATAA |
| 4556 | AAGGAATATGTACAAAGAATAAA |
| 4557 | AGGAATATGTACAAAGAATAAAT |
| 4558 | GGAATATGTACAAAGAATAAATT |
| 4559 | GAATATGTACAAAGAATAAATTT |
| 4560 | AATATGTACAAAGAATAAATTTT |
| 4561 | ATATGTACAAAGAATAAATTTTC |
| 4562 | TATGTACAAAGAATAAATTTTCT |
| 4563 | ATGTACAAAGAATAAATTTTCTG |
| 4564 | TGTACAAAGAATAAATTTTCTGC |
| 4565 | GTACAAAGAATAAATTTTCTGCT |
| 4566 | TACAAAGAATAAATTTTCTGCTC |
| 4567 | ACAAAGAATAAATTTTCTGCTCA |
| 4568 | CAAAGAATAAATTTTCTGCTCAC |
| 4569 | AAAGAATAAATTTTCTGCTCACG |
| 4570 | AAGAATAAATTTTCTGCTCACGA |
| 4571 | AGAATAAATTTTCTGCTCACGAT |
| 4572 | GAATAAATTTTCTGCTCACGATG |
| 4573 | AATAAATTTTCTGCTCACGATGA |
| 4574 | ATAAATTTTCTGCTCACGATGAG |
| 4575 | TAAATTTTCTGCTCACGATGAGT |
| 4576 | AAATTTTCTGCTCACGATGAGTT |
| 4577 | AATTTTCTGCTCACGATGAGTTT |
| 4578 | ATTTTCTGCTCACGATGAGTTTA |
| 4579 | TTTTCTGCTCACGATGAGTTTAG |

| ID | SEQUENCE |
|---|---|
| 4580 | TTTCTGCTCACGATGAGTTTAGT |
| 4581 | TTCTGCTCACGATGAGTTTAGTG |
| 4582 | TCTGCTCACGATGAGTTTAGTGT |
| 4583 | CTGCTCACGATGAGTTTAGTGTG |
| 4584 | TGCTCACGATGAGTTTAGTGTGT |
| 4585 | GCTCACGATGAGTTTAGTGTGTA |
| 4586 | CTCACGATGAGTTTAGTGTGTAA |
| 4587 | TCACGATGAGTTTAGTGTGTAAA |
| 4588 | CACGATGAGTTTAGTGTGTAAAG |
| 4589 | ACGATGAGTTTAGTGTGTAAAGT |
| 4590 | CGATGAGTTTAGTGTGTAAAGTT |
| 4591 | GATGAGTTTAGTGTGTAAAGTTT |
| 4592 | ATGAGTTTAGTGTGTAAAGTTTA |
| 4593 | TGAGTTTAGTGTGTAAAGTTTAG |
| 4594 | GAGTTTAGTGTGTAAAGTTTAGA |
| 4595 | AGTTTAGTGTGTAAAGTTTAGAG |
| 4596 | GTTTAGTGTGTAAAGTTTAGAGA |
| 4597 | TTTAGTGTGTAAAGTTTAGAGAC |
| 4598 | TTAGTGTGTAAAGTTTAGAGACA |
| 4599 | TAGTGTGTAAAGTTTAGAGACAT |
| 4600 | AGTGTGTAAAGTTTAGAGACATC |
| 4601 | GTGTGTAAAGTTTAGAGACATCT |
| 4602 | TGTGTAAAGTTTAGAGACATCTG |
| 4603 | GTGTAAAGTTTAGAGACATCTGA |
| 4604 | TGTAAAGTTTAGAGACATCTGAC |
| 4605 | GTAAAGTTTAGAGACATCTGACT |
| 4606 | TAAAGTTTAGAGACATCTGACTT |
| 4607 | AAAGTTTAGAGACATCTGACTTT |
| 4608 | AAGTTTAGAGACATCTGACTTTG |
| 4609 | AGTTTAGAGACATCTGACTTTGA |
| 4610 | GTTTAGAGACATCTGACTTTGAT |
| 4611 | TTTAGAGACATCTGACTTTGATA |
| 4612 | TTAGAGACATCTGACTTTGATAG |
| 4613 | TAGAGACATCTGACTTTGATAGC |
| 4614 | AGAGACATCTGACTTTGATAGCT |
| 4615 | GAGACATCTGACTTTGATAGCTA |
| 4616 | AGACATCTGACTTTGATAGCTAA |
| 4617 | GACATCTGACTTTGATAGCTAAA |
| 4618 | ACATCTGACTTTGATAGCTAAAT |
| 4619 | CATCTGACTTTGATAGCTAAATT |
| 4620 | ATCTGACTTTGATAGCTAAATTA |
| 4621 | TCTGACTTTGATAGCTAAATTAA |
| 4622 | CTGACTTTGATAGCTAAATTAAA |
| 4623 | TGACTTTGATAGCTAAATTAAAC |
| 4624 | GACTTTGATAGCTAAATTAAACC |
| 4625 | ACTTTGATAGCTAAATTAAACCA |
| 4626 | CTTTGATAGCTAAATTAAACCAA |
| 4627 | TTTGATAGCTAAATTAAACCAAA |
| 4628 | TTGATAGCTAAATTAAACCAAAC |
| 4629 | TGATAGCTAAATTAAACCAAACC |
| 4630 | GATAGCTAAATTAAACCAAACCC |
| 4631 | ATAGCTAAATTAAACCAAACCCT |
| 4632 | TAGCTAAATTAAACCAAACCCTA |
| 4633 | AGCTAAATTAAACCAAACCCTAT |
| 4634 | GCTAAATTAAACCAAACCCTATT |
| 4635 | CTAAATTAAACCAAACCCTATTG |
| 4636 | TAAATTAAACCAAACCCTATTGA |
| 4637 | AAATTAAACCAAACCCTATTGAA |

| ID | SEQUENCE |
|---|---|
| 4638 | AATTAAACCAAACCCTATTGAAG |
| 4639 | ATTAAACCAAACCCTATTGAAGA |
| 4640 | TTAAACCAAACCCTATTGAAGAA |
| 4641 | TAAACCAAACCCTATTGAAGAAT |
| 4642 | AAACCAAACCCTATTGAAGAATT |
| 4643 | AACCAAACCCTATTGAAGAATTG |
| 4644 | ACCAAACCCTATTGAAGAATTGA |
| 4645 | CCAAACCCTATTGAAGAATTGAA |
| 4646 | CAAACCCTATTGAAGAATTGAAT |
| 4647 | AAACCCTATTGAAGAATTGAATA |
| 4648 | AACCCTATTGAAGAATTGAATAT |
| 4649 | ACCCTATTGAAGAATTGAATATA |
| 4650 | CCCTATTGAAGAATTGAATATAT |
| 4651 | CCTATTGAAGAATTGAATATATG |
| 4652 | CTATTGAAGAATTGAATATATGC |
| 4653 | TATTGAAGAATTGAATATATGCT |
| 4654 | ATTGAAGAATTGAATATATGCTA |
| 4655 | TTGAAGAATTGAATATATGCTAC |
| 4656 | TGAAGAATTGAATATATGCTACT |
| 4657 | GAAGAATTGAATATATGCTACTT |
| 4658 | AAGAATTGAATATATGCTACTTC |
| 4659 | AGAATTGAATATATGCTACTTCA |
| 4660 | GAATTGAATATATGCTACTTCAA |
| 4661 | AATTGAATATATGCTACTTCAAG |
| 4662 | ATTGAATATATGCTACTTCAAGA |
| 4663 | TTGAATATATGCTACTTCAAGAA |
| 4664 | TGAATATATGCTACTTCAAGAAA |
| 4665 | GAATATATGCTACTTCAAGAAAC |
| 4666 | AATATATGCTACTTCAAGAAACT |
| 4667 | ATATATGCTACTTCAAGAAACTA |
| 4668 | TATATGCTACTTCAAGAAACTAA |
| 4669 | ATATGCTACTTCAAGAAACTAAA |
| 4670 | TATGCTACTTCAAGAAACTAAAT |
| 4671 | ATGCTACTTCAAGAAACTAAATT |
| 4672 | TGCTACTTCAAGAAACTAAATTG |
| 4673 | GCTACTTCAAGAAACTAAATTGA |
| 4674 | CTACTTCAAGAAACTAAATTGAT |
| 4675 | TACTTCAAGAAACTAAATTGATC |
| 4676 | ACTTCAAGAAACTAAATTGATCT |
| 4677 | CTTCAAGAAACTAAATTGATCTC |
| 4678 | TTCAAGAAACTAAATTGATCTCG |
| 4679 | TCAAGAAACTAAATTGATCTCGT |
| 4680 | CAAGAAACTAAATTGATCTCGTA |
| 4681 | AAGAAACTAAATTGATCTCGTAG |
| 4682 | AGAAACTAAATTGATCTCGTAGA |
| 4683 | GAAACTAAATTGATCTCGTAGAA |
| 4684 | AAACTAAATTGATCTCGTAGAAT |
| 4685 | AACTAAATTGATCTCGTAGAATT |
| 4686 | ACTAAATTGATCTCGTAGAATTA |
| 4687 | CTAAATTGATCTCGTAGAATTAT |
| 4688 | TAAATTGATCTCGTAGAATTATC |
| 4689 | AAATTGATCTCGTAGAATTATCT |
| 4690 | AATTGATCTCGTAGAATTATCTT |
| 4691 | ATTGATCTCGTAGAATTATCTTA |
| 4692 | TTGATCTCGTAGAATTATCTTAA |
| 4693 | TGATCTCGTAGAATTATCTTAAT |
| 4694 | GATCTCGTAGAATTATCTTAATA |
| 4695 | ATCTCGTAGAATTATCTTAATAA |

| ID | SEQUENCE |
|---|---|
| 4696 | TCTCGTAGAATTATCTTAATAAA |
| 4697 | CTCGTAGAATTATCTTAATAAAA |
| 4698 | TCGTAGAATTATCTTAATAAAAT |
| 4699 | CGTAGAATTATCTTAATAAAATA |
| 4700 | GTAGAATTATCTTAATAAAATAA |
| 4701 | TAGAATTATCTTAATAAAATAAT |
| 4702 | AGAATTATCTTAATAAAATAATG |
| 4703 | GAATTATCTTAATAAAATAATGG |
| 4704 | AATTATCTTAATAAAATAATGGC |
| 4705 | ATTATCTTAATAAAATAATGGCT |
| 4706 | TTATCTTAATAAAATAATGGCTA |
| 4707 | TATCTTAATAAAATAATGGCTAT |
| 4708 | ATCTTAATAAAATAATGGCTATA |
| 4709 | TCTTAATAAAATAATGGCTATAA |
| 4710 | CTTAATAAAATAATGGCTATAAT |
| 4711 | TTAATAAAATAATGGCTATAATT |
| 4712 | TAATAAAATAATGGCTATAATTT |
| 4713 | AATAAAATAATGGCTATAATTTC |
| 4714 | ATAAAATAATGGCTATAATTTCT |
| 4715 | TAAAATAATGGCTATAATTTCTC |
| 4716 | AAAATAATGGCTATAATTTCTCT |
| 4717 | AAATAATGGCTATAATTTCTCTG |
| 4718 | AATAATGGCTATAATTTCTCTGC |
| 4719 | ATAATGGCTATAATTTCTCTGCA |
| 4720 | TAATGGCTATAATTTCTCTGCAA |
| 4721 | AATGGCTATAATTTCTCTGCAAA |
| 4722 | ATGGCTATAATTTCTCTGCAAAA |
| 4723 | TGGCTATAATTTCTCTGCAAAAT |
| 4724 | GGCTATAATTTCTCTGCAAAATC |
| 4725 | GCTATAATTTCTCTGCAAAATCA |
| 4726 | CTATAATTTCTCTGCAAAATCAG |
| 4727 | TATAATTTCTCTGCAAAATCAGA |
| 4728 | ATAATTTCTCTGCAAAATCAGAT |
| 4729 | TAATTTCTCTGCAAAATCAGATG |
| 4730 | AATTTCTCTGCAAAATCAGATGT |
| 4731 | ATTTCTCTGCAAAATCAGATGTC |
| 4732 | TTTCTCTGCAAAATCAGATGTCA |
| 4733 | TTCTCTGCAAAATCAGATGTCAG |
| 4734 | TCTCTGCAAAATCAGATGTCAGC |
| 4735 | CTCTGCAAAATCAGATGTCAGCA |
| 4736 | TCTGCAAAATCAGATGTCAGCAT |
| 4737 | CTGCAAAATCAGATGTCAGCATA |
| 4738 | TGCAAAATCAGATGTCAGCATAA |
| 4739 | GCAAAATCAGATGTCAGCATAAG |
| 4740 | CAAAATCAGATGTCAGCATAAGC |
| 4741 | AAAATCAGATGTCAGCATAAGCG |
| 4742 | AAATCAGATGTCAGCATAAGCGA |
| 4743 | AATCAGATGTCAGCATAAGCGAT |
| 4744 | ATCAGATGTCAGCATAAGCGATG |
| 4745 | TCAGATGTCAGCATAAGCGATGG |
| 4746 | CAGATGTCAGCATAAGCGATGGA |
| 4747 | AGATGTCAGCATAAGCGATGGAT |
| 4748 | GATGTCAGCATAAGCGATGGATA |
| 4749 | ATGTCAGCATAAGCGATGGATAA |
| 4750 | TGTCAGCATAAGCGATGGATAAT |
| 4751 | GTCAGCATAAGCGATGGATAATA |
| 4752 | TCAGCATAAGCGATGGATAATAC |
| 4753 | CAGCATAAGCGATGGATAATACC |

| ID | SEQUENCE |
|---|---|
| 4754 | AGCATAAGCGATGGATAATACCT |
| 4755 | GCATAAGCGATGGATAATACCTA |
| 4756 | CATAAGCGATGGATAATACCTAA |
| 4757 | ATAAGCGATGGATAATACCTAAT |
| 4758 | TAAGCGATGGATAATACCTAATA |
| 4759 | AAGCGATGGATAATACCTAATAA |
| 4760 | AGCGATGGATAATACCTAATAAA |
| 4761 | GCGATGGATAATACCTAATAAAC |
| 4762 | CGATGGATAATACCTAATAAACT |
| 4763 | GATGGATAATACCTAATAAACTG |
| 4764 | ATGGATAATACCTAATAAACTGC |
| 4765 | TGGATAATACCTAATAAACTGCC |
| 4766 | GGATAATACCTAATAAACTGCCC |
| 4767 | GATAATACCTAATAAACTGCCCT |
| 4768 | ATAATACCTAATAAACTGCCCTC |
| 4769 | TAATACCTAATAAACTGCCCTCA |
| 4770 | AATACCTAATAAACTGCCCTCAG |
| 4771 | ATACCTAATAAACTGCCCTCAGT |
| 4772 | TACCTAATAAACTGCCCTCAGTA |
| 4773 | ACCTAATAAACTGCCCTCAGTAA |
| 4774 | CCTAATAAACTGCCCTCAGTAAA |
| 4775 | CTAATAAACTGCCCTCAGTAAAT |
| 4776 | TAATAAACTGCCCTCAGTAAATC |
| 4777 | AATAAACTGCCCTCAGTAAATCC |
| 4778 | ATAAACTGCCCTCAGTAAATCCA |
| 4779 | TAAACTGCCCTCAGTAAATCCAT |
| 4780 | AAACTGCCCTCAGTAAATCCATG |
| 4781 | AACTGCCCTCAGTAAATCCATGG |
| 4782 | ACTGCCCTCAGTAAATCCATGGT |
| 4783 | CTGCCCTCAGTAAATCCATGGTT |
| 4784 | TGCCCTCAGTAAATCCATGGTTA |
| 4785 | GCCCTCAGTAAATCCATGGTTAA |
| 4786 | CCCTCAGTAAATCCATGGTTAAT |
| 4787 | CCTCAGTAAATCCATGGTTAATA |
| 4788 | CTCAGTAAATCCATGGTTAATAA |
| 4789 | TCAGTAAATCCATGGTTAATAAA |
| 4790 | CAGTAAATCCATGGTTAATAAAT |
| 4791 | AGTAAATCCATGGTTAATAAATG |
| 4792 | GTAAATCCATGGTTAATAAATGT |
| 4793 | TAAATCCATGGTTAATAAATGTG |
| 4794 | AAATCCATGGTTAATAAATGTGG |
| 4795 | AATCCATGGTTAATAAATGTGGT |
| 4796 | ATCCATGGTTAATAAATGTGGTT |
| 4797 | TCCATGGTTAATAAATGTGGTTT |
| 4798 | CCATGGTTAATAAATGTGGTTTC |
| 4799 | CATGGTTAATAAATGTGGTTTCT |
| 4800 | ATGGTTAATAAATGTGGTTTCTA |
| 4801 | TGGTTAATAAATGTGGTTTCTAC |
| 4802 | GGTTAATAAATGTGGTTTCTACA |
| 4803 | GTTAATAAATGTGGTTTCTACAT |
| 4804 | TTAATAAATGTGGTTTCTACATT |

| ID | SEQUENCE |
|---|---|
| 1 | GCGGCCGCAGCAGCCTCCGCCCC |
| 2 | CGGCCGCAGCAGCCTCCGCCCCC |
| 3 | CCCCCCGCACGGTGTGAGCGCCC |
| 4 | CCCCCGCACGGTGTGAGCGCCCG |
| 5 | CCCCGCACGGTGTGAGCGCCCGA |
| 6 | CCCGCACGGTGTGAGCGCCCGAC |
| 7 | CCGCACGGTGTGAGCGCCCGACG |
| 8 | CGCACGGTGTGAGCGCCCGACGC |
| 9 | GCACGGTGTGAGCGCCCGACGCG |
| 10 | CACGGTGTGAGCGCCCGACGCGG |
| 11 | ACGGTGTGAGCGCCCGACGCGGC |
| 12 | CGGTGTGAGCGCCCGACGCGGCC |
| 13 | GGTGTGAGCGCCCGACGCGGCCG |
| 14 | GTGTGAGCGCCCGACGCGGCCGA |
| 15 | TGTGAGCGCCCGACGCGGCCGAG |
| 16 | GTGAGCGCCCGACGCGGCCGAGG |
| 17 | TGAGCGCCCGACGCGGCCGAGGC |
| 18 | GAGCGCCCGACGCGGCCGAGGCG |
| 19 | AGCGCCCGACGCGGCCGAGGCGG |
| 20 | GCGCCCGACGCGGCCGAGGCGGC |
| 21 | CGCCCGACGCGGCCGAGGCGGCC |
| 22 | GCCCGACGCGGCCGAGGCGGCCG |
| 23 | GCGGCCGGAGTCCCGAGCTAGCC |
| 24 | CGGCCGGAGTCCCGAGCTAGCCC |
| 25 | GGCCGGAGTCCCGAGCTAGCCCC |
| 26 | GCCGGAGTCCCGAGCTAGCCCCG |
| 27 | CCGGAGTCCCGAGCTAGCCCCGG |
| 28 | CGGAGTCCCGAGCTAGCCCCGGC |
| 29 | CGCCGCCCAGACCGGACGACAGG |
| 30 | GCCGCCCAGACCGGACGACAGGC |
| 31 | CCGCCCAGACCGGACGACAGGCC |
| 32 | CGCCCAGACCGGACGACAGGCCA |
| 33 | GCCCAGACCGGACGACAGGCCAC |
| 34 | CCCAGACCGGACGACAGGCCACC |
| 35 | CCAGACCGGACGACAGGCCACCT |
| 36 | CAGACCGGACGACAGGCCACCTC |
| 37 | AGACCGGACGACAGGCCACCTCG |
| 38 | GACCGGACGACAGGCCACCTCGT |
| 39 | ACCGGACGACAGGCCACCTCGTC |
| 40 | CCGGACGACAGGCCACCTCGTCG |
| 41 | CGGACGACAGGCCACCTCGTCGG |
| 42 | GGACGACAGGCCACCTCGTCGGC |
| 43 | GACGACAGGCCACCTCGTCGGCG |
| 44 | ACGACAGGCCACCTCGTCGGCGT |
| 45 | CGACAGGCCACCTCGTCGGCGTC |
| 46 | GACAGGCCACCTCGTCGGCGTCC |
| 47 | ACAGGCCACCTCGTCGGCGTCCG |
| 48 | CAGGCCACCTCGTCGGCGTCCGC |
| 49 | AGGCCACCTCGTCGGCGTCCGCC |
| 50 | GGCCACCTCGTCGGCGTCCGCCC |
| 51 | GCCACCTCGTCGGCGTCCGCCCG |
| 52 | CCACCTCGTCGGCGTCCGCCCGA |
| 53 | CACCTCGTCGGCGTCCGCCCGAG |
| 54 | ACCTCGTCGGCGTCCGCCCGAGT |
| 55 | CCTCGTCGGCGTCCGCCCGAGTC |
| 56 | CTCGTCGGCGTCCGCCCGAGTCC |
| 57 | TCGTCGGCGTCCGCCCGAGTCCC |
| 58 | CGTCGGCGTCCGCCCGAGTCCCC |

| ID | SEQUENCE |
|---|---|
| 59 | GTCGGCGTCCGCCCGAGTCCCCG |
| 60 | TCGGCGTCCGCCCGAGTCCCCGC |
| 61 | CGGCGTCCGCCCGAGTCCCCGCC |
| 62 | GGCGTCCGCCCGAGTCCCCGCCT |
| 63 | GCGTCCGCCCGAGTCCCCGCCTC |
| 64 | CGTCCGCCCGAGTCCCCGCCTCG |
| 65 | GTCCGCCCGAGTCCCCGCCTCGC |
| 66 | TCCGCCCGAGTCCCCGCCTCGCC |
| 67 | CCGCCCGAGTCCCCGCCTCGCCG |
| 68 | CGCCCGAGTCCCCGCCTCGCCGC |
| 69 | GCCCGAGTCCCCGCCTCGCCGCC |
| 70 | CCCGAGTCCCCGCCTCGCCGCCA |
| 71 | CCGAGTCCCCGCCTCGCCGCCAA |
| 72 | CGAGTCCCCGCCTCGCCGCCAAC |
| 73 | GAGTCCCCGCCTCGCCGCCAACG |
| 74 | AGTCCCCGCCTCGCCGCCAACGC |
| 75 | GTCCCCGCCTCGCCGCCAACGCC |
| 76 | TCCCCGCCTCGCCGCCAACGCCA |
| 77 | CCCCGCCTCGCCGCCAACGCCAC |
| 78 | CCCGCCTCGCCGCCAACGCCACA |
| 79 | CCGCCTCGCCGCCAACGCCACAA |
| 80 | CGCCTCGCCGCCAACGCCACAAC |
| 81 | GCCTCGCCGCCAACGCCACAACC |
| 82 | CCTCGCCGCCAACGCCACAACCA |
| 83 | CTCGCCGCCAACGCCACAACCAC |
| 84 | TCGCCGCCAACGCCACAACCACC |
| 85 | CGCCGCCAACGCCACAACCACCG |
| 86 | GCCGCCAACGCCACAACCACCGC |
| 87 | CCGCCAACGCCACAACCACCGCG |
| 88 | CGCCAACGCCACAACCACCGCGC |
| 89 | GCCAACGCCACAACCACCGCGCA |
| 90 | CCAACGCCACAACCACCGCGCAC |
| 91 | CAACGCCACAACCACCGCGCACG |
| 92 | AACGCCACAACCACCGCGCACGG |
| 93 | ACGCCACAACCACCGCGCACGGC |
| 94 | CGCCACAACCACCGCGCACGGCC |
| 95 | GCCACAACCACCGCGCACGGCCC |
| 96 | CCACAACCACCGCGCACGGCCCC |
| 97 | CACAACCACCGCGCACGGCCCCC |
| 98 | ACAACCACCGCGCACGGCCCCCT |
| 99 | CAACCACCGCGCACGGCCCCCTG |
| 100 | AACCACCGCGCACGGCCCCCTGA |
| 101 | ACCACCGCGCACGGCCCCCTGAC |
| 102 | CCACCGCGCACGGCCCCCTGACT |
| 103 | CACCGCGCACGGCCCCCTGACTC |
| 104 | ACCGCGCACGGCCCCCTGACTCC |
| 105 | CCGCGCACGGCCCCCTGACTCCG |
| 106 | CGCGCACGGCCCCCTGACTCCGT |
| 107 | GCGCACGGCCCCCTGACTCCGTC |
| 108 | CGCACGGCCCCCTGACTCCGTCC |
| 109 | GCACGGCCCCCTGACTCCGTCCA |
| 110 | CACGGCCCCCTGACTCCGTCCAG |
| 111 | ACGGCCCCCTGACTCCGTCCAGT |
| 112 | CGGCCCCCTGACTCCGTCCAGTA |
| 113 | GGCCCCCTGACTCCGTCCAGTAT |
| 114 | GCCCCCTGACTCCGTCCAGTATT |
| 115 | CCCCCTGACTCCGTCCAGTATTG |
| 116 | CCCCTGACTCCGTCCAGTATTGA |

| ID | SEQUENCE |
|---|---|
| 117 | CCCTGACTCCGTCCAGTATTGAT |
| 118 | CCTGACTCCGTCCAGTATTGATC |
| 119 | CTGACTCCGTCCAGTATTGATCG |
| 120 | TGACTCCGTCCAGTATTGATCGG |
| 121 | GACTCCGTCCAGTATTGATCGGG |
| 122 | ACTCCGTCCAGTATTGATCGGGA |
| 123 | CTCCGTCCAGTATTGATCGGGAG |
| 124 | TCCGTCCAGTATTGATCGGGAGA |
| 125 | CCGTCCAGTATTGATCGGGAGAG |
| 126 | CGTCCAGTATTGATCGGGAGAGC |
| 127 | GTCCAGTATTGATCGGGAGAGCC |
| 128 | TCCAGTATTGATCGGGAGAGCCG |
| 129 | CCAGTATTGATCGGGAGAGCCGG |
| 130 | CAGTATTGATCGGGAGAGCCGGA |
| 131 | AGTATTGATCGGGAGAGCCGGAG |
| 132 | GTATTGATCGGGAGAGCCGGAGC |
| 133 | TATTGATCGGGAGAGCCGGAGCG |
| 134 | ATTGATCGGGAGAGCCGGAGCGA |
| 135 | TTGATCGGGAGAGCCGGAGCGAG |
| 136 | TGATCGGGAGAGCCGGAGCGAGC |
| 137 | GATCGGGAGAGCCGGAGCGAGCT |
| 138 | ATCGGGAGAGCCGGAGCGAGCTC |
| 139 | TCGGGAGAGCCGGAGCGAGCTCT |
| 140 | CGGGAGAGCCGGAGCGAGCTCTT |
| 141 | GGGAGAGCCGGAGCGAGCTCTTC |
| 142 | GGAGAGCCGGAGCGAGCTCTTCG |
| 143 | GAGAGCCGGAGCGAGCTCTTCGG |
| 144 | AGAGCCGGAGCGAGCTCTTCGGG |
| 145 | GAGCCGGAGCGAGCTCTTCGGGG |
| 146 | AGCCGGAGCGAGCTCTTCGGGGA |
| 147 | GCCGGAGCGAGCTCTTCGGGGAG |
| 148 | CCGGAGCGAGCTCTTCGGGGAGC |
| 149 | CGGAGCGAGCTCTTCGGGGAGCA |
| 150 | GGAGCGAGCTCTTCGGGGAGCAG |
| 151 | GAGCGAGCTCTTCGGGGAGCAGC |
| 152 | ATGCGACCCTCCGGGACGGCCGG |
| 153 | TGCGACCCTCCGGGACGGCCGGG |
| 154 | GCCGGGGCAGCGCTCCTGGCGCT |
| 155 | CCGGGGCAGCGCTCCTGGCGCTG |
| 156 | CGGGGCAGCGCTCCTGGCGCTGC |
| 157 | GGGGCAGCGCTCCTGGCGCTGCT |
| 158 | GGGCAGCGCTCCTGGCGCTGCTG |
| 159 | GGCAGCGCTCCTGGCGCTGCTGG |
| 160 | GCAGCGCTCCTGGCGCTGCTGGC |
| 161 | CAGCGCTCCTGGCGCTGCTGGCT |
| 162 | AGCGCTCCTGGCGCTGCTGGCTG |
| 163 | GCGCTCCTGGCGCTGCTGGCTGC |
| 164 | CGCTCCTGGCGCTGCTGGCTGCG |
| 165 | GCTCCTGGCGCTGCTGGCTGCGC |
| 166 | CTCCTGGCGCTGCTGGCTGCGCT |
| 167 | TCCTGGCGCTGCTGGCTGCGCTC |
| 168 | CCTGGCGCTGCTGGCTGCGCTCT |
| 169 | CTGGCGCTGCTGGCTGCGCTCTG |
| 170 | TGGCGCTGCTGGCTGCGCTCTGC |
| 171 | GGCGCTGCTGGCTGCGCTCTGCC |
| 172 | GCGCTGCTGGCTGCGCTCTGCCC |
| 173 | CGCTGCTGGCTGCGCTCTGCCCG |
| 174 | GCTGCTGGCTGCGCTCTGCCCGG |

| ID | SEQUENCE |
|---|---|
| 175 | CTGCTGGCTGCGCTCTGCCCGGC |
| 176 | TGCTGGCTGCGCTCTGCCCGGCG |
| 177 | GCTGGCTGCGCTCTGCCCGGCGA |
| 178 | CTGGCTGCGCTCTGCCCGGCGAG |
| 179 | TGGCTGCGCTCTGCCCGGCGAGT |
| 180 | GGCTGCGCTCTGCCCGGCGAGTC |
| 181 | GCTGCGCTCTGCCCGGCGAGTCG |
| 182 | CTGCGCTCTGCCCGGCGAGTCGG |
| 183 | TGCGCTCTGCCCGGCGAGTCGGG |
| 184 | GCGCTCTGCCCGGCGAGTCGGGC |
| 185 | CGCTCTGCCCGGCGAGTCGGGCT |
| 186 | GCTCTGCCCGGCGAGTCGGGCTC |
| 187 | CTCTGCCCGGCGAGTCGGGCTCT |
| 188 | TCTGCCCGGCGAGTCGGGCTCTG |
| 189 | CTGCCCGGCGAGTCGGGCTCTGG |
| 190 | TGCCCGGCGAGTCGGGCTCTGGA |
| 191 | GCCCGGCGAGTCGGGCTCTGGAG |
| 192 | CCCGGCGAGTCGGGCTCTGGAGG |
| 193 | CCGGCGAGTCGGGCTCTGGAGGA |
| 194 | CGGCGAGTCGGGCTCTGGAGGAA |
| 195 | GGCGAGTCGGGCTCTGGAGGAAA |
| 196 | GCGAGTCGGGCTCTGGAGGAAAA |
| 197 | CGAGTCGGGCTCTGGAGGAAAAG |
| 198 | GAGTCGGGCTCTGGAGGAAAAGA |
| 199 | AGTCGGGCTCTGGAGGAAAAGAA |
| 200 | GTCGGGCTCTGGAGGAAAAGAAA |
| 201 | TCGGGCTCTGGAGGAAAAGAAAG |
| 202 | CGGGCTCTGGAGGAAAAGAAAGT |
| 203 | GGGCTCTGGAGGAAAAGAAAGTT |
| 204 | GGCTCTGGAGGAAAAGAAAGTTT |
| 205 | GCTCTGGAGGAAAAGAAAGTTTG |
| 206 | CTCTGGAGGAAAAGAAAGTTTGC |
| 207 | TCTGGAGGAAAAGAAAGTTTGCC |
| 208 | CTGGAGGAAAAGAAAGTTTGCCA |
| 209 | TGGAGGAAAAGAAAGTTTGCCAA |
| 210 | GGAGGAAAAGAAAGTTTGCCAAG |
| 211 | GAGGAAAAGAAAGTTTGCCAAGG |
| 212 | AGGAAAAGAAAGTTTGCCAAGGC |
| 213 | GGAAAAGAAAGTTTGCCAAGGCA |
| 214 | GAAAAGAAAGTTTGCCAAGGCAC |
| 215 | AAAAGAAAGTTTGCCAAGGCACG |
| 216 | AAAGAAAGTTTGCCAAGGCACGA |
| 217 | AAGAAAGTTTGCCAAGGCACGAG |
| 218 | AGAAAGTTTGCCAAGGCACGAGT |
| 219 | GAAAGTTTGCCAAGGCACGAGTA |
| 220 | AAAGTTTGCCAAGGCACGAGTAA |
| 221 | AAGTTTGCCAAGGCACGAGTAAC |
| 222 | AGTTTGCCAAGGCACGAGTAACA |
| 223 | GTTTGCCAAGGCACGAGTAACAA |
| 224 | TTTGCCAAGGCACGAGTAACAAG |
| 225 | TTGCCAAGGCACGAGTAACAAGC |
| 226 | TGCCAAGGCACGAGTAACAAGCT |
| 227 | GCCAAGGCACGAGTAACAAGCTC |
| 228 | CCAAGGCACGAGTAACAAGCTCA |
| 229 | CAAGGCACGAGTAACAAGCTCAC |
| 230 | AAGGCACGAGTAACAAGCTCACG |
| 231 | AGGCACGAGTAACAAGCTCACGC |
| 232 | GGCACGAGTAACAAGCTCACGCA |

| ID | SEQUENCE |
|---|---|
| 233 | GCACGAGTAACAAGCTCACGCAG |
| 234 | CACGAGTAACAAGCTCACGCAGT |
| 235 | ACGAGTAACAAGCTCACGCAGTT |
| 236 | CGAGTAACAAGCTCACGCAGTTG |
| 237 | GAGTAACAAGCTCACGCAGTTGG |
| 238 | AGTAACAAGCTCACGCAGTTGGG |
| 239 | GTAACAAGCTCACGCAGTTGGGC |
| 240 | TAACAAGCTCACGCAGTTGGGCA |
| 241 | AACAAGCTCACGCAGTTGGGCAC |
| 242 | ACAAGCTCACGCAGTTGGGCACT |
| 243 | CAAGCTCACGCAGTTGGGCACTT |
| 244 | AAGCTCACGCAGTTGGGCACTTT |
| 245 | AGCTCACGCAGTTGGGCACTTTT |
| 246 | GCTCACGCAGTTGGGCACTTTTG |
| 247 | CTCACGCAGTTGGGCACTTTTGA |
| 248 | TCACGCAGTTGGGCACTTTTGAA |
| 249 | CACGCAGTTGGGCACTTTTGAAG |
| 250 | ACGCAGTTGGGCACTTTTGAAGA |
| 251 | CGCAGTTGGGCACTTTTGAAGAT |
| 252 | GCAGTTGGGCACTTTTGAAGATC |
| 253 | CAGTTGGGCACTTTTGAAGATCA |
| 254 | AGTTGGGCACTTTTGAAGATCAT |
| 255 | GTTGGGCACTTTTGAAGATCATT |
| 256 | TTGGGCACTTTTGAAGATCATTT |
| 257 | TGGGCACTTTTGAAGATCATTTT |
| 258 | GGGCACTTTTGAAGATCATTTTC |
| 259 | GGCACTTTTGAAGATCATTTTCT |
| 260 | GCACTTTTGAAGATCATTTTCTC |
| 261 | CACTTTTGAAGATCATTTTCTCA |
| 262 | ACTTTTGAAGATCATTTTCTCAG |
| 263 | CTTTTGAAGATCATTTTCTCAGC |
| 264 | TTTTGAAGATCATTTTCTCAGCC |
| 265 | TTTGAAGATCATTTTCTCAGCCT |
| 266 | TTGAAGATCATTTTCTCAGCCTC |
| 267 | TGAAGATCATTTTCTCAGCCTCC |
| 268 | GAAGATCATTTTCTCAGCCTCCA |
| 269 | AAGATCATTTTCTCAGCCTCCAG |
| 270 | AGATCATTTTCTCAGCCTCCAGA |
| 271 | GATCATTTTCTCAGCCTCCAGAG |
| 272 | ATCATTTTCTCAGCCTCCAGAGG |
| 273 | TCATTTTCTCAGCCTCCAGAGGA |
| 274 | CATTTTCTCAGCCTCCAGAGGAT |
| 275 | ATTTTCTCAGCCTCCAGAGGATG |
| 276 | TTTTCTCAGCCTCCAGAGGATGT |
| 277 | TTTCTCAGCCTCCAGAGGATGTT |
| 278 | TTCTCAGCCTCCAGAGGATGTTC |
| 279 | TCTCAGCCTCCAGAGGATGTTCA |
| 280 | CTCAGCCTCCAGAGGATGTTCAA |
| 281 | TCAGCCTCCAGAGGATGTTCAAT |
| 282 | CAGCCTCCAGAGGATGTTCAATA |
| 283 | AGCCTCCAGAGGATGTTCAATAA |
| 284 | GCCTCCAGAGGATGTTCAATAAC |
| 285 | CCTCCAGAGGATGTTCAATAACT |
| 286 | CTCCAGAGGATGTTCAATAACTG |
| 287 | TCCAGAGGATGTTCAATAACTGT |
| 288 | CCAGAGGATGTTCAATAACTGTG |
| 289 | CAGAGGATGTTCAATAACTGTGA |
| 290 | AGAGGATGTTCAATAACTGTGAG |

| ID | SEQUENCE |
|---|---|
| 291 | GAGGATGTTCAATAACTGTGAGG |
| 292 | AGGATGTTCAATAACTGTGAGGT |
| 293 | GGATGTTCAATAACTGTGAGGTG |
| 294 | GATGTTCAATAACTGTGAGGTGG |
| 295 | ATGTTCAATAACTGTGAGGTGGT |
| 296 | TGTTCAATAACTGTGAGGTGGTC |
| 297 | GTTCAATAACTGTGAGGTGGTCC |
| 298 | TTCAATAACTGTGAGGTGGTCCT |
| 299 | TCAATAACTGTGAGGTGGTCCTT |
| 300 | CAATAACTGTGAGGTGGTCCTTG |
| 301 | AATAACTGTGAGGTGGTCCTTGG |
| 302 | ATAACTGTGAGGTGGTCCTTGGG |
| 303 | TAACTGTGAGGTGGTCCTTGGGA |
| 304 | AACTGTGAGGTGGTCCTTGGGAA |
| 305 | ACTGTGAGGTGGTCCTTGGGAAT |
| 306 | CTGTGAGGTGGTCCTTGGGAATT |
| 307 | TGTGAGGTGGTCCTTGGGAATTT |
| 308 | GTGAGGTGGTCCTTGGGAATTTG |
| 309 | TGAGGTGGTCCTTGGGAATTTGG |
| 310 | GAGGTGGTCCTTGGGAATTTGGA |
| 311 | AGGTGGTCCTTGGGAATTTGGAA |
| 312 | GGTGGTCCTTGGGAATTTGGAAA |
| 313 | GTGGTCCTTGGGAATTTGGAAAT |
| 314 | TGGTCCTTGGGAATTTGGAAATT |
| 315 | GGTCCTTGGGAATTTGGAAATTA |
| 316 | GTCCTTGGGAATTTGGAAATTAC |
| 317 | TCCTTGGGAATTTGGAAATTACC |
| 318 | CCTTGGGAATTTGGAAATTACCT |
| 319 | CTTGGGAATTTGGAAATTACCTA |
| 320 | TTGGGAATTTGGAAATTACCTAT |
| 321 | TGGGAATTTGGAAATTACCTATG |
| 322 | GGGAATTTGGAAATTACCTATGT |
| 323 | GGAATTTGGAAATTACCTATGTG |
| 324 | GAATTTGGAAATTACCTATGTGC |
| 325 | AATTTGGAAATTACCTATGTGCA |
| 326 | ATTTGGAAATTACCTATGTGCAG |
| 327 | TTTGGAAATTACCTATGTGCAGA |
| 328 | TTGGAAATTACCTATGTGCAGAG |
| 329 | TGGAAATTACCTATGTGCAGAGG |
| 330 | GGAAATTACCTATGTGCAGAGGA |
| 331 | GAAATTACCTATGTGCAGAGGAA |
| 332 | AAATTACCTATGTGCAGAGGAAT |
| 333 | AATTACCTATGTGCAGAGGAATT |
| 334 | ATTACCTATGTGCAGAGGAATTA |
| 335 | TTACCTATGTGCAGAGGAATTAT |
| 336 | TACCTATGTGCAGAGGAATTATG |
| 337 | ACCTATGTGCAGAGGAATTATGA |
| 338 | CCTATGTGCAGAGGAATTATGAT |
| 339 | CTATGTGCAGAGGAATTATGATC |
| 340 | TATGTGCAGAGGAATTATGATCT |
| 341 | ATGTGCAGAGGAATTATGATCTT |
| 342 | TGTGCAGAGGAATTATGATCTTT |
| 343 | GTGCAGAGGAATTATGATCTTTC |
| 344 | TGCAGAGGAATTATGATCTTTCC |
| 345 | GCAGAGGAATTATGATCTTTCCT |
| 346 | CAGAGGAATTATGATCTTTCCTT |
| 347 | AGAGGAATTATGATCTTTCCTTC |
| 348 | GAGGAATTATGATCTTTCCTTCT |

| ID | SEQUENCE |
|---|---|
| 349 | AGGAATTATGATCTTTCCTTCTT |
| 350 | GGAATTATGATCTTTCCTTCTTA |
| 351 | GAATTATGATCTTTCCTTCTTAA |
| 352 | AATTATGATCTTTCCTTCTTAAA |
| 353 | ATTATGATCTTTCCTTCTTAAAG |
| 354 | TTATGATCTTTCCTTCTTAAAGA |
| 355 | TATGATCTTTCCTTCTTAAAGAC |
| 356 | ATGATCTTTCCTTCTTAAAGACC |
| 357 | TGATCTTTCCTTCTTAAAGACCA |
| 358 | GATCTTTCCTTCTTAAAGACCAT |
| 359 | ATCTTTCCTTCTTAAAGACCATC |
| 360 | TCTTTCCTTCTTAAAGACCATCC |
| 361 | CTTTCCTTCTTAAAGACCATCCA |
| 362 | TTTCCTTCTTAAAGACCATCCAG |
| 363 | TTCCTTCTTAAAGACCATCCAGG |
| 364 | TCCTTCTTAAAGACCATCCAGGA |
| 365 | CCTTCTTAAAGACCATCCAGGAG |
| 366 | CTTCTTAAAGACCATCCAGGAGG |
| 367 | TTCTTAAAGACCATCCAGGAGGT |
| 368 | TCTTAAAGACCATCCAGGAGGTG |
| 369 | CTTAAAGACCATCCAGGAGGTGG |
| 370 | TTAAAGACCATCCAGGAGGTGGC |
| 371 | TAAAGACCATCCAGGAGGTGGCT |
| 372 | AAAGACCATCCAGGAGGTGGCTG |
| 373 | AAGACCATCCAGGAGGTGGCTGG |
| 374 | AGACCATCCAGGAGGTGGCTGGT |
| 375 | GACCATCCAGGAGGTGGCTGGTT |
| 376 | ACCATCCAGGAGGTGGCTGGTTA |
| 377 | CCATCCAGGAGGTGGCTGGTTAT |
| 378 | CATCCAGGAGGTGGCTGGTTATG |
| 379 | ATCCAGGAGGTGGCTGGTTATGT |
| 380 | TCCAGGAGGTGGCTGGTTATGTC |
| 381 | CCAGGAGGTGGCTGGTTATGTCC |
| 382 | CAGGAGGTGGCTGGTTATGTCCT |
| 383 | AGGAGGTGGCTGGTTATGTCCTC |
| 384 | GGAGGTGGCTGGTTATGTCCTCA |
| 385 | GAGGTGGCTGGTTATGTCCTCAT |
| 386 | AGGTGGCTGGTTATGTCCTCATT |
| 387 | GGTGGCTGGTTATGTCCTCATTG |
| 388 | GTGGCTGGTTATGTCCTCATTGC |
| 389 | TGGCTGGTTATGTCCTCATTGCC |
| 390 | GGCTGGTTATGTCCTCATTGCCC |
| 391 | GCTGGTTATGTCCTCATTGCCCT |
| 392 | CTGGTTATGTCCTCATTGCCCTC |
| 393 | TGGTTATGTCCTCATTGCCCTCA |
| 394 | GGTTATGTCCTCATTGCCCTCAA |
| 395 | GTTATGTCCTCATTGCCCTCAAC |
| 396 | TTATGTCCTCATTGCCCTCAACA |
| 397 | TATGTCCTCATTGCCCTCAACAC |
| 398 | ATGTCCTCATTGCCCTCAACACA |
| 399 | TGTCCTCATTGCCCTCAACACAG |
| 400 | GTCCTCATTGCCCTCAACACAGT |
| 401 | TCCTCATTGCCCTCAACACAGTG |
| 402 | CCTCATTGCCCTCAACACAGTGG |
| 403 | CTCATTGCCCTCAACACAGTGGA |
| 404 | TCATTGCCCTCAACACAGTGGAG |
| 405 | CATTGCCCTCAACACAGTGGAGC |
| 406 | ATTGCCCTCAACACAGTGGAGCG |

| ID | SEQUENCE |
|---|---|
| 407 | TTGCCCTCAACACAGTGGAGCGA |
| 408 | TGCCCTCAACACAGTGGAGCGAA |
| 409 | GCCCTCAACACAGTGGAGCGAAT |
| 410 | CCCTCAACACAGTGGAGCGAATT |
| 411 | CCTCAACACAGTGGAGCGAATTC |
| 412 | CTCAACACAGTGGAGCGAATTCC |
| 413 | TCAACACAGTGGAGCGAATTCCT |
| 414 | CAACACAGTGGAGCGAATTCCTT |
| 415 | AACACAGTGGAGCGAATTCCTTT |
| 416 | ACACAGTGGAGCGAATTCCTTTG |
| 417 | CACAGTGGAGCGAATTCCTTTGG |
| 418 | ACAGTGGAGCGAATTCCTTTGGA |
| 419 | CAGTGGAGCGAATTCCTTTGGAA |
| 420 | AGTGGAGCGAATTCCTTTGGAAA |
| 421 | GTGGAGCGAATTCCTTTGGAAAA |
| 422 | TGGAGCGAATTCCTTTGGAAAAC |
| 423 | GGAGCGAATTCCTTTGGAAAACC |
| 424 | GAGCGAATTCCTTTGGAAAACCT |
| 425 | AGCGAATTCCTTTGGAAAACCTG |
| 426 | GCGAATTCCTTTGGAAAACCTGC |
| 427 | CGAATTCCTTTGGAAAACCTGCA |
| 428 | GAATTCCTTTGGAAAACCTGCAG |
| 429 | AATTCCTTTGGAAAACCTGCAGA |
| 430 | ATTCCTTTGGAAAACCTGCAGAT |
| 431 | TTCCTTTGGAAAACCTGCAGATC |
| 432 | TCCTTTGGAAAACCTGCAGATCA |
| 433 | CCTTTGGAAAACCTGCAGATCAT |
| 434 | CTTTGGAAAACCTGCAGATCATC |
| 435 | TTTGGAAAACCTGCAGATCATCA |
| 436 | TTGGAAAACCTGCAGATCATCAG |
| 437 | TGGAAAACCTGCAGATCATCAGA |
| 438 | GGAAAACCTGCAGATCATCAGAG |
| 439 | GAAAACCTGCAGATCATCAGAGG |
| 440 | AAAACCTGCAGATCATCAGAGGA |
| 441 | AAACCTGCAGATCATCAGAGGAA |
| 442 | AACCTGCAGATCATCAGAGGAAA |
| 443 | ACCTGCAGATCATCAGAGGAAAT |
| 444 | CCTGCAGATCATCAGAGGAAATA |
| 445 | CTGCAGATCATCAGAGGAAATAT |
| 446 | TGCAGATCATCAGAGGAAATATG |
| 447 | GCAGATCATCAGAGGAAATATGT |
| 448 | CAGATCATCAGAGGAAATATGTA |
| 449 | AGATCATCAGAGGAAATATGTAC |
| 450 | GATCATCAGAGGAAATATGTACT |
| 451 | ATCATCAGAGGAAATATGTACTA |
| 452 | TCATCAGAGGAAATATGTACTAC |
| 453 | CATCAGAGGAAATATGTACTACG |
| 454 | ATCAGAGGAAATATGTACTACGA |
| 455 | TCAGAGGAAATATGTACTACGAA |
| 456 | CAGAGGAAATATGTACTACGAAA |
| 457 | AGAGGAAATATGTACTACGAAAA |
| 458 | GAGGAAATATGTACTACGAAAAT |
| 459 | AGGAAATATGTACTACGAAAATT |
| 460 | GGAAATATGTACTACGAAAATTC |
| 461 | GAAATATGTACTACGAAAATTCC |
| 462 | AAATATGTACTACGAAAATTCCT |
| 463 | AATATGTACTACGAAAATTCCTA |
| 464 | ATATGTACTACGAAAATTCCTAT |

| ID | SEQUENCE |
|---|---|
| 465 | TATGTACTACGAAAATTCCTATG |
| 466 | ATGTACTACGAAAATTCCTATGC |
| 467 | TGTACTACGAAAATTCCTATGCC |
| 468 | GTACTACGAAAATTCCTATGCCT |
| 469 | TACTACGAAAATTCCTATGCCTT |
| 470 | ACTACGAAAATTCCTATGCCTTA |
| 471 | CTACGAAAATTCCTATGCCTTAG |
| 472 | TACGAAAATTCCTATGCCTTAGC |
| 473 | ACGAAAATTCCTATGCCTTAGCA |
| 474 | CGAAAATTCCTATGCCTTAGCAG |
| 475 | GAAAATTCCTATGCCTTAGCAGT |
| 476 | AAAATTCCTATGCCTTAGCAGTC |
| 477 | AAATTCCTATGCCTTAGCAGTCT |
| 478 | AATTCCTATGCCTTAGCAGTCTT |
| 479 | ATTCCTATGCCTTAGCAGTCTTA |
| 480 | TTCCTATGCCTTAGCAGTCTTAT |
| 481 | TCCTATGCCTTAGCAGTCTTATC |
| 482 | CCTATGCCTTAGCAGTCTTATCT |
| 483 | CTATGCCTTAGCAGTCTTATCTA |
| 484 | TATGCCTTAGCAGTCTTATCTAA |
| 485 | ATGCCTTAGCAGTCTTATCTAAC |
| 486 | TGCCTTAGCAGTCTTATCTAACT |
| 487 | GCCTTAGCAGTCTTATCTAACTA |
| 488 | CCTTAGCAGTCTTATCTAACTAT |
| 489 | CTTAGCAGTCTTATCTAACTATG |
| 490 | TTAGCAGTCTTATCTAACTATGA |
| 491 | TAGCAGTCTTATCTAACTATGAT |
| 492 | AGCAGTCTTATCTAACTATGATG |
| 493 | GCAGTCTTATCTAACTATGATGC |
| 494 | CAGTCTTATCTAACTATGATGCA |
| 495 | AGTCTTATCTAACTATGATGCAA |
| 496 | GTCTTATCTAACTATGATGCAAA |
| 497 | TCTTATCTAACTATGATGCAAAT |
| 498 | CTTATCTAACTATGATGCAAATA |
| 499 | TTATCTAACTATGATGCAAATAA |
| 500 | TATCTAACTATGATGCAAATAAA |
| 501 | ATCTAACTATGATGCAAATAAAA |
| 502 | TCTAACTATGATGCAAATAAAAC |
| 503 | CTAACTATGATGCAAATAAAACC |
| 504 | TAACTATGATGCAAATAAAACCG |
| 505 | AACTATGATGCAAATAAAACCGG |
| 506 | ACTATGATGCAAATAAAACCGGA |
| 507 | CTATGATGCAAATAAAACCGGAC |
| 508 | TATGATGCAAATAAAACCGGACT |
| 509 | ATGATGCAAATAAAACCGGACTG |
| 510 | TGATGCAAATAAAACCGGACTGA |
| 511 | GATGCAAATAAAACCGGACTGAA |
| 512 | ATGCAAATAAAACCGGACTGAAG |
| 513 | TGCAAATAAAACCGGACTGAAGG |
| 514 | GCAAATAAAACCGGACTGAAGGA |
| 515 | CAAATAAAACCGGACTGAAGGAG |
| 516 | AAATAAAACCGGACTGAAGGAGC |
| 517 | AATAAAACCGGACTGAAGGAGCT |
| 518 | ATAAAACCGGACTGAAGGAGCTG |
| 519 | TAAAACCGGACTGAAGGAGCTGC |
| 520 | AAAACCGGACTGAAGGAGCTGCC |
| 521 | AAACCGGACTGAAGGAGCTGCCC |
| 522 | AACCGGACTGAAGGAGCTGCCCA |

| ID | SEQUENCE |
|---|---|
| 523 | ACCGGACTGAAGGAGCTGCCCAT |
| 524 | CCGGACTGAAGGAGCTGCCCATG |
| 525 | CGGACTGAAGGAGCTGCCCATGA |
| 526 | GGACTGAAGGAGCTGCCCATGAG |
| 527 | GACTGAAGGAGCTGCCCATGAGA |
| 528 | ACTGAAGGAGCTGCCCATGAGAA |
| 529 | CTGAAGGAGCTGCCCATGAGAAA |
| 530 | TGAAGGAGCTGCCCATGAGAAAT |
| 531 | GAAGGAGCTGCCCATGAGAAATT |
| 532 | AAGGAGCTGCCCATGAGAAATTT |
| 533 | AGGAGCTGCCCATGAGAAATTTA |
| 534 | GGAGCTGCCCATGAGAAATTTAC |
| 535 | GAGCTGCCCATGAGAAATTTACA |
| 536 | AGCTGCCCATGAGAAATTTACAG |
| 537 | GCTGCCCATGAGAAATTTACAGG |
| 538 | CTGCCCATGAGAAATTTACAGGA |
| 539 | TGCCCATGAGAAATTTACAGGAA |
| 540 | GCCCATGAGAAATTTACAGGAAA |
| 541 | CCCATGAGAAATTTACAGGAAAT |
| 542 | CCATGAGAAATTTACAGGAAATC |
| 543 | CATGAGAAATTTACAGGAAATCC |
| 544 | ATGAGAAATTTACAGGAAATCCT |
| 545 | TGAGAAATTTACAGGAAATCCTG |
| 546 | GAGAAATTTACAGGAAATCCTGC |
| 547 | AGAAATTTACAGGAAATCCTGCA |
| 548 | GAAATTTACAGGAAATCCTGCAT |
| 549 | AAATTTACAGGAAATCCTGCATG |
| 550 | AATTTACAGGAAATCCTGCATGG |
| 551 | ATTTACAGGAAATCCTGCATGGC |
| 552 | TTTACAGGAAATCCTGCATGGCG |
| 553 | TTACAGGAAATCCTGCATGGCGC |
| 554 | TACAGGAAATCCTGCATGGCGCC |
| 555 | ACAGGAAATCCTGCATGGCGCCG |
| 556 | CAGGAAATCCTGCATGGCGCCGT |
| 557 | AGGAAATCCTGCATGGCGCCGTG |
| 558 | GGAAATCCTGCATGGCGCCGTGC |
| 559 | GAAATCCTGCATGGCGCCGTGCG |
| 560 | AAATCCTGCATGGCGCCGTGCGG |
| 561 | AATCCTGCATGGCGCCGTGCGGT |
| 562 | ATCCTGCATGGCGCCGTGCGGTT |
| 563 | TCCTGCATGGCGCCGTGCGGTTC |
| 564 | CCTGCATGGCGCCGTGCGGTTCA |
| 565 | CTGCATGGCGCCGTGCGGTTCAG |
| 566 | TGCATGGCGCCGTGCGGTTCAGC |
| 567 | GCATGGCGCCGTGCGGTTCAGCA |
| 568 | CATGGCGCCGTGCGGTTCAGCAA |
| 569 | ATGGCGCCGTGCGGTTCAGCAAC |
| 570 | TGGCGCCGTGCGGTTCAGCAACA |
| 571 | GGCGCCGTGCGGTTCAGCAACAA |
| 572 | GCGCCGTGCGGTTCAGCAACAAC |
| 573 | CGCCGTGCGGTTCAGCAACAACC |
| 574 | GCCGTGCGGTTCAGCAACAACCC |
| 575 | CCGTGCGGTTCAGCAACAACCCT |
| 576 | CGTGCGGTTCAGCAACAACCCTG |
| 577 | GTGCGGTTCAGCAACAACCCTGC |
| 578 | TGCGGTTCAGCAACAACCCTGCC |
| 579 | GCGGTTCAGCAACAACCCTGCCC |
| 580 | CGGTTCAGCAACAACCCTGCCCT |

| ID | SEQUENCE |
|---|---|
| 581 | GGTTCAGCAACAACCCTGCCCTG |
| 582 | GTTCAGCAACAACCCTGCCCTGT |
| 583 | TTCAGCAACAACCCTGCCCTGTG |
| 584 | TCAGCAACAACCCTGCCCTGTGC |
| 585 | CAGCAACAACCCTGCCCTGTGCA |
| 586 | AGCAACAACCCTGCCCTGTGCAA |
| 587 | GCAACAACCCTGCCCTGTGCAAC |
| 588 | CAACAACCCTGCCCTGTGCAACG |
| 589 | AACAACCCTGCCCTGTGCAACGT |
| 590 | ACAACCCTGCCCTGTGCAACGTG |
| 591 | CAACCCTGCCCTGTGCAACGTGG |
| 592 | AACCCTGCCCTGTGCAACGTGGA |
| 593 | ACCCTGCCCTGTGCAACGTGGAG |
| 594 | CCCTGCCCTGTGCAACGTGGAGA |
| 595 | CCTGCCCTGTGCAACGTGGAGAG |
| 596 | CTGCCCTGTGCAACGTGGAGAGC |
| 597 | TGCCCTGTGCAACGTGGAGAGCA |
| 598 | GCCCTGTGCAACGTGGAGAGCAT |
| 599 | CCCTGTGCAACGTGGAGAGCATC |
| 600 | CCTGTGCAACGTGGAGAGCATCC |
| 601 | CTGTGCAACGTGGAGAGCATCCA |
| 602 | TGTGCAACGTGGAGAGCATCCAG |
| 603 | GTGCAACGTGGAGAGCATCCAGT |
| 604 | TGCAACGTGGAGAGCATCCAGTG |
| 605 | GCAACGTGGAGAGCATCCAGTGG |
| 606 | CAACGTGGAGAGCATCCAGTGGC |
| 607 | AACGTGGAGAGCATCCAGTGGCG |
| 608 | ACGTGGAGAGCATCCAGTGGCGG |
| 609 | CGTGGAGAGCATCCAGTGGCGGG |
| 610 | GTGGAGAGCATCCAGTGGCGGGA |
| 611 | TGGAGAGCATCCAGTGGCGGGAC |
| 612 | GGAGAGCATCCAGTGGCGGGACA |
| 613 | GAGAGCATCCAGTGGCGGGACAT |
| 614 | AGAGCATCCAGTGGCGGGACATA |
| 615 | GAGCATCCAGTGGCGGGACATAG |
| 616 | AGCATCCAGTGGCGGGACATAGT |
| 617 | GCATCCAGTGGCGGGACATAGTC |
| 618 | CATCCAGTGGCGGGACATAGTCA |
| 619 | ATCCAGTGGCGGGACATAGTCAG |
| 620 | TCCAGTGGCGGGACATAGTCAGC |
| 621 | CCAGTGGCGGGACATAGTCAGCA |
| 622 | CAGTGGCGGGACATAGTCAGCAG |
| 623 | AGTGGCGGGACATAGTCAGCAGT |
| 624 | GTGGCGGGACATAGTCAGCAGTG |
| 625 | TGGCGGGACATAGTCAGCAGTGA |
| 626 | GGCGGGACATAGTCAGCAGTGAC |
| 627 | GCGGGACATAGTCAGCAGTGACT |
| 628 | CGGGACATAGTCAGCAGTGACTT |
| 629 | GGGACATAGTCAGCAGTGACTTT |
| 630 | GGACATAGTCAGCAGTGACTTTC |
| 631 | GACATAGTCAGCAGTGACTTTCT |
| 632 | ACATAGTCAGCAGTGACTTTCTC |
| 633 | CATAGTCAGCAGTGACTTTCTCA |
| 634 | ATAGTCAGCAGTGACTTTCTCAG |
| 635 | TAGTCAGCAGTGACTTTCTCAGC |
| 636 | AGTCAGCAGTGACTTTCTCAGCA |
| 637 | GTCAGCAGTGACTTTCTCAGCAA |
| 638 | TCAGCAGTGACTTTCTCAGCAAC |

| ID | SEQUENCE |
|---|---|
| 639 | CAGCAGTGACTTTCTCAGCAACA |
| 640 | AGCAGTGACTTTCTCAGCAACAT |
| 641 | GCAGTGACTTTCTCAGCAACATG |
| 642 | CAGTGACTTTCTCAGCAACATGT |
| 643 | AGTGACTTTCTCAGCAACATGTC |
| 644 | GTGACTTTCTCAGCAACATGTCG |
| 645 | TGACTTTCTCAGCAACATGTCGA |
| 646 | GACTTTCTCAGCAACATGTCGAT |
| 647 | ACTTTCTCAGCAACATGTCGATG |
| 648 | CTTTCTCAGCAACATGTCGATGG |
| 649 | TTTCTCAGCAACATGTCGATGGA |
| 650 | TTCTCAGCAACATGTCGATGGAC |
| 651 | TCTCAGCAACATGTCGATGGACT |
| 652 | CTCAGCAACATGTCGATGGACTT |
| 653 | TCAGCAACATGTCGATGGACTTC |
| 654 | CAGCAACATGTCGATGGACTTCC |
| 655 | AGCAACATGTCGATGGACTTCCA |
| 656 | GCAACATGTCGATGGACTTCCAG |
| 657 | CAACATGTCGATGGACTTCCAGA |
| 658 | AACATGTCGATGGACTTCCAGAA |
| 659 | ACATGTCGATGGACTTCCAGAAC |
| 660 | CATGTCGATGGACTTCCAGAACC |
| 661 | ATGTCGATGGACTTCCAGAACCA |
| 662 | TGTCGATGGACTTCCAGAACCAC |
| 663 | GTCGATGGACTTCCAGAACCACC |
| 664 | TCGATGGACTTCCAGAACCACCT |
| 665 | CGATGGACTTCCAGAACCACCTG |
| 666 | GATGGACTTCCAGAACCACCTGG |
| 667 | ATGGACTTCCAGAACCACCTGGG |
| 668 | TGGACTTCCAGAACCACCTGGGC |
| 669 | GGACTTCCAGAACCACCTGGGCA |
| 670 | GACTTCCAGAACCACCTGGGCAG |
| 671 | ACTTCCAGAACCACCTGGGCAGC |
| 672 | CTTCCAGAACCACCTGGGCAGCT |
| 673 | TTCCAGAACCACCTGGGCAGCTG |
| 674 | TCCAGAACCACCTGGGCAGCTGC |
| 675 | CCAGAACCACCTGGGCAGCTGCC |
| 676 | CAGAACCACCTGGGCAGCTGCCA |
| 677 | AGAACCACCTGGGCAGCTGCCAA |
| 678 | GAACCACCTGGGCAGCTGCCAAA |
| 679 | AACCACCTGGGCAGCTGCCAAAA |
| 680 | ACCACCTGGGCAGCTGCCAAAAG |
| 681 | CCACCTGGGCAGCTGCCAAAAGT |
| 682 | CACCTGGGCAGCTGCCAAAAGTG |
| 683 | ACCTGGGCAGCTGCCAAAAGTGT |
| 684 | CCTGGGCAGCTGCCAAAAGTGTG |
| 685 | CTGGGCAGCTGCCAAAAGTGTGA |
| 686 | TGGGCAGCTGCCAAAAGTGTGAT |
| 687 | GGGCAGCTGCCAAAAGTGTGATC |
| 688 | GGCAGCTGCCAAAAGTGTGATCC |
| 689 | GCAGCTGCCAAAAGTGTGATCCA |
| 690 | CAGCTGCCAAAAGTGTGATCCAA |
| 691 | AGCTGCCAAAAGTGTGATCCAAG |
| 692 | GCTGCCAAAAGTGTGATCCAAGC |
| 693 | CTGCCAAAAGTGTGATCCAAGCT |
| 694 | TGCCAAAAGTGTGATCCAAGCTG |
| 695 | GCCAAAAGTGTGATCCAAGCTGT |
| 696 | CCAAAAGTGTGATCCAAGCTGTC |

| ID | SEQUENCE |
|---|---|
| 697 | CAAAAGTGTGATCCAAGCTGTCC |
| 698 | AAAAGTGTGATCCAAGCTGTCCC |
| 699 | AAAGTGTGATCCAAGCTGTCCCA |
| 700 | AAGTGTGATCCAAGCTGTCCCAA |
| 701 | AGTGTGATCCAAGCTGTCCCAAT |
| 702 | GTGTGATCCAAGCTGTCCCAATG |
| 703 | TGTGATCCAAGCTGTCCCAATGG |
| 704 | GTGATCCAAGCTGTCCCAATGGG |
| 705 | TGATCCAAGCTGTCCCAATGGGA |
| 706 | GATCCAAGCTGTCCCAATGGGAG |
| 707 | ATCCAAGCTGTCCCAATGGGAGC |
| 708 | TCCAAGCTGTCCCAATGGGAGCT |
| 709 | CCAAGCTGTCCCAATGGGAGCTG |
| 710 | CAAGCTGTCCCAATGGGAGCTGC |
| 711 | AAGCTGTCCCAATGGGAGCTGCT |
| 712 | AGCTGTCCCAATGGGAGCTGCTG |
| 713 | GCTGTCCCAATGGGAGCTGCTGG |
| 714 | CTGTCCCAATGGGAGCTGCTGGG |
| 715 | TGTCCCAATGGGAGCTGCTGGGG |
| 716 | GTCCCAATGGGAGCTGCTGGGGT |
| 717 | TCCCAATGGGAGCTGCTGGGGTG |
| 718 | CCCAATGGGAGCTGCTGGGGTGC |
| 719 | CCAATGGGAGCTGCTGGGGTGCA |
| 720 | CAATGGGAGCTGCTGGGGTGCAG |
| 721 | AATGGGAGCTGCTGGGGTGCAGG |
| 722 | ATGGGAGCTGCTGGGGTGCAGGA |
| 723 | TGGGAGCTGCTGGGGTGCAGGAG |
| 724 | GGGAGCTGCTGGGGTGCAGGAGA |
| 725 | GGAGCTGCTGGGGTGCAGGAGAG |
| 726 | GAGCTGCTGGGGTGCAGGAGAGG |
| 727 | AGCTGCTGGGGTGCAGGAGAGGA |
| 728 | GCTGCTGGGGTGCAGGAGAGGAG |
| 729 | CTGCTGGGGTGCAGGAGAGGAGA |
| 730 | TGCTGGGGTGCAGGAGAGGAGAA |
| 731 | GCTGGGGTGCAGGAGAGGAGAAC |
| 732 | CTGGGGTGCAGGAGAGGAGAACT |
| 733 | TGGGGTGCAGGAGAGGAGAACTG |
| 734 | GGGGTGCAGGAGAGGAGAACTGC |
| 735 | GGGTGCAGGAGAGGAGAACTGCC |
| 736 | GGTGCAGGAGAGGAGAACTGCCA |
| 737 | GTGCAGGAGAGGAGAACTGCCAG |
| 738 | TGCAGGAGAGGAGAACTGCCAGA |
| 739 | GCAGGAGAGGAGAACTGCCAGAA |
| 740 | CAGGAGAGGAGAACTGCCAGAAA |
| 741 | AGGAGAGGAGAACTGCCAGAAAC |
| 742 | GGAGAGGAGAACTGCCAGAAACT |
| 743 | GAGAGGAGAACTGCCAGAAACTG |
| 744 | AGAGGAGAACTGCCAGAAACTGA |
| 745 | GAGGAGAACTGCCAGAAACTGAC |
| 746 | AGGAGAACTGCCAGAAACTGACC |
| 747 | GGAGAACTGCCAGAAACTGACCA |
| 748 | GAGAACTGCCAGAAACTGACCAA |
| 749 | AGAACTGCCAGAAACTGACCAAA |
| 750 | GAACTGCCAGAAACTGACCAAAA |
| 751 | AACTGCCAGAAACTGACCAAAAT |
| 752 | ACTGCCAGAAACTGACCAAAATC |
| 753 | CTGCCAGAAACTGACCAAAATCA |
| 754 | TGCCAGAAACTGACCAAAATCAT |

| ID | SEQUENCE |
|---|---|
| 755 | GCCAGAAACTGACCAAAATCATC |
| 756 | CCAGAAACTGACCAAAATCATCT |
| 757 | CAGAAACTGACCAAAATCATCTG |
| 758 | AGAAACTGACCAAAATCATCTGT |
| 759 | GAAACTGACCAAAATCATCTGTG |
| 760 | AAACTGACCAAAATCATCTGTGC |
| 761 | AACTGACCAAAATCATCTGTGCC |
| 762 | ACTGACCAAAATCATCTGTGCCC |
| 763 | CTGACCAAAATCATCTGTGCCCA |
| 764 | TGACCAAAATCATCTGTGCCCAG |
| 765 | GACCAAAATCATCTGTGCCCAGC |
| 766 | ACCAAAATCATCTGTGCCCAGCA |
| 767 | CCAAAATCATCTGTGCCCAGCAG |
| 768 | CAAAATCATCTGTGCCCAGCAGT |
| 769 | AAAATCATCTGTGCCCAGCAGTG |
| 770 | AAATCATCTGTGCCCAGCAGTGC |
| 771 | AATCATCTGTGCCCAGCAGTGCT |
| 772 | ATCATCTGTGCCCAGCAGTGCTC |
| 773 | TCATCTGTGCCCAGCAGTGCTCC |
| 774 | CATCTGTGCCCAGCAGTGCTCCG |
| 775 | ATCTGTGCCCAGCAGTGCTCCGG |
| 776 | TCTGTGCCCAGCAGTGCTCCGGG |
| 777 | CTGTGCCCAGCAGTGCTCCGGGC |
| 778 | TGTGCCCAGCAGTGCTCCGGGCG |
| 779 | GTGCCCAGCAGTGCTCCGGGCGC |
| 780 | TGCCCAGCAGTGCTCCGGGCGCT |
| 781 | GCCCAGCAGTGCTCCGGGCGCTG |
| 782 | CCCAGCAGTGCTCCGGGCGCTGC |
| 783 | CCAGCAGTGCTCCGGGCGCTGCC |
| 784 | CAGCAGTGCTCCGGGCGCTGCCG |
| 785 | AGCAGTGCTCCGGGCGCTGCCGT |
| 786 | GCAGTGCTCCGGGCGCTGCCGTG |
| 787 | CAGTGCTCCGGGCGCTGCCGTGG |
| 788 | AGTGCTCCGGGCGCTGCCGTGGC |
| 789 | GTGCTCCGGGCGCTGCCGTGGCA |
| 790 | TGCTCCGGGCGCTGCCGTGGCAA |
| 791 | GCTCCGGGCGCTGCCGTGGCAAG |
| 792 | CTCCGGGCGCTGCCGTGGCAAGT |
| 793 | TCCGGGCGCTGCCGTGGCAAGTC |
| 794 | CCGGGCGCTGCCGTGGCAAGTCC |
| 795 | CGGGCGCTGCCGTGGCAAGTCCC |
| 796 | GGGCGCTGCCGTGGCAAGTCCCC |
| 797 | GGCGCTGCCGTGGCAAGTCCCCC |
| 798 | GCGCTGCCGTGGCAAGTCCCCCA |
| 799 | CGCTGCCGTGGCAAGTCCCCCAG |
| 800 | GCTGCCGTGGCAAGTCCCCCAGT |
| 801 | CTGCCGTGGCAAGTCCCCCAGTG |
| 802 | TGCCGTGGCAAGTCCCCCAGTGA |
| 803 | GCCGTGGCAAGTCCCCCAGTGAC |
| 804 | CCGTGGCAAGTCCCCCAGTGACT |
| 805 | CGTGGCAAGTCCCCCAGTGACTG |
| 806 | GTGGCAAGTCCCCCAGTGACTGC |
| 807 | TGGCAAGTCCCCCAGTGACTGCT |
| 808 | GGCAAGTCCCCCAGTGACTGCTG |
| 809 | GCAAGTCCCCCAGTGACTGCTGC |
| 810 | CAAGTCCCCCAGTGACTGCTGCC |
| 811 | AAGTCCCCCAGTGACTGCTGCCA |
| 812 | AGTCCCCCAGTGACTGCTGCCAC |

| ID | SEQUENCE |
|---|---|
| 813 | GTCCCCCAGTGACTGCTGCCACA |
| 814 | TCCCCCAGTGACTGCTGCCACAA |
| 815 | CCCCCAGTGACTGCTGCCACAAC |
| 816 | CCCCAGTGACTGCTGCCACAACC |
| 817 | CCCAGTGACTGCTGCCACAACCA |
| 818 | CCAGTGACTGCTGCCACAACCAG |
| 819 | CAGTGACTGCTGCCACAACCAGT |
| 820 | AGTGACTGCTGCCACAACCAGTG |
| 821 | GTGACTGCTGCCACAACCAGTGT |
| 822 | TGACTGCTGCCACAACCAGTGTG |
| 823 | GACTGCTGCCACAACCAGTGTGC |
| 824 | ACTGCTGCCACAACCAGTGTGCT |
| 825 | CTGCTGCCACAACCAGTGTGCTG |
| 826 | TGCTGCCACAACCAGTGTGCTGC |
| 827 | GCTGCCACAACCAGTGTGCTGCA |
| 828 | CTGCCACAACCAGTGTGCTGCAG |
| 829 | TGCCACAACCAGTGTGCTGCAGG |
| 830 | GCCACAACCAGTGTGCTGCAGGC |
| 831 | CCACAACCAGTGTGCTGCAGGCT |
| 832 | CACAACCAGTGTGCTGCAGGCTG |
| 833 | ACAACCAGTGTGCTGCAGGCTGC |
| 834 | CAACCAGTGTGCTGCAGGCTGCA |
| 835 | AACCAGTGTGCTGCAGGCTGCAC |
| 836 | ACCAGTGTGCTGCAGGCTGCACA |
| 837 | CCAGTGTGCTGCAGGCTGCACAG |
| 838 | CAGTGTGCTGCAGGCTGCACAGG |
| 839 | AGTGTGCTGCAGGCTGCACAGGC |
| 840 | GTGTGCTGCAGGCTGCACAGGCC |
| 841 | TGTGCTGCAGGCTGCACAGGCCC |
| 842 | GTGCTGCAGGCTGCACAGGCCCC |
| 843 | TGCTGCAGGCTGCACAGGCCCCC |
| 844 | GCTGCAGGCTGCACAGGCCCCCG |
| 845 | CCCCGGGAGAGCGACTGCCTGG |
| 846 | CCCCGGGAGAGCGACTGCCTGGT |
| 847 | CCCGGGAGAGCGACTGCCTGGTC |
| 848 | CCGGGAGAGCGACTGCCTGGTCT |
| 849 | CGGGAGAGCGACTGCCTGGTCTG |
| 850 | GGGAGAGCGACTGCCTGGTCTGC |
| 851 | GGAGAGCGACTGCCTGGTCTGCC |
| 852 | GAGAGCGACTGCCTGGTCTGCCG |
| 853 | AGAGCGACTGCCTGGTCTGCCGC |
| 854 | GAGCGACTGCCTGGTCTGCCGCA |
| 855 | AGCGACTGCCTGGTCTGCCGCAA |
| 856 | GCGACTGCCTGGTCTGCCGCAAA |
| 857 | CGACTGCCTGGTCTGCCGCAAAT |
| 858 | GACTGCCTGGTCTGCCGCAAATT |
| 859 | ACTGCCTGGTCTGCCGCAAATTC |
| 860 | CTGCCTGGTCTGCCGCAAATTCC |
| 861 | TGCCTGGTCTGCCGCAAATTCCG |
| 862 | GCCTGGTCTGCCGCAAATTCCGA |
| 863 | CCTGGTCTGCCGCAAATTCCGAG |
| 864 | CTGGTCTGCCGCAAATTCCGAGA |
| 865 | TGGTCTGCCGCAAATTCCGAGAC |
| 866 | GGTCTGCCGCAAATTCCGAGACG |
| 867 | GTCTGCCGCAAATTCCGAGACGA |
| 868 | TCTGCCGCAAATTCCGAGACGAA |
| 869 | CTGCCGCAAATTCCGAGACGAAG |
| 870 | TGCCGCAAATTCCGAGACGAAGC |

| ID | SEQUENCE |
|---|---|
| 871 | GCCGCAAATTCCGAGACGAAGCC |
| 872 | CCGCAAATTCCGAGACGAAGCCA |
| 873 | CGCAAATTCCGAGACGAAGCCAC |
| 874 | GCAAATTCCGAGACGAAGCCACG |
| 875 | CAAATTCCGAGACGAAGCCACGT |
| 876 | AAATTCCGAGACGAAGCCACGTG |
| 877 | AATTCCGAGACGAAGCCACGTGC |
| 878 | ATTCCGAGACGAAGCCACGTGCA |
| 879 | TTCCGAGACGAAGCCACGTGCAA |
| 880 | TCCGAGACGAAGCCACGTGCAAG |
| 881 | CCGAGACGAAGCCACGTGCAAGG |
| 882 | CGAGACGAAGCCACGTGCAAGGA |
| 883 | GAGACGAAGCCACGTGCAAGGAC |
| 884 | AGACGAAGCCACGTGCAAGGACA |
| 885 | GACGAAGCCACGTGCAAGGACAC |
| 886 | ACGAAGCCACGTGCAAGGACACC |
| 887 | CGAAGCCACGTGCAAGGACACCT |
| 888 | GAAGCCACGTGCAAGGACACCTG |
| 889 | AAGCCACGTGCAAGGACACCTGC |
| 890 | AGCCACGTGCAAGGACACCTGCC |
| 891 | GCCACGTGCAAGGACACCTGCCC |
| 892 | CCACGTGCAAGGACACCTGCCCC |
| 893 | CACGTGCAAGGACACCTGCCCCC |
| 894 | ACGTGCAAGGACACCTGCCCCCC |
| 895 | CGTGCAAGGACACCTGCCCCCCA |
| 896 | GTGCAAGGACACCTGCCCCCCAC |
| 897 | TGCAAGGACACCTGCCCCCCACT |
| 898 | GCAAGGACACCTGCCCCCCACTC |
| 899 | CAAGGACACCTGCCCCCCACTCA |
| 900 | AAGGACACCTGCCCCCCACTCAT |
| 901 | AGGACACCTGCCCCCCACTCATG |
| 902 | GGACACCTGCCCCCCACTCATGC |
| 903 | GACACCTGCCCCCCACTCATGCT |
| 904 | ACACCTGCCCCCCACTCATGCTC |
| 905 | CACCTGCCCCCCACTCATGCTCT |
| 906 | ACCTGCCCCCCACTCATGCTCTA |
| 907 | CCTGCCCCCCACTCATGCTCTAC |
| 908 | CTGCCCCCCACTCATGCTCTACA |
| 909 | TGCCCCCCACTCATGCTCTACAA |
| 910 | GCCCCCCACTCATGCTCTACAAC |
| 911 | CCCCCCACTCATGCTCTACAACC |
| 912 | CCCCCACTCATGCTCTACAACCC |
| 913 | CCCCACTCATGCTCTACAACCCC |
| 914 | CCCACTCATGCTCTACAACCCCA |
| 915 | CCACTCATGCTCTACAACCCCAC |
| 916 | CACTCATGCTCTACAACCCCACC |
| 917 | ACTCATGCTCTACAACCCCACCA |
| 918 | CTCATGCTCTACAACCCCACCAC |
| 919 | TCATGCTCTACAACCCCACCACG |
| 920 | CATGCTCTACAACCCCACCACGT |
| 921 | ATGCTCTACAACCCCACCACGTA |
| 922 | TGCTCTACAACCCCACCACGTAC |
| 923 | GCTCTACAACCCCACCACGTACC |
| 924 | CTCTACAACCCCACCACGTACCA |
| 925 | TCTACAACCCCACCACGTACCAG |
| 926 | CTACAACCCCACCACGTACCAGA |
| 927 | TACAACCCCACCACGTACCAGAT |
| 928 | ACAACCCCACCACGTACCAGATG |

| ID | SEQUENCE |
|---|---|
| 929 | CAACCCCACCACGTACCAGATGG |
| 930 | AACCCCACCACGTACCAGATGGA |
| 931 | ACCCCACCACGTACCAGATGGAT |
| 932 | CCCCACCACGTACCAGATGGATG |
| 933 | CCCACCACGTACCAGATGGATGT |
| 934 | CCACCACGTACCAGATGGATGTG |
| 935 | CACCACGTACCAGATGGATGTGA |
| 936 | ACCACGTACCAGATGGATGTGAA |
| 937 | CCACGTACCAGATGGATGTGAAC |
| 938 | CACGTACCAGATGGATGTGAACC |
| 939 | ACGTACCAGATGGATGTGAACCC |
| 940 | CGTACCAGATGGATGTGAACCCC |
| 941 | GTACCAGATGGATGTGAACCCCG |
| 942 | TACCAGATGGATGTGAACCCCGA |
| 943 | ACCAGATGGATGTGAACCCCGAG |
| 944 | CCAGATGGATGTGAACCCCGAGG |
| 945 | CAGATGGATGTGAACCCCGAGGG |
| 946 | AGATGGATGTGAACCCCGAGGGC |
| 947 | GATGGATGTGAACCCCGAGGGCA |
| 948 | ATGGATGTGAACCCCGAGGGCAA |
| 949 | TGGATGTGAACCCCGAGGGCAAA |
| 950 | GGATGTGAACCCCGAGGGCAAAT |
| 951 | GATGTGAACCCCGAGGGCAAATA |
| 952 | ATGTGAACCCCGAGGGCAAATAC |
| 953 | TGTGAACCCCGAGGGCAAATACA |
| 954 | GTGAACCCCGAGGGCAAATACAG |
| 955 | TGAACCCCGAGGGCAAATACAGC |
| 956 | GAACCCCGAGGGCAAATACAGCT |
| 957 | AACCCCGAGGGCAAATACAGCTT |
| 958 | ACCCCGAGGGCAAATACAGCTTT |
| 959 | CCCCGAGGGCAAATACAGCTTTG |
| 960 | CCCGAGGGCAAATACAGCTTTGG |
| 961 | CCGAGGGCAAATACAGCTTTGGT |
| 962 | CGAGGGCAAATACAGCTTTGGTG |
| 963 | GAGGGCAAATACAGCTTTGGTGC |
| 964 | AGGGCAAATACAGCTTTGGTGCC |
| 965 | GGGCAAATACAGCTTTGGTGCCA |
| 966 | GGCAAATACAGCTTTGGTGCCAC |
| 967 | GCAAATACAGCTTTGGTGCCACC |
| 968 | CAAATACAGCTTTGGTGCCACCT |
| 969 | AAATACAGCTTTGGTGCCACCTG |
| 970 | AATACAGCTTTGGTGCCACCTGC |
| 971 | ATACAGCTTTGGTGCCACCTGCG |
| 972 | TACAGCTTTGGTGCCACCTGCGT |
| 973 | ACAGCTTTGGTGCCACCTGCGTG |
| 974 | CAGCTTTGGTGCCACCTGCGTGA |
| 975 | AGCTTTGGTGCCACCTGCGTGAA |
| 976 | GCTTTGGTGCCACCTGCGTGAAG |
| 977 | CTTTGGTGCCACCTGCGTGAAGA |
| 978 | TTTGGTGCCACCTGCGTGAAGAA |
| 979 | TTGGTGCCACCTGCGTGAAGAAG |
| 980 | TGGTGCCACCTGCGTGAAGAAGT |
| 981 | GGTGCCACCTGCGTGAAGAAGTG |
| 982 | GTGCCACCTGCGTGAAGAAGTGT |
| 983 | TGCCACCTGCGTGAAGAAGTGTC |
| 984 | GCCACCTGCGTGAAGAAGTGTCC |
| 985 | CCACCTGCGTGAAGAAGTGTCCC |
| 986 | CACCTGCGTGAAGAAGTGTCCCC |

| ID | SEQUENCE |
|---|---|
| 987 | ACCTGCGTGAAGAAGTGTCCCCG |
| 988 | CCTGCGTGAAGAAGTGTCCCCGT |
| 989 | CTGCGTGAAGAAGTGTCCCCGTA |
| 990 | TGCGTGAAGAAGTGTCCCCGTAA |
| 991 | GCGTGAAGAAGTGTCCCCGTAAT |
| 992 | CGTGAAGAAGTGTCCCCGTAATT |
| 993 | GTGAAGAAGTGTCCCCGTAATTA |
| 994 | TGAAGAAGTGTCCCCGTAATTAT |
| 995 | GAAGAAGTGTCCCCGTAATTATG |
| 996 | AAGAAGTGTCCCCGTAATTATGT |
| 997 | AGAAGTGTCCCCGTAATTATGTG |
| 998 | GAAGTGTCCCCGTAATTATGTGG |
| 999 | AAGTGTCCCCGTAATTATGTGGT |
| 1000 | AGTGTCCCCGTAATTATGTGGTG |
| 1001 | GTGTCCCCGTAATTATGTGGTGA |
| 1002 | TGTCCCCGTAATTATGTGGTGAC |
| 1003 | GTCCCCGTAATTATGTGGTGACA |
| 1004 | TCCCCGTAATTATGTGGTGACAG |
| 1005 | CCCCGTAATTATGTGGTGACAGA |
| 1006 | CCCGTAATTATGTGGTGACAGAT |
| 1007 | CCGTAATTATGTGGTGACAGATC |
| 1008 | CGTAATTATGTGGTGACAGATCA |
| 1009 | GTAATTATGTGGTGACAGATCAC |
| 1010 | TAATTATGTGGTGACAGATCACG |
| 1011 | AATTATGTGGTGACAGATCACGG |
| 1012 | ATTATGTGGTGACAGATCACGGC |
| 1013 | TTATGTGGTGACAGATCACGGCT |
| 1014 | TATGTGGTGACAGATCACGGCTC |
| 1015 | ATGTGGTGACAGATCACGGCTCG |
| 1016 | TGTGGTGACAGATCACGGCTCGT |
| 1017 | GTGGTGACAGATCACGGCTCGTG |
| 1018 | TGGTGACAGATCACGGCTCGTGC |
| 1019 | GGTGACAGATCACGGCTCGTGCG |
| 1020 | GTGACAGATCACGGCTCGTGCGT |
| 1021 | TGACAGATCACGGCTCGTGCGTC |
| 1022 | GACAGATCACGGCTCGTGCGTCC |
| 1023 | ACAGATCACGGCTCGTGCGTCCG |
| 1024 | CAGATCACGGCTCGTGCGTCCGA |
| 1025 | AGATCACGGCTCGTGCGTCCGAG |
| 1026 | GATCACGGCTCGTGCGTCCGAGC |
| 1027 | ATCACGGCTCGTGCGTCCGAGCC |
| 1028 | TCACGGCTCGTGCGTCCGAGCCT |
| 1029 | CACGGCTCGTGCGTCCGAGCCTG |
| 1030 | ACGGCTCGTGCGTCCGAGCCTGT |
| 1031 | CGGCTCGTGCGTCCGAGCCTGTG |
| 1032 | GGCTCGTGCGTCCGAGCCTGTGG |
| 1033 | GCTCGTGCGTCCGAGCCTGTGGG |
| 1034 | CTCGTGCGTCCGAGCCTGTGGGG |
| 1035 | TCGTGCGTCCGAGCCTGTGGGGC |
| 1036 | CGTGCGTCCGAGCCTGTGGGGCC |
| 1037 | GTGCGTCCGAGCCTGTGGGGCCG |
| 1038 | TGCGTCCGAGCCTGTGGGGCCGA |
| 1039 | GCGTCCGAGCCTGTGGGGCCGAC |
| 1040 | CGTCCGAGCCTGTGGGGCCGACA |
| 1041 | GTCCGAGCCTGTGGGGCCGACAG |
| 1042 | TCCGAGCCTGTGGGGCCGACAGC |
| 1043 | CCGAGCCTGTGGGGCCGACAGCT |
| 1044 | CGAGCCTGTGGGGCCGACAGCTA |

| ID | SEQUENCE |
|---|---|
| 1045 | GAGCCTGTGGGGCCGACAGCTAT |
| 1046 | AGCCTGTGGGGCCGACAGCTATG |
| 1047 | GCCTGTGGGGCCGACAGCTATGA |
| 1048 | CCTGTGGGGCCGACAGCTATGAG |
| 1049 | CTGTGGGGCCGACAGCTATGAGA |
| 1050 | TGTGGGGCCGACAGCTATGAGAT |
| 1051 | GTGGGGCCGACAGCTATGAGATG |
| 1052 | TGGGGCCGACAGCTATGAGATGG |
| 1053 | GGGGCCGACAGCTATGAGATGGA |
| 1054 | GGGCCGACAGCTATGAGATGGAG |
| 1055 | GGCCGACAGCTATGAGATGGAGG |
| 1056 | GCCGACAGCTATGAGATGGAGGA |
| 1057 | CCGACAGCTATGAGATGGAGGAA |
| 1058 | CGACAGCTATGAGATGGAGGAAG |
| 1059 | GACAGCTATGAGATGGAGGAAGA |
| 1060 | ACAGCTATGAGATGGAGGAAGAC |
| 1061 | CAGCTATGAGATGGAGGAAGACG |
| 1062 | AGCTATGAGATGGAGGAAGACGG |
| 1063 | GCTATGAGATGGAGGAAGACGGC |
| 1064 | CTATGAGATGGAGGAAGACGGCG |
| 1065 | TATGAGATGGAGGAAGACGGCGT |
| 1066 | ATGAGATGGAGGAAGACGGCGTC |
| 1067 | TGAGATGGAGGAAGACGGCGTCC |
| 1068 | GAGATGGAGGAAGACGGCGTCCG |
| 1069 | AGATGGAGGAAGACGGCGTCCGC |
| 1070 | GATGGAGGAAGACGGCGTCCGCA |
| 1071 | ATGGAGGAAGACGGCGTCCGCAA |
| 1072 | TGGAGGAAGACGGCGTCCGCAAG |
| 1073 | GGAGGAAGACGGCGTCCGCAAGT |
| 1074 | GAGGAAGACGGCGTCCGCAAGTG |
| 1075 | AGGAAGACGGCGTCCGCAAGTGT |
| 1076 | GGAAGACGGCGTCCGCAAGTGTA |
| 1077 | GAAGACGGCGTCCGCAAGTGTAA |
| 1078 | AAGACGGCGTCCGCAAGTGTAAG |
| 1079 | AGACGGCGTCCGCAAGTGTAAGA |
| 1080 | GACGGCGTCCGCAAGTGTAAGAA |
| 1081 | ACGGCGTCCGCAAGTGTAAGAAG |
| 1082 | CGGCGTCCGCAAGTGTAAGAAGT |
| 1083 | GGCGTCCGCAAGTGTAAGAAGTG |
| 1084 | GCGTCCGCAAGTGTAAGAAGTGC |
| 1085 | CGTCCGCAAGTGTAAGAAGTGCG |
| 1086 | GTCCGCAAGTGTAAGAAGTGCGA |
| 1087 | TCCGCAAGTGTAAGAAGTGCGAA |
| 1088 | CCGCAAGTGTAAGAAGTGCGAAG |
| 1089 | CGCAAGTGTAAGAAGTGCGAAGG |
| 1090 | GCAAGTGTAAGAAGTGCGAAGGG |
| 1091 | CAAGTGTAAGAAGTGCGAAGGGC |
| 1092 | AAGTGTAAGAAGTGCGAAGGGCC |
| 1093 | AGTGTAAGAAGTGCGAAGGGCCT |
| 1094 | GTGTAAGAAGTGCGAAGGGCCTT |
| 1095 | TGTAAGAAGTGCGAAGGGCCTTG |
| 1096 | GTAAGAAGTGCGAAGGGCCTTGC |
| 1097 | TAAGAAGTGCGAAGGGCCTTGCC |
| 1098 | AAGAAGTGCGAAGGGCCTTGCCG |
| 1099 | AGAAGTGCGAAGGGCCTTGCCGC |
| 1100 | GAAGTGCGAAGGGCCTTGCCGCA |
| 1101 | AAGTGCGAAGGGCCTTGCCGCAA |
| 1102 | AGTGCGAAGGGCCTTGCCGCAAA |

| ID | SEQUENCE |
|---|---|
| 1103 | GTGCGAAGGGCCTTGCCGCAAAG |
| 1104 | TGCGAAGGGCCTTGCCGCAAAGT |
| 1105 | GCGAAGGGCCTTGCCGCAAAGTG |
| 1106 | CGAAGGGCCTTGCCGCAAAGTGT |
| 1107 | GAAGGGCCTTGCCGCAAAGTGTG |
| 1108 | AAGGGCCTTGCCGCAAAGTGTGT |
| 1109 | AGGGCCTTGCCGCAAAGTGTGTA |
| 1110 | GGGCCTTGCCGCAAAGTGTGTAA |
| 1111 | GGCCTTGCCGCAAAGTGTGTAAC |
| 1112 | GCCTTGCCGCAAAGTGTGTAACG |
| 1113 | CCTTGCCGCAAAGTGTGTAACGG |
| 1114 | CTTGCCGCAAAGTGTGTAACGGA |
| 1115 | TTGCCGCAAAGTGTGTAACGGAA |
| 1116 | TGCCGCAAAGTGTGTAACGGAAT |
| 1117 | GCCGCAAAGTGTGTAACGGAATA |
| 1118 | CCGCAAAGTGTGTAACGGAATAG |
| 1119 | CGCAAAGTGTGTAACGGAATAGG |
| 1120 | GCAAAGTGTGTAACGGAATAGGT |
| 1121 | CAAAGTGTGTAACGGAATAGGTA |
| 1122 | AAAGTGTGTAACGGAATAGGTAT |
| 1123 | AAGTGTGTAACGGAATAGGTATT |
| 1124 | AGTGTGTAACGGAATAGGTATTG |
| 1125 | GTGTGTAACGGAATAGGTATTGG |
| 1126 | TGTGTAACGGAATAGGTATTGGT |
| 1127 | GTGTAACGGAATAGGTATTGGTG |
| 1128 | TGTAACGGAATAGGTATTGGTGA |
| 1129 | GTAACGGAATAGGTATTGGTGAA |
| 1130 | TAACGGAATAGGTATTGGTGAAT |
| 1131 | AACGGAATAGGTATTGGTGAATT |
| 1132 | ACGGAATAGGTATTGGTGAATTT |
| 1133 | CGGAATAGGTATTGGTGAATTTA |
| 1134 | GGAATAGGTATTGGTGAATTTAA |
| 1135 | GAATAGGTATTGGTGAATTTAAA |
| 1136 | AATAGGTATTGGTGAATTTAAAG |
| 1137 | ATAGGTATTGGTGAATTTAAAGA |
| 1138 | TAGGTATTGGTGAATTTAAAGAC |
| 1139 | AGGTATTGGTGAATTTAAAGACT |
| 1140 | GGTATTGGTGAATTTAAAGACTC |
| 1141 | GTATTGGTGAATTTAAAGACTCA |
| 1142 | TATTGGTGAATTTAAAGACTCAC |
| 1143 | ATTGGTGAATTTAAAGACTCACT |
| 1144 | TTGGTGAATTTAAAGACTCACTC |
| 1145 | TGGTGAATTTAAAGACTCACTCT |
| 1146 | GGTGAATTTAAAGACTCACTCTC |
| 1147 | GTGAATTTAAAGACTCACTCTCC |
| 1148 | TGAATTTAAAGACTCACTCTCCA |
| 1149 | GAATTTAAAGACTCACTCTCCAT |
| 1150 | AATTTAAAGACTCACTCTCCATA |
| 1151 | ATTTAAAGACTCACTCTCCATAA |
| 1152 | TTTAAAGACTCACTCTCCATAAA |
| 1153 | TTAAAGACTCACTCTCCATAAAT |
| 1154 | TAAAGACTCACTCTCCATAAATG |
| 1155 | AAAGACTCACTCTCCATAAATGC |
| 1156 | AAGACTCACTCTCCATAAATGCT |
| 1157 | AGACTCACTCTCCATAAATGCTA |
| 1158 | GACTCACTCTCCATAAATGCTAC |
| 1159 | ACTCACTCTCCATAAATGCTACG |
| 1160 | CTCACTCTCCATAAATGCTACGA |

| ID | SEQUENCE |
|---|---|
| 1161 | TCACTCTCCATAAATGCTACGAA |
| 1162 | CACTCTCCATAAATGCTACGAAT |
| 1163 | ACTCTCCATAAATGCTACGAATA |
| 1164 | CTCTCCATAAATGCTACGAATAT |
| 1165 | TCTCCATAAATGCTACGAATATT |
| 1166 | CTCCATAAATGCTACGAATATTA |
| 1167 | TCCATAAATGCTACGAATATTAA |
| 1168 | CCATAAATGCTACGAATATTAAA |
| 1169 | CATAAATGCTACGAATATTAAAC |
| 1170 | ATAAATGCTACGAATATTAAACA |
| 1171 | TAAATGCTACGAATATTAAACAC |
| 1172 | AAATGCTACGAATATTAAACACT |
| 1173 | AATGCTACGAATATTAAACACTT |
| 1174 | ATGCTACGAATATTAAACACTTC |
| 1175 | TGCTACGAATATTAAACACTTCA |
| 1176 | GCTACGAATATTAAACACTTCAA |
| 1177 | CTACGAATATTAAACACTTCAAA |
| 1178 | TACGAATATTAAACACTTCAAAA |
| 1179 | ACGAATATTAAACACTTCAAAAA |
| 1180 | CGAATATTAAACACTTCAAAAAC |
| 1181 | GAATATTAAACACTTCAAAAACT |
| 1182 | AATATTAAACACTTCAAAAACTG |
| 1183 | ATATTAAACACTTCAAAAACTGC |
| 1184 | TATTAAACACTTCAAAAACTGCA |
| 1185 | ATTAAACACTTCAAAAACTGCAC |
| 1186 | TTAAACACTTCAAAAACTGCACC |
| 1187 | TAAACACTTCAAAAACTGCACCT |
| 1188 | AAACACTTCAAAAACTGCACCTC |
| 1189 | AACACTTCAAAAACTGCACCTCC |
| 1190 | ACACTTCAAAAACTGCACCTCCA |
| 1191 | CACTTCAAAAACTGCACCTCCAT |
| 1192 | ACTTCAAAAACTGCACCTCCATC |
| 1193 | CTTCAAAAACTGCACCTCCATCA |
| 1194 | TTCAAAAACTGCACCTCCATCAG |
| 1195 | TCAAAAACTGCACCTCCATCAGT |
| 1196 | CAAAAACTGCACCTCCATCAGTG |
| 1197 | AAAAACTGCACCTCCATCAGTGG |
| 1198 | AAAACTGCACCTCCATCAGTGGC |
| 1199 | AAACTGCACCTCCATCAGTGGCG |
| 1200 | AACTGCACCTCCATCAGTGGCGA |
| 1201 | ACTGCACCTCCATCAGTGGCGAT |
| 1202 | CTGCACCTCCATCAGTGGCGATC |
| 1203 | TGCACCTCCATCAGTGGCGATCT |
| 1204 | GCACCTCCATCAGTGGCGATCTC |
| 1205 | CACCTCCATCAGTGGCGATCTCC |
| 1206 | ACCTCCATCAGTGGCGATCTCCA |
| 1207 | CCTCCATCAGTGGCGATCTCCAC |
| 1208 | CTCCATCAGTGGCGATCTCCACA |
| 1209 | TCCATCAGTGGCGATCTCCACAT |
| 1210 | CCATCAGTGGCGATCTCCACATC |
| 1211 | CATCAGTGGCGATCTCCACATCC |
| 1212 | ATCAGTGGCGATCTCCACATCCT |
| 1213 | TCAGTGGCGATCTCCACATCCTG |
| 1214 | CAGTGGCGATCTCCACATCCTGC |
| 1215 | AGTGGCGATCTCCACATCCTGCC |
| 1216 | GTGGCGATCTCCACATCCTGCCG |
| 1217 | TGGCGATCTCCACATCCTGCCGG |
| 1218 | GGCGATCTCCACATCCTGCCGGT |

| ID | SEQUENCE |
|---|---|
| 1219 | GCGATCTCCACATCCTGCCGGTG |
| 1220 | CGATCTCCACATCCTGCCGGTGG |
| 1221 | GATCTCCACATCCTGCCGGTGGC |
| 1222 | ATCTCCACATCCTGCCGGTGGCA |
| 1223 | TCTCCACATCCTGCCGGTGGCAT |
| 1224 | CTCCACATCCTGCCGGTGGCATT |
| 1225 | TCCACATCCTGCCGGTGGCATTT |
| 1226 | CCACATCCTGCCGGTGGCATTTA |
| 1227 | CACATCCTGCCGGTGGCATTTAG |
| 1228 | ACATCCTGCCGGTGGCATTTAGG |
| 1229 | CATCCTGCCGGTGGCATTTAGGG |
| 1230 | ATCCTGCCGGTGGCATTTAGGGG |
| 1231 | TCCTGCCGGTGGCATTTAGGGGT |
| 1232 | CCTGCCGGTGGCATTTAGGGGTG |
| 1233 | CTGCCGGTGGCATTTAGGGGTGA |
| 1234 | TGCCGGTGGCATTTAGGGGTGAC |
| 1235 | GCCGGTGGCATTTAGGGGTGACT |
| 1236 | CCGGTGGCATTTAGGGGTGACTC |
| 1237 | CGGTGGCATTTAGGGGTGACTCC |
| 1238 | GGTGGCATTTAGGGGTGACTCCT |
| 1239 | GTGGCATTTAGGGGTGACTCCTT |
| 1240 | TGGCATTTAGGGGTGACTCCTTC |
| 1241 | GGCATTTAGGGGTGACTCCTTCA |
| 1242 | GCATTTAGGGGTGACTCCTTCAC |
| 1243 | CATTTAGGGGTGACTCCTTCACA |
| 1244 | ATTTAGGGGTGACTCCTTCACAC |
| 1245 | TTTAGGGGTGACTCCTTCACACA |
| 1246 | TTAGGGGTGACTCCTTCACACAT |
| 1247 | TAGGGGTGACTCCTTCACACATA |
| 1248 | AGGGGTGACTCCTTCACACATAC |
| 1249 | GGGGTGACTCCTTCACACATACT |
| 1250 | GGGTGACTCCTTCACACATACTC |
| 1251 | GGTGACTCCTTCACACATACTCC |
| 1252 | GTGACTCCTTCACACATACTCCT |
| 1253 | TGACTCCTTCACACATACTCCTC |
| 1254 | GACTCCTTCACACATACTCCTCC |
| 1255 | ACTCCTTCACACATACTCCTCCT |
| 1256 | CTCCTTCACACATACTCCTCCTC |
| 1257 | TCCTTCACACATACTCCTCCTCT |
| 1258 | CCTTCACACATACTCCTCCTCTG |
| 1259 | CTTCACACATACTCCTCCTCTGG |
| 1260 | TTCACACATACTCCTCCTCTGGA |
| 1261 | TCACACATACTCCTCCTCTGGAT |
| 1262 | CACACATACTCCTCCTCTGGATC |
| 1263 | ACACATACTCCTCCTCTGGATCC |
| 1264 | CACATACTCCTCCTCTGGATCCA |
| 1265 | ACATACTCCTCCTCTGGATCCAC |
| 1266 | CATACTCCTCCTCTGGATCCACA |
| 1267 | ATACTCCTCCTCTGGATCCACAG |
| 1268 | TACTCCTCCTCTGGATCCACAGG |
| 1269 | ACTCCTCCTCTGGATCCACAGGA |
| 1270 | CTCCTCCTCTGGATCCACAGGAA |
| 1271 | TCCTCCTCTGGATCCACAGGAAC |
| 1272 | CCTCCTCTGGATCCACAGGAACT |
| 1273 | CTCCTCTGGATCCACAGGAACTG |
| 1274 | TCCTCTGGATCCACAGGAACTGG |
| 1275 | CCTCTGGATCCACAGGAACTGGA |
| 1276 | CTCTGGATCCACAGGAACTGGAT |

| ID | SEQUENCE |
|---|---|
| 1277 | TCTGGATCCACAGGAACTGGATA |
| 1278 | CTGGATCCACAGGAACTGGATAT |
| 1279 | TGGATCCACAGGAACTGGATATT |
| 1280 | GGATCCACAGGAACTGGATATTC |
| 1281 | GATCCACAGGAACTGGATATTCT |
| 1282 | ATCCACAGGAACTGGATATTCTG |
| 1283 | TCCACAGGAACTGGATATTCTGA |
| 1284 | CCACAGGAACTGGATATTCTGAA |
| 1285 | CACAGGAACTGGATATTCTGAAA |
| 1286 | ACAGGAACTGGATATTCTGAAAA |
| 1287 | CAGGAACTGGATATTCTGAAAAC |
| 1288 | AGGAACTGGATATTCTGAAAACC |
| 1289 | GGAACTGGATATTCTGAAAACCG |
| 1290 | GAACTGGATATTCTGAAAACCGT |
| 1291 | AACTGGATATTCTGAAAACCGTA |
| 1292 | ACTGGATATTCTGAAAACCGTAA |
| 1293 | CTGGATATTCTGAAAACCGTAAA |
| 1294 | TGGATATTCTGAAAACCGTAAAG |
| 1295 | GGATATTCTGAAAACCGTAAAGG |
| 1296 | GATATTCTGAAAACCGTAAAGGA |
| 1297 | ATATTCTGAAAACCGTAAAGGAA |
| 1298 | TATTCTGAAAACCGTAAAGGAAA |
| 1299 | ATTCTGAAAACCGTAAAGGAAAT |
| 1300 | TTCTGAAAACCGTAAAGGAAATC |
| 1301 | TCTGAAAACCGTAAAGGAAATCA |
| 1302 | CTGAAAACCGTAAAGGAAATCAC |
| 1303 | TGAAAACCGTAAAGGAAATCACA |
| 1304 | GAAAACCGTAAAGGAAATCACAG |
| 1305 | AAAACCGTAAAGGAAATCACAGG |
| 1306 | AAACCGTAAAGGAAATCACAGGG |
| 1307 | AACCGTAAAGGAAATCACAGGGT |
| 1308 | ACCGTAAAGGAAATCACAGGGTT |
| 1309 | CCGTAAAGGAAATCACAGGGTTT |
| 1310 | CGTAAAGGAAATCACAGGGTTTT |
| 1311 | GTAAAGGAAATCACAGGGTTTTT |
| 1312 | TAAAGGAAATCACAGGGTTTTTG |
| 1313 | AAAGGAAATCACAGGGTTTTTGC |
| 1314 | AAGGAAATCACAGGGTTTTTGCT |
| 1315 | AGGAAATCACAGGGTTTTTGCTG |
| 1316 | GGAAATCACAGGGTTTTTGCTGA |
| 1317 | GAAATCACAGGGTTTTTGCTGAT |
| 1318 | AAATCACAGGGTTTTTGCTGATT |
| 1319 | AATCACAGGGTTTTTGCTGATTC |
| 1320 | ATCACAGGGTTTTTGCTGATTCA |
| 1321 | TCACAGGGTTTTTGCTGATTCAG |
| 1322 | CACAGGGTTTTTGCTGATTCAGG |
| 1323 | ACAGGGTTTTTGCTGATTCAGGC |
| 1324 | CAGGGTTTTTGCTGATTCAGGCT |
| 1325 | AGGGTTTTTGCTGATTCAGGCTT |
| 1326 | GGGTTTTTGCTGATTCAGGCTTG |
| 1327 | GGTTTTTGCTGATTCAGGCTTGG |
| 1328 | GTTTTTGCTGATTCAGGCTTGGC |
| 1329 | TTTTTGCTGATTCAGGCTTGGCC |
| 1330 | TTTTGCTGATTCAGGCTTGGCCT |
| 1331 | TTTGCTGATTCAGGCTTGGCCTG |
| 1332 | TTGCTGATTCAGGCTTGGCCTGA |
| 1333 | TGCTGATTCAGGCTTGGCCTGAA |
| 1334 | GCTGATTCAGGCTTGGCCTGAAA |

| ID | SEQUENCE |
|---|---|
| 1335 | CTGATTCAGGCTTGGCCTGAAAA |
| 1336 | TGATTCAGGCTTGGCCTGAAAAC |
| 1337 | GATTCAGGCTTGGCCTGAAAACA |
| 1338 | ATTCAGGCTTGGCCTGAAAACAG |
| 1339 | TTCAGGCTTGGCCTGAAAACAGG |
| 1340 | TCAGGCTTGGCCTGAAAACAGGA |
| 1341 | CAGGCTTGGCCTGAAAACAGGAC |
| 1342 | AGGCTTGGCCTGAAAACAGGACG |
| 1343 | GGCTTGGCCTGAAAACAGGACGG |
| 1344 | GCTTGGCCTGAAAACAGGACGGA |
| 1345 | CTTGGCCTGAAAACAGGACGGAC |
| 1346 | TTGGCCTGAAAACAGGACGGACC |
| 1347 | TGGCCTGAAAACAGGACGGACCT |
| 1348 | GGCCTGAAAACAGGACGGACCTC |
| 1349 | GCCTGAAAACAGGACGGACCTCC |
| 1350 | CCTGAAAACAGGACGGACCTCCA |
| 1351 | CTGAAAACAGGACGGACCTCCAT |
| 1352 | TGAAAACAGGACGGACCTCCATG |
| 1353 | GAAAACAGGACGGACCTCCATGC |
| 1354 | AAAACAGGACGGACCTCCATGCC |
| 1355 | AAACAGGACGGACCTCCATGCCT |
| 1356 | AACAGGACGGACCTCCATGCCTT |
| 1357 | ACAGGACGGACCTCCATGCCTTT |
| 1358 | CAGGACGGACCTCCATGCCTTTG |
| 1359 | AGGACGGACCTCCATGCCTTTGA |
| 1360 | GGACGGACCTCCATGCCTTTGAG |
| 1361 | GACGGACCTCCATGCCTTTGAGA |
| 1362 | ACGGACCTCCATGCCTTTGAGAA |
| 1363 | CGGACCTCCATGCCTTTGAGAAC |
| 1364 | GGACCTCCATGCCTTTGAGAACC |
| 1365 | GACCTCCATGCCTTTGAGAACCT |
| 1366 | ACCTCCATGCCTTTGAGAACCTA |
| 1367 | CCTCCATGCCTTTGAGAACCTAG |
| 1368 | CTCCATGCCTTTGAGAACCTAGA |
| 1369 | TCCATGCCTTTGAGAACCTAGAA |
| 1370 | CCATGCCTTTGAGAACCTAGAAA |
| 1371 | CATGCCTTTGAGAACCTAGAAAT |
| 1372 | ATGCCTTTGAGAACCTAGAAATC |
| 1373 | TGCCTTTGAGAACCTAGAAATCA |
| 1374 | GCCTTTGAGAACCTAGAAATCAT |
| 1375 | CCTTTGAGAACCTAGAAATCATA |
| 1376 | CTTTGAGAACCTAGAAATCATAC |
| 1377 | TTTGAGAACCTAGAAATCATACG |
| 1378 | TTGAGAACCTAGAAATCATACGC |
| 1379 | TGAGAACCTAGAAATCATACGCG |
| 1380 | GAGAACCTAGAAATCATACGCGG |
| 1381 | AGAACCTAGAAATCATACGCGGC |
| 1382 | GAACCTAGAAATCATACGCGGCA |
| 1383 | AACCTAGAAATCATACGCGGCAG |
| 1384 | ACCTAGAAATCATACGCGGCAGG |
| 1385 | CCTAGAAATCATACGCGGCAGGA |
| 1386 | CTAGAAATCATACGCGGCAGGAC |
| 1387 | TAGAAATCATACGCGGCAGGACC |
| 1388 | AGAAATCATACGCGGCAGGACCA |
| 1389 | GAAATCATACGCGGCAGGACCAA |
| 1390 | AAATCATACGCGGCAGGACCAAG |
| 1391 | AATCATACGCGGCAGGACCAAGC |
| 1392 | ATCATACGCGGCAGGACCAAGCA |

| ID | SEQUENCE |
|---|---|
| 1393 | TCATACGCGGCAGGACCAAGCAA |
| 1394 | CATACGCGGCAGGACCAAGCAAC |
| 1395 | ATACGCGGCAGGACCAAGCAACA |
| 1396 | TACGCGGCAGGACCAAGCAACAT |
| 1397 | ACGCGGCAGGACCAAGCAACATG |
| 1398 | CGCGGCAGGACCAAGCAACATGG |
| 1399 | GCGGCAGGACCAAGCAACATGGT |
| 1400 | CGGCAGGACCAAGCAACATGGTC |
| 1401 | GGCAGGACCAAGCAACATGGTCA |
| 1402 | GCAGGACCAAGCAACATGGTCAG |
| 1403 | CAGGACCAAGCAACATGGTCAGT |
| 1404 | AGGACCAAGCAACATGGTCAGTT |
| 1405 | GGACCAAGCAACATGGTCAGTTT |
| 1406 | GACCAAGCAACATGGTCAGTTTT |
| 1407 | ACCAAGCAACATGGTCAGTTTTC |
| 1408 | CCAAGCAACATGGTCAGTTTTCT |
| 1409 | CAAGCAACATGGTCAGTTTTCTC |
| 1410 | AAGCAACATGGTCAGTTTTCTCT |
| 1411 | AGCAACATGGTCAGTTTTCTCTT |
| 1412 | GCAACATGGTCAGTTTTCTCTTG |
| 1413 | CAACATGGTCAGTTTTCTCTTGC |
| 1414 | AACATGGTCAGTTTTCTCTTGCA |
| 1415 | ACATGGTCAGTTTTCTCTTGCAG |
| 1416 | CATGGTCAGTTTTCTCTTGCAGT |
| 1417 | ATGGTCAGTTTTCTCTTGCAGTC |
| 1418 | TGGTCAGTTTTCTCTTGCAGTCG |
| 1419 | GGTCAGTTTTCTCTTGCAGTCGT |
| 1420 | GTCAGTTTTCTCTTGCAGTCGTC |
| 1421 | TCAGTTTTCTCTTGCAGTCGTCA |
| 1422 | CAGTTTTCTCTTGCAGTCGTCAG |
| 1423 | AGTTTTCTCTTGCAGTCGTCAGC |
| 1424 | GTTTTCTCTTGCAGTCGTCAGCC |
| 1425 | TTTTCTCTTGCAGTCGTCAGCCT |
| 1426 | TTTCTCTTGCAGTCGTCAGCCTG |
| 1427 | TTCTCTTGCAGTCGTCAGCCTGA |
| 1428 | TCTCTTGCAGTCGTCAGCCTGAA |
| 1429 | CTCTTGCAGTCGTCAGCCTGAAC |
| 1430 | TCTTGCAGTCGTCAGCCTGAACA |
| 1431 | CTTGCAGTCGTCAGCCTGAACAT |
| 1432 | TTGCAGTCGTCAGCCTGAACATA |
| 1433 | TGCAGTCGTCAGCCTGAACATAA |
| 1434 | GCAGTCGTCAGCCTGAACATAAC |
| 1435 | CAGTCGTCAGCCTGAACATAACA |
| 1436 | AGTCGTCAGCCTGAACATAACAT |
| 1437 | GTCGTCAGCCTGAACATAACATC |
| 1438 | TCGTCAGCCTGAACATAACATCC |
| 1439 | CGTCAGCCTGAACATAACATCCT |
| 1440 | GTCAGCCTGAACATAACATCCTT |
| 1441 | TCAGCCTGAACATAACATCCTTG |
| 1442 | CAGCCTGAACATAACATCCTTGG |
| 1443 | AGCCTGAACATAACATCCTTGGG |
| 1444 | GCCTGAACATAACATCCTTGGGA |
| 1445 | CCTGAACATAACATCCTTGGGAT |
| 1446 | CTGAACATAACATCCTTGGGATT |
| 1447 | TGAACATAACATCCTTGGGATTA |
| 1448 | GAACATAACATCCTTGGGATTAC |
| 1449 | AACATAACATCCTTGGGATTACG |
| 1450 | ACATAACATCCTTGGGATTACGC |

| ID | SEQUENCE |
|---|---|
| 1451 | CATAACATCCTTGGGATTACGCT |
| 1452 | ATAACATCCTTGGGATTACGCTC |
| 1453 | TAACATCCTTGGGATTACGCTCC |
| 1454 | AACATCCTTGGGATTACGCTCCC |
| 1455 | ACATCCTTGGGATTACGCTCCCT |
| 1456 | CATCCTTGGGATTACGCTCCCTC |
| 1457 | ATCCTTGGGATTACGCTCCCTCA |
| 1458 | TCCTTGGGATTACGCTCCCTCAA |
| 1459 | CCTTGGGATTACGCTCCCTCAAG |
| 1460 | CTTGGGATTACGCTCCCTCAAGG |
| 1461 | TTGGGATTACGCTCCCTCAAGGA |
| 1462 | TGGGATTACGCTCCCTCAAGGAG |
| 1463 | GGGATTACGCTCCCTCAAGGAGA |
| 1464 | GGATTACGCTCCCTCAAGGAGAT |
| 1465 | GATTACGCTCCCTCAAGGAGATA |
| 1466 | ATTACGCTCCCTCAAGGAGATAA |
| 1467 | TTACGCTCCCTCAAGGAGATAAG |
| 1468 | TACGCTCCCTCAAGGAGATAAGT |
| 1469 | ACGCTCCCTCAAGGAGATAAGTG |
| 1470 | CGCTCCCTCAAGGAGATAAGTGA |
| 1471 | GCTCCCTCAAGGAGATAAGTGAT |
| 1472 | CTCCCTCAAGGAGATAAGTGATG |
| 1473 | TCCCTCAAGGAGATAAGTGATGG |
| 1474 | CCCTCAAGGAGATAAGTGATGGA |
| 1475 | CCTCAAGGAGATAAGTGATGGAG |
| 1476 | CTCAAGGAGATAAGTGATGGAGA |
| 1477 | TCAAGGAGATAAGTGATGGAGAT |
| 1478 | CAAGGAGATAAGTGATGGAGATG |
| 1479 | AAGGAGATAAGTGATGGAGATGT |
| 1480 | AGGAGATAAGTGATGGAGATGTG |
| 1481 | GGAGATAAGTGATGGAGATGTGA |
| 1482 | GAGATAAGTGATGGAGATGTGAT |
| 1483 | AGATAAGTGATGGAGATGTGATA |
| 1484 | GATAAGTGATGGAGATGTGATAA |
| 1485 | ATAAGTGATGGAGATGTGATAAT |
| 1486 | TAAGTGATGGAGATGTGATAATT |
| 1487 | AAGTGATGGAGATGTGATAATTT |
| 1488 | AGTGATGGAGATGTGATAATTTC |
| 1489 | GTGATGGAGATGTGATAATTTCA |
| 1490 | TGATGGAGATGTGATAATTTCAG |
| 1491 | GATGGAGATGTGATAATTTCAGG |
| 1492 | ATGGAGATGTGATAATTTCAGGA |
| 1493 | TGGAGATGTGATAATTTCAGGAA |
| 1494 | GGAGATGTGATAATTTCAGGAAA |
| 1495 | GAGATGTGATAATTTCAGGAAAC |
| 1496 | AGATGTGATAATTTCAGGAAACA |
| 1497 | GATGTGATAATTTCAGGAAACAA |
| 1498 | ATGTGATAATTTCAGGAAACAAA |
| 1499 | TGTGATAATTTCAGGAAACAAAA |
| 1500 | GTGATAATTTCAGGAAACAAAAA |
| 1501 | TGATAATTTCAGGAAACAAAAAT |
| 1502 | GATAATTTCAGGAAACAAAAATT |
| 1503 | ATAATTTCAGGAAACAAAAATTT |
| 1504 | TAATTTCAGGAAACAAAAATTTG |
| 1505 | AATTTCAGGAAACAAAAATTTGT |
| 1506 | ATTTCAGGAAACAAAAATTTGTG |
| 1507 | TTTCAGGAAACAAAAATTTGTGC |
| 1508 | TTCAGGAAACAAAAATTTGTGCT |

| ID | SEQUENCE |
|---|---|
| 1509 | TCAGGAAACAAAAATTTGTGCTA |
| 1510 | CAGGAAACAAAAATTTGTGCTAT |
| 1511 | AGGAAACAAAAATTTGTGCTATG |
| 1512 | GGAAACAAAAATTTGTGCTATGC |
| 1513 | GAAACAAAAATTTGTGCTATGCA |
| 1514 | AAACAAAAATTTGTGCTATGCAA |
| 1515 | AACAAAAATTTGTGCTATGCAAA |
| 1516 | ACAAAAATTTGTGCTATGCAAAT |
| 1517 | CAAAAATTTGTGCTATGCAAATA |
| 1518 | AAAAATTTGTGCTATGCAAATAC |
| 1519 | AAAATTTGTGCTATGCAAATACA |
| 1520 | AAATTTGTGCTATGCAAATACAA |
| 1521 | AATTTGTGCTATGCAAATACAAT |
| 1522 | ATTTGTGCTATGCAAATACAATA |
| 1523 | TTTGTGCTATGCAAATACAATAA |
| 1524 | TTGTGCTATGCAAATACAATAAA |
| 1525 | TGTGCTATGCAAATACAATAAAC |
| 1526 | GTGCTATGCAAATACAATAAACT |
| 1527 | TGCTATGCAAATACAATAAACTG |
| 1528 | GCTATGCAAATACAATAAACTGG |
| 1529 | CTATGCAAATACAATAAACTGGA |
| 1530 | TATGCAAATACAATAAACTGGAA |
| 1531 | ATGCAAATACAATAAACTGGAAA |
| 1532 | TGCAAATACAATAAACTGGAAAA |
| 1533 | GCAAATACAATAAACTGGAAAAA |
| 1534 | CAAATACAATAAACTGGAAAAAA |
| 1535 | AAATACAATAAACTGGAAAAAAC |
| 1536 | AATACAATAAACTGGAAAAAACT |
| 1537 | ATACAATAAACTGGAAAAAACTG |
| 1538 | TACAATAAACTGGAAAAAACTGT |
| 1539 | ACAATAAACTGGAAAAAACTGTT |
| 1540 | CAATAAACTGGAAAAAACTGTTT |
| 1541 | AATAAACTGGAAAAAACTGTTTG |
| 1542 | ATAAACTGGAAAAAACTGTTTGG |
| 1543 | TAAACTGGAAAAAACTGTTTGGG |
| 1544 | AAACTGGAAAAAACTGTTTGGGA |
| 1545 | AACTGGAAAAAACTGTTTGGGAC |
| 1546 | ACTGGAAAAAACTGTTTGGGACC |
| 1547 | CTGGAAAAAACTGTTTGGGACCT |
| 1548 | TGGAAAAAACTGTTTGGGACCTC |
| 1549 | GGAAAAAACTGTTTGGGACCTCC |
| 1550 | GAAAAAACTGTTTGGGACCTCCG |
| 1551 | AAAAAACTGTTTGGGACCTCCGG |
| 1552 | AAAAACTGTTTGGGACCTCCGGT |
| 1553 | AAAACTGTTTGGGACCTCCGGTC |
| 1554 | AAACTGTTTGGGACCTCCGGTCA |
| 1555 | AACTGTTTGGGACCTCCGGTCAG |
| 1556 | ACTGTTTGGGACCTCCGGTCAGA |
| 1557 | CTGTTTGGGACCTCCGGTCAGAA |
| 1558 | TGTTTGGGACCTCCGGTCAGAAA |
| 1559 | GTTTGGGACCTCCGGTCAGAAAA |
| 1560 | TTTGGGACCTCCGGTCAGAAAAC |
| 1561 | TTGGGACCTCCGGTCAGAAAACC |
| 1562 | TGGGACCTCCGGTCAGAAAACCA |
| 1563 | GGGACCTCCGGTCAGAAAACCAA |
| 1564 | GGACCTCCGGTCAGAAAACCAAA |
| 1565 | GACCTCCGGTCAGAAAACCAAAA |
| 1566 | ACCTCCGGTCAGAAAACCAAAAT |

| ID | SEQUENCE |
|---|---|
| 1567 | CCTCCGGTCAGAAAACCAAAATT |
| 1568 | CTCCGGTCAGAAAACCAAAATTA |
| 1569 | TCCGGTCAGAAAACCAAAATTAT |
| 1570 | CCGGTCAGAAAACCAAAATTATA |
| 1571 | CGGTCAGAAAACCAAAATTATAA |
| 1572 | GGTCAGAAAACCAAAATTATAAG |
| 1573 | GTCAGAAAACCAAAATTATAAGC |
| 1574 | TCAGAAAACCAAAATTATAAGCA |
| 1575 | CAGAAAACCAAAATTATAAGCAA |
| 1576 | AGAAAACCAAAATTATAAGCAAC |
| 1577 | GAAAACCAAAATTATAAGCAACA |
| 1578 | AAAACCAAAATTATAAGCAACAG |
| 1579 | AAACCAAAATTATAAGCAACAGA |
| 1580 | AACCAAAATTATAAGCAACAGAG |
| 1581 | ACCAAAATTATAAGCAACAGAGG |
| 1582 | CCAAAATTATAAGCAACAGAGGT |
| 1583 | CAAAATTATAAGCAACAGAGGTG |
| 1584 | AAAATTATAAGCAACAGAGGTGA |
| 1585 | AAATTATAAGCAACAGAGGTGAA |
| 1586 | AATTATAAGCAACAGAGGTGAAA |
| 1587 | ATTATAAGCAACAGAGGTGAAAA |
| 1588 | TTATAAGCAACAGAGGTGAAAAC |
| 1589 | TATAAGCAACAGAGGTGAAAACA |
| 1590 | ATAAGCAACAGAGGTGAAAACAG |
| 1591 | TAAGCAACAGAGGTGAAAACAGC |
| 1592 | AAGCAACAGAGGTGAAAACAGCT |
| 1593 | AGCAACAGAGGTGAAAACAGCTG |
| 1594 | GCAACAGAGGTGAAAACAGCTGC |
| 1595 | CAACAGAGGTGAAAACAGCTGCA |
| 1596 | AACAGAGGTGAAAACAGCTGCAA |
| 1597 | ACAGAGGTGAAAACAGCTGCAAG |
| 1598 | CAGAGGTGAAAACAGCTGCAAGG |
| 1599 | AGAGGTGAAAACAGCTGCAAGGC |
| 1600 | GAGGTGAAAACAGCTGCAAGGCC |
| 1601 | AGGTGAAAACAGCTGCAAGGCCA |
| 1602 | GGTGAAAACAGCTGCAAGGCCAC |
| 1603 | GTGAAAACAGCTGCAAGGCCACA |
| 1604 | TGAAAACAGCTGCAAGGCCACAG |
| 1605 | GAAAACAGCTGCAAGGCCACAGG |
| 1606 | AAAACAGCTGCAAGGCCACAGGC |
| 1607 | AAACAGCTGCAAGGCCACAGGCC |
| 1608 | AACAGCTGCAAGGCCACAGGCCA |
| 1609 | ACAGCTGCAAGGCCACAGGCCAG |
| 1610 | CAGCTGCAAGGCCACAGGCCAGG |
| 1611 | AGCTGCAAGGCCACAGGCCAGGT |
| 1612 | GCTGCAAGGCCACAGGCCAGGTC |
| 1613 | CTGCAAGGCCACAGGCCAGGTCT |
| 1614 | TGCAAGGCCACAGGCCAGGTCTG |
| 1615 | GCAAGGCCACAGGCCAGGTCTGC |
| 1616 | CAAGGCCACAGGCCAGGTCTGCC |
| 1617 | AAGGCCACAGGCCAGGTCTGCCA |
| 1618 | AGGCCACAGGCCAGGTCTGCCAT |
| 1619 | GGCCACAGGCCAGGTCTGCCATG |
| 1620 | GCCACAGGCCAGGTCTGCCATGC |
| 1621 | CCACAGGCCAGGTCTGCCATGCC |
| 1622 | CACAGGCCAGGTCTGCCATGCCT |
| 1623 | ACAGGCCAGGTCTGCCATGCCTT |
| 1624 | CAGGCCAGGTCTGCCATGCCTTG |

| ID | SEQUENCE |
|---|---|
| 1625 | AGGCCAGGTCTGCCATGCCTTGT |
| 1626 | GGCCAGGTCTGCCATGCCTTGTG |
| 1627 | GCCAGGTCTGCCATGCCTTGTGC |
| 1628 | CCAGGTCTGCCATGCCTTGTGCT |
| 1629 | CAGGTCTGCCATGCCTTGTGCTC |
| 1630 | AGGTCTGCCATGCCTTGTGCTCC |
| 1631 | GGTCTGCCATGCCTTGTGCTCCC |
| 1632 | GTCTGCCATGCCTTGTGCTCCCC |
| 1633 | TCTGCCATGCCTTGTGCTCCCCC |
| 1634 | CTGCCATGCCTTGTGCTCCCCCG |
| 1635 | TGCCATGCCTTGTGCTCCCCCGA |
| 1636 | GCCATGCCTTGTGCTCCCCCGAG |
| 1637 | CCATGCCTTGTGCTCCCCCGAGG |
| 1638 | CATGCCTTGTGCTCCCCCGAGGG |
| 1639 | ATGCCTTGTGCTCCCCCGAGGGC |
| 1640 | TGCCTTGTGCTCCCCCGAGGGCT |
| 1641 | GCCTTGTGCTCCCCCGAGGGCTG |
| 1642 | CCTTGTGCTCCCCCGAGGGCTGC |
| 1643 | CTTGTGCTCCCCCGAGGGCTGCT |
| 1644 | TTGTGCTCCCCCGAGGGCTGCTG |
| 1645 | TGTGCTCCCCCGAGGGCTGCTGG |
| 1646 | GTGCTCCCCCGAGGGCTGCTGGG |
| 1647 | TGCTCCCCCGAGGGCTGCTGGGG |
| 1648 | GCTCCCCCGAGGGCTGCTGGGGC |
| 1649 | CTCCCCCGAGGGCTGCTGGGGCC |
| 1650 | TCCCCCGAGGGCTGCTGGGGCCC |
| 1651 | CCCCCGAGGGCTGCTGGGGCCCG |
| 1652 | GGGCCCGGAGCCCAGGGACTGCG |
| 1653 | GGCCCGGAGCCCAGGGACTGCGT |
| 1654 | GCCCGGAGCCCAGGGACTGCGTC |
| 1655 | CCCGGAGCCCAGGGACTGCGTCT |
| 1656 | CCGGAGCCCAGGGACTGCGTCTC |
| 1657 | CGGAGCCCAGGGACTGCGTCTCT |
| 1658 | GGAGCCCAGGGACTGCGTCTCTT |
| 1659 | GAGCCCAGGGACTGCGTCTCTTG |
| 1660 | AGCCCAGGGACTGCGTCTCTTGC |
| 1661 | GCCCAGGGACTGCGTCTCTTGCC |
| 1662 | CCCAGGGACTGCGTCTCTTGCCG |
| 1663 | CCAGGGACTGCGTCTCTTGCCGG |
| 1664 | CAGGGACTGCGTCTCTTGCCGGA |
| 1665 | AGGGACTGCGTCTCTTGCCGGAA |
| 1666 | GGGACTGCGTCTCTTGCCGGAAT |
| 1667 | GGACTGCGTCTCTTGCCGGAATG |
| 1668 | GACTGCGTCTCTTGCCGGAATGT |
| 1669 | ACTGCGTCTCTTGCCGGAATGTC |
| 1670 | CTGCGTCTCTTGCCGGAATGTCA |
| 1671 | TGCGTCTCTTGCCGGAATGTCAG |
| 1672 | GCGTCTCTTGCCGGAATGTCAGC |
| 1673 | CGTCTCTTGCCGGAATGTCAGCC |
| 1674 | GTCTCTTGCCGGAATGTCAGCCG |
| 1675 | TCTCTTGCCGGAATGTCAGCCGA |
| 1676 | CTCTTGCCGGAATGTCAGCCGAG |
| 1677 | TCTTGCCGGAATGTCAGCCGAGG |
| 1678 | CTTGCCGGAATGTCAGCCGAGGC |
| 1679 | TTGCCGGAATGTCAGCCGAGGCA |
| 1680 | TGCCGGAATGTCAGCCGAGGCAG |
| 1681 | GCCGGAATGTCAGCCGAGGCAGG |
| 1682 | CCGGAATGTCAGCCGAGGCAGGG |

| ID | SEQUENCE |
|---|---|
| 1683 | CGGAATGTCAGCCGAGGCAGGGA |
| 1684 | GGAATGTCAGCCGAGGCAGGGAA |
| 1685 | GAATGTCAGCCGAGGCAGGGAAT |
| 1686 | AATGTCAGCCGAGGCAGGGAATG |
| 1687 | ATGTCAGCCGAGGCAGGGAATGC |
| 1688 | TGTCAGCCGAGGCAGGGAATGCG |
| 1689 | GTCAGCCGAGGCAGGGAATGCGT |
| 1690 | TCAGCCGAGGCAGGGAATGCGTG |
| 1691 | CAGCCGAGGCAGGGAATGCGTGG |
| 1692 | AGCCGAGGCAGGGAATGCGTGGA |
| 1693 | GCCGAGGCAGGGAATGCGTGGAC |
| 1694 | CCGAGGCAGGGAATGCGTGGACA |
| 1695 | CGAGGCAGGGAATGCGTGGACAA |
| 1696 | GAGGCAGGGAATGCGTGGACAAG |
| 1697 | AGGCAGGGAATGCGTGGACAAGT |
| 1698 | GGCAGGGAATGCGTGGACAAGTG |
| 1699 | GCAGGGAATGCGTGGACAAGTGC |
| 1700 | CAGGGAATGCGTGGACAAGTGCA |
| 1701 | AGGGAATGCGTGGACAAGTGCAA |
| 1702 | GGGAATGCGTGGACAAGTGCAAC |
| 1703 | GGAATGCGTGGACAAGTGCAACC |
| 1704 | GAATGCGTGGACAAGTGCAACCT |
| 1705 | AATGCGTGGACAAGTGCAACCTT |
| 1706 | ATGCGTGGACAAGTGCAACCTTC |
| 1707 | TGCGTGGACAAGTGCAACCTTCT |
| 1708 | GCGTGGACAAGTGCAACCTTCTG |
| 1709 | CGTGGACAAGTGCAACCTTCTGG |
| 1710 | GTGGACAAGTGCAACCTTCTGGA |
| 1711 | TGGACAAGTGCAACCTTCTGGAG |
| 1712 | GGACAAGTGCAACCTTCTGGAGG |
| 1713 | GACAAGTGCAACCTTCTGGAGGG |
| 1714 | ACAAGTGCAACCTTCTGGAGGGT |
| 1715 | CAAGTGCAACCTTCTGGAGGGTG |
| 1716 | AAGTGCAACCTTCTGGAGGGTGA |
| 1717 | AGTGCAACCTTCTGGAGGGTGAG |
| 1718 | GTGCAACCTTCTGGAGGGTGAGC |
| 1719 | TGCAACCTTCTGGAGGGTGAGCC |
| 1720 | GCAACCTTCTGGAGGGTGAGCCA |
| 1721 | CAACCTTCTGGAGGGTGAGCCAA |
| 1722 | AACCTTCTGGAGGGTGAGCCAAG |
| 1723 | ACCTTCTGGAGGGTGAGCCAAGG |
| 1724 | CCTTCTGGAGGGTGAGCCAAGGG |
| 1725 | CTTCTGGAGGGTGAGCCAAGGGA |
| 1726 | TTCTGGAGGGTGAGCCAAGGGAG |
| 1727 | TCTGGAGGGTGAGCCAAGGGAGT |
| 1728 | CTGGAGGGTGAGCCAAGGGAGTT |
| 1729 | TGGAGGGTGAGCCAAGGGAGTTT |
| 1730 | GGAGGGTGAGCCAAGGGAGTTTG |
| 1731 | GAGGGTGAGCCAAGGGAGTTTGT |
| 1732 | AGGGTGAGCCAAGGGAGTTTGTG |
| 1733 | GGGTGAGCCAAGGGAGTTTGTGG |
| 1734 | GGTGAGCCAAGGGAGTTTGTGGA |
| 1735 | GTGAGCCAAGGGAGTTTGTGGAG |
| 1736 | TGAGCCAAGGGAGTTTGTGGAGA |
| 1737 | GAGCCAAGGGAGTTTGTGGAGAA |
| 1738 | AGCCAAGGGAGTTTGTGGAGAAC |
| 1739 | GCCAAGGGAGTTTGTGGAGAACT |
| 1740 | CCAAGGGAGTTTGTGGAGAACTC |

| ID | SEQUENCE |
|---|---|
| 1741 | CAAGGGAGTTTGTGGAGAACTCT |
| 1742 | AAGGGAGTTTGTGGAGAACTCTG |
| 1743 | AGGGAGTTTGTGGAGAACTCTGA |
| 1744 | GGGAGTTTGTGGAGAACTCTGAG |
| 1745 | GGAGTTTGTGGAGAACTCTGAGT |
| 1746 | GAGTTTGTGGAGAACTCTGAGTG |
| 1747 | AGTTTGTGGAGAACTCTGAGTGC |
| 1748 | GTTTGTGGAGAACTCTGAGTGCA |
| 1749 | TTTGTGGAGAACTCTGAGTGCAT |
| 1750 | TTGTGGAGAACTCTGAGTGCATA |
| 1751 | TGTGGAGAACTCTGAGTGCATAC |
| 1752 | GTGGAGAACTCTGAGTGCATACA |
| 1753 | TGGAGAACTCTGAGTGCATACAG |
| 1754 | GGAGAACTCTGAGTGCATACAGT |
| 1755 | GAGAACTCTGAGTGCATACAGTG |
| 1756 | AGAACTCTGAGTGCATACAGTGC |
| 1757 | GAACTCTGAGTGCATACAGTGCC |
| 1758 | AACTCTGAGTGCATACAGTGCCA |
| 1759 | ACTCTGAGTGCATACAGTGCCAC |
| 1760 | CTCTGAGTGCATACAGTGCCACC |
| 1761 | TCTGAGTGCATACAGTGCCACCC |
| 1762 | CTGAGTGCATACAGTGCCACCCA |
| 1763 | TGAGTGCATACAGTGCCACCCAG |
| 1764 | GAGTGCATACAGTGCCACCCAGA |
| 1765 | AGTGCATACAGTGCCACCCAGAG |
| 1766 | GTGCATACAGTGCCACCCAGAGT |
| 1767 | TGCATACAGTGCCACCCAGAGTG |
| 1768 | GCATACAGTGCCACCCAGAGTGC |
| 1769 | CATACAGTGCCACCCAGAGTGCC |
| 1770 | ATACAGTGCCACCCAGAGTGCCT |
| 1771 | TACAGTGCCACCCAGAGTGCCTG |
| 1772 | ACAGTGCCACCCAGAGTGCCTGC |
| 1773 | CAGTGCCACCCAGAGTGCCTGCC |
| 1774 | AGTGCCACCCAGAGTGCCTGCCT |
| 1775 | GTGCCACCCAGAGTGCCTGCCTC |
| 1776 | TGCCACCCAGAGTGCCTGCCTCA |
| 1777 | GCCACCCAGAGTGCCTGCCTCAG |
| 1778 | CCACCCAGAGTGCCTGCCTCAGG |
| 1779 | CACCCAGAGTGCCTGCCTCAGGC |
| 1780 | ACCCAGAGTGCCTGCCTCAGGCC |
| 1781 | CCCAGAGTGCCTGCCTCAGGCCA |
| 1782 | CCAGAGTGCCTGCCTCAGGCCAT |
| 1783 | CAGAGTGCCTGCCTCAGGCCATG |
| 1784 | AGAGTGCCTGCCTCAGGCCATGA |
| 1785 | GAGTGCCTGCCTCAGGCCATGAA |
| 1786 | AGTGCCTGCCTCAGGCCATGAAC |
| 1787 | GTGCCTGCCTCAGGCCATGAACA |
| 1788 | TGCCTGCCTCAGGCCATGAACAT |
| 1789 | GCCTGCCTCAGGCCATGAACATC |
| 1790 | CCTGCCTCAGGCCATGAACATCA |
| 1791 | CTGCCTCAGGCCATGAACATCAC |
| 1792 | TGCCTCAGGCCATGAACATCACC |
| 1793 | GCCTCAGGCCATGAACATCACCT |
| 1794 | CCTCAGGCCATGAACATCACCTG |
| 1795 | CTCAGGCCATGAACATCACCTGC |
| 1796 | TCAGGCCATGAACATCACCTGCA |
| 1797 | CAGGCCATGAACATCACCTGCAC |
| 1798 | AGGCCATGAACATCACCTGCACA |

| ID | SEQUENCE |
|---|---|
| 1799 | GGCCATGAACATCACCTGCACAG |
| 1800 | GCCATGAACATCACCTGCACAGG |
| 1801 | CCATGAACATCACCTGCACAGGA |
| 1802 | CATGAACATCACCTGCACAGGAC |
| 1803 | ATGAACATCACCTGCACAGGACG |
| 1804 | TGAACATCACCTGCACAGGACGG |
| 1805 | GAACATCACCTGCACAGGACGGG |
| 1806 | AACATCACCTGCACAGGACGGGG |
| 1807 | ACATCACCTGCACAGGACGGGGA |
| 1808 | CATCACCTGCACAGGACGGGGAC |
| 1809 | ATCACCTGCACAGGACGGGGACC |
| 1810 | TCACCTGCACAGGACGGGGACCA |
| 1811 | CACCTGCACAGGACGGGGACCAG |
| 1812 | ACCTGCACAGGACGGGGACCAGA |
| 1813 | CCTGCACAGGACGGGGACCAGAC |
| 1814 | CTGCACAGGACGGGGACCAGACA |
| 1815 | TGCACAGGACGGGGACCAGACAA |
| 1816 | GCACAGGACGGGGACCAGACAAC |
| 1817 | CACAGGACGGGGACCAGACAACT |
| 1818 | ACAGGACGGGGACCAGACAACTG |
| 1819 | CAGGACGGGGACCAGACAACTGT |
| 1820 | AGGACGGGGACCAGACAACTGTA |
| 1821 | GGACGGGGACCAGACAACTGTAT |
| 1822 | GACGGGGACCAGACAACTGTATC |
| 1823 | ACGGGGACCAGACAACTGTATCC |
| 1824 | CGGGGACCAGACAACTGTATCCA |
| 1825 | GGGGACCAGACAACTGTATCCAG |
| 1826 | GGGACCAGACAACTGTATCCAGT |
| 1827 | GGACCAGACAACTGTATCCAGTG |
| 1828 | GACCAGACAACTGTATCCAGTGT |
| 1829 | ACCAGACAACTGTATCCAGTGTG |
| 1830 | CCAGACAACTGTATCCAGTGTGC |
| 1831 | CAGACAACTGTATCCAGTGTGCC |
| 1832 | AGACAACTGTATCCAGTGTGCCC |
| 1833 | GACAACTGTATCCAGTGTGCCCA |
| 1834 | ACAACTGTATCCAGTGTGCCCAC |
| 1835 | CAACTGTATCCAGTGTGCCCACT |
| 1836 | AACTGTATCCAGTGTGCCCACTA |
| 1837 | ACTGTATCCAGTGTGCCCACTAC |
| 1838 | CTGTATCCAGTGTGCCCACTACA |
| 1839 | TGTATCCAGTGTGCCCACTACAT |
| 1840 | GTATCCAGTGTGCCCACTACATT |
| 1841 | TATCCAGTGTGCCCACTACATTG |
| 1842 | ATCCAGTGTGCCCACTACATTGA |
| 1843 | TCCAGTGTGCCCACTACATTGAC |
| 1844 | CCAGTGTGCCCACTACATTGACG |
| 1845 | CAGTGTGCCCACTACATTGACGG |
| 1846 | AGTGTGCCCACTACATTGACGGC |
| 1847 | GTGTGCCCACTACATTGACGGCC |
| 1848 | TGTGCCCACTACATTGACGGCCC |
| 1849 | GTGCCCACTACATTGACGGCCCC |
| 1850 | TGCCCACTACATTGACGGCCCCC |
| 1851 | GCCCACTACATTGACGGCCCCCA |
| 1852 | CCCACTACATTGACGGCCCCCAC |
| 1853 | CCACTACATTGACGGCCCCCACT |
| 1854 | CACTACATTGACGGCCCCCACTG |
| 1855 | ACTACATTGACGGCCCCCACTGC |
| 1856 | CTACATTGACGGCCCCCACTGCG |

| ID | SEQUENCE |
|---|---|
| 1857 | TACATTGACGGCCCCCACTGCGT |
| 1858 | ACATTGACGGCCCCCACTGCGTC |
| 1859 | CATTGACGGCCCCCACTGCGTCA |
| 1860 | ATTGACGGCCCCCACTGCGTCAA |
| 1861 | TTGACGGCCCCCACTGCGTCAAG |
| 1862 | TGACGGCCCCCACTGCGTCAAGA |
| 1863 | GACGGCCCCCACTGCGTCAAGAC |
| 1864 | ACGGCCCCCACTGCGTCAAGACC |
| 1865 | CGGCCCCCACTGCGTCAAGACCT |
| 1866 | GGCCCCCACTGCGTCAAGACCTG |
| 1867 | GCCCCCACTGCGTCAAGACCTGC |
| 1868 | CCCCCACTGCGTCAAGACCTGCC |
| 1869 | CCCCACTGCGTCAAGACCTGCCC |
| 1870 | CCCACTGCGTCAAGACCTGCCCG |
| 1871 | CCACTGCGTCAAGACCTGCCCGG |
| 1872 | CACTGCGTCAAGACCTGCCCGGC |
| 1873 | ACTGCGTCAAGACCTGCCCGGCA |
| 1874 | CTGCGTCAAGACCTGCCCGGCAG |
| 1875 | TGCGTCAAGACCTGCCCGGCAGG |
| 1876 | GCGTCAAGACCTGCCCGGCAGGA |
| 1877 | CGTCAAGACCTGCCCGGCAGGAG |
| 1878 | GTCAAGACCTGCCCGGCAGGAGT |
| 1879 | TCAAGACCTGCCCGGCAGGAGTC |
| 1880 | CAAGACCTGCCCGGCAGGAGTCA |
| 1881 | AAGACCTGCCCGGCAGGAGTCAT |
| 1882 | AGACCTGCCCGGCAGGAGTCATG |
| 1883 | GACCTGCCCGGCAGGAGTCATGG |
| 1884 | ACCTGCCCGGCAGGAGTCATGGG |
| 1885 | CCTGCCCGGCAGGAGTCATGGGA |
| 1886 | CTGCCCGGCAGGAGTCATGGGAG |
| 1887 | TGCCCGGCAGGAGTCATGGGAGA |
| 1888 | GCCCGGCAGGAGTCATGGGAGAA |
| 1889 | CCCGGCAGGAGTCATGGGAGAAA |
| 1890 | CCGGCAGGAGTCATGGGAGAAAA |
| 1891 | CGGCAGGAGTCATGGGAGAAAAC |
| 1892 | GGCAGGAGTCATGGGAGAAAACA |
| 1893 | GCAGGAGTCATGGGAGAAAACAA |
| 1894 | CAGGAGTCATGGGAGAAAACAAC |
| 1895 | AGGAGTCATGGGAGAAAACAACA |
| 1896 | GGAGTCATGGGAGAAAACAACAC |
| 1897 | GAGTCATGGGAGAAAACAACACC |
| 1898 | AGTCATGGGAGAAAACAACACCC |
| 1899 | GTCATGGGAGAAAACAACACCCT |
| 1900 | TCATGGGAGAAAACAACACCCTG |
| 1901 | CATGGGAGAAAACAACACCCTGG |
| 1902 | ATGGGAGAAAACAACACCCTGGT |
| 1903 | TGGGAGAAAACAACACCCTGGTC |
| 1904 | GGGAGAAAACAACACCCTGGTCT |
| 1905 | GGAGAAAACAACACCCTGGTCTG |
| 1906 | GAGAAAACAACACCCTGGTCTGG |
| 1907 | AGAAAACAACACCCTGGTCTGGA |
| 1908 | GAAAACAACACCCTGGTCTGGAA |
| 1909 | AAAACAACACCCTGGTCTGGAAG |
| 1910 | AAACAACACCCTGGTCTGGAAGT |
| 1911 | AACAACACCCTGGTCTGGAAGTA |
| 1912 | ACAACACCCTGGTCTGGAAGTAC |
| 1913 | CAACACCCTGGTCTGGAAGTACG |
| 1914 | AACACCCTGGTCTGGAAGTACGC |

| ID | SEQUENCE |
|---|---|
| 1915 | ACACCCTGGTCTGGAAGTACGCA |
| 1916 | CACCCTGGTCTGGAAGTACGCAG |
| 1917 | ACCCTGGTCTGGAAGTACGCAGA |
| 1918 | CCCTGGTCTGGAAGTACGCAGAC |
| 1919 | CCTGGTCTGGAAGTACGCAGACG |
| 1920 | CTGGTCTGGAAGTACGCAGACGC |
| 1921 | TGGTCTGGAAGTACGCAGACGCC |
| 1922 | GGTCTGGAAGTACGCAGACGCCG |
| 1923 | GTCTGGAAGTACGCAGACGCCGG |
| 1924 | TCTGGAAGTACGCAGACGCCGGC |
| 1925 | CTGGAAGTACGCAGACGCCGGCC |
| 1926 | TGGAAGTACGCAGACGCCGGCCA |
| 1927 | GGAAGTACGCAGACGCCGGCCAT |
| 1928 | GAAGTACGCAGACGCCGGCCATG |
| 1929 | AAGTACGCAGACGCCGGCCATGT |
| 1930 | AGTACGCAGACGCCGGCCATGTG |
| 1931 | GTACGCAGACGCCGGCCATGTGT |
| 1932 | TACGCAGACGCCGGCCATGTGTG |
| 1933 | ACGCAGACGCCGGCCATGTGTGC |
| 1934 | CGCAGACGCCGGCCATGTGTGCC |
| 1935 | GCAGACGCCGGCCATGTGTGCCA |
| 1936 | CAGACGCCGGCCATGTGTGCCAC |
| 1937 | AGACGCCGGCCATGTGTGCCACC |
| 1938 | GACGCCGGCCATGTGTGCCACCT |
| 1939 | ACGCCGGCCATGTGTGCCACCTG |
| 1940 | CGCCGGCCATGTGTGCCACCTGT |
| 1941 | GCCGGCCATGTGTGCCACCTGTG |
| 1942 | CCGGCCATGTGTGCCACCTGTGC |
| 1943 | CGGCCATGTGTGCCACCTGTGCC |
| 1944 | GGCCATGTGTGCCACCTGTGCCA |
| 1945 | GCCATGTGTGCCACCTGTGCCAT |
| 1946 | CCATGTGTGCCACCTGTGCCATC |
| 1947 | CATGTGTGCCACCTGTGCCATCC |
| 1948 | ATGTGTGCCACCTGTGCCATCCA |
| 1949 | TGTGTGCCACCTGTGCCATCCAA |
| 1950 | GTGTGCCACCTGTGCCATCCAAA |
| 1951 | TGTGCCACCTGTGCCATCCAAAC |
| 1952 | GTGCCACCTGTGCCATCCAAACT |
| 1953 | TGCCACCTGTGCCATCCAAACTG |
| 1954 | GCCACCTGTGCCATCCAAACTGC |
| 1955 | CCACCTGTGCCATCCAAACTGCA |
| 1956 | CACCTGTGCCATCCAAACTGCAC |
| 1957 | ACCTGTGCCATCCAAACTGCACC |
| 1958 | CCTGTGCCATCCAAACTGCACCT |
| 1959 | CTGTGCCATCCAAACTGCACCTA |
| 1960 | TGTGCCATCCAAACTGCACCTAC |
| 1961 | GTGCCATCCAAACTGCACCTACG |
| 1962 | TGCCATCCAAACTGCACCTACGG |
| 1963 | GCCATCCAAACTGCACCTACGGA |
| 1964 | CCATCCAAACTGCACCTACGGAT |
| 1965 | CATCCAAACTGCACCTACGGATG |
| 1966 | ATCCAAACTGCACCTACGGATGC |
| 1967 | TCCAAACTGCACCTACGGATGCA |
| 1968 | CCAAACTGCACCTACGGATGCAC |
| 1969 | CAAACTGCACCTACGGATGCACT |
| 1970 | AAACTGCACCTACGGATGCACTG |
| 1971 | AACTGCACCTACGGATGCACTGG |
| 1972 | ACTGCACCTACGGATGCACTGGG |

| ID | SEQUENCE |
|---|---|
| 1973 | CTGCACCTACGGATGCACTGGGC |
| 1974 | TGCACCTACGGATGCACTGGGCC |
| 1975 | GCACCTACGGATGCACTGGGCCA |
| 1976 | CACCTACGGATGCACTGGGCCAG |
| 1977 | ACCTACGGATGCACTGGGCCAGG |
| 1978 | CCTACGGATGCACTGGGCCAGGT |
| 1979 | CTACGGATGCACTGGGCCAGGTC |
| 1980 | TACGGATGCACTGGGCCAGGTCT |
| 1981 | ACGGATGCACTGGGCCAGGTCTT |
| 1982 | CGGATGCACTGGGCCAGGTCTTG |
| 1983 | GGATGCACTGGGCCAGGTCTTGA |
| 1984 | GATGCACTGGGCCAGGTCTTGAA |
| 1985 | ATGCACTGGGCCAGGTCTTGAAG |
| 1986 | TGCACTGGGCCAGGTCTTGAAGG |
| 1987 | GCACTGGGCCAGGTCTTGAAGGC |
| 1988 | CACTGGGCCAGGTCTTGAAGGCT |
| 1989 | ACTGGGCCAGGTCTTGAAGGCTG |
| 1990 | CTGGGCCAGGTCTTGAAGGCTGT |
| 1991 | TGGGCCAGGTCTTGAAGGCTGTC |
| 1992 | GGGCCAGGTCTTGAAGGCTGTCC |
| 1993 | GGCCAGGTCTTGAAGGCTGTCCA |
| 1994 | GCCAGGTCTTGAAGGCTGTCCAA |
| 1995 | CCAGGTCTTGAAGGCTGTCCAAC |
| 1996 | CAGGTCTTGAAGGCTGTCCAACG |
| 1997 | AGGTCTTGAAGGCTGTCCAACGA |
| 1998 | GGTCTTGAAGGCTGTCCAACGAA |
| 1999 | GTCTTGAAGGCTGTCCAACGAAT |
| 2000 | TCTTGAAGGCTGTCCAACGAATG |
| 2001 | CTTGAAGGCTGTCCAACGAATGG |
| 2002 | TTGAAGGCTGTCCAACGAATGGG |
| 2003 | TGAAGGCTGTCCAACGAATGGGC |
| 2004 | GAAGGCTGTCCAACGAATGGGCC |
| 2005 | AAGGCTGTCCAACGAATGGGCCT |
| 2006 | AGGCTGTCCAACGAATGGGCCTA |
| 2007 | GGCTGTCCAACGAATGGGCCTAA |
| 2008 | GCTGTCCAACGAATGGGCCTAAG |
| 2009 | CTGTCCAACGAATGGGCCTAAGA |
| 2010 | TGTCCAACGAATGGGCCTAAGAT |
| 2011 | GTCCAACGAATGGGCCTAAGATC |
| 2012 | TCCAACGAATGGGCCTAAGATCC |
| 2013 | CCAACGAATGGGCCTAAGATCCC |
| 2014 | CAACGAATGGGCCTAAGATCCCG |
| 2015 | AACGAATGGGCCTAAGATCCCGT |
| 2016 | ACGAATGGGCCTAAGATCCCGTC |
| 2017 | CGAATGGGCCTAAGATCCCGTCC |
| 2018 | GAATGGGCCTAAGATCCCGTCCA |
| 2019 | AATGGGCCTAAGATCCCGTCCAT |
| 2020 | ATGGGCCTAAGATCCCGTCCATC |
| 2021 | TGGGCCTAAGATCCCGTCCATCG |
| 2022 | GGGCCTAAGATCCCGTCCATCGC |
| 2023 | GGCCTAAGATCCCGTCCATCGCC |
| 2024 | GCCTAAGATCCCGTCCATCGCCA |
| 2025 | CCTAAGATCCCGTCCATCGCCAC |
| 2026 | CTAAGATCCCGTCCATCGCCACT |
| 2027 | TAAGATCCCGTCCATCGCCACTG |
| 2028 | AAGATCCCGTCCATCGCCACTGG |
| 2029 | AGATCCCGTCCATCGCCACTGGG |
| 2030 | GATCCCGTCCATCGCCACTGGGA |

| ID | SEQUENCE |
|---|---|
| 2031 | ATCCCGTCCATCGCCACTGGGAT |
| 2032 | TCCCGTCCATCGCCACTGGGATG |
| 2033 | CCCGTCCATCGCCACTGGGATGG |
| 2034 | CCGTCCATCGCCACTGGGATGGT |
| 2035 | CGTCCATCGCCACTGGGATGGTG |
| 2036 | GTCCATCGCCACTGGGATGGTGG |
| 2037 | TCCATCGCCACTGGGATGGTGGG |
| 2038 | CCATCGCCACTGGGATGGTGGGG |
| 2039 | CATCGCCACTGGGATGGTGGGGG |
| 2040 | ATCGCCACTGGGATGGTGGGGGC |
| 2041 | TCGCCACTGGGATGGTGGGGGCC |
| 2042 | CGCCACTGGGATGGTGGGGGCCC |
| 2043 | GCCACTGGGATGGTGGGGGCCCT |
| 2044 | CCACTGGGATGGTGGGGGCCCTC |
| 2045 | CACTGGGATGGTGGGGGCCCTCC |
| 2046 | ACTGGGATGGTGGGGGCCCTCCT |
| 2047 | CTGGGATGGTGGGGGCCCTCCTC |
| 2048 | TGGGATGGTGGGGGCCCTCCTCT |
| 2049 | GGGATGGTGGGGGCCCTCCTCTT |
| 2050 | GGATGGTGGGGGCCCTCCTCTTG |
| 2051 | GATGGTGGGGGCCCTCCTCTTGC |
| 2052 | ATGGTGGGGGCCCTCCTCTTGCT |
| 2053 | TGGTGGGGGCCCTCCTCTTGCTG |
| 2054 | GGTGGGGGCCCTCCTCTTGCTGC |
| 2055 | GTGGGGGCCCTCCTCTTGCTGCT |
| 2056 | TGGGGGCCCTCCTCTTGCTGCTG |
| 2057 | GGGGGCCCTCCTCTTGCTGCTGG |
| 2058 | GGGGCCCTCCTCTTGCTGCTGGT |
| 2059 | GGGCCCTCCTCTTGCTGCTGGTG |
| 2060 | GGCCCTCCTCTTGCTGCTGGTGG |
| 2061 | GCCCTCCTCTTGCTGCTGGTGGT |
| 2062 | CCCTCCTCTTGCTGCTGGTGGTG |
| 2063 | CCTCCTCTTGCTGCTGGTGGTGG |
| 2064 | CTCCTCTTGCTGCTGGTGGTGGC |
| 2065 | TCCTCTTGCTGCTGGTGGTGGCC |
| 2066 | CCTCTTGCTGCTGGTGGTGGCCC |
| 2067 | CTCTTGCTGCTGGTGGTGGCCCT |
| 2068 | TCTTGCTGCTGGTGGTGGCCCTG |
| 2069 | CTTGCTGCTGGTGGTGGCCCTGG |
| 2070 | TTGCTGCTGGTGGTGGCCCTGGG |
| 2071 | TGCTGCTGGTGGTGGCCCTGGGG |
| 2072 | GCTGCTGGTGGTGGCCCTGGGGA |
| 2073 | CTGCTGGTGGTGGCCCTGGGGAT |
| 2074 | TGCTGGTGGTGGCCCTGGGGATC |
| 2075 | GCTGGTGGTGGCCCTGGGGATCG |
| 2076 | CTGGTGGTGGCCCTGGGGATCGG |
| 2077 | TGGTGGTGGCCCTGGGGATCGGC |
| 2078 | GGTGGTGGCCCTGGGGATCGGCC |
| 2079 | GTGGTGGCCCTGGGGATCGGCCT |
| 2080 | TGGTGGCCCTGGGGATCGGCCTC |
| 2081 | GGTGGCCCTGGGGATCGGCCTCT |
| 2082 | GTGGCCCTGGGGATCGGCCTCTT |
| 2083 | TGGCCCTGGGGATCGGCCTCTTC |
| 2084 | GGCCCTGGGGATCGGCCTCTTCA |
| 2085 | GCCCTGGGGATCGGCCTCTTCAT |
| 2086 | CCCTGGGGATCGGCCTCTTCATG |
| 2087 | CCTGGGGATCGGCCTCTTCATGC |
| 2088 | CTGGGGATCGGCCTCTTCATGCG |

| ID | SEQUENCE |
|---|---|
| 2089 | TGGGGATCGGCCTCTTCATGCGA |
| 2090 | GGGGATCGGCCTCTTCATGCGAA |
| 2091 | GGGATCGGCCTCTTCATGCGAAG |
| 2092 | GGATCGGCCTCTTCATGCGAAGG |
| 2093 | GATCGGCCTCTTCATGCGAAGGC |
| 2094 | ATCGGCCTCTTCATGCGAAGGCG |
| 2095 | TCGGCCTCTTCATGCGAAGGCGC |
| 2096 | CGGCCTCTTCATGCGAAGGCGCC |
| 2097 | GGCCTCTTCATGCGAAGGCGCCA |
| 2098 | GCCTCTTCATGCGAAGGCGCCAC |
| 2099 | CCTCTTCATGCGAAGGCGCCACA |
| 2100 | CTCTTCATGCGAAGGCGCCACAT |
| 2101 | TCTTCATGCGAAGGCGCCACATC |
| 2102 | CTTCATGCGAAGGCGCCACATCG |
| 2103 | TTCATGCGAAGGCGCCACATCGT |
| 2104 | TCATGCGAAGGCGCCACATCGTT |
| 2105 | CATGCGAAGGCGCCACATCGTTC |
| 2106 | ATGCGAAGGCGCCACATCGTTCG |
| 2107 | TGCGAAGGCGCCACATCGTTCGG |
| 2108 | GCGAAGGCGCCACATCGTTCGGA |
| 2109 | CGAAGGCGCCACATCGTTCGGAA |
| 2110 | GAAGGCGCCACATCGTTCGGAAG |
| 2111 | AAGGCGCCACATCGTTCGGAAGC |
| 2112 | AGGCGCCACATCGTTCGGAAGCG |
| 2113 | GGCGCCACATCGTTCGGAAGCGC |
| 2114 | GCGCCACATCGTTCGGAAGCGCA |
| 2115 | CGCCACATCGTTCGGAAGCGCAC |
| 2116 | GCCACATCGTTCGGAAGCGCACG |
| 2117 | CCACATCGTTCGGAAGCGCACGC |
| 2118 | CACATCGTTCGGAAGCGCACGCT |
| 2119 | ACATCGTTCGGAAGCGCACGCTG |
| 2120 | CATCGTTCGGAAGCGCACGCTGC |
| 2121 | ATCGTTCGGAAGCGCACGCTGCG |
| 2122 | TCGTTCGGAAGCGCACGCTGCGG |
| 2123 | CGTTCGGAAGCGCACGCTGCGGA |
| 2124 | GTTCGGAAGCGCACGCTGCGGAG |
| 2125 | TTCGGAAGCGCACGCTGCGGAGG |
| 2126 | TCGGAAGCGCACGCTGCGGAGGC |
| 2127 | CGGAAGCGCACGCTGCGGAGGCT |
| 2128 | GGAAGCGCACGCTGCGGAGGCTG |
| 2129 | GAAGCGCACGCTGCGGAGGCTGC |
| 2130 | AAGCGCACGCTGCGGAGGCTGCT |
| 2131 | AGCGCACGCTGCGGAGGCTGCTG |
| 2132 | GCGCACGCTGCGGAGGCTGCTGC |
| 2133 | CGCACGCTGCGGAGGCTGCTGCA |
| 2134 | GCACGCTGCGGAGGCTGCTGCAG |
| 2135 | CACGCTGCGGAGGCTGCTGCAGG |
| 2136 | ACGCTGCGGAGGCTGCTGCAGGA |
| 2137 | CGCTGCGGAGGCTGCTGCAGGAG |
| 2138 | GCTGCGGAGGCTGCTGCAGGAGA |
| 2139 | CTGCGGAGGCTGCTGCAGGAGAG |
| 2140 | TGCGGAGGCTGCTGCAGGAGAGG |
| 2141 | GCGGAGGCTGCTGCAGGAGAGGG |
| 2142 | CGGAGGCTGCTGCAGGAGAGGGA |
| 2143 | GGAGGCTGCTGCAGGAGAGGGAG |
| 2144 | GAGGCTGCTGCAGGAGAGGGAGC |
| 2145 | AGGCTGCTGCAGGAGAGGGAGCT |
| 2146 | GGCTGCTGCAGGAGAGGGAGCTT |

| ID | SEQUENCE |
|---|---|
| 2147 | GCTGCTGCAGGAGAGGGAGCTTG |
| 2148 | CTGCTGCAGGAGAGGGAGCTTGT |
| 2149 | TGCTGCAGGAGAGGGAGCTTGTG |
| 2150 | GCTGCAGGAGAGGGAGCTTGTGG |
| 2151 | CTGCAGGAGAGGGAGCTTGTGGA |
| 2152 | TGCAGGAGAGGGAGCTTGTGGAG |
| 2153 | GCAGGAGAGGGAGCTTGTGGAGC |
| 2154 | CAGGAGAGGGAGCTTGTGGAGCC |
| 2155 | AGGAGAGGGAGCTTGTGGAGCCT |
| 2156 | GGAGAGGGAGCTTGTGGAGCCTC |
| 2157 | GAGAGGGAGCTTGTGGAGCCTCT |
| 2158 | AGAGGGAGCTTGTGGAGCCTCTT |
| 2159 | GAGGGAGCTTGTGGAGCCTCTTA |
| 2160 | AGGGAGCTTGTGGAGCCTCTTAC |
| 2161 | GGGAGCTTGTGGAGCCTCTTACA |
| 2162 | GGAGCTTGTGGAGCCTCTTACAC |
| 2163 | GAGCTTGTGGAGCCTCTTACACC |
| 2164 | AGCTTGTGGAGCCTCTTACACCC |
| 2165 | GCTTGTGGAGCCTCTTACACCCA |
| 2166 | CTTGTGGAGCCTCTTACACCCAG |
| 2167 | TTGTGGAGCCTCTTACACCCAGT |
| 2168 | TGTGGAGCCTCTTACACCCAGTG |
| 2169 | GTGGAGCCTCTTACACCCAGTGG |
| 2170 | TGGAGCCTCTTACACCCAGTGGA |
| 2171 | GGAGCCTCTTACACCCAGTGGAG |
| 2172 | GAGCCTCTTACACCCAGTGGAGA |
| 2173 | AGCCTCTTACACCCAGTGGAGAA |
| 2174 | GCCTCTTACACCCAGTGGAGAAG |
| 2175 | CCTCTTACACCCAGTGGAGAAGC |
| 2176 | CTCTTACACCCAGTGGAGAAGCT |
| 2177 | TCTTACACCCAGTGGAGAAGCTC |
| 2178 | CTTACACCCAGTGGAGAAGCTCC |
| 2179 | TTACACCCAGTGGAGAAGCTCCC |
| 2180 | TACACCCAGTGGAGAAGCTCCCA |
| 2181 | ACACCCAGTGGAGAAGCTCCCAA |
| 2182 | CACCCAGTGGAGAAGCTCCCAAC |
| 2183 | ACCCAGTGGAGAAGCTCCCAACC |
| 2184 | CCCAGTGGAGAAGCTCCCAACCA |
| 2185 | CCAGTGGAGAAGCTCCCAACCAA |
| 2186 | CAGTGGAGAAGCTCCCAACCAAG |
| 2187 | AGTGGAGAAGCTCCCAACCAAGC |
| 2188 | GTGGAGAAGCTCCCAACCAAGCT |
| 2189 | TGGAGAAGCTCCCAACCAAGCTC |
| 2190 | GGAGAAGCTCCCAACCAAGCTCT |
| 2191 | GAGAAGCTCCCAACCAAGCTCTC |
| 2192 | AGAAGCTCCCAACCAAGCTCTCT |
| 2193 | GAAGCTCCCAACCAAGCTCTCTT |
| 2194 | AAGCTCCCAACCAAGCTCTCTTG |
| 2195 | AGCTCCCAACCAAGCTCTCTTGA |
| 2196 | GCTCCCAACCAAGCTCTCTTGAG |
| 2197 | CTCCCAACCAAGCTCTCTTGAGG |
| 2198 | TCCCAACCAAGCTCTCTTGAGGA |
| 2199 | CCCAACCAAGCTCTCTTGAGGAT |
| 2200 | CCAACCAAGCTCTCTTGAGGATC |
| 2201 | CAACCAAGCTCTCTTGAGGATCT |
| 2202 | AACCAAGCTCTCTTGAGGATCTT |
| 2203 | ACCAAGCTCTCTTGAGGATCTTG |
| 2204 | CCAAGCTCTCTTGAGGATCTTGA |

| ID | SEQUENCE |
|---|---|
| 2205 | CAAGCTCTCTTGAGGATCTTGAA |
| 2206 | AAGCTCTCTTGAGGATCTTGAAG |
| 2207 | AGCTCTCTTGAGGATCTTGAAGG |
| 2208 | GCTCTCTTGAGGATCTTGAAGGA |
| 2209 | CTCTCTTGAGGATCTTGAAGGAA |
| 2210 | TCTCTTGAGGATCTTGAAGGAAA |
| 2211 | CTCTTGAGGATCTTGAAGGAAAC |
| 2212 | TCTTGAGGATCTTGAAGGAAACT |
| 2213 | CTTGAGGATCTTGAAGGAAACTG |
| 2214 | TTGAGGATCTTGAAGGAAACTGA |
| 2215 | TGAGGATCTTGAAGGAAACTGAA |
| 2216 | GAGGATCTTGAAGGAAACTGAAT |
| 2217 | AGGATCTTGAAGGAAACTGAATT |
| 2218 | GGATCTTGAAGGAAACTGAATTC |
| 2219 | GATCTTGAAGGAAACTGAATTCA |
| 2220 | ATCTTGAAGGAAACTGAATTCAA |
| 2221 | TCTTGAAGGAAACTGAATTCAAA |
| 2222 | CTTGAAGGAAACTGAATTCAAAA |
| 2223 | TTGAAGGAAACTGAATTCAAAAA |
| 2224 | TGAAGGAAACTGAATTCAAAAAG |
| 2225 | GAAGGAAACTGAATTCAAAAAGA |
| 2226 | AAGGAAACTGAATTCAAAAAGAT |
| 2227 | AGGAAACTGAATTCAAAAAGATC |
| 2228 | GGAAACTGAATTCAAAAAGATCA |
| 2229 | GAAACTGAATTCAAAAAGATCAA |
| 2230 | AAACTGAATTCAAAAAGATCAAA |
| 2231 | AACTGAATTCAAAAAGATCAAAG |
| 2232 | ACTGAATTCAAAAAGATCAAAGT |
| 2233 | CTGAATTCAAAAAGATCAAAGTG |
| 2234 | TGAATTCAAAAAGATCAAAGTGC |
| 2235 | GAATTCAAAAAGATCAAAGTGCT |
| 2236 | AATTCAAAAAGATCAAAGTGCTG |
| 2237 | ATTCAAAAAGATCAAAGTGCTGG |
| 2238 | TTCAAAAAGATCAAAGTGCTGGG |
| 2239 | TCAAAAAGATCAAAGTGCTGGGC |
| 2240 | CAAAAAGATCAAAGTGCTGGGCT |
| 2241 | AAAAAGATCAAAGTGCTGGGCTC |
| 2242 | AAAAGATCAAAGTGCTGGGCTCC |
| 2243 | AAAGATCAAAGTGCTGGGCTCCG |
| 2244 | AAGATCAAAGTGCTGGGCTCCGG |
| 2245 | AGATCAAAGTGCTGGGCTCCGGT |
| 2246 | GATCAAAGTGCTGGGCTCCGGTG |
| 2247 | ATCAAAGTGCTGGGCTCCGGTGC |
| 2248 | TCAAAGTGCTGGGCTCCGGTGCG |
| 2249 | CAAAGTGCTGGGCTCCGGTGCGT |
| 2250 | AAAGTGCTGGGCTCCGGTGCGTT |
| 2251 | AAGTGCTGGGCTCCGGTGCGTTC |
| 2252 | AGTGCTGGGCTCCGGTGCGTTCG |
| 2253 | GTGCTGGGCTCCGGTGCGTTCGG |
| 2254 | TGCTGGGCTCCGGTGCGTTCGGC |
| 2255 | GCTGGGCTCCGGTGCGTTCGGCA |
| 2256 | CTGGGCTCCGGTGCGTTCGGCAC |
| 2257 | TGGGCTCCGGTGCGTTCGGCACG |
| 2258 | GGGCTCCGGTGCGTTCGGCACGG |
| 2259 | GGCTCCGGTGCGTTCGGCACGGT |
| 2260 | GCTCCGGTGCGTTCGGCACGGTG |
| 2261 | CTCCGGTGCGTTCGGCACGGTGT |
| 2262 | TCCGGTGCGTTCGGCACGGTGTA |

| ID | SEQUENCE |
|---|---|
| 2263 | CCGGTGCGTTCGGCACGGTGTAT |
| 2264 | CGGTGCGTTCGGCACGGTGTATA |
| 2265 | GGTGCGTTCGGCACGGTGTATAA |
| 2266 | GTGCGTTCGGCACGGTGTATAAG |
| 2267 | TGCGTTCGGCACGGTGTATAAGG |
| 2268 | GCGTTCGGCACGGTGTATAAGGG |
| 2269 | CGTTCGGCACGGTGTATAAGGGA |
| 2270 | GTTCGGCACGGTGTATAAGGGAC |
| 2271 | TTCGGCACGGTGTATAAGGGACT |
| 2272 | TCGGCACGGTGTATAAGGGACTC |
| 2273 | CGGCACGGTGTATAAGGGACTCT |
| 2274 | GGCACGGTGTATAAGGGACTCTG |
| 2275 | GCACGGTGTATAAGGGACTCTGG |
| 2276 | CACGGTGTATAAGGGACTCTGGA |
| 2277 | ACGGTGTATAAGGGACTCTGGAT |
| 2278 | CGGTGTATAAGGGACTCTGGATC |
| 2279 | GGTGTATAAGGGACTCTGGATCC |
| 2280 | GTGTATAAGGGACTCTGGATCCC |
| 2281 | TGTATAAGGGACTCTGGATCCCA |
| 2282 | GTATAAGGGACTCTGGATCCCAG |
| 2283 | TATAAGGGACTCTGGATCCCAGA |
| 2284 | ATAAGGGACTCTGGATCCCAGAA |
| 2285 | TAAGGGACTCTGGATCCCAGAAG |
| 2286 | AAGGGACTCTGGATCCCAGAAGG |
| 2287 | AGGGACTCTGGATCCCAGAAGGT |
| 2288 | GGGACTCTGGATCCCAGAAGGTG |
| 2289 | GGACTCTGGATCCCAGAAGGTGA |
| 2290 | GACTCTGGATCCCAGAAGGTGAG |
| 2291 | ACTCTGGATCCCAGAAGGTGAGA |
| 2292 | CTCTGGATCCCAGAAGGTGAGAA |
| 2293 | TCTGGATCCCAGAAGGTGAGAAA |
| 2294 | CTGGATCCCAGAAGGTGAGAAAG |
| 2295 | TGGATCCCAGAAGGTGAGAAAGT |
| 2296 | GGATCCCAGAAGGTGAGAAAGTT |
| 2297 | GATCCCAGAAGGTGAGAAAGTTA |
| 2298 | ATCCCAGAAGGTGAGAAAGTTAA |
| 2299 | TCCCAGAAGGTGAGAAAGTTAAA |
| 2300 | CCCAGAAGGTGAGAAAGTTAAAA |
| 2301 | CCAGAAGGTGAGAAAGTTAAAAT |
| 2302 | CAGAAGGTGAGAAAGTTAAAATT |
| 2303 | AGAAGGTGAGAAAGTTAAAATTC |
| 2304 | GAAGGTGAGAAAGTTAAAATTCC |
| 2305 | AAGGTGAGAAAGTTAAAATTCCC |
| 2306 | AGGTGAGAAAGTTAAAATTCCCG |
| 2307 | GGTGAGAAAGTTAAAATTCCCGT |
| 2308 | GTGAGAAAGTTAAAATTCCCGTC |
| 2309 | TGAGAAAGTTAAAATTCCCGTCG |
| 2310 | GAGAAAGTTAAAATTCCCGTCGC |
| 2311 | AGAAAGTTAAAATTCCCGTCGCT |
| 2312 | GAAAGTTAAAATTCCCGTCGCTA |
| 2313 | AAAGTTAAAATTCCCGTCGCTAT |
| 2314 | AAGTTAAAATTCCCGTCGCTATC |
| 2315 | AGTTAAAATTCCCGTCGCTATCA |
| 2316 | GTTAAAATTCCCGTCGCTATCAA |
| 2317 | TTAAAATTCCCGTCGCTATCAAG |
| 2318 | TAAAATTCCCGTCGCTATCAAGG |
| 2319 | AAAATTCCCGTCGCTATCAAGGA |
| 2320 | AAATTCCCGTCGCTATCAAGGAA |

| ID | SEQUENCE |
|---|---|
| 2321 | AATTCCCGTCGCTATCAAGGAAT |
| 2322 | ATTCCCGTCGCTATCAAGGAATT |
| 2323 | TTCCCGTCGCTATCAAGGAATTA |
| 2324 | TCCCGTCGCTATCAAGGAATTAA |
| 2325 | CCCGTCGCTATCAAGGAATTAAG |
| 2326 | CCGTCGCTATCAAGGAATTAAGA |
| 2327 | CGTCGCTATCAAGGAATTAAGAG |
| 2328 | GTCGCTATCAAGGAATTAAGAGA |
| 2329 | TCGCTATCAAGGAATTAAGAGAA |
| 2330 | CGCTATCAAGGAATTAAGAGAAG |
| 2331 | GCTATCAAGGAATTAAGAGAAGC |
| 2332 | CTATCAAGGAATTAAGAGAAGCA |
| 2333 | TATCAAGGAATTAAGAGAAGCAA |
| 2334 | ATCAAGGAATTAAGAGAAGCAAC |
| 2335 | TCAAGGAATTAAGAGAAGCAACA |
| 2336 | CAAGGAATTAAGAGAAGCAACAT |
| 2337 | AAGGAATTAAGAGAAGCAACATC |
| 2338 | AGGAATTAAGAGAAGCAACATCT |
| 2339 | GGAATTAAGAGAAGCAACATCTC |
| 2340 | GAATTAAGAGAAGCAACATCTCC |
| 2341 | AATTAAGAGAAGCAACATCTCCG |
| 2342 | ATTAAGAGAAGCAACATCTCCGA |
| 2343 | TTAAGAGAAGCAACATCTCCGAA |
| 2344 | TAAGAGAAGCAACATCTCCGAAA |
| 2345 | AAGAGAAGCAACATCTCCGAAAG |
| 2346 | AGAGAAGCAACATCTCCGAAAGC |
| 2347 | GAGAAGCAACATCTCCGAAAGCC |
| 2348 | AGAAGCAACATCTCCGAAAGCCA |
| 2349 | GAAGCAACATCTCCGAAAGCCAA |
| 2350 | AAGCAACATCTCCGAAAGCCAAC |
| 2351 | AGCAACATCTCCGAAAGCCAACA |
| 2352 | GCAACATCTCCGAAAGCCAACAA |
| 2353 | CAACATCTCCGAAAGCCAACAAG |
| 2354 | AACATCTCCGAAAGCCAACAAGG |
| 2355 | ACATCTCCGAAAGCCAACAAGGA |
| 2356 | CATCTCCGAAAGCCAACAAGGAA |
| 2357 | ATCTCCGAAAGCCAACAAGGAAA |
| 2358 | TCTCCGAAAGCCAACAAGGAAAT |
| 2359 | CTCCGAAAGCCAACAAGGAAATC |
| 2360 | TCCGAAAGCCAACAAGGAAATCC |
| 2361 | CCGAAAGCCAACAAGGAAATCCT |
| 2362 | CGAAAGCCAACAAGGAAATCCTC |
| 2363 | GAAAGCCAACAAGGAAATCCTCG |
| 2364 | AAAGCCAACAAGGAAATCCTCGA |
| 2365 | AAGCCAACAAGGAAATCCTCGAT |
| 2366 | AGCCAACAAGGAAATCCTCGATG |
| 2367 | GCCAACAAGGAAATCCTCGATGA |
| 2368 | CCAACAAGGAAATCCTCGATGAA |
| 2369 | CAACAAGGAAATCCTCGATGAAG |
| 2370 | AACAAGGAAATCCTCGATGAAGC |
| 2371 | ACAAGGAAATCCTCGATGAAGCC |
| 2372 | CAAGGAAATCCTCGATGAAGCCT |
| 2373 | AAGGAAATCCTCGATGAAGCCTA |
| 2374 | AGGAAATCCTCGATGAAGCCTAC |
| 2375 | GGAAATCCTCGATGAAGCCTACG |
| 2376 | GAAATCCTCGATGAAGCCTACGT |
| 2377 | AAATCCTCGATGAAGCCTACGTG |
| 2378 | AATCCTCGATGAAGCCTACGTGA |

| ID | SEQUENCE |
|---|---|
| 2379 | ATCCTCGATGAAGCCTACGTGAT |
| 2380 | TCCTCGATGAAGCCTACGTGATG |
| 2381 | CCTCGATGAAGCCTACGTGATGG |
| 2382 | CTCGATGAAGCCTACGTGATGGC |
| 2383 | TCGATGAAGCCTACGTGATGGCC |
| 2384 | CGATGAAGCCTACGTGATGGCCA |
| 2385 | GATGAAGCCTACGTGATGGCCAG |
| 2386 | ATGAAGCCTACGTGATGGCCAGC |
| 2387 | TGAAGCCTACGTGATGGCCAGCG |
| 2388 | GAAGCCTACGTGATGGCCAGCGT |
| 2389 | AAGCCTACGTGATGGCCAGCGTG |
| 2390 | AGCCTACGTGATGGCCAGCGTGG |
| 2391 | GCCTACGTGATGGCCAGCGTGGA |
| 2392 | CCTACGTGATGGCCAGCGTGGAC |
| 2393 | CTACGTGATGGCCAGCGTGGACA |
| 2394 | TACGTGATGGCCAGCGTGGACAA |
| 2395 | ACGTGATGGCCAGCGTGGACAAC |
| 2396 | CGTGATGGCCAGCGTGGACAACC |
| 2397 | GTGATGGCCAGCGTGGACAACCC |
| 2398 | TGATGGCCAGCGTGGACAACCCC |
| 2399 | GATGGCCAGCGTGGACAACCCCC |
| 2400 | ATGGCCAGCGTGGACAACCCCCA |
| 2401 | TGGCCAGCGTGGACAACCCCCAC |
| 2402 | GGCCAGCGTGGACAACCCCCACG |
| 2403 | GCCAGCGTGGACAACCCCCACGT |
| 2404 | CCAGCGTGGACAACCCCCACGTG |
| 2405 | CAGCGTGGACAACCCCCACGTGT |
| 2406 | AGCGTGGACAACCCCCACGTGTG |
| 2407 | GCGTGGACAACCCCCACGTGTGC |
| 2408 | CGTGGACAACCCCCACGTGTGCC |
| 2409 | GTGGACAACCCCCACGTGTGCCG |
| 2410 | TGGACAACCCCCACGTGTGCCGC |
| 2411 | GGACAACCCCCACGTGTGCCGCC |
| 2412 | GACAACCCCCACGTGTGCCGCCT |
| 2413 | ACAACCCCCACGTGTGCCGCCTG |
| 2414 | CAACCCCCACGTGTGCCGCCTGC |
| 2415 | AACCCCCACGTGTGCCGCCTGCT |
| 2416 | ACCCCCACGTGTGCCGCCTGCTG |
| 2417 | CCCCCACGTGTGCCGCCTGCTGG |
| 2418 | CCCCACGTGTGCCGCCTGCTGGG |
| 2419 | CCCACGTGTGCCGCCTGCTGGGC |
| 2420 | CCACGTGTGCCGCCTGCTGGGCA |
| 2421 | CACGTGTGCCGCCTGCTGGGCAT |
| 2422 | ACGTGTGCCGCCTGCTGGGCATC |
| 2423 | CGTGTGCCGCCTGCTGGGCATCT |
| 2424 | GTGTGCCGCCTGCTGGGCATCTG |
| 2425 | TGTGCCGCCTGCTGGGCATCTGC |
| 2426 | GTGCCGCCTGCTGGGCATCTGCC |
| 2427 | TGCCGCCTGCTGGGCATCTGCCT |
| 2428 | GCCGCCTGCTGGGCATCTGCCTC |
| 2429 | CCGCCTGCTGGGCATCTGCCTCA |
| 2430 | CGCCTGCTGGGCATCTGCCTCAC |
| 2431 | GCCTGCTGGGCATCTGCCTCACC |
| 2432 | CCTGCTGGGCATCTGCCTCACCT |
| 2433 | CTGCTGGGCATCTGCCTCACCTC |
| 2434 | TGCTGGGCATCTGCCTCACCTCC |
| 2435 | GCTGGGCATCTGCCTCACCTCCA |
| 2436 | CTGGGCATCTGCCTCACCTCCAC |

| ID | SEQUENCE |
|---|---|
| 2437 | TGGGCATCTGCCTCACCTCCACC |
| 2438 | GGGCATCTGCCTCACCTCCACCG |
| 2439 | GGCATCTGCCTCACCTCCACCGT |
| 2440 | GCATCTGCCTCACCTCCACCGTG |
| 2441 | CATCTGCCTCACCTCCACCGTGC |
| 2442 | ATCTGCCTCACCTCCACCGTGCA |
| 2443 | TCTGCCTCACCTCCACCGTGCAG |
| 2444 | CTGCCTCACCTCCACCGTGCAGC |
| 2445 | TGCCTCACCTCCACCGTGCAGCT |
| 2446 | GCCTCACCTCCACCGTGCAGCTC |
| 2447 | CCTCACCTCCACCGTGCAGCTCA |
| 2448 | CTCACCTCCACCGTGCAGCTCAT |
| 2449 | TCACCTCCACCGTGCAGCTCATC |
| 2450 | CACCTCCACCGTGCAGCTCATCA |
| 2451 | ACCTCCACCGTGCAGCTCATCAC |
| 2452 | CCTCCACCGTGCAGCTCATCACG |
| 2453 | CTCCACCGTGCAGCTCATCACGC |
| 2454 | TCCACCGTGCAGCTCATCACGCA |
| 2455 | CCACCGTGCAGCTCATCACGCAG |
| 2456 | CACCGTGCAGCTCATCACGCAGC |
| 2457 | ACCGTGCAGCTCATCACGCAGCT |
| 2458 | CCGTGCAGCTCATCACGCAGCTC |
| 2459 | CGTGCAGCTCATCACGCAGCTCA |
| 2460 | GTGCAGCTCATCACGCAGCTCAT |
| 2461 | TGCAGCTCATCACGCAGCTCATG |
| 2462 | GCAGCTCATCACGCAGCTCATGC |
| 2463 | CAGCTCATCACGCAGCTCATGCC |
| 2464 | AGCTCATCACGCAGCTCATGCCC |
| 2465 | GCTCATCACGCAGCTCATGCCCT |
| 2466 | CTCATCACGCAGCTCATGCCCTT |
| 2467 | TCATCACGCAGCTCATGCCCTTC |
| 2468 | CATCACGCAGCTCATGCCCTTCG |
| 2469 | ATCACGCAGCTCATGCCCTTCGG |
| 2470 | TCACGCAGCTCATGCCCTTCGGC |
| 2471 | CACGCAGCTCATGCCCTTCGGCT |
| 2472 | ACGCAGCTCATGCCCTTCGGCTG |
| 2473 | CGCAGCTCATGCCCTTCGGCTGC |
| 2474 | GCAGCTCATGCCCTTCGGCTGCC |
| 2475 | CAGCTCATGCCCTTCGGCTGCCT |
| 2476 | AGCTCATGCCCTTCGGCTGCCTC |
| 2477 | GCTCATGCCCTTCGGCTGCCTCC |
| 2478 | CTCATGCCCTTCGGCTGCCTCCT |
| 2479 | TCATGCCCTTCGGCTGCCTCCTG |
| 2480 | CATGCCCTTCGGCTGCCTCCTGG |
| 2481 | ATGCCCTTCGGCTGCCTCCTGGA |
| 2482 | TGCCCTTCGGCTGCCTCCTGGAC |
| 2483 | GCCCTTCGGCTGCCTCCTGGACT |
| 2484 | CCCTTCGGCTGCCTCCTGGACTA |
| 2485 | CCTTCGGCTGCCTCCTGGACTAT |
| 2486 | CTTCGGCTGCCTCCTGGACTATG |
| 2487 | TTCGGCTGCCTCCTGGACTATGT |
| 2488 | TCGGCTGCCTCCTGGACTATGTC |
| 2489 | CGGCTGCCTCCTGGACTATGTCC |
| 2490 | GGCTGCCTCCTGGACTATGTCCG |
| 2491 | GCTGCCTCCTGGACTATGTCCGG |
| 2492 | CTGCCTCCTGGACTATGTCCGGG |
| 2493 | TGCCTCCTGGACTATGTCCGGGA |
| 2494 | GCCTCCTGGACTATGTCCGGGAA |

| ID | SEQUENCE |
|---|---|
| 2495 | CCTCCTGGACTATGTCCGGGAAC |
| 2496 | CTCCTGGACTATGTCCGGGAACA |
| 2497 | TCCTGGACTATGTCCGGGAACAC |
| 2498 | CCTGGACTATGTCCGGGAACACA |
| 2499 | CTGGACTATGTCCGGGAACACAA |
| 2500 | TGGACTATGTCCGGGAACACAAA |
| 2501 | GGACTATGTCCGGGAACACAAAG |
| 2502 | GACTATGTCCGGGAACACAAAGA |
| 2503 | ACTATGTCCGGGAACACAAAGAC |
| 2504 | CTATGTCCGGGAACACAAAGACA |
| 2505 | TATGTCCGGGAACACAAAGACAA |
| 2506 | ATGTCCGGGAACACAAAGACAAT |
| 2507 | TGTCCGGGAACACAAAGACAATA |
| 2508 | GTCCGGGAACACAAAGACAATAT |
| 2509 | TCCGGGAACACAAAGACAATATT |
| 2510 | CCGGGAACACAAAGACAATATTG |
| 2511 | CGGGAACACAAAGACAATATTGG |
| 2512 | GGGAACACAAAGACAATATTGGC |
| 2513 | GGAACACAAAGACAATATTGGCT |
| 2514 | GAACACAAAGACAATATTGGCTC |
| 2515 | AACACAAAGACAATATTGGCTCC |
| 2516 | ACACAAAGACAATATTGGCTCCC |
| 2517 | CACAAAGACAATATTGGCTCCCA |
| 2518 | ACAAAGACAATATTGGCTCCCAG |
| 2519 | CAAAGACAATATTGGCTCCCAGT |
| 2520 | AAAGACAATATTGGCTCCCAGTA |
| 2521 | AAGACAATATTGGCTCCCAGTAC |
| 2522 | AGACAATATTGGCTCCCAGTACC |
| 2523 | GACAATATTGGCTCCCAGTACCT |
| 2524 | ACAATATTGGCTCCCAGTACCTG |
| 2525 | CAATATTGGCTCCCAGTACCTGC |
| 2526 | AATATTGGCTCCCAGTACCTGCT |
| 2527 | ATATTGGCTCCCAGTACCTGCTC |
| 2528 | TATTGGCTCCCAGTACCTGCTCA |
| 2529 | ATTGGCTCCCAGTACCTGCTCAA |
| 2530 | TTGGCTCCCAGTACCTGCTCAAC |
| 2531 | TGGCTCCCAGTACCTGCTCAACT |
| 2532 | GGCTCCCAGTACCTGCTCAACTG |
| 2533 | GCTCCCAGTACCTGCTCAACTGG |
| 2534 | CTCCCAGTACCTGCTCAACTGGT |
| 2535 | TCCCAGTACCTGCTCAACTGGTG |
| 2536 | CCCAGTACCTGCTCAACTGGTGT |
| 2537 | CCAGTACCTGCTCAACTGGTGTG |
| 2538 | CAGTACCTGCTCAACTGGTGTGT |
| 2539 | AGTACCTGCTCAACTGGTGTGTG |
| 2540 | GTACCTGCTCAACTGGTGTGTGC |
| 2541 | TACCTGCTCAACTGGTGTGTGCA |
| 2542 | ACCTGCTCAACTGGTGTGTGCAG |
| 2543 | CCTGCTCAACTGGTGTGTGCAGA |
| 2544 | CTGCTCAACTGGTGTGTGCAGAT |
| 2545 | TGCTCAACTGGTGTGTGCAGATC |
| 2546 | GCTCAACTGGTGTGTGCAGATCG |
| 2547 | CTCAACTGGTGTGTGCAGATCGC |
| 2548 | TCAACTGGTGTGTGCAGATCGCA |
| 2549 | CAACTGGTGTGTGCAGATCGCAA |
| 2550 | AACTGGTGTGTGCAGATCGCAAA |
| 2551 | ACTGGTGTGTGCAGATCGCAAAG |
| 2552 | CTGGTGTGTGCAGATCGCAAAGG |

| ID | SEQUENCE |
|---|---|
| 2553 | TGGTGTGTGCAGATCGCAAAGGG |
| 2554 | GGTGTGTGCAGATCGCAAAGGGC |
| 2555 | GTGTGTGCAGATCGCAAAGGGCA |
| 2556 | TGTGTGCAGATCGCAAAGGGCAT |
| 2557 | GTGTGCAGATCGCAAAGGGCATG |
| 2558 | TGTGCAGATCGCAAAGGGCATGA |
| 2559 | GTGCAGATCGCAAAGGGCATGAA |
| 2560 | TGCAGATCGCAAAGGGCATGAAC |
| 2561 | GCAGATCGCAAAGGGCATGAACT |
| 2562 | CAGATCGCAAAGGGCATGAACTA |
| 2563 | AGATCGCAAAGGGCATGAACTAC |
| 2564 | GATCGCAAAGGGCATGAACTACT |
| 2565 | ATCGCAAAGGGCATGAACTACTT |
| 2566 | TCGCAAAGGGCATGAACTACTTG |
| 2567 | CGCAAAGGGCATGAACTACTTGG |
| 2568 | GCAAAGGGCATGAACTACTTGGA |
| 2569 | CAAAGGGCATGAACTACTTGGAG |
| 2570 | AAAGGGCATGAACTACTTGGAGG |
| 2571 | AAGGGCATGAACTACTTGGAGGA |
| 2572 | AGGGCATGAACTACTTGGAGGAC |
| 2573 | GGGCATGAACTACTTGGAGGACC |
| 2574 | GGCATGAACTACTTGGAGGACCG |
| 2575 | GCATGAACTACTTGGAGGACCGT |
| 2576 | CATGAACTACTTGGAGGACCGTC |
| 2577 | ATGAACTACTTGGAGGACCGTCG |
| 2578 | TGAACTACTTGGAGGACCGTCGC |
| 2579 | GAACTACTTGGAGGACCGTCGCT |
| 2580 | AACTACTTGGAGGACCGTCGCTT |
| 2581 | ACTACTTGGAGGACCGTCGCTTG |
| 2582 | CTACTTGGAGGACCGTCGCTTGG |
| 2583 | TACTTGGAGGACCGTCGCTTGGT |
| 2584 | ACTTGGAGGACCGTCGCTTGGTG |
| 2585 | CTTGGAGGACCGTCGCTTGGTGC |
| 2586 | TTGGAGGACCGTCGCTTGGTGCA |
| 2587 | TGGAGGACCGTCGCTTGGTGCAC |
| 2588 | GGAGGACCGTCGCTTGGTGCACC |
| 2589 | GAGGACCGTCGCTTGGTGCACCG |
| 2590 | AGGACCGTCGCTTGGTGCACCGC |
| 2591 | GGACCGTCGCTTGGTGCACCGCG |
| 2592 | GACCGTCGCTTGGTGCACCGCGA |
| 2593 | ACCGTCGCTTGGTGCACCGCGAC |
| 2594 | CCGTCGCTTGGTGCACCGCGACC |
| 2595 | CGTCGCTTGGTGCACCGCGACCT |
| 2596 | GTCGCTTGGTGCACCGCGACCTG |
| 2597 | TCGCTTGGTGCACCGCGACCTGG |
| 2598 | CGCTTGGTGCACCGCGACCTGGC |
| 2599 | GCTTGGTGCACCGCGACCTGGCA |
| 2600 | CTTGGTGCACCGCGACCTGGCAG |
| 2601 | TTGGTGCACCGCGACCTGGCAGC |
| 2602 | TGGTGCACCGCGACCTGGCAGCC |
| 2603 | GGTGCACCGCGACCTGGCAGCCA |
| 2604 | GTGCACCGCGACCTGGCAGCCAG |
| 2605 | TGCACCGCGACCTGGCAGCCAGG |
| 2606 | GCACCGCGACCTGGCAGCCAGGA |
| 2607 | CACCGCGACCTGGCAGCCAGGAA |
| 2608 | ACCGCGACCTGGCAGCCAGGAAC |
| 2609 | CCGCGACCTGGCAGCCAGGAACG |
| 2610 | CGCGACCTGGCAGCCAGGAACGT |

| ID | SEQUENCE |
|---|---|
| 2611 | GCGACCTGGCAGCCAGGAACGTA |
| 2612 | CGACCTGGCAGCCAGGAACGTAC |
| 2613 | GACCTGGCAGCCAGGAACGTACT |
| 2614 | ACCTGGCAGCCAGGAACGTACTG |
| 2615 | CCTGGCAGCCAGGAACGTACTGG |
| 2616 | CTGGCAGCCAGGAACGTACTGGT |
| 2617 | TGGCAGCCAGGAACGTACTGGTG |
| 2618 | GGCAGCCAGGAACGTACTGGTGA |
| 2619 | GCAGCCAGGAACGTACTGGTGAA |
| 2620 | CAGCCAGGAACGTACTGGTGAAA |
| 2621 | AGCCAGGAACGTACTGGTGAAAA |
| 2622 | GCCAGGAACGTACTGGTGAAAAC |
| 2623 | CCAGGAACGTACTGGTGAAAACA |
| 2624 | CAGGAACGTACTGGTGAAAACAC |
| 2625 | AGGAACGTACTGGTGAAAACACC |
| 2626 | GGAACGTACTGGTGAAAACACCG |
| 2627 | GAACGTACTGGTGAAAACACCGC |
| 2628 | AACGTACTGGTGAAAACACCGCA |
| 2629 | ACGTACTGGTGAAAACACCGCAG |
| 2630 | CGTACTGGTGAAAACACCGCAGC |
| 2631 | GTACTGGTGAAAACACCGCAGCA |
| 2632 | TACTGGTGAAAACACCGCAGCAT |
| 2633 | ACTGGTGAAAACACCGCAGCATG |
| 2634 | CTGGTGAAAACACCGCAGCATGT |
| 2635 | TGGTGAAAACACCGCAGCATGTC |
| 2636 | GGTGAAAACACCGCAGCATGTCA |
| 2637 | GTGAAAACACCGCAGCATGTCAA |
| 2638 | TGAAAACACCGCAGCATGTCAAG |
| 2639 | GAAAACACCGCAGCATGTCAAGA |
| 2640 | AAAACACCGCAGCATGTCAAGAT |
| 2641 | AAACACCGCAGCATGTCAAGATC |
| 2642 | AACACCGCAGCATGTCAAGATCA |
| 2643 | ACACCGCAGCATGTCAAGATCAC |
| 2644 | CACCGCAGCATGTCAAGATCACA |
| 2645 | ACCGCAGCATGTCAAGATCACAG |
| 2646 | CCGCAGCATGTCAAGATCACAGA |
| 2647 | CGCAGCATGTCAAGATCACAGAT |
| 2648 | GCAGCATGTCAAGATCACAGATT |
| 2649 | CAGCATGTCAAGATCACAGATTT |
| 2650 | AGCATGTCAAGATCACAGATTTT |
| 2651 | GCATGTCAAGATCACAGATTTTG |
| 2652 | CATGTCAAGATCACAGATTTTGG |
| 2653 | ATGTCAAGATCACAGATTTTGGG |
| 2654 | TGTCAAGATCACAGATTTTGGGC |
| 2655 | GTCAAGATCACAGATTTTGGGCT |
| 2656 | TCAAGATCACAGATTTTGGGCTG |
| 2657 | CAAGATCACAGATTTTGGGCTGG |
| 2658 | AAGATCACAGATTTTGGGCTGGC |
| 2659 | AGATCACAGATTTTGGGCTGGCC |
| 2660 | GATCACAGATTTTGGGCTGGCCA |
| 2661 | ATCACAGATTTTGGGCTGGCCAA |
| 2662 | TCACAGATTTTGGGCTGGCCAAA |
| 2663 | CACAGATTTTGGGCTGGCCAAAC |
| 2664 | ACAGATTTTGGGCTGGCCAAACT |
| 2665 | CAGATTTTGGGCTGGCCAAACTG |
| 2666 | AGATTTTGGGCTGGCCAAACTGC |
| 2667 | GATTTTGGGCTGGCCAAACTGCT |
| 2668 | ATTTTGGGCTGGCCAAACTGCTG |

| ID | SEQUENCE |
|---|---|
| 2669 | TTTTGGGCTGGCCAAACTGCTGG |
| 2670 | TTTGGGCTGGCCAAACTGCTGGG |
| 2671 | TTGGGCTGGCCAAACTGCTGGGT |
| 2672 | TGGGCTGGCCAAACTGCTGGGTG |
| 2673 | GGGCTGGCCAAACTGCTGGGTGC |
| 2674 | GGCTGGCCAAACTGCTGGGTGCG |
| 2675 | GCTGGCCAAACTGCTGGGTGCGG |
| 2676 | CTGGCCAAACTGCTGGGTGCGGA |
| 2677 | TGGCCAAACTGCTGGGTGCGGAA |
| 2678 | GGCCAAACTGCTGGGTGCGGAAG |
| 2679 | GCCAAACTGCTGGGTGCGGAAGA |
| 2680 | CCAAACTGCTGGGTGCGGAAGAG |
| 2681 | CAAACTGCTGGGTGCGGAAGAGA |
| 2682 | AAACTGCTGGGTGCGGAAGAGAA |
| 2683 | AACTGCTGGGTGCGGAAGAGAAA |
| 2684 | ACTGCTGGGTGCGGAAGAGAAAG |
| 2685 | CTGCTGGGTGCGGAAGAGAAAGA |
| 2686 | TGCTGGGTGCGGAAGAGAAAGAA |
| 2687 | GCTGGGTGCGGAAGAGAAAGAAT |
| 2688 | CTGGGTGCGGAAGAGAAAGAATA |
| 2689 | TGGGTGCGGAAGAGAAAGAATAC |
| 2690 | GGGTGCGGAAGAGAAAGAATACC |
| 2691 | GGTGCGGAAGAGAAAGAATACCA |
| 2692 | GTGCGGAAGAGAAAGAATACCAT |
| 2693 | TGCGGAAGAGAAAGAATACCATG |
| 2694 | GCGGAAGAGAAAGAATACCATGC |
| 2695 | CGGAAGAGAAAGAATACCATGCA |
| 2696 | GGAAGAGAAAGAATACCATGCAG |
| 2697 | GAAGAGAAAGAATACCATGCAGA |
| 2698 | AAGAGAAAGAATACCATGCAGAA |
| 2699 | AGAGAAAGAATACCATGCAGAAG |
| 2700 | GAGAAAGAATACCATGCAGAAGG |
| 2701 | AGAAAGAATACCATGCAGAAGGA |
| 2702 | GAAAGAATACCATGCAGAAGGAG |
| 2703 | AAAGAATACCATGCAGAAGGAGG |
| 2704 | AAGAATACCATGCAGAAGGAGGC |
| 2705 | AGAATACCATGCAGAAGGAGGCA |
| 2706 | GAATACCATGCAGAAGGAGGCAA |
| 2707 | AATACCATGCAGAAGGAGGCAAA |
| 2708 | ATACCATGCAGAAGGAGGCAAAG |
| 2709 | TACCATGCAGAAGGAGGCAAAGT |
| 2710 | ACCATGCAGAAGGAGGCAAAGTG |
| 2711 | CCATGCAGAAGGAGGCAAAGTGC |
| 2712 | CATGCAGAAGGAGGCAAAGTGCC |
| 2713 | ATGCAGAAGGAGGCAAAGTGCCT |
| 2714 | TGCAGAAGGAGGCAAAGTGCCTA |
| 2715 | GCAGAAGGAGGCAAAGTGCCTAT |
| 2716 | CAGAAGGAGGCAAAGTGCCTATC |
| 2717 | AGAAGGAGGCAAAGTGCCTATCA |
| 2718 | GAAGGAGGCAAAGTGCCTATCAA |
| 2719 | AAGGAGGCAAAGTGCCTATCAAG |
| 2720 | AGGAGGCAAAGTGCCTATCAAGT |
| 2721 | GGAGGCAAAGTGCCTATCAAGTG |
| 2722 | GAGGCAAAGTGCCTATCAAGTGG |
| 2723 | AGGCAAAGTGCCTATCAAGTGGA |
| 2724 | GGCAAAGTGCCTATCAAGTGGAT |
| 2725 | GCAAAGTGCCTATCAAGTGGATG |
| 2726 | CAAAGTGCCTATCAAGTGGATGG |

| ID | SEQUENCE |
|---|---|
| 2727 | AAAGTGCCTATCAAGTGGATGGC |
| 2728 | AAGTGCCTATCAAGTGGATGGCA |
| 2729 | AGTGCCTATCAAGTGGATGGCAT |
| 2730 | GTGCCTATCAAGTGGATGGCATT |
| 2731 | TGCCTATCAAGTGGATGGCATTG |
| 2732 | GCCTATCAAGTGGATGGCATTGG |
| 2733 | CCTATCAAGTGGATGGCATTGGA |
| 2734 | CTATCAAGTGGATGGCATTGGAA |
| 2735 | TATCAAGTGGATGGCATTGGAAT |
| 2736 | ATCAAGTGGATGGCATTGGAATC |
| 2737 | TCAAGTGGATGGCATTGGAATCA |
| 2738 | CAAGTGGATGGCATTGGAATCAA |
| 2739 | AAGTGGATGGCATTGGAATCAAT |
| 2740 | AGTGGATGGCATTGGAATCAATT |
| 2741 | GTGGATGGCATTGGAATCAATTT |
| 2742 | TGGATGGCATTGGAATCAATTTT |
| 2743 | GGATGGCATTGGAATCAATTTTA |
| 2744 | GATGGCATTGGAATCAATTTTAC |
| 2745 | ATGGCATTGGAATCAATTTTACA |
| 2746 | TGGCATTGGAATCAATTTTACAC |
| 2747 | GGCATTGGAATCAATTTTACACA |
| 2748 | GCATTGGAATCAATTTTACACAG |
| 2749 | CATTGGAATCAATTTTACACAGA |
| 2750 | ATTGGAATCAATTTTACACAGAA |
| 2751 | TTGGAATCAATTTTACACAGAAT |
| 2752 | TGGAATCAATTTTACACAGAATC |
| 2753 | GGAATCAATTTTACACAGAATCT |
| 2754 | GAATCAATTTTACACAGAATCTA |
| 2755 | AATCAATTTTACACAGAATCTAT |
| 2756 | ATCAATTTTACACAGAATCTATA |
| 2757 | TCAATTTTACACAGAATCTATAC |
| 2758 | CAATTTTACACAGAATCTATACC |
| 2759 | AATTTTACACAGAATCTATACCC |
| 2760 | ATTTTACACAGAATCTATACCCA |
| 2761 | TTTTACACAGAATCTATACCCAC |
| 2762 | TTTACACAGAATCTATACCCACC |
| 2763 | TTACACAGAATCTATACCCACCA |
| 2764 | TACACAGAATCTATACCCACCAG |
| 2765 | ACACAGAATCTATACCCACCAGA |
| 2766 | CACAGAATCTATACCCACCAGAG |
| 2767 | ACAGAATCTATACCCACCAGAGT |
| 2768 | CAGAATCTATACCCACCAGAGTG |
| 2769 | AGAATCTATACCCACCAGAGTGA |
| 2770 | GAATCTATACCCACCAGAGTGAT |
| 2771 | AATCTATACCCACCAGAGTGATG |
| 2772 | ATCTATACCCACCAGAGTGATGT |
| 2773 | TCTATACCCACCAGAGTGATGTC |
| 2774 | CTATACCCACCAGAGTGATGTCT |
| 2775 | TATACCCACCAGAGTGATGTCTG |
| 2776 | ATACCCACCAGAGTGATGTCTGG |
| 2777 | TACCCACCAGAGTGATGTCTGGA |
| 2778 | ACCCACCAGAGTGATGTCTGGAG |
| 2779 | CCCACCAGAGTGATGTCTGGAGC |
| 2780 | CCACCAGAGTGATGTCTGGAGCT |
| 2781 | CACCAGAGTGATGTCTGGAGCTA |
| 2782 | ACCAGAGTGATGTCTGGAGCTAC |
| 2783 | CCAGAGTGATGTCTGGAGCTACG |
| 2784 | CAGAGTGATGTCTGGAGCTACGG |

| ID | SEQUENCE |
|---|---|
| 2785 | AGAGTGATGTCTGGAGCTACGGG |
| 2786 | GAGTGATGTCTGGAGCTACGGGG |
| 2787 | AGTGATGTCTGGAGCTACGGGGT |
| 2788 | GTGATGTCTGGAGCTACGGGGTG |
| 2789 | TGATGTCTGGAGCTACGGGGTGA |
| 2790 | GATGTCTGGAGCTACGGGGTGAC |
| 2791 | ATGTCTGGAGCTACGGGGTGACC |
| 2792 | TGTCTGGAGCTACGGGGTGACCG |
| 2793 | GTCTGGAGCTACGGGGTGACCGT |
| 2794 | TCTGGAGCTACGGGGTGACCGTT |
| 2795 | CTGGAGCTACGGGGTGACCGTTT |
| 2796 | TGGAGCTACGGGGTGACCGTTTG |
| 2797 | GGAGCTACGGGGTGACCGTTTGG |
| 2798 | GAGCTACGGGGTGACCGTTTGGG |
| 2799 | AGCTACGGGGTGACCGTTTGGGA |
| 2800 | GCTACGGGGTGACCGTTTGGGAG |
| 2801 | CTACGGGGTGACCGTTTGGGAGT |
| 2802 | TACGGGGTGACCGTTTGGGAGTT |
| 2803 | ACGGGGTGACCGTTTGGGAGTTG |
| 2804 | CGGGGTGACCGTTTGGGAGTTGA |
| 2805 | GGGGTGACCGTTTGGGAGTTGAT |
| 2806 | GGGTGACCGTTTGGGAGTTGATG |
| 2807 | GGTGACCGTTTGGGAGTTGATGA |
| 2808 | GTGACCGTTTGGGAGTTGATGAC |
| 2809 | TGACCGTTTGGGAGTTGATGACC |
| 2810 | GACCGTTTGGGAGTTGATGACCT |
| 2811 | ACCGTTTGGGAGTTGATGACCTT |
| 2812 | CCGTTTGGGAGTTGATGACCTTT |
| 2813 | CGTTTGGGAGTTGATGACCTTTG |
| 2814 | GTTTGGGAGTTGATGACCTTTGG |
| 2815 | TTTGGGAGTTGATGACCTTTGGA |
| 2816 | TTGGGAGTTGATGACCTTTGGAT |
| 2817 | TGGGAGTTGATGACCTTTGGATC |
| 2818 | GGGAGTTGATGACCTTTGGATCC |
| 2819 | GGAGTTGATGACCTTTGGATCCA |
| 2820 | GAGTTGATGACCTTTGGATCCAA |
| 2821 | AGTTGATGACCTTTGGATCCAAG |
| 2822 | GTTGATGACCTTTGGATCCAAGC |
| 2823 | TTGATGACCTTTGGATCCAAGCC |
| 2824 | TGATGACCTTTGGATCCAAGCCA |
| 2825 | GATGACCTTTGGATCCAAGCCAT |
| 2826 | ATGACCTTTGGATCCAAGCCATA |
| 2827 | TGACCTTTGGATCCAAGCCATAT |
| 2828 | GACCTTTGGATCCAAGCCATATG |
| 2829 | ACCTTTGGATCCAAGCCATATGA |
| 2830 | CCTTTGGATCCAAGCCATATGAC |
| 2831 | CTTTGGATCCAAGCCATATGACG |
| 2832 | TTTGGATCCAAGCCATATGACGG |
| 2833 | TTGGATCCAAGCCATATGACGGA |
| 2834 | TGGATCCAAGCCATATGACGGAA |
| 2835 | GGATCCAAGCCATATGACGGAAT |
| 2836 | GATCCAAGCCATATGACGGAATC |
| 2837 | ATCCAAGCCATATGACGGAATCC |
| 2838 | TCCAAGCCATATGACGGAATCCC |
| 2839 | CCAAGCCATATGACGGAATCCCT |
| 2840 | CAAGCCATATGACGGAATCCCTG |
| 2841 | AAGCCATATGACGGAATCCCTGC |
| 2842 | AGCCATATGACGGAATCCCTGCC |

| ID | SEQUENCE |
|---|---|
| 2843 | GCCATATGACGGAATCCCTGCCA |
| 2844 | CCATATGACGGAATCCCTGCCAG |
| 2845 | CATATGACGGAATCCCTGCCAGC |
| 2846 | ATATGACGGAATCCCTGCCAGCG |
| 2847 | TATGACGGAATCCCTGCCAGCGA |
| 2848 | ATGACGGAATCCCTGCCAGCGAG |
| 2849 | TGACGGAATCCCTGCCAGCGAGA |
| 2850 | GACGGAATCCCTGCCAGCGAGAT |
| 2851 | ACGGAATCCCTGCCAGCGAGATC |
| 2852 | CGGAATCCCTGCCAGCGAGATCT |
| 2853 | GGAATCCCTGCCAGCGAGATCTC |
| 2854 | GAATCCCTGCCAGCGAGATCTCC |
| 2855 | AATCCCTGCCAGCGAGATCTCCT |
| 2856 | ATCCCTGCCAGCGAGATCTCCTC |
| 2857 | TCCCTGCCAGCGAGATCTCCTCC |
| 2858 | CCCTGCCAGCGAGATCTCCTCCA |
| 2859 | CCTGCCAGCGAGATCTCCTCCAT |
| 2860 | CTGCCAGCGAGATCTCCTCCATC |
| 2861 | TGCCAGCGAGATCTCCTCCATCC |
| 2862 | GCCAGCGAGATCTCCTCCATCCT |
| 2863 | CCAGCGAGATCTCCTCCATCCTG |
| 2864 | CAGCGAGATCTCCTCCATCCTGG |
| 2865 | AGCGAGATCTCCTCCATCCTGGA |
| 2866 | GCGAGATCTCCTCCATCCTGGAG |
| 2867 | CGAGATCTCCTCCATCCTGGAGA |
| 2868 | GAGATCTCCTCCATCCTGGAGAA |
| 2869 | AGATCTCCTCCATCCTGGAGAAA |
| 2870 | GATCTCCTCCATCCTGGAGAAAG |
| 2871 | ATCTCCTCCATCCTGGAGAAAGG |
| 2872 | TCTCCTCCATCCTGGAGAAAGGA |
| 2873 | CTCCTCCATCCTGGAGAAAGGAG |
| 2874 | TCCTCCATCCTGGAGAAAGGAGA |
| 2875 | CCTCCATCCTGGAGAAAGGAGAA |
| 2876 | CTCCATCCTGGAGAAAGGAGAAC |
| 2877 | TCCATCCTGGAGAAAGGAGAACG |
| 2878 | CCATCCTGGAGAAAGGAGAACGC |
| 2879 | CATCCTGGAGAAAGGAGAACGCC |
| 2880 | ATCCTGGAGAAAGGAGAACGCCT |
| 2881 | TCCTGGAGAAAGGAGAACGCCTC |
| 2882 | CCTGGAGAAAGGAGAACGCCTCC |
| 2883 | CTGGAGAAAGGAGAACGCCTCCC |
| 2884 | TGGAGAAAGGAGAACGCCTCCCT |
| 2885 | GGAGAAAGGAGAACGCCTCCCTC |
| 2886 | GAGAAAGGAGAACGCCTCCCTCA |
| 2887 | AGAAAGGAGAACGCCTCCCTCAG |
| 2888 | GAAAGGAGAACGCCTCCCTCAGC |
| 2889 | AAAGGAGAACGCCTCCCTCAGCC |
| 2890 | AAGGAGAACGCCTCCCTCAGCCA |
| 2891 | AGGAGAACGCCTCCCTCAGCCAC |
| 2892 | GGAGAACGCCTCCCTCAGCCACC |
| 2893 | GAGAACGCCTCCCTCAGCCACCC |
| 2894 | AGAACGCCTCCCTCAGCCACCCA |
| 2895 | GAACGCCTCCCTCAGCCACCCAT |
| 2896 | AACGCCTCCCTCAGCCACCCATA |
| 2897 | ACGCCTCCCTCAGCCACCCATAT |
| 2898 | CGCCTCCCTCAGCCACCCATATG |
| 2899 | GCCTCCCTCAGCCACCCATATGT |
| 2900 | CCTCCCTCAGCCACCCATATGTA |

| ID | SEQUENCE |
|---|---|
| 2901 | CTCCCTCAGCCACCCATATGTAC |
| 2902 | TCCCTCAGCCACCCATATGTACC |
| 2903 | CCCTCAGCCACCCATATGTACCA |
| 2904 | CCTCAGCCACCCATATGTACCAT |
| 2905 | CTCAGCCACCCATATGTACCATC |
| 2906 | TCAGCCACCCATATGTACCATCG |
| 2907 | CAGCCACCCATATGTACCATCGA |
| 2908 | AGCCACCCATATGTACCATCGAT |
| 2909 | GCCACCCATATGTACCATCGATG |
| 2910 | CCACCCATATGTACCATCGATGT |
| 2911 | CACCCATATGTACCATCGATGTC |
| 2912 | ACCCATATGTACCATCGATGTCT |
| 2913 | CCCATATGTACCATCGATGTCTA |
| 2914 | CCATATGTACCATCGATGTCTAC |
| 2915 | CATATGTACCATCGATGTCTACA |
| 2916 | ATATGTACCATCGATGTCTACAT |
| 2917 | TATGTACCATCGATGTCTACATG |
| 2918 | ATGTACCATCGATGTCTACATGA |
| 2919 | TGTACCATCGATGTCTACATGAT |
| 2920 | GTACCATCGATGTCTACATGATC |
| 2921 | TACCATCGATGTCTACATGATCA |
| 2922 | ACCATCGATGTCTACATGATCAT |
| 2923 | CCATCGATGTCTACATGATCATG |
| 2924 | CATCGATGTCTACATGATCATGG |
| 2925 | ATCGATGTCTACATGATCATGGT |
| 2926 | TCGATGTCTACATGATCATGGTC |
| 2927 | CGATGTCTACATGATCATGGTCA |
| 2928 | GATGTCTACATGATCATGGTCAA |
| 2929 | ATGTCTACATGATCATGGTCAAG |
| 2930 | TGTCTACATGATCATGGTCAAGT |
| 2931 | GTCTACATGATCATGGTCAAGTG |
| 2932 | TCTACATGATCATGGTCAAGTGC |
| 2933 | CTACATGATCATGGTCAAGTGCT |
| 2934 | TACATGATCATGGTCAAGTGCTG |
| 2935 | ACATGATCATGGTCAAGTGCTGG |
| 2936 | CATGATCATGGTCAAGTGCTGGA |
| 2937 | ATGATCATGGTCAAGTGCTGGAT |
| 2938 | TGATCATGGTCAAGTGCTGGATG |
| 2939 | GATCATGGTCAAGTGCTGGATGA |
| 2940 | ATCATGGTCAAGTGCTGGATGAT |
| 2941 | TCATGGTCAAGTGCTGGATGATA |
| 2942 | CATGGTCAAGTGCTGGATGATAG |
| 2943 | ATGGTCAAGTGCTGGATGATAGA |
| 2944 | TGGTCAAGTGCTGGATGATAGAC |
| 2945 | GGTCAAGTGCTGGATGATAGACG |
| 2946 | GTCAAGTGCTGGATGATAGACGC |
| 2947 | TCAAGTGCTGGATGATAGACGCA |
| 2948 | CAAGTGCTGGATGATAGACGCAG |
| 2949 | AAGTGCTGGATGATAGACGCAGA |
| 2950 | AGTGCTGGATGATAGACGCAGAT |
| 2951 | GTGCTGGATGATAGACGCAGATA |
| 2952 | TGCTGGATGATAGACGCAGATAG |
| 2953 | GCTGGATGATAGACGCAGATAGT |
| 2954 | CTGGATGATAGACGCAGATAGTC |
| 2955 | TGGATGATAGACGCAGATAGTCG |
| 2956 | GGATGATAGACGCAGATAGTCGC |
| 2957 | GATGATAGACGCAGATAGTCGCC |
| 2958 | ATGATAGACGCAGATAGTCGCCC |

| ID | SEQUENCE |
|---|---|
| 2959 | TGATAGACGCAGATAGTCGCCCA |
| 2960 | GATAGACGCAGATAGTCGCCCAA |
| 2961 | ATAGACGCAGATAGTCGCCCAAA |
| 2962 | TAGACGCAGATAGTCGCCCAAAG |
| 2963 | AGACGCAGATAGTCGCCCAAAGT |
| 2964 | GACGCAGATAGTCGCCCAAAGTT |
| 2965 | ACGCAGATAGTCGCCCAAAGTTC |
| 2966 | CGCAGATAGTCGCCCAAAGTTCC |
| 2967 | GCAGATAGTCGCCCAAAGTTCCG |
| 2968 | CAGATAGTCGCCCAAAGTTCCGT |
| 2969 | AGATAGTCGCCCAAAGTTCCGTG |
| 2970 | GATAGTCGCCCAAAGTTCCGTGA |
| 2971 | ATAGTCGCCCAAAGTTCCGTGAG |
| 2972 | TAGTCGCCCAAAGTTCCGTGAGT |
| 2973 | AGTCGCCCAAAGTTCCGTGAGTT |
| 2974 | GTCGCCCAAAGTTCCGTGAGTTG |
| 2975 | TCGCCCAAAGTTCCGTGAGTTGA |
| 2976 | CGCCCAAAGTTCCGTGAGTTGAT |
| 2977 | GCCCAAAGTTCCGTGAGTTGATC |
| 2978 | CCCAAAGTTCCGTGAGTTGATCA |
| 2979 | CCAAAGTTCCGTGAGTTGATCAT |
| 2980 | CAAAGTTCCGTGAGTTGATCATC |
| 2981 | AAAGTTCCGTGAGTTGATCATCG |
| 2982 | AAGTTCCGTGAGTTGATCATCGA |
| 2983 | AGTTCCGTGAGTTGATCATCGAA |
| 2984 | GTTCCGTGAGTTGATCATCGAAT |
| 2985 | TTCCGTGAGTTGATCATCGAATT |
| 2986 | TCCGTGAGTTGATCATCGAATTC |
| 2987 | CCGTGAGTTGATCATCGAATTCT |
| 2988 | CGTGAGTTGATCATCGAATTCTC |
| 2989 | GTGAGTTGATCATCGAATTCTCC |
| 2990 | TGAGTTGATCATCGAATTCTCCA |
| 2991 | GAGTTGATCATCGAATTCTCCAA |
| 2992 | AGTTGATCATCGAATTCTCCAAA |
| 2993 | GTTGATCATCGAATTCTCCAAAA |
| 2994 | TTGATCATCGAATTCTCCAAAAT |
| 2995 | TGATCATCGAATTCTCCAAAATG |
| 2996 | GATCATCGAATTCTCCAAAATGG |
| 2997 | ATCATCGAATTCTCCAAAATGGC |
| 2998 | TCATCGAATTCTCCAAAATGGCC |
| 2999 | CATCGAATTCTCCAAAATGGCCC |
| 3000 | ATCGAATTCTCCAAAATGGCCCG |
| 3001 | TCGAATTCTCCAAAATGGCCCGA |
| 3002 | CGAATTCTCCAAAATGGCCCGAG |
| 3003 | GAATTCTCCAAAATGGCCCGAGA |
| 3004 | AATTCTCCAAAATGGCCCGAGAC |
| 3005 | ATTCTCCAAAATGGCCCGAGACC |
| 3006 | TTCTCCAAAATGGCCCGAGACCC |
| 3007 | TCTCCAAAATGGCCCGAGACCCC |
| 3008 | CTCCAAAATGGCCCGAGACCCCC |
| 3009 | TCCAAAATGGCCCGAGACCCCCA |
| 3010 | CCAAAATGGCCCGAGACCCCCAG |
| 3011 | CAAAATGGCCCGAGACCCCCAGC |
| 3012 | AAAATGGCCCGAGACCCCCAGCG |
| 3013 | AAATGGCCCGAGACCCCCAGCGC |
| 3014 | AATGGCCCGAGACCCCCAGCGCT |
| 3015 | ATGGCCCGAGACCCCCAGCGCTA |
| 3016 | TGGCCCGAGACCCCCAGCGCTAC |

| ID | SEQUENCE |
|---|---|
| 3017 | GGCCCGAGACCCCCAGCGCTACC |
| 3018 | GCCCGAGACCCCCAGCGCTACCT |
| 3019 | CCCGAGACCCCCAGCGCTACCTT |
| 3020 | CCGAGACCCCCAGCGCTACCTTG |
| 3021 | CGAGACCCCCAGCGCTACCTTGT |
| 3022 | GAGACCCCCAGCGCTACCTTGTC |
| 3023 | AGACCCCCAGCGCTACCTTGTCA |
| 3024 | GACCCCCAGCGCTACCTTGTCAT |
| 3025 | ACCCCCAGCGCTACCTTGTCATT |
| 3026 | CCCCCAGCGCTACCTTGTCATTC |
| 3027 | CCCCAGCGCTACCTTGTCATTCA |
| 3028 | CCCAGCGCTACCTTGTCATTCAG |
| 3029 | CCAGCGCTACCTTGTCATTCAGG |
| 3030 | CAGCGCTACCTTGTCATTCAGGG |
| 3031 | AGCGCTACCTTGTCATTCAGGGG |
| 3032 | GCGCTACCTTGTCATTCAGGGGG |
| 3033 | CGCTACCTTGTCATTCAGGGGGA |
| 3034 | GCTACCTTGTCATTCAGGGGGAT |
| 3035 | CTACCTTGTCATTCAGGGGGATG |
| 3036 | TACCTTGTCATTCAGGGGGATGA |
| 3037 | ACCTTGTCATTCAGGGGGATGAA |
| 3038 | CCTTGTCATTCAGGGGGATGAAA |
| 3039 | CTTGTCATTCAGGGGGATGAAAG |
| 3040 | TTGTCATTCAGGGGGATGAAAGA |
| 3041 | TGTCATTCAGGGGGATGAAAGAA |
| 3042 | GTCATTCAGGGGGATGAAAGAAT |
| 3043 | TCATTCAGGGGGATGAAAGAATG |
| 3044 | CATTCAGGGGGATGAAAGAATGC |
| 3045 | ATTCAGGGGGATGAAAGAATGCA |
| 3046 | TTCAGGGGGATGAAAGAATGCAT |
| 3047 | TCAGGGGGATGAAAGAATGCATT |
| 3048 | CAGGGGGATGAAAGAATGCATTT |
| 3049 | AGGGGGATGAAAGAATGCATTTG |
| 3050 | GGGGGATGAAAGAATGCATTTGC |
| 3051 | GGGGATGAAAGAATGCATTTGCC |
| 3052 | GGGATGAAAGAATGCATTTGCCA |
| 3053 | GGATGAAAGAATGCATTTGCCAA |
| 3054 | GATGAAAGAATGCATTTGCCAAG |
| 3055 | ATGAAAGAATGCATTTGCCAAGT |
| 3056 | TGAAAGAATGCATTTGCCAAGTC |
| 3057 | GAAAGAATGCATTTGCCAAGTCC |
| 3058 | AAAGAATGCATTTGCCAAGTCCT |
| 3059 | AAGAATGCATTTGCCAAGTCCTA |
| 3060 | AGAATGCATTTGCCAAGTCCTAC |
| 3061 | GAATGCATTTGCCAAGTCCTACA |
| 3062 | AATGCATTTGCCAAGTCCTACAG |
| 3063 | ATGCATTTGCCAAGTCCTACAGA |
| 3064 | TGCATTTGCCAAGTCCTACAGAC |
| 3065 | GCATTTGCCAAGTCCTACAGACT |
| 3066 | CATTTGCCAAGTCCTACAGACTC |
| 3067 | ATTTGCCAAGTCCTACAGACTCC |
| 3068 | TTTGCCAAGTCCTACAGACTCCA |
| 3069 | TTGCCAAGTCCTACAGACTCCAA |
| 3070 | TGCCAAGTCCTACAGACTCCAAC |
| 3071 | GCCAAGTCCTACAGACTCCAACT |
| 3072 | CCAAGTCCTACAGACTCCAACTT |
| 3073 | CAAGTCCTACAGACTCCAACTTC |
| 3074 | AAGTCCTACAGACTCCAACTTCT |

| ID | SEQUENCE |
|---|---|
| 3075 | AGTCCTACAGACTCCAACTTCTA |
| 3076 | GTCCTACAGACTCCAACTTCTAC |
| 3077 | TCCTACAGACTCCAACTTCTACC |
| 3078 | CCTACAGACTCCAACTTCTACCG |
| 3079 | CTACAGACTCCAACTTCTACCGT |
| 3080 | TACAGACTCCAACTTCTACCGTG |
| 3081 | ACAGACTCCAACTTCTACCGTGC |
| 3082 | CAGACTCCAACTTCTACCGTGCC |
| 3083 | AGACTCCAACTTCTACCGTGCCC |
| 3084 | GACTCCAACTTCTACCGTGCCCT |
| 3085 | ACTCCAACTTCTACCGTGCCCTG |
| 3086 | CTCCAACTTCTACCGTGCCCTGA |
| 3087 | TCCAACTTCTACCGTGCCCTGAT |
| 3088 | CCAACTTCTACCGTGCCCTGATG |
| 3089 | CAACTTCTACCGTGCCCTGATGG |
| 3090 | AACTTCTACCGTGCCCTGATGGA |
| 3091 | ACTTCTACCGTGCCCTGATGGAT |
| 3092 | CTTCTACCGTGCCCTGATGGATG |
| 3093 | TTCTACCGTGCCCTGATGGATGA |
| 3094 | TCTACCGTGCCCTGATGGATGAA |
| 3095 | CTACCGTGCCCTGATGGATGAAG |
| 3096 | TACCGTGCCCTGATGGATGAAGA |
| 3097 | ACCGTGCCCTGATGGATGAAGAA |
| 3098 | CCGTGCCCTGATGGATGAAGAAG |
| 3099 | CGTGCCCTGATGGATGAAGAAGA |
| 3100 | GTGCCCTGATGGATGAAGAAGAC |
| 3101 | TGCCCTGATGGATGAAGAAGACA |
| 3102 | GCCCTGATGGATGAAGAAGACAT |
| 3103 | CCCTGATGGATGAAGAAGACATG |
| 3104 | CCTGATGGATGAAGAAGACATGG |
| 3105 | CTGATGGATGAAGAAGACATGGA |
| 3106 | TGATGGATGAAGAAGACATGGAC |
| 3107 | GATGGATGAAGAAGACATGGACG |
| 3108 | ATGGATGAAGAAGACATGGACGA |
| 3109 | TGGATGAAGAAGACATGGACGAC |
| 3110 | GGATGAAGAAGACATGGACGACG |
| 3111 | GATGAAGAAGACATGGACGACGT |
| 3112 | ATGAAGAAGACATGGACGACGTG |
| 3113 | TGAAGAAGACATGGACGACGTGG |
| 3114 | GAAGAAGACATGGACGACGTGGT |
| 3115 | AAGAAGACATGGACGACGTGGTG |
| 3116 | AGAAGACATGGACGACGTGGTGG |
| 3117 | GAAGACATGGACGACGTGGTGGA |
| 3118 | AAGACATGGACGACGTGGTGGAT |
| 3119 | AGACATGGACGACGTGGTGGATG |
| 3120 | GACATGGACGACGTGGTGGATGC |
| 3121 | ACATGGACGACGTGGTGGATGCC |
| 3122 | CATGGACGACGTGGTGGATGCCG |
| 3123 | ATGGACGACGTGGTGGATGCCGA |
| 3124 | TGGACGACGTGGTGGATGCCGAC |
| 3125 | GGACGACGTGGTGGATGCCGACG |
| 3126 | GACGACGTGGTGGATGCCGACGA |
| 3127 | ACGACGTGGTGGATGCCGACGAG |
| 3128 | CGACGTGGTGGATGCCGACGAGT |
| 3129 | GACGTGGTGGATGCCGACGAGTA |
| 3130 | ACGTGGTGGATGCCGACGAGTAC |
| 3131 | CGTGGTGGATGCCGACGAGTACC |
| 3132 | GTGGTGGATGCCGACGAGTACCT |

| ID | SEQUENCE |
|---|---|
| 3133 | TGGTGGATGCCGACGAGTACCTC |
| 3134 | GGTGGATGCCGACGAGTACCTCA |
| 3135 | GTGGATGCCGACGAGTACCTCAT |
| 3136 | TGGATGCCGACGAGTACCTCATC |
| 3137 | GGATGCCGACGAGTACCTCATCC |
| 3138 | GATGCCGACGAGTACCTCATCCC |
| 3139 | ATGCCGACGAGTACCTCATCCCA |
| 3140 | TGCCGACGAGTACCTCATCCCAC |
| 3141 | GCCGACGAGTACCTCATCCCACA |
| 3142 | CCGACGAGTACCTCATCCCACAG |
| 3143 | CGACGAGTACCTCATCCCACAGC |
| 3144 | GACGAGTACCTCATCCCACAGCA |
| 3145 | ACGAGTACCTCATCCCACAGCAG |
| 3146 | CGAGTACCTCATCCCACAGCAGG |
| 3147 | GAGTACCTCATCCCACAGCAGGG |
| 3148 | AGTACCTCATCCCACAGCAGGGC |
| 3149 | GTACCTCATCCCACAGCAGGGCT |
| 3150 | TACCTCATCCCACAGCAGGGCTT |
| 3151 | ACCTCATCCCACAGCAGGGCTTC |
| 3152 | CCTCATCCCACAGCAGGGCTTCT |
| 3153 | CTCATCCCACAGCAGGGCTTCTT |
| 3154 | TCATCCCACAGCAGGGCTTCTTC |
| 3155 | CATCCCACAGCAGGGCTTCTTCA |
| 3156 | ATCCCACAGCAGGGCTTCTTCAG |
| 3157 | TCCCACAGCAGGGCTTCTTCAGC |
| 3158 | CCCACAGCAGGGCTTCTTCAGCA |
| 3159 | CCACAGCAGGGCTTCTTCAGCAG |
| 3160 | CACAGCAGGGCTTCTTCAGCAGC |
| 3161 | ACAGCAGGGCTTCTTCAGCAGCC |
| 3162 | CAGCAGGGCTTCTTCAGCAGCCC |
| 3163 | AGCAGGGCTTCTTCAGCAGCCCC |
| 3164 | GCAGGGCTTCTTCAGCAGCCCCT |
| 3165 | CAGGGCTTCTTCAGCAGCCCCTC |
| 3166 | AGGGCTTCTTCAGCAGCCCCTCC |
| 3167 | GGGCTTCTTCAGCAGCCCCTCCA |
| 3168 | GGCTTCTTCAGCAGCCCCTCCAC |
| 3169 | GCTTCTTCAGCAGCCCCTCCACG |
| 3170 | CTTCTTCAGCAGCCCCTCCACGT |
| 3171 | TTCTTCAGCAGCCCCTCCACGTC |
| 3172 | TCTTCAGCAGCCCCTCCACGTCA |
| 3173 | CTTCAGCAGCCCCTCCACGTCAC |
| 3174 | TTCAGCAGCCCCTCCACGTCACG |
| 3175 | TCAGCAGCCCCTCCACGTCACGG |
| 3176 | CAGCAGCCCCTCCACGTCACGGA |
| 3177 | AGCAGCCCCTCCACGTCACGGAC |
| 3178 | GCAGCCCCTCCACGTCACGGACT |
| 3179 | CAGCCCCTCCACGTCACGGACTC |
| 3180 | AGCCCCTCCACGTCACGGACTCC |
| 3181 | GCCCCTCCACGTCACGGACTCCC |
| 3182 | CCCCTCCACGTCACGGACTCCCC |
| 3183 | CCCTCCACGTCACGGACTCCCCT |
| 3184 | CCTCCACGTCACGGACTCCCCTC |
| 3185 | CTCCACGTCACGGACTCCCCTCC |
| 3186 | TCCACGTCACGGACTCCCCTCCT |
| 3187 | CCACGTCACGGACTCCCCTCCTG |
| 3188 | CACGTCACGGACTCCCCTCCTGA |
| 3189 | ACGTCACGGACTCCCCTCCTGAG |
| 3190 | CGTCACGGACTCCCCTCCTGAGC |

| ID | SEQUENCE |
|---|---|
| 3191 | GTCACGGACTCCCCTCCTGAGCT |
| 3192 | TCACGGACTCCCCTCCTGAGCTC |
| 3193 | CACGGACTCCCCTCCTGAGCTCT |
| 3194 | ACGGACTCCCCTCCTGAGCTCTC |
| 3195 | CGGACTCCCCTCCTGAGCTCTCT |
| 3196 | GGACTCCCCTCCTGAGCTCTCTG |
| 3197 | GACTCCCCTCCTGAGCTCTCTGA |
| 3198 | ACTCCCCTCCTGAGCTCTCTGAG |
| 3199 | CTCCCCTCCTGAGCTCTCTGAGT |
| 3200 | TCCCCTCCTGAGCTCTCTGAGTG |
| 3201 | CCCCTCCTGAGCTCTCTGAGTGC |
| 3202 | CCCTCCTGAGCTCTCTGAGTGCA |
| 3203 | CCTCCTGAGCTCTCTGAGTGCAA |
| 3204 | CTCCTGAGCTCTCTGAGTGCAAC |
| 3205 | TCCTGAGCTCTCTGAGTGCAACC |
| 3206 | CCTGAGCTCTCTGAGTGCAACCA |
| 3207 | CTGAGCTCTCTGAGTGCAACCAG |
| 3208 | TGAGCTCTCTGAGTGCAACCAGC |
| 3209 | GAGCTCTCTGAGTGCAACCAGCA |
| 3210 | AGCTCTCTGAGTGCAACCAGCAA |
| 3211 | GCTCTCTGAGTGCAACCAGCAAC |
| 3212 | CTCTCTGAGTGCAACCAGCAACA |
| 3213 | TCTCTGAGTGCAACCAGCAACAA |
| 3214 | CTCTGAGTGCAACCAGCAACAAT |
| 3215 | TCTGAGTGCAACCAGCAACAATT |
| 3216 | CTGAGTGCAACCAGCAACAATTC |
| 3217 | TGAGTGCAACCAGCAACAATTCC |
| 3218 | GAGTGCAACCAGCAACAATTCCA |
| 3219 | AGTGCAACCAGCAACAATTCCAC |
| 3220 | GTGCAACCAGCAACAATTCCACC |
| 3221 | TGCAACCAGCAACAATTCCACCG |
| 3222 | GCAACCAGCAACAATTCCACCGT |
| 3223 | CAACCAGCAACAATTCCACCGTG |
| 3224 | AACCAGCAACAATTCCACCGTGG |
| 3225 | ACCAGCAACAATTCCACCGTGGC |
| 3226 | CCAGCAACAATTCCACCGTGGCT |
| 3227 | CAGCAACAATTCCACCGTGGCTT |
| 3228 | AGCAACAATTCCACCGTGGCTTG |
| 3229 | GCAACAATTCCACCGTGGCTTGC |
| 3230 | CAACAATTCCACCGTGGCTTGCA |
| 3231 | AACAATTCCACCGTGGCTTGCAT |
| 3232 | ACAATTCCACCGTGGCTTGCATT |
| 3233 | CAATTCCACCGTGGCTTGCATTG |
| 3234 | AATTCCACCGTGGCTTGCATTGA |
| 3235 | ATTCCACCGTGGCTTGCATTGAT |
| 3236 | TTCCACCGTGGCTTGCATTGATA |
| 3237 | TCCACCGTGGCTTGCATTGATAG |
| 3238 | CCACCGTGGCTTGCATTGATAGA |
| 3239 | CACCGTGGCTTGCATTGATAGAA |
| 3240 | ACCGTGGCTTGCATTGATAGAAA |
| 3241 | CCGTGGCTTGCATTGATAGAAAT |
| 3242 | CGTGGCTTGCATTGATAGAAATG |
| 3243 | GTGGCTTGCATTGATAGAAATGG |
| 3244 | TGGCTTGCATTGATAGAAATGGG |
| 3245 | GGCTTGCATTGATAGAAATGGGC |
| 3246 | GCTTGCATTGATAGAAATGGGCT |
| 3247 | CTTGCATTGATAGAAATGGGCTG |
| 3248 | TTGCATTGATAGAAATGGGCTGC |

| ID | SEQUENCE |
|---|---|
| 3249 | TGCATTGATAGAAATGGGCTGCA |
| 3250 | GCATTGATAGAAATGGGCTGCAA |
| 3251 | CATTGATAGAAATGGGCTGCAAA |
| 3252 | ATTGATAGAAATGGGCTGCAAAG |
| 3253 | TTGATAGAAATGGGCTGCAAAGC |
| 3254 | TGATAGAAATGGGCTGCAAAGCT |
| 3255 | GATAGAAATGGGCTGCAAAGCTG |
| 3256 | ATAGAAATGGGCTGCAAAGCTGT |
| 3257 | TAGAAATGGGCTGCAAAGCTGTC |
| 3258 | AGAAATGGGCTGCAAAGCTGTCC |
| 3259 | GAAATGGGCTGCAAAGCTGTCCC |
| 3260 | AAATGGGCTGCAAAGCTGTCCCA |
| 3261 | AATGGGCTGCAAAGCTGTCCCAT |
| 3262 | ATGGGCTGCAAAGCTGTCCCATC |
| 3263 | TGGGCTGCAAAGCTGTCCCATCA |
| 3264 | GGGCTGCAAAGCTGTCCCATCAA |
| 3265 | GGCTGCAAAGCTGTCCCATCAAG |
| 3266 | GCTGCAAAGCTGTCCCATCAAGG |
| 3267 | CTGCAAAGCTGTCCCATCAAGGA |
| 3268 | TGCAAAGCTGTCCCATCAAGGAA |
| 3269 | GCAAAGCTGTCCCATCAAGGAAG |
| 3270 | CAAAGCTGTCCCATCAAGGAAGA |
| 3271 | AAAGCTGTCCCATCAAGGAAGAC |
| 3272 | AAGCTGTCCCATCAAGGAAGACA |
| 3273 | AGCTGTCCCATCAAGGAAGACAG |
| 3274 | GCTGTCCCATCAAGGAAGACAGC |
| 3275 | CTGTCCCATCAAGGAAGACAGCT |
| 3276 | TGTCCCATCAAGGAAGACAGCTT |
| 3277 | GTCCCATCAAGGAAGACAGCTTC |
| 3278 | TCCCATCAAGGAAGACAGCTTCT |
| 3279 | CCCATCAAGGAAGACAGCTTCTT |
| 3280 | CCATCAAGGAAGACAGCTTCTTG |
| 3281 | CATCAAGGAAGACAGCTTCTTGC |
| 3282 | ATCAAGGAAGACAGCTTCTTGCA |
| 3283 | TCAAGGAAGACAGCTTCTTGCAG |
| 3284 | CAAGGAAGACAGCTTCTTGCAGC |
| 3285 | AAGGAAGACAGCTTCTTGCAGCG |
| 3286 | AGGAAGACAGCTTCTTGCAGCGA |
| 3287 | GGAAGACAGCTTCTTGCAGCGAT |
| 3288 | GAAGACAGCTTCTTGCAGCGATA |
| 3289 | AAGACAGCTTCTTGCAGCGATAC |
| 3290 | AGACAGCTTCTTGCAGCGATACA |
| 3291 | GACAGCTTCTTGCAGCGATACAG |
| 3292 | ACAGCTTCTTGCAGCGATACAGC |
| 3293 | CAGCTTCTTGCAGCGATACAGCT |
| 3294 | AGCTTCTTGCAGCGATACAGCTC |
| 3295 | GCTTCTTGCAGCGATACAGCTCA |
| 3296 | CTTCTTGCAGCGATACAGCTCAG |
| 3297 | TTCTTGCAGCGATACAGCTCAGA |
| 3298 | TCTTGCAGCGATACAGCTCAGAC |
| 3299 | CTTGCAGCGATACAGCTCAGACC |
| 3300 | TTGCAGCGATACAGCTCAGACCC |
| 3301 | TGCAGCGATACAGCTCAGACCCC |
| 3302 | GCAGCGATACAGCTCAGACCCCA |
| 3303 | CAGCGATACAGCTCAGACCCCAC |
| 3304 | AGCGATACAGCTCAGACCCCACA |
| 3305 | GCGATACAGCTCAGACCCCACAG |
| 3306 | CGATACAGCTCAGACCCCACAGG |

| ID | SEQUENCE |
|---|---|
| 3307 | GATACAGCTCAGACCCCACAGGC |
| 3308 | ATACAGCTCAGACCCCACAGGCG |
| 3309 | TACAGCTCAGACCCCACAGGCGC |
| 3310 | ACAGCTCAGACCCCACAGGCGCC |
| 3311 | CAGCTCAGACCCCACAGGCGCCT |
| 3312 | AGCTCAGACCCCACAGGCGCCTT |
| 3313 | GCTCAGACCCCACAGGCGCCTTG |
| 3314 | CTCAGACCCCACAGGCGCCTTGA |
| 3315 | TCAGACCCCACAGGCGCCTTGAC |
| 3316 | CAGACCCCACAGGCGCCTTGACT |
| 3317 | AGACCCCACAGGCGCCTTGACTG |
| 3318 | GACCCCACAGGCGCCTTGACTGA |
| 3319 | ACCCCACAGGCGCCTTGACTGAG |
| 3320 | CCCCACAGGCGCCTTGACTGAGG |
| 3321 | CCCACAGGCGCCTTGACTGAGGA |
| 3322 | CCACAGGCGCCTTGACTGAGGAC |
| 3323 | CACAGGCGCCTTGACTGAGGACA |
| 3324 | ACAGGCGCCTTGACTGAGGACAG |
| 3325 | CAGGCGCCTTGACTGAGGACAGC |
| 3326 | AGGCGCCTTGACTGAGGACAGCA |
| 3327 | GGCGCCTTGACTGAGGACAGCAT |
| 3328 | GCGCCTTGACTGAGGACAGCATA |
| 3329 | CGCCTTGACTGAGGACAGCATAG |
| 3330 | GCCTTGACTGAGGACAGCATAGA |
| 3331 | CCTTGACTGAGGACAGCATAGAC |
| 3332 | CTTGACTGAGGACAGCATAGACG |
| 3333 | TTGACTGAGGACAGCATAGACGA |
| 3334 | TGACTGAGGACAGCATAGACGAC |
| 3335 | GACTGAGGACAGCATAGACGACA |
| 3336 | ACTGAGGACAGCATAGACGACAC |
| 3337 | CTGAGGACAGCATAGACGACACC |
| 3338 | TGAGGACAGCATAGACGACACCT |
| 3339 | GAGGACAGCATAGACGACACCTT |
| 3340 | AGGACAGCATAGACGACACCTTC |
| 3341 | GGACAGCATAGACGACACCTTCC |
| 3342 | GACAGCATAGACGACACCTTCCT |
| 3343 | ACAGCATAGACGACACCTTCCTC |
| 3344 | CAGCATAGACGACACCTTCCTCC |
| 3345 | AGCATAGACGACACCTTCCTCCC |
| 3346 | GCATAGACGACACCTTCCTCCCA |
| 3347 | CATAGACGACACCTTCCTCCCAG |
| 3348 | ATAGACGACACCTTCCTCCCAGT |
| 3349 | TAGACGACACCTTCCTCCCAGTG |
| 3350 | AGACGACACCTTCCTCCCAGTGC |
| 3351 | GACGACACCTTCCTCCCAGTGCC |
| 3352 | ACGACACCTTCCTCCCAGTGCCT |
| 3353 | CGACACCTTCCTCCCAGTGCCTG |
| 3354 | GACACCTTCCTCCCAGTGCCTGA |
| 3355 | ACACCTTCCTCCCAGTGCCTGAA |
| 3356 | CACCTTCCTCCCAGTGCCTGAAT |
| 3357 | ACCTTCCTCCCAGTGCCTGAATA |
| 3358 | CCTTCCTCCCAGTGCCTGAATAC |
| 3359 | CTTCCTCCCAGTGCCTGAATACA |
| 3360 | TTCCTCCCAGTGCCTGAATACAT |
| 3361 | TCCTCCCAGTGCCTGAATACATA |
| 3362 | CCTCCCAGTGCCTGAATACATAA |
| 3363 | CTCCCAGTGCCTGAATACATAAA |
| 3364 | TCCCAGTGCCTGAATACATAAAC |

| ID | SEQUENCE |
|---|---|
| 3365 | CCCAGTGCCTGAATACATAAACC |
| 3366 | CCAGTGCCTGAATACATAAACCA |
| 3367 | CAGTGCCTGAATACATAAACCAG |
| 3368 | AGTGCCTGAATACATAAACCAGT |
| 3369 | GTGCCTGAATACATAAACCAGTC |
| 3370 | TGCCTGAATACATAAACCAGTCC |
| 3371 | GCCTGAATACATAAACCAGTCCG |
| 3372 | CCTGAATACATAAACCAGTCCGT |
| 3373 | CTGAATACATAAACCAGTCCGTT |
| 3374 | TGAATACATAAACCAGTCCGTTC |
| 3375 | GAATACATAAACCAGTCCGTTCC |
| 3376 | AATACATAAACCAGTCCGTTCCC |
| 3377 | ATACATAAACCAGTCCGTTCCCA |
| 3378 | TACATAAACCAGTCCGTTCCCAA |
| 3379 | ACATAAACCAGTCCGTTCCCAAA |
| 3380 | CATAAACCAGTCCGTTCCCAAAA |
| 3381 | ATAAACCAGTCCGTTCCCAAAAG |
| 3382 | TAAACCAGTCCGTTCCCAAAAGG |
| 3383 | AAACCAGTCCGTTCCCAAAAGGC |
| 3384 | AACCAGTCCGTTCCCAAAAGGCC |
| 3385 | ACCAGTCCGTTCCCAAAAGGCCC |
| 3386 | CCAGTCCGTTCCCAAAAGGCCCG |
| 3387 | CAGTCCGTTCCCAAAAGGCCCGC |
| 3388 | AGTCCGTTCCCAAAAGGCCCGCT |
| 3389 | GTCCGTTCCCAAAAGGCCCGCTG |
| 3390 | TCCGTTCCCAAAAGGCCCGCTGG |
| 3391 | CCGTTCCCAAAAGGCCCGCTGGC |
| 3392 | CGTTCCCAAAAGGCCCGCTGGCT |
| 3393 | GTTCCCAAAAGGCCCGCTGGCTC |
| 3394 | TTCCCAAAAGGCCCGCTGGCTCT |
| 3395 | TCCCAAAAGGCCCGCTGGCTCTG |
| 3396 | CCCAAAAGGCCCGCTGGCTCTGT |
| 3397 | CCAAAAGGCCCGCTGGCTCTGTG |
| 3398 | CAAAAGGCCCGCTGGCTCTGTGC |
| 3399 | AAAAGGCCCGCTGGCTCTGTGCA |
| 3400 | AAAGGCCCGCTGGCTCTGTGCAG |
| 3401 | AAGGCCCGCTGGCTCTGTGCAGA |
| 3402 | AGGCCCGCTGGCTCTGTGCAGAA |
| 3403 | GGCCCGCTGGCTCTGTGCAGAAT |
| 3404 | GCCCGCTGGCTCTGTGCAGAATC |
| 3405 | CCCGCTGGCTCTGTGCAGAATCC |
| 3406 | CCGCTGGCTCTGTGCAGAATCCT |
| 3407 | CGCTGGCTCTGTGCAGAATCCTG |
| 3408 | GCTGGCTCTGTGCAGAATCCTGT |
| 3409 | CTGGCTCTGTGCAGAATCCTGTC |
| 3410 | TGGCTCTGTGCAGAATCCTGTCT |
| 3411 | GGCTCTGTGCAGAATCCTGTCTA |
| 3412 | GCTCTGTGCAGAATCCTGTCTAT |
| 3413 | CTCTGTGCAGAATCCTGTCTATC |
| 3414 | TCTGTGCAGAATCCTGTCTATCA |
| 3415 | CTGTGCAGAATCCTGTCTATCAC |
| 3416 | TGTGCAGAATCCTGTCTATCACA |
| 3417 | GTGCAGAATCCTGTCTATCACAA |
| 3418 | TGCAGAATCCTGTCTATCACAAT |
| 3419 | GCAGAATCCTGTCTATCACAATC |
| 3420 | CAGAATCCTGTCTATCACAATCA |
| 3421 | AGAATCCTGTCTATCACAATCAG |
| 3422 | GAATCCTGTCTATCACAATCAGC |

| ID | SEQUENCE |
|---|---|
| 3423 | AATCCTGTCTATCACAATCAGCC |
| 3424 | ATCCTGTCTATCACAATCAGCCT |
| 3425 | TCCTGTCTATCACAATCAGCCTC |
| 3426 | CCTGTCTATCACAATCAGCCTCT |
| 3427 | CTGTCTATCACAATCAGCCTCTG |
| 3428 | TGTCTATCACAATCAGCCTCTGA |
| 3429 | GTCTATCACAATCAGCCTCTGAA |
| 3430 | TCTATCACAATCAGCCTCTGAAC |
| 3431 | CTATCACAATCAGCCTCTGAACC |
| 3432 | TATCACAATCAGCCTCTGAACCC |
| 3433 | ATCACAATCAGCCTCTGAACCCC |
| 3434 | TCACAATCAGCCTCTGAACCCCG |
| 3435 | CACAATCAGCCTCTGAACCCCGC |
| 3436 | ACAATCAGCCTCTGAACCCCGCG |
| 3437 | CAATCAGCCTCTGAACCCCGCGC |
| 3438 | CCGCGCCCAGCAGAGACCCACAC |
| 3439 | CGCGCCCAGCAGAGACCCACACT |
| 3440 | GCGCCCAGCAGAGACCCACACTA |
| 3441 | CGCCCAGCAGAGACCCACACTAC |
| 3442 | GCCCAGCAGAGACCCACACTACC |
| 3443 | CCCAGCAGAGACCCACACTACCA |
| 3444 | CCAGCAGAGACCCACACTACCAG |
| 3445 | CAGCAGAGACCCACACTACCAGG |
| 3446 | AGCAGAGACCCACACTACCAGGA |
| 3447 | GCAGAGACCCACACTACCAGGAC |
| 3448 | CAGAGACCCACACTACCAGGACC |
| 3449 | AGAGACCCACACTACCAGGACCC |
| 3450 | GAGACCCACACTACCAGGACCCC |
| 3451 | AGACCCACACTACCAGGACCCCC |
| 3452 | GACCCACACTACCAGGACCCCCA |
| 3453 | ACCCACACTACCAGGACCCCCAC |
| 3454 | CCCACACTACCAGGACCCCCACA |
| 3455 | CCACACTACCAGGACCCCCACAG |
| 3456 | CACACTACCAGGACCCCCACAGC |
| 3457 | ACACTACCAGGACCCCCACAGCA |
| 3458 | CACTACCAGGACCCCCACAGCAC |
| 3459 | ACTACCAGGACCCCCACAGCACT |
| 3460 | CTACCAGGACCCCCACAGCACTG |
| 3461 | TACCAGGACCCCCACAGCACTGC |
| 3462 | ACCAGGACCCCCACAGCACTGCA |
| 3463 | CCAGGACCCCCACAGCACTGCAG |
| 3464 | CAGGACCCCCACAGCACTGCAGT |
| 3465 | AGGACCCCCACAGCACTGCAGTG |
| 3466 | GGACCCCCACAGCACTGCAGTGG |
| 3467 | GACCCCCACAGCACTGCAGTGGG |
| 3468 | ACCCCCACAGCACTGCAGTGGGC |
| 3469 | CCCCCACAGCACTGCAGTGGGCA |
| 3470 | CCCCACAGCACTGCAGTGGGCAA |
| 3471 | CCCACAGCACTGCAGTGGGCAAC |
| 3472 | CCACAGCACTGCAGTGGGCAACC |
| 3473 | CACAGCACTGCAGTGGGCAACCC |
| 3474 | ACAGCACTGCAGTGGGCAACCCC |
| 3475 | CAGCACTGCAGTGGGCAACCCCG |
| 3476 | AGCACTGCAGTGGGCAACCCCGA |
| 3477 | GCACTGCAGTGGGCAACCCCGAG |
| 3478 | CACTGCAGTGGGCAACCCCGAGT |
| 3479 | ACTGCAGTGGGCAACCCCGAGTA |
| 3480 | CTGCAGTGGGCAACCCCGAGTAT |

| ID | SEQUENCE |
|---|---|
| 3481 | TGCAGTGGGCAACCCCGAGTATC |
| 3482 | GCAGTGGGCAACCCCGAGTATCT |
| 3483 | CAGTGGGCAACCCCGAGTATCTC |
| 3484 | AGTGGGCAACCCCGAGTATCTCA |
| 3485 | GTGGGCAACCCCGAGTATCTCAA |
| 3486 | TGGGCAACCCCGAGTATCTCAAC |
| 3487 | GGGCAACCCCGAGTATCTCAACA |
| 3488 | GGCAACCCCGAGTATCTCAACAC |
| 3489 | GCAACCCCGAGTATCTCAACACT |
| 3490 | CAACCCCGAGTATCTCAACACTG |
| 3491 | AACCCCGAGTATCTCAACACTGT |
| 3492 | ACCCCGAGTATCTCAACACTGTC |
| 3493 | CCCCGAGTATCTCAACACTGTCC |
| 3494 | CCCGAGTATCTCAACACTGTCCA |
| 3495 | CCGAGTATCTCAACACTGTCCAG |
| 3496 | CGAGTATCTCAACACTGTCCAGC |
| 3497 | GAGTATCTCAACACTGTCCAGCC |
| 3498 | AGTATCTCAACACTGTCCAGCCC |
| 3499 | GTATCTCAACACTGTCCAGCCCA |
| 3500 | TATCTCAACACTGTCCAGCCCAC |
| 3501 | ATCTCAACACTGTCCAGCCCACC |
| 3502 | TCTCAACACTGTCCAGCCCACCT |
| 3503 | CTCAACACTGTCCAGCCCACCTG |
| 3504 | TCAACACTGTCCAGCCCACCTGT |
| 3505 | CAACACTGTCCAGCCCACCTGTG |
| 3506 | AACACTGTCCAGCCCACCTGTGT |
| 3507 | ACACTGTCCAGCCCACCTGTGTC |
| 3508 | CACTGTCCAGCCCACCTGTGTCA |
| 3509 | ACTGTCCAGCCCACCTGTGTCAA |
| 3510 | CTGTCCAGCCCACCTGTGTCAAC |
| 3511 | TGTCCAGCCCACCTGTGTCAACA |
| 3512 | GTCCAGCCCACCTGTGTCAACAG |
| 3513 | TCCAGCCCACCTGTGTCAACAGC |
| 3514 | CCAGCCCACCTGTGTCAACAGCA |
| 3515 | CAGCCCACCTGTGTCAACAGCAC |
| 3516 | AGCCCACCTGTGTCAACAGCACA |
| 3517 | GCCCACCTGTGTCAACAGCACAT |
| 3518 | CCCACCTGTGTCAACAGCACATT |
| 3519 | CCACCTGTGTCAACAGCACATTC |
| 3520 | CACCTGTGTCAACAGCACATTCG |
| 3521 | ACCTGTGTCAACAGCACATTCGA |
| 3522 | CCTGTGTCAACAGCACATTCGAC |
| 3523 | CTGTGTCAACAGCACATTCGACA |
| 3524 | TGTGTCAACAGCACATTCGACAG |
| 3525 | GTGTCAACAGCACATTCGACAGC |
| 3526 | TGTCAACAGCACATTCGACAGCC |
| 3527 | GTCAACAGCACATTCGACAGCCC |
| 3528 | TCAACAGCACATTCGACAGCCCT |
| 3529 | CAACAGCACATTCGACAGCCCTG |
| 3530 | AACAGCACATTCGACAGCCCTGC |
| 3531 | ACAGCACATTCGACAGCCCTGCC |
| 3532 | CAGCACATTCGACAGCCCTGCCC |
| 3533 | AGCACATTCGACAGCCCTGCCCA |
| 3534 | GCACATTCGACAGCCCTGCCCAC |
| 3535 | CACATTCGACAGCCCTGCCCACT |
| 3536 | ACATTCGACAGCCCTGCCCACTG |
| 3537 | CATTCGACAGCCCTGCCCACTGG |
| 3538 | ATTCGACAGCCCTGCCCACTGGG |

| ID | SEQUENCE |
|---|---|
| 3539 | TTCGACAGCCCTGCCCACTGGGC |
| 3540 | TCGACAGCCCTGCCCACTGGGCC |
| 3541 | CGACAGCCCTGCCCACTGGGCCC |
| 3542 | GACAGCCCTGCCCACTGGGCCCA |
| 3543 | ACAGCCCTGCCCACTGGGCCCAG |
| 3544 | CAGCCCTGCCCACTGGGCCCAGA |
| 3545 | AGCCCTGCCCACTGGGCCCAGAA |
| 3546 | GCCCTGCCCACTGGGCCCAGAAA |
| 3547 | CCCTGCCCACTGGGCCCAGAAAG |
| 3548 | CCTGCCCACTGGGCCCAGAAAGG |
| 3549 | CTGCCCACTGGGCCCAGAAAGGC |
| 3550 | TGCCCACTGGGCCCAGAAAGGCA |
| 3551 | GCCCACTGGGCCCAGAAAGGCAG |
| 3552 | CCCACTGGGCCCAGAAAGGCAGC |
| 3553 | CCACTGGGCCCAGAAAGGCAGCC |
| 3554 | CACTGGGCCCAGAAAGGCAGCCA |
| 3555 | ACTGGGCCCAGAAAGGCAGCCAC |
| 3556 | CTGGGCCCAGAAAGGCAGCCACC |
| 3557 | TGGGCCCAGAAAGGCAGCCACCA |
| 3558 | GGGCCCAGAAAGGCAGCCACCAA |
| 3559 | GGCCCAGAAAGGCAGCCACCAAA |
| 3560 | GCCCAGAAAGGCAGCCACCAAAT |
| 3561 | CCCAGAAAGGCAGCCACCAAATT |
| 3562 | CCAGAAAGGCAGCCACCAAATTA |
| 3563 | CAGAAAGGCAGCCACCAAATTAG |
| 3564 | AGAAAGGCAGCCACCAAATTAGC |
| 3565 | GAAAGGCAGCCACCAAATTAGCC |
| 3566 | AAAGGCAGCCACCAAATTAGCCT |
| 3567 | AAGGCAGCCACCAAATTAGCCTG |
| 3568 | AGGCAGCCACCAAATTAGCCTGG |
| 3569 | GGCAGCCACCAAATTAGCCTGGA |
| 3570 | GCAGCCACCAAATTAGCCTGGAC |
| 3571 | CAGCCACCAAATTAGCCTGGACA |
| 3572 | AGCCACCAAATTAGCCTGGACAA |
| 3573 | GCCACCAAATTAGCCTGGACAAC |
| 3574 | CCACCAAATTAGCCTGGACAACC |
| 3575 | CACCAAATTAGCCTGGACAACCC |
| 3576 | ACCAAATTAGCCTGGACAACCCT |
| 3577 | CCAAATTAGCCTGGACAACCCTG |
| 3578 | CAAATTAGCCTGGACAACCCTGA |
| 3579 | AAATTAGCCTGGACAACCCTGAC |
| 3580 | AATTAGCCTGGACAACCCTGACT |
| 3581 | ATTAGCCTGGACAACCCTGACTA |
| 3582 | TTAGCCTGGACAACCCTGACTAC |
| 3583 | TAGCCTGGACAACCCTGACTACC |
| 3584 | AGCCTGGACAACCCTGACTACCA |
| 3585 | GCCTGGACAACCCTGACTACCAG |
| 3586 | CCTGGACAACCCTGACTACCAGC |
| 3587 | CTGGACAACCCTGACTACCAGCA |
| 3588 | TGGACAACCCTGACTACCAGCAG |
| 3589 | GGACAACCCTGACTACCAGCAGG |
| 3590 | GACAACCCTGACTACCAGCAGGA |
| 3591 | ACAACCCTGACTACCAGCAGGAC |
| 3592 | CAACCCTGACTACCAGCAGGACT |
| 3593 | AACCCTGACTACCAGCAGGACTT |
| 3594 | ACCCTGACTACCAGCAGGACTTC |
| 3595 | CCCTGACTACCAGCAGGACTTCT |
| 3596 | CCTGACTACCAGCAGGACTTCTT |

| ID | SEQUENCE |
|---|---|
| 3597 | CTGACTACCAGCAGGACTTCTTT |
| 3598 | TGACTACCAGCAGGACTTCTTTC |
| 3599 | GACTACCAGCAGGACTTCTTTCC |
| 3600 | ACTACCAGCAGGACTTCTTTCCC |
| 3601 | CTACCAGCAGGACTTCTTTCCCA |
| 3602 | TACCAGCAGGACTTCTTTCCCAA |
| 3603 | ACCAGCAGGACTTCTTTCCCAAG |
| 3604 | CCAGCAGGACTTCTTTCCCAAGG |
| 3605 | CAGCAGGACTTCTTTCCCAAGGA |
| 3606 | AGCAGGACTTCTTTCCCAAGGAA |
| 3607 | GCAGGACTTCTTTCCCAAGGAAG |
| 3608 | CAGGACTTCTTTCCCAAGGAAGC |
| 3609 | AGGACTTCTTTCCCAAGGAAGCC |
| 3610 | GGACTTCTTTCCCAAGGAAGCCA |
| 3611 | GACTTCTTTCCCAAGGAAGCCAA |
| 3612 | ACTTCTTTCCCAAGGAAGCCAAG |
| 3613 | CTTCTTTCCCAAGGAAGCCAAGC |
| 3614 | TTCTTTCCCAAGGAAGCCAAGCC |
| 3615 | TCTTTCCCAAGGAAGCCAAGCCA |
| 3616 | CTTTCCCAAGGAAGCCAAGCCAA |
| 3617 | TTTCCCAAGGAAGCCAAGCCAAA |
| 3618 | TTCCCAAGGAAGCCAAGCCAAAT |
| 3619 | TCCCAAGGAAGCCAAGCCAAATG |
| 3620 | CCCAAGGAAGCCAAGCCAAATGG |
| 3621 | CCAAGGAAGCCAAGCCAAATGGC |
| 3622 | CAAGGAAGCCAAGCCAAATGGCA |
| 3623 | AAGGAAGCCAAGCCAAATGGCAT |
| 3624 | AGGAAGCCAAGCCAAATGGCATC |
| 3625 | GGAAGCCAAGCCAAATGGCATCT |
| 3626 | GAAGCCAAGCCAAATGGCATCTT |
| 3627 | AAGCCAAGCCAAATGGCATCTTT |
| 3628 | AGCCAAGCCAAATGGCATCTTTA |
| 3629 | GCCAAGCCAAATGGCATCTTTAA |
| 3630 | CCAAGCCAAATGGCATCTTTAAG |
| 3631 | CAAGCCAAATGGCATCTTTAAGG |
| 3632 | AAGCCAAATGGCATCTTTAAGGG |
| 3633 | AGCCAAATGGCATCTTTAAGGGC |
| 3634 | GCCAAATGGCATCTTTAAGGGCT |
| 3635 | CCAAATGGCATCTTTAAGGGCTC |
| 3636 | CAAATGGCATCTTTAAGGGCTCC |
| 3637 | AAATGGCATCTTTAAGGGCTCCA |
| 3638 | AATGGCATCTTTAAGGGCTCCAC |
| 3639 | ATGGCATCTTTAAGGGCTCCACA |
| 3640 | TGGCATCTTTAAGGGCTCCACAG |
| 3641 | GGCATCTTTAAGGGCTCCACAGC |
| 3642 | GCATCTTTAAGGGCTCCACAGCT |
| 3643 | CATCTTTAAGGGCTCCACAGCTG |
| 3644 | ATCTTTAAGGGCTCCACAGCTGA |
| 3645 | TCTTTAAGGGCTCCACAGCTGAA |
| 3646 | CTTTAAGGGCTCCACAGCTGAAA |
| 3647 | TTTAAGGGCTCCACAGCTGAAAA |
| 3648 | TTAAGGGCTCCACAGCTGAAAAT |
| 3649 | TAAGGGCTCCACAGCTGAAAATG |
| 3650 | AAGGGCTCCACAGCTGAAAATGC |
| 3651 | AGGGCTCCACAGCTGAAAATGCA |
| 3652 | GGGCTCCACAGCTGAAAATGCAG |
| 3653 | GGCTCCACAGCTGAAAATGCAGA |
| 3654 | GCTCCACAGCTGAAAATGCAGAA |

| ID | SEQUENCE |
|---|---|
| 3655 | CTCCACAGCTGAAAATGCAGAAT |
| 3656 | TCCACAGCTGAAAATGCAGAATA |
| 3657 | CCACAGCTGAAAATGCAGAATAC |
| 3658 | CACAGCTGAAAATGCAGAATACC |
| 3659 | ACAGCTGAAAATGCAGAATACCT |
| 3660 | CAGCTGAAAATGCAGAATACCTA |
| 3661 | AGCTGAAAATGCAGAATACCTAA |
| 3662 | GCTGAAAATGCAGAATACCTAAG |
| 3663 | CTGAAAATGCAGAATACCTAAGG |
| 3664 | TGAAAATGCAGAATACCTAAGGG |
| 3665 | GAAAATGCAGAATACCTAAGGGT |
| 3666 | AAAATGCAGAATACCTAAGGGTC |
| 3667 | AAATGCAGAATACCTAAGGGTCG |
| 3668 | AATGCAGAATACCTAAGGGTCGC |
| 3669 | ATGCAGAATACCTAAGGGTCGCG |
| 3670 | TGCAGAATACCTAAGGGTCGCGC |
| 3671 | GCAGAATACCTAAGGGTCGCGCC |
| 3672 | CAGAATACCTAAGGGTCGCGCCA |
| 3673 | AGAATACCTAAGGGTCGCGCCAC |
| 3674 | GAATACCTAAGGGTCGCGCCACA |
| 3675 | AATACCTAAGGGTCGCGCCACAA |
| 3676 | ATACCTAAGGGTCGCGCCACAAA |
| 3677 | TACCTAAGGGTCGCGCCACAAAG |
| 3678 | ACCTAAGGGTCGCGCCACAAAGC |
| 3679 | CCTAAGGGTCGCGCCACAAAGCA |
| 3680 | CTAAGGGTCGCGCCACAAAGCAG |
| 3681 | TAAGGGTCGCGCCACAAAGCAGT |
| 3682 | AAGGGTCGCGCCACAAAGCAGTG |
| 3683 | AGGGTCGCGCCACAAAGCAGTGA |
| 3684 | GGGTCGCGCCACAAAGCAGTGAA |
| 3685 | GGTCGCGCCACAAAGCAGTGAAT |
| 3686 | GTCGCGCCACAAAGCAGTGAATT |
| 3687 | TCGCGCCACAAAGCAGTGAATTT |
| 3688 | CGCGCCACAAAGCAGTGAATTTA |
| 3689 | GCGCCACAAAGCAGTGAATTTAT |
| 3690 | CGCCACAAAGCAGTGAATTTATT |
| 3691 | GCCACAAAGCAGTGAATTTATTG |
| 3692 | CCACAAAGCAGTGAATTTATTGG |
| 3693 | CACAAAGCAGTGAATTTATTGGA |
| 3694 | ACAAAGCAGTGAATTTATTGGAG |
| 3695 | CAAAGCAGTGAATTTATTGGAGC |
| 3696 | AAAGCAGTGAATTTATTGGAGCA |
| 3697 | AAGCAGTGAATTTATTGGAGCAT |
| 3698 | AGCAGTGAATTTATTGGAGCATG |
| 3699 | CCACGGAGGATAGTATGAGCCCT |
| 3700 | CACGGAGGATAGTATGAGCCCTA |
| 3701 | ACGGAGGATAGTATGAGCCCTAA |
| 3702 | CGGAGGATAGTATGAGCCCTAAA |
| 3703 | GGAGGATAGTATGAGCCCTAAAA |
| 3704 | GAGGATAGTATGAGCCCTAAAAA |
| 3705 | AGGATAGTATGAGCCCTAAAAAT |
| 3706 | GGATAGTATGAGCCCTAAAAATC |
| 3707 | GATAGTATGAGCCCTAAAAATCC |
| 3708 | ATAGTATGAGCCCTAAAAATCCA |
| 3709 | TAGTATGAGCCCTAAAAATCCAG |
| 3710 | AGTATGAGCCCTAAAAATCCAGA |
| 3711 | GTATGAGCCCTAAAAATCCAGAC |
| 3712 | TATGAGCCCTAAAAATCCAGACT |

| ID | SEQUENCE |
|---|---|
| 3713 | ATGAGCCCTAAAAATCCAGACTC |
| 3714 | TGAGCCCTAAAAATCCAGACTCT |
| 3715 | GAGCCCTAAAAATCCAGACTCTT |
| 3716 | AGCCCTAAAAATCCAGACTCTTT |
| 3717 | GCCCTAAAAATCCAGACTCTTTC |
| 3718 | CCCTAAAAATCCAGACTCTTTCG |
| 3719 | CCTAAAAATCCAGACTCTTTCGA |
| 3720 | CTAAAAATCCAGACTCTTTCGAT |
| 3721 | TAAAAATCCAGACTCTTTCGATA |
| 3722 | AAAAATCCAGACTCTTTCGATAC |
| 3723 | AAAATCCAGACTCTTTCGATACC |
| 3724 | AAATCCAGACTCTTTCGATACCC |
| 3725 | AATCCAGACTCTTTCGATACCCA |
| 3726 | ATCCAGACTCTTTCGATACCCAG |
| 3727 | TCCAGACTCTTTCGATACCCAGG |
| 3728 | CCAGACTCTTTCGATACCCAGGA |
| 3729 | CAGACTCTTTCGATACCCAGGAC |
| 3730 | AGACTCTTTCGATACCCAGGACC |
| 3731 | GACTCTTTCGATACCCAGGACCA |
| 3732 | ACTCTTTCGATACCCAGGACCAA |
| 3733 | CTCTTTCGATACCCAGGACCAAG |
| 3734 | TCTTTCGATACCCAGGACCAAGC |
| 3735 | CTTTCGATACCCAGGACCAAGCC |
| 3736 | TTTCGATACCCAGGACCAAGCCA |
| 3737 | TTCGATACCCAGGACCAAGCCAC |
| 3738 | TCGATACCCAGGACCAAGCCACA |
| 3739 | CGATACCCAGGACCAAGCCACAG |
| 3740 | GATACCCAGGACCAAGCCACAGC |
| 3741 | ATACCCAGGACCAAGCCACAGCA |
| 3742 | TACCCAGGACCAAGCCACAGCAG |
| 3743 | ACCCAGGACCAAGCCACAGCAGG |
| 3744 | CCCAGGACCAAGCCACAGCAGGT |
| 3745 | CCAGGACCAAGCCACAGCAGGTC |
| 3746 | CAGGACCAAGCCACAGCAGGTCC |
| 3747 | AGGACCAAGCCACAGCAGGTCCT |
| 3748 | GGACCAAGCCACAGCAGGTCCTC |
| 3749 | GACCAAGCCACAGCAGGTCCTCC |
| 3750 | ACCAAGCCACAGCAGGTCCTCCA |
| 3751 | CCAAGCCACAGCAGGTCCTCCAT |
| 3752 | CAAGCCACAGCAGGTCCTCCATC |
| 3753 | AAGCCACAGCAGGTCCTCCATCC |
| 3754 | AGCCACAGCAGGTCCTCCATCCC |
| 3755 | GCCACAGCAGGTCCTCCATCCCA |
| 3756 | CCACAGCAGGTCCTCCATCCCAA |
| 3757 | CACAGCAGGTCCTCCATCCCAAC |
| 3758 | ACAGCAGGTCCTCCATCCCAACA |
| 3759 | CAGCAGGTCCTCCATCCCAACAG |
| 3760 | AGCAGGTCCTCCATCCCAACAGC |
| 3761 | GCAGGTCCTCCATCCCAACAGCC |
| 3762 | CAGGTCCTCCATCCCAACAGCCA |
| 3763 | AGGTCCTCCATCCCAACAGCCAT |
| 3764 | GGTCCTCCATCCCAACAGCCATG |
| 3765 | GTCCTCCATCCCAACAGCCATGC |
| 3766 | TCCTCCATCCCAACAGCCATGCC |
| 3767 | CCTCCATCCCAACAGCCATGCCC |
| 3768 | CTCCATCCCAACAGCCATGCCCG |
| 3769 | TCCATCCCAACAGCCATGCCCGC |
| 3770 | CCATCCCAACAGCCATGCCCGCA |

| ID | SEQUENCE |
|---|---|
| 3771 | CATCCCAACAGCCATGCCCGCAT |
| 3772 | ATCCCAACAGCCATGCCCGCATT |
| 3773 | TCCCAACAGCCATGCCCGCATTA |
| 3774 | CCCAACAGCCATGCCCGCATTAG |
| 3775 | CCAACAGCCATGCCCGCATTAGC |
| 3776 | CAACAGCCATGCCCGCATTAGCT |
| 3777 | AACAGCCATGCCCGCATTAGCTC |
| 3778 | ACAGCCATGCCCGCATTAGCTCT |
| 3779 | CAGCCATGCCCGCATTAGCTCTT |
| 3780 | AGCCATGCCCGCATTAGCTCTTA |
| 3781 | GCCATGCCCGCATTAGCTCTTAG |
| 3782 | CCATGCCCGCATTAGCTCTTAGA |
| 3783 | CATGCCCGCATTAGCTCTTAGAC |
| 3784 | ATGCCCGCATTAGCTCTTAGACC |
| 3785 | TGCCCGCATTAGCTCTTAGACCC |
| 3786 | GCCCGCATTAGCTCTTAGACCCA |
| 3787 | CCCGCATTAGCTCTTAGACCCAC |
| 3788 | CCGCATTAGCTCTTAGACCCACA |
| 3789 | CGCATTAGCTCTTAGACCCACAG |
| 3790 | GCATTAGCTCTTAGACCCACAGA |
| 3791 | CATTAGCTCTTAGACCCACAGAC |
| 3792 | ATTAGCTCTTAGACCCACAGACT |
| 3793 | TTAGCTCTTAGACCCACAGACTG |
| 3794 | TAGCTCTTAGACCCACAGACTGG |
| 3795 | AGCTCTTAGACCCACAGACTGGT |
| 3796 | GCTCTTAGACCCACAGACTGGTT |
| 3797 | CTCTTAGACCCACAGACTGGTTT |
| 3798 | TCTTAGACCCACAGACTGGTTTT |
| 3799 | CTTAGACCCACAGACTGGTTTTG |
| 3800 | TTAGACCCACAGACTGGTTTTGC |
| 3801 | TAGACCCACAGACTGGTTTTGCA |
| 3802 | AGACCCACAGACTGGTTTTGCAA |
| 3803 | GACCCACAGACTGGTTTTGCAAC |
| 3804 | ACCCACAGACTGGTTTTGCAACG |
| 3805 | CCCACAGACTGGTTTTGCAACGT |
| 3806 | CCACAGACTGGTTTTGCAACGTT |
| 3807 | CACAGACTGGTTTTGCAACGTTT |
| 3808 | ACAGACTGGTTTTGCAACGTTTA |
| 3809 | CAGACTGGTTTTGCAACGTTTAC |
| 3810 | AGACTGGTTTTGCAACGTTTACA |
| 3811 | GACTGGTTTTGCAACGTTTACAC |
| 3812 | ACTGGTTTTGCAACGTTTACACC |
| 3813 | CTGGTTTTGCAACGTTTACACCG |
| 3814 | TGGTTTTGCAACGTTTACACCGA |
| 3815 | GGTTTTGCAACGTTTACACCGAC |
| 3816 | GTTTTGCAACGTTTACACCGACT |
| 3817 | TTTTGCAACGTTTACACCGACTA |
| 3818 | TTTGCAACGTTTACACCGACTAG |
| 3819 | TTGCAACGTTTACACCGACTAGC |
| 3820 | TGCAACGTTTACACCGACTAGCC |
| 3821 | GCAACGTTTACACCGACTAGCCA |
| 3822 | CAACGTTTACACCGACTAGCCAG |
| 3823 | AACGTTTACACCGACTAGCCAGG |
| 3824 | ACGTTTACACCGACTAGCCAGGA |
| 3825 | CGTTTACACCGACTAGCCAGGAA |
| 3826 | GTTTACACCGACTAGCCAGGAAG |
| 3827 | TTTACACCGACTAGCCAGGAAGT |
| 3828 | TTACACCGACTAGCCAGGAAGTA |

| ID | SEQUENCE |
|---|---|
| 3829 | TACACCGACTAGCCAGGAAGTAC |
| 3830 | ACACCGACTAGCCAGGAAGTACT |
| 3831 | CACCGACTAGCCAGGAAGTACTT |
| 3832 | ACCGACTAGCCAGGAAGTACTTC |
| 3833 | CCGACTAGCCAGGAAGTACTTCC |
| 3834 | CGACTAGCCAGGAAGTACTTCCA |
| 3835 | GACTAGCCAGGAAGTACTTCCAC |
| 3836 | ACTAGCCAGGAAGTACTTCCACC |
| 3837 | CTAGCCAGGAAGTACTTCCACCT |
| 3838 | TAGCCAGGAAGTACTTCCACCTC |
| 3839 | AGCCAGGAAGTACTTCCACCTCG |
| 3840 | GCCAGGAAGTACTTCCACCTCGG |
| 3841 | CCAGGAAGTACTTCCACCTCGGG |
| 3842 | CAGGAAGTACTTCCACCTCGGGC |
| 3843 | AGGAAGTACTTCCACCTCGGGCA |
| 3844 | GGAAGTACTTCCACCTCGGGCAC |
| 3845 | GAAGTACTTCCACCTCGGGCACA |
| 3846 | AAGTACTTCCACCTCGGGCACAT |
| 3847 | AGTACTTCCACCTCGGGCACATT |
| 3848 | GTACTTCCACCTCGGGCACATTT |
| 3849 | TACTTCCACCTCGGGCACATTTT |
| 3850 | ACTTCCACCTCGGGCACATTTTG |
| 3851 | CTTCCACCTCGGGCACATTTTGG |
| 3852 | TTCCACCTCGGGCACATTTTGGG |
| 3853 | TCCACCTCGGGCACATTTTGGGA |
| 3854 | CCACCTCGGGCACATTTTGGGAA |
| 3855 | CACCTCGGGCACATTTTGGGAAG |
| 3856 | ACCTCGGGCACATTTTGGGAAGT |
| 3857 | CCTCGGGCACATTTTGGGAAGTT |
| 3858 | CTCGGGCACATTTTGGGAAGTTG |
| 3859 | TCGGGCACATTTTGGGAAGTTGC |
| 3860 | CGGGCACATTTTGGGAAGTTGCA |
| 3861 | GGGCACATTTTGGGAAGTTGCAT |
| 3862 | GGCACATTTTGGGAAGTTGCATT |
| 3863 | GCACATTTTGGGAAGTTGCATTC |
| 3864 | CACATTTTGGGAAGTTGCATTCC |
| 3865 | ACATTTTGGGAAGTTGCATTCCT |
| 3866 | CATTTTGGGAAGTTGCATTCCTT |
| 3867 | ATTTTGGGAAGTTGCATTCCTTT |
| 3868 | TTTTGGGAAGTTGCATTCCTTTG |
| 3869 | TTTGGGAAGTTGCATTCCTTTGT |
| 3870 | TTGGGAAGTTGCATTCCTTTGTC |
| 3871 | TGGGAAGTTGCATTCCTTTGTCT |
| 3872 | GGGAAGTTGCATTCCTTTGTCTT |
| 3873 | GGAAGTTGCATTCCTTTGTCTTC |
| 3874 | GAAGTTGCATTCCTTTGTCTTCA |
| 3875 | AAGTTGCATTCCTTTGTCTTCAA |
| 3876 | AGTTGCATTCCTTTGTCTTCAAA |
| 3877 | GTTGCATTCCTTTGTCTTCAAAC |
| 3878 | TTGCATTCCTTTGTCTTCAAACT |
| 3879 | TGCATTCCTTTGTCTTCAAACTG |
| 3880 | GCATTCCTTTGTCTTCAAACTGT |
| 3881 | CATTCCTTTGTCTTCAAACTGTG |
| 3882 | ATTCCTTTGTCTTCAAACTGTGA |
| 3883 | TTCCTTTGTCTTCAAACTGTGAA |
| 3884 | TCCTTTGTCTTCAAACTGTGAAG |
| 3885 | CCTTTGTCTTCAAACTGTGAAGC |
| 3886 | CTTTGTCTTCAAACTGTGAAGCA |

| ID | SEQUENCE |
|---|---|
| 3887 | TTTGTCTTCAAACTGTGAAGCAT |
| 3888 | TTGTCTTCAAACTGTGAAGCATT |
| 3889 | TGTCTTCAAACTGTGAAGCATTT |
| 3890 | GTCTTCAAACTGTGAAGCATTTA |
| 3891 | TCTTCAAACTGTGAAGCATTTAC |
| 3892 | CTTCAAACTGTGAAGCATTTACA |
| 3893 | TTCAAACTGTGAAGCATTTACAG |
| 3894 | TCAAACTGTGAAGCATTTACAGA |
| 3895 | CAAACTGTGAAGCATTTACAGAA |
| 3896 | AAACTGTGAAGCATTTACAGAAA |
| 3897 | AACTGTGAAGCATTTACAGAAAC |
| 3898 | ACTGTGAAGCATTTACAGAAACG |
| 3899 | CTGTGAAGCATTTACAGAAACGC |
| 3900 | TGTGAAGCATTTACAGAAACGCA |
| 3901 | GTGAAGCATTTACAGAAACGCAT |
| 3902 | TGAAGCATTTACAGAAACGCATC |
| 3903 | GAAGCATTTACAGAAACGCATCC |
| 3904 | AAGCATTTACAGAAACGCATCCA |
| 3905 | AGCATTTACAGAAACGCATCCAG |
| 3906 | GCATTTACAGAAACGCATCCAGC |
| 3907 | CATTTACAGAAACGCATCCAGCA |
| 3908 | ATTTACAGAAACGCATCCAGCAA |
| 3909 | TTTACAGAAACGCATCCAGCAAG |
| 3910 | TTACAGAAACGCATCCAGCAAGA |
| 3911 | TACAGAAACGCATCCAGCAAGAA |
| 3912 | ACAGAAACGCATCCAGCAAGAAT |
| 3913 | CAGAAACGCATCCAGCAAGAATA |
| 3914 | AGAAACGCATCCAGCAAGAATAT |
| 3915 | GAAACGCATCCAGCAAGAATATT |
| 3916 | AAACGCATCCAGCAAGAATATTG |
| 3917 | AACGCATCCAGCAAGAATATTGT |
| 3918 | ACGCATCCAGCAAGAATATTGTC |
| 3919 | CGCATCCAGCAAGAATATTGTCC |
| 3920 | GCATCCAGCAAGAATATTGTCCC |
| 3921 | CATCCAGCAAGAATATTGTCCCT |
| 3922 | ATCCAGCAAGAATATTGTCCCTT |
| 3923 | TCCAGCAAGAATATTGTCCCTTT |
| 3924 | CCAGCAAGAATATTGTCCCTTTG |
| 3925 | CAGCAAGAATATTGTCCCTTTGA |
| 3926 | AGCAAGAATATTGTCCCTTTGAG |
| 3927 | GCAAGAATATTGTCCCTTTGAGC |
| 3928 | CAAGAATATTGTCCCTTTGAGCA |
| 3929 | AAGAATATTGTCCCTTTGAGCAG |
| 3930 | AGAATATTGTCCCTTTGAGCAGA |
| 3931 | GAATATTGTCCCTTTGAGCAGAA |
| 3932 | AATATTGTCCCTTTGAGCAGAAA |
| 3933 | ATATTGTCCCTTTGAGCAGAAAT |
| 3934 | TATTGTCCCTTTGAGCAGAAATT |
| 3935 | ATTGTCCCTTTGAGCAGAAATTT |
| 3936 | TTGTCCCTTTGAGCAGAAATTTA |
| 3937 | TGTCCCTTTGAGCAGAAATTTAT |
| 3938 | GTCCCTTTGAGCAGAAATTTATC |
| 3939 | TCCCTTTGAGCAGAAATTTATCT |
| 3940 | CCCTTTGAGCAGAAATTTATCTT |
| 3941 | CCTTTGAGCAGAAATTTATCTTT |
| 3942 | CTTTGAGCAGAAATTTATCTTTC |
| 3943 | TTTGAGCAGAAATTTATCTTTCA |
| 3944 | TTGAGCAGAAATTTATCTTTCAA |

| ID | SEQUENCE |
|---|---|
| 3945 | TGAGCAGAAATTTATCTTTCAAA |
| 3946 | GAGCAGAAATTTATCTTTCAAAG |
| 3947 | AGCAGAAATTTATCTTTCAAAGA |
| 3948 | GCAGAAATTTATCTTTCAAAGAG |
| 3949 | CAGAAATTTATCTTTCAAAGAGG |
| 3950 | AGAAATTTATCTTTCAAAGAGGT |
| 3951 | GAAATTTATCTTTCAAAGAGGTA |
| 3952 | AAATTTATCTTTCAAAGAGGTAT |
| 3953 | AATTTATCTTTCAAAGAGGTATA |
| 3954 | ATTTATCTTTCAAAGAGGTATAT |
| 3955 | TTTATCTTTCAAAGAGGTATATT |
| 3956 | TTATCTTTCAAAGAGGTATATTT |
| 3957 | TATCTTTCAAAGAGGTATATTTG |
| 3958 | ATCTTTCAAAGAGGTATATTTGA |
| 3959 | TCTTTCAAAGAGGTATATTTGAA |
| 3960 | CTTTCAAAGAGGTATATTTGAAA |
| 3961 | TTTCAAAGAGGTATATTTGAAAA |
| 3962 | TTCAAAGAGGTATATTTGAAAAA |
| 3963 | TCAAAGAGGTATATTTGAAAAAA |
| 3964 | CAAAGAGGTATATTTGAAAAAAA |
| 3965 | AAAGAGGTATATTTGAAAAAAAA |
| 3966 | AAAAAAAAGTATATGTGAGGATT |
| 3967 | AAAAAAAGTATATGTGAGGATTT |
| 3968 | AAAAAAGTATATGTGAGGATTTT |
| 3969 | AAAAAGTATATGTGAGGATTTTT |
| 3970 | AAAAGTATATGTGAGGATTTTTA |
| 3971 | AAAGTATATGTGAGGATTTTTAT |
| 3972 | AAGTATATGTGAGGATTTTTATT |
| 3973 | AGTATATGTGAGGATTTTTATTG |
| 3974 | GTATATGTGAGGATTTTTATTGA |
| 3975 | TATATGTGAGGATTTTTATTGAT |
| 3976 | ATATGTGAGGATTTTTATTGATT |
| 3977 | TATGTGAGGATTTTTATTGATTG |
| 3978 | ATGTGAGGATTTTTATTGATTGG |
| 3979 | TGTGAGGATTTTTATTGATTGGG |
| 3980 | GTGAGGATTTTTATTGATTGGGG |
| 3981 | TGAGGATTTTTATTGATTGGGGA |
| 3982 | GAGGATTTTTATTGATTGGGGAT |
| 3983 | AGGATTTTTATTGATTGGGGATC |
| 3984 | GGATTTTTATTGATTGGGGATCT |
| 3985 | GATTTTTATTGATTGGGGATCTT |
| 3986 | ATTTTTATTGATTGGGGATCTTG |
| 3987 | TTTTTATTGATTGGGGATCTTGG |
| 3988 | TTTTATTGATTGGGGATCTTGGA |
| 3989 | TTTATTGATTGGGGATCTTGGAG |
| 3990 | TTATTGATTGGGGATCTTGGAGT |
| 3991 | TATTGATTGGGGATCTTGGAGTT |
| 3992 | ATTGATTGGGGATCTTGGAGTTT |
| 3993 | TTGATTGGGGATCTTGGAGTTTT |
| 3994 | TGATTGGGGATCTTGGAGTTTTT |
| 3995 | GATTGGGGATCTTGGAGTTTTTC |
| 3996 | ATTGGGGATCTTGGAGTTTTTCA |
| 3997 | TTGGGGATCTTGGAGTTTTTCAT |
| 3998 | TGGGGATCTTGGAGTTTTTCATT |
| 3999 | GGGGATCTTGGAGTTTTTCATTG |
| 4000 | GGGATCTTGGAGTTTTTCATTGT |
| 4001 | GGATCTTGGAGTTTTTCATTGTC |
| 4002 | GATCTTGGAGTTTTTCATTGTCG |

| ID | SEQUENCE |
|---|---|
| 4003 | ATCTTGGAGTTTTTCATTGTCGC |
| 4004 | TCTTGGAGTTTTTCATTGTCGCT |
| 4005 | CTTGGAGTTTTTCATTGTCGCTA |
| 4006 | TTGGAGTTTTTCATTGTCGCTAT |
| 4007 | TGGAGTTTTTCATTGTCGCTATT |
| 4008 | GGAGTTTTTCATTGTCGCTATTG |
| 4009 | GAGTTTTTCATTGTCGCTATTGA |
| 4010 | AGTTTTTCATTGTCGCTATTGAT |
| 4011 | GTTTTTCATTGTCGCTATTGATT |
| 4012 | TTTTTCATTGTCGCTATTGATTT |
| 4013 | TTTTCATTGTCGCTATTGATTTT |
| 4014 | TTTCATTGTCGCTATTGATTTTT |
| 4015 | TTCATTGTCGCTATTGATTTTTA |
| 4016 | TCATTGTCGCTATTGATTTTTAC |
| 4017 | CATTGTCGCTATTGATTTTTACT |
| 4018 | ATTGTCGCTATTGATTTTTACTT |
| 4019 | TTGTCGCTATTGATTTTTACTTC |
| 4020 | TGTCGCTATTGATTTTTACTTCA |
| 4021 | GTCGCTATTGATTTTTACTTCAA |
| 4022 | TCGCTATTGATTTTTACTTCAAT |
| 4023 | CGCTATTGATTTTTACTTCAATG |
| 4024 | GCTATTGATTTTTACTTCAATGG |
| 4025 | CTATTGATTTTTACTTCAATGGG |
| 4026 | TATTGATTTTTACTTCAATGGGC |
| 4027 | ATTGATTTTTACTTCAATGGGCT |
| 4028 | TTGATTTTTACTTCAATGGGCTC |
| 4029 | TGATTTTTACTTCAATGGGCTCT |
| 4030 | GATTTTTACTTCAATGGGCTCTT |
| 4031 | ATTTTTACTTCAATGGGCTCTTC |
| 4032 | TTTTTACTTCAATGGGCTCTTCC |
| 4033 | TTTTACTTCAATGGGCTCTTCCA |
| 4034 | TTTACTTCAATGGGCTCTTCCAA |
| 4035 | TTACTTCAATGGGCTCTTCCAAC |
| 4036 | TACTTCAATGGGCTCTTCCAACA |
| 4037 | ACTTCAATGGGCTCTTCCAACAA |
| 4038 | CTTCAATGGGCTCTTCCAACAAG |
| 4039 | TTCAATGGGCTCTTCCAACAAGG |
| 4040 | TCAATGGGCTCTTCCAACAAGGA |
| 4041 | CAATGGGCTCTTCCAACAAGGAA |
| 4042 | AATGGGCTCTTCCAACAAGGAAG |
| 4043 | ATGGGCTCTTCCAACAAGGAAGA |
| 4044 | TGGGCTCTTCCAACAAGGAAGAA |
| 4045 | GGGCTCTTCCAACAAGGAAGAAG |
| 4046 | GGCTCTTCCAACAAGGAAGAAGC |
| 4047 | GCTCTTCCAACAAGGAAGAAGCT |
| 4048 | CTCTTCCAACAAGGAAGAAGCTT |
| 4049 | TCTTCCAACAAGGAAGAAGCTTG |
| 4050 | CTTCCAACAAGGAAGAAGCTTGC |
| 4051 | TTCCAACAAGGAAGAAGCTTGCT |
| 4052 | TCCAACAAGGAAGAAGCTTGCTG |
| 4053 | CCAACAAGGAAGAAGCTTGCTGG |
| 4054 | CAACAAGGAAGAAGCTTGCTGGT |
| 4055 | AACAAGGAAGAAGCTTGCTGGTA |
| 4056 | ACAAGGAAGAAGCTTGCTGGTAG |
| 4057 | CAAGGAAGAAGCTTGCTGGTAGC |
| 4058 | AAGGAAGAAGCTTGCTGGTAGCA |
| 4059 | AGGAAGAAGCTTGCTGGTAGCAC |
| 4060 | GGAAGAAGCTTGCTGGTAGCACT |

| ID | SEQUENCE |
|---|---|
| 4061 | GAAGAAGCTTGCTGGTAGCACTT |
| 4062 | AAGAAGCTTGCTGGTAGCACTTG |
| 4063 | AGAAGCTTGCTGGTAGCACTTGC |
| 4064 | GAAGCTTGCTGGTAGCACTTGCT |
| 4065 | AAGCTTGCTGGTAGCACTTGCTA |
| 4066 | AGCTTGCTGGTAGCACTTGCTAC |
| 4067 | GCTTGCTGGTAGCACTTGCTACC |
| 4068 | CTTGCTGGTAGCACTTGCTACCC |
| 4069 | TTGCTGGTAGCACTTGCTACCCT |
| 4070 | TGCTGGTAGCACTTGCTACCCTG |
| 4071 | GCTGGTAGCACTTGCTACCCTGA |
| 4072 | CTGGTAGCACTTGCTACCCTGAG |
| 4073 | TGGTAGCACTTGCTACCCTGAGT |
| 4074 | GGTAGCACTTGCTACCCTGAGTT |
| 4075 | GTAGCACTTGCTACCCTGAGTTC |
| 4076 | TAGCACTTGCTACCCTGAGTTCA |
| 4077 | AGCACTTGCTACCCTGAGTTCAT |
| 4078 | GCACTTGCTACCCTGAGTTCATC |
| 4079 | CACTTGCTACCCTGAGTTCATCC |
| 4080 | ACTTGCTACCCTGAGTTCATCCA |
| 4081 | CTTGCTACCCTGAGTTCATCCAG |
| 4082 | TTGCTACCCTGAGTTCATCCAGG |
| 4083 | TGCTACCCTGAGTTCATCCAGGC |
| 4084 | GCTACCCTGAGTTCATCCAGGCC |
| 4085 | CTACCCTGAGTTCATCCAGGCCC |
| 4086 | TACCCTGAGTTCATCCAGGCCCA |
| 4087 | ACCCTGAGTTCATCCAGGCCCAA |
| 4088 | CCCTGAGTTCATCCAGGCCCAAC |
| 4089 | CCTGAGTTCATCCAGGCCCAACT |
| 4090 | CTGAGTTCATCCAGGCCCAACTG |
| 4091 | TGAGTTCATCCAGGCCCAACTGT |
| 4092 | GAGTTCATCCAGGCCCAACTGTG |
| 4093 | AGTTCATCCAGGCCCAACTGTGA |
| 4094 | GTTCATCCAGGCCCAACTGTGAG |
| 4095 | TTCATCCAGGCCCAACTGTGAGC |
| 4096 | TCATCCAGGCCCAACTGTGAGCA |
| 4097 | CATCCAGGCCCAACTGTGAGCAA |
| 4098 | ATCCAGGCCCAACTGTGAGCAAG |
| 4099 | TCCAGGCCCAACTGTGAGCAAGG |
| 4100 | CCAGGCCCAACTGTGAGCAAGGA |
| 4101 | CAGGCCCAACTGTGAGCAAGGAG |
| 4102 | AGGCCCAACTGTGAGCAAGGAGC |
| 4103 | GGCCCAACTGTGAGCAAGGAGCA |
| 4104 | GCCCAACTGTGAGCAAGGAGCAC |
| 4105 | CCCAACTGTGAGCAAGGAGCACA |
| 4106 | CCAACTGTGAGCAAGGAGCACAA |
| 4107 | CAACTGTGAGCAAGGAGCACAAG |
| 4108 | AACTGTGAGCAAGGAGCACAAGC |
| 4109 | ACTGTGAGCAAGGAGCACAAGCC |
| 4110 | CTGTGAGCAAGGAGCACAAGCCA |
| 4111 | TGTGAGCAAGGAGCACAAGCCAC |
| 4112 | GTGAGCAAGGAGCACAAGCCACA |
| 4113 | TGAGCAAGGAGCACAAGCCACAA |
| 4114 | GAGCAAGGAGCACAAGCCACAAG |
| 4115 | AGCAAGGAGCACAAGCCACAAGT |
| 4116 | GCAAGGAGCACAAGCCACAAGTC |
| 4117 | CAAGGAGCACAAGCCACAAGTCT |
| 4118 | AAGGAGCACAAGCCACAAGTCTT |

| ID | SEQUENCE |
|---|---|
| 4119 | AGGAGCACAAGCCACAAGTCTTC |
| 4120 | GGAGCACAAGCCACAAGTCTTCC |
| 4121 | GAGCACAAGCCACAAGTCTTCCA |
| 4122 | AGCACAAGCCACAAGTCTTCCAG |
| 4123 | GCACAAGCCACAAGTCTTCCAGA |
| 4124 | CACAAGCCACAAGTCTTCCAGAG |
| 4125 | ACAAGCCACAAGTCTTCCAGAGG |
| 4126 | CAAGCCACAAGTCTTCCAGAGGA |
| 4127 | AAGCCACAAGTCTTCCAGAGGAT |
| 4128 | AGCCACAAGTCTTCCAGAGGATG |
| 4129 | GCCACAAGTCTTCCAGAGGATGC |
| 4130 | CCACAAGTCTTCCAGAGGATGCT |
| 4131 | CACAAGTCTTCCAGAGGATGCTT |
| 4132 | ACAAGTCTTCCAGAGGATGCTTG |
| 4133 | CAAGTCTTCCAGAGGATGCTTGA |
| 4134 | AAGTCTTCCAGAGGATGCTTGAT |
| 4135 | AGTCTTCCAGAGGATGCTTGATT |
| 4136 | GTCTTCCAGAGGATGCTTGATTC |
| 4137 | TCTTCCAGAGGATGCTTGATTCC |
| 4138 | CTTCCAGAGGATGCTTGATTCCA |
| 4139 | TTCCAGAGGATGCTTGATTCCAG |
| 4140 | TCCAGAGGATGCTTGATTCCAGT |
| 4141 | CCAGAGGATGCTTGATTCCAGTG |
| 4142 | CAGAGGATGCTTGATTCCAGTGG |
| 4143 | AGAGGATGCTTGATTCCAGTGGT |
| 4144 | GAGGATGCTTGATTCCAGTGGTT |
| 4145 | AGGATGCTTGATTCCAGTGGTTC |
| 4146 | GGATGCTTGATTCCAGTGGTTCT |
| 4147 | GATGCTTGATTCCAGTGGTTCTG |
| 4148 | ATGCTTGATTCCAGTGGTTCTGC |
| 4149 | TGCTTGATTCCAGTGGTTCTGCT |
| 4150 | GCTTGATTCCAGTGGTTCTGCTT |
| 4151 | CTTGATTCCAGTGGTTCTGCTTC |
| 4152 | TTGATTCCAGTGGTTCTGCTTCA |
| 4153 | TGATTCCAGTGGTTCTGCTTCAA |
| 4154 | GATTCCAGTGGTTCTGCTTCAAG |
| 4155 | ATTCCAGTGGTTCTGCTTCAAGG |
| 4156 | TTCCAGTGGTTCTGCTTCAAGGC |
| 4157 | TCCAGTGGTTCTGCTTCAAGGCT |
| 4158 | CCAGTGGTTCTGCTTCAAGGCTT |
| 4159 | CAGTGGTTCTGCTTCAAGGCTTC |
| 4160 | AGTGGTTCTGCTTCAAGGCTTCC |
| 4161 | GTGGTTCTGCTTCAAGGCTTCCA |
| 4162 | TGGTTCTGCTTCAAGGCTTCCAC |
| 4163 | GGTTCTGCTTCAAGGCTTCCACT |
| 4164 | GTTCTGCTTCAAGGCTTCCACTG |
| 4165 | TTCTGCTTCAAGGCTTCCACTGC |
| 4166 | TCTGCTTCAAGGCTTCCACTGCA |
| 4167 | CTGCTTCAAGGCTTCCACTGCAA |
| 4168 | TGCTTCAAGGCTTCCACTGCAAA |
| 4169 | GCTTCAAGGCTTCCACTGCAAAA |
| 4170 | CTTCAAGGCTTCCACTGCAAAAC |
| 4171 | TTCAAGGCTTCCACTGCAAAACA |
| 4172 | TCAAGGCTTCCACTGCAAAACAC |
| 4173 | CAAGGCTTCCACTGCAAAACACT |
| 4174 | AAGGCTTCCACTGCAAAACACTA |
| 4175 | AGGCTTCCACTGCAAAACACTAA |
| 4176 | GGCTTCCACTGCAAAACACTAAA |

| ID | SEQUENCE |
|---|---|
| 4177 | GCTTCCACTGCAAAACACTAAAG |
| 4178 | CTTCCACTGCAAAACACTAAAGA |
| 4179 | TTCCACTGCAAAACACTAAAGAT |
| 4180 | TCCACTGCAAAACACTAAAGATC |
| 4181 | CCACTGCAAAACACTAAAGATCC |
| 4182 | CACTGCAAAACACTAAAGATCCA |
| 4183 | ACTGCAAAACACTAAAGATCCAA |
| 4184 | CTGCAAAACACTAAAGATCCAAG |
| 4185 | TGCAAAACACTAAAGATCCAAGA |
| 4186 | GCAAAACACTAAAGATCCAAGAA |
| 4187 | CAAAACACTAAAGATCCAAGAAG |
| 4188 | AAAACACTAAAGATCCAAGAAGG |
| 4189 | AAACACTAAAGATCCAAGAAGGC |
| 4190 | AACACTAAAGATCCAAGAAGGCC |
| 4191 | ACACTAAAGATCCAAGAAGGCCT |
| 4192 | CACTAAAGATCCAAGAAGGCCTT |
| 4193 | ACTAAAGATCCAAGAAGGCCTTC |
| 4194 | CTAAAGATCCAAGAAGGCCTTCA |
| 4195 | TAAAGATCCAAGAAGGCCTTCAT |
| 4196 | AAAGATCCAAGAAGGCCTTCATG |
| 4197 | AAGATCCAAGAAGGCCTTCATGG |
| 4198 | AGATCCAAGAAGGCCTTCATGGC |
| 4199 | GATCCAAGAAGGCCTTCATGGCC |
| 4200 | ATCCAAGAAGGCCTTCATGGCCC |
| 4201 | TCCAAGAAGGCCTTCATGGCCCC |
| 4202 | CCAAGAAGGCCTTCATGGCCCCA |
| 4203 | CAAGAAGGCCTTCATGGCCCCAG |
| 4204 | AAGAAGGCCTTCATGGCCCCAGC |
| 4205 | AGAAGGCCTTCATGGCCCCAGCA |
| 4206 | GAAGGCCTTCATGGCCCCAGCAG |
| 4207 | AAGGCCTTCATGGCCCCAGCAGG |
| 4208 | AGGCCTTCATGGCCCCAGCAGGC |
| 4209 | GGCCTTCATGGCCCCAGCAGGCC |
| 4210 | GCCTTCATGGCCCCAGCAGGCCG |
| 4211 | CCTTCATGGCCCCAGCAGGCCGG |
| 4212 | CTTCATGGCCCCAGCAGGCCGGA |
| 4213 | TTCATGGCCCCAGCAGGCCGGAT |
| 4214 | TCATGGCCCCAGCAGGCCGGATC |
| 4215 | CATGGCCCCAGCAGGCCGGATCG |
| 4216 | ATGGCCCCAGCAGGCCGGATCGG |
| 4217 | TGGCCCCAGCAGGCCGGATCGGT |
| 4218 | GGCCCCAGCAGGCCGGATCGGTA |
| 4219 | GCCCCAGCAGGCCGGATCGGTAC |
| 4220 | CCCCAGCAGGCCGGATCGGTACT |
| 4221 | CCCAGCAGGCCGGATCGGTACTG |
| 4222 | CCAGCAGGCCGGATCGGTACTGT |
| 4223 | CAGCAGGCCGGATCGGTACTGTA |
| 4224 | AGCAGGCCGGATCGGTACTGTAT |
| 4225 | GCAGGCCGGATCGGTACTGTATC |
| 4226 | CAGGCCGGATCGGTACTGTATCA |
| 4227 | AGGCCGGATCGGTACTGTATCAA |
| 4228 | GGCCGGATCGGTACTGTATCAAG |
| 4229 | GCCGGATCGGTACTGTATCAAGT |
| 4230 | CCGGATCGGTACTGTATCAAGTC |
| 4231 | CGGATCGGTACTGTATCAAGTCA |
| 4232 | GGATCGGTACTGTATCAAGTCAT |
| 4233 | GATCGGTACTGTATCAAGTCATG |
| 4234 | ATCGGTACTGTATCAAGTCATGG |

| ID | SEQUENCE |
|---|---|
| 4235 | TCGGTACTGTATCAAGTCATGGC |
| 4236 | CGGTACTGTATCAAGTCATGGCA |
| 4237 | GGTACTGTATCAAGTCATGGCAG |
| 4238 | GTACTGTATCAAGTCATGGCAGG |
| 4239 | TACTGTATCAAGTCATGGCAGGT |
| 4240 | ACTGTATCAAGTCATGGCAGGTA |
| 4241 | CTGTATCAAGTCATGGCAGGTAC |
| 4242 | TGTATCAAGTCATGGCAGGTACA |
| 4243 | GTATCAAGTCATGGCAGGTACAG |
| 4244 | TATCAAGTCATGGCAGGTACAGT |
| 4245 | ATCAAGTCATGGCAGGTACAGTA |
| 4246 | TCAAGTCATGGCAGGTACAGTAG |
| 4247 | CAAGTCATGGCAGGTACAGTAGG |
| 4248 | AAGTCATGGCAGGTACAGTAGGA |
| 4249 | AGTCATGGCAGGTACAGTAGGAT |
| 4250 | GTCATGGCAGGTACAGTAGGATA |
| 4251 | TCATGGCAGGTACAGTAGGATAA |
| 4252 | CATGGCAGGTACAGTAGGATAAG |
| 4253 | ATGGCAGGTACAGTAGGATAAGC |
| 4254 | TGGCAGGTACAGTAGGATAAGCC |
| 4255 | GGCAGGTACAGTAGGATAAGCCA |
| 4256 | GCAGGTACAGTAGGATAAGCCAC |
| 4257 | CAGGTACAGTAGGATAAGCCACT |
| 4258 | AGGTACAGTAGGATAAGCCACTC |
| 4259 | GGTACAGTAGGATAAGCCACTCT |
| 4260 | GTACAGTAGGATAAGCCACTCTG |
| 4261 | TACAGTAGGATAAGCCACTCTGT |
| 4262 | ACAGTAGGATAAGCCACTCTGTC |
| 4263 | CAGTAGGATAAGCCACTCTGTCC |
| 4264 | AGTAGGATAAGCCACTCTGTCCC |
| 4265 | GTAGGATAAGCCACTCTGTCCCT |
| 4266 | TAGGATAAGCCACTCTGTCCCTT |
| 4267 | AGGATAAGCCACTCTGTCCCTTC |
| 4268 | GGATAAGCCACTCTGTCCCTTCC |
| 4269 | GATAAGCCACTCTGTCCCTTCCT |
| 4270 | ATAAGCCACTCTGTCCCTTCCTG |
| 4271 | TAAGCCACTCTGTCCCTTCCTGG |
| 4272 | AAGCCACTCTGTCCCTTCCTGGG |
| 4273 | AGCCACTCTGTCCCTTCCTGGGC |
| 4274 | GCCACTCTGTCCCTTCCTGGGCA |
| 4275 | CCACTCTGTCCCTTCCTGGGCAA |
| 4276 | CACTCTGTCCCTTCCTGGGCAAA |
| 4277 | ACTCTGTCCCTTCCTGGGCAAAG |
| 4278 | CTCTGTCCCTTCCTGGGCAAAGA |
| 4279 | TCTGTCCCTTCCTGGGCAAAGAA |
| 4280 | CTGTCCCTTCCTGGGCAAAGAAG |
| 4281 | TGTCCCTTCCTGGGCAAAGAAGA |
| 4282 | GTCCCTTCCTGGGCAAAGAAGAA |
| 4283 | TCCCTTCCTGGGCAAAGAAGAAA |
| 4284 | CCCTTCCTGGGCAAAGAAGAAAC |
| 4285 | CCTTCCTGGGCAAAGAAGAAACG |
| 4286 | CTTCCTGGGCAAAGAAGAAACGG |
| 4287 | TTCCTGGGCAAAGAAGAAACGGA |
| 4288 | TCCTGGGCAAAGAAGAAACGGAG |
| 4289 | CCTGGGCAAAGAAGAAACGGAGG |
| 4290 | CTGGGCAAAGAAGAAACGGAGGG |
| 4291 | TGGGCAAAGAAGAAACGGAGGGG |
| 4292 | GGGCAAAGAAGAAACGGAGGGGA |

| ID | SEQUENCE |
|---|---|
| 4293 | GGCAAAGAAGAAACGGAGGGGAT |
| 4294 | GCAAAGAAGAAACGGAGGGGATG |
| 4295 | CAAAGAAGAAACGGAGGGGATGG |
| 4296 | AAAGAAGAAACGGAGGGGATGGA |
| 4297 | AAGAAGAAACGGAGGGGATGGAA |
| 4298 | AGAAGAAACGGAGGGGATGGAAT |
| 4299 | GAAGAAACGGAGGGGATGGAATT |
| 4300 | AAGAAACGGAGGGGATGGAATTC |
| 4301 | AGAAACGGAGGGGATGGAATTCT |
| 4302 | GAAACGGAGGGGATGGAATTCTT |
| 4303 | AAACGGAGGGGATGGAATTCTTC |
| 4304 | AACGGAGGGGATGGAATTCTTCC |
| 4305 | ACGGAGGGGATGGAATTCTTCCT |
| 4306 | CGGAGGGGATGGAATTCTTCCTT |
| 4307 | GGAGGGGATGGAATTCTTCCTTA |
| 4308 | GAGGGGATGGAATTCTTCCTTAG |
| 4309 | AGGGGATGGAATTCTTCCTTAGA |
| 4310 | GGGGATGGAATTCTTCCTTAGAC |
| 4311 | GGGATGGAATTCTTCCTTAGACT |
| 4312 | GGATGGAATTCTTCCTTAGACTT |
| 4313 | GATGGAATTCTTCCTTAGACTTA |
| 4314 | ATGGAATTCTTCCTTAGACTTAC |
| 4315 | TGGAATTCTTCCTTAGACTTACT |
| 4316 | GGAATTCTTCCTTAGACTTACTT |
| 4317 | GAATTCTTCCTTAGACTTACTTT |
| 4318 | AATTCTTCCTTAGACTTACTTTT |
| 4319 | ATTCTTCCTTAGACTTACTTTTG |
| 4320 | TTCTTCCTTAGACTTACTTTTGT |
| 4321 | TCTTCCTTAGACTTACTTTTGTA |
| 4322 | CTTCCTTAGACTTACTTTTGTAA |
| 4323 | TTCCTTAGACTTACTTTTGTAAA |
| 4324 | TCCTTAGACTTACTTTTGTAAAA |
| 4325 | CCTTAGACTTACTTTTGTAAAAA |
| 4326 | CTTAGACTTACTTTTGTAAAAAT |
| 4327 | TTAGACTTACTTTTGTAAAAATG |
| 4328 | TAGACTTACTTTTGTAAAAATGT |
| 4329 | AGACTTACTTTTGTAAAAATGTC |
| 4330 | GACTTACTTTTGTAAAAATGTCC |
| 4331 | ACTTACTTTTGTAAAAATGTCCC |
| 4332 | CTTACTTTTGTAAAAATGTCCCC |
| 4333 | TTACTTTTGTAAAAATGTCCCCA |
| 4334 | TACTTTTGTAAAAATGTCCCCAC |
| 4335 | ACTTTTGTAAAAATGTCCCCACG |
| 4336 | CTTTTGTAAAAATGTCCCCACGG |
| 4337 | TTTTGTAAAAATGTCCCCACGGT |
| 4338 | TTTGTAAAAATGTCCCCACGGTA |
| 4339 | TTGTAAAAATGTCCCCACGGTAC |
| 4340 | TGTAAAAATGTCCCCACGGTACT |
| 4341 | GTAAAAATGTCCCCACGGTACTT |
| 4342 | TAAAAATGTCCCCACGGTACTTA |
| 4343 | AAAAATGTCCCCACGGTACTTAC |
| 4344 | AAAATGTCCCCACGGTACTTACT |
| 4345 | AAATGTCCCCACGGTACTTACTC |
| 4346 | AATGTCCCCACGGTACTTACTCC |
| 4347 | ATGTCCCCACGGTACTTACTCCC |
| 4348 | TGTCCCCACGGTACTTACTCCCC |
| 4349 | GTCCCCACGGTACTTACTCCCCA |
| 4350 | TCCCCACGGTACTTACTCCCCAC |

| ID | SEQUENCE |
|---|---|
| 4351 | CCCCACGGTACTTACTCCCCACT |
| 4352 | CCCACGGTACTTACTCCCCACTG |
| 4353 | CCACGGTACTTACTCCCCACTGA |
| 4354 | CACGGTACTTACTCCCCACTGAT |
| 4355 | ACGGTACTTACTCCCCACTGATG |
| 4356 | CGGTACTTACTCCCCACTGATGG |
| 4357 | GGTACTTACTCCCCACTGATGGA |
| 4358 | GTACTTACTCCCCACTGATGGAC |
| 4359 | TACTTACTCCCCACTGATGGACC |
| 4360 | ACTTACTCCCCACTGATGGACCA |
| 4361 | CTTACTCCCCACTGATGGACCAG |
| 4362 | TTACTCCCCACTGATGGACCAGT |
| 4363 | TACTCCCCACTGATGGACCAGTG |
| 4364 | ACTCCCCACTGATGGACCAGTGG |
| 4365 | CTCCCCACTGATGGACCAGTGGT |
| 4366 | TCCCCACTGATGGACCAGTGGTT |
| 4367 | CCCCACTGATGGACCAGTGGTTT |
| 4368 | CCCACTGATGGACCAGTGGTTTC |
| 4369 | CCACTGATGGACCAGTGGTTTCC |
| 4370 | CACTGATGGACCAGTGGTTTCCA |
| 4371 | ACTGATGGACCAGTGGTTTCCAG |
| 4372 | CTGATGGACCAGTGGTTTCCAGT |
| 4373 | TGATGGACCAGTGGTTTCCAGTC |
| 4374 | GATGGACCAGTGGTTTCCAGTCA |
| 4375 | ATGGACCAGTGGTTTCCAGTCAT |
| 4376 | TGGACCAGTGGTTTCCAGTCATG |
| 4377 | GGACCAGTGGTTTCCAGTCATGA |
| 4378 | GACCAGTGGTTTCCAGTCATGAG |
| 4379 | ACCAGTGGTTTCCAGTCATGAGC |
| 4380 | CCAGTGGTTTCCAGTCATGAGCG |
| 4381 | CAGTGGTTTCCAGTCATGAGCGT |
| 4382 | AGTGGTTTCCAGTCATGAGCGTT |
| 4383 | GTGGTTTCCAGTCATGAGCGTTA |
| 4384 | TGGTTTCCAGTCATGAGCGTTAG |
| 4385 | GGTTTCCAGTCATGAGCGTTAGA |
| 4386 | GTTTCCAGTCATGAGCGTTAGAC |
| 4387 | TTTCCAGTCATGAGCGTTAGACT |
| 4388 | TTCCAGTCATGAGCGTTAGACTG |
| 4389 | TCCAGTCATGAGCGTTAGACTGA |
| 4390 | CCAGTCATGAGCGTTAGACTGAC |
| 4391 | CAGTCATGAGCGTTAGACTGACT |
| 4392 | AGTCATGAGCGTTAGACTGACTT |
| 4393 | GTCATGAGCGTTAGACTGACTTG |
| 4394 | TCATGAGCGTTAGACTGACTTGT |
| 4395 | CATGAGCGTTAGACTGACTTGTT |
| 4396 | ATGAGCGTTAGACTGACTTGTTT |
| 4397 | TGAGCGTTAGACTGACTTGTTTG |
| 4398 | GAGCGTTAGACTGACTTGTTTGT |
| 4399 | AGCGTTAGACTGACTTGTTTGTC |
| 4400 | GCGTTAGACTGACTTGTTTGTCT |
| 4401 | CGTTAGACTGACTTGTTTGTCTT |
| 4402 | GTTAGACTGACTTGTTTGTCTTC |
| 4403 | TTAGACTGACTTGTTTGTCTTCC |
| 4404 | TAGACTGACTTGTTTGTCTTCCA |
| 4405 | AGACTGACTTGTTTGTCTTCCAT |
| 4406 | GACTGACTTGTTTGTCTTCCATT |
| 4407 | ACTGACTTGTTTGTCTTCCATTC |
| 4408 | CTGACTTGTTTGTCTTCCATTCC |

| ID | SEQUENCE |
|---|---|
| 4409 | TGACTTGTTTGTCTTCCATTCCA |
| 4410 | GACTTGTTTGTCTTCCATTCCAT |
| 4411 | ACTTGTTTGTCTTCCATTCCATT |
| 4412 | CTTGTTTGTCTTCCATTCCATTG |
| 4413 | TTGTTTGTCTTCCATTCCATTGT |
| 4414 | TGTTTGTCTTCCATTCCATTGTT |
| 4415 | GTTTGTCTTCCATTCCATTGTTT |
| 4416 | TTTGTCTTCCATTCCATTGTTTT |
| 4417 | TTGTCTTCCATTCCATTGTTTTG |
| 4418 | TGTCTTCCATTCCATTGTTTTGA |
| 4419 | GTCTTCCATTCCATTGTTTTGAA |
| 4420 | TCTTCCATTCCATTGTTTTGAAA |
| 4421 | CTTCCATTCCATTGTTTTGAAAC |
| 4422 | TTCCATTCCATTGTTTTGAAACT |
| 4423 | TCCATTCCATTGTTTTGAAACTC |
| 4424 | CCATTCCATTGTTTTGAAACTCA |
| 4425 | CATTCCATTGTTTTGAAACTCAG |
| 4426 | ATTCCATTGTTTTGAAACTCAGT |
| 4427 | TTCCATTGTTTTGAAACTCAGTA |
| 4428 | TCCATTGTTTTGAAACTCAGTAT |
| 4429 | CCATTGTTTTGAAACTCAGTATG |
| 4430 | CATTGTTTTGAAACTCAGTATGC |
| 4431 | ATTGTTTTGAAACTCAGTATGCT |
| 4432 | TTGTTTTGAAACTCAGTATGCTG |
| 4433 | TGTTTTGAAACTCAGTATGCTGC |
| 4434 | GTTTTGAAACTCAGTATGCTGCC |
| 4435 | TTTTGAAACTCAGTATGCTGCCC |
| 4436 | TTTGAAACTCAGTATGCTGCCCC |
| 4437 | TTGAAACTCAGTATGCTGCCCCT |
| 4438 | TGAAACTCAGTATGCTGCCCCTG |
| 4439 | GAAACTCAGTATGCTGCCCCTGT |
| 4440 | AAACTCAGTATGCTGCCCCTGTC |
| 4441 | AACTCAGTATGCTGCCCCTGTCT |
| 4442 | ACTCAGTATGCTGCCCCTGTCTT |
| 4443 | CTCAGTATGCTGCCCCTGTCTTG |
| 4444 | TCAGTATGCTGCCCCTGTCTTGC |
| 4445 | CAGTATGCTGCCCCTGTCTTGCT |
| 4446 | AGTATGCTGCCCCTGTCTTGCTG |
| 4447 | GTATGCTGCCCCTGTCTTGCTGT |
| 4448 | TATGCTGCCCCTGTCTTGCTGTC |
| 4449 | ATGCTGCCCCTGTCTTGCTGTCA |
| 4450 | TGCTGCCCCTGTCTTGCTGTCAT |
| 4451 | GCTGCCCCTGTCTTGCTGTCATG |
| 4452 | CTGCCCCTGTCTTGCTGTCATGA |
| 4453 | TGCCCCTGTCTTGCTGTCATGAA |
| 4454 | GCCCCTGTCTTGCTGTCATGAAA |
| 4455 | CCCCTGTCTTGCTGTCATGAAAT |
| 4456 | CCCTGTCTTGCTGTCATGAAATC |
| 4457 | CCTGTCTTGCTGTCATGAAATCA |
| 4458 | CTGTCTTGCTGTCATGAAATCAG |
| 4459 | TGTCTTGCTGTCATGAAATCAGC |
| 4460 | GTCTTGCTGTCATGAAATCAGCA |
| 4461 | TCTTGCTGTCATGAAATCAGCAA |
| 4462 | CTTGCTGTCATGAAATCAGCAAG |
| 4463 | TTGCTGTCATGAAATCAGCAAGA |
| 4464 | TGCTGTCATGAAATCAGCAAGAG |
| 4465 | GCTGTCATGAAATCAGCAAGAGA |
| 4466 | CTGTCATGAAATCAGCAAGAGAG |

| ID | SEQUENCE |
|---|---|
| 4467 | TGTCATGAAATCAGCAAGAGAGG |
| 4468 | GTCATGAAATCAGCAAGAGAGGA |
| 4469 | TCATGAAATCAGCAAGAGAGGAT |
| 4470 | CATGAAATCAGCAAGAGAGGATG |
| 4471 | ATGAAATCAGCAAGAGAGGATGA |
| 4472 | TGAAATCAGCAAGAGAGGATGAC |
| 4473 | GAAATCAGCAAGAGAGGATGACA |
| 4474 | AAATCAGCAAGAGAGGATGACAC |
| 4475 | AATCAGCAAGAGAGGATGACACA |
| 4476 | ATCAGCAAGAGAGGATGACACAT |
| 4477 | TCAGCAAGAGAGGATGACACATC |
| 4478 | CAGCAAGAGAGGATGACACATCA |
| 4479 | AGCAAGAGAGGATGACACATCAA |
| 4480 | GCAAGAGAGGATGACACATCAAA |
| 4481 | CAAGAGAGGATGACACATCAAAT |
| 4482 | AAGAGAGGATGACACATCAAATA |
| 4483 | AGAGAGGATGACACATCAAATAA |
| 4484 | GAGAGGATGACACATCAAATAAT |
| 4485 | AGAGGATGACACATCAAATAATA |
| 4486 | GAGGATGACACATCAAATAATAA |
| 4487 | AGGATGACACATCAAATAATAAC |
| 4488 | GGATGACACATCAAATAATAACT |
| 4489 | GATGACACATCAAATAATAACTC |
| 4490 | ATGACACATCAAATAATAACTCG |
| 4491 | TGACACATCAAATAATAACTCGG |
| 4492 | GACACATCAAATAATAACTCGGA |
| 4493 | ACACATCAAATAATAACTCGGAT |
| 4494 | CACATCAAATAATAACTCGGATT |
| 4495 | ACATCAAATAATAACTCGGATTC |
| 4496 | CATCAAATAATAACTCGGATTCC |
| 4497 | ATCAAATAATAACTCGGATTCCA |
| 4498 | TCAAATAATAACTCGGATTCCAG |
| 4499 | CAAATAATAACTCGGATTCCAGC |
| 4500 | AAATAATAACTCGGATTCCAGCC |
| 4501 | AATAATAACTCGGATTCCAGCCC |
| 4502 | ATAATAACTCGGATTCCAGCCCA |
| 4503 | TAATAACTCGGATTCCAGCCCAC |
| 4504 | AATAACTCGGATTCCAGCCCACA |
| 4505 | ATAACTCGGATTCCAGCCCACAT |
| 4506 | TAACTCGGATTCCAGCCCACATT |
| 4507 | AACTCGGATTCCAGCCCACATTG |
| 4508 | ACTCGGATTCCAGCCCACATTGG |
| 4509 | CTCGGATTCCAGCCCACATTGGA |
| 4510 | TCGGATTCCAGCCCACATTGGAT |
| 4511 | CGGATTCCAGCCCACATTGGATT |
| 4512 | GGATTCCAGCCCACATTGGATTC |
| 4513 | GATTCCAGCCCACATTGGATTCA |
| 4514 | ATTCCAGCCCACATTGGATTCAT |
| 4515 | TTCCAGCCCACATTGGATTCATC |
| 4516 | TCCAGCCCACATTGGATTCATCA |
| 4517 | CCAGCCCACATTGGATTCATCAG |
| 4518 | CAGCCCACATTGGATTCATCAGC |
| 4519 | AGCCCACATTGGATTCATCAGCA |
| 4520 | GCCCACATTGGATTCATCAGCAT |
| 4521 | CCCACATTGGATTCATCAGCATT |
| 4522 | CCACATTGGATTCATCAGCATTT |
| 4523 | CACATTGGATTCATCAGCATTTG |
| 4524 | ACATTGGATTCATCAGCATTTGG |

| ID | SEQUENCE |
|---|---|
| 4525 | CATTGGATTCATCAGCATTTGGA |
| 4526 | ATTGGATTCATCAGCATTTGGAC |
| 4527 | TTGGATTCATCAGCATTTGGACC |
| 4528 | TGGATTCATCAGCATTTGGACCA |
| 4529 | GGATTCATCAGCATTTGGACCAA |
| 4530 | GATTCATCAGCATTTGGACCAAT |
| 4531 | ATTCATCAGCATTTGGACCAATA |
| 4532 | TTCATCAGCATTTGGACCAATAG |
| 4533 | TCATCAGCATTTGGACCAATAGC |
| 4534 | CATCAGCATTTGGACCAATAGCC |
| 4535 | ATCAGCATTTGGACCAATAGCCC |
| 4536 | TCAGCATTTGGACCAATAGCCCA |
| 4537 | CAGCATTTGGACCAATAGCCCAC |
| 4538 | AGCATTTGGACCAATAGCCCACA |
| 4539 | GCATTTGGACCAATAGCCCACAG |
| 4540 | CATTTGGACCAATAGCCCACAGC |
| 4541 | ATTTGGACCAATAGCCCACAGCT |
| 4542 | TTTGGACCAATAGCCCACAGCTG |
| 4543 | TTGGACCAATAGCCCACAGCTGA |
| 4544 | TGGACCAATAGCCCACAGCTGAG |
| 4545 | GGACCAATAGCCCACAGCTGAGA |
| 4546 | GACCAATAGCCCACAGCTGAGAA |
| 4547 | ACCAATAGCCCACAGCTGAGAAT |
| 4548 | CCAATAGCCCACAGCTGAGAATG |
| 4549 | CAATAGCCCACAGCTGAGAATGT |
| 4550 | AATAGCCCACAGCTGAGAATGTG |
| 4551 | ATAGCCCACAGCTGAGAATGTGG |
| 4552 | TAGCCCACAGCTGAGAATGTGGA |
| 4553 | AGCCCACAGCTGAGAATGTGGAA |
| 4554 | GCCCACAGCTGAGAATGTGGAAT |
| 4555 | CCCACAGCTGAGAATGTGGAATA |
| 4556 | CCACAGCTGAGAATGTGGAATAC |
| 4557 | CACAGCTGAGAATGTGGAATACC |
| 4558 | ACAGCTGAGAATGTGGAATACCT |
| 4559 | CAGCTGAGAATGTGGAATACCTA |
| 4560 | AGCTGAGAATGTGGAATACCTAA |
| 4561 | GCTGAGAATGTGGAATACCTAAG |
| 4562 | CTGAGAATGTGGAATACCTAAGG |
| 4563 | TGAGAATGTGGAATACCTAAGGA |
| 4564 | GAGAATGTGGAATACCTAAGGAT |
| 4565 | AGAATGTGGAATACCTAAGGATA |
| 4566 | GAATGTGGAATACCTAAGGATAG |
| 4567 | AATGTGGAATACCTAAGGATAGC |
| 4568 | ATGTGGAATACCTAAGGATAGCA |
| 4569 | TGTGGAATACCTAAGGATAGCAC |
| 4570 | GTGGAATACCTAAGGATAGCACC |
| 4571 | TGGAATACCTAAGGATAGCACCG |
| 4572 | GGAATACCTAAGGATAGCACCGC |
| 4573 | GAATACCTAAGGATAGCACCGCT |
| 4574 | AATACCTAAGGATAGCACCGCTT |
| 4575 | ATACCTAAGGATAGCACCGCTTT |
| 4576 | TACCTAAGGATAGCACCGCTTTT |
| 4577 | ACCTAAGGATAGCACCGCTTTTG |
| 4578 | CCTAAGGATAGCACCGCTTTTGT |
| 4579 | CTAAGGATAGCACCGCTTTTGTT |
| 4580 | TAAGGATAGCACCGCTTTTGTTC |
| 4581 | AAGGATAGCACCGCTTTTGTTCT |
| 4582 | AGGATAGCACCGCTTTTGTTCTC |

| ID | SEQUENCE |
|---|---|
| 4583 | GGATAGCACCGCTTTTGTTCTCG |
| 4584 | GATAGCACCGCTTTTGTTCTCGC |
| 4585 | ATAGCACCGCTTTTGTTCTCGCA |
| 4586 | TAGCACCGCTTTTGTTCTCGCAA |
| 4587 | AGCACCGCTTTTGTTCTCGCAAA |
| 4588 | GCACCGCTTTTGTTCTCGCAAAA |
| 4589 | CACCGCTTTTGTTCTCGCAAAAA |
| 4590 | ACCGCTTTTGTTCTCGCAAAAAC |
| 4591 | CCGCTTTTGTTCTCGCAAAAACG |
| 4592 | CGCTTTTGTTCTCGCAAAAACGT |
| 4593 | GCTTTTGTTCTCGCAAAAACGTA |
| 4594 | CTTTTGTTCTCGCAAAAACGTAT |
| 4595 | TTTTGTTCTCGCAAAAACGTATC |
| 4596 | TTTGTTCTCGCAAAAACGTATCT |
| 4597 | TTGTTCTCGCAAAAACGTATCTC |
| 4598 | TGTTCTCGCAAAAACGTATCTCC |
| 4599 | GTTCTCGCAAAAACGTATCTCCT |
| 4600 | TTCTCGCAAAAACGTATCTCCTA |
| 4601 | TCTCGCAAAAACGTATCTCCTAA |
| 4602 | CTCGCAAAAACGTATCTCCTAAT |
| 4603 | TCGCAAAAACGTATCTCCTAATT |
| 4604 | CGCAAAAACGTATCTCCTAATTT |
| 4605 | GCAAAAACGTATCTCCTAATTTG |
| 4606 | CAAAAACGTATCTCCTAATTTGA |
| 4607 | AAAAACGTATCTCCTAATTTGAG |
| 4608 | AAAACGTATCTCCTAATTTGAGG |
| 4609 | AAACGTATCTCCTAATTTGAGGC |
| 4610 | AACGTATCTCCTAATTTGAGGCT |
| 4611 | ACGTATCTCCTAATTTGAGGCTC |
| 4612 | CGTATCTCCTAATTTGAGGCTCA |
| 4613 | GTATCTCCTAATTTGAGGCTCAG |
| 4614 | TATCTCCTAATTTGAGGCTCAGA |
| 4615 | ATCTCCTAATTTGAGGCTCAGAT |
| 4616 | TCTCCTAATTTGAGGCTCAGATG |
| 4617 | CTCCTAATTTGAGGCTCAGATGA |
| 4618 | TCCTAATTTGAGGCTCAGATGAA |
| 4619 | CCTAATTTGAGGCTCAGATGAAA |
| 4620 | CTAATTTGAGGCTCAGATGAAAT |
| 4621 | TAATTTGAGGCTCAGATGAAATG |
| 4622 | AATTTGAGGCTCAGATGAAATGC |
| 4623 | ATTTGAGGCTCAGATGAAATGCA |
| 4624 | TTTGAGGCTCAGATGAAATGCAT |
| 4625 | TTGAGGCTCAGATGAAATGCATC |
| 4626 | TGAGGCTCAGATGAAATGCATCA |
| 4627 | GAGGCTCAGATGAAATGCATCAG |
| 4628 | AGGCTCAGATGAAATGCATCAGG |
| 4629 | GGCTCAGATGAAATGCATCAGGT |
| 4630 | GCTCAGATGAAATGCATCAGGTC |
| 4631 | CTCAGATGAAATGCATCAGGTCC |
| 4632 | TCAGATGAAATGCATCAGGTCCT |
| 4633 | CAGATGAAATGCATCAGGTCCTT |
| 4634 | AGATGAAATGCATCAGGTCCTTT |
| 4635 | GATGAAATGCATCAGGTCCTTTG |
| 4636 | ATGAAATGCATCAGGTCCTTTGG |
| 4637 | TGAAATGCATCAGGTCCTTTGGG |
| 4638 | GAAATGCATCAGGTCCTTTGGGG |
| 4639 | AAATGCATCAGGTCCTTTGGGGC |
| 4640 | AATGCATCAGGTCCTTTGGGGCA |

| ID | SEQUENCE |
|---|---|
| 4641 | ATGCATCAGGTCCTTTGGGGCAT |
| 4642 | TGCATCAGGTCCTTTGGGGCATA |
| 4643 | GCATCAGGTCCTTTGGGGCATAG |
| 4644 | CATCAGGTCCTTTGGGGCATAGA |
| 4645 | ATCAGGTCCTTTGGGGCATAGAT |
| 4646 | TCAGGTCCTTTGGGGCATAGATC |
| 4647 | CAGGTCCTTTGGGGCATAGATCA |
| 4648 | AGGTCCTTTGGGGCATAGATCAG |
| 4649 | GGTCCTTTGGGGCATAGATCAGA |
| 4650 | GTCCTTTGGGGCATAGATCAGAA |
| 4651 | TCCTTTGGGGCATAGATCAGAAG |
| 4652 | CCTTTGGGGCATAGATCAGAAGA |
| 4653 | CTTTGGGGCATAGATCAGAAGAC |
| 4654 | TTTGGGGCATAGATCAGAAGACT |
| 4655 | TTGGGGCATAGATCAGAAGACTA |
| 4656 | TGGGGCATAGATCAGAAGACTAC |
| 4657 | GGGGCATAGATCAGAAGACTACA |
| 4658 | GGGCATAGATCAGAAGACTACAA |
| 4659 | GGCATAGATCAGAAGACTACAAA |
| 4660 | GCATAGATCAGAAGACTACAAAA |
| 4661 | CATAGATCAGAAGACTACAAAAA |
| 4662 | ATAGATCAGAAGACTACAAAAAT |
| 4663 | TAGATCAGAAGACTACAAAAATG |
| 4664 | AGATCAGAAGACTACAAAAATGA |
| 4665 | GATCAGAAGACTACAAAAATGAA |
| 4666 | ATCAGAAGACTACAAAAATGAAG |
| 4667 | TCAGAAGACTACAAAAATGAAGC |
| 4668 | CAGAAGACTACAAAAATGAAGCT |
| 4669 | AGAAGACTACAAAAATGAAGCTG |
| 4670 | GAAGACTACAAAAATGAAGCTGC |
| 4671 | AAGACTACAAAAATGAAGCTGCT |
| 4672 | AGACTACAAAAATGAAGCTGCTC |
| 4673 | GACTACAAAAATGAAGCTGCTCT |
| 4674 | ACTACAAAAATGAAGCTGCTCTG |
| 4675 | CTACAAAAATGAAGCTGCTCTGA |
| 4676 | TACAAAAATGAAGCTGCTCTGAA |
| 4677 | ACAAAAATGAAGCTGCTCTGAAA |
| 4678 | CAAAAATGAAGCTGCTCTGAAAT |
| 4679 | AAAAATGAAGCTGCTCTGAAATC |
| 4680 | AAAATGAAGCTGCTCTGAAATCT |
| 4681 | AAATGAAGCTGCTCTGAAATCTC |
| 4682 | AATGAAGCTGCTCTGAAATCTCC |
| 4683 | ATGAAGCTGCTCTGAAATCTCCT |
| 4684 | TGAAGCTGCTCTGAAATCTCCTT |
| 4685 | GAAGCTGCTCTGAAATCTCCTTT |
| 4686 | AAGCTGCTCTGAAATCTCCTTTA |
| 4687 | AGCTGCTCTGAAATCTCCTTTAG |
| 4688 | GCTGCTCTGAAATCTCCTTTAGC |
| 4689 | CTGCTCTGAAATCTCCTTTAGCC |
| 4690 | TGCTCTGAAATCTCCTTTAGCCA |
| 4691 | GCTCTGAAATCTCCTTTAGCCAT |
| 4692 | CTCTGAAATCTCCTTTAGCCATC |
| 4693 | TCTGAAATCTCCTTTAGCCATCA |
| 4694 | CTGAAATCTCCTTTAGCCATCAC |
| 4695 | TGAAATCTCCTTTAGCCATCACC |
| 4696 | GAAATCTCCTTTAGCCATCACCC |
| 4697 | AAATCTCCTTTAGCCATCACCCC |
| 4698 | AATCTCCTTTAGCCATCACCCCA |

| ID | SEQUENCE |
|---|---|
| 4699 | ATCTCCTTTAGCCATCACCCCAA |
| 4700 | TCTCCTTTAGCCATCACCCCAAC |
| 4701 | CTCCTTTAGCCATCACCCCAACC |
| 4702 | TCCTTTAGCCATCACCCCAACCC |
| 4703 | CCTTTAGCCATCACCCCAACCCC |
| 4704 | CTTTAGCCATCACCCCAACCCCC |
| 4705 | TTTAGCCATCACCCCAACCCCCC |
| 4706 | TTAGCCATCACCCCAACCCCCCA |
| 4707 | TAGCCATCACCCCAACCCCCCAA |
| 4708 | AGCCATCACCCCAACCCCCCAAA |
| 4709 | GCCATCACCCCAACCCCCCAAAA |
| 4710 | CCATCACCCCAACCCCCCAAAAT |
| 4711 | CATCACCCCAACCCCCCAAAATT |
| 4712 | ATCACCCCAACCCCCCAAAATTA |
| 4713 | TCACCCCAACCCCCCAAAATTAG |
| 4714 | CACCCCAACCCCCCAAAATTAGT |
| 4715 | ACCCCAACCCCCCAAAATTAGTT |
| 4716 | CCCCAACCCCCCAAAATTAGTTT |
| 4717 | CCCAACCCCCCAAAATTAGTTTG |
| 4718 | CCAACCCCCCAAAATTAGTTTGT |
| 4719 | CAACCCCCCAAAATTAGTTTGTG |
| 4720 | AACCCCCCAAAATTAGTTTGTGT |
| 4721 | ACCCCCCAAAATTAGTTTGTGTT |
| 4722 | CCCCCCAAAATTAGTTTGTGTTA |
| 4723 | CCCCCAAAATTAGTTTGTGTTAC |
| 4724 | CCCCAAAATTAGTTTGTGTTACT |
| 4725 | CCCAAAATTAGTTTGTGTTACTT |
| 4726 | CCAAAATTAGTTTGTGTTACTTA |
| 4727 | CAAAATTAGTTTGTGTTACTTAT |
| 4728 | AAAATTAGTTTGTGTTACTTATG |
| 4729 | AAATTAGTTTGTGTTACTTATGG |
| 4730 | AATTAGTTTGTGTTACTTATGGA |
| 4731 | ATTAGTTTGTGTTACTTATGGAA |
| 4732 | TTAGTTTGTGTTACTTATGGAAG |
| 4733 | TAGTTTGTGTTACTTATGGAAGA |
| 4734 | AGTTTGTGTTACTTATGGAAGAT |
| 4735 | GTTTGTGTTACTTATGGAAGATA |
| 4736 | TTTGTGTTACTTATGGAAGATAG |
| 4737 | TTGTGTTACTTATGGAAGATAGT |
| 4738 | TGTGTTACTTATGGAAGATAGTT |
| 4739 | GTGTTACTTATGGAAGATAGTTT |
| 4740 | TGTTACTTATGGAAGATAGTTTT |
| 4741 | GTTACTTATGGAAGATAGTTTTC |
| 4742 | TTACTTATGGAAGATAGTTTTCT |
| 4743 | TACTTATGGAAGATAGTTTTCTC |
| 4744 | ACTTATGGAAGATAGTTTTCTCC |
| 4745 | CTTATGGAAGATAGTTTTCTCCT |
| 4746 | TTATGGAAGATAGTTTTCTCCTT |
| 4747 | TATGGAAGATAGTTTTCTCCTTT |
| 4748 | ATGGAAGATAGTTTTCTCCTTTT |
| 4749 | TGGAAGATAGTTTTCTCCTTTTA |
| 4750 | GGAAGATAGTTTTCTCCTTTTAC |
| 4751 | GAAGATAGTTTTCTCCTTTTACT |
| 4752 | AAGATAGTTTTCTCCTTTTACTT |
| 4753 | AGATAGTTTTCTCCTTTTACTTC |
| 4754 | GATAGTTTTCTCCTTTTACTTCA |
| 4755 | ATAGTTTTCTCCTTTTACTTCAC |
| 4756 | TAGTTTTCTCCTTTTACTTCACT |

| ID | SEQUENCE |
|---|---|
| 4757 | AGTTTTCTCCTTTTACTTCACTT |
| 4758 | GTTTTCTCCTTTTACTTCACTTC |
| 4759 | TTTTCTCCTTTTACTTCACTTCA |
| 4760 | TTTCTCCTTTTACTTCACTTCAA |
| 4761 | TTCTCCTTTTACTTCACTTCAAA |
| 4762 | TCTCCTTTTACTTCACTTCAAAA |
| 4763 | CTCCTTTTACTTCACTTCAAAAG |
| 4764 | TCCTTTTACTTCACTTCAAAAGC |
| 4765 | CCTTTTACTTCACTTCAAAAGCT |
| 4766 | CTTTTACTTCACTTCAAAAGCTT |
| 4767 | TTTTACTTCACTTCAAAAGCTTT |
| 4768 | TTTACTTCACTTCAAAAGCTTTT |
| 4769 | TTACTTCACTTCAAAAGCTTTTT |
| 4770 | TACTTCACTTCAAAAGCTTTTTA |
| 4771 | ACTTCACTTCAAAAGCTTTTTAC |
| 4772 | CTTCACTTCAAAAGCTTTTTACT |
| 4773 | TTCACTTCAAAAGCTTTTTACTC |
| 4774 | TCACTTCAAAAGCTTTTTACTCA |
| 4775 | CACTTCAAAAGCTTTTTACTCAA |
| 4776 | ACTTCAAAAGCTTTTTACTCAAA |
| 4777 | CTTCAAAAGCTTTTTACTCAAAG |
| 4778 | TTCAAAAGCTTTTTACTCAAAGA |
| 4779 | TCAAAAGCTTTTTACTCAAAGAG |
| 4780 | CAAAAGCTTTTTACTCAAAGAGT |
| 4781 | AAAAGCTTTTTACTCAAAGAGTA |
| 4782 | AAAGCTTTTTACTCAAAGAGTAT |
| 4783 | AAGCTTTTTACTCAAAGAGTATA |
| 4784 | AGCTTTTTACTCAAAGAGTATAT |
| 4785 | GCTTTTTACTCAAAGAGTATATG |
| 4786 | CTTTTTACTCAAAGAGTATATGT |
| 4787 | TTTTTACTCAAAGAGTATATGTT |
| 4788 | TTTTACTCAAAGAGTATATGTTC |
| 4789 | TTTACTCAAAGAGTATATGTTCC |
| 4790 | TTACTCAAAGAGTATATGTTCCC |
| 4791 | TACTCAAAGAGTATATGTTCCCT |
| 4792 | ACTCAAAGAGTATATGTTCCCTC |
| 4793 | CTCAAAGAGTATATGTTCCCTCC |
| 4794 | TCAAAGAGTATATGTTCCCTCCA |
| 4795 | CAAAGAGTATATGTTCCCTCCAG |
| 4796 | AAAGAGTATATGTTCCCTCCAGG |
| 4797 | AAGAGTATATGTTCCCTCCAGGT |
| 4798 | AGAGTATATGTTCCCTCCAGGTC |
| 4799 | GAGTATATGTTCCCTCCAGGTCA |
| 4800 | AGTATATGTTCCCTCCAGGTCAG |
| 4801 | GTATATGTTCCCTCCAGGTCAGC |
| 4802 | TATATGTTCCCTCCAGGTCAGCT |
| 4803 | ATATGTTCCCTCCAGGTCAGCTG |
| 4804 | TATGTTCCCTCCAGGTCAGCTGC |
| 4805 | ATGTTCCCTCCAGGTCAGCTGCC |
| 4806 | TGTTCCCTCCAGGTCAGCTGCCC |
| 4807 | GTTCCCTCCAGGTCAGCTGCCCC |
| 4808 | TTCCCTCCAGGTCAGCTGCCCCC |
| 4809 | TCCCTCCAGGTCAGCTGCCCCCA |
| 4810 | CCCTCCAGGTCAGCTGCCCCCAA |
| 4811 | CCTCCAGGTCAGCTGCCCCCAAA |
| 4812 | CTCCAGGTCAGCTGCCCCCAAAC |
| 4813 | TCCAGGTCAGCTGCCCCCAAACC |
| 4814 | CCAGGTCAGCTGCCCCCAAACCC |

| ID | SEQUENCE |
|---|---|
| 4815 | CAGGTCAGCTGCCCCCAAACCCC |
| 4816 | AGGTCAGCTGCCCCCAAACCCCC |
| 4817 | GGTCAGCTGCCCCCAAACCCCCT |
| 4818 | GTCAGCTGCCCCCAAACCCCCTC |
| 4819 | TCAGCTGCCCCCAAACCCCCTCC |
| 4820 | CAGCTGCCCCCAAACCCCCTCCT |
| 4821 | AGCTGCCCCCAAACCCCCTCCTT |
| 4822 | GCTGCCCCCAAACCCCCTCCTTA |
| 4823 | CTGCCCCCAAACCCCCTCCTTAC |
| 4824 | TGCCCCCAAACCCCCTCCTTACG |
| 4825 | GCCCCCAAACCCCCTCCTTACGC |
| 4826 | CCCCCAAACCCCCTCCTTACGCT |
| 4827 | CCCCAAACCCCCTCCTTACGCTT |
| 4828 | CCCAAACCCCCTCCTTACGCTTT |
| 4829 | CCAAACCCCCTCCTTACGCTTTG |
| 4830 | CAAACCCCCTCCTTACGCTTTGT |
| 4831 | AAACCCCCTCCTTACGCTTTGTC |
| 4832 | AACCCCCTCCTTACGCTTTGTCA |
| 4833 | ACCCCCTCCTTACGCTTTGTCAC |
| 4834 | CCCCCTCCTTACGCTTTGTCACA |
| 4835 | CCCCTCCTTACGCTTTGTCACAC |
| 4836 | CCCTCCTTACGCTTTGTCACACA |
| 4837 | CCTCCTTACGCTTTGTCACACAA |
| 4838 | CTCCTTACGCTTTGTCACACAAA |
| 4839 | TCCTTACGCTTTGTCACACAAAA |
| 4840 | CCTTACGCTTTGTCACACAAAAA |
| 4841 | CTTACGCTTTGTCACACAAAAAG |
| 4842 | TTACGCTTTGTCACACAAAAAGT |
| 4843 | TACGCTTTGTCACACAAAAAGTG |
| 4844 | ACGCTTTGTCACACAAAAAGTGT |
| 4845 | CGCTTTGTCACACAAAAAGTGTC |
| 4846 | GCTTTGTCACACAAAAAGTGTCT |
| 4847 | CTTTGTCACACAAAAAGTGTCTC |
| 4848 | TTTGTCACACAAAAAGTGTCTCT |
| 4849 | TTGTCACACAAAAAGTGTCTCTG |
| 4850 | TGTCACACAAAAAGTGTCTCTGC |
| 4851 | GTCACACAAAAAGTGTCTCTGCC |
| 4852 | TCACACAAAAAGTGTCTCTGCCT |
| 4853 | CACACAAAAAGTGTCTCTGCCTT |
| 4854 | ACACAAAAAGTGTCTCTGCCTTG |
| 4855 | CACAAAAAGTGTCTCTGCCTTGA |
| 4856 | ACAAAAAGTGTCTCTGCCTTGAG |
| 4857 | CAAAAAGTGTCTCTGCCTTGAGT |
| 4858 | AAAAAGTGTCTCTGCCTTGAGTC |
| 4859 | AAAAGTGTCTCTGCCTTGAGTCA |
| 4860 | AAAGTGTCTCTGCCTTGAGTCAT |
| 4861 | AAGTGTCTCTGCCTTGAGTCATC |
| 4862 | AGTGTCTCTGCCTTGAGTCATCT |
| 4863 | GTGTCTCTGCCTTGAGTCATCTA |
| 4864 | TGTCTCTGCCTTGAGTCATCTAT |
| 4865 | GTCTCTGCCTTGAGTCATCTATT |
| 4866 | TCTCTGCCTTGAGTCATCTATTC |
| 4867 | CTCTGCCTTGAGTCATCTATTCA |
| 4868 | TCTGCCTTGAGTCATCTATTCAA |
| 4869 | CTGCCTTGAGTCATCTATTCAAG |
| 4870 | TGCCTTGAGTCATCTATTCAAGC |
| 4871 | GCCTTGAGTCATCTATTCAAGCA |
| 4872 | CCTTGAGTCATCTATTCAAGCAC |

| ID | SEQUENCE |
|---|---|
| 4873 | CTTGAGTCATCTATTCAAGCACT |
| 4874 | TTGAGTCATCTATTCAAGCACTT |
| 4875 | TGAGTCATCTATTCAAGCACTTA |
| 4876 | GAGTCATCTATTCAAGCACTTAC |
| 4877 | AGTCATCTATTCAAGCACTTACA |
| 4878 | GTCATCTATTCAAGCACTTACAG |
| 4879 | TCATCTATTCAAGCACTTACAGC |
| 4880 | CATCTATTCAAGCACTTACAGCT |
| 4881 | ATCTATTCAAGCACTTACAGCTC |
| 4882 | TCTATTCAAGCACTTACAGCTCT |
| 4883 | CTATTCAAGCACTTACAGCTCTG |
| 4884 | TATTCAAGCACTTACAGCTCTGG |
| 4885 | ATTCAAGCACTTACAGCTCTGGC |
| 4886 | TTCAAGCACTTACAGCTCTGGCC |
| 4887 | TCAAGCACTTACAGCTCTGGCCA |
| 4888 | CAAGCACTTACAGCTCTGGCCAC |
| 4889 | AAGCACTTACAGCTCTGGCCACA |
| 4890 | AGCACTTACAGCTCTGGCCACAA |
| 4891 | GCACTTACAGCTCTGGCCACAAC |
| 4892 | CACTTACAGCTCTGGCCACAACA |
| 4893 | ACTTACAGCTCTGGCCACAACAG |
| 4894 | CTTACAGCTCTGGCCACAACAGG |
| 4895 | TTACAGCTCTGGCCACAACAGGG |
| 4896 | TACAGCTCTGGCCACAACAGGGC |
| 4897 | ACAGCTCTGGCCACAACAGGGCA |
| 4898 | CAGCTCTGGCCACAACAGGGCAT |
| 4899 | AGCTCTGGCCACAACAGGGCATT |
| 4900 | GCTCTGGCCACAACAGGGCATTT |
| 4901 | CTCTGGCCACAACAGGGCATTTT |
| 4902 | TCTGGCCACAACAGGGCATTTTA |
| 4903 | CTGGCCACAACAGGGCATTTTAC |
| 4904 | TGGCCACAACAGGGCATTTTACA |
| 4905 | GGCCACAACAGGGCATTTTACAG |
| 4906 | GCCACAACAGGGCATTTTACAGG |
| 4907 | CCACAACAGGGCATTTTACAGGT |
| 4908 | CACAACAGGGCATTTTACAGGTG |
| 4909 | ACAACAGGGCATTTTACAGGTGC |
| 4910 | CAACAGGGCATTTTACAGGTGCG |
| 4911 | AACAGGGCATTTTACAGGTGCGA |
| 4912 | ACAGGGCATTTTACAGGTGCGAA |
| 4913 | CAGGGCATTTTACAGGTGCGAAT |
| 4914 | AGGGCATTTTACAGGTGCGAATG |
| 4915 | GGGCATTTTACAGGTGCGAATGA |
| 4916 | GGCATTTTACAGGTGCGAATGAC |
| 4917 | GCATTTTACAGGTGCGAATGACA |
| 4918 | CATTTTACAGGTGCGAATGACAG |
| 4919 | ATTTTACAGGTGCGAATGACAGT |
| 4920 | TTTTACAGGTGCGAATGACAGTA |
| 4921 | TTTACAGGTGCGAATGACAGTAG |
| 4922 | TTACAGGTGCGAATGACAGTAGC |
| 4923 | TACAGGTGCGAATGACAGTAGCA |
| 4924 | ACAGGTGCGAATGACAGTAGCAT |
| 4925 | CAGGTGCGAATGACAGTAGCATT |
| 4926 | AGGTGCGAATGACAGTAGCATTA |
| 4927 | GGTGCGAATGACAGTAGCATTAT |
| 4928 | GTGCGAATGACAGTAGCATTATG |
| 4929 | TGCGAATGACAGTAGCATTATGA |
| 4930 | GCGAATGACAGTAGCATTATGAG |

| ID | SEQUENCE |
|---|---|
| 4931 | CGAATGACAGTAGCATTATGAGT |
| 4932 | GAATGACAGTAGCATTATGAGTA |
| 4933 | AATGACAGTAGCATTATGAGTAG |
| 4934 | ATGACAGTAGCATTATGAGTAGT |
| 4935 | TGACAGTAGCATTATGAGTAGTG |
| 4936 | GACAGTAGCATTATGAGTAGTGT |
| 4937 | ACAGTAGCATTATGAGTAGTGTG |
| 4938 | CAGTAGCATTATGAGTAGTGTGG |
| 4939 | AGTAGCATTATGAGTAGTGTGGA |
| 4940 | GTAGCATTATGAGTAGTGTGGAA |
| 4941 | TAGCATTATGAGTAGTGTGGAAT |
| 4942 | AGCATTATGAGTAGTGTGGAATT |
| 4943 | GCATTATGAGTAGTGTGGAATTC |
| 4944 | CATTATGAGTAGTGTGGAATTCA |
| 4945 | ATTATGAGTAGTGTGGAATTCAG |
| 4946 | TTATGAGTAGTGTGGAATTCAGG |
| 4947 | TATGAGTAGTGTGGAATTCAGGT |
| 4948 | ATGAGTAGTGTGGAATTCAGGTA |
| 4949 | TGAGTAGTGTGGAATTCAGGTAG |
| 4950 | GAGTAGTGTGGAATTCAGGTAGT |
| 4951 | AGTAGTGTGGAATTCAGGTAGTA |
| 4952 | GTAGTGTGGAATTCAGGTAGTAA |
| 4953 | TAGTGTGGAATTCAGGTAGTAAA |
| 4954 | AGTGTGGAATTCAGGTAGTAAAT |
| 4955 | GTGTGGAATTCAGGTAGTAAATA |
| 4956 | TGTGGAATTCAGGTAGTAAATAT |
| 4957 | GTGGAATTCAGGTAGTAAATATG |
| 4958 | TGGAATTCAGGTAGTAAATATGA |
| 4959 | GGAATTCAGGTAGTAAATATGAA |
| 4960 | GAATTCAGGTAGTAAATATGAAA |
| 4961 | AATTCAGGTAGTAAATATGAAAC |
| 4962 | ATTCAGGTAGTAAATATGAAACT |
| 4963 | TTCAGGTAGTAAATATGAAACTA |
| 4964 | TCAGGTAGTAAATATGAAACTAG |
| 4965 | CAGGTAGTAAATATGAAACTAGG |
| 4966 | AGGTAGTAAATATGAAACTAGGG |
| 4967 | GGTAGTAAATATGAAACTAGGGT |
| 4968 | GTAGTAAATATGAAACTAGGGTT |
| 4969 | TAGTAAATATGAAACTAGGGTTT |
| 4970 | AGTAAATATGAAACTAGGGTTTG |
| 4971 | GTAAATATGAAACTAGGGTTTGA |
| 4972 | TAAATATGAAACTAGGGTTTGAA |
| 4973 | AAATATGAAACTAGGGTTTGAAA |
| 4974 | AATATGAAACTAGGGTTTGAAAT |
| 4975 | ATATGAAACTAGGGTTTGAAATT |
| 4976 | TATGAAACTAGGGTTTGAAATTG |
| 4977 | ATGAAACTAGGGTTTGAAATTGA |
| 4978 | TGAAACTAGGGTTTGAAATTGAT |
| 4979 | GAAACTAGGGTTTGAAATTGATA |
| 4980 | AAACTAGGGTTTGAAATTGATAA |
| 4981 | AACTAGGGTTTGAAATTGATAAT |
| 4982 | ACTAGGGTTTGAAATTGATAATG |
| 4983 | CTAGGGTTTGAAATTGATAATGC |
| 4984 | TAGGGTTTGAAATTGATAATGCT |
| 4985 | AGGGTTTGAAATTGATAATGCTT |
| 4986 | GGGTTTGAAATTGATAATGCTTT |
| 4987 | GGTTTGAAATTGATAATGCTTTC |
| 4988 | GTTTGAAATTGATAATGCTTTCA |

| ID | SEQUENCE |
|---|---|
| 4989 | TTTGAAATTGATAATGCTTTCAC |
| 4990 | TTGAAATTGATAATGCTTTCACA |
| 4991 | TGAAATTGATAATGCTTTCACAA |
| 4992 | GAAATTGATAATGCTTTCACAAC |
| 4993 | AAATTGATAATGCTTTCACAACA |
| 4994 | AATTGATAATGCTTTCACAACAT |
| 4995 | ATTGATAATGCTTTCACAACATT |
| 4996 | TTGATAATGCTTTCACAACATTT |
| 4997 | TGATAATGCTTTCACAACATTTG |
| 4998 | GATAATGCTTTCACAACATTTGC |
| 4999 | ATAATGCTTTCACAACATTTGCA |
| 5000 | TAATGCTTTCACAACATTTGCAG |
| 5001 | AATGCTTTCACAACATTTGCAGA |
| 5002 | ATGCTTTCACAACATTTGCAGAT |
| 5003 | TGCTTTCACAACATTTGCAGATG |
| 5004 | GCTTTCACAACATTTGCAGATGT |
| 5005 | CTTTCACAACATTTGCAGATGTT |
| 5006 | TTTCACAACATTTGCAGATGTTT |
| 5007 | TTCACAACATTTGCAGATGTTTT |
| 5008 | TCACAACATTTGCAGATGTTTTA |
| 5009 | CACAACATTTGCAGATGTTTTAG |
| 5010 | ACAACATTTGCAGATGTTTTAGA |
| 5011 | CAACATTTGCAGATGTTTTAGAA |
| 5012 | AACATTTGCAGATGTTTTAGAAG |
| 5013 | ACATTTGCAGATGTTTTAGAAGG |
| 5014 | CATTTGCAGATGTTTTAGAAGGA |
| 5015 | ATTTGCAGATGTTTTAGAAGGAA |
| 5016 | TTTGCAGATGTTTTAGAAGGAAA |
| 5017 | TTGCAGATGTTTTAGAAGGAAAA |
| 5018 | TGCAGATGTTTTAGAAGGAAAAA |
| 5019 | GCAGATGTTTTAGAAGGAAAAAA |
| 5020 | CAGATGTTTTAGAAGGAAAAAAG |
| 5021 | AGATGTTTTAGAAGGAAAAAAGT |
| 5022 | GATGTTTTAGAAGGAAAAAAGTT |
| 5023 | ATGTTTTAGAAGGAAAAAAGTTC |
| 5024 | TGTTTTAGAAGGAAAAAAGTTCC |
| 5025 | GTTTTAGAAGGAAAAAAGTTCCT |
| 5026 | TTTTAGAAGGAAAAAAGTTCCTT |
| 5027 | TTTAGAAGGAAAAAAGTTCCTTC |
| 5028 | TTAGAAGGAAAAAAGTTCCTTCC |
| 5029 | TAGAAGGAAAAAAGTTCCTTCCT |
| 5030 | AGAAGGAAAAAAGTTCCTTCCTA |
| 5031 | GAAGGAAAAAAGTTCCTTCCTAA |
| 5032 | AAGGAAAAAAGTTCCTTCCTAAA |
| 5033 | AGGAAAAAAGTTCCTTCCTAAAA |
| 5034 | GGAAAAAAGTTCCTTCCTAAAAT |
| 5035 | GAAAAAAGTTCCTTCCTAAAATA |
| 5036 | AAAAAAGTTCCTTCCTAAAATAA |
| 5037 | AAAAAGTTCCTTCCTAAAATAAT |
| 5038 | AAAAGTTCCTTCCTAAAATAATT |
| 5039 | AAAGTTCCTTCCTAAAATAATTT |
| 5040 | AAGTTCCTTCCTAAAATAATTTC |
| 5041 | AGTTCCTTCCTAAAATAATTTCT |
| 5042 | GTTCCTTCCTAAAATAATTTCTC |
| 5043 | TTCCTTCCTAAAATAATTTCTCT |
| 5044 | TCCTTCCTAAAATAATTTCTCTA |
| 5045 | CCTTCCTAAAATAATTTCTCTAC |
| 5046 | CTTCCTAAAATAATTTCTCTACA |

| ID | SEQUENCE |
|---|---|
| 5047 | TTCCTAAAATAATTTCTCTACAA |
| 5048 | TCCTAAAATAATTTCTCTACAAT |
| 5049 | CCTAAAATAATTTCTCTACAATT |
| 5050 | CTAAAATAATTTCTCTACAATTG |
| 5051 | TAAAATAATTTCTCTACAATTGG |
| 5052 | AAAATAATTTCTCTACAATTGGA |
| 5053 | AAATAATTTCTCTACAATTGGAA |
| 5054 | AATAATTTCTCTACAATTGGAAG |
| 5055 | ATAATTTCTCTACAATTGGAAGA |
| 5056 | TAATTTCTCTACAATTGGAAGAT |
| 5057 | AATTTCTCTACAATTGGAAGATT |
| 5058 | ATTTCTCTACAATTGGAAGATTG |
| 5059 | TTTCTCTACAATTGGAAGATTGG |
| 5060 | TTCTCTACAATTGGAAGATTGGA |
| 5061 | TCTCTACAATTGGAAGATTGGAA |
| 5062 | CTCTACAATTGGAAGATTGGAAG |
| 5063 | TCTACAATTGGAAGATTGGAAGA |
| 5064 | CTACAATTGGAAGATTGGAAGAT |
| 5065 | TACAATTGGAAGATTGGAAGATT |
| 5066 | ACAATTGGAAGATTGGAAGATTC |
| 5067 | CAATTGGAAGATTGGAAGATTCA |
| 5068 | AATTGGAAGATTGGAAGATTCAG |
| 5069 | ATTGGAAGATTGGAAGATTCAGC |
| 5070 | TTGGAAGATTGGAAGATTCAGCT |
| 5071 | TGGAAGATTGGAAGATTCAGCTA |
| 5072 | GGAAGATTGGAAGATTCAGCTAG |
| 5073 | GAAGATTGGAAGATTCAGCTAGT |
| 5074 | AAGATTGGAAGATTCAGCTAGTT |
| 5075 | AGATTGGAAGATTCAGCTAGTTA |
| 5076 | GATTGGAAGATTCAGCTAGTTAG |
| 5077 | ATTGGAAGATTCAGCTAGTTAGG |
| 5078 | TTGGAAGATTCAGCTAGTTAGGA |
| 5079 | TGGAAGATTCAGCTAGTTAGGAG |
| 5080 | GGAAGATTCAGCTAGTTAGGAGC |
| 5081 | GAAGATTCAGCTAGTTAGGAGCC |
| 5082 | AAGATTCAGCTAGTTAGGAGCCC |
| 5083 | AGATTCAGCTAGTTAGGAGCCCA |
| 5084 | GATTCAGCTAGTTAGGAGCCCAC |
| 5085 | ATTCAGCTAGTTAGGAGCCCACC |
| 5086 | TTCAGCTAGTTAGGAGCCCACCT |
| 5087 | TCAGCTAGTTAGGAGCCCACCTT |
| 5088 | CAGCTAGTTAGGAGCCCACCTTT |
| 5089 | AGCTAGTTAGGAGCCCACCTTTT |
| 5090 | GCTAGTTAGGAGCCCACCTTTTT |
| 5091 | CTAGTTAGGAGCCCACCTTTTTT |
| 5092 | TAGTTAGGAGCCCACCTTTTTTC |
| 5093 | AGTTAGGAGCCCACCTTTTTTCC |
| 5094 | GTTAGGAGCCCACCTTTTTTCCT |
| 5095 | TTAGGAGCCCACCTTTTTTCCTA |
| 5096 | TAGGAGCCCACCTTTTTTCCTAA |
| 5097 | AGGAGCCCACCTTTTTTCCTAAT |
| 5098 | GGAGCCCACCTTTTTTCCTAATC |
| 5099 | GAGCCCACCTTTTTTCCTAATCT |
| 5100 | AGCCCACCTTTTTTCCTAATCTG |
| 5101 | GCCCACCTTTTTTCCTAATCTGT |
| 5102 | CCCACCTTTTTTCCTAATCTGTG |
| 5103 | CCACCTTTTTTCCTAATCTGTGT |
| 5104 | CACCTTTTTTCCTAATCTGTGTG |

| ID | SEQUENCE |
|---|---|
| 5105 | ACCTTTTTCCTAATCTGTGTGT |
| 5106 | CCTTTTTCCTAATCTGTGTGTG |
| 5107 | CTTTTTTCCTAATCTGTGTGTGC |
| 5108 | TTTTTTCCTAATCTGTGTGTGCC |
| 5109 | TTTTTCCTAATCTGTGTGTGCCC |
| 5110 | TTTTCCTAATCTGTGTGTGCCCT |
| 5111 | TTTCCTAATCTGTGTGTGCCCTG |
| 5112 | TTCCTAATCTGTGTGTGCCCTGT |
| 5113 | TCCTAATCTGTGTGTGCCCTGTA |
| 5114 | CCTAATCTGTGTGTGCCCTGTAA |
| 5115 | CTAATCTGTGTGTGCCCTGTAAC |
| 5116 | TAATCTGTGTGTGCCCTGTAACC |
| 5117 | AATCTGTGTGTGCCCTGTAACCT |
| 5118 | ATCTGTGTGTGCCCTGTAACCTG |
| 5119 | TCTGTGTGTGCCCTGTAACCTGA |
| 5120 | CTGTGTGTGCCCTGTAACCTGAC |
| 5121 | TGTGTGTGCCCTGTAACCTGACT |
| 5122 | GTGTGTGCCCTGTAACCTGACTG |
| 5123 | TGTGTGCCCTGTAACCTGACTGG |
| 5124 | GTGTGCCCTGTAACCTGACTGGT |
| 5125 | TGTGCCCTGTAACCTGACTGGTT |
| 5126 | GTGCCCTGTAACCTGACTGGTTA |
| 5127 | TGCCCTGTAACCTGACTGGTTAA |
| 5128 | GCCCTGTAACCTGACTGGTTAAC |
| 5129 | CCCTGTAACCTGACTGGTTAACA |
| 5130 | CCTGTAACCTGACTGGTTAACAG |
| 5131 | CTGTAACCTGACTGGTTAACAGC |
| 5132 | TGTAACCTGACTGGTTAACAGCA |
| 5133 | GTAACCTGACTGGTTAACAGCAG |
| 5134 | TAACCTGACTGGTTAACAGCAGT |
| 5135 | AACCTGACTGGTTAACAGCAGTC |
| 5136 | ACCTGACTGGTTAACAGCAGTCC |
| 5137 | CCTGACTGGTTAACAGCAGTCCT |
| 5138 | CTGACTGGTTAACAGCAGTCCTT |
| 5139 | TGACTGGTTAACAGCAGTCCTTT |
| 5140 | GACTGGTTAACAGCAGTCCTTTG |
| 5141 | ACTGGTTAACAGCAGTCCTTTGT |
| 5142 | CTGGTTAACAGCAGTCCTTTGTA |
| 5143 | TGGTTAACAGCAGTCCTTTGTAA |
| 5144 | GGTTAACAGCAGTCCTTTGTAAA |
| 5145 | GTTAACAGCAGTCCTTTGTAAAC |
| 5146 | TTAACAGCAGTCCTTTGTAAACA |
| 5147 | TAACAGCAGTCCTTTGTAAACAG |
| 5148 | AACAGCAGTCCTTTGTAAACAGT |
| 5149 | ACAGCAGTCCTTTGTAAACAGTG |
| 5150 | CAGCAGTCCTTTGTAAACAGTGT |
| 5151 | AGCAGTCCTTTGTAAACAGTGTT |
| 5152 | GCAGTCCTTTGTAAACAGTGTTT |
| 5153 | CAGTCCTTTGTAAACAGTGTTTT |
| 5154 | AGTCCTTTGTAAACAGTGTTTTA |
| 5155 | GTCCTTTGTAAACAGTGTTTTAA |
| 5156 | TCCTTTGTAAACAGTGTTTTAAA |
| 5157 | CCTTTGTAAACAGTGTTTTAAAC |
| 5158 | CTTTGTAAACAGTGTTTTAAACT |
| 5159 | TTTGTAAACAGTGTTTTAAACTC |
| 5160 | TTGTAAACAGTGTTTTAAACTCT |
| 5161 | TGTAAACAGTGTTTTAAACTCTC |
| 5162 | GTAAACAGTGTTTTAAACTCTCC |

| ID | SEQUENCE |
|---|---|
| 5163 | TAAACAGTGTTTTAAACTCTCCT |
| 5164 | AAACAGTGTTTTAAACTCTCCTA |
| 5165 | AACAGTGTTTTAAACTCTCCTAG |
| 5166 | ACAGTGTTTTAAACTCTCCTAGT |
| 5167 | CAGTGTTTTAAACTCTCCTAGTC |
| 5168 | AGTGTTTTAAACTCTCCTAGTCA |
| 5169 | GTGTTTTAAACTCTCCTAGTCAA |
| 5170 | TGTTTTAAACTCTCCTAGTCAAT |
| 5171 | GTTTTAAACTCTCCTAGTCAATA |
| 5172 | TTTTAAACTCTCCTAGTCAATAT |
| 5173 | TTTAAACTCTCCTAGTCAATATC |
| 5174 | TTAAACTCTCCTAGTCAATATCC |
| 5175 | TAAACTCTCCTAGTCAATATCCA |
| 5176 | AAACTCTCCTAGTCAATATCCAC |
| 5177 | AACTCTCCTAGTCAATATCCACC |
| 5178 | ACTCTCCTAGTCAATATCCACCC |
| 5179 | CTCTCCTAGTCAATATCCACCCC |
| 5180 | TCTCCTAGTCAATATCCACCCCA |
| 5181 | CTCCTAGTCAATATCCACCCCAT |
| 5182 | TCCTAGTCAATATCCACCCCATC |
| 5183 | CCTAGTCAATATCCACCCCATCC |
| 5184 | CTAGTCAATATCCACCCCATCCA |
| 5185 | TAGTCAATATCCACCCCATCCAA |
| 5186 | AGTCAATATCCACCCCATCCAAT |
| 5187 | GTCAATATCCACCCCATCCAATT |
| 5188 | TCAATATCCACCCCATCCAATTT |
| 5189 | CAATATCCACCCCATCCAATTTA |
| 5190 | AATATCCACCCCATCCAATTTAT |
| 5191 | ATATCCACCCCATCCAATTTATC |
| 5192 | TATCCACCCCATCCAATTTATCA |
| 5193 | ATCCACCCCATCCAATTTATCAA |
| 5194 | TCCACCCCATCCAATTTATCAAG |
| 5195 | CCACCCCATCCAATTTATCAAGG |
| 5196 | CACCCCATCCAATTTATCAAGGA |
| 5197 | ACCCCATCCAATTTATCAAGGAA |
| 5198 | CCCCATCCAATTTATCAAGGAAG |
| 5199 | CCCATCCAATTTATCAAGGAAGA |
| 5200 | CCATCCAATTTATCAAGGAAGAA |
| 5201 | CATCCAATTTATCAAGGAAGAAA |
| 5202 | ATCCAATTTATCAAGGAAGAAAT |
| 5203 | TCCAATTTATCAAGGAAGAAATG |
| 5204 | CCAATTTATCAAGGAAGAAATGG |
| 5205 | CAATTTATCAAGGAAGAAATGGT |
| 5206 | AATTTATCAAGGAAGAAATGGTT |
| 5207 | ATTTATCAAGGAAGAAATGGTTC |
| 5208 | TTTATCAAGGAAGAAATGGTTCA |
| 5209 | TTATCAAGGAAGAAATGGTTCAG |
| 5210 | TATCAAGGAAGAAATGGTTCAGA |
| 5211 | ATCAAGGAAGAAATGGTTCAGAA |
| 5212 | TCAAGGAAGAAATGGTTCAGAAA |
| 5213 | CAAGGAAGAAATGGTTCAGAAAA |
| 5214 | AAGGAAGAAATGGTTCAGAAAAT |
| 5215 | AGGAAGAAATGGTTCAGAAAATA |
| 5216 | GGAAGAAATGGTTCAGAAAATAT |
| 5217 | GAAGAAATGGTTCAGAAAATATT |
| 5218 | AAGAAATGGTTCAGAAAATATTT |
| 5219 | AGAAATGGTTCAGAAAATATTTT |
| 5220 | GAAATGGTTCAGAAAATATTTTC |

| ID | SEQUENCE |
|---|---|
| 5221 | AAATGGTTCAGAAAATATTTTCA |
| 5222 | AATGGTTCAGAAAATATTTTCAG |
| 5223 | ATGGTTCAGAAAATATTTTCAGC |
| 5224 | TGGTTCAGAAAATATTTTCAGCC |
| 5225 | GGTTCAGAAAATATTTTCAGCCT |
| 5226 | GTTCAGAAAATATTTTCAGCCTA |
| 5227 | TTCAGAAAATATTTTCAGCCTAC |
| 5228 | TCAGAAAATATTTTCAGCCTACA |
| 5229 | CAGAAAATATTTTCAGCCTACAG |
| 5230 | AGAAAATATTTTCAGCCTACAGT |
| 5231 | GAAAATATTTTCAGCCTACAGTT |
| 5232 | AAAATATTTTCAGCCTACAGTTA |
| 5233 | AAATATTTTCAGCCTACAGTTAT |
| 5234 | AATATTTTCAGCCTACAGTTATG |
| 5235 | ATATTTTCAGCCTACAGTTATGT |
| 5236 | TATTTTCAGCCTACAGTTATGTT |
| 5237 | ATTTTCAGCCTACAGTTATGTTC |
| 5238 | TTTTCAGCCTACAGTTATGTTCA |
| 5239 | TTTCAGCCTACAGTTATGTTCAG |
| 5240 | TTCAGCCTACAGTTATGTTCAGT |
| 5241 | TCAGCCTACAGTTATGTTCAGTC |
| 5242 | CAGCCTACAGTTATGTTCAGTCA |
| 5243 | AGCCTACAGTTATGTTCAGTCAC |
| 5244 | GCCTACAGTTATGTTCAGTCACA |
| 5245 | CCTACAGTTATGTTCAGTCACAC |
| 5246 | CTACAGTTATGTTCAGTCACACA |
| 5247 | TACAGTTATGTTCAGTCACACAC |
| 5248 | ACAGTTATGTTCAGTCACACACA |
| 5249 | CAGTTATGTTCAGTCACACACAC |
| 5250 | AGTTATGTTCAGTCACACACACA |
| 5251 | GTTATGTTCAGTCACACACACAT |
| 5252 | TTATGTTCAGTCACACACACATA |
| 5253 | TATGTTCAGTCACACACACATAC |
| 5254 | ATGTTCAGTCACACACACATACA |
| 5255 | TGTTCAGTCACACACACATACAA |
| 5256 | GTTCAGTCACACACACATACAAA |
| 5257 | TTCAGTCACACACACATACAAAA |
| 5258 | TCAGTCACACACACATACAAAAT |
| 5259 | CAGTCACACACACATACAAAATG |
| 5260 | AGTCACACACACATACAAAATGT |
| 5261 | GTCACACACACATACAAAATGTT |
| 5262 | TCACACACACATACAAAATGTTC |
| 5263 | CACACACACATACAAAATGTTCC |
| 5264 | ACACACACATACAAAATGTTCCT |
| 5265 | CACACACATACAAAATGTTCCTT |
| 5266 | ACACACATACAAAATGTTCCTTT |
| 5267 | CACACATACAAAATGTTCCTTTT |
| 5268 | ACACATACAAAATGTTCCTTTTG |
| 5269 | CACATACAAAATGTTCCTTTTGC |
| 5270 | ACATACAAAATGTTCCTTTTGCT |
| 5271 | CATACAAAATGTTCCTTTTGCTT |
| 5272 | ATACAAAATGTTCCTTTTGCTTT |
| 5273 | TACAAAATGTTCCTTTTGCTTTT |
| 5274 | ACAAAATGTTCCTTTTGCTTTTA |
| 5275 | CAAAATGTTCCTTTTGCTTTTAA |
| 5276 | AAAATGTTCCTTTTGCTTTTAAA |
| 5277 | AAATGTTCCTTTTGCTTTTAAAG |
| 5278 | AATGTTCCTTTTGCTTTTAAAGT |

| ID | SEQUENCE |
|---|---|
| 5279 | ATGTTCCTTTTGCTTTTAAAGTA |
| 5280 | TGTTCCTTTTGCTTTTAAAGTAA |
| 5281 | GTTCCTTTTGCTTTTAAAGTAAT |
| 5282 | TTCCTTTTGCTTTTAAAGTAATT |
| 5283 | TCCTTTTGCTTTTAAAGTAATTT |
| 5284 | CCTTTTGCTTTTAAAGTAATTTT |
| 5285 | CTTTTGCTTTTAAAGTAATTTTT |
| 5286 | TTTTGCTTTTAAAGTAATTTTTG |
| 5287 | TTTGCTTTTAAAGTAATTTTTGA |
| 5288 | TTGCTTTTAAAGTAATTTTTGAC |
| 5289 | TGCTTTTAAAGTAATTTTTGACT |
| 5290 | GCTTTTAAAGTAATTTTTGACTC |
| 5291 | CTTTTAAAGTAATTTTTGACTCC |
| 5292 | TTTTAAAGTAATTTTTGACTCCC |
| 5293 | TTTAAAGTAATTTTTGACTCCCA |
| 5294 | TTAAAGTAATTTTTGACTCCCAG |
| 5295 | TAAAGTAATTTTTGACTCCCAGA |
| 5296 | AAAGTAATTTTTGACTCCCAGAT |
| 5297 | AAGTAATTTTTGACTCCCAGATC |
| 5298 | AGTAATTTTTGACTCCCAGATCA |
| 5299 | GTAATTTTTGACTCCCAGATCAG |
| 5300 | TAATTTTTGACTCCCAGATCAGT |
| 5301 | AATTTTTGACTCCCAGATCAGTC |
| 5302 | ATTTTTGACTCCCAGATCAGTCA |
| 5303 | TTTTTGACTCCCAGATCAGTCAG |
| 5304 | TTTTGACTCCCAGATCAGTCAGA |
| 5305 | TTTGACTCCCAGATCAGTCAGAG |
| 5306 | TTGACTCCCAGATCAGTCAGAGC |
| 5307 | TGACTCCCAGATCAGTCAGAGCC |
| 5308 | GACTCCCAGATCAGTCAGAGCCC |
| 5309 | ACTCCCAGATCAGTCAGAGCCCC |
| 5310 | CTCCCAGATCAGTCAGAGCCCCT |
| 5311 | TCCCAGATCAGTCAGAGCCCCTA |
| 5312 | CCCAGATCAGTCAGAGCCCCTAC |
| 5313 | CCAGATCAGTCAGAGCCCCTACA |
| 5314 | CAGATCAGTCAGAGCCCCTACAG |
| 5315 | AGATCAGTCAGAGCCCCTACAGC |
| 5316 | GATCAGTCAGAGCCCCTACAGCA |
| 5317 | ATCAGTCAGAGCCCCTACAGCAT |
| 5318 | TCAGTCAGAGCCCCTACAGCATT |
| 5319 | CAGTCAGAGCCCCTACAGCATTG |
| 5320 | AGTCAGAGCCCCTACAGCATTGT |
| 5321 | GTCAGAGCCCCTACAGCATTGTT |
| 5322 | TCAGAGCCCCTACAGCATTGTTA |
| 5323 | CAGAGCCCCTACAGCATTGTTAA |
| 5324 | AGAGCCCCTACAGCATTGTTAAG |
| 5325 | GAGCCCCTACAGCATTGTTAAGA |
| 5326 | AGCCCCTACAGCATTGTTAAGAA |
| 5327 | GCCCCTACAGCATTGTTAAGAAA |
| 5328 | CCCCTACAGCATTGTTAAGAAAG |
| 5329 | CCCTACAGCATTGTTAAGAAAGT |
| 5330 | CCTACAGCATTGTTAAGAAAGTA |
| 5331 | CTACAGCATTGTTAAGAAAGTAT |
| 5332 | TACAGCATTGTTAAGAAAGTATT |
| 5333 | ACAGCATTGTTAAGAAAGTATTT |
| 5334 | CAGCATTGTTAAGAAAGTATTTG |
| 5335 | AGCATTGTTAAGAAAGTATTTGA |
| 5336 | GCATTGTTAAGAAAGTATTTGAT |

| ID | SEQUENCE |
|---|---|
| 5337 | CATTGTTAAGAAAGTATTTGATT |
| 5338 | ATTGTTAAGAAAGTATTTGATTT |
| 5339 | TTGTTAAGAAAGTATTTGATTTT |
| 5340 | TGTTAAGAAAGTATTTGATTTTT |
| 5341 | GTTAAGAAAGTATTTGATTTTTG |
| 5342 | TTAAGAAAGTATTTGATTTTTGT |
| 5343 | TAAGAAAGTATTTGATTTTTGTC |
| 5344 | AAGAAAGTATTTGATTTTTGTCT |
| 5345 | AGAAAGTATTTGATTTTTGTCTC |
| 5346 | GAAAGTATTTGATTTTTGTCTCA |
| 5347 | AAAGTATTTGATTTTTGTCTCAA |
| 5348 | AAGTATTTGATTTTTGTCTCAAT |
| 5349 | AGTATTTGATTTTTGTCTCAATG |
| 5350 | GTATTTGATTTTTGTCTCAATGA |
| 5351 | TATTTGATTTTTGTCTCAATGAA |
| 5352 | ATTTGATTTTTGTCTCAATGAAA |
| 5353 | TTTGATTTTTGTCTCAATGAAAA |
| 5354 | TTGATTTTTGTCTCAATGAAAAT |
| 5355 | TGATTTTTGTCTCAATGAAAATA |
| 5356 | GATTTTTGTCTCAATGAAAATAA |
| 5357 | ATTTTTGTCTCAATGAAAATAAA |
| 5358 | TTTTTGTCTCAATGAAAATAAAA |
| 5359 | TTTTGTCTCAATGAAAATAAAAC |
| 5360 | TTTGTCTCAATGAAAATAAAACT |
| 5361 | TTGTCTCAATGAAAATAAAACTA |
| 5362 | TGTCTCAATGAAAATAAAACTAT |
| 5363 | GTCTCAATGAAAATAAAACTATA |
| 5364 | TCTCAATGAAAATAAAACTATAT |
| 5365 | CTCAATGAAAATAAAACTATATT |
| 5366 | TCAATGAAAATAAAACTATATTC |
| 5367 | CAATGAAAATAAAACTATATTCA |
| 5368 | AATGAAAATAAAACTATATTCAT |
| 5369 | ATGAAAATAAAACTATATTCATT |
| 5370 | TGAAAATAAAACTATATTCATTT |
| 5371 | GAAAATAAAACTATATTCATTTC |
| 5372 | AAAATAAAACTATATTCATTTCC |
| 5373 | AAATAAAACTATATTCATTTCCA |
| 5374 | AATAAAACTATATTCATTTCCAC |
| 5375 | ATAAAACTATATTCATTTCCACT |
| 5376 | TAAAACTATATTCATTTCCACTC |
| 5377 | AAAACTATATTCATTTCCACTCT |
| 5378 | AAACTATATTCATTTCCACTCTA |
| 5379 | AACTATATTCATTTCCACTCTAA |
| 5380 | ACTATATTCATTTCCACTCTAAA |
| 5381 | CTATATTCATTTCCACTCTAAAA |
| 5382 | TATATTCATTTCCACTCTAAAAA |
| 5383 | ATATTCATTTCCACTCTAAAAAA |
| 5384 | TATTCATTTCCACTCTAAAAAAA |
| 5385 | ATTCATTTCCACTCTAAAAAAAA |

| ID | SEQUENCE |
|---|---|
| 1 | TTTCCAGATTGGGGCTCGGGCCG |
| 2 | TTCCAGATTGGGGCTCGGGCCGC |
| 3 | GCCGCGCCTCCTCCGGGACCCTC |
| 4 | CCGCGCCTCCTCCGGGACCCTCC |
| 5 | CGCGCCTCCTCCGGGACCCTCCC |
| 6 | GCGCCTCCTCCGGGACCCTCCCC |
| 7 | CGCCTCCTCCGGGACCCTCCCCT |
| 8 | GCCTCCTCCGGGACCCTCCCCTT |
| 9 | CCTCCTCCGGGACCCTCCCCTTG |
| 10 | CTCCTCCGGGACCCTCCCCTTGG |
| 11 | TCCTCCGGGACCCTCCCCTTGGA |
| 12 | CCTCCGGGACCCTCCCCTTGGAC |
| 13 | CTCCGGGACCCTCCCCTTGGACC |
| 14 | TCCGGGACCCTCCCCTTGGACCG |
| 15 | CCGGGACCCTCCCCTTGGACCGA |
| 16 | CGGGACCCTCCCCTTGGACCGAG |
| 17 | GGGACCCTCCCCTTGGACCGAGC |
| 18 | GGACCCTCCCCTTGGACCGAGCC |
| 19 | GACCCTCCCCTTGGACCGAGCCG |
| 20 | ACCCTCCCCTTGGACCGAGCCGA |
| 21 | CCCTCCCCTTGGACCGAGCCGAT |
| 22 | CCTCCCCTTGGACCGAGCCGATC |
| 23 | CTCCCCTTGGACCGAGCCGATCG |
| 24 | TCCCCTTGGACCGAGCCGATCGC |
| 25 | CCCCTTGGACCGAGCCGATCGCC |
| 26 | CCCTTGGACCGAGCCGATCGCCG |
| 27 | CCTTGGACCGAGCCGATCGCCGC |
| 28 | CTTGGACCGAGCCGATCGCCGCG |
| 29 | TTGGACCGAGCCGATCGCCGCGG |
| 30 | GGGCCGGCTGTCCTGGCGCGAAA |
| 31 | GGCCGGCTGTCCTGGCGCGAAAA |
| 32 | GCCGGCTGTCCTGGCGCGAAAAG |
| 33 | CCGGCTGTCCTGGCGCGAAAAGG |
| 34 | CGGCTGTCCTGGCGCGAAAAGGT |
| 35 | GGCTGTCCTGGCGCGAAAAGGTG |
| 36 | GCTGTCCTGGCGCGAAAAGGTGG |
| 37 | CTGTCCTGGCGCGAAAAGGTGGA |
| 38 | TGTCCTGGCGCGAAAAGGTGGAC |
| 39 | GTCCTGGCGCGAAAAGGTGGACA |
| 40 | TCCTGGCGCGAAAAGGTGGACAA |
| 41 | CCTGGCGCGAAAAGGTGGACAAG |
| 42 | CTGGCGCGAAAAGGTGGACAAGT |
| 43 | TGGCGCGAAAAGGTGGACAAGTC |
| 44 | GGCGCGAAAAGGTGGACAAGTCC |
| 45 | GCGCGAAAAGGTGGACAAGTCCT |
| 46 | CGCGAAAAGGTGGACAAGTCCTA |
| 47 | GCGAAAAGGTGGACAAGTCCTAT |
| 48 | CGAAAAGGTGGACAAGTCCTATT |

| ID | SEQUENCE |
|---|---|
| 49 | GAAAAGGTGGACAAGTCCTATTT |
| 50 | AAAAGGTGGACAAGTCCTATTTT |
| 51 | AAAGGTGGACAAGTCCTATTTTC |
| 52 | AAGGTGGACAAGTCCTATTTTCA |
| 53 | AGGTGGACAAGTCCTATTTTCAA |
| 54 | GGTGGACAAGTCCTATTTTCAAG |
| 55 | GTGGACAAGTCCTATTTTCAAGA |
| 56 | TGGACAAGTCCTATTTTCAAGAG |
| 57 | GGACAAGTCCTATTTTCAAGAGA |
| 58 | GACAAGTCCTATTTTCAAGAGAA |
| 59 | ATGACTTTTAACAGTTTTGAAGG |
| 60 | TGACTTTTAACAGTTTTGAAGGA |
| 61 | GACTTTTAACAGTTTTGAAGGAT |
| 62 | ACTTTTAACAGTTTTGAAGGATC |
| 63 | CTTTTAACAGTTTTGAAGGATCT |
| 64 | TTTTAACAGTTTTGAAGGATCTA |
| 65 | TTTAACAGTTTTGAAGGATCTAA |
| 66 | TTAACAGTTTTGAAGGATCTAAA |
| 67 | TAACAGTTTTGAAGGATCTAAAA |
| 68 | AACAGTTTTGAAGGATCTAAAAC |
| 69 | ACAGTTTTGAAGGATCTAAAACT |
| 70 | CAGTTTTGAAGGATCTAAAACTT |
| 71 | AGTTTTGAAGGATCTAAAACTTG |
| 72 | GTTTTGAAGGATCTAAAACTTGT |
| 73 | TTTTGAAGGATCTAAAACTTGTG |
| 74 | TTTGAAGGATCTAAAACTTGTGT |
| 75 | TTGAAGGATCTAAAACTTGTGTA |
| 76 | TGAAGGATCTAAAACTTGTGTAC |
| 77 | GAAGGATCTAAAACTTGTGTACC |
| 78 | AAGGATCTAAAACTTGTGTACCT |
| 79 | AGGATCTAAAACTTGTGTACCTG |
| 80 | GGATCTAAAACTTGTGTACCTGC |
| 81 | GATCTAAAACTTGTGTACCTGCA |
| 82 | ATCTAAAACTTGTGTACCTGCAG |
| 83 | TCTAAAACTTGTGTACCTGCAGA |
| 84 | CTAAAACTTGTGTACCTGCAGAC |
| 85 | TAAAACTTGTGTACCTGCAGACA |
| 86 | AAAACTTGTGTACCTGCAGACAT |
| 87 | AAACTTGTGTACCTGCAGACATC |
| 88 | AACTTGTGTACCTGCAGACATCA |
| 89 | ACTTGTGTACCTGCAGACATCAA |
| 90 | CTTGTGTACCTGCAGACATCAAT |
| 91 | TTGTGTACCTGCAGACATCAATA |
| 92 | TGTGTACCTGCAGACATCAATAA |
| 93 | GTGTACCTGCAGACATCAATAAG |
| 94 | TGTACCTGCAGACATCAATAAGG |
| 95 | GTACCTGCAGACATCAATAAGGA |
| 96 | TACCTGCAGACATCAATAAGGAA |

| ID | SEQUENCE |
|---|---|
| 97 | ACCTGCAGACATCAATAAGGAAG |
| 98 | CCTGCAGACATCAATAAGGAAGA |
| 99 | CTGCAGACATCAATAAGGAAGAA |
| 100 | TGCAGACATCAATAAGGAAGAAG |
| 101 | GCAGACATCAATAAGGAAGAAGA |
| 102 | CAGACATCAATAAGGAAGAAGAA |
| 103 | AGACATCAATAAGGAAGAAGAAT |
| 104 | GACATCAATAAGGAAGAAGAATT |
| 105 | ACATCAATAAGGAAGAAGAATTT |
| 106 | CATCAATAAGGAAGAAGAATTTG |
| 107 | ATCAATAAGGAAGAAGAATTTGT |
| 108 | TCAATAAGGAAGAAGAATTTGTA |
| 109 | CAATAAGGAAGAAGAATTTGTAG |
| 110 | AATAAGGAAGAAGAATTTGTAGA |
| 111 | ATAAGGAAGAAGAATTTGTAGAA |
| 112 | TAAGGAAGAAGAATTTGTAGAAG |
| 113 | AAGGAAGAAGAATTTGTAGAAGA |
| 114 | AGGAAGAAGAATTTGTAGAAGAG |
| 115 | GGAAGAAGAATTTGTAGAAGAGT |
| 116 | GAAGAAGAATTTGTAGAAGAGTT |
| 117 | AAGAAGAATTTGTAGAAGAGTTT |
| 118 | AGAAGAATTTGTAGAAGAGTTTA |
| 119 | GAAGAATTTGTAGAAGAGTTTAA |
| 120 | AAGAATTTGTAGAAGAGTTTAAT |
| 121 | AGAATTTGTAGAAGAGTTTAATA |
| 122 | GAATTTGTAGAAGAGTTTAATAG |
| 123 | AATTTGTAGAAGAGTTTAATAGA |
| 124 | ATTTGTAGAAGAGTTTAATAGAT |
| 125 | TTTGTAGAAGAGTTTAATAGATT |
| 126 | TTGTAGAAGAGTTTAATAGATTA |
| 127 | TGTAGAAGAGTTTAATAGATTAA |
| 128 | GTAGAAGAGTTTAATAGATTAAA |
| 129 | TAGAAGAGTTTAATAGATTAAAA |
| 130 | AGAAGAGTTTAATAGATTAAAAA |
| 131 | GAAGAGTTTAATAGATTAAAAAC |
| 132 | AAGAGTTTAATAGATTAAAAACT |
| 133 | AGAGTTTAATAGATTAAAAACTT |
| 134 | GAGTTTAATAGATTAAAAACTTT |
| 135 | AGTTTAATAGATTAAAAACTTTT |
| 136 | GTTTAATAGATTAAAAACTTTTG |
| 137 | TTTAATAGATTAAAAACTTTTGC |
| 138 | TTAATAGATTAAAAACTTTTGCT |
| 139 | TAATAGATTAAAAACTTTTGCTA |
| 140 | AATAGATTAAAAACTTTTGCTAA |
| 141 | ATAGATTAAAAACTTTTGCTAAT |
| 142 | TAGATTAAAAACTTTTGCTAATT |
| 143 | AGATTAAAAACTTTTGCTAATTT |
| 144 | GATTAAAAACTTTTGCTAATTTT |

| ID | SEQUENCE |
|---|---|
| 145 | ATTAAAAACTTTTGCTAATTTTC |
| 146 | TTAAAAACTTTTGCTAATTTTCC |
| 147 | TAAAAACTTTTGCTAATTTTCCA |
| 148 | AAAAACTTTTGCTAATTTTCCAA |
| 149 | AAAACTTTTGCTAATTTTCCAAG |
| 150 | AAACTTTTGCTAATTTTCCAAGT |
| 151 | AACTTTTGCTAATTTTCCAAGTG |
| 152 | ACTTTTGCTAATTTTCCAAGTGG |
| 153 | CTTTTGCTAATTTTCCAAGTGGT |
| 154 | TTTTGCTAATTTTCCAAGTGGTA |
| 155 | TTTGCTAATTTTCCAAGTGGTAG |
| 156 | TTGCTAATTTTCCAAGTGGTAGT |
| 157 | TGCTAATTTTCCAAGTGGTAGTC |
| 158 | GCTAATTTTCCAAGTGGTAGTCC |
| 159 | CTAATTTTCCAAGTGGTAGTCCT |
| 160 | TAATTTTCCAAGTGGTAGTCCTG |
| 161 | AATTTTCCAAGTGGTAGTCCTGT |
| 162 | ATTTTCCAAGTGGTAGTCCTGTT |
| 163 | TTTTCCAAGTGGTAGTCCTGTTT |
| 164 | TTTCCAAGTGGTAGTCCTGTTTC |
| 165 | TTCCAAGTGGTAGTCCTGTTTCA |
| 166 | TCCAAGTGGTAGTCCTGTTTCAG |
| 167 | CCAAGTGGTAGTCCTGTTTCAGC |
| 168 | CAAGTGGTAGTCCTGTTTCAGCA |
| 169 | AAGTGGTAGTCCTGTTTCAGCAT |
| 170 | AGTGGTAGTCCTGTTTCAGCATC |
| 171 | GTGGTAGTCCTGTTTCAGCATCA |
| 172 | TGGTAGTCCTGTTTCAGCATCAA |
| 173 | GGTAGTCCTGTTTCAGCATCAAC |
| 174 | GTAGTCCTGTTTCAGCATCAACA |
| 175 | TAGTCCTGTTTCAGCATCAACAC |
| 176 | AGTCCTGTTTCAGCATCAACACT |
| 177 | GTCCTGTTTCAGCATCAACACTG |
| 178 | TCCTGTTTCAGCATCAACACTGG |
| 179 | CCTGTTTCAGCATCAACACTGGC |
| 180 | CTGTTTCAGCATCAACACTGGCA |
| 181 | TGTTTCAGCATCAACACTGGCAC |
| 182 | GTTTCAGCATCAACACTGGCACG |
| 183 | TTTCAGCATCAACACTGGCACGA |
| 184 | TTCAGCATCAACACTGGCACGAG |
| 185 | TCAGCATCAACACTGGCACGAGC |
| 186 | CAGCATCAACACTGGCACGAGCA |
| 187 | AGCATCAACACTGGCACGAGCAG |
| 188 | GCATCAACACTGGCACGAGCAGG |
| 189 | CATCAACACTGGCACGAGCAGGG |
| 190 | ATCAACACTGGCACGAGCAGGGT |
| 191 | TCAACACTGGCACGAGCAGGGTT |
| 192 | CAACACTGGCACGAGCAGGGTTT |

| ID | SEQUENCE |
|---|---|
| 193 | AACACTGGCACGAGCAGGGTTTC |
| 194 | ACACTGGCACGAGCAGGGTTTCT |
| 195 | CACTGGCACGAGCAGGGTTTCTT |
| 196 | ACTGGCACGAGCAGGGTTTCTTT |
| 197 | CTGGCACGAGCAGGGTTTCTTTA |
| 198 | TGGCACGAGCAGGGTTTCTTTAT |
| 199 | GGCACGAGCAGGGTTTCTTTATA |
| 200 | GCACGAGCAGGGTTTCTTTATAC |
| 201 | CACGAGCAGGGTTTCTTTATACT |
| 202 | ACGAGCAGGGTTTCTTTATACTG |
| 203 | CGAGCAGGGTTTCTTTATACTGG |
| 204 | GAGCAGGGTTTCTTTATACTGGT |
| 205 | AGCAGGGTTTCTTTATACTGGTG |
| 206 | GCAGGGTTTCTTTATACTGGTGA |
| 207 | CAGGGTTTCTTTATACTGGTGAA |
| 208 | AGGGTTTCTTTATACTGGTGAAG |
| 209 | GGGTTTCTTTATACTGGTGAAGG |
| 210 | GGTTTCTTTATACTGGTGAAGGA |
| 211 | GTTTCTTTATACTGGTGAAGGAG |
| 212 | TTTCTTTATACTGGTGAAGGAGA |
| 213 | TTCTTTATACTGGTGAAGGAGAT |
| 214 | TCTTTATACTGGTGAAGGAGATA |
| 215 | CTTTATACTGGTGAAGGAGATAC |
| 216 | TTTATACTGGTGAAGGAGATACC |
| 217 | TTATACTGGTGAAGGAGATACCG |
| 218 | TATACTGGTGAAGGAGATACCGT |
| 219 | ATACTGGTGAAGGAGATACCGTG |
| 220 | TACTGGTGAAGGAGATACCGTGC |
| 221 | ACTGGTGAAGGAGATACCGTGCG |
| 222 | CTGGTGAAGGAGATACCGTGCGG |
| 223 | TGGTGAAGGAGATACCGTGCGGT |
| 224 | GGTGAAGGAGATACCGTGCGGTG |
| 225 | GTGAAGGAGATACCGTGCGGTGC |
| 226 | TGAAGGAGATACCGTGCGGTGCT |
| 227 | GAAGGAGATACCGTGCGGTGCTT |
| 228 | AAGGAGATACCGTGCGGTGCTTT |
| 229 | AGGAGATACCGTGCGGTGCTTTA |
| 230 | GGAGATACCGTGCGGTGCTTTAG |
| 231 | GAGATACCGTGCGGTGCTTTAGT |
| 232 | AGATACCGTGCGGTGCTTTAGTT |
| 233 | GATACCGTGCGGTGCTTTAGTTG |
| 234 | ATACCGTGCGGTGCTTTAGTTGT |
| 235 | TACCGTGCGGTGCTTTAGTTGTC |
| 236 | ACCGTGCGGTGCTTTAGTTGTCA |
| 237 | CCGTGCGGTGCTTTAGTTGTCAT |
| 238 | CGTGCGGTGCTTTAGTTGTCATG |
| 239 | GTGCGGTGCTTTAGTTGTCATGC |
| 240 | TGCGGTGCTTTAGTTGTCATGCA |

| ID | SEQUENCE |
|---|---|
| 241 | GCGGTGCTTTAGTTGTCATGCAG |
| 242 | CGGTGCTTTAGTTGTCATGCAGC |
| 243 | GGTGCTTTAGTTGTCATGCAGCT |
| 244 | GTGCTTTAGTTGTCATGCAGCTG |
| 245 | TGCTTTAGTTGTCATGCAGCTGT |
| 246 | GCTTTAGTTGTCATGCAGCTGTA |
| 247 | CTTTAGTTGTCATGCAGCTGTAG |
| 248 | TTTAGTTGTCATGCAGCTGTAGA |
| 249 | TTAGTTGTCATGCAGCTGTAGAT |
| 250 | TAGTTGTCATGCAGCTGTAGATA |
| 251 | AGTTGTCATGCAGCTGTAGATAG |
| 252 | GTTGTCATGCAGCTGTAGATAGA |
| 253 | TTGTCATGCAGCTGTAGATAGAT |
| 254 | TGTCATGCAGCTGTAGATAGATG |
| 255 | GTCATGCAGCTGTAGATAGATGG |
| 256 | TCATGCAGCTGTAGATAGATGGC |
| 257 | CATGCAGCTGTAGATAGATGGCA |
| 258 | ATGCAGCTGTAGATAGATGGCAA |
| 259 | TGCAGCTGTAGATAGATGGCAAT |
| 260 | GCAGCTGTAGATAGATGGCAATA |
| 261 | CAGCTGTAGATAGATGGCAATAT |
| 262 | AGCTGTAGATAGATGGCAATATG |
| 263 | GCTGTAGATAGATGGCAATATGG |
| 264 | CTGTAGATAGATGGCAATATGGA |
| 265 | TGTAGATAGATGGCAATATGGAG |
| 266 | GTAGATAGATGGCAATATGGAGA |
| 267 | TAGATAGATGGCAATATGGAGAC |
| 268 | AGATAGATGGCAATATGGAGACT |
| 269 | GATAGATGGCAATATGGAGACTC |
| 270 | ATAGATGGCAATATGGAGACTCA |
| 271 | TAGATGGCAATATGGAGACTCAG |
| 272 | AGATGGCAATATGGAGACTCAGC |
| 273 | GATGGCAATATGGAGACTCAGCA |
| 274 | ATGGCAATATGGAGACTCAGCAG |
| 275 | TGGCAATATGGAGACTCAGCAGT |
| 276 | GGCAATATGGAGACTCAGCAGTT |
| 277 | GCAATATGGAGACTCAGCAGTTG |
| 278 | CAATATGGAGACTCAGCAGTTGG |
| 279 | AATATGGAGACTCAGCAGTTGGA |
| 280 | ATATGGAGACTCAGCAGTTGGAA |
| 281 | TATGGAGACTCAGCAGTTGGAAG |
| 282 | ATGGAGACTCAGCAGTTGGAAGA |
| 283 | TGGAGACTCAGCAGTTGGAAGAC |
| 284 | GGAGACTCAGCAGTTGGAAGACA |
| 285 | GAGACTCAGCAGTTGGAAGACAC |
| 286 | AGACTCAGCAGTTGGAAGACACA |
| 287 | GACTCAGCAGTTGGAAGACACAG |
| 288 | ACTCAGCAGTTGGAAGACACAGG |

| ID | SEQUENCE |
|---|---|
| 289 | CTCAGCAGTTGGAAGACACAGGA |
| 290 | TCAGCAGTTGGAAGACACAGGAA |
| 291 | CAGCAGTTGGAAGACACAGGAAA |
| 292 | AGCAGTTGGAAGACACAGGAAAG |
| 293 | GCAGTTGGAAGACACAGGAAAGT |
| 294 | CAGTTGGAAGACACAGGAAAGTA |
| 295 | AGTTGGAAGACACAGGAAAGTAT |
| 296 | GTTGGAAGACACAGGAAAGTATC |
| 297 | TTGGAAGACACAGGAAAGTATCC |
| 298 | TGGAAGACACAGGAAAGTATCCC |
| 299 | GGAAGACACAGGAAAGTATCCCC |
| 300 | GAAGACACAGGAAAGTATCCCCA |
| 301 | AAGACACAGGAAAGTATCCCCAA |
| 302 | AGACACAGGAAAGTATCCCCAAA |
| 303 | GACACAGGAAAGTATCCCCAAAT |
| 304 | ACACAGGAAAGTATCCCCAAATT |
| 305 | CACAGGAAAGTATCCCCAAATTG |
| 306 | ACAGGAAAGTATCCCCAAATTGC |
| 307 | CAGGAAAGTATCCCCAAATTGCA |
| 308 | AGGAAAGTATCCCCAAATTGCAG |
| 309 | GGAAAGTATCCCCAAATTGCAGA |
| 310 | GAAAGTATCCCCAAATTGCAGAT |
| 311 | AAAGTATCCCCAAATTGCAGATT |
| 312 | AAGTATCCCCAAATTGCAGATTT |
| 313 | AGTATCCCCAAATTGCAGATTTA |
| 314 | GTATCCCCAAATTGCAGATTTAT |
| 315 | TATCCCCAAATTGCAGATTTATC |
| 316 | ATCCCCAAATTGCAGATTTATCA |
| 317 | TCCCCAAATTGCAGATTTATCAA |
| 318 | CCCCAAATTGCAGATTTATCAAC |
| 319 | CCCAAATTGCAGATTTATCAACG |
| 320 | CCAAATTGCAGATTTATCAACGG |
| 321 | CAAATTGCAGATTTATCAACGGC |
| 322 | AAATTGCAGATTTATCAACGGCT |
| 323 | AATTGCAGATTTATCAACGGCTT |
| 324 | ATTGCAGATTTATCAACGGCTTT |
| 325 | TTGCAGATTTATCAACGGCTTTT |
| 326 | TGCAGATTTATCAACGGCTTTTA |
| 327 | GCAGATTTATCAACGGCTTTTAT |
| 328 | CAGATTTATCAACGGCTTTTATC |
| 329 | AGATTTATCAACGGCTTTTATCT |
| 330 | GATTTATCAACGGCTTTTATCTT |
| 331 | ATTTATCAACGGCTTTTATCTTG |
| 332 | TTTATCAACGGCTTTTATCTTGA |
| 333 | TTATCAACGGCTTTTATCTTGAA |
| 334 | TATCAACGGCTTTTATCTTGAAA |
| 335 | ATCAACGGCTTTTATCTTGAAAA |
| 336 | TCAACGGCTTTTATCTTGAAAAT |

| ID | SEQUENCE |
|---|---|
| 337 | CAACGGCTTTTATCTTGAAAATA |
| 338 | AACGGCTTTTATCTTGAAAATAG |
| 339 | ACGGCTTTTATCTTGAAAATAGT |
| 340 | CGGCTTTTATCTTGAAAATAGTG |
| 341 | GGCTTTTATCTTGAAAATAGTGC |
| 342 | GCTTTTATCTTGAAAATAGTGCC |
| 343 | CTTTTATCTTGAAAATAGTGCCA |
| 344 | TTTTATCTTGAAAATAGTGCCAC |
| 345 | TTTATCTTGAAAATAGTGCCACG |
| 346 | TTATCTTGAAAATAGTGCCACGC |
| 347 | TATCTTGAAAATAGTGCCACGCA |
| 348 | ATCTTGAAAATAGTGCCACGCAG |
| 349 | TCTTGAAAATAGTGCCACGCAGT |
| 350 | CTTGAAAATAGTGCCACGCAGTC |
| 351 | TTGAAAATAGTGCCACGCAGTCT |
| 352 | TGAAAATAGTGCCACGCAGTCTA |
| 353 | GAAAATAGTGCCACGCAGTCTAC |
| 354 | AAAATAGTGCCACGCAGTCTACA |
| 355 | AAATAGTGCCACGCAGTCTACAA |
| 356 | AATAGTGCCACGCAGTCTACAAA |
| 357 | ATAGTGCCACGCAGTCTACAAAT |
| 358 | TAGTGCCACGCAGTCTACAAATT |
| 359 | AGTGCCACGCAGTCTACAAATTC |
| 360 | GTGCCACGCAGTCTACAAATTCT |
| 361 | TGCCACGCAGTCTACAAATTCTG |
| 362 | GCCACGCAGTCTACAAATTCTGG |
| 363 | CCACGCAGTCTACAAATTCTGGT |
| 364 | CACGCAGTCTACAAATTCTGGTA |
| 365 | ACGCAGTCTACAAATTCTGGTAT |
| 366 | CGCAGTCTACAAATTCTGGTATC |
| 367 | GCAGTCTACAAATTCTGGTATCC |
| 368 | CAGTCTACAAATTCTGGTATCCA |
| 369 | AGTCTACAAATTCTGGTATCCAG |
| 370 | GTCTACAAATTCTGGTATCCAGA |
| 371 | TCTACAAATTCTGGTATCCAGAA |
| 372 | CTACAAATTCTGGTATCCAGAAT |
| 373 | TACAAATTCTGGTATCCAGAATG |
| 374 | ACAAATTCTGGTATCCAGAATGG |
| 375 | CAAATTCTGGTATCCAGAATGGT |
| 376 | AAATTCTGGTATCCAGAATGGTC |
| 377 | AATTCTGGTATCCAGAATGGTCA |
| 378 | ATTCTGGTATCCAGAATGGTCAG |
| 379 | TTCTGGTATCCAGAATGGTCAGT |
| 380 | TCTGGTATCCAGAATGGTCAGTA |
| 381 | CTGGTATCCAGAATGGTCAGTAC |
| 382 | TGGTATCCAGAATGGTCAGTACA |
| 383 | GGTATCCAGAATGGTCAGTACAA |
| 384 | GTATCCAGAATGGTCAGTACAAA |

| ID | SEQUENCE |
|---|---|
| 385 | TATCCAGAATGGTCAGTACAAAG |
| 386 | ATCCAGAATGGTCAGTACAAAGT |
| 387 | TCCAGAATGGTCAGTACAAAGTT |
| 388 | CCAGAATGGTCAGTACAAAGTTG |
| 389 | CAGAATGGTCAGTACAAAGTTGA |
| 390 | AGAATGGTCAGTACAAAGTTGAA |
| 391 | GAATGGTCAGTACAAAGTTGAAA |
| 392 | AATGGTCAGTACAAAGTTGAAAA |
| 393 | ATGGTCAGTACAAAGTTGAAAAC |
| 394 | TGGTCAGTACAAAGTTGAAAACT |
| 395 | GGTCAGTACAAAGTTGAAAACTA |
| 396 | GTCAGTACAAAGTTGAAAACTAT |
| 397 | TCAGTACAAAGTTGAAAACTATC |
| 398 | CAGTACAAAGTTGAAAACTATCT |
| 399 | AGTACAAAGTTGAAAACTATCTG |
| 400 | GTACAAAGTTGAAAACTATCTGG |
| 401 | TACAAAGTTGAAAACTATCTGGG |
| 402 | ACAAAGTTGAAAACTATCTGGGA |
| 403 | CAAAGTTGAAAACTATCTGGGAA |
| 404 | AAAGTTGAAAACTATCTGGGAAG |
| 405 | AAGTTGAAAACTATCTGGGAAGC |
| 406 | AGTTGAAAACTATCTGGGAAGCA |
| 407 | GTTGAAAACTATCTGGGAAGCAG |
| 408 | TTGAAAACTATCTGGGAAGCAGA |
| 409 | TGAAAACTATCTGGGAAGCAGAG |
| 410 | GAAAACTATCTGGGAAGCAGAGA |
| 411 | AAAACTATCTGGGAAGCAGAGAT |
| 412 | AAACTATCTGGGAAGCAGAGATC |
| 413 | AACTATCTGGGAAGCAGAGATCA |
| 414 | ACTATCTGGGAAGCAGAGATCAT |
| 415 | CTATCTGGGAAGCAGAGATCATT |
| 416 | TATCTGGGAAGCAGAGATCATTT |
| 417 | ATCTGGGAAGCAGAGATCATTTT |
| 418 | TCTGGGAAGCAGAGATCATTTTG |
| 419 | CTGGGAAGCAGAGATCATTTTGC |
| 420 | TGGGAAGCAGAGATCATTTTGCC |
| 421 | GGGAAGCAGAGATCATTTTGCCT |
| 422 | GGAAGCAGAGATCATTTTGCCTT |
| 423 | GAAGCAGAGATCATTTTGCCTTA |
| 424 | AAGCAGAGATCATTTTGCCTTAG |
| 425 | AGCAGAGATCATTTTGCCTTAGA |
| 426 | GCAGAGATCATTTTGCCTTAGAC |
| 427 | CAGAGATCATTTTGCCTTAGACA |
| 428 | AGAGATCATTTTGCCTTAGACAG |
| 429 | GAGATCATTTTGCCTTAGACAGG |
| 430 | AGATCATTTTGCCTTAGACAGGC |
| 431 | GATCATTTTGCCTTAGACAGGCC |
| 432 | ATCATTTTGCCTTAGACAGGCCA |

| ID | SEQUENCE |
|---|---|
| 433 | TCATTTTGCCTTAGACAGGCCAT |
| 434 | CATTTTGCCTTAGACAGGCCATC |
| 435 | ATTTTGCCTTAGACAGGCCATCT |
| 436 | TTTTGCCTTAGACAGGCCATCTG |
| 437 | TTTGCCTTAGACAGGCCATCTGA |
| 438 | TTGCCTTAGACAGGCCATCTGAG |
| 439 | TGCCTTAGACAGGCCATCTGAGA |
| 440 | GCCTTAGACAGGCCATCTGAGAC |
| 441 | CCTTAGACAGGCCATCTGAGACA |
| 442 | CTTAGACAGGCCATCTGAGACAC |
| 443 | TTAGACAGGCCATCTGAGACACA |
| 444 | TAGACAGGCCATCTGAGACACAT |
| 445 | AGACAGGCCATCTGAGACACATG |
| 446 | GACAGGCCATCTGAGACACATGC |
| 447 | ACAGGCCATCTGAGACACATGCA |
| 448 | CAGGCCATCTGAGACACATGCAG |
| 449 | AGGCCATCTGAGACACATGCAGA |
| 450 | GGCCATCTGAGACACATGCAGAC |
| 451 | GCCATCTGAGACACATGCAGACT |
| 452 | CCATCTGAGACACATGCAGACTA |
| 453 | CATCTGAGACACATGCAGACTAT |
| 454 | ATCTGAGACACATGCAGACTATC |
| 455 | TCTGAGACACATGCAGACTATCT |
| 456 | CTGAGACACATGCAGACTATCTT |
| 457 | TGAGACACATGCAGACTATCTTT |
| 458 | GAGACACATGCAGACTATCTTTT |
| 459 | AGACACATGCAGACTATCTTTTG |
| 460 | GACACATGCAGACTATCTTTTGA |
| 461 | ACACATGCAGACTATCTTTTGAG |
| 462 | CACATGCAGACTATCTTTTGAGA |
| 463 | ACATGCAGACTATCTTTTGAGAA |
| 464 | CATGCAGACTATCTTTTGAGAAC |
| 465 | ATGCAGACTATCTTTTGAGAACT |
| 466 | TGCAGACTATCTTTTGAGAACTG |
| 467 | GCAGACTATCTTTTGAGAACTGG |
| 468 | CAGACTATCTTTTGAGAACTGGG |
| 469 | AGACTATCTTTTGAGAACTGGGC |
| 470 | GACTATCTTTTGAGAACTGGGCA |
| 471 | ACTATCTTTTGAGAACTGGGCAG |
| 472 | CTATCTTTTGAGAACTGGGCAGG |
| 473 | TATCTTTTGAGAACTGGGCAGGT |
| 474 | ATCTTTTGAGAACTGGGCAGGTT |
| 475 | TCTTTTGAGAACTGGGCAGGTTG |
| 476 | CTTTTGAGAACTGGGCAGGTTGT |
| 477 | TTTTGAGAACTGGGCAGGTTGTA |
| 478 | TTTGAGAACTGGGCAGGTTGTAG |
| 479 | TTGAGAACTGGGCAGGTTGTAGA |
| 480 | TGAGAACTGGGCAGGTTGTAGAT |

| ID | SEQUENCE |
|---|---|
| 481 | GAGAACTGGGCAGGTTGTAGATA |
| 482 | AGAACTGGGCAGGTTGTAGATAT |
| 483 | GAACTGGGCAGGTTGTAGATATA |
| 484 | AACTGGGCAGGTTGTAGATATAT |
| 485 | ACTGGGCAGGTTGTAGATATATC |
| 486 | CTGGGCAGGTTGTAGATATATCA |
| 487 | TGGGCAGGTTGTAGATATATCAG |
| 488 | GGGCAGGTTGTAGATATATCAGA |
| 489 | GGCAGGTTGTAGATATATCAGAC |
| 490 | GCAGGTTGTAGATATATCAGACA |
| 491 | CAGGTTGTAGATATATCAGACAC |
| 492 | AGGTTGTAGATATATCAGACACC |
| 493 | GGTTGTAGATATATCAGACACCA |
| 494 | GTTGTAGATATATCAGACACCAT |
| 495 | TTGTAGATATATCAGACACCATA |
| 496 | TGTAGATATATCAGACACCATAT |
| 497 | GTAGATATATCAGACACCATATA |
| 498 | TAGATATATCAGACACCATATAC |
| 499 | AGATATATCAGACACCATATACC |
| 500 | GATATATCAGACACCATATACCC |
| 501 | ATATATCAGACACCATATACCCG |
| 502 | TATATCAGACACCATATACCCGA |
| 503 | ATATCAGACACCATATACCCGAG |
| 504 | TATCAGACACCATATACCCGAGG |
| 505 | ATCAGACACCATATACCCGAGGA |
| 506 | TCAGACACCATATACCCGAGGAA |
| 507 | CAGACACCATATACCCGAGGAAC |
| 508 | AGACACCATATACCCGAGGAACC |
| 509 | GACACCATATACCCGAGGAACCC |
| 510 | ACACCATATACCCGAGGAACCCT |
| 511 | CACCATATACCCGAGGAACCCTG |
| 512 | ACCATATACCCGAGGAACCCTGC |
| 513 | CCATATACCCGAGGAACCCTGCC |
| 514 | CATATACCCGAGGAACCCTGCCA |
| 515 | ATATACCCGAGGAACCCTGCCAT |
| 516 | TATACCCGAGGAACCCTGCCATG |
| 517 | ATACCCGAGGAACCCTGCCATGT |
| 518 | TACCCGAGGAACCCTGCCATGTA |
| 519 | ACCCGAGGAACCCTGCCATGTAT |
| 520 | CCCGAGGAACCCTGCCATGTATA |
| 521 | CCGAGGAACCCTGCCATGTATAG |
| 522 | CGAGGAACCCTGCCATGTATAGT |
| 523 | GAGGAACCCTGCCATGTATAGTG |
| 524 | AGGAACCCTGCCATGTATAGTGA |
| 525 | GGAACCCTGCCATGTATAGTGAA |
| 526 | GAACCCTGCCATGTATAGTGAAG |
| 527 | AACCCTGCCATGTATAGTGAAGA |
| 528 | ACCCTGCCATGTATAGTGAAGAA |

| ID | SEQUENCE |
|---|---|
| 529 | CCCTGCCATGTATAGTGAAGAAG |
| 530 | CCTGCCATGTATAGTGAAGAAGC |
| 531 | CTGCCATGTATAGTGAAGAAGCT |
| 532 | TGCCATGTATAGTGAAGAAGCTA |
| 533 | GCCATGTATAGTGAAGAAGCTAG |
| 534 | CCATGTATAGTGAAGAAGCTAGA |
| 535 | CATGTATAGTGAAGAAGCTAGAT |
| 536 | ATGTATAGTGAAGAAGCTAGATT |
| 537 | TGTATAGTGAAGAAGCTAGATTA |
| 538 | GTATAGTGAAGAAGCTAGATTAA |
| 539 | TATAGTGAAGAAGCTAGATTAAA |
| 540 | ATAGTGAAGAAGCTAGATTAAAG |
| 541 | TAGTGAAGAAGCTAGATTAAAGT |
| 542 | AGTGAAGAAGCTAGATTAAAGTC |
| 543 | GTGAAGAAGCTAGATTAAAGTCC |
| 544 | TGAAGAAGCTAGATTAAAGTCCT |
| 545 | GAAGAAGCTAGATTAAAGTCCTT |
| 546 | AAGAAGCTAGATTAAAGTCCTTT |
| 547 | AGAAGCTAGATTAAAGTCCTTTC |
| 548 | GAAGCTAGATTAAAGTCCTTTCA |
| 549 | AAGCTAGATTAAAGTCCTTTCAG |
| 550 | AGCTAGATTAAAGTCCTTTCAGA |
| 551 | GCTAGATTAAAGTCCTTTCAGAA |
| 552 | CTAGATTAAAGTCCTTTCAGAAC |
| 553 | TAGATTAAAGTCCTTTCAGAACT |
| 554 | AGATTAAAGTCCTTTCAGAACTG |
| 555 | GATTAAAGTCCTTTCAGAACTGG |
| 556 | ATTAAAGTCCTTTCAGAACTGGC |
| 557 | TTAAAGTCCTTTCAGAACTGGCC |
| 558 | TAAAGTCCTTTCAGAACTGGCCA |
| 559 | AAAGTCCTTTCAGAACTGGCCAG |
| 560 | AAGTCCTTTCAGAACTGGCCAGA |
| 561 | AGTCCTTTCAGAACTGGCCAGAC |
| 562 | GTCCTTTCAGAACTGGCCAGACT |
| 563 | TCCTTTCAGAACTGGCCAGACTA |
| 564 | CCTTTCAGAACTGGCCAGACTAT |
| 565 | CTTTCAGAACTGGCCAGACTATG |
| 566 | TTTCAGAACTGGCCAGACTATGC |
| 567 | TTCAGAACTGGCCAGACTATGCT |
| 568 | TCAGAACTGGCCAGACTATGCTC |
| 569 | CAGAACTGGCCAGACTATGCTCA |
| 570 | AGAACTGGCCAGACTATGCTCAC |
| 571 | GAACTGGCCAGACTATGCTCACC |
| 572 | AACTGGCCAGACTATGCTCACCT |
| 573 | ACTGGCCAGACTATGCTCACCTA |
| 574 | CTGGCCAGACTATGCTCACCTAA |
| 575 | TGGCCAGACTATGCTCACCTAAC |
| 576 | GGCCAGACTATGCTCACCTAACC |

| ID | SEQUENCE |
|---|---|
| 577 | GCCAGACTATGCTCACCTAACCC |
| 578 | CCAGACTATGCTCACCTAACCCC |
| 579 | CAGACTATGCTCACCTAACCCCA |
| 580 | AGACTATGCTCACCTAACCCCAA |
| 581 | GACTATGCTCACCTAACCCCAAG |
| 582 | ACTATGCTCACCTAACCCCAAGA |
| 583 | CTATGCTCACCTAACCCCAAGAG |
| 584 | TATGCTCACCTAACCCCAAGAGA |
| 585 | ATGCTCACCTAACCCCAAGAGAG |
| 586 | TGCTCACCTAACCCCAAGAGAGT |
| 587 | GCTCACCTAACCCCAAGAGAGTT |
| 588 | CTCACCTAACCCCAAGAGAGTTA |
| 589 | TCACCTAACCCCAAGAGAGTTAG |
| 590 | CACCTAACCCCAAGAGAGTTAGC |
| 591 | ACCTAACCCCAAGAGAGTTAGCA |
| 592 | CCTAACCCCAAGAGAGTTAGCAA |
| 593 | CTAACCCCAAGAGAGTTAGCAAG |
| 594 | TAACCCCAAGAGAGTTAGCAAGT |
| 595 | AACCCCAAGAGAGTTAGCAAGTG |
| 596 | ACCCCAAGAGAGTTAGCAAGTGC |
| 597 | CCCCAAGAGAGTTAGCAAGTGCT |
| 598 | CCCAAGAGAGTTAGCAAGTGCTG |
| 599 | CCAAGAGAGTTAGCAAGTGCTGG |
| 600 | CAAGAGAGTTAGCAAGTGCTGGA |
| 601 | AAGAGAGTTAGCAAGTGCTGGAC |
| 602 | AGAGAGTTAGCAAGTGCTGGACT |
| 603 | GAGAGTTAGCAAGTGCTGGACTC |
| 604 | AGAGTTAGCAAGTGCTGGACTCT |
| 605 | GAGTTAGCAAGTGCTGGACTCTA |
| 606 | AGTTAGCAAGTGCTGGACTCTAC |
| 607 | GTTAGCAAGTGCTGGACTCTACT |
| 608 | TTAGCAAGTGCTGGACTCTACTA |
| 609 | TAGCAAGTGCTGGACTCTACTAC |
| 610 | AGCAAGTGCTGGACTCTACTACA |
| 611 | GCAAGTGCTGGACTCTACTACAC |
| 612 | CAAGTGCTGGACTCTACTACACA |
| 613 | AAGTGCTGGACTCTACTACACAG |
| 614 | AGTGCTGGACTCTACTACACAGG |
| 615 | GTGCTGGACTCTACTACACAGGT |
| 616 | TGCTGGACTCTACTACACAGGTA |
| 617 | GCTGGACTCTACTACACAGGTAT |
| 618 | CTGGACTCTACTACACAGGTATT |
| 619 | TGGACTCTACTACACAGGTATTG |
| 620 | GGACTCTACTACACAGGTATTGG |
| 621 | GACTCTACTACACAGGTATTGGT |
| 622 | ACTCTACTACACAGGTATTGGTG |
| 623 | CTCTACTACACAGGTATTGGTGA |
| 624 | TCTACTACACAGGTATTGGTGAC |

| ID | SEQUENCE |
|---|---|
| 625 | CTACTACACAGGTATTGGTGACC |
| 626 | TACTACACAGGTATTGGTGACCA |
| 627 | ACTACACAGGTATTGGTGACCAA |
| 628 | CTACACAGGTATTGGTGACCAAG |
| 629 | TACACAGGTATTGGTGACCAAGT |
| 630 | ACACAGGTATTGGTGACCAAGTG |
| 631 | CACAGGTATTGGTGACCAAGTGC |
| 632 | ACAGGTATTGGTGACCAAGTGCA |
| 633 | CAGGTATTGGTGACCAAGTGCAG |
| 634 | AGGTATTGGTGACCAAGTGCAGT |
| 635 | GGTATTGGTGACCAAGTGCAGTG |
| 636 | GTATTGGTGACCAAGTGCAGTGC |
| 637 | TATTGGTGACCAAGTGCAGTGCT |
| 638 | ATTGGTGACCAAGTGCAGTGCTT |
| 639 | TTGGTGACCAAGTGCAGTGCTTT |
| 640 | TGGTGACCAAGTGCAGTGCTTTT |
| 641 | GGTGACCAAGTGCAGTGCTTTTG |
| 642 | GTGACCAAGTGCAGTGCTTTTGT |
| 643 | TGACCAAGTGCAGTGCTTTTGTT |
| 644 | GACCAAGTGCAGTGCTTTTGTTG |
| 645 | ACCAAGTGCAGTGCTTTTGTTGT |
| 646 | CCAAGTGCAGTGCTTTTGTTGTG |
| 647 | CAAGTGCAGTGCTTTTGTTGTGG |
| 648 | AAGTGCAGTGCTTTTGTTGTGGT |
| 649 | AGTGCAGTGCTTTTGTTGTGGTG |
| 650 | GTGCAGTGCTTTTGTTGTGGTGG |
| 651 | TGCAGTGCTTTTGTTGTGGTGGA |
| 652 | GCAGTGCTTTTGTTGTGGTGGAA |
| 653 | CAGTGCTTTTGTTGTGGTGGAAA |
| 654 | AGTGCTTTTGTTGTGGTGGAAAA |
| 655 | GTGCTTTTGTTGTGGTGGAAAAC |
| 656 | TGCTTTTGTTGTGGTGGAAAACT |
| 657 | GCTTTTGTTGTGGTGGAAAACTG |
| 658 | CTTTTGTTGTGGTGGAAAACTGA |
| 659 | TTTTGTTGTGGTGGAAAACTGAA |
| 660 | TTTGTTGTGGTGGAAAACTGAAA |
| 661 | TTGTTGTGGTGGAAAACTGAAAA |
| 662 | TGTTGTGGTGGAAAACTGAAAAA |
| 663 | GTTGTGGTGGAAAACTGAAAAAT |
| 664 | TTGTGGTGGAAAACTGAAAAATT |
| 665 | TGTGGTGGAAAACTGAAAAATTG |
| 666 | GTGGTGGAAAACTGAAAAATTGG |
| 667 | TGGTGGAAAACTGAAAAATTGGG |
| 668 | GGTGGAAAACTGAAAAATTGGGA |
| 669 | GTGGAAAACTGAAAAATTGGGAA |
| 670 | TGGAAAACTGAAAAATTGGGAAC |
| 671 | GGAAAACTGAAAAATTGGGAACC |
| 672 | GAAAACTGAAAAATTGGGAACCT |

| ID | SEQUENCE |
|---|---|
| 673 | AAAACTGAAAAATTGGGAACCTT |
| 674 | AAACTGAAAAATTGGGAACCTTG |
| 675 | AACTGAAAAATTGGGAACCTTGT |
| 676 | ACTGAAAAATTGGGAACCTTGTG |
| 677 | CTGAAAAATTGGGAACCTTGTGA |
| 678 | TGAAAAATTGGGAACCTTGTGAT |
| 679 | GAAAAATTGGGAACCTTGTGATC |
| 680 | AAAAATTGGGAACCTTGTGATCG |
| 681 | AAAATTGGGAACCTTGTGATCGT |
| 682 | AAATTGGGAACCTTGTGATCGTG |
| 683 | AATTGGGAACCTTGTGATCGTGC |
| 684 | ATTGGGAACCTTGTGATCGTGCC |
| 685 | TTGGGAACCTTGTGATCGTGCCT |
| 686 | TGGGAACCTTGTGATCGTGCCTG |
| 687 | GGGAACCTTGTGATCGTGCCTGG |
| 688 | GGAACCTTGTGATCGTGCCTGGT |
| 689 | GAACCTTGTGATCGTGCCTGGTC |
| 690 | AACCTTGTGATCGTGCCTGGTCA |
| 691 | ACCTTGTGATCGTGCCTGGTCAG |
| 692 | CCTTGTGATCGTGCCTGGTCAGA |
| 693 | CTTGTGATCGTGCCTGGTCAGAA |
| 694 | TTGTGATCGTGCCTGGTCAGAAC |
| 695 | TGTGATCGTGCCTGGTCAGAACA |
| 696 | GTGATCGTGCCTGGTCAGAACAC |
| 697 | TGATCGTGCCTGGTCAGAACACA |
| 698 | GATCGTGCCTGGTCAGAACACAG |
| 699 | ATCGTGCCTGGTCAGAACACAGG |
| 700 | TCGTGCCTGGTCAGAACACAGGC |
| 701 | CGTGCCTGGTCAGAACACAGGCG |
| 702 | GTGCCTGGTCAGAACACAGGCGA |
| 703 | TGCCTGGTCAGAACACAGGCGAC |
| 704 | GCCTGGTCAGAACACAGGCGACA |
| 705 | CCTGGTCAGAACACAGGCGACAC |
| 706 | CTGGTCAGAACACAGGCGACACT |
| 707 | TGGTCAGAACACAGGCGACACTT |
| 708 | GGTCAGAACACAGGCGACACTTT |
| 709 | GTCAGAACACAGGCGACACTTTC |
| 710 | TCAGAACACAGGCGACACTTTCC |
| 711 | CAGAACACAGGCGACACTTTCCT |
| 712 | AGAACACAGGCGACACTTTCCTA |
| 713 | GAACACAGGCGACACTTTCCTAA |
| 714 | AACACAGGCGACACTTTCCTAAT |
| 715 | ACACAGGCGACACTTTCCTAATT |
| 716 | CACAGGCGACACTTTCCTAATTG |
| 717 | ACAGGCGACACTTTCCTAATTGC |
| 718 | CAGGCGACACTTTCCTAATTGCT |
| 719 | AGGCGACACTTTCCTAATTGCTT |
| 720 | GGCGACACTTTCCTAATTGCTTC |

| ID | SEQUENCE |
|---|---|
| 721 | GCGACACTTTCCTAATTGCTTCT |
| 722 | CGACACTTTCCTAATTGCTTCTT |
| 723 | GACACTTTCCTAATTGCTTCTTT |
| 724 | ACACTTTCCTAATTGCTTCTTTG |
| 725 | CACTTTCCTAATTGCTTCTTTGT |
| 726 | ACTTTCCTAATTGCTTCTTTGTT |
| 727 | CTTTCCTAATTGCTTCTTTGTTT |
| 728 | TTTCCTAATTGCTTCTTTGTTTT |
| 729 | TTCCTAATTGCTTCTTTGTTTTG |
| 730 | TCCTAATTGCTTCTTTGTTTTGG |
| 731 | CCTAATTGCTTCTTTGTTTTGGG |
| 732 | CTAATTGCTTCTTTGTTTTGGGC |
| 733 | TAATTGCTTCTTTGTTTTGGGCC |
| 734 | AATTGCTTCTTTGTTTTGGGCCG |
| 735 | ATTGCTTCTTTGTTTTGGGCCGG |
| 736 | TTGCTTCTTTGTTTTGGGCCGGA |
| 737 | TGCTTCTTTGTTTTGGGCCGGAA |
| 738 | GCTTCTTTGTTTTGGGCCGGAAT |
| 739 | CTTCTTTGTTTTGGGCCGGAATC |
| 740 | TTCTTTGTTTTGGGCCGGAATCT |
| 741 | TCTTTGTTTTGGGCCGGAATCTT |
| 742 | CTTTGTTTTGGGCCGGAATCTTA |
| 743 | TTTGTTTTGGGCCGGAATCTTAA |
| 744 | TTGTTTTGGGCCGGAATCTTAAT |
| 745 | TGTTTTGGGCCGGAATCTTAATA |
| 746 | GTTTTGGGCCGGAATCTTAATAT |
| 747 | TTTTGGGCCGGAATCTTAATATT |
| 748 | TTTGGGCCGGAATCTTAATATTC |
| 749 | TTGGGCCGGAATCTTAATATTCG |
| 750 | TGGGCCGGAATCTTAATATTCGA |
| 751 | GGGCCGGAATCTTAATATTCGAA |
| 752 | GGCCGGAATCTTAATATTCGAAG |
| 753 | GCCGGAATCTTAATATTCGAAGT |
| 754 | CCGGAATCTTAATATTCGAAGTG |
| 755 | CGGAATCTTAATATTCGAAGTGA |
| 756 | GGAATCTTAATATTCGAAGTGAA |
| 757 | GAATCTTAATATTCGAAGTGAAT |
| 758 | AATCTTAATATTCGAAGTGAATC |
| 759 | ATCTTAATATTCGAAGTGAATCT |
| 760 | TCTTAATATTCGAAGTGAATCTG |
| 761 | CTTAATATTCGAAGTGAATCTGA |
| 762 | TTAATATTCGAAGTGAATCTGAT |
| 763 | TAATATTCGAAGTGAATCTGATG |
| 764 | AATATTCGAAGTGAATCTGATGC |
| 765 | ATATTCGAAGTGAATCTGATGCT |
| 766 | TATTCGAAGTGAATCTGATGCTG |
| 767 | ATTCGAAGTGAATCTGATGCTGT |
| 768 | TTCGAAGTGAATCTGATGCTGTG |

| ID | SEQUENCE |
|---|---|
| 769 | TCGAAGTGAATCTGATGCTGTGA |
| 770 | CGAAGTGAATCTGATGCTGTGAG |
| 771 | GAAGTGAATCTGATGCTGTGAGT |
| 772 | AAGTGAATCTGATGCTGTGAGTT |
| 773 | AGTGAATCTGATGCTGTGAGTTC |
| 774 | GTGAATCTGATGCTGTGAGTTCT |
| 775 | TGAATCTGATGCTGTGAGTTCTG |
| 776 | GAATCTGATGCTGTGAGTTCTGA |
| 777 | AATCTGATGCTGTGAGTTCTGAT |
| 778 | ATCTGATGCTGTGAGTTCTGATA |
| 779 | TCTGATGCTGTGAGTTCTGATAG |
| 780 | CTGATGCTGTGAGTTCTGATAGG |
| 781 | TGATGCTGTGAGTTCTGATAGGA |
| 782 | GATGCTGTGAGTTCTGATAGGAA |
| 783 | ATGCTGTGAGTTCTGATAGGAAT |
| 784 | TGCTGTGAGTTCTGATAGGAATT |
| 785 | GCTGTGAGTTCTGATAGGAATTT |
| 786 | CTGTGAGTTCTGATAGGAATTTC |
| 787 | TGTGAGTTCTGATAGGAATTTCC |
| 788 | GTGAGTTCTGATAGGAATTTCCC |
| 789 | TGAGTTCTGATAGGAATTTCCCA |
| 790 | GAGTTCTGATAGGAATTTCCCAA |
| 791 | AGTTCTGATAGGAATTTCCCAAA |
| 792 | GTTCTGATAGGAATTTCCCAAAT |
| 793 | TTCTGATAGGAATTTCCCAAATT |
| 794 | TCTGATAGGAATTTCCCAAATTC |
| 795 | CTGATAGGAATTTCCCAAATTCA |
| 796 | TGATAGGAATTTCCCAAATTCAA |
| 797 | GATAGGAATTTCCCAAATTCAAC |
| 798 | ATAGGAATTTCCCAAATTCAACA |
| 799 | TAGGAATTTCCCAAATTCAACAA |
| 800 | AGGAATTTCCCAAATTCAACAAA |
| 801 | GGAATTTCCCAAATTCAACAAAT |
| 802 | GAATTTCCCAAATTCAACAAATC |
| 803 | AATTTCCCAAATTCAACAAATCT |
| 804 | ATTTCCCAAATTCAACAAATCTT |
| 805 | TTTCCCAAATTCAACAAATCTTC |
| 806 | TTCCCAAATTCAACAAATCTTCC |
| 807 | TCCCAAATTCAACAAATCTTCCA |
| 808 | CCCAAATTCAACAAATCTTCCAA |
| 809 | CCAAATTCAACAAATCTTCCAAG |
| 810 | CAAATTCAACAAATCTTCCAAGA |
| 811 | AAATTCAACAAATCTTCCAAGAA |
| 812 | AATTCAACAAATCTTCCAAGAAA |
| 813 | ATTCAACAAATCTTCCAAGAAAT |
| 814 | TTCAACAAATCTTCCAAGAAATC |
| 815 | TCAACAAATCTTCCAAGAAATCC |
| 816 | CAACAAATCTTCCAAGAAATCCA |

| ID | SEQUENCE |
|---|---|
| 817 | AACAAATCTTCCAAGAAATCCAT |
| 818 | ACAAATCTTCCAAGAAATCCATC |
| 819 | CAAATCTTCCAAGAAATCCATCC |
| 820 | AAATCTTCCAAGAAATCCATCCA |
| 821 | AATCTTCCAAGAAATCCATCCAT |
| 822 | ATCTTCCAAGAAATCCATCCATG |
| 823 | TCTTCCAAGAAATCCATCCATGG |
| 824 | CTTCCAAGAAATCCATCCATGGC |
| 825 | TTCCAAGAAATCCATCCATGGCA |
| 826 | TCCAAGAAATCCATCCATGGCAG |
| 827 | CCAAGAAATCCATCCATGGCAGA |
| 828 | CAAGAAATCCATCCATGGCAGAT |
| 829 | AAGAAATCCATCCATGGCAGATT |
| 830 | AGAAATCCATCCATGGCAGATTA |
| 831 | GAAATCCATCCATGGCAGATTAT |
| 832 | AAATCCATCCATGGCAGATTATG |
| 833 | AATCCATCCATGGCAGATTATGA |
| 834 | ATCCATCCATGGCAGATTATGAA |
| 835 | TCCATCCATGGCAGATTATGAAG |
| 836 | CCATCCATGGCAGATTATGAAGC |
| 837 | CATCCATGGCAGATTATGAAGCA |
| 838 | ATCCATGGCAGATTATGAAGCAC |
| 839 | TCCATGGCAGATTATGAAGCACG |
| 840 | CCATGGCAGATTATGAAGCACGG |
| 841 | CATGGCAGATTATGAAGCACGGA |
| 842 | ATGGCAGATTATGAAGCACGGAT |
| 843 | TGGCAGATTATGAAGCACGGATC |
| 844 | GGCAGATTATGAAGCACGGATCT |
| 845 | GCAGATTATGAAGCACGGATCTT |
| 846 | CAGATTATGAAGCACGGATCTTT |
| 847 | AGATTATGAAGCACGGATCTTTA |
| 848 | GATTATGAAGCACGGATCTTTAC |
| 849 | ATTATGAAGCACGGATCTTTACT |
| 850 | TTATGAAGCACGGATCTTTACTT |
| 851 | TATGAAGCACGGATCTTTACTTT |
| 852 | ATGAAGCACGGATCTTTACTTTT |
| 853 | TGAAGCACGGATCTTTACTTTTG |
| 854 | GAAGCACGGATCTTTACTTTTGG |
| 855 | AAGCACGGATCTTTACTTTTGGG |
| 856 | AGCACGGATCTTTACTTTTGGGA |
| 857 | GCACGGATCTTTACTTTTGGGAC |
| 858 | CACGGATCTTTACTTTTGGGACA |
| 859 | ACGGATCTTTACTTTTGGGACAT |
| 860 | CGGATCTTTACTTTTGGGACATG |
| 861 | GGATCTTTACTTTTGGGACATGG |
| 862 | GATCTTTACTTTTGGGACATGGA |
| 863 | ATCTTTACTTTTGGGACATGGAT |
| 864 | TCTTTACTTTTGGGACATGGATA |

| ID | SEQUENCE |
|---|---|
| 865 | CTTTACTTTTGGGACATGGATAT |
| 866 | TTTACTTTTGGGACATGGATATA |
| 867 | TTACTTTTGGGACATGGATATAC |
| 868 | TACTTTTGGGACATGGATATACT |
| 869 | ACTTTTGGGACATGGATATACTC |
| 870 | CTTTTGGGACATGGATATACTCA |
| 871 | TTTTGGGACATGGATATACTCAG |
| 872 | TTTGGGACATGGATATACTCAGT |
| 873 | TTGGGACATGGATATACTCAGTT |
| 874 | TGGGACATGGATATACTCAGTTA |
| 875 | GGGACATGGATATACTCAGTTAA |
| 876 | GGACATGGATATACTCAGTTAAC |
| 877 | GACATGGATATACTCAGTTAACA |
| 878 | ACATGGATATACTCAGTTAACAA |
| 879 | CATGGATATACTCAGTTAACAAG |
| 880 | ATGGATATACTCAGTTAACAAGG |
| 881 | TGGATATACTCAGTTAACAAGGA |
| 882 | GGATATACTCAGTTAACAAGGAG |
| 883 | GATATACTCAGTTAACAAGGAGC |
| 884 | ATATACTCAGTTAACAAGGAGCA |
| 885 | TATACTCAGTTAACAAGGAGCAG |
| 886 | ATACTCAGTTAACAAGGAGCAGC |
| 887 | TACTCAGTTAACAAGGAGCAGCT |
| 888 | ACTCAGTTAACAAGGAGCAGCTT |
| 889 | CTCAGTTAACAAGGAGCAGCTTG |
| 890 | TCAGTTAACAAGGAGCAGCTTGC |
| 891 | CAGTTAACAAGGAGCAGCTTGCA |
| 892 | AGTTAACAAGGAGCAGCTTGCAA |
| 893 | GTTAACAAGGAGCAGCTTGCAAG |
| 894 | TTAACAAGGAGCAGCTTGCAAGA |
| 895 | TAACAAGGAGCAGCTTGCAAGAG |
| 896 | AACAAGGAGCAGCTTGCAAGAGC |
| 897 | ACAAGGAGCAGCTTGCAAGAGCT |
| 898 | CAAGGAGCAGCTTGCAAGAGCTG |
| 899 | AAGGAGCAGCTTGCAAGAGCTGG |
| 900 | AGGAGCAGCTTGCAAGAGCTGGA |
| 901 | GGAGCAGCTTGCAAGAGCTGGAT |
| 902 | GAGCAGCTTGCAAGAGCTGGATT |
| 903 | AGCAGCTTGCAAGAGCTGGATTT |
| 904 | GCAGCTTGCAAGAGCTGGATTTT |
| 905 | CAGCTTGCAAGAGCTGGATTTTA |
| 906 | AGCTTGCAAGAGCTGGATTTTAT |
| 907 | GCTTGCAAGAGCTGGATTTTATG |
| 908 | CTTGCAAGAGCTGGATTTTATGC |
| 909 | TTGCAAGAGCTGGATTTTATGCT |
| 910 | TGCAAGAGCTGGATTTTATGCTT |
| 911 | GCAAGAGCTGGATTTTATGCTTT |
| 912 | CAAGAGCTGGATTTTATGCTTTA |

| ID | SEQUENCE |
|---|---|
| 913 | AAGAGCTGGATTTTATGCTTTAG |
| 914 | AGAGCTGGATTTTATGCTTTAGG |
| 915 | GAGCTGGATTTTATGCTTTAGGT |
| 916 | AGCTGGATTTTATGCTTTAGGTG |
| 917 | GCTGGATTTTATGCTTTAGGTGA |
| 918 | CTGGATTTTATGCTTTAGGTGAA |
| 919 | TGGATTTTATGCTTTAGGTGAAG |
| 920 | GGATTTTATGCTTTAGGTGAAGG |
| 921 | GATTTTATGCTTTAGGTGAAGGT |
| 922 | ATTTTATGCTTTAGGTGAAGGTG |
| 923 | TTTTATGCTTTAGGTGAAGGTGA |
| 924 | TTTATGCTTTAGGTGAAGGTGAT |
| 925 | TTATGCTTTAGGTGAAGGTGATA |
| 926 | TATGCTTTAGGTGAAGGTGATAA |
| 927 | ATGCTTTAGGTGAAGGTGATAAA |
| 928 | TGCTTTAGGTGAAGGTGATAAAG |
| 929 | GCTTTAGGTGAAGGTGATAAAGT |
| 930 | CTTTAGGTGAAGGTGATAAAGTA |
| 931 | TTTAGGTGAAGGTGATAAAGTAA |
| 932 | TTAGGTGAAGGTGATAAAGTAAA |
| 933 | TAGGTGAAGGTGATAAAGTAAAG |
| 934 | AGGTGAAGGTGATAAAGTAAAGT |
| 935 | GGTGAAGGTGATAAAGTAAAGTG |
| 936 | GTGAAGGTGATAAAGTAAAGTGC |
| 937 | TGAAGGTGATAAAGTAAAGTGCT |
| 938 | GAAGGTGATAAAGTAAAGTGCTT |
| 939 | AAGGTGATAAAGTAAAGTGCTTT |
| 940 | AGGTGATAAAGTAAAGTGCTTTC |
| 941 | GGTGATAAAGTAAAGTGCTTTCA |
| 942 | GTGATAAAGTAAAGTGCTTTCAC |
| 943 | TGATAAAGTAAAGTGCTTTCACT |
| 944 | GATAAAGTAAAGTGCTTTCACTG |
| 945 | ATAAAGTAAAGTGCTTTCACTGT |
| 946 | TAAAGTAAAGTGCTTTCACTGTG |
| 947 | AAAGTAAAGTGCTTTCACTGTGG |
| 948 | AAGTAAAGTGCTTTCACTGTGGA |
| 949 | AGTAAAGTGCTTTCACTGTGGAG |
| 950 | GTAAAGTGCTTTCACTGTGGAGG |
| 951 | TAAAGTGCTTTCACTGTGGAGGA |
| 952 | AAAGTGCTTTCACTGTGGAGGAG |
| 953 | AAGTGCTTTCACTGTGGAGGAGG |
| 954 | AGTGCTTTCACTGTGGAGGAGGG |
| 955 | GTGCTTTCACTGTGGAGGAGGGC |
| 956 | TGCTTTCACTGTGGAGGAGGGCT |
| 957 | GCTTTCACTGTGGAGGAGGGCTA |
| 958 | CTTTCACTGTGGAGGAGGGCTAA |
| 959 | TTTCACTGTGGAGGAGGGCTAAC |
| 960 | TTCACTGTGGAGGAGGGCTAACT |

| ID | SEQUENCE |
|---|---|
| 961 | TCACTGTGGAGGAGGGCTAACTG |
| 962 | CACTGTGGAGGAGGGCTAACTGA |
| 963 | ACTGTGGAGGAGGGCTAACTGAT |
| 964 | CTGTGGAGGAGGGCTAACTGATT |
| 965 | TGTGGAGGAGGGCTAACTGATTG |
| 966 | GTGGAGGAGGGCTAACTGATTGG |
| 967 | TGGAGGAGGGCTAACTGATTGGA |
| 968 | GGAGGAGGGCTAACTGATTGGAA |
| 969 | GAGGAGGGCTAACTGATTGGAAG |
| 970 | AGGAGGGCTAACTGATTGGAAGC |
| 971 | GGAGGGCTAACTGATTGGAAGCC |
| 972 | GAGGGCTAACTGATTGGAAGCCC |
| 973 | AGGGCTAACTGATTGGAAGCCCA |
| 974 | GGGCTAACTGATTGGAAGCCCAG |
| 975 | GGCTAACTGATTGGAAGCCCAGT |
| 976 | GCTAACTGATTGGAAGCCCAGTG |
| 977 | CTAACTGATTGGAAGCCCAGTGA |
| 978 | TAACTGATTGGAAGCCCAGTGAA |
| 979 | AACTGATTGGAAGCCCAGTGAAG |
| 980 | ACTGATTGGAAGCCCAGTGAAGA |
| 981 | CTGATTGGAAGCCCAGTGAAGAC |
| 982 | TGATTGGAAGCCCAGTGAAGACC |
| 983 | GATTGGAAGCCCAGTGAAGACCC |
| 984 | ATTGGAAGCCCAGTGAAGACCCT |
| 985 | TTGGAAGCCCAGTGAAGACCCTT |
| 986 | TGGAAGCCCAGTGAAGACCCTTG |
| 987 | GGAAGCCCAGTGAAGACCCTTGG |
| 988 | GAAGCCCAGTGAAGACCCTTGGG |
| 989 | AAGCCCAGTGAAGACCCTTGGGA |
| 990 | AGCCCAGTGAAGACCCTTGGGAA |
| 991 | GCCCAGTGAAGACCCTTGGGAAC |
| 992 | CCCAGTGAAGACCCTTGGGAACA |
| 993 | CCAGTGAAGACCCTTGGGAACAA |
| 994 | CAGTGAAGACCCTTGGGAACAAC |
| 995 | AGTGAAGACCCTTGGGAACAACA |
| 996 | GTGAAGACCCTTGGGAACAACAT |
| 997 | TGAAGACCCTTGGGAACAACATG |
| 998 | GAAGACCCTTGGGAACAACATGC |
| 999 | AAGACCCTTGGGAACAACATGCT |
| 1000 | AGACCCTTGGGAACAACATGCTA |
| 1001 | GACCCTTGGGAACAACATGCTAA |
| 1002 | ACCCTTGGGAACAACATGCTAAA |
| 1003 | CCCTTGGGAACAACATGCTAAAT |
| 1004 | CCTTGGGAACAACATGCTAAATG |
| 1005 | CTTGGGAACAACATGCTAAATGG |
| 1006 | TTGGGAACAACATGCTAAATGGT |
| 1007 | TGGGAACAACATGCTAAATGGTA |
| 1008 | GGGAACAACATGCTAAATGGTAT |

| ID | SEQUENCE |
|---|---|
| 1009 | GGAACAACATGCTAAATGGTATC |
| 1010 | GAACAACATGCTAAATGGTATCC |
| 1011 | AACAACATGCTAAATGGTATCCA |
| 1012 | ACAACATGCTAAATGGTATCCAG |
| 1013 | CAACATGCTAAATGGTATCCAGG |
| 1014 | AACATGCTAAATGGTATCCAGGG |
| 1015 | ACATGCTAAATGGTATCCAGGGT |
| 1016 | CATGCTAAATGGTATCCAGGGTG |
| 1017 | ATGCTAAATGGTATCCAGGGTGC |
| 1018 | TGCTAAATGGTATCCAGGGTGCA |
| 1019 | GCTAAATGGTATCCAGGGTGCAA |
| 1020 | CTAAATGGTATCCAGGGTGCAAA |
| 1021 | TAAATGGTATCCAGGGTGCAAAT |
| 1022 | AAATGGTATCCAGGGTGCAAATA |
| 1023 | AATGGTATCCAGGGTGCAAATAT |
| 1024 | ATGGTATCCAGGGTGCAAATATC |
| 1025 | TGGTATCCAGGGTGCAAATATCT |
| 1026 | GGTATCCAGGGTGCAAATATCTG |
| 1027 | GTATCCAGGGTGCAAATATCTGT |
| 1028 | TATCCAGGGTGCAAATATCTGTT |
| 1029 | ATCCAGGGTGCAAATATCTGTTA |
| 1030 | TCCAGGGTGCAAATATCTGTTAG |
| 1031 | CCAGGGTGCAAATATCTGTTAGA |
| 1032 | CAGGGTGCAAATATCTGTTAGAA |
| 1033 | AGGGTGCAAATATCTGTTAGAAC |
| 1034 | GGGTGCAAATATCTGTTAGAACA |
| 1035 | GGTGCAAATATCTGTTAGAACAG |
| 1036 | GTGCAAATATCTGTTAGAACAGA |
| 1037 | TGCAAATATCTGTTAGAACAGAA |
| 1038 | GCAAATATCTGTTAGAACAGAAG |
| 1039 | CAAATATCTGTTAGAACAGAAGG |
| 1040 | AAATATCTGTTAGAACAGAAGGG |
| 1041 | AATATCTGTTAGAACAGAAGGGA |
| 1042 | ATATCTGTTAGAACAGAAGGGAC |
| 1043 | TATCTGTTAGAACAGAAGGGACA |
| 1044 | ATCTGTTAGAACAGAAGGGACAA |
| 1045 | TCTGTTAGAACAGAAGGGACAAG |
| 1046 | CTGTTAGAACAGAAGGGACAAGA |
| 1047 | TGTTAGAACAGAAGGGACAAGAA |
| 1048 | GTTAGAACAGAAGGGACAAGAAT |
| 1049 | TTAGAACAGAAGGGACAAGAATA |
| 1050 | TAGAACAGAAGGGACAAGAATAT |
| 1051 | AGAACAGAAGGGACAAGAATATA |
| 1052 | GAACAGAAGGGACAAGAATATAT |
| 1053 | AACAGAAGGGACAAGAATATATA |
| 1054 | ACAGAAGGGACAAGAATATATAA |
| 1055 | CAGAAGGGACAAGAATATATAAA |
| 1056 | AGAAGGGACAAGAATATATAAAC |

| ID | SEQUENCE |
|---|---|
| 1057 | GAAGGGACAAGAATATATAAACA |
| 1058 | AAGGGACAAGAATATATAAACAA |
| 1059 | AGGGACAAGAATATATAAACAAT |
| 1060 | GGGACAAGAATATATAAACAATA |
| 1061 | GGACAAGAATATATAAACAATAT |
| 1062 | GACAAGAATATATAAACAATATT |
| 1063 | ACAAGAATATATAAACAATATTC |
| 1064 | CAAGAATATATAAACAATATTCA |
| 1065 | AAGAATATATAAACAATATTCAT |
| 1066 | AGAATATATAAACAATATTCATT |
| 1067 | GAATATATAAACAATATTCATTT |
| 1068 | AATATATAAACAATATTCATTTA |
| 1069 | ATATATAAACAATATTCATTTAA |
| 1070 | TATATAAACAATATTCATTTAAC |
| 1071 | ATATAAACAATATTCATTTAACT |
| 1072 | TATAAACAATATTCATTTAACTC |
| 1073 | ATAAACAATATTCATTTAACTCA |
| 1074 | TAAACAATATTCATTTAACTCAT |
| 1075 | AAACAATATTCATTTAACTCATT |
| 1076 | AACAATATTCATTTAACTCATTC |
| 1077 | ACAATATTCATTTAACTCATTCA |
| 1078 | CAATATTCATTTAACTCATTCAC |
| 1079 | AATATTCATTTAACTCATTCACT |
| 1080 | ATATTCATTTAACTCATTCACTT |
| 1081 | TATTCATTTAACTCATTCACTTG |
| 1082 | ATTCATTTAACTCATTCACTTGA |
| 1083 | TTCATTTAACTCATTCACTTGAG |
| 1084 | TCATTTAACTCATTCACTTGAGG |
| 1085 | CATTTAACTCATTCACTTGAGGA |
| 1086 | ATTTAACTCATTCACTTGAGGAG |
| 1087 | TTTAACTCATTCACTTGAGGAGT |
| 1088 | TTAACTCATTCACTTGAGGAGTG |
| 1089 | TAACTCATTCACTTGAGGAGTGT |
| 1090 | AACTCATTCACTTGAGGAGTGTC |
| 1091 | ACTCATTCACTTGAGGAGTGTCT |
| 1092 | CTCATTCACTTGAGGAGTGTCTG |
| 1093 | TCATTCACTTGAGGAGTGTCTGG |
| 1094 | CATTCACTTGAGGAGTGTCTGGT |
| 1095 | ATTCACTTGAGGAGTGTCTGGTA |
| 1096 | TTCACTTGAGGAGTGTCTGGTAA |
| 1097 | TCACTTGAGGAGTGTCTGGTAAG |
| 1098 | CACTTGAGGAGTGTCTGGTAAGA |
| 1099 | ACTTGAGGAGTGTCTGGTAAGAA |
| 1100 | CTTGAGGAGTGTCTGGTAAGAAC |
| 1101 | TTGAGGAGTGTCTGGTAAGAACT |
| 1102 | TGAGGAGTGTCTGGTAAGAACTA |
| 1103 | GAGGAGTGTCTGGTAAGAACTAC |
| 1104 | AGGAGTGTCTGGTAAGAACTACT |

| ID | SEQUENCE |
|---|---|
| 1105 | GGAGTGTCTGGTAAGAACTACTG |
| 1106 | GAGTGTCTGGTAAGAACTACTGA |
| 1107 | AGTGTCTGGTAAGAACTACTGAG |
| 1108 | GTGTCTGGTAAGAACTACTGAGA |
| 1109 | TGTCTGGTAAGAACTACTGAGAA |
| 1110 | GTCTGGTAAGAACTACTGAGAAA |
| 1111 | TCTGGTAAGAACTACTGAGAAAA |
| 1112 | CTGGTAAGAACTACTGAGAAAAC |
| 1113 | TGGTAAGAACTACTGAGAAAACA |
| 1114 | GGTAAGAACTACTGAGAAAACAC |
| 1115 | GTAAGAACTACTGAGAAAACACC |
| 1116 | TAAGAACTACTGAGAAAACACCA |
| 1117 | AAGAACTACTGAGAAAACACCAT |
| 1118 | AGAACTACTGAGAAAACACCATC |
| 1119 | GAACTACTGAGAAAACACCATCA |
| 1120 | AACTACTGAGAAAACACCATCAC |
| 1121 | ACTACTGAGAAAACACCATCACT |
| 1122 | CTACTGAGAAAACACCATCACTA |
| 1123 | TACTGAGAAAACACCATCACTAA |
| 1124 | ACTGAGAAAACACCATCACTAAC |
| 1125 | CTGAGAAAACACCATCACTAACT |
| 1126 | TGAGAAAACACCATCACTAACTA |
| 1127 | GAGAAAACACCATCACTAACTAG |
| 1128 | AGAAAACACCATCACTAACTAGA |
| 1129 | GAAAACACCATCACTAACTAGAA |
| 1130 | AAAACACCATCACTAACTAGAAG |
| 1131 | AAACACCATCACTAACTAGAAGA |
| 1132 | AACACCATCACTAACTAGAAGAA |
| 1133 | ACACCATCACTAACTAGAAGAAT |
| 1134 | CACCATCACTAACTAGAAGAATT |
| 1135 | ACCATCACTAACTAGAAGAATTG |
| 1136 | CCATCACTAACTAGAAGAATTGA |
| 1137 | CATCACTAACTAGAAGAATTGAT |
| 1138 | ATCACTAACTAGAAGAATTGATG |
| 1139 | TCACTAACTAGAAGAATTGATGA |
| 1140 | CACTAACTAGAAGAATTGATGAT |
| 1141 | ACTAACTAGAAGAATTGATGATA |
| 1142 | CTAACTAGAAGAATTGATGATAC |
| 1143 | TAACTAGAAGAATTGATGATACC |
| 1144 | AACTAGAAGAATTGATGATACCA |
| 1145 | ACTAGAAGAATTGATGATACCAT |
| 1146 | CTAGAAGAATTGATGATACCATC |
| 1147 | TAGAAGAATTGATGATACCATCT |
| 1148 | AGAAGAATTGATGATACCATCTT |
| 1149 | GAAGAATTGATGATACCATCTTC |
| 1150 | AAGAATTGATGATACCATCTTCC |
| 1151 | AGAATTGATGATACCATCTTCCA |
| 1152 | GAATTGATGATACCATCTTCCAA |

| ID | SEQUENCE |
|---|---|
| 1153 | AATTGATGATACCATCTTCCAAA |
| 1154 | ATTGATGATACCATCTTCCAAAA |
| 1155 | TTGATGATACCATCTTCCAAAAT |
| 1156 | TGATGATACCATCTTCCAAAATC |
| 1157 | GATGATACCATCTTCCAAAATCC |
| 1158 | ATGATACCATCTTCCAAAATCCT |
| 1159 | TGATACCATCTTCCAAAATCCTA |
| 1160 | GATACCATCTTCCAAAATCCTAT |
| 1161 | ATACCATCTTCCAAAATCCTATG |
| 1162 | TACCATCTTCCAAAATCCTATGG |
| 1163 | ACCATCTTCCAAAATCCTATGGT |
| 1164 | CCATCTTCCAAAATCCTATGGTA |
| 1165 | CATCTTCCAAAATCCTATGGTAC |
| 1166 | ATCTTCCAAAATCCTATGGTACA |
| 1167 | TCTTCCAAAATCCTATGGTACAA |
| 1168 | CTTCCAAAATCCTATGGTACAAG |
| 1169 | TTCCAAAATCCTATGGTACAAGA |
| 1170 | TCCAAAATCCTATGGTACAAGAA |
| 1171 | CCAAAATCCTATGGTACAAGAAG |
| 1172 | CAAAATCCTATGGTACAAGAAGC |
| 1173 | AAAATCCTATGGTACAAGAAGCT |
| 1174 | AAATCCTATGGTACAAGAAGCTA |
| 1175 | AATCCTATGGTACAAGAAGCTAT |
| 1176 | ATCCTATGGTACAAGAAGCTATA |
| 1177 | TCCTATGGTACAAGAAGCTATAC |
| 1178 | CCTATGGTACAAGAAGCTATACG |
| 1179 | CTATGGTACAAGAAGCTATACGA |
| 1180 | TATGGTACAAGAAGCTATACGAA |
| 1181 | ATGGTACAAGAAGCTATACGAAT |
| 1182 | TGGTACAAGAAGCTATACGAATG |
| 1183 | GGTACAAGAAGCTATACGAATGG |
| 1184 | GTACAAGAAGCTATACGAATGGG |
| 1185 | TACAAGAAGCTATACGAATGGGG |
| 1186 | ACAAGAAGCTATACGAATGGGGT |
| 1187 | CAAGAAGCTATACGAATGGGGTT |
| 1188 | AAGAAGCTATACGAATGGGGTTC |
| 1189 | AGAAGCTATACGAATGGGGTTCA |
| 1190 | GAAGCTATACGAATGGGGTTCAG |
| 1191 | AAGCTATACGAATGGGGTTCAGT |
| 1192 | AGCTATACGAATGGGGTTCAGTT |
| 1193 | GCTATACGAATGGGGTTCAGTTT |
| 1194 | CTATACGAATGGGGTTCAGTTTC |
| 1195 | TATACGAATGGGGTTCAGTTTCA |
| 1196 | ATACGAATGGGGTTCAGTTTCAA |
| 1197 | TACGAATGGGGTTCAGTTTCAAG |
| 1198 | ACGAATGGGGTTCAGTTTCAAGG |
| 1199 | CGAATGGGGTTCAGTTTCAAGGA |
| 1200 | GAATGGGGTTCAGTTTCAAGGAC |

| ID | SEQUENCE |
|---|---|
| 1201 | AATGGGGTTCAGTTTCAAGGACA |
| 1202 | ATGGGGTTCAGTTTCAAGGACAT |
| 1203 | TGGGGTTCAGTTTCAAGGACATT |
| 1204 | GGGGTTCAGTTTCAAGGACATTA |
| 1205 | GGGTTCAGTTTCAAGGACATTAA |
| 1206 | GGTTCAGTTTCAAGGACATTAAG |
| 1207 | GTTCAGTTTCAAGGACATTAAGA |
| 1208 | TTCAGTTTCAAGGACATTAAGAA |
| 1209 | TCAGTTTCAAGGACATTAAGAAA |
| 1210 | CAGTTTCAAGGACATTAAGAAAA |
| 1211 | AGTTTCAAGGACATTAAGAAAAT |
| 1212 | GTTTCAAGGACATTAAGAAAATA |
| 1213 | TTTCAAGGACATTAAGAAAATAA |
| 1214 | TTCAAGGACATTAAGAAAATAAT |
| 1215 | TCAAGGACATTAAGAAAATAATG |
| 1216 | CAAGGACATTAAGAAAATAATGG |
| 1217 | AAGGACATTAAGAAAATAATGGA |
| 1218 | AGGACATTAAGAAAATAATGGAG |
| 1219 | GGACATTAAGAAAATAATGGAGG |
| 1220 | GACATTAAGAAAATAATGGAGGA |
| 1221 | ACATTAAGAAAATAATGGAGGAA |
| 1222 | CATTAAGAAAATAATGGAGGAAA |
| 1223 | ATTAAGAAAATAATGGAGGAAAA |
| 1224 | TTAAGAAAATAATGGAGGAAAAA |
| 1225 | TAAGAAAATAATGGAGGAAAAAA |
| 1226 | AAGAAAATAATGGAGGAAAAAAT |
| 1227 | AGAAAATAATGGAGGAAAAAATT |
| 1228 | GAAAATAATGGAGGAAAAAATTC |
| 1229 | AAAATAATGGAGGAAAAAATTCA |
| 1230 | AAATAATGGAGGAAAAAATTCAG |
| 1231 | AATAATGGAGGAAAAAATTCAGA |
| 1232 | ATAATGGAGGAAAAAATTCAGAT |
| 1233 | TAATGGAGGAAAAAATTCAGATA |
| 1234 | AATGGAGGAAAAAATTCAGATAT |
| 1235 | ATGGAGGAAAAAATTCAGATATC |
| 1236 | TGGAGGAAAAAATTCAGATATCT |
| 1237 | GGAGGAAAAAATTCAGATATCTG |
| 1238 | GAGGAAAAAATTCAGATATCTGG |
| 1239 | AGGAAAAAATTCAGATATCTGGG |
| 1240 | GGAAAAAATTCAGATATCTGGGA |
| 1241 | GAAAAAATTCAGATATCTGGGAG |
| 1242 | AAAAAATTCAGATATCTGGGAGC |
| 1243 | AAAAATTCAGATATCTGGGAGCA |
| 1244 | AAAATTCAGATATCTGGGAGCAA |
| 1245 | AAATTCAGATATCTGGGAGCAAC |
| 1246 | AATTCAGATATCTGGGAGCAACT |
| 1247 | ATTCAGATATCTGGGAGCAACTA |
| 1248 | TTCAGATATCTGGGAGCAACTAT |

| ID | SEQUENCE |
|---|---|
| 1249 | TCAGATATCTGGGAGCAACTATA |
| 1250 | CAGATATCTGGGAGCAACTATAA |
| 1251 | AGATATCTGGGAGCAACTATAAA |
| 1252 | GATATCTGGGAGCAACTATAAAT |
| 1253 | ATATCTGGGAGCAACTATAAATC |
| 1254 | TATCTGGGAGCAACTATAAATCA |
| 1255 | ATCTGGGAGCAACTATAAATCAC |
| 1256 | TCTGGGAGCAACTATAAATCACT |
| 1257 | CTGGGAGCAACTATAAATCACTT |
| 1258 | TGGGAGCAACTATAAATCACTTG |
| 1259 | GGGAGCAACTATAAATCACTTGA |
| 1260 | GGAGCAACTATAAATCACTTGAG |
| 1261 | GAGCAACTATAAATCACTTGAGG |
| 1262 | AGCAACTATAAATCACTTGAGGT |
| 1263 | GCAACTATAAATCACTTGAGGTT |
| 1264 | CAACTATAAATCACTTGAGGTTC |
| 1265 | AACTATAAATCACTTGAGGTTCT |
| 1266 | ACTATAAATCACTTGAGGTTCTG |
| 1267 | CTATAAATCACTTGAGGTTCTGG |
| 1268 | TATAAATCACTTGAGGTTCTGGT |
| 1269 | ATAAATCACTTGAGGTTCTGGTT |
| 1270 | TAAATCACTTGAGGTTCTGGTTG |
| 1271 | AAATCACTTGAGGTTCTGGTTGC |
| 1272 | AATCACTTGAGGTTCTGGTTGCA |
| 1273 | ATCACTTGAGGTTCTGGTTGCAG |
| 1274 | TCACTTGAGGTTCTGGTTGCAGA |
| 1275 | CACTTGAGGTTCTGGTTGCAGAT |
| 1276 | ACTTGAGGTTCTGGTTGCAGATC |
| 1277 | CTTGAGGTTCTGGTTGCAGATCT |
| 1278 | TTGAGGTTCTGGTTGCAGATCTA |
| 1279 | TGAGGTTCTGGTTGCAGATCTAG |
| 1280 | GAGGTTCTGGTTGCAGATCTAGT |
| 1281 | AGGTTCTGGTTGCAGATCTAGTG |
| 1282 | GGTTCTGGTTGCAGATCTAGTGA |
| 1283 | GTTCTGGTTGCAGATCTAGTGAA |
| 1284 | TTCTGGTTGCAGATCTAGTGAAT |
| 1285 | TCTGGTTGCAGATCTAGTGAATG |
| 1286 | CTGGTTGCAGATCTAGTGAATGC |
| 1287 | TGGTTGCAGATCTAGTGAATGCT |
| 1288 | GGTTGCAGATCTAGTGAATGCTC |
| 1289 | GTTGCAGATCTAGTGAATGCTCA |
| 1290 | TTGCAGATCTAGTGAATGCTCAG |
| 1291 | TGCAGATCTAGTGAATGCTCAGA |
| 1292 | GCAGATCTAGTGAATGCTCAGAA |
| 1293 | CAGATCTAGTGAATGCTCAGAAA |
| 1294 | AGATCTAGTGAATGCTCAGAAAG |
| 1295 | GATCTAGTGAATGCTCAGAAAGA |
| 1296 | ATCTAGTGAATGCTCAGAAAGAC |

| ID | SEQUENCE |
|---|---|
| 1297 | TCTAGTGAATGCTCAGAAAGACA |
| 1298 | CTAGTGAATGCTCAGAAAGACAG |
| 1299 | TAGTGAATGCTCAGAAAGACAGT |
| 1300 | AGTGAATGCTCAGAAAGACAGTA |
| 1301 | GTGAATGCTCAGAAAGACAGTAT |
| 1302 | TGAATGCTCAGAAAGACAGTATG |
| 1303 | GAATGCTCAGAAAGACAGTATGC |
| 1304 | AATGCTCAGAAAGACAGTATGCA |
| 1305 | ATGCTCAGAAAGACAGTATGCAA |
| 1306 | TGCTCAGAAAGACAGTATGCAAG |
| 1307 | GCTCAGAAAGACAGTATGCAAGA |
| 1308 | CTCAGAAAGACAGTATGCAAGAT |
| 1309 | TCAGAAAGACAGTATGCAAGATG |
| 1310 | CAGAAAGACAGTATGCAAGATGA |
| 1311 | AGAAAGACAGTATGCAAGATGAG |
| 1312 | GAAAGACAGTATGCAAGATGAGT |
| 1313 | AAAGACAGTATGCAAGATGAGTC |
| 1314 | AAGACAGTATGCAAGATGAGTCA |
| 1315 | AGACAGTATGCAAGATGAGTCAA |
| 1316 | GACAGTATGCAAGATGAGTCAAG |
| 1317 | ACAGTATGCAAGATGAGTCAAGT |
| 1318 | CAGTATGCAAGATGAGTCAAGTC |
| 1319 | AGTATGCAAGATGAGTCAAGTCA |
| 1320 | GTATGCAAGATGAGTCAAGTCAG |
| 1321 | TATGCAAGATGAGTCAAGTCAGA |
| 1322 | ATGCAAGATGAGTCAAGTCAGAC |
| 1323 | TGCAAGATGAGTCAAGTCAGACT |
| 1324 | GCAAGATGAGTCAAGTCAGACTT |
| 1325 | CAAGATGAGTCAAGTCAGACTTC |
| 1326 | AAGATGAGTCAAGTCAGACTTCA |
| 1327 | AGATGAGTCAAGTCAGACTTCAT |
| 1328 | GATGAGTCAAGTCAGACTTCATT |
| 1329 | ATGAGTCAAGTCAGACTTCATTA |
| 1330 | TGAGTCAAGTCAGACTTCATTAC |
| 1331 | GAGTCAAGTCAGACTTCATTACA |
| 1332 | AGTCAAGTCAGACTTCATTACAG |
| 1333 | GTCAAGTCAGACTTCATTACAGA |
| 1334 | TCAAGTCAGACTTCATTACAGAA |
| 1335 | CAAGTCAGACTTCATTACAGAAA |
| 1336 | AAGTCAGACTTCATTACAGAAAG |
| 1337 | AGTCAGACTTCATTACAGAAAGA |
| 1338 | GTCAGACTTCATTACAGAAAGAG |
| 1339 | TCAGACTTCATTACAGAAAGAGA |
| 1340 | CAGACTTCATTACAGAAAGAGAT |
| 1341 | AGACTTCATTACAGAAAGAGATT |
| 1342 | GACTTCATTACAGAAAGAGATTA |
| 1343 | ACTTCATTACAGAAAGAGATTAG |
| 1344 | CTTCATTACAGAAAGAGATTAGT |

| ID | SEQUENCE |
|---|---|
| 1345 | TTCATTACAGAAAGAGATTAGTA |
| 1346 | TCATTACAGAAAGAGATTAGTAC |
| 1347 | CATTACAGAAAGAGATTAGTACT |
| 1348 | ATTACAGAAAGAGATTAGTACTG |
| 1349 | TTACAGAAAGAGATTAGTACTGA |
| 1350 | TACAGAAAGAGATTAGTACTGAA |
| 1351 | ACAGAAAGAGATTAGTACTGAAG |
| 1352 | CAGAAAGAGATTAGTACTGAAGA |
| 1353 | AGAAAGAGATTAGTACTGAAGAG |
| 1354 | GAAAGAGATTAGTACTGAAGAGC |
| 1355 | AAAGAGATTAGTACTGAAGAGCA |
| 1356 | AAGAGATTAGTACTGAAGAGCAG |
| 1357 | AGAGATTAGTACTGAAGAGCAGC |
| 1358 | GAGATTAGTACTGAAGAGCAGCT |
| 1359 | AGATTAGTACTGAAGAGCAGCTA |
| 1360 | GATTAGTACTGAAGAGCAGCTAA |
| 1361 | ATTAGTACTGAAGAGCAGCTAAG |
| 1362 | TTAGTACTGAAGAGCAGCTAAGG |
| 1363 | TAGTACTGAAGAGCAGCTAAGGC |
| 1364 | AGTACTGAAGAGCAGCTAAGGCG |
| 1365 | GTACTGAAGAGCAGCTAAGGCGC |
| 1366 | TACTGAAGAGCAGCTAAGGCGCC |
| 1367 | ACTGAAGAGCAGCTAAGGCGCCT |
| 1368 | CTGAAGAGCAGCTAAGGCGCCTG |
| 1369 | TGAAGAGCAGCTAAGGCGCCTGC |
| 1370 | GAAGAGCAGCTAAGGCGCCTGCA |
| 1371 | AAGAGCAGCTAAGGCGCCTGCAA |
| 1372 | AGAGCAGCTAAGGCGCCTGCAAG |
| 1373 | GAGCAGCTAAGGCGCCTGCAAGA |
| 1374 | AGCAGCTAAGGCGCCTGCAAGAG |
| 1375 | GCAGCTAAGGCGCCTGCAAGAGG |
| 1376 | CAGCTAAGGCGCCTGCAAGAGGA |
| 1377 | AGCTAAGGCGCCTGCAAGAGGAG |
| 1378 | GCTAAGGCGCCTGCAAGAGGAGA |
| 1379 | CTAAGGCGCCTGCAAGAGGAGAA |
| 1380 | TAAGGCGCCTGCAAGAGGAGAAG |
| 1381 | AAGGCGCCTGCAAGAGGAGAAGC |
| 1382 | AGGCGCCTGCAAGAGGAGAAGCT |
| 1383 | GGCGCCTGCAAGAGGAGAAGCTT |
| 1384 | GCGCCTGCAAGAGGAGAAGCTTT |
| 1385 | CGCCTGCAAGAGGAGAAGCTTTG |
| 1386 | GCCTGCAAGAGGAGAAGCTTTGC |
| 1387 | CCTGCAAGAGGAGAAGCTTTGCA |
| 1388 | CTGCAAGAGGAGAAGCTTTGCAA |
| 1389 | TGCAAGAGGAGAAGCTTTGCAAA |
| 1390 | GCAAGAGGAGAAGCTTTGCAAAA |
| 1391 | CAAGAGGAGAAGCTTTGCAAAAT |
| 1392 | AAGAGGAGAAGCTTTGCAAAATC |

| ID | SEQUENCE |
|---|---|
| 1393 | AGAGGAGAAGCTTTGCAAAATCT |
| 1394 | GAGGAGAAGCTTTGCAAAATCTG |
| 1395 | AGGAGAAGCTTTGCAAAATCTGT |
| 1396 | GGAGAAGCTTTGCAAAATCTGTA |
| 1397 | GAGAAGCTTTGCAAAATCTGTAT |
| 1398 | AGAAGCTTTGCAAAATCTGTATG |
| 1399 | GAAGCTTTGCAAAATCTGTATGG |
| 1400 | AAGCTTTGCAAAATCTGTATGGA |
| 1401 | AGCTTTGCAAAATCTGTATGGAT |
| 1402 | GCTTTGCAAAATCTGTATGGATA |
| 1403 | CTTTGCAAAATCTGTATGGATAG |
| 1404 | TTTGCAAAATCTGTATGGATAGA |
| 1405 | TTGCAAAATCTGTATGGATAGAA |
| 1406 | TGCAAAATCTGTATGGATAGAAA |
| 1407 | GCAAAATCTGTATGGATAGAAAT |
| 1408 | CAAAATCTGTATGGATAGAAATA |
| 1409 | AAAATCTGTATGGATAGAAATAT |
| 1410 | AAATCTGTATGGATAGAAATATT |
| 1411 | AATCTGTATGGATAGAAATATTG |
| 1412 | ATCTGTATGGATAGAAATATTGC |
| 1413 | TCTGTATGGATAGAAATATTGCT |
| 1414 | CTGTATGGATAGAAATATTGCTA |
| 1415 | TGTATGGATAGAAATATTGCTAT |
| 1416 | GTATGGATAGAAATATTGCTATC |
| 1417 | TATGGATAGAAATATTGCTATCG |
| 1418 | ATGGATAGAAATATTGCTATCGT |
| 1419 | TGGATAGAAATATTGCTATCGTT |
| 1420 | GGATAGAAATATTGCTATCGTTT |
| 1421 | GATAGAAATATTGCTATCGTTTT |
| 1422 | ATAGAAATATTGCTATCGTTTTT |
| 1423 | TAGAAATATTGCTATCGTTTTTG |
| 1424 | AGAAATATTGCTATCGTTTTTGT |
| 1425 | GAAATATTGCTATCGTTTTTGTT |
| 1426 | AAATATTGCTATCGTTTTTGTTC |
| 1427 | AATATTGCTATCGTTTTTGTTCC |
| 1428 | ATATTGCTATCGTTTTTGTTCCT |
| 1429 | TATTGCTATCGTTTTTGTTCCTT |
| 1430 | ATTGCTATCGTTTTTGTTCCTTG |
| 1431 | TTGCTATCGTTTTTGTTCCTTGT |
| 1432 | TGCTATCGTTTTTGTTCCTTGTG |
| 1433 | GCTATCGTTTTTGTTCCTTGTGG |
| 1434 | CTATCGTTTTTGTTCCTTGTGGA |
| 1435 | TATCGTTTTTGTTCCTTGTGGAC |
| 1436 | ATCGTTTTTGTTCCTTGTGGACA |
| 1437 | TCGTTTTTGTTCCTTGTGGACAT |
| 1438 | CGTTTTTGTTCCTTGTGGACATC |
| 1439 | GTTTTTGTTCCTTGTGGACATCT |
| 1440 | TTTTTGTTCCTTGTGGACATCTA |

| ID | SEQUENCE |
|---|---|
| 1441 | TTTTGTTCCTTGTGGACATCTAG |
| 1442 | TTTGTTCCTTGTGGACATCTAGT |
| 1443 | TTGTTCCTTGTGGACATCTAGTC |
| 1444 | TGTTCCTTGTGGACATCTAGTCA |
| 1445 | GTTCCTTGTGGACATCTAGTCAC |
| 1446 | TTCCTTGTGGACATCTAGTCACT |
| 1447 | TCCTTGTGGACATCTAGTCACTT |
| 1448 | CCTTGTGGACATCTAGTCACTTG |
| 1449 | CTTGTGGACATCTAGTCACTTGT |
| 1450 | TTGTGGACATCTAGTCACTTGTA |
| 1451 | TGTGGACATCTAGTCACTTGTAA |
| 1452 | GTGGACATCTAGTCACTTGTAAA |
| 1453 | TGGACATCTAGTCACTTGTAAAC |
| 1454 | GGACATCTAGTCACTTGTAAACA |
| 1455 | GACATCTAGTCACTTGTAAACAA |
| 1456 | ACATCTAGTCACTTGTAAACAAT |
| 1457 | CATCTAGTCACTTGTAAACAATG |
| 1458 | ATCTAGTCACTTGTAAACAATGT |
| 1459 | TCTAGTCACTTGTAAACAATGTG |
| 1460 | CTAGTCACTTGTAAACAATGTGC |
| 1461 | TAGTCACTTGTAAACAATGTGCT |
| 1462 | AGTCACTTGTAAACAATGTGCTG |
| 1463 | GTCACTTGTAAACAATGTGCTGA |
| 1464 | TCACTTGTAAACAATGTGCTGAA |
| 1465 | CACTTGTAAACAATGTGCTGAAG |
| 1466 | ACTTGTAAACAATGTGCTGAAGC |
| 1467 | CTTGTAAACAATGTGCTGAAGCA |
| 1468 | TTGTAAACAATGTGCTGAAGCAG |
| 1469 | TGTAAACAATGTGCTGAAGCAGT |
| 1470 | GTAAACAATGTGCTGAAGCAGTT |
| 1471 | TAAACAATGTGCTGAAGCAGTTG |
| 1472 | AAACAATGTGCTGAAGCAGTTGA |
| 1473 | AACAATGTGCTGAAGCAGTTGAC |
| 1474 | ACAATGTGCTGAAGCAGTTGACA |
| 1475 | CAATGTGCTGAAGCAGTTGACAA |
| 1476 | AATGTGCTGAAGCAGTTGACAAG |
| 1477 | ATGTGCTGAAGCAGTTGACAAGT |
| 1478 | TGTGCTGAAGCAGTTGACAAGTG |
| 1479 | GTGCTGAAGCAGTTGACAAGTGT |
| 1480 | TGCTGAAGCAGTTGACAAGTGTC |
| 1481 | GCTGAAGCAGTTGACAAGTGTCC |
| 1482 | CTGAAGCAGTTGACAAGTGTCCC |
| 1483 | TGAAGCAGTTGACAAGTGTCCCA |
| 1484 | GAAGCAGTTGACAAGTGTCCCAT |
| 1485 | AAGCAGTTGACAAGTGTCCCATG |
| 1486 | AGCAGTTGACAAGTGTCCCATGT |
| 1487 | GCAGTTGACAAGTGTCCCATGTG |
| 1488 | CAGTTGACAAGTGTCCCATGTGC |

| ID | SEQUENCE |
|---|---|
| 1489 | AGTTGACAAGTGTCCCATGTGCT |
| 1490 | GTTGACAAGTGTCCCATGTGCTA |
| 1491 | TTGACAAGTGTCCCATGTGCTAC |
| 1492 | TGACAAGTGTCCCATGTGCTACA |
| 1493 | GACAAGTGTCCCATGTGCTACAC |
| 1494 | ACAAGTGTCCCATGTGCTACACA |
| 1495 | CAAGTGTCCCATGTGCTACACAG |
| 1496 | AAGTGTCCCATGTGCTACACAGT |
| 1497 | AGTGTCCCATGTGCTACACAGTC |
| 1498 | GTGTCCCATGTGCTACACAGTCA |
| 1499 | TGTCCCATGTGCTACACAGTCAT |
| 1500 | GTCCCATGTGCTACACAGTCATT |
| 1501 | TCCCATGTGCTACACAGTCATTA |
| 1502 | CCCATGTGCTACACAGTCATTAC |
| 1503 | CCATGTGCTACACAGTCATTACT |
| 1504 | CATGTGCTACACAGTCATTACTT |
| 1505 | ATGTGCTACACAGTCATTACTTT |
| 1506 | TGTGCTACACAGTCATTACTTTC |
| 1507 | GTGCTACACAGTCATTACTTTCA |
| 1508 | TGCTACACAGTCATTACTTTCAA |
| 1509 | GCTACACAGTCATTACTTTCAAG |
| 1510 | CTACACAGTCATTACTTTCAAGC |
| 1511 | TACACAGTCATTACTTTCAAGCA |
| 1512 | ACACAGTCATTACTTTCAAGCAA |
| 1513 | CACAGTCATTACTTTCAAGCAAA |
| 1514 | ACAGTCATTACTTTCAAGCAAAA |
| 1515 | CAGTCATTACTTTCAAGCAAAAA |
| 1516 | AGTCATTACTTTCAAGCAAAAAA |
| 1517 | GTCATTACTTTCAAGCAAAAAAT |
| 1518 | TCATTACTTTCAAGCAAAAAATT |
| 1519 | CATTACTTTCAAGCAAAAAATTT |
| 1520 | ATTACTTTCAAGCAAAAAATTTT |
| 1521 | TTACTTTCAAGCAAAAAATTTTT |
| 1522 | TACTTTCAAGCAAAAAATTTTTA |
| 1523 | ACTTTCAAGCAAAAAATTTTTAT |
| 1524 | CTTTCAAGCAAAAAATTTTTATG |
| 1525 | TTTCAAGCAAAAAATTTTTATGT |
| 1526 | TTCAAGCAAAAAATTTTTATGTC |
| 1527 | TCAAGCAAAAAATTTTTATGTCT |
| 1528 | CAAGCAAAAAATTTTTATGTCTT |
| 1529 | AAGCAAAAAATTTTTATGTCTTA |
| 1530 | TCTAACTCTATAGTAGGCATGTT |
| 1531 | CTAACTCTATAGTAGGCATGTTA |
| 1532 | TAACTCTATAGTAGGCATGTTAT |
| 1533 | AACTCTATAGTAGGCATGTTATG |
| 1534 | ACTCTATAGTAGGCATGTTATGT |
| 1535 | CTCTATAGTAGGCATGTTATGTT |
| 1536 | TCTATAGTAGGCATGTTATGTTG |

| ID | SEQUENCE |
|---|---|
| 1537 | CTATAGTAGGCATGTTATGTTGT |
| 1538 | TATAGTAGGCATGTTATGTTGTT |
| 1539 | ATAGTAGGCATGTTATGTTGTTC |
| 1540 | TAGTAGGCATGTTATGTTGTTCT |
| 1541 | AGTAGGCATGTTATGTTGTTCTT |
| 1542 | GTAGGCATGTTATGTTGTTCTTA |
| 1543 | TAGGCATGTTATGTTGTTCTTAT |
| 1544 | AGGCATGTTATGTTGTTCTTATT |
| 1545 | GGCATGTTATGTTGTTCTTATTA |
| 1546 | GCATGTTATGTTGTTCTTATTAC |
| 1547 | CATGTTATGTTGTTCTTATTACC |
| 1548 | ATGTTATGTTGTTCTTATTACCC |
| 1549 | TGTTATGTTGTTCTTATTACCCT |
| 1550 | GTTATGTTGTTCTTATTACCCTG |
| 1551 | TTATGTTGTTCTTATTACCCTGA |
| 1552 | TATGTTGTTCTTATTACCCTGAT |
| 1553 | ATGTTGTTCTTATTACCCTGATT |
| 1554 | TGTTGTTCTTATTACCCTGATTG |
| 1555 | GTTGTTCTTATTACCCTGATTGA |
| 1556 | TTGTTCTTATTACCCTGATTGAA |
| 1557 | TGTTCTTATTACCCTGATTGAAT |
| 1558 | GTTCTTATTACCCTGATTGAATG |
| 1559 | TTCTTATTACCCTGATTGAATGT |
| 1560 | TCTTATTACCCTGATTGAATGTG |
| 1561 | CTTATTACCCTGATTGAATGTGT |
| 1562 | TTATTACCCTGATTGAATGTGTG |
| 1563 | TATTACCCTGATTGAATGTGTGA |
| 1564 | ATTACCCTGATTGAATGTGTGAT |
| 1565 | TTACCCTGATTGAATGTGTGATG |
| 1566 | TACCCTGATTGAATGTGTGATGT |
| 1567 | ACCCTGATTGAATGTGTGATGTG |
| 1568 | CCCTGATTGAATGTGTGATGTGA |
| 1569 | CCTGATTGAATGTGTGATGTGAA |
| 1570 | CTGATTGAATGTGTGATGTGAAC |
| 1571 | TGATTGAATGTGTGATGTGAACT |
| 1572 | GATTGAATGTGTGATGTGAACTG |
| 1573 | ATTGAATGTGTGATGTGAACTGA |
| 1574 | TTGAATGTGTGATGTGAACTGAC |
| 1575 | TGAATGTGTGATGTGAACTGACT |
| 1576 | GAATGTGTGATGTGAACTGACTT |
| 1577 | AATGTGTGATGTGAACTGACTTT |
| 1578 | ATGTGTGATGTGAACTGACTTTA |
| 1579 | TGTGTGATGTGAACTGACTTTAA |
| 1580 | GTGTGATGTGAACTGACTTTAAG |
| 1581 | TGTGATGTGAACTGACTTTAAGT |
| 1582 | GTGATGTGAACTGACTTTAAGTA |
| 1583 | TGATGTGAACTGACTTTAAGTAA |
| 1584 | GATGTGAACTGACTTTAAGTAAT |

| ID | SEQUENCE |
|---|---|
| 1585 | ATGTGAACTGACTTTAAGTAATC |
| 1586 | TGTGAACTGACTTTAAGTAATCA |
| 1587 | GTGAACTGACTTTAAGTAATCAG |
| 1588 | TGAACTGACTTTAAGTAATCAGG |
| 1589 | GAACTGACTTTAAGTAATCAGGA |
| 1590 | AACTGACTTTAAGTAATCAGGAT |
| 1591 | ACTGACTTTAAGTAATCAGGATT |
| 1592 | CTGACTTTAAGTAATCAGGATTG |
| 1593 | TGACTTTAAGTAATCAGGATTGA |
| 1594 | GACTTTAAGTAATCAGGATTGAA |
| 1595 | ACTTTAAGTAATCAGGATTGAAT |
| 1596 | CTTTAAGTAATCAGGATTGAATT |
| 1597 | TTTAAGTAATCAGGATTGAATTC |
| 1598 | TTAAGTAATCAGGATTGAATTCC |
| 1599 | TAAGTAATCAGGATTGAATTCCA |
| 1600 | AAGTAATCAGGATTGAATTCCAT |
| 1601 | AGTAATCAGGATTGAATTCCATT |
| 1602 | GTAATCAGGATTGAATTCCATTA |
| 1603 | TAATCAGGATTGAATTCCATTAG |
| 1604 | AATCAGGATTGAATTCCATTAGC |
| 1605 | ATCAGGATTGAATTCCATTAGCA |
| 1606 | TCAGGATTGAATTCCATTAGCAT |
| 1607 | CAGGATTGAATTCCATTAGCATT |
| 1608 | AGGATTGAATTCCATTAGCATTT |
| 1609 | GGATTGAATTCCATTAGCATTTG |
| 1610 | GATTGAATTCCATTAGCATTTGC |
| 1611 | ATTGAATTCCATTAGCATTTGCT |
| 1612 | TTGAATTCCATTAGCATTTGCTA |
| 1613 | TGAATTCCATTAGCATTTGCTAC |
| 1614 | GAATTCCATTAGCATTTGCTACC |
| 1615 | AATTCCATTAGCATTTGCTACCA |
| 1616 | ATTCCATTAGCATTTGCTACCAA |
| 1617 | TTCCATTAGCATTTGCTACCAAG |
| 1618 | TCCATTAGCATTTGCTACCAAGT |
| 1619 | CCATTAGCATTTGCTACCAAGTA |
| 1620 | CATTAGCATTTGCTACCAAGTAG |
| 1621 | ATTAGCATTTGCTACCAAGTAGG |
| 1622 | TTAGCATTTGCTACCAAGTAGGA |
| 1623 | TAGCATTTGCTACCAAGTAGGAA |
| 1624 | AGCATTTGCTACCAAGTAGGAAA |
| 1625 | GCATTTGCTACCAAGTAGGAAAA |
| 1626 | CATTTGCTACCAAGTAGGAAAAA |
| 1627 | ATTTGCTACCAAGTAGGAAAAAA |
| 1628 | TTTGCTACCAAGTAGGAAAAAAA |
| 1629 | TTGCTACCAAGTAGGAAAAAAAA |
| 1630 | TGCTACCAAGTAGGAAAAAAAAT |
| 1631 | GCTACCAAGTAGGAAAAAAAATG |
| 1632 | CTACCAAGTAGGAAAAAAAATGT |

| ID | SEQUENCE |
|---|---|
| 1633 | TACCAAGTAGGAAAAAAAATGTA |
| 1634 | ACCAAGTAGGAAAAAAATGTAC |
| 1635 | CCAAGTAGGAAAAAAATGTACA |
| 1636 | CAAGTAGGAAAAAAATGTACAT |
| 1637 | AAGTAGGAAAAAAATGTACATG |
| 1638 | AGTAGGAAAAAAATGTACATGG |
| 1639 | GTAGGAAAAAAATGTACATGGC |
| 1640 | TAGGAAAAAAATGTACATGGCA |
| 1641 | AGGAAAAAAATGTACATGGCAG |
| 1642 | GGAAAAAAATGTACATGGCAGT |
| 1643 | GAAAAAAATGTACATGGCAGTG |
| 1644 | AAAAAAATGTACATGGCAGTGT |
| 1645 | AAAAAATGTACATGGCAGTGTT |
| 1646 | AAAAATGTACATGGCAGTGTTT |
| 1647 | AAAATGTACATGGCAGTGTTTT |
| 1648 | AAATGTACATGGCAGTGTTTTA |
| 1649 | AATGTACATGGCAGTGTTTTAG |
| 1650 | ATGTACATGGCAGTGTTTTAGT |
| 1651 | ATGTACATGGCAGTGTTTTAGTT |
| 1652 | TGTACATGGCAGTGTTTTAGTTG |
| 1653 | GTACATGGCAGTGTTTTAGTTGG |
| 1654 | TACATGGCAGTGTTTTAGTTGGC |
| 1655 | ACATGGCAGTGTTTTAGTTGGCA |
| 1656 | CATGGCAGTGTTTTAGTTGGCAA |
| 1657 | ATGGCAGTGTTTTAGTTGGCAAT |
| 1658 | TGGCAGTGTTTTAGTTGGCAATA |
| 1659 | GGCAGTGTTTTAGTTGGCAATAT |
| 1660 | GCAGTGTTTTAGTTGGCAATATA |
| 1661 | CAGTGTTTTAGTTGGCAATATAA |
| 1662 | AGTGTTTTAGTTGGCAATATAAT |
| 1663 | GTGTTTTAGTTGGCAATATAATC |
| 1664 | TGTTTTAGTTGGCAATATAATCT |
| 1665 | GTTTTAGTTGGCAATATAATCTT |
| 1666 | TTTTAGTTGGCAATATAATCTTT |
| 1667 | TTTAGTTGGCAATATAATCTTTG |
| 1668 | TTAGTTGGCAATATAATCTTTGA |
| 1669 | TAGTTGGCAATATAATCTTTGAA |
| 1670 | AGTTGGCAATATAATCTTTGAAT |
| 1671 | GTTGGCAATATAATCTTTGAATT |
| 1672 | TTGGCAATATAATCTTTGAATTT |
| 1673 | TGGCAATATAATCTTTGAATTTC |
| 1674 | GGCAATATAATCTTTGAATTTCT |
| 1675 | GCAATATAATCTTTGAATTTCTT |
| 1676 | CAATATAATCTTTGAATTTCTTG |
| 1677 | AATATAATCTTTGAATTTCTTGA |
| 1678 | ATATAATCTTTGAATTTCTTGAT |
| 1679 | TATAATCTTTGAATTTCTTGATT |
| 1680 | ATAATCTTTGAATTTCTTGATTT |

| ID | SEQUENCE |
|---|---|
| 1681 | TAATCTTTGAATTTCTTGATTTT |
| 1682 | AATCTTTGAATTTCTTGATTTTT |
| 1683 | ATCTTTGAATTTCTTGATTTTTC |
| 1684 | TCTTTGAATTTCTTGATTTTTCA |
| 1685 | CTTTGAATTTCTTGATTTTTCAG |
| 1686 | TTTGAATTTCTTGATTTTTCAGG |
| 1687 | TTGAATTTCTTGATTTTTCAGGG |
| 1688 | TGAATTTCTTGATTTTTCAGGGT |
| 1689 | GAATTTCTTGATTTTTCAGGGTA |
| 1690 | AATTTCTTGATTTTTCAGGGTAT |
| 1691 | ATTTCTTGATTTTTCAGGGTATT |
| 1692 | TTTCTTGATTTTTCAGGGTATTA |
| 1693 | TTCTTGATTTTTCAGGGTATTAG |
| 1694 | TCTTGATTTTTCAGGGTATTAGC |
| 1695 | CTTGATTTTTCAGGGTATTAGCT |
| 1696 | TTGATTTTTCAGGGTATTAGCTG |
| 1697 | TGATTTTTCAGGGTATTAGCTGT |
| 1698 | GATTTTTCAGGGTATTAGCTGTA |
| 1699 | ATTTTTCAGGGTATTAGCTGTAT |
| 1700 | TTTTTCAGGGTATTAGCTGTATT |
| 1701 | TTTTCAGGGTATTAGCTGTATTA |
| 1702 | TTTCAGGGTATTAGCTGTATTAT |
| 1703 | TTCAGGGTATTAGCTGTATTATC |
| 1704 | TCAGGGTATTAGCTGTATTATCC |
| 1705 | CAGGGTATTAGCTGTATTATCCA |
| 1706 | AGGGTATTAGCTGTATTATCCAT |
| 1707 | GGGTATTAGCTGTATTATCCATT |
| 1708 | GGTATTAGCTGTATTATCCATTT |
| 1709 | GTATTAGCTGTATTATCCATTTT |
| 1710 | TATTAGCTGTATTATCCATTTTT |
| 1711 | ATTAGCTGTATTATCCATTTTTT |
| 1712 | TTAGCTGTATTATCCATTTTTTT |
| 1713 | TAGCTGTATTATCCATTTTTTTA |
| 1714 | AGCTGTATTATCCATTTTTTTAC |
| 1715 | GCTGTATTATCCATTTTTTTACT |
| 1716 | CTGTATTATCCATTTTTTTACTG |
| 1717 | TGTATTATCCATTTTTTTACTGT |
| 1718 | GTATTATCCATTTTTTTACTGTT |
| 1719 | TATTATCCATTTTTTTACTGTTA |
| 1720 | ATTATCCATTTTTTTACTGTTAT |
| 1721 | TTATCCATTTTTTTACTGTTATT |
| 1722 | TATCCATTTTTTTACTGTTATTT |
| 1723 | ATCCATTTTTTTACTGTTATTTA |
| 1724 | TCCATTTTTTTACTGTTATTTAA |
| 1725 | CCATTTTTTTACTGTTATTTAAT |
| 1726 | CATTTTTTTACTGTTATTTAATT |
| 1727 | ATTTTTTTACTGTTATTTAATTG |
| 1728 | TTTTTTTACTGTTATTTAATTG |

| ID | SEQUENCE |
|---|---|
| 1729 | TTTTTTTACTGTTATTTAATTGA |
| 1730 | TTTTTTACTGTTATTTAATTGAA |
| 1731 | TTTTTACTGTTATTTAATTGAAA |
| 1732 | TTTTACTGTTATTTAATTGAAAC |
| 1733 | TTTACTGTTATTTAATTGAAACC |
| 1734 | TTACTGTTATTTAATTGAAACCA |
| 1735 | TACTGTTATTTAATTGAAACCAT |
| 1736 | ACTGTTATTTAATTGAAACCATA |
| 1737 | CTGTTATTTAATTGAAACCATAG |
| 1738 | TGTTATTTAATTGAAACCATAGA |
| 1739 | GTTATTTAATTGAAACCATAGAC |
| 1740 | TTATTTAATTGAAACCATAGACT |
| 1741 | TATTTAATTGAAACCATAGACTA |
| 1742 | ATTTAATTGAAACCATAGACTAA |
| 1743 | TTTAATTGAAACCATAGACTAAG |
| 1744 | TTAATTGAAACCATAGACTAAGA |
| 1745 | TAATTGAAACCATAGACTAAGAA |
| 1746 | AATTGAAACCATAGACTAAGAAT |
| 1747 | ATTGAAACCATAGACTAAGAATA |
| 1748 | TTGAAACCATAGACTAAGAATAA |
| 1749 | TGAAACCATAGACTAAGAATAAG |
| 1750 | GAAACCATAGACTAAGAATAAGA |
| 1751 | AAACCATAGACTAAGAATAAGAA |
| 1752 | AACCATAGACTAAGAATAAGAAG |
| 1753 | ACCATAGACTAAGAATAAGAAGC |
| 1754 | CCATAGACTAAGAATAAGAAGCA |
| 1755 | CATAGACTAAGAATAAGAAGCAT |
| 1756 | ATAGACTAAGAATAAGAAGCATC |
| 1757 | TAGACTAAGAATAAGAAGCATCA |
| 1758 | AGACTAAGAATAAGAAGCATCAT |
| 1759 | GACTAAGAATAAGAAGCATCATA |
| 1760 | ACTAAGAATAAGAAGCATCATAC |
| 1761 | CTAAGAATAAGAAGCATCATACT |
| 1762 | TAAGAATAAGAAGCATCATACTA |
| 1763 | AAGAATAAGAAGCATCATACTAT |
| 1764 | AGAATAAGAAGCATCATACTATA |
| 1765 | GAATAAGAAGCATCATACTATAA |
| 1766 | AATAAGAAGCATCATACTATAAC |
| 1767 | ATAAGAAGCATCATACTATAACT |
| 1768 | TAAGAAGCATCATACTATAACTG |
| 1769 | AAGAAGCATCATACTATAACTGA |
| 1770 | AGAAGCATCATACTATAACTGAA |
| 1771 | GAAGCATCATACTATAACTGAAC |
| 1772 | AAGCATCATACTATAACTGAACA |
| 1773 | AGCATCATACTATAACTGAACAC |
| 1774 | GCATCATACTATAACTGAACACA |
| 1775 | CATCATACTATAACTGAACACAA |
| 1776 | ATCATACTATAACTGAACACAAT |

| ID | SEQUENCE |
|---|---|
| 1777 | TCATACTATAACTGAACACAATG |
| 1778 | CATACTATAACTGAACACAATGT |
| 1779 | ATACTATAACTGAACACAATGTG |
| 1780 | TACTATAACTGAACACAATGTGT |
| 1781 | ACTATAACTGAACACAATGTGTA |
| 1782 | CTATAACTGAACACAATGTGTAT |
| 1783 | TATAACTGAACACAATGTGTATT |
| 1784 | ATAACTGAACACAATGTGTATTC |
| 1785 | TAACTGAACACAATGTGTATTCA |
| 1786 | AACTGAACACAATGTGTATTCAT |
| 1787 | ACTGAACACAATGTGTATTCATA |
| 1788 | CTGAACACAATGTGTATTCATAG |
| 1789 | TGAACACAATGTGTATTCATAGT |
| 1790 | GAACACAATGTGTATTCATAGTA |
| 1791 | AACACAATGTGTATTCATAGTAT |
| 1792 | ACACAATGTGTATTCATAGTATA |
| 1793 | CACAATGTGTATTCATAGTATAC |
| 1794 | ACAATGTGTATTCATAGTATACT |
| 1795 | CAATGTGTATTCATAGTATACTG |
| 1796 | AATGTGTATTCATAGTATACTGA |
| 1797 | ATGTGTATTCATAGTATACTGAT |
| 1798 | TGTGTATTCATAGTATACTGATT |
| 1799 | GTGTATTCATAGTATACTGATTT |
| 1800 | TGTATTCATAGTATACTGATTTA |
| 1801 | GTATTCATAGTATACTGATTTAA |
| 1802 | TATTCATAGTATACTGATTTAAT |
| 1803 | ATTCATAGTATACTGATTTAATT |
| 1804 | TTCATAGTATACTGATTTAATTT |
| 1805 | TCATAGTATACTGATTTAATTTC |
| 1806 | CATAGTATACTGATTTAATTTCT |
| 1807 | ATAGTATACTGATTTAATTTCTA |
| 1808 | TAGTATACTGATTTAATTTCTAA |
| 1809 | AGTATACTGATTTAATTTCTAAG |
| 1810 | GTATACTGATTTAATTTCTAAGT |
| 1811 | TATACTGATTTAATTTCTAAGTG |
| 1812 | ATACTGATTTAATTTCTAAGTGT |
| 1813 | TACTGATTTAATTTCTAAGTGTA |
| 1814 | ACTGATTTAATTTCTAAGTGTAA |
| 1815 | CTGATTTAATTTCTAAGTGTAAG |
| 1816 | TGATTTAATTTCTAAGTGTAAGT |
| 1817 | GATTTAATTTCTAAGTGTAAGTG |
| 1818 | ATTTAATTTCTAAGTGTAAGTGA |
| 1819 | TTTAATTTCTAAGTGTAAGTGAA |
| 1820 | TTAATTTCTAAGTGTAAGTGAAT |
| 1821 | TAATTTCTAAGTGTAAGTGAATT |
| 1822 | AATTTCTAAGTGTAAGTGAATTA |
| 1823 | ATTTCTAAGTGTAAGTGAATTAA |
| 1824 | TTTCTAAGTGTAAGTGAATTAAT |

| ID | SEQUENCE |
|---|---|
| 1825 | TTCTAAGTGTAAGTGAATTAATC |
| 1826 | TCTAAGTGTAAGTGAATTAATCA |
| 1827 | CTAAGTGTAAGTGAATTAATCAT |
| 1828 | TAAGTGTAAGTGAATTAATCATC |
| 1829 | AAGTGTAAGTGAATTAATCATCT |
| 1830 | AGTGTAAGTGAATTAATCATCTG |
| 1831 | GTGTAAGTGAATTAATCATCTGG |
| 1832 | TGTAAGTGAATTAATCATCTGGA |
| 1833 | GTAAGTGAATTAATCATCTGGAT |
| 1834 | TAAGTGAATTAATCATCTGGATT |
| 1835 | AAGTGAATTAATCATCTGGATTT |
| 1836 | AGTGAATTAATCATCTGGATTTT |
| 1837 | GTGAATTAATCATCTGGATTTTT |
| 1838 | TGAATTAATCATCTGGATTTTTT |
| 1839 | GAATTAATCATCTGGATTTTTTA |
| 1840 | AATTAATCATCTGGATTTTTTAT |
| 1841 | ATTAATCATCTGGATTTTTTATT |
| 1842 | TTAATCATCTGGATTTTTTATTC |
| 1843 | TAATCATCTGGATTTTTTATTCT |
| 1844 | AATCATCTGGATTTTTTATTCTT |
| 1845 | ATCATCTGGATTTTTTATTCTTT |
| 1846 | TCATCTGGATTTTTTATTCTTTT |
| 1847 | CATCTGGATTTTTTATTCTTTTC |
| 1848 | ATCTGGATTTTTTATTCTTTTCA |
| 1849 | TCTGGATTTTTTATTCTTTTCAG |
| 1850 | CTGGATTTTTTATTCTTTTCAGA |
| 1851 | TGGATTTTTTATTCTTTTCAGAT |
| 1852 | GGATTTTTTATTCTTTTCAGATA |
| 1853 | GATTTTTTATTCTTTTCAGATAG |
| 1854 | ATTTTTTATTCTTTTCAGATAGG |
| 1855 | TTTTTTATTCTTTTCAGATAGGC |
| 1856 | TTTTTATTCTTTTCAGATAGGCT |
| 1857 | TTTTATTCTTTTCAGATAGGCTT |
| 1858 | TTTATTCTTTTCAGATAGGCTTA |
| 1859 | TTATTCTTTTCAGATAGGCTTAA |
| 1860 | TATTCTTTTCAGATAGGCTTAAC |
| 1861 | ATTCTTTTCAGATAGGCTTAACA |
| 1862 | TTCTTTTCAGATAGGCTTAACAA |
| 1863 | TCTTTTCAGATAGGCTTAACAAA |
| 1864 | CTTTTCAGATAGGCTTAACAAAT |
| 1865 | TTTTCAGATAGGCTTAACAAATG |
| 1866 | TTTCAGATAGGCTTAACAAATGG |
| 1867 | TTCAGATAGGCTTAACAAATGGA |
| 1868 | TCAGATAGGCTTAACAAATGGAG |
| 1869 | CAGATAGGCTTAACAAATGGAGC |
| 1870 | AGATAGGCTTAACAAATGGAGCT |
| 1871 | GATAGGCTTAACAAATGGAGCTT |
| 1872 | ATAGGCTTAACAAATGGAGCTTT |

| ID | SEQUENCE |
|---|---|
| 1873 | TAGGCTTAACAAATGGAGCTTTC |
| 1874 | AGGCTTAACAAATGGAGCTTTCT |
| 1875 | GGCTTAACAAATGGAGCTTTCTG |
| 1876 | GCTTAACAAATGGAGCTTTCTGT |
| 1877 | CTTAACAAATGGAGCTTTCTGTA |
| 1878 | TTAACAAATGGAGCTTTCTGTAT |
| 1879 | TAACAAATGGAGCTTTCTGTATA |
| 1880 | AACAAATGGAGCTTTCTGTATAT |
| 1881 | ACAAATGGAGCTTTCTGTATATA |
| 1882 | CAAATGGAGCTTTCTGTATATAA |
| 1883 | AAATGGAGCTTTCTGTATATAAA |
| 1884 | AATGGAGCTTTCTGTATATAAAT |
| 1885 | ATGGAGCTTTCTGTATATAAATG |
| 1886 | TGGAGCTTTCTGTATATAAATGT |
| 1887 | GGAGCTTTCTGTATATAAATGTG |
| 1888 | GAGCTTTCTGTATATAAATGTGG |
| 1889 | AGCTTTCTGTATATAAATGTGGA |
| 1890 | GCTTTCTGTATATAAATGTGGAG |
| 1891 | CTTTCTGTATATAAATGTGGAGA |
| 1892 | TTTCTGTATATAAATGTGGAGAT |
| 1893 | TTCTGTATATAAATGTGGAGATT |
| 1894 | TCTGTATATAAATGTGGAGATTA |
| 1895 | CTGTATATAAATGTGGAGATTAG |
| 1896 | TGTATATAAATGTGGAGATTAGA |
| 1897 | GTATATAAATGTGGAGATTAGAG |
| 1898 | TATATAAATGTGGAGATTAGAGT |
| 1899 | ATATAAATGTGGAGATTAGAGTT |
| 1900 | TATAAATGTGGAGATTAGAGTTA |
| 1901 | ATAAATGTGGAGATTAGAGTTAA |
| 1902 | TAAATGTGGAGATTAGAGTTAAT |
| 1903 | AAATGTGGAGATTAGAGTTAATC |
| 1904 | AATGTGGAGATTAGAGTTAATCT |
| 1905 | ATGTGGAGATTAGAGTTAATCTC |
| 1906 | TGTGGAGATTAGAGTTAATCTCC |
| 1907 | GTGGAGATTAGAGTTAATCTCCC |
| 1908 | TGGAGATTAGAGTTAATCTCCCC |
| 1909 | GGAGATTAGAGTTAATCTCCCCA |
| 1910 | GAGATTAGAGTTAATCTCCCCAA |
| 1911 | AGATTAGAGTTAATCTCCCCAAT |
| 1912 | GATTAGAGTTAATCTCCCCAATC |
| 1913 | ATTAGAGTTAATCTCCCCAATCA |
| 1914 | TTAGAGTTAATCTCCCCAATCAC |
| 1915 | TAGAGTTAATCTCCCCAATCACA |
| 1916 | AGAGTTAATCTCCCCAATCACAT |
| 1917 | GAGTTAATCTCCCCAATCACATA |
| 1918 | AGTTAATCTCCCCAATCACATAA |
| 1919 | GTTAATCTCCCCAATCACATAAT |
| 1920 | TTAATCTCCCCAATCACATAATT |

| ID | SEQUENCE |
|---|---|
| 1921 | TAATCTCCCCAATCACATAATTT |
| 1922 | AATCTCCCCAATCACATAATTTG |
| 1923 | ATCTCCCCAATCACATAATTTGT |
| 1924 | TCTCCCCAATCACATAATTTGTT |
| 1925 | CTCCCCAATCACATAATTTGTTT |
| 1926 | TCCCCAATCACATAATTTGTTTT |
| 1927 | CCCCAATCACATAATTTGTTTTG |
| 1928 | CCCAATCACATAATTTGTTTTGT |
| 1929 | CCAATCACATAATTTGTTTTGTG |
| 1930 | CAATCACATAATTTGTTTTGTGT |
| 1931 | AATCACATAATTTGTTTTGTGTG |
| 1932 | ATCACATAATTTGTTTTGTGTGA |
| 1933 | TCACATAATTTGTTTTGTGTGAA |
| 1934 | CACATAATTTGTTTTGTGTGAAA |
| 1935 | ACATAATTTGTTTTGTGTGAAAA |
| 1936 | CATAATTTGTTTTGTGTGAAAAA |
| 1937 | ATAATTTGTTTTGTGTGAAAAAG |
| 1938 | TAATTTGTTTTGTGTGAAAAAGG |
| 1939 | AATTTGTTTTGTGTGAAAAAGGA |
| 1940 | ATTTGTTTTGTGTGAAAAAGGAA |
| 1941 | TTTGTTTTGTGTGAAAAAGGAAT |
| 1942 | TTGTTTTGTGTGAAAAAGGAATA |
| 1943 | TGTTTTGTGTGAAAAAGGAATAA |
| 1944 | GTTTTGTGTGAAAAAGGAATAAA |
| 1945 | TTTTGTGTGAAAAAGGAATAAAT |
| 1946 | TTTGTGTGAAAAAGGAATAAATT |
| 1947 | TTGTGTGAAAAAGGAATAAATTG |
| 1948 | TGTGTGAAAAAGGAATAAATTGT |
| 1949 | GTGTGAAAAAGGAATAAATTGTT |
| 1950 | TGTGAAAAAGGAATAAATTGTTC |
| 1951 | GTGAAAAAGGAATAAATTGTTCC |
| 1952 | TGAAAAAGGAATAAATTGTTCCA |
| 1953 | GAAAAAGGAATAAATTGTTCCAT |
| 1954 | AAAAAGGAATAAATTGTTCCATG |
| 1955 | AAAAGGAATAAATTGTTCCATGC |
| 1956 | AAAGGAATAAATTGTTCCATGCT |
| 1957 | AAGGAATAAATTGTTCCATGCTG |
| 1958 | AGGAATAAATTGTTCCATGCTGG |
| 1959 | GGAATAAATTGTTCCATGCTGGT |
| 1960 | GAATAAATTGTTCCATGCTGGTG |
| 1961 | AATAAATTGTTCCATGCTGGTGG |
| 1962 | ATAAATTGTTCCATGCTGGTGGA |
| 1963 | TAAATTGTTCCATGCTGGTGGAA |
| 1964 | AAATTGTTCCATGCTGGTGGAAA |
| 1965 | AATTGTTCCATGCTGGTGGAAAG |
| 1966 | ATTGTTCCATGCTGGTGGAAAGA |
| 1967 | TTGTTCCATGCTGGTGGAAAGAT |
| 1968 | TGTTCCATGCTGGTGGAAAGATA |

| ID | SEQUENCE |
|---|---|
| 1969 | GTTCCATGCTGGTGGAAAGATAG |
| 1970 | TTCCATGCTGGTGGAAAGATAGA |
| 1971 | TCCATGCTGGTGGAAAGATAGAG |
| 1972 | CCATGCTGGTGGAAAGATAGAGA |
| 1973 | CATGCTGGTGGAAAGATAGAGAT |
| 1974 | ATGCTGGTGGAAAGATAGAGATT |
| 1975 | TGCTGGTGGAAAGATAGAGATTG |
| 1976 | GCTGGTGGAAAGATAGAGATTGT |
| 1977 | CTGGTGGAAAGATAGAGATTGTT |
| 1978 | TGGTGGAAAGATAGAGATTGTTT |
| 1979 | GGTGGAAAGATAGAGATTGTTTT |
| 1980 | GTGGAAAGATAGAGATTGTTTTT |
| 1981 | TGGAAAGATAGAGATTGTTTTTA |
| 1982 | GGAAAGATAGAGATTGTTTTTAG |
| 1983 | GAAAGATAGAGATTGTTTTTAGA |
| 1984 | AAAGATAGAGATTGTTTTTAGAG |
| 1985 | AAGATAGAGATTGTTTTTAGAGG |
| 1986 | AGATAGAGATTGTTTTTAGAGGT |
| 1987 | GATAGAGATTGTTTTTAGAGGTT |
| 1988 | ATAGAGATTGTTTTTAGAGGTTG |
| 1989 | TAGAGATTGTTTTTAGAGGTTGG |
| 1990 | AGAGATTGTTTTTAGAGGTTGGT |
| 1991 | GAGATTGTTTTTAGAGGTTGGTT |
| 1992 | AGATTGTTTTTAGAGGTTGGTTG |
| 1993 | GATTGTTTTTAGAGGTTGGTTGT |
| 1994 | ATTGTTTTTAGAGGTTGGTTGTT |
| 1995 | TTGTTTTTAGAGGTTGGTTGTTG |
| 1996 | TGTTTTTAGAGGTTGGTTGTTGT |
| 1997 | GTTTTTAGAGGTTGGTTGTTGTG |
| 1998 | TTTTTAGAGGTTGGTTGTTGTGT |
| 1999 | TTTTAGAGGTTGGTTGTTGTGTT |
| 2000 | TTTAGAGGTTGGTTGTTGTGTTT |
| 2001 | TTAGAGGTTGGTTGTTGTGTTTT |
| 2002 | TAGAGGTTGGTTGTTGTGTTTTA |
| 2003 | AGAGGTTGGTTGTTGTGTTTTAG |
| 2004 | GAGGTTGGTTGTTGTGTTTTAGG |
| 2005 | AGGTTGGTTGTTGTGTTTTAGGA |
| 2006 | GGTTGGTTGTTGTGTTTTAGGAT |
| 2007 | GTTGGTTGTTGTGTTTTAGGATT |
| 2008 | TTGGTTGTTGTGTTTTAGGATTC |
| 2009 | TGGTTGTTGTGTTTTAGGATTCT |
| 2010 | GGTTGTTGTGTTTTAGGATTCTG |
| 2011 | GTTGTTGTGTTTTAGGATTCTGT |
| 2012 | TTGTTGTGTTTTAGGATTCTGTC |
| 2013 | TGTTGTGTTTTAGGATTCTGTCC |
| 2014 | GTTGTGTTTTAGGATTCTGTCCA |
| 2015 | TTGTGTTTTAGGATTCTGTCCAT |
| 2016 | TGTGTTTTAGGATTCTGTCCATT |

| ID | SEQUENCE |
|---|---|
| 2017 | GTGTTTTAGGATTCTGTCCATTT |
| 2018 | TGTTTTAGGATTCTGTCCATTTT |
| 2019 | GTTTTAGGATTCTGTCCATTTTC |
| 2020 | TTTTAGGATTCTGTCCATTTTCT |
| 2021 | TTTAGGATTCTGTCCATTTTCTT |
| 2022 | TTAGGATTCTGTCCATTTTCTTT |
| 2023 | TAGGATTCTGTCCATTTTCTTTT |
| 2024 | AGGATTCTGTCCATTTTCTTTTA |
| 2025 | GGATTCTGTCCATTTTCTTTTAA |
| 2026 | GATTCTGTCCATTTTCTTTTAAA |
| 2027 | ATTCTGTCCATTTTCTTTTAAAG |
| 2028 | TTCTGTCCATTTTCTTTTAAAGT |
| 2029 | TCTGTCCATTTTCTTTTAAAGTT |
| 2030 | CTGTCCATTTTCTTTTAAAGTTA |
| 2031 | TGTCCATTTTCTTTTAAAGTTAT |
| 2032 | GTCCATTTTCTTTTAAAGTTATA |
| 2033 | TCCATTTTCTTTTAAAGTTATAA |
| 2034 | CCATTTTCTTTTAAAGTTATAAA |
| 2035 | CATTTTCTTTTAAAGTTATAAAC |
| 2036 | ATTTTCTTTTAAAGTTATAAACA |
| 2037 | TTTTCTTTTAAAGTTATAAACAC |
| 2038 | TTTCTTTTAAAGTTATAAACACG |
| 2039 | TTCTTTTAAAGTTATAAACACGT |
| 2040 | TCTTTTAAAGTTATAAACACGTA |
| 2041 | CTTTTAAAGTTATAAACACGTAC |
| 2042 | TTTTAAAGTTATAAACACGTACT |
| 2043 | TTTAAAGTTATAAACACGTACTT |
| 2044 | TTAAAGTTATAAACACGTACTTG |
| 2045 | TAAAGTTATAAACACGTACTTGT |
| 2046 | AAAGTTATAAACACGTACTTGTG |
| 2047 | AAGTTATAAACACGTACTTGTGC |
| 2048 | AGTTATAAACACGTACTTGTGCG |
| 2049 | GTTATAAACACGTACTTGTGCGA |
| 2050 | TTATAAACACGTACTTGTGCGAA |
| 2051 | TATAAACACGTACTTGTGCGAAT |
| 2052 | ATAAACACGTACTTGTGCGAATT |
| 2053 | TAAACACGTACTTGTGCGAATTA |
| 2054 | AAACACGTACTTGTGCGAATTAT |
| 2055 | AACACGTACTTGTGCGAATTATT |
| 2056 | ACACGTACTTGTGCGAATTATTT |
| 2057 | CACGTACTTGTGCGAATTATTTT |
| 2058 | ACGTACTTGTGCGAATTATTTTT |
| 2059 | CGTACTTGTGCGAATTATTTTTT |
| 2060 | GTACTTGTGCGAATTATTTTTTT |
| 2061 | TACTTGTGCGAATTATTTTTTTA |
| 2062 | ACTTGTGCGAATTATTTTTTTAA |
| 2063 | CTTGTGCGAATTATTTTTTTAAA |
| 2064 | TTGTGCGAATTATTTTTTTAAAG |

| ID | SEQUENCE |
|---|---|
| 2065 | TGTGCGAATTATTTTTTAAAGT |
| 2066 | GTGCGAATTATTTTTTAAAGTG |
| 2067 | TGCGAATTATTTTTTAAAGTGA |
| 2068 | GCGAATTATTTTTTAAAGTGAT |
| 2069 | CGAATTATTTTTTAAAGTGATT |
| 2070 | GAATTATTTTTTAAAGTGATTT |
| 2071 | AATTATTTTTTAAAGTGATTTG |
| 2072 | ATTATTTTTTAAAGTGATTTGC |
| 2073 | TTATTTTTTAAAGTGATTTGCC |
| 2074 | TATTTTTTAAAGTGATTTGCCA |
| 2075 | ATTTTTTAAAGTGATTTGCCAT |
| 2076 | TTTTTTAAAGTGATTTGCCATT |
| 2077 | TTTTTAAAGTGATTTGCCATTT |
| 2078 | TTTTAAAGTGATTTGCCATTTT |
| 2079 | TTTAAAGTGATTTGCCATTTTT |
| 2080 | TTAAAGTGATTTGCCATTTTTG |
| 2081 | TAAAGTGATTTGCCATTTTTGA |
| 2082 | AAAGTGATTTGCCATTTTTGAA |
| 2083 | AAGTGATTTGCCATTTTTGAAA |
| 2084 | AGTGATTTGCCATTTTTGAAAG |
| 2085 | GTGATTTGCCATTTTTGAAAGC |
| 2086 | TGATTTGCCATTTTTGAAAGCG |
| 2087 | GATTTGCCATTTTTGAAAGCGT |
| 2088 | ATTTGCCATTTTTGAAAGCGTA |
| 2089 | TTTGCCATTTTTGAAAGCGTAT |
| 2090 | TTGCCATTTTTGAAAGCGTATT |
| 2091 | TGCCATTTTTGAAAGCGTATTT |
| 2092 | GCCATTTTTGAAAGCGTATTTA |
| 2093 | CCATTTTTGAAAGCGTATTTAA |
| 2094 | CATTTTTGAAAGCGTATTTAAT |
| 2095 | ATTTTTGAAAGCGTATTTAATG |
| 2096 | TTTTTGAAAGCGTATTTAATGA |
| 2097 | TTTTGAAAGCGTATTTAATGAT |
| 2098 | TTTGAAAGCGTATTTAATGATA |
| 2099 | TTGAAAGCGTATTTAATGATAG |
| 2100 | TGAAAGCGTATTTAATGATAGA |
| 2101 | GAAAGCGTATTTAATGATAGAA |
| 2102 | AAAGCGTATTTAATGATAGAAT |
| 2103 | AAGCGTATTTAATGATAGAATA |
| 2104 | AGCGTATTTAATGATAGAATAC |
| 2105 | GCGTATTTAATGATAGAATACT |
| 2106 | CGTATTTAATGATAGAATACTA |
| 2107 | GTATTTAATGATAGAATACTAT |
| 2108 | TATTTAATGATAGAATACTATC |
| 2109 | ATTTAATGATAGAATACTATCG |
| 2110 | TTTAATGATAGAATACTATCGA |
| 2111 | TTAATGATAGAATACTATCGAG |
| 2112 | TAATGATAGAATACTATCGAGC |

| ID | SEQUENCE |
|---|---|
| 2113 | TAATGATAGAATACTATCGAGCC |
| 2114 | AATGATAGAATACTATCGAGCCA |
| 2115 | ATGATAGAATACTATCGAGCCAA |
| 2116 | TGATAGAATACTATCGAGCCAAC |
| 2117 | GATAGAATACTATCGAGCCAACA |
| 2118 | ATAGAATACTATCGAGCCAACAT |
| 2119 | TAGAATACTATCGAGCCAACATG |
| 2120 | AGAATACTATCGAGCCAACATGT |
| 2121 | GAATACTATCGAGCCAACATGTA |
| 2122 | AATACTATCGAGCCAACATGTAC |
| 2123 | ATACTATCGAGCCAACATGTACT |
| 2124 | TACTATCGAGCCAACATGTACTG |
| 2125 | ACTATCGAGCCAACATGTACTGA |
| 2126 | CTATCGAGCCAACATGTACTGAC |
| 2127 | TATCGAGCCAACATGTACTGACA |
| 2128 | ATCGAGCCAACATGTACTGACAT |
| 2129 | TCGAGCCAACATGTACTGACATG |
| 2130 | CGAGCCAACATGTACTGACATGG |
| 2131 | GAGCCAACATGTACTGACATGGA |
| 2132 | AGCCAACATGTACTGACATGGAA |
| 2133 | GCCAACATGTACTGACATGGAAA |
| 2134 | CCAACATGTACTGACATGGAAAG |
| 2135 | CAACATGTACTGACATGGAAAGA |
| 2136 | AACATGTACTGACATGGAAAGAT |
| 2137 | ACATGTACTGACATGGAAAGATG |
| 2138 | CATGTACTGACATGGAAAGATGT |
| 2139 | ATGTACTGACATGGAAAGATGTC |
| 2140 | TGTACTGACATGGAAAGATGTCA |
| 2141 | GTACTGACATGGAAAGATGTCAA |
| 2142 | TACTGACATGGAAAGATGTCAAA |
| 2143 | ACTGACATGGAAAGATGTCAAAG |
| 2144 | CTGACATGGAAAGATGTCAAAGA |
| 2145 | TGACATGGAAAGATGTCAAAGAT |
| 2146 | GACATGGAAAGATGTCAAAGATA |
| 2147 | ACATGGAAAGATGTCAAAGATAT |
| 2148 | CATGGAAAGATGTCAAAGATATG |
| 2149 | ATGGAAAGATGTCAAAGATATGT |
| 2150 | TGGAAAGATGTCAAAGATATGTT |
| 2151 | GGAAAGATGTCAAAGATATGTTA |
| 2152 | GAAAGATGTCAAAGATATGTTAA |
| 2153 | AAAGATGTCAAAGATATGTTAAG |
| 2154 | AAGATGTCAAAGATATGTTAAGT |
| 2155 | AGATGTCAAAGATATGTTAAGTG |
| 2156 | GATGTCAAAGATATGTTAAGTGT |
| 2157 | ATGTCAAAGATATGTTAAGTGTA |
| 2158 | TGTCAAAGATATGTTAAGTGTAA |
| 2159 | GTCAAAGATATGTTAAGTGTAAA |
| 2160 | TCAAAGATATGTTAAGTGTAAAA |

| ID | SEQUENCE |
|---|---|
| 2161 | CAAAGATATGTTAAGTGTAAAAT |
| 2162 | AAAGATATGTTAAGTGTAAAATG |
| 2163 | AAGATATGTTAAGTGTAAAATGC |
| 2164 | AGATATGTTAAGTGTAAAATGCA |
| 2165 | GATATGTTAAGTGTAAAATGCAA |
| 2166 | ATATGTTAAGTGTAAAATGCAAG |
| 2167 | TATGTTAAGTGTAAAATGCAAGT |
| 2168 | ATGTTAAGTGTAAAATGCAAGTG |
| 2169 | TGTTAAGTGTAAAATGCAAGTGG |
| 2170 | GTTAAGTGTAAAATGCAAGTGGC |
| 2171 | TTAAGTGTAAAATGCAAGTGGCA |
| 2172 | TAAGTGTAAAATGCAAGTGGCAA |
| 2173 | AAGTGTAAAATGCAAGTGGCAAA |
| 2174 | AGTGTAAAATGCAAGTGGCAAAA |
| 2175 | GTGTAAAATGCAAGTGGCAAAAC |
| 2176 | TGTAAAATGCAAGTGGCAAAACA |
| 2177 | GTAAAATGCAAGTGGCAAAACAC |
| 2178 | TAAAATGCAAGTGGCAAAACACT |
| 2179 | AAAATGCAAGTGGCAAAACACTA |
| 2180 | AAATGCAAGTGGCAAAACACTAT |
| 2181 | AATGCAAGTGGCAAAACACTATG |
| 2182 | ATGCAAGTGGCAAAACACTATGT |
| 2183 | TGCAAGTGGCAAAACACTATGTA |
| 2184 | GCAAGTGGCAAAACACTATGTAT |
| 2185 | CAAGTGGCAAAACACTATGTATA |
| 2186 | AAGTGGCAAAACACTATGTATAG |
| 2187 | AGTGGCAAAACACTATGTATAGT |
| 2188 | GTGGCAAAACACTATGTATAGTC |
| 2189 | TGGCAAAACACTATGTATAGTCT |
| 2190 | GGCAAAACACTATGTATAGTCTG |
| 2191 | GCAAAACACTATGTATAGTCTGA |
| 2192 | CAAAACACTATGTATAGTCTGAG |
| 2193 | AAAACACTATGTATAGTCTGAGC |
| 2194 | AAACACTATGTATAGTCTGAGCC |
| 2195 | AACACTATGTATAGTCTGAGCCA |
| 2196 | ACACTATGTATAGTCTGAGCCAG |
| 2197 | CACTATGTATAGTCTGAGCCAGA |
| 2198 | ACTATGTATAGTCTGAGCCAGAT |
| 2199 | CTATGTATAGTCTGAGCCAGATC |
| 2200 | TATGTATAGTCTGAGCCAGATCA |
| 2201 | ATGTATAGTCTGAGCCAGATCAA |
| 2202 | TGTATAGTCTGAGCCAGATCAAA |
| 2203 | GTATAGTCTGAGCCAGATCAAAG |
| 2204 | TATAGTCTGAGCCAGATCAAAGT |
| 2205 | ATAGTCTGAGCCAGATCAAAGTA |
| 2206 | TAGTCTGAGCCAGATCAAAGTAT |
| 2207 | AGTCTGAGCCAGATCAAAGTATG |
| 2208 | GTCTGAGCCAGATCAAAGTATGT |

| ID | SEQUENCE |
|---|---|
| 2209 | TCTGAGCCAGATCAAAGTATGTA |
| 2210 | CTGAGCCAGATCAAAGTATGTAT |
| 2211 | TGAGCCAGATCAAAGTATGTATG |
| 2212 | GAGCCAGATCAAAGTATGTATGT |
| 2213 | AGCCAGATCAAAGTATGTATGTT |
| 2214 | GCCAGATCAAAGTATGTATGTTT |
| 2215 | CCAGATCAAAGTATGTATGTTTT |
| 2216 | CAGATCAAAGTATGTATGTTTTT |
| 2217 | AGATCAAAGTATGTATGTTTTTA |
| 2218 | GATCAAAGTATGTATGTTTTTAA |
| 2219 | ATCAAAGTATGTATGTTTTTAAT |
| 2220 | TCAAAGTATGTATGTTTTTAATA |
| 2221 | CAAAGTATGTATGTTTTTAATAT |
| 2222 | AAAGTATGTATGTTTTTAATATG |
| 2223 | AAGTATGTATGTTTTTAATATGC |
| 2224 | AGTATGTATGTTTTTAATATGCA |
| 2225 | GTATGTATGTTTTTAATATGCAT |
| 2226 | TATGTATGTTTTTAATATGCATA |
| 2227 | ATGTATGTTTTTAATATGCATAG |
| 2228 | TGTATGTTTTTAATATGCATAGA |
| 2229 | GTATGTTTTTAATATGCATAGAA |
| 2230 | TATGTTTTTAATATGCATAGAAC |
| 2231 | ATGTTTTTAATATGCATAGAACA |
| 2232 | TGTTTTTAATATGCATAGAACAA |
| 2233 | GTTTTTAATATGCATAGAACAAA |
| 2234 | TTTTTAATATGCATAGAACAAAA |
| 2235 | TTTTAATATGCATAGAACAAAAG |
| 2236 | TTTAATATGCATAGAACAAAAGA |
| 2237 | TTAATATGCATAGAACAAAAGAT |
| 2238 | TAATATGCATAGAACAAAAGATT |
| 2239 | AATATGCATAGAACAAAAGATTT |
| 2240 | ATATGCATAGAACAAAAGATTTG |
| 2241 | TATGCATAGAACAAAAGATTTGG |
| 2242 | ATGCATAGAACAAAAGATTTGGA |
| 2243 | TGCATAGAACAAAAGATTTGGAA |
| 2244 | GCATAGAACAAAAGATTTGGAAA |
| 2245 | CATAGAACAAAAGATTTGGAAAG |
| 2246 | ATAGAACAAAAGATTTGGAAAGA |
| 2247 | TAGAACAAAAGATTTGGAAAGAT |
| 2248 | AGAACAAAAGATTTGGAAAGATA |
| 2249 | GAACAAAAGATTTGGAAAGATAT |
| 2250 | AACAAAAGATTTGGAAAGATATA |
| 2251 | ACAAAAGATTTGGAAAGATATAC |
| 2252 | CAAAAGATTTGGAAAGATATACA |
| 2253 | AAAAGATTTGGAAAGATATACAC |
| 2254 | AAAGATTTGGAAAGATATACACC |
| 2255 | AAGATTTGGAAAGATATACACCA |
| 2256 | AGATTTGGAAAGATATACACCAA |

| ID | SEQUENCE |
|---|---|
| 2257 | GATTTGGAAAGATATACACCAAA |
| 2258 | ATTTGGAAAGATATACACCAAAC |
| 2259 | TTTGGAAAGATATACACCAAACT |
| 2260 | TTGGAAAGATATACACCAAACTG |
| 2261 | TGGAAAGATATACACCAAACTGT |
| 2262 | GGAAAGATATACACCAAACTGTT |
| 2263 | GAAAGATATACACCAAACTGTTA |
| 2264 | AAAGATATACACCAAACTGTTAA |
| 2265 | AAGATATACACCAAACTGTTAAA |
| 2266 | AGATATACACCAAACTGTTAAAT |
| 2267 | GATATACACCAAACTGTTAAATG |
| 2268 | ATATACACCAAACTGTTAAATGT |
| 2269 | TATACACCAAACTGTTAAATGTG |
| 2270 | ATACACCAAACTGTTAAATGTGG |
| 2271 | TACACCAAACTGTTAAATGTGGT |
| 2272 | ACACCAAACTGTTAAATGTGGTT |
| 2273 | CACCAAACTGTTAAATGTGGTTT |
| 2274 | ACCAAACTGTTAAATGTGGTTTC |
| 2275 | CCAAACTGTTAAATGTGGTTTCT |
| 2276 | CAAACTGTTAAATGTGGTTTCTC |
| 2277 | AAACTGTTAAATGTGGTTTCTCT |
| 2278 | AACTGTTAAATGTGGTTTCTCTT |
| 2279 | ACTGTTAAATGTGGTTTCTCTTC |
| 2280 | CTGTTAAATGTGGTTTCTCTTCG |
| 2281 | TGTTAAATGTGGTTTCTCTTCGG |
| 2282 | GTTAAATGTGGTTTCTCTTCGGG |
| 2283 | TTAAATGTGGTTTCTCTTCGGGG |
| 2284 | TAAATGTGGTTTCTCTTCGGGGA |
| 2285 | AAATGTGGTTTCTCTTCGGGGAG |
| 2286 | AATGTGGTTTCTCTTCGGGGAGG |
| 2287 | ATGTGGTTTCTCTTCGGGGAGGG |
| 2288 | TGTGGTTTCTCTTCGGGGAGGGG |
| 2289 | GTGGTTTCTCTTCGGGGAGGGGG |
| 2290 | TGGTTTCTCTTCGGGGAGGGGGG |
| 2291 | GGTTTCTCTTCGGGGAGGGGGGG |
| 2292 | GTTTCTCTTCGGGGAGGGGGGGA |
| 2293 | TTTCTCTTCGGGGAGGGGGGGAT |
| 2294 | TTCTCTTCGGGGAGGGGGGGATT |
| 2295 | TCTCTTCGGGGAGGGGGGGATTG |
| 2296 | CTCTTCGGGGAGGGGGGGATTGG |
| 2297 | TCTTCGGGGAGGGGGGGATTGGG |
| 2298 | CTTCGGGGAGGGGGGGATTGGGG |
| 2299 | TTCGGGGAGGGGGGGATTGGGGG |
| 2300 | TCGGGGAGGGGGGGATTGGGGGA |
| 2301 | CGGGGAGGGGGGGATTGGGGGAG |
| 2302 | GGGGAGGGGGGGATTGGGGGAGG |
| 2303 | GGGAGGGGGGGATTGGGGGAGGG |
| 2304 | GGAGGGGGGGATTGGGGGAGGGG |

| ID | SEQUENCE |
|---|---|
| 2305 | GAGGGGGGGATTGGGGGAGGGGC |
| 2306 | AGGGGGGGATTGGGGGAGGGGCC |
| 2307 | GGGGGGGATTGGGGGAGGGGCCC |
| 2308 | GGGGGGATTGGGGGAGGGGCCCC |
| 2309 | GGGGGATTGGGGGAGGGGCCCCA |
| 2310 | GGGGATTGGGGGAGGGGCCCCAG |
| 2311 | GGGATTGGGGGAGGGGCCCCAGA |
| 2312 | GGATTGGGGGAGGGGCCCCAGAG |
| 2313 | GATTGGGGGAGGGGCCCCAGAGG |
| 2314 | ATTGGGGGAGGGGCCCCAGAGGG |
| 2315 | TTGGGGGAGGGGCCCCAGAGGGG |
| 2316 | TGGGGGAGGGGCCCCAGAGGGGT |
| 2317 | GGGGGAGGGGCCCCAGAGGGGTT |
| 2318 | GGGGAGGGGCCCCAGAGGGGTTT |
| 2319 | GGGAGGGGCCCCAGAGGGGTTTT |
| 2320 | GGAGGGGCCCCAGAGGGGTTTTA |
| 2321 | GAGGGGCCCCAGAGGGGTTTTAT |
| 2322 | AGGGGCCCCAGAGGGGTTTTATA |
| 2323 | GGGGCCCCAGAGGGGTTTTATAG |
| 2324 | GGGCCCCAGAGGGGTTTTATAGG |
| 2325 | GGCCCCAGAGGGGTTTTATAGGG |
| 2326 | GCCCCAGAGGGGTTTTATAGGGG |
| 2327 | CCCCAGAGGGGTTTTATAGGGGC |
| 2328 | CCCAGAGGGGTTTTATAGGGGCC |
| 2329 | CCAGAGGGGTTTTATAGGGGCCT |
| 2330 | CAGAGGGGTTTTATAGGGGCCTT |
| 2331 | AGAGGGGTTTTATAGGGGCCTTT |
| 2332 | GAGGGGTTTTATAGGGGCCTTTT |
| 2333 | AGGGGTTTTATAGGGGCCTTTTC |
| 2334 | GGGGTTTTATAGGGGCCTTTTCA |
| 2335 | GGGTTTTATAGGGGCCTTTTCAC |
| 2336 | GGTTTTATAGGGGCCTTTTCACT |
| 2337 | GTTTTATAGGGGCCTTTTCACTT |
| 2338 | TTTTATAGGGGCCTTTTCACTTT |
| 2339 | TTTATAGGGGCCTTTTCACTTTC |
| 2340 | TTATAGGGGCCTTTTCACTTTCT |
| 2341 | TATAGGGGCCTTTTCACTTTCTA |
| 2342 | ATAGGGGCCTTTTCACTTTCTAC |
| 2343 | TAGGGGCCTTTTCACTTTCTACT |
| 2344 | AGGGGCCTTTTCACTTTCTACTT |
| 2345 | GGGGCCTTTTCACTTTCTACTTT |
| 2346 | GGGCCTTTTCACTTTCTACTTTT |
| 2347 | GGCCTTTTCACTTTCTACTTTTT |
| 2348 | GCCTTTTCACTTTCTACTTTTTT |
| 2349 | CCTTTTCACTTTCTACTTTTTTC |
| 2350 | CTTTTCACTTTCTACTTTTTTCA |
| 2351 | TTTTCACTTTCTACTTTTTTCAT |
| 2352 | TTTCACTTTCTACTTTTTTCATT |

| ID | SEQUENCE |
|---|---|
| 2353 | TTCACTTTCTACTTTTTCATTT |
| 2354 | TCACTTTCTACTTTTTCATTTT |
| 2355 | CACTTTCTACTTTTTCATTTTG |
| 2356 | ACTTTCTACTTTTTCATTTTGT |
| 2357 | CTTTCTACTTTTTCATTTGTT |
| 2358 | TTTCTACTTTTTCATTTGTTC |
| 2359 | TTCTACTTTTTCATTTGTTCT |
| 2360 | TCTACTTTTTCATTTGTTCTG |
| 2361 | CTACTTTTTCATTTGTTCTGT |
| 2362 | TACTTTTTCATTTGTTCTGTT |
| 2363 | ACTTTTTCATTTGTTCTGTTC |
| 2364 | CTTTTTCATTTGTTCTGTTCG |
| 2365 | TTTTTCATTTGTTCTGTTCGA |
| 2366 | TTTTCATTTGTTCTGTTCGAA |
| 2367 | TTTCATTTGTTCTGTTCGAAT |
| 2368 | TTCATTTGTTCTGTTCGAATT |
| 2369 | TCATTTGTTCTGTTCGAATTT |
| 2370 | CATTTGTTCTGTTCGAATTTT |
| 2371 | ATTTGTTCTGTTCGAATTTTT |
| 2372 | TTTGTTCTGTTCGAATTTTTA |
| 2373 | TTGTTCTGTTCGAATTTTTAT |
| 2374 | TGTTCTGTTCGAATTTTTATA |
| 2375 | GTTCTGTTCGAATTTTTATAA |
| 2376 | TTCTGTTCGAATTTTTATAAG |
| 2377 | TCTGTTCGAATTTTTATAAGT |
| 2378 | CTGTTCGAATTTTTATAAGTA |
| 2379 | TGTTCGAATTTTTATAAGTAT |
| 2380 | GTTCGAATTTTTATAAGTATG |
| 2381 | TTCGAATTTTTATAAGTATGT |
| 2382 | TCGAATTTTTATAAGTATGTA |
| 2383 | CGAATTTTTATAAGTATGTAT |
| 2384 | GAATTTTTATAAGTATGTATT |
| 2385 | AATTTTTATAAGTATGTATTA |
| 2386 | ATTTTTATAAGTATGTATTAC |
| 2387 | TTTTTATAAGTATGTATTACT |
| 2388 | TTTTATAAGTATGTATTACTT |
| 2389 | TTTATAAGTATGTATTACTTT |
| 2390 | TTATAAGTATGTATTACTTTG |
| 2391 | TATAAGTATGTATTACTTTGT |
| 2392 | ATAAGTATGTATTACTTTGTA |
| 2393 | TAAGTATGTATTACTTTGTAA |
| 2394 | AAGTATGTATTACTTTGTAAT |
| 2395 | AGTATGTATTACTTTGTAATC |
| 2396 | GTATGTATTACTTTGTAATCA |
| 2397 | TATGTATTACTTTGTAATCAG |
| 2398 | ATGTATTACTTTGTAATCAGA |
| 2399 | GTATGTATTACTTTGTAATCAG |
| 2400 | TATGTATTACTTTGTAATCAGA |

| ID | SEQUENCE |
|---|---|
| 2401 | ATGTATTACTTTTGTAATCAGAA |
| 2402 | TGTATTACTTTTGTAATCAGAAT |
| 2403 | GTATTACTTTTGTAATCAGAATT |
| 2404 | TATTACTTTTGTAATCAGAATTT |
| 2405 | ATTACTTTTGTAATCAGAATTTT |
| 2406 | TTACTTTTGTAATCAGAATTTTT |
| 2407 | TACTTTTGTAATCAGAATTTTTA |
| 2408 | ACTTTTGTAATCAGAATTTTTAG |
| 2409 | CTTTTGTAATCAGAATTTTTAGA |
| 2410 | TTTTGTAATCAGAATTTTTAGAA |
| 2411 | TTTGTAATCAGAATTTTTAGAAA |
| 2412 | TTGTAATCAGAATTTTTAGAAAG |
| 2413 | TGTAATCAGAATTTTTAGAAAGT |
| 2414 | GTAATCAGAATTTTTAGAAAGTA |
| 2415 | TAATCAGAATTTTTAGAAAGTAT |
| 2416 | AATCAGAATTTTTAGAAAGTATT |
| 2417 | ATCAGAATTTTTAGAAAGTATTT |
| 2418 | TCAGAATTTTTAGAAAGTATTTT |
| 2419 | CAGAATTTTTAGAAAGTATTTTG |
| 2420 | AGAATTTTTAGAAAGTATTTTGC |
| 2421 | GAATTTTTAGAAAGTATTTTGCT |
| 2422 | AATTTTTAGAAAGTATTTTGCTG |
| 2423 | ATTTTTAGAAAGTATTTTGCTGA |
| 2424 | TTTTTAGAAAGTATTTTGCTGAT |
| 2425 | TTTTAGAAAGTATTTTGCTGATT |
| 2426 | TTTAGAAAGTATTTTGCTGATTT |
| 2427 | TTAGAAAGTATTTTGCTGATTTA |
| 2428 | TAGAAAGTATTTTGCTGATTTAA |
| 2429 | AGAAAGTATTTTGCTGATTTAAA |
| 2430 | GAAAGTATTTTGCTGATTTAAAG |
| 2431 | AAAGTATTTTGCTGATTTAAAGG |
| 2432 | AAGTATTTTGCTGATTTAAAGGC |
| 2433 | AGTATTTTGCTGATTTAAAGGCT |
| 2434 | GTATTTTGCTGATTTAAAGGCTT |
| 2435 | TATTTTGCTGATTTAAAGGCTTA |
| 2436 | ATTTTGCTGATTTAAAGGCTTAG |
| 2437 | TTTTGCTGATTTAAAGGCTTAGG |
| 2438 | TTTGCTGATTTAAAGGCTTAGGC |
| 2439 | TTGCTGATTTAAAGGCTTAGGCA |
| 2440 | TGCTGATTTAAAGGCTTAGGCAT |
| 2441 | GCTGATTTAAAGGCTTAGGCATG |
| 2442 | CTGATTTAAAGGCTTAGGCATGT |
| 2443 | TGATTTAAAGGCTTAGGCATGTT |
| 2444 | GATTTAAAGGCTTAGGCATGTTC |
| 2445 | ATTTAAAGGCTTAGGCATGTTCA |
| 2446 | TTTAAAGGCTTAGGCATGTTCAA |
| 2447 | TTAAAGGCTTAGGCATGTTCAAA |
| 2448 | TAAAGGCTTAGGCATGTTCAAAC |

| ID | SEQUENCE |
|---|---|
| 2449 | AAAGGCTTAGGCATGTTCAAACG |
| 2450 | AAGGCTTAGGCATGTTCAAACGC |
| 2451 | AGGCTTAGGCATGTTCAAACGCC |
| 2452 | GGCTTAGGCATGTTCAAACGCCT |
| 2453 | GCTTAGGCATGTTCAAACGCCTG |
| 2454 | CTTAGGCATGTTCAAACGCCTGC |
| 2455 | TTAGGCATGTTCAAACGCCTGCA |
| 2456 | TAGGCATGTTCAAACGCCTGCAA |
| 2457 | AGGCATGTTCAAACGCCTGCAAA |
| 2458 | GGCATGTTCAAACGCCTGCAAAA |
| 2459 | GCATGTTCAAACGCCTGCAAAAC |
| 2460 | CATGTTCAAACGCCTGCAAAACT |
| 2461 | ATGTTCAAACGCCTGCAAAACTA |
| 2462 | TGTTCAAACGCCTGCAAAACTAC |
| 2463 | GTTCAAACGCCTGCAAAACTACT |
| 2464 | TTCAAACGCCTGCAAAACTACTT |
| 2465 | TCAAACGCCTGCAAAACTACTTA |
| 2466 | CAAACGCCTGCAAAACTACTTAT |
| 2467 | AAACGCCTGCAAAACTACTTATC |
| 2468 | AACGCCTGCAAAACTACTTATCA |
| 2469 | ACGCCTGCAAAACTACTTATCAC |
| 2470 | CGCCTGCAAAACTACTTATCACT |
| 2471 | GCCTGCAAAACTACTTATCACTC |
| 2472 | CCTGCAAAACTACTTATCACTCA |
| 2473 | CTGCAAAACTACTTATCACTCAG |
| 2474 | TGCAAAACTACTTATCACTCAGC |
| 2475 | GCAAAACTACTTATCACTCAGCT |
| 2476 | CAAAACTACTTATCACTCAGCTT |
| 2477 | AAAACTACTTATCACTCAGCTTT |
| 2478 | AAACTACTTATCACTCAGCTTTA |
| 2479 | AACTACTTATCACTCAGCTTTAG |
| 2480 | ACTACTTATCACTCAGCTTTAGT |
| 2481 | CTACTTATCACTCAGCTTTAGTT |
| 2482 | TACTTATCACTCAGCTTTAGTTT |
| 2483 | ACTTATCACTCAGCTTTAGTTTT |
| 2484 | CTTATCACTCAGCTTTAGTTTTT |
| 2485 | TTATCACTCAGCTTTAGTTTTTC |
| 2486 | TATCACTCAGCTTTAGTTTTTCT |
| 2487 | ATCACTCAGCTTTAGTTTTTCTA |
| 2488 | TCACTCAGCTTTAGTTTTTCTAA |
| 2489 | CACTCAGCTTTAGTTTTTCTAAT |
| 2490 | ACTCAGCTTTAGTTTTTCTAATC |
| 2491 | CTCAGCTTTAGTTTTTCTAATCC |
| 2492 | TCAGCTTTAGTTTTTCTAATCCA |
| 2493 | CAGCTTTAGTTTTTCTAATCCAA |
| 2494 | AGCTTTAGTTTTTCTAATCCAAG |
| 2495 | GCTTTAGTTTTTCTAATCCAAGA |
| 2496 | CTTTAGTTTTTCTAATCCAAGAA |

| ID | SEQUENCE |
|---|---|
| 2497 | TTTAGTTTTTCTAATCCAAGAAG |
| 2498 | TTAGTTTTTCTAATCCAAGAAGG |
| 2499 | TAGTTTTTCTAATCCAAGAAGGC |
| 2500 | AGTTTTTCTAATCCAAGAAGGCA |
| 2501 | GTTTTTCTAATCCAAGAAGGCAG |
| 2502 | TTTTTCTAATCCAAGAAGGCAGG |
| 2503 | TTTTCTAATCCAAGAAGGCAGGG |
| 2504 | TTTCTAATCCAAGAAGGCAGGGC |
| 2505 | TTCTAATCCAAGAAGGCAGGGCA |
| 2506 | TCTAATCCAAGAAGGCAGGGCAG |
| 2507 | CTAATCCAAGAAGGCAGGGCAGT |
| 2508 | TAATCCAAGAAGGCAGGGCAGTT |
| 2509 | AATCCAAGAAGGCAGGGCAGTTA |
| 2510 | ATCCAAGAAGGCAGGGCAGTTAA |
| 2511 | TCCAAGAAGGCAGGGCAGTTAAC |
| 2512 | CCAAGAAGGCAGGGCAGTTAACC |
| 2513 | CAAGAAGGCAGGGCAGTTAACCT |
| 2514 | AAGAAGGCAGGGCAGTTAACCTT |
| 2515 | AGAAGGCAGGGCAGTTAACCTTT |
| 2516 | GAAGGCAGGGCAGTTAACCTTTT |
| 2517 | AAGGCAGGGCAGTTAACCTTTTT |
| 2518 | AGGCAGGGCAGTTAACCTTTTTG |
| 2519 | GGCAGGGCAGTTAACCTTTTTGG |
| 2520 | GCAGGGCAGTTAACCTTTTTGGT |
| 2521 | CAGGGCAGTTAACCTTTTTGGTG |
| 2522 | AGGGCAGTTAACCTTTTTGGTGC |
| 2523 | GGGCAGTTAACCTTTTTGGTGCC |
| 2524 | GGCAGTTAACCTTTTTGGTGCCA |
| 2525 | GCAGTTAACCTTTTTGGTGCCAA |
| 2526 | CAGTTAACCTTTTTGGTGCCAAT |
| 2527 | AGTTAACCTTTTTGGTGCCAATG |
| 2528 | GTTAACCTTTTTGGTGCCAATGT |
| 2529 | TTAACCTTTTTGGTGCCAATGTG |
| 2530 | TAACCTTTTTGGTGCCAATGTGA |
| 2531 | AACCTTTTTGGTGCCAATGTGAA |
| 2532 | ACCTTTTTGGTGCCAATGTGAAA |
| 2533 | CCTTTTTGGTGCCAATGTGAAAT |
| 2534 | CTTTTTGGTGCCAATGTGAAATG |
| 2535 | TTTTTGGTGCCAATGTGAAATGT |
| 2536 | TTTTGGTGCCAATGTGAAATGTA |
| 2537 | TTTGGTGCCAATGTGAAATGTAA |
| 2538 | TTGGTGCCAATGTGAAATGTAAA |
| 2539 | TGGTGCCAATGTGAAATGTAAAT |
| 2540 | GGTGCCAATGTGAAATGTAAATG |
| 2541 | GTGCCAATGTGAAATGTAAATGA |
| 2542 | TGCCAATGTGAAATGTAAATGAT |
| 2543 | GCCAATGTGAAATGTAAATGATT |
| 2544 | CCAATGTGAAATGTAAATGATTT |

| ID | SEQUENCE |
|---|---|
| 2545 | CAATGTGAAATGTAAATGATTTT |
| 2546 | AATGTGAAATGTAAATGATTTTA |
| 2547 | ATGTGAAATGTAAATGATTTTAT |
| 2548 | TGTGAAATGTAAATGATTTTATG |
| 2549 | GTGAAATGTAAATGATTTTATGT |
| 2550 | TGAAATGTAAATGATTTTATGTT |
| 2551 | GAAATGTAAATGATTTTATGTTT |
| 2552 | AAATGTAAATGATTTTATGTTTT |
| 2553 | AATGTAAATGATTTTATGTTTTT |
| 2554 | ATGTAAATGATTTTATGTTTTTC |
| 2555 | TGTAAATGATTTTATGTTTTTCC |
| 2556 | GTAAATGATTTTATGTTTTTCCT |
| 2557 | TAAATGATTTTATGTTTTTCCTG |
| 2558 | AAATGATTTTATGTTTTTCCTGC |
| 2559 | AATGATTTTATGTTTTTCCTGCT |
| 2560 | ATGATTTTATGTTTTTCCTGCTT |
| 2561 | TGATTTTATGTTTTTCCTGCTTT |
| 2562 | GATTTTATGTTTTTCCTGCTTTG |
| 2563 | ATTTTATGTTTTTCCTGCTTTGT |
| 2564 | TTTTATGTTTTTCCTGCTTTGTG |
| 2565 | TTTATGTTTTTCCTGCTTTGTGG |
| 2566 | TTATGTTTTTCCTGCTTTGTGGA |
| 2567 | TATGTTTTTCCTGCTTTGTGGAT |
| 2568 | ATGTTTTTCCTGCTTTGTGGATG |
| 2569 | TGTTTTTCCTGCTTTGTGGATGA |
| 2570 | GTTTTTCCTGCTTTGTGGATGAA |
| 2571 | TTTTTCCTGCTTTGTGGATGAAA |
| 2572 | TTTTCCTGCTTTGTGGATGAAAA |
| 2573 | TTTCCTGCTTTGTGGATGAAAAA |
| 2574 | TTCCTGCTTTGTGGATGAAAAAT |
| 2575 | TCCTGCTTTGTGGATGAAAAATA |
| 2576 | CCTGCTTTGTGGATGAAAAATAT |
| 2577 | CTGCTTTGTGGATGAAAAATATT |
| 2578 | TGCTTTGTGGATGAAAAATATTT |
| 2579 | GCTTTGTGGATGAAAAATATTTC |
| 2580 | CTTTGTGGATGAAAAATATTTCT |
| 2581 | TTTGTGGATGAAAAATATTTCTG |
| 2582 | TTGTGGATGAAAAATATTTCTGA |
| 2583 | TGTGGATGAAAAATATTTCTGAG |
| 2584 | GTGGATGAAAAATATTTCTGAGT |
| 2585 | TGGATGAAAAATATTTCTGAGTG |
| 2586 | GGATGAAAAATATTTCTGAGTGG |
| 2587 | GATGAAAAATATTTCTGAGTGGT |
| 2588 | ATGAAAAATATTTCTGAGTGGTA |
| 2589 | TGAAAAATATTTCTGAGTGGTAG |
| 2590 | GAAAAATATTTCTGAGTGGTAGT |
| 2591 | AAAAATATTTCTGAGTGGTAGTT |
| 2592 | AAAATATTTCTGAGTGGTAGTTT |

| ID | SEQUENCE |
|---|---|
| 2593 | AAATATTTCTGAGTGGTAGTTTT |
| 2594 | AATATTTCTGAGTGGTAGTTTTT |
| 2595 | ATATTTCTGAGTGGTAGTTTTTT |
| 2596 | TATTTCTGAGTGGTAGTTTTTTG |
| 2597 | ATTTCTGAGTGGTAGTTTTTTGA |
| 2598 | TTTCTGAGTGGTAGTTTTTTGAC |
| 2599 | TTCTGAGTGGTAGTTTTTTGACA |
| 2600 | TCTGAGTGGTAGTTTTTTGACAG |
| 2601 | CTGAGTGGTAGTTTTTTGACAGG |
| 2602 | TGAGTGGTAGTTTTTTGACAGGT |
| 2603 | GAGTGGTAGTTTTTTGACAGGTA |
| 2604 | AGTGGTAGTTTTTTGACAGGTAG |
| 2605 | GTGGTAGTTTTTTGACAGGTAGA |
| 2606 | TGGTAGTTTTTTGACAGGTAGAC |
| 2607 | GGTAGTTTTTTGACAGGTAGACC |
| 2608 | GTAGTTTTTTGACAGGTAGACCA |
| 2609 | TAGTTTTTTGACAGGTAGACCAT |
| 2610 | AGTTTTTTGACAGGTAGACCATG |
| 2611 | GTTTTTTGACAGGTAGACCATGT |
| 2612 | TTTTTTGACAGGTAGACCATGTC |
| 2613 | TTTTTGACAGGTAGACCATGTCT |
| 2614 | TTTTGACAGGTAGACCATGTCTT |
| 2615 | TTTGACAGGTAGACCATGTCTTA |
| 2616 | TTGACAGGTAGACCATGTCTTAT |
| 2617 | TGACAGGTAGACCATGTCTTATC |
| 2618 | GACAGGTAGACCATGTCTTATCT |
| 2619 | ACAGGTAGACCATGTCTTATCTT |
| 2620 | CAGGTAGACCATGTCTTATCTTG |
| 2621 | AGGTAGACCATGTCTTATCTTGT |
| 2622 | GGTAGACCATGTCTTATCTTGTT |
| 2623 | GTAGACCATGTCTTATCTTGTTT |
| 2624 | TAGACCATGTCTTATCTTGTTTC |
| 2625 | AGACCATGTCTTATCTTGTTTCA |
| 2626 | GACCATGTCTTATCTTGTTTCAA |
| 2627 | ACCATGTCTTATCTTGTTTCAAA |
| 2628 | CCATGTCTTATCTTGTTTCAAAA |
| 2629 | CATGTCTTATCTTGTTTCAAAAT |
| 2630 | ATGTCTTATCTTGTTTCAAAATA |
| 2631 | TGTCTTATCTTGTTTCAAAATAA |
| 2632 | GTCTTATCTTGTTTCAAAATAAG |
| 2633 | TCTTATCTTGTTTCAAAATAAGT |
| 2634 | CTTATCTTGTTTCAAAATAAGTA |
| 2635 | TTATCTTGTTTCAAAATAAGTAT |
| 2636 | TATCTTGTTTCAAAATAAGTATT |
| 2637 | ATCTTGTTTCAAAATAAGTATTT |
| 2638 | TCTTGTTTCAAAATAAGTATTTC |
| 2639 | CTTGTTTCAAAATAAGTATTTCT |
| 2640 | TTGTTTCAAAATAAGTATTTCTG |

| ID | SEQUENCE |
|---|---|
| 2641 | TGTTTCAAAATAAGTATTTCTGA |
| 2642 | GTTTCAAAATAAGTATTTCTGAT |
| 2643 | TTTCAAAATAAGTATTTCTGATT |
| 2644 | TTCAAAATAAGTATTTCTGATTT |
| 2645 | TCAAAATAAGTATTTCTGATTTT |
| 2646 | CAAAATAAGTATTTCTGATTTTG |
| 2647 | AAAATAAGTATTTCTGATTTTGT |
| 2648 | AAATAAGTATTTCTGATTTTGTA |
| 2649 | AATAAGTATTTCTGATTTTGTAA |
| 2650 | ATAAGTATTTCTGATTTTGTAAA |
| 2651 | TAAGTATTTCTGATTTTGTAAAA |
| 2652 | AAGTATTTCTGATTTTGTAAAAT |
| 2653 | AGTATTTCTGATTTTGTAAAATG |
| 2654 | GTATTTCTGATTTTGTAAAATGA |
| 2655 | TATTTCTGATTTTGTAAAATGAA |
| 2656 | ATTTCTGATTTTGTAAAATGAAA |
| 2657 | TTTCTGATTTTGTAAAATGAAAT |
| 2658 | TTCTGATTTTGTAAAATGAAATA |
| 2659 | TCTGATTTTGTAAAATGAAATAT |
| 2660 | CTGATTTTGTAAAATGAAATATA |
| 2661 | TGATTTTGTAAAATGAAATATAA |
| 2662 | GATTTTGTAAAATGAAATATAAA |
| 2663 | ATTTTGTAAAATGAAATATAAAA |
| 2664 | TTTTGTAAAATGAAATATAAAAT |
| 2665 | TTTGTAAAATGAAATATAAAATA |
| 2666 | TTGTAAAATGAAATATAAAATAT |
| 2667 | TGTAAAATGAAATATAAAATATG |
| 2668 | GTAAAATGAAATATAAAATATGT |
| 2669 | TAAAATGAAATATAAAATATGTC |
| 2670 | AAAATGAAATATAAAATATGTCT |
| 2671 | AAATGAAATATAAAATATGTCTC |
| 2672 | AATGAAATATAAAATATGTCTCA |
| 2673 | ATGAAATATAAAATATGTCTCAG |
| 2674 | TGAAATATAAAATATGTCTCAGA |
| 2675 | GAAATATAAAATATGTCTCAGAT |
| 2676 | AAATATAAAATATGTCTCAGATC |
| 2677 | AATATAAAATATGTCTCAGATCT |
| 2678 | ATATAAAATATGTCTCAGATCTT |
| 2679 | TATAAAATATGTCTCAGATCTTC |
| 2680 | ATAAAATATGTCTCAGATCTTCC |
| 2681 | TAAAATATGTCTCAGATCTTCCA |
| 2682 | AAAATATGTCTCAGATCTTCCAA |
| 2683 | AAATATGTCTCAGATCTTCCAAT |
| 2684 | AATATGTCTCAGATCTTCCAATT |
| 2685 | ATATGTCTCAGATCTTCCAATTA |
| 2686 | TATGTCTCAGATCTTCCAATTAA |
| 2687 | ATGTCTCAGATCTTCCAATTAAT |
| 2688 | TGTCTCAGATCTTCCAATTAATT |

| ID | SEQUENCE |
|---|---|
| 2689 | GTCTCAGATCTTCCAATTAATTA |
| 2690 | TCTCAGATCTTCCAATTAATTAG |
| 2691 | CTCAGATCTTCCAATTAATTAGT |
| 2692 | TCAGATCTTCCAATTAATTAGTA |
| 2693 | CAGATCTTCCAATTAATTAGTAA |
| 2694 | AGATCTTCCAATTAATTAGTAAG |
| 2695 | GATCTTCCAATTAATTAGTAAGG |
| 2696 | ATCTTCCAATTAATTAGTAAGGA |
| 2697 | TCTTCCAATTAATTAGTAAGGAT |
| 2698 | CTTCCAATTAATTAGTAAGGATT |
| 2699 | TTCCAATTAATTAGTAAGGATTC |
| 2700 | TCCAATTAATTAGTAAGGATTCA |
| 2701 | CCAATTAATTAGTAAGGATTCAT |
| 2702 | CAATTAATTAGTAAGGATTCATC |
| 2703 | AATTAATTAGTAAGGATTCATCC |
| 2704 | ATTAATTAGTAAGGATTCATCCT |
| 2705 | TTAATTAGTAAGGATTCATCCTT |
| 2706 | TAATTAGTAAGGATTCATCCTTA |
| 2707 | AATTAGTAAGGATTCATCCTTAA |
| 2708 | ATTAGTAAGGATTCATCCTTAAT |
| 2709 | TTAGTAAGGATTCATCCTTAATC |
| 2710 | TAGTAAGGATTCATCCTTAATCC |
| 2711 | AGTAAGGATTCATCCTTAATCCT |
| 2712 | GTAAGGATTCATCCTTAATCCTT |
| 2713 | TAAGGATTCATCCTTAATCCTTG |
| 2714 | AAGGATTCATCCTTAATCCTTGC |
| 2715 | AGGATTCATCCTTAATCCTTGCT |
| 2716 | GGATTCATCCTTAATCCTTGCTA |
| 2717 | GATTCATCCTTAATCCTTGCTAG |
| 2718 | ATTCATCCTTAATCCTTGCTAGT |
| 2719 | TTCATCCTTAATCCTTGCTAGTT |
| 2720 | TCATCCTTAATCCTTGCTAGTTT |
| 2721 | CATCCTTAATCCTTGCTAGTTTA |
| 2722 | ATCCTTAATCCTTGCTAGTTTAA |
| 2723 | TCCTTAATCCTTGCTAGTTTAAG |
| 2724 | CCTTAATCCTTGCTAGTTTAAGC |
| 2725 | CTTAATCCTTGCTAGTTTAAGCC |
| 2726 | TTAATCCTTGCTAGTTTAAGCCT |
| 2727 | TAATCCTTGCTAGTTTAAGCCTG |
| 2728 | AATCCTTGCTAGTTTAAGCCTGC |
| 2729 | ATCCTTGCTAGTTTAAGCCTGCC |
| 2730 | TCCTTGCTAGTTTAAGCCTGCCT |
| 2731 | CCTTGCTAGTTTAAGCCTGCCTA |
| 2732 | CTTGCTAGTTTAAGCCTGCCTAA |
| 2733 | TTGCTAGTTTAAGCCTGCCTAAG |
| 2734 | TGCTAGTTTAAGCCTGCCTAAGT |
| 2735 | GCTAGTTTAAGCCTGCCTAAGTC |
| 2736 | CTAGTTTAAGCCTGCCTAAGTCA |

| ID | SEQUENCE |
|---|---|
| 2737 | TAGTTTAAGCCTGCCTAAGTCAC |
| 2738 | AGTTTAAGCCTGCCTAAGTCACT |
| 2739 | GTTTAAGCCTGCCTAAGTCACTT |
| 2740 | TTTAAGCCTGCCTAAGTCACTTT |
| 2741 | TTAAGCCTGCCTAAGTCACTTTA |
| 2742 | TAAGCCTGCCTAAGTCACTTTAC |
| 2743 | AAGCCTGCCTAAGTCACTTTACT |
| 2744 | AGCCTGCCTAAGTCACTTTACTA |
| 2745 | GCCTGCCTAAGTCACTTTACTAA |
| 2746 | CCTGCCTAAGTCACTTTACTAAA |
| 2747 | CTGCCTAAGTCACTTTACTAAAA |
| 2748 | TGCCTAAGTCACTTTACTAAAAG |
| 2749 | GCCTAAGTCACTTTACTAAAAGA |
| 2750 | CCTAAGTCACTTTACTAAAAGAT |
| 2751 | CTAAGTCACTTTACTAAAAGATC |
| 2752 | TAAGTCACTTTACTAAAAGATCT |
| 2753 | AAGTCACTTTACTAAAAGATCTT |
| 2754 | AGTCACTTTACTAAAAGATCTTT |
| 2755 | GTCACTTTACTAAAAGATCTTTG |
| 2756 | TCACTTTACTAAAAGATCTTTGT |
| 2757 | CACTTTACTAAAAGATCTTTGTT |
| 2758 | ACTTTACTAAAAGATCTTTGTTA |
| 2759 | CTTTACTAAAAGATCTTTGTTAA |
| 2760 | TTTACTAAAAGATCTTTGTTAAC |
| 2761 | TTACTAAAAGATCTTTGTTAACT |
| 2762 | TACTAAAAGATCTTTGTTAACTC |
| 2763 | ACTAAAAGATCTTTGTTAACTCA |
| 2764 | CTAAAAGATCTTTGTTAACTCAG |
| 2765 | TAAAAGATCTTTGTTAACTCAGT |
| 2766 | AAAAGATCTTTGTTAACTCAGTA |
| 2767 | AAAGATCTTTGTTAACTCAGTAT |
| 2768 | AAGATCTTTGTTAACTCAGTATT |
| 2769 | AGATCTTTGTTAACTCAGTATTT |
| 2770 | GATCTTTGTTAACTCAGTATTTT |
| 2771 | ATCTTTGTTAACTCAGTATTTTA |
| 2772 | TCTTTGTTAACTCAGTATTTTAA |
| 2773 | CTTTGTTAACTCAGTATTTTAAA |
| 2774 | TTTGTTAACTCAGTATTTTAAAC |
| 2775 | TTGTTAACTCAGTATTTTAAACA |
| 2776 | TGTTAACTCAGTATTTTAAACAT |
| 2777 | GTTAACTCAGTATTTTAAACATC |
| 2778 | TTAACTCAGTATTTTAAACATCT |
| 2779 | TAACTCAGTATTTTAAACATCTG |
| 2780 | AACTCAGTATTTTAAACATCTGT |
| 2781 | ACTCAGTATTTTAAACATCTGTC |
| 2782 | CTCAGTATTTTAAACATCTGTCA |
| 2783 | TCAGTATTTTAAACATCTGTCAG |
| 2784 | CAGTATTTTAAACATCTGTCAGC |

| ID | SEQUENCE |
|---|---|
| 2785 | AGTATTTTAAACATCTGTCAGCT |
| 2786 | GTATTTTAAACATCTGTCAGCTT |
| 2787 | TATTTTAAACATCTGTCAGCTTA |
| 2788 | ATTTTAAACATCTGTCAGCTTAT |
| 2789 | TTTTAAACATCTGTCAGCTTATG |
| 2790 | TTTAAACATCTGTCAGCTTATGT |
| 2791 | TTAAACATCTGTCAGCTTATGTA |
| 2792 | TAAACATCTGTCAGCTTATGTAG |
| 2793 | AAACATCTGTCAGCTTATGTAGG |
| 2794 | AACATCTGTCAGCTTATGTAGGT |
| 2795 | ACATCTGTCAGCTTATGTAGGTA |
| 2796 | CATCTGTCAGCTTATGTAGGTAA |
| 2797 | ATCTGTCAGCTTATGTAGGTAAA |
| 2798 | TCTGTCAGCTTATGTAGGTAAAA |
| 2799 | CTGTCAGCTTATGTAGGTAAAAG |
| 2800 | TGTCAGCTTATGTAGGTAAAAGT |
| 2801 | GTCAGCTTATGTAGGTAAAAGTA |
| 2802 | TCAGCTTATGTAGGTAAAAGTAG |
| 2803 | CAGCTTATGTAGGTAAAAGTAGA |
| 2804 | AGCTTATGTAGGTAAAAGTAGAA |
| 2805 | GCTTATGTAGGTAAAAGTAGAAG |
| 2806 | CTTATGTAGGTAAAAGTAGAAGC |
| 2807 | TTATGTAGGTAAAAGTAGAAGCA |
| 2808 | TATGTAGGTAAAAGTAGAAGCAT |
| 2809 | ATGTAGGTAAAAGTAGAAGCATG |
| 2810 | TGTAGGTAAAAGTAGAAGCATGT |
| 2811 | GTAGGTAAAAGTAGAAGCATGTT |
| 2812 | TAGGTAAAAGTAGAAGCATGTTT |
| 2813 | AGGTAAAAGTAGAAGCATGTTTG |
| 2814 | GGTAAAAGTAGAAGCATGTTTGT |
| 2815 | GTAAAAGTAGAAGCATGTTTGTA |
| 2816 | TAAAAGTAGAAGCATGTTTGTAC |
| 2817 | AAAAGTAGAAGCATGTTTGTACA |
| 2818 | AAAGTAGAAGCATGTTTGTACAC |
| 2819 | AAGTAGAAGCATGTTTGTACACT |
| 2820 | AGTAGAAGCATGTTTGTACACTG |
| 2821 | GTAGAAGCATGTTTGTACACTGC |
| 2822 | TAGAAGCATGTTTGTACACTGCT |
| 2823 | AGAAGCATGTTTGTACACTGCTT |
| 2824 | GAAGCATGTTTGTACACTGCTTG |
| 2825 | AAGCATGTTTGTACACTGCTTGT |
| 2826 | AGCATGTTTGTACACTGCTTGTA |
| 2827 | GCATGTTTGTACACTGCTTGTAG |
| 2828 | CATGTTTGTACACTGCTTGTAGT |
| 2829 | ATGTTTGTACACTGCTTGTAGTT |
| 2830 | TGTTTGTACACTGCTTGTAGTTA |
| 2831 | GTTTGTACACTGCTTGTAGTTAT |
| 2832 | TTTGTACACTGCTTGTAGTTATA |

| ID | SEQUENCE |
|---|---|
| 2833 | TTGTACACTGCTTGTAGTTATAG |
| 2834 | TGTACACTGCTTGTAGTTATAGT |
| 2835 | GTACACTGCTTGTAGTTATAGTG |
| 2836 | TACACTGCTTGTAGTTATAGTGA |
| 2837 | ACACTGCTTGTAGTTATAGTGAC |
| 2838 | CACTGCTTGTAGTTATAGTGACA |
| 2839 | ACTGCTTGTAGTTATAGTGACAG |
| 2840 | CTGCTTGTAGTTATAGTGACAGC |
| 2841 | TGCTTGTAGTTATAGTGACAGCT |
| 2842 | GCTTGTAGTTATAGTGACAGCTT |
| 2843 | CTTGTAGTTATAGTGACAGCTTT |
| 2844 | TTGTAGTTATAGTGACAGCTTTC |
| 2845 | TGTAGTTATAGTGACAGCTTTCC |
| 2846 | GTAGTTATAGTGACAGCTTTCCA |
| 2847 | TAGTTATAGTGACAGCTTTCCAT |
| 2848 | AGTTATAGTGACAGCTTTCCATG |
| 2849 | GTTATAGTGACAGCTTTCCATGT |
| 2850 | TTATAGTGACAGCTTTCCATGTT |
| 2851 | TATAGTGACAGCTTTCCATGTTG |
| 2852 | ATAGTGACAGCTTTCCATGTTGA |
| 2853 | TAGTGACAGCTTTCCATGTTGAG |
| 2854 | AGTGACAGCTTTCCATGTTGAGA |
| 2855 | GTGACAGCTTTCCATGTTGAGAT |
| 2856 | TGACAGCTTTCCATGTTGAGATT |
| 2857 | GACAGCTTTCCATGTTGAGATTC |
| 2858 | ACAGCTTTCCATGTTGAGATTCT |
| 2859 | CAGCTTTCCATGTTGAGATTCTC |
| 2860 | AGCTTTCCATGTTGAGATTCTCA |
| 2861 | GCTTTCCATGTTGAGATTCTCAT |
| 2862 | CTTTCCATGTTGAGATTCTCATA |
| 2863 | TTTCCATGTTGAGATTCTCATAT |
| 2864 | TTCCATGTTGAGATTCTCATATC |
| 2865 | TCCATGTTGAGATTCTCATATCA |
| 2866 | CCATGTTGAGATTCTCATATCAT |
| 2867 | CATGTTGAGATTCTCATATCATC |
| 2868 | ATGTTGAGATTCTCATATCATCT |
| 2869 | TGTTGAGATTCTCATATCATCTT |
| 2870 | GTTGAGATTCTCATATCATCTTG |
| 2871 | TTGAGATTCTCATATCATCTTGT |
| 2872 | TGAGATTCTCATATCATCTTGTA |
| 2873 | GAGATTCTCATATCATCTTGTAT |
| 2874 | AGATTCTCATATCATCTTGTATC |
| 2875 | GATTCTCATATCATCTTGTATCT |
| 2876 | ATTCTCATATCATCTTGTATCTT |
| 2877 | TTCTCATATCATCTTGTATCTTA |
| 2878 | TCTCATATCATCTTGTATCTTAA |
| 2879 | CTCATATCATCTTGTATCTTAAA |
| 2880 | TCATATCATCTTGTATCTTAAAG |

| ID | SEQUENCE |
|---|---|
| 2881 | CATATCATCTTGTATCTTAAAGT |
| 2882 | ATATCATCTTGTATCTTAAAGTT |
| 2883 | TATCATCTTGTATCTTAAAGTTT |
| 2884 | ATCATCTTGTATCTTAAAGTTTC |
| 2885 | TCATCTTGTATCTTAAAGTTTCA |
| 2886 | CATCTTGTATCTTAAAGTTTCAT |
| 2887 | ATCTTGTATCTTAAAGTTTCATG |
| 2888 | TCTTGTATCTTAAAGTTTCATGT |
| 2889 | CTTGTATCTTAAAGTTTCATGTG |
| 2890 | TTGTATCTTAAAGTTTCATGTGA |
| 2891 | TGTATCTTAAAGTTTCATGTGAG |
| 2892 | GTATCTTAAAGTTTCATGTGAGT |
| 2893 | TATCTTAAAGTTTCATGTGAGTT |
| 2894 | ATCTTAAAGTTTCATGTGAGTTT |
| 2895 | TCTTAAAGTTTCATGTGAGTTTT |
| 2896 | CTTAAAGTTTCATGTGAGTTTTT |
| 2897 | TTAAAGTTTCATGTGAGTTTTTA |
| 2898 | TAAAGTTTCATGTGAGTTTTTAC |
| 2899 | AAAGTTTCATGTGAGTTTTTACC |
| 2900 | AAGTTTCATGTGAGTTTTTACCG |
| 2901 | AGTTTCATGTGAGTTTTTACCGT |
| 2902 | GTTTCATGTGAGTTTTTACCGTT |
| 2903 | TTTCATGTGAGTTTTTACCGTTA |
| 2904 | TTCATGTGAGTTTTTACCGTTAG |
| 2905 | TCATGTGAGTTTTTACCGTTAGG |
| 2906 | CATGTGAGTTTTTACCGTTAGGA |
| 2907 | ATGTGAGTTTTTACCGTTAGGAT |
| 2908 | TGTGAGTTTTTACCGTTAGGATG |
| 2909 | GTGAGTTTTTACCGTTAGGATGA |
| 2910 | TGAGTTTTTACCGTTAGGATGAT |
| 2911 | GAGTTTTTACCGTTAGGATGATT |
| 2912 | AGTTTTTACCGTTAGGATGATTA |
| 2913 | GTTTTTACCGTTAGGATGATTAA |
| 2914 | TTTTTACCGTTAGGATGATTAAG |
| 2915 | TTTTACCGTTAGGATGATTAAGA |
| 2916 | TTTACCGTTAGGATGATTAAGAT |
| 2917 | TTACCGTTAGGATGATTAAGATG |
| 2918 | TACCGTTAGGATGATTAAGATGT |
| 2919 | ACCGTTAGGATGATTAAGATGTA |
| 2920 | CCGTTAGGATGATTAAGATGTAT |
| 2921 | CGTTAGGATGATTAAGATGTATA |
| 2922 | GTTAGGATGATTAAGATGTATAT |
| 2923 | TTAGGATGATTAAGATGTATATA |
| 2924 | TAGGATGATTAAGATGTATATAG |
| 2925 | AGGATGATTAAGATGTATATAGG |
| 2926 | GGATGATTAAGATGTATATAGGA |
| 2927 | GATGATTAAGATGTATATAGGAC |
| 2928 | ATGATTAAGATGTATATAGGACA |

| ID | SEQUENCE |
|---|---|
| 2929 | TGATTAAGATGTATATAGGACAA |
| 2930 | GATTAAGATGTATATAGGACAAA |
| 2931 | ATTAAGATGTATATAGGACAAAA |
| 2932 | TTAAGATGTATATAGGACAAAAT |
| 2933 | TAAGATGTATATAGGACAAAATG |
| 2934 | AAGATGTATATAGGACAAAATGT |
| 2935 | AGATGTATATAGGACAAAATGTT |
| 2936 | GATGTATATAGGACAAAATGTTA |
| 2937 | ATGTATATAGGACAAAATGTTAA |
| 2938 | TGTATATAGGACAAAATGTTAAG |
| 2939 | GTATATAGGACAAAATGTTAAGT |
| 2940 | TATATAGGACAAAATGTTAAGTC |
| 2941 | ATATAGGACAAAATGTTAAGTCT |
| 2942 | TATAGGACAAAATGTTAAGTCTT |
| 2943 | ATAGGACAAAATGTTAAGTCTTT |
| 2944 | TAGGACAAAATGTTAAGTCTTTC |
| 2945 | AGGACAAAATGTTAAGTCTTTCC |
| 2946 | GGACAAAATGTTAAGTCTTTCCT |
| 2947 | GACAAAATGTTAAGTCTTTCCTC |
| 2948 | ACAAAATGTTAAGTCTTTCCTCT |
| 2949 | CAAAATGTTAAGTCTTTCCTCTA |
| 2950 | AAAATGTTAAGTCTTTCCTCTAC |
| 2951 | AAATGTTAAGTCTTTCCTCTACC |
| 2952 | AATGTTAAGTCTTTCCTCTACCT |
| 2953 | ATGTTAAGTCTTTCCTCTACCTA |
| 2954 | TGTTAAGTCTTTCCTCTACCTAC |
| 2955 | GTTAAGTCTTTCCTCTACCTACA |
| 2956 | TTAAGTCTTTCCTCTACCTACAT |
| 2957 | TAAGTCTTTCCTCTACCTACATT |
| 2958 | AAGTCTTTCCTCTACCTACATTT |
| 2959 | AGTCTTTCCTCTACCTACATTTG |
| 2960 | GTCTTTCCTCTACCTACATTTGT |
| 2961 | TCTTTCCTCTACCTACATTTGTT |
| 2962 | CTTTCCTCTACCTACATTTGTTT |
| 2963 | TTTCCTCTACCTACATTTGTTTT |
| 2964 | TTCCTCTACCTACATTTGTTTTC |
| 2965 | TCCTCTACCTACATTTGTTTTCT |
| 2966 | CCTCTACCTACATTTGTTTTCTT |
| 2967 | CTCTACCTACATTTGTTTTCTTG |
| 2968 | TCTACCTACATTTGTTTTCTTGG |
| 2969 | CTACCTACATTTGTTTTCTTGGC |
| 2970 | TACCTACATTTGTTTTCTTGGCT |
| 2971 | ACCTACATTTGTTTTCTTGGCTA |
| 2972 | CCTACATTTGTTTTCTTGGCTAG |
| 2973 | CTACATTTGTTTTCTTGGCTAGT |
| 2974 | TACATTTGTTTTCTTGGCTAGTA |
| 2975 | ACATTTGTTTTCTTGGCTAGTAA |
| 2976 | CATTTGTTTTCTTGGCTAGTAAT |

| ID | SEQUENCE |
|---|---|
| 2977 | ATTTGTTTTCTTGGCTAGTAATA |
| 2978 | TTTGTTTTCTTGGCTAGTAATAG |
| 2979 | TTGTTTTCTTGGCTAGTAATAGT |
| 2980 | TGTTTTCTTGGCTAGTAATAGTA |
| 2981 | GTTTTCTTGGCTAGTAATAGTAG |
| 2982 | TTTTCTTGGCTAGTAATAGTAGT |
| 2983 | TTTCTTGGCTAGTAATAGTAGTA |
| 2984 | TTCTTGGCTAGTAATAGTAGTAG |
| 2985 | TCTTGGCTAGTAATAGTAGTAGA |
| 2986 | CTTGGCTAGTAATAGTAGTAGAT |
| 2987 | TTGGCTAGTAATAGTAGTAGATA |
| 2988 | TGGCTAGTAATAGTAGTAGATAC |
| 2989 | GGCTAGTAATAGTAGTAGATACT |
| 2990 | GCTAGTAATAGTAGTAGATACTT |
| 2991 | CTAGTAATAGTAGTAGATACTTC |
| 2992 | TAGTAATAGTAGTAGATACTTCT |
| 2993 | AGTAATAGTAGTAGATACTTCTG |
| 2994 | GTAATAGTAGTAGATACTTCTGA |
| 2995 | TAATAGTAGTAGATACTTCTGAA |
| 2996 | AATAGTAGTAGATACTTCTGAAA |
| 2997 | ATAGTAGTAGATACTTCTGAAAT |
| 2998 | TAGTAGTAGATACTTCTGAAATA |
| 2999 | AGTAGTAGATACTTCTGAAATAA |
| 3000 | GTAGTAGATACTTCTGAAATAAA |
| 3001 | TAGTAGATACTTCTGAAATAAAT |
| 3002 | AGTAGATACTTCTGAAATAAATG |
| 3003 | GTAGATACTTCTGAAATAAATGT |
| 3004 | TAGATACTTCTGAAATAAATGTT |
| 3005 | AGATACTTCTGAAATAAATGTTC |
| 3006 | GATACTTCTGAAATAAATGTTCT |
| 3007 | ATACTTCTGAAATAAATGTTCTC |
| 3008 | TACTTCTGAAATAAATGTTCTCT |
| 3009 | ACTTCTGAAATAAATGTTCTCTC |
| 3010 | CTTCTGAAATAAATGTTCTCTCA |
| 3011 | TTCTGAAATAAATGTTCTCTCAA |
| 3012 | TCTGAAATAAATGTTCTCTCAAG |
| 3013 | CTGAAATAAATGTTCTCTCAAGA |
| 3014 | TGAAATAAATGTTCTCTCAAGAT |
| 3015 | GAAATAAATGTTCTCTCAAGATC |
| 3016 | AAATAAATGTTCTCTCAAGATCC |
| 3017 | AATAAATGTTCTCTCAAGATCCT |
| 3018 | ATAAATGTTCTCTCAAGATCCTT |
| 3019 | TAAATGTTCTCTCAAGATCCTTA |
| 3020 | AAATGTTCTCTCAAGATCCTTAA |
| 3021 | AATGTTCTCTCAAGATCCTTAAA |
| 3022 | ATGTTCTCTCAAGATCCTTAAAA |
| 3023 | TGTTCTCTCAAGATCCTTAAAAC |
| 3024 | GTTCTCTCAAGATCCTTAAAACC |

| ID | SEQUENCE |
|---|---|
| 3025 | TTCTCTCAAGATCCTTAAAACCT |
| 3026 | TCTCTCAAGATCCTTAAAACCTC |
| 3027 | CTCTCAAGATCCTTAAAACCTCT |
| 3028 | TCTCAAGATCCTTAAAACCTCTT |
| 3029 | CTCAAGATCCTTAAAACCTCTTG |
| 3030 | TCAAGATCCTTAAAACCTCTTGG |
| 3031 | CAAGATCCTTAAAACCTCTTGGA |
| 3032 | AAGATCCTTAAAACCTCTTGGAA |
| 3033 | AGATCCTTAAAACCTCTTGGAAA |
| 3034 | GATCCTTAAAACCTCTTGGAAAT |
| 3035 | ATCCTTAAAACCTCTTGGAAATT |
| 3036 | TCCTTAAAACCTCTTGGAAATTA |
| 3037 | CCTTAAAACCTCTTGGAAATTAT |
| 3038 | CTTAAAACCTCTTGGAAATTATA |
| 3039 | TTAAAACCTCTTGGAAATTATAA |
| 3040 | TAAAACCTCTTGGAAATTATAAA |
| 3041 | AAAACCTCTTGGAAATTATAAAA |
| 3042 | AAACCTCTTGGAAATTATAAAAA |
| 3043 | AACCTCTTGGAAATTATAAAAAT |
| 3044 | ACCTCTTGGAAATTATAAAAATA |
| 3045 | CCTCTTGGAAATTATAAAAATAT |
| 3046 | CTCTTGGAAATTATAAAAATATT |
| 3047 | TCTTGGAAATTATAAAAATATTG |
| 3048 | CTTGGAAATTATAAAAATATTGG |
| 3049 | TTGGAAATTATAAAAATATTGGC |
| 3050 | TGGAAATTATAAAAATATTGGCA |
| 3051 | GGAAATTATAAAAATATTGGCAA |
| 3052 | GAAATTATAAAAATATTGGCAAG |
| 3053 | AAATTATAAAAATATTGGCAAGA |
| 3054 | AATTATAAAAATATTGGCAAGAA |
| 3055 | ATTATAAAAATATTGGCAAGAAA |
| 3056 | TTATAAAAATATTGGCAAGAAAA |
| 3057 | TATAAAAATATTGGCAAGAAAAG |
| 3058 | ATAAAAATATTGGCAAGAAAAGA |
| 3059 | TAAAAATATTGGCAAGAAAAGAA |
| 3060 | AAAAATATTGGCAAGAAAAGAAG |
| 3061 | AAAATATTGGCAAGAAAAGAAGA |
| 3062 | AAATATTGGCAAGAAAAGAAGAA |
| 3063 | AATATTGGCAAGAAAAGAAGAAT |
| 3064 | ATATTGGCAAGAAAAGAAGAATA |
| 3065 | TATTGGCAAGAAAAGAAGAATAG |
| 3066 | ATTGGCAAGAAAAGAAGAATAGT |
| 3067 | TTGGCAAGAAAAGAAGAATAGTT |
| 3068 | TGGCAAGAAAAGAAGAATAGTTG |
| 3069 | GGCAAGAAAAGAAGAATAGTTGT |
| 3070 | GCAAGAAAAGAAGAATAGTTGTT |
| 3071 | CAAGAAAAGAAGAATAGTTGTTT |
| 3072 | AAGAAAAGAAGAATAGTTGTTTA |

| ID | SEQUENCE |
|---|---|
| 3073 | AGAAAAGAAGAATAGTTGTTTAA |
| 3074 | GAAAAGAAGAATAGTTGTTTAAA |
| 3075 | AAAAGAAGAATAGTTGTTTAAAT |
| 3076 | AAAGAAGAATAGTTGTTTAAATA |
| 3077 | AAGAAGAATAGTTGTTTAAATAT |
| 3078 | AGAAGAATAGTTGTTTAAATATT |
| 3079 | GAAGAATAGTTGTTTAAATATTT |
| 3080 | AAGAATAGTTGTTTAAATATTTT |
| 3081 | AGAATAGTTGTTTAAATATTTTT |
| 3082 | GAATAGTTGTTTAAATATTTTTT |
| 3083 | AATAGTTGTTTAAATATTTTTTA |
| 3084 | ATAGTTGTTTAAATATTTTTTAA |
| 3085 | TAGTTGTTTAAATATTTTTTAAA |
| 3086 | AGTTGTTTAAATATTTTTTAAAA |
| 3087 | GTTGTTTAAATATTTTTTAAAAA |
| 3088 | TTGTTTAAATATTTTTTAAAAAA |
| 3089 | TGTTTAAATATTTTTTAAAAAAC |
| 3090 | GTTTAAATATTTTTTAAAAAACA |
| 3091 | TTTAAATATTTTTTAAAAAACAC |
| 3092 | TTAAATATTTTTTAAAAAACACT |
| 3093 | TAAATATTTTTTAAAAAACACTT |
| 3094 | AAATATTTTTTAAAAAACACTTG |
| 3095 | AATATTTTTTAAAAAACACTTGA |
| 3096 | ATATTTTTTAAAAAACACTTGAA |
| 3097 | TATTTTTTAAAAAACACTTGAAT |
| 3098 | ATTTTTTAAAAAACACTTGAATA |
| 3099 | TTTTTTAAAAAACACTTGAATAA |
| 3100 | TTTTTAAAAAACACTTGAATAAG |
| 3101 | TTTTAAAAAACACTTGAATAAGA |
| 3102 | TTTAAAAAACACTTGAATAAGAA |
| 3103 | TTAAAAAACACTTGAATAAGAAT |
| 3104 | TAAAAAACACTTGAATAAGAATC |
| 3105 | AAAAAACACTTGAATAAGAATCA |
| 3106 | AAAAACACTTGAATAAGAATCAG |
| 3107 | AAAACACTTGAATAAGAATCAGT |
| 3108 | AAACACTTGAATAAGAATCAGTA |
| 3109 | AACACTTGAATAAGAATCAGTAG |
| 3110 | ACACTTGAATAAGAATCAGTAGG |
| 3111 | CACTTGAATAAGAATCAGTAGGG |
| 3112 | ACTTGAATAAGAATCAGTAGGGT |
| 3113 | CTTGAATAAGAATCAGTAGGGTA |
| 3114 | TTGAATAAGAATCAGTAGGGTAT |
| 3115 | TGAATAAGAATCAGTAGGGTATA |
| 3116 | GAATAAGAATCAGTAGGGTATAA |
| 3117 | AATAAGAATCAGTAGGGTATAAA |
| 3118 | ATAAGAATCAGTAGGGTATAAAC |
| 3119 | TAAGAATCAGTAGGGTATAAACT |
| 3120 | AAGAATCAGTAGGGTATAAACTA |

| ID | SEQUENCE |
|---|---|
| 3121 | AGAATCAGTAGGGTATAAACTAG |
| 3122 | GAATCAGTAGGGTATAAACTAGA |
| 3123 | AATCAGTAGGGTATAAACTAGAA |
| 3124 | ATCAGTAGGGTATAAACTAGAAG |
| 3125 | TCAGTAGGGTATAAACTAGAAGT |
| 3126 | CAGTAGGGTATAAACTAGAAGTT |
| 3127 | AGTAGGGTATAAACTAGAAGTTT |
| 3128 | GTAGGGTATAAACTAGAAGTTTA |
| 3129 | TAGGGTATAAACTAGAAGTTTAA |
| 3130 | AGGGTATAAACTAGAAGTTTAAA |
| 3131 | GGGTATAAACTAGAAGTTTAAAA |
| 3132 | GGTATAAACTAGAAGTTTAAAAA |
| 3133 | GTATAAACTAGAAGTTTAAAAAT |
| 3134 | TATAAACTAGAAGTTTAAAAATG |
| 3135 | ATAAACTAGAAGTTTAAAAATGC |
| 3136 | TAAACTAGAAGTTTAAAAATGCT |
| 3137 | AAACTAGAAGTTTAAAAATGCTT |
| 3138 | AACTAGAAGTTTAAAAATGCTTC |
| 3139 | ACTAGAAGTTTAAAAATGCTTCA |
| 3140 | CTAGAAGTTTAAAAATGCTTCAT |
| 3141 | TAGAAGTTTAAAAATGCTTCATA |
| 3142 | AGAAGTTTAAAAATGCTTCATAG |
| 3143 | GAAGTTTAAAAATGCTTCATAGA |
| 3144 | AAGTTTAAAAATGCTTCATAGAA |
| 3145 | AGTTTAAAAATGCTTCATAGAAC |
| 3146 | GTTTAAAAATGCTTCATAGAACG |
| 3147 | TTTAAAAATGCTTCATAGAACGT |
| 3148 | TTAAAAATGCTTCATAGAACGTC |
| 3149 | TAAAAATGCTTCATAGAACGTCC |
| 3150 | AAAAATGCTTCATAGAACGTCCA |
| 3151 | AAAATGCTTCATAGAACGTCCAG |
| 3152 | AAATGCTTCATAGAACGTCCAGG |
| 3153 | AATGCTTCATAGAACGTCCAGGG |
| 3154 | ATGCTTCATAGAACGTCCAGGGT |
| 3155 | TGCTTCATAGAACGTCCAGGGTT |
| 3156 | GCTTCATAGAACGTCCAGGGTTT |
| 3157 | CTTCATAGAACGTCCAGGGTTTA |
| 3158 | TTCATAGAACGTCCAGGGTTTAC |
| 3159 | TCATAGAACGTCCAGGGTTTACA |
| 3160 | CATAGAACGTCCAGGGTTTACAT |
| 3161 | ATAGAACGTCCAGGGTTTACATT |
| 3162 | TAGAACGTCCAGGGTTTACATTA |
| 3163 | AGAACGTCCAGGGTTTACATTAC |
| 3164 | GAACGTCCAGGGTTTACATTACA |
| 3165 | AACGTCCAGGGTTTACATTACAA |
| 3166 | ACGTCCAGGGTTTACATTACAAG |
| 3167 | CGTCCAGGGTTTACATTACAAGA |
| 3168 | GTCCAGGGTTTACATTACAAGAT |

| ID | SEQUENCE |
|---|---|
| 3169 | TCCAGGGTTTACATTACAAGATT |
| 3170 | CCAGGGTTTACATTACAAGATTC |
| 3171 | CAGGGTTTACATTACAAGATTCT |
| 3172 | AGGGTTTACATTACAAGATTCTC |
| 3173 | GGGTTTACATTACAAGATTCTCA |
| 3174 | GGTTTACATTACAAGATTCTCAC |
| 3175 | GTTTACATTACAAGATTCTCACA |
| 3176 | TTTACATTACAAGATTCTCACAA |
| 3177 | TTACATTACAAGATTCTCACAAC |
| 3178 | TACATTACAAGATTCTCACAACA |
| 3179 | ACATTACAAGATTCTCACAACAA |
| 3180 | CATTACAAGATTCTCACAACAAA |
| 3181 | ATTACAAGATTCTCACAACAAAC |
| 3182 | TTACAAGATTCTCACAACAAACC |
| 3183 | TACAAGATTCTCACAACAAACCT |
| 3184 | ACAAGATTCTCACAACAAACCTA |
| 3185 | CAAGATTCTCACAACAAACCTAT |
| 3186 | AAGATTCTCACAACAAACCTATT |
| 3187 | AGATTCTCACAACAAACCTATTG |
| 3188 | GATTCTCACAACAAACCTATTGT |
| 3189 | ATTCTCACAACAAACCTATTGTA |
| 3190 | TTCTCACAACAAACCTATTGTAG |
| 3191 | TCTCACAACAAACCTATTGTAGA |
| 3192 | CTCACAACAAACCTATTGTAGAG |
| 3193 | TCACAACAAACCTATTGTAGAGG |
| 3194 | CACAACAAACCTATTGTAGAGGT |
| 3195 | ACAACAAACCTATTGTAGAGGTG |
| 3196 | CAACAAACCTATTGTAGAGGTGA |
| 3197 | AACAAACCTATTGTAGAGGTGAG |
| 3198 | ACAAACCTATTGTAGAGGTGAGT |
| 3199 | CAAACCTATTGTAGAGGTGAGTA |
| 3200 | AAACCTATTGTAGAGGTGAGTAA |
| 3201 | AACCTATTGTAGAGGTGAGTAAG |
| 3202 | ACCTATTGTAGAGGTGAGTAAGG |
| 3203 | CCTATTGTAGAGGTGAGTAAGGC |
| 3204 | CTATTGTAGAGGTGAGTAAGGCA |
| 3205 | TATTGTAGAGGTGAGTAAGGCAT |
| 3206 | ATTGTAGAGGTGAGTAAGGCATG |
| 3207 | TTGTAGAGGTGAGTAAGGCATGT |
| 3208 | TGTAGAGGTGAGTAAGGCATGTT |
| 3209 | GTAGAGGTGAGTAAGGCATGTTA |
| 3210 | TAGAGGTGAGTAAGGCATGTTAC |
| 3211 | AGAGGTGAGTAAGGCATGTTACT |
| 3212 | GAGGTGAGTAAGGCATGTTACTA |
| 3213 | AGGTGAGTAAGGCATGTTACTAC |
| 3214 | GGTGAGTAAGGCATGTTACTACA |
| 3215 | GTGAGTAAGGCATGTTACTACAG |
| 3216 | TGAGTAAGGCATGTTACTACAGA |

| ID | SEQUENCE |
|---|---|
| 3217 | GAGTAAGGCATGTTACTACAGAG |
| 3218 | AGTAAGGCATGTTACTACAGAGG |
| 3219 | GTAAGGCATGTTACTACAGAGGA |
| 3220 | TAAGGCATGTTACTACAGAGGAA |
| 3221 | AAGGCATGTTACTACAGAGGAAA |
| 3222 | AGGCATGTTACTACAGAGGAAAG |
| 3223 | GGCATGTTACTACAGAGGAAAGT |
| 3224 | GCATGTTACTACAGAGGAAAGTT |
| 3225 | CATGTTACTACAGAGGAAAGTTT |
| 3226 | ATGTTACTACAGAGGAAAGTTTG |
| 3227 | TGTTACTACAGAGGAAAGTTTGA |
| 3228 | GTTACTACAGAGGAAAGTTTGAG |
| 3229 | TTACTACAGAGGAAAGTTTGAGA |
| 3230 | TACTACAGAGGAAAGTTTGAGAG |
| 3231 | ACTACAGAGGAAAGTTTGAGAGT |
| 3232 | CTACAGAGGAAAGTTTGAGAGTA |
| 3233 | TACAGAGGAAAGTTTGAGAGTAA |
| 3234 | ACAGAGGAAAGTTTGAGAGTAAA |
| 3235 | CAGAGGAAAGTTTGAGAGTAAAA |
| 3236 | AGAGGAAAGTTTGAGAGTAAAAC |
| 3237 | GAGGAAAGTTTGAGAGTAAAACT |
| 3238 | AGGAAAGTTTGAGAGTAAAACTG |
| 3239 | GGAAAGTTTGAGAGTAAAACTGT |
| 3240 | GAAAGTTTGAGAGTAAAACTGTA |
| 3241 | AAAGTTTGAGAGTAAAACTGTAA |
| 3242 | AAGTTTGAGAGTAAAACTGTAAA |
| 3243 | AGTTTGAGAGTAAAACTGTAAAA |
| 3244 | GTTTGAGAGTAAAACTGTAAAAA |
| 3245 | TTTGAGAGTAAAACTGTAAAAAA |
| 3246 | TTGAGAGTAAAACTGTAAAAAAT |
| 3247 | TGAGAGTAAAACTGTAAAAAATT |
| 3248 | GAGAGTAAAACTGTAAAAAATTA |
| 3249 | AGAGTAAAACTGTAAAAAATTAT |
| 3250 | GAGTAAAACTGTAAAAAATTATA |
| 3251 | AGTAAAACTGTAAAAAATTATAT |
| 3252 | GTAAAACTGTAAAAAATTATATT |
| 3253 | TAAAACTGTAAAAAATTATATTT |
| 3254 | AAAACTGTAAAAAATTATATTTT |
| 3255 | AAACTGTAAAAAATTATATTTTT |
| 3256 | AACTGTAAAAAATTATATTTTTG |
| 3257 | ACTGTAAAAAATTATATTTTTGT |
| 3258 | CTGTAAAAAATTATATTTTTGTT |
| 3259 | TGTAAAAAATTATATTTTTGTTG |
| 3260 | GTAAAAAATTATATTTTTGTTGT |
| 3261 | TAAAAAATTATATTTTTGTTGTA |
| 3262 | AAAAAATTATATTTTTGTTGTAC |
| 3263 | AAAAATTATATTTTTGTTGTACT |
| 3264 | AAAATTATATTTTTGTTGTACTT |

| ID | SEQUENCE |
|---|---|
| 3265 | AAATTATATTTTGTTGTACTTT |
| 3266 | AATTATATTTTGTTGTACTTTC |
| 3267 | ATTATATTTTGTTGTACTTTCT |
| 3268 | TTATATTTTGTTGTACTTTCTA |
| 3269 | TATATTTTGTTGTACTTTCTAA |
| 3270 | ATATTTTGTTGTACTTTCTAAG |
| 3271 | TATTTTGTTGTACTTTCTAAGA |
| 3272 | ATTTTGTTGTACTTTCTAAGAG |
| 3273 | TTTTTGTTGTACTTTCTAAGAGA |
| 3274 | TTTTGTTGTACTTTCTAAGAGAA |
| 3275 | TTTGTTGTACTTTCTAAGAGAAA |
| 3276 | TTGTTGTACTTTCTAAGAGAAAG |
| 3277 | TGTTGTACTTTCTAAGAGAAAGA |
| 3278 | GTTGTACTTTCTAAGAGAAAGAG |
| 3279 | TTGTACTTTCTAAGAGAAAGAGT |
| 3280 | TGTACTTTCTAAGAGAAAGAGTA |
| 3281 | GTACTTTCTAAGAGAAAGAGTAT |
| 3282 | TACTTTCTAAGAGAAAGAGTATT |
| 3283 | ACTTTCTAAGAGAAAGAGTATTG |
| 3284 | CTTTCTAAGAGAAAGAGTATTGT |
| 3285 | TTTCTAAGAGAAAGAGTATTGTT |
| 3286 | TTCTAAGAGAAAGAGTATTGTTA |
| 3287 | TCTAAGAGAAAGAGTATTGTTAT |
| 3288 | CTAAGAGAAAGAGTATTGTTATG |
| 3289 | TAAGAGAAAGAGTATTGTTATGT |
| 3290 | AAGAGAAAGAGTATTGTTATGTT |
| 3291 | AGAGAAAGAGTATTGTTATGTTC |
| 3292 | GAGAAAGAGTATTGTTATGTTCT |
| 3293 | AGAAAGAGTATTGTTATGTTCTC |
| 3294 | GAAAGAGTATTGTTATGTTCTCC |
| 3295 | AAAGAGTATTGTTATGTTCTCCT |
| 3296 | AAGAGTATTGTTATGTTCTCCTA |
| 3297 | AGAGTATTGTTATGTTCTCCTAA |
| 3298 | GAGTATTGTTATGTTCTCCTAAC |
| 3299 | AGTATTGTTATGTTCTCCTAACT |
| 3300 | GTATTGTTATGTTCTCCTAACTT |
| 3301 | TATTGTTATGTTCTCCTAACTTC |
| 3302 | ATTGTTATGTTCTCCTAACTTCT |
| 3303 | TTGTTATGTTCTCCTAACTTCTG |
| 3304 | TGTTATGTTCTCCTAACTTCTGT |
| 3305 | GTTATGTTCTCCTAACTTCTGTT |
| 3306 | TTATGTTCTCCTAACTTCTGTTG |
| 3307 | TATGTTCTCCTAACTTCTGTTGA |
| 3308 | ATGTTCTCCTAACTTCTGTTGAT |
| 3309 | TGTTCTCCTAACTTCTGTTGATT |
| 3310 | GTTCTCCTAACTTCTGTTGATTA |
| 3311 | TTCTCCTAACTTCTGTTGATTAC |
| 3312 | TCTCCTAACTTCTGTTGATTACT |

| ID | SEQUENCE |
|---|---|
| 3313 | CTCCTAACTTCTGTTGATTACTA |
| 3314 | TCCTAACTTCTGTTGATTACTAC |
| 3315 | CCTAACTTCTGTTGATTACTACT |
| 3316 | CTAACTTCTGTTGATTACTACTT |
| 3317 | TAACTTCTGTTGATTACTACTTT |
| 3318 | AACTTCTGTTGATTACTACTTTA |
| 3319 | ACTTCTGTTGATTACTACTTTAA |
| 3320 | CTTCTGTTGATTACTACTTTAAG |
| 3321 | TTCTGTTGATTACTACTTTAAGT |
| 3322 | TCTGTTGATTACTACTTTAAGTG |
| 3323 | CTGTTGATTACTACTTTAAGTGA |
| 3324 | TGTTGATTACTACTTTAAGTGAT |
| 3325 | GTTGATTACTACTTTAAGTGATA |
| 3326 | TTGATTACTACTTTAAGTGATAT |
| 3327 | TGATTACTACTTTAAGTGATATT |
| 3328 | GATTACTACTTTAAGTGATATTC |
| 3329 | ATTACTACTTTAAGTGATATTCA |
| 3330 | TTACTACTTTAAGTGATATTCAT |
| 3331 | TACTACTTTAAGTGATATTCATT |
| 3332 | ACTACTTTAAGTGATATTCATTT |
| 3333 | CTACTTTAAGTGATATTCATTTA |
| 3334 | TACTTTAAGTGATATTCATTTAA |
| 3335 | ACTTTAAGTGATATTCATTTAAA |
| 3336 | CTTTAAGTGATATTCATTTAAAA |
| 3337 | TTTAAGTGATATTCATTTAAAAC |
| 3338 | TTAAGTGATATTCATTTAAAACA |
| 3339 | TAAGTGATATTCATTTAAAACAT |
| 3340 | AAGTGATATTCATTTAAAACATT |
| 3341 | AGTGATATTCATTTAAAACATTG |
| 3342 | GTGATATTCATTTAAAACATTGC |
| 3343 | TGATATTCATTTAAAACATTGCA |
| 3344 | GATATTCATTTAAAACATTGCAA |
| 3345 | ATATTCATTTAAAACATTGCAAA |
| 3346 | TATTCATTTAAAACATTGCAAAT |
| 3347 | ATTCATTTAAAACATTGCAAATT |
| 3348 | TTCATTTAAAACATTGCAAATTT |
| 3349 | TCATTTAAAACATTGCAAATTTA |
| 3350 | CATTTAAAACATTGCAAATTTAT |
| 3351 | ATTTAAAACATTGCAAATTTATT |
| 3352 | TTTAAAACATTGCAAATTTATTT |
| 3353 | TTAAAACATTGCAAATTTATTTT |
| 3354 | TAAAACATTGCAAATTTATTTTA |
| 3355 | AAAACATTGCAAATTTATTTTAT |
| 3356 | AAACATTGCAAATTTATTTTATT |
| 3357 | AACATTGCAAATTTATTTTATTT |
| 3358 | ACATTGCAAATTTATTTTATTTA |
| 3359 | CATTGCAAATTTATTTTATTTAT |
| 3360 | ATTGCAAATTTATTTTATTTATT |

| ID | SEQUENCE |
|---|---|
| 3361 | TTGCAAATTTATTTTATTTATTT |
| 3362 | TGCAAATTTATTTTATTTATTTA |
| 3363 | GCAAATTTATTTTATTTATTTAA |
| 3364 | CAAATTTATTTTATTTATTTAAT |
| 3365 | AAATTTATTTTATTTATTTAATT |
| 3366 | AATTTATTTTATTTATTTAATTT |
| 3367 | ATTTATTTTATTTATTTAATTTT |
| 3368 | TTTATTTTATTTATTTAATTTTC |
| 3369 | TTATTTTATTTATTTAATTTTCT |
| 3370 | TATTTTATTTATTTAATTTTCTT |
| 3371 | ATTTTATTTATTTAATTTTCTTT |
| 3372 | TTTTATTTATTTAATTTTCTTTT |
| 3373 | TTTATTTATTTAATTTTCTTTTT |
| 3374 | TTATTTATTTAATTTTCTTTTTG |
| 3375 | TATTTATTTAATTTTCTTTTTGA |
| 3376 | ATTTATTTAATTTTCTTTTTGAG |
| 3377 | TTTATTTAATTTTCTTTTTGAGA |
| 3378 | TTATTTAATTTTCTTTTTGAGAT |
| 3379 | TATTTAATTTTCTTTTTGAGATG |
| 3380 | ATTTAATTTTCTTTTTGAGATGG |
| 3381 | TTTAATTTTCTTTTTGAGATGGA |
| 3382 | TTAATTTTCTTTTTGAGATGGAG |
| 3383 | TAATTTTCTTTTTGAGATGGAGT |
| 3384 | AATTTTCTTTTTGAGATGGAGTC |
| 3385 | ATTTTCTTTTTGAGATGGAGTCT |
| 3386 | TTTTCTTTTTGAGATGGAGTCTT |
| 3387 | TTTCTTTTTGAGATGGAGTCTTG |
| 3388 | TTCTTTTTGAGATGGAGTCTTGC |
| 3389 | TCTTTTTGAGATGGAGTCTTGCT |
| 3390 | CTTTTTGAGATGGAGTCTTGCTT |
| 3391 | TTTTTGAGATGGAGTCTTGCTTG |
| 3392 | TTTTGAGATGGAGTCTTGCTTGT |
| 3393 | TTTGAGATGGAGTCTTGCTTGTC |
| 3394 | TTGAGATGGAGTCTTGCTTGTCA |
| 3395 | TGAGATGGAGTCTTGCTTGTCAC |
| 3396 | GAGATGGAGTCTTGCTTGTCACC |
| 3397 | AGATGGAGTCTTGCTTGTCACCC |
| 3398 | GATGGAGTCTTGCTTGTCACCCA |
| 3399 | ATGGAGTCTTGCTTGTCACCCAG |
| 3400 | TGGAGTCTTGCTTGTCACCCAGG |
| 3401 | GGAGTCTTGCTTGTCACCCAGGC |
| 3402 | GAGTCTTGCTTGTCACCCAGGCT |
| 3403 | AGTCTTGCTTGTCACCCAGGCTG |
| 3404 | GTCTTGCTTGTCACCCAGGCTGG |
| 3405 | TCTTGCTTGTCACCCAGGCTGGA |
| 3406 | CTTGCTTGTCACCCAGGCTGGAG |
| 3407 | TTGCTTGTCACCCAGGCTGGAGT |
| 3408 | TGCTTGTCACCCAGGCTGGAGTG |

| ID | SEQUENCE |
|---|---|
| 3409 | GCTTGTCACCCAGGCTGGAGTGC |
| 3410 | CTTGTCACCCAGGCTGGAGTGCA |
| 3411 | TTGTCACCCAGGCTGGAGTGCAG |
| 3412 | TGTCACCCAGGCTGGAGTGCAGT |
| 3413 | GTCACCCAGGCTGGAGTGCAGTG |
| 3414 | TCACCCAGGCTGGAGTGCAGTGG |
| 3415 | CACCCAGGCTGGAGTGCAGTGGA |
| 3416 | ACCCAGGCTGGAGTGCAGTGGAG |
| 3417 | CCCAGGCTGGAGTGCAGTGGAGT |
| 3418 | CCAGGCTGGAGTGCAGTGGAGTG |
| 3419 | CAGGCTGGAGTGCAGTGGAGTGA |
| 3420 | AGGCTGGAGTGCAGTGGAGTGAT |
| 3421 | GGCTGGAGTGCAGTGGAGTGATC |
| 3422 | GCTGGAGTGCAGTGGAGTGATCT |
| 3423 | CTGGAGTGCAGTGGAGTGATCTC |
| 3424 | TGGAGTGCAGTGGAGTGATCTCT |
| 3425 | GGAGTGCAGTGGAGTGATCTCTG |
| 3426 | GAGTGCAGTGGAGTGATCTCTGC |
| 3427 | AGTGCAGTGGAGTGATCTCTGCT |
| 3428 | GTGCAGTGGAGTGATCTCTGCTC |
| 3429 | TGCAGTGGAGTGATCTCTGCTCA |
| 3430 | GCAGTGGAGTGATCTCTGCTCAC |
| 3431 | CAGTGGAGTGATCTCTGCTCACT |
| 3432 | AGTGGAGTGATCTCTGCTCACTG |
| 3433 | GTGGAGTGATCTCTGCTCACTGC |
| 3434 | TGGAGTGATCTCTGCTCACTGCA |
| 3435 | GGAGTGATCTCTGCTCACTGCAA |
| 3436 | GAGTGATCTCTGCTCACTGCAAC |
| 3437 | AGTGATCTCTGCTCACTGCAACC |
| 3438 | GTGATCTCTGCTCACTGCAACCT |
| 3439 | TGATCTCTGCTCACTGCAACCTC |
| 3440 | GATCTCTGCTCACTGCAACCTCC |
| 3441 | ATCTCTGCTCACTGCAACCTCCG |
| 3442 | TCTCTGCTCACTGCAACCTCCGC |
| 3443 | CTCTGCTCACTGCAACCTCCGCC |
| 3444 | TCTGCTCACTGCAACCTCCGCCT |
| 3445 | CTGCTCACTGCAACCTCCGCCTT |
| 3446 | TGCTCACTGCAACCTCCGCCTTC |
| 3447 | GCTCACTGCAACCTCCGCCTTCT |
| 3448 | CTCACTGCAACCTCCGCCTTCTG |
| 3449 | TCACTGCAACCTCCGCCTTCTGG |
| 3450 | CACTGCAACCTCCGCCTTCTGGG |
| 3451 | ACTGCAACCTCCGCCTTCTGGGT |
| 3452 | CTGCAACCTCCGCCTTCTGGGTT |
| 3453 | TGCAACCTCCGCCTTCTGGGTTC |
| 3454 | GCAACCTCCGCCTTCTGGGTTCA |
| 3455 | CAACCTCCGCCTTCTGGGTTCAA |
| 3456 | AACCTCCGCCTTCTGGGTTCAAG |

| ID | SEQUENCE |
|---|---|
| 3457 | ACCTCCGCCTTCTGGGTTCAAGC |
| 3458 | CCTCCGCCTTCTGGGTTCAAGCG |
| 3459 | CTCCGCCTTCTGGGTTCAAGCGA |
| 3460 | TCCGCCTTCTGGGTTCAAGCGAT |
| 3461 | CCGCCTTCTGGGTTCAAGCGATT |
| 3462 | CGCCTTCTGGGTTCAAGCGATTC |
| 3463 | GCCTTCTGGGTTCAAGCGATTCT |
| 3464 | CCTTCTGGGTTCAAGCGATTCTC |
| 3465 | CTTCTGGGTTCAAGCGATTCTCG |
| 3466 | TTCTGGGTTCAAGCGATTCTCGT |
| 3467 | TCTGGGTTCAAGCGATTCTCGTG |
| 3468 | CTGGGTTCAAGCGATTCTCGTGC |
| 3469 | TGGGTTCAAGCGATTCTCGTGCC |
| 3470 | GGGTTCAAGCGATTCTCGTGCCT |
| 3471 | GGTTCAAGCGATTCTCGTGCCTC |
| 3472 | GTTCAAGCGATTCTCGTGCCTCA |
| 3473 | TTCAAGCGATTCTCGTGCCTCAG |
| 3474 | TCAAGCGATTCTCGTGCCTCAGC |
| 3475 | CAAGCGATTCTCGTGCCTCAGCT |
| 3476 | AAGCGATTCTCGTGCCTCAGCTT |
| 3477 | AGCGATTCTCGTGCCTCAGCTTC |
| 3478 | GCGATTCTCGTGCCTCAGCTTCC |
| 3479 | CGATTCTCGTGCCTCAGCTTCCT |
| 3480 | GATTCTCGTGCCTCAGCTTCCTG |
| 3481 | ATTCTCGTGCCTCAGCTTCCTGA |
| 3482 | TTCTCGTGCCTCAGCTTCCTGAG |
| 3483 | TCTCGTGCCTCAGCTTCCTGAGT |
| 3484 | CTCGTGCCTCAGCTTCCTGAGTA |
| 3485 | TCGTGCCTCAGCTTCCTGAGTAG |
| 3486 | CGTGCCTCAGCTTCCTGAGTAGC |
| 3487 | GTGCCTCAGCTTCCTGAGTAGCT |
| 3488 | TGCCTCAGCTTCCTGAGTAGCTG |
| 3489 | GCCTCAGCTTCCTGAGTAGCTGG |
| 3490 | CCTCAGCTTCCTGAGTAGCTGGA |
| 3491 | CTCAGCTTCCTGAGTAGCTGGAA |
| 3492 | TCAGCTTCCTGAGTAGCTGGAAT |
| 3493 | CAGCTTCCTGAGTAGCTGGAATT |
| 3494 | AGCTTCCTGAGTAGCTGGAATTA |
| 3495 | GCTTCCTGAGTAGCTGGAATTAC |
| 3496 | CTTCCTGAGTAGCTGGAATTACA |
| 3497 | TTCCTGAGTAGCTGGAATTACAG |
| 3498 | TCCTGAGTAGCTGGAATTACAGG |
| 3499 | CCTGAGTAGCTGGAATTACAGGC |
| 3500 | CTGAGTAGCTGGAATTACAGGCA |
| 3501 | TGAGTAGCTGGAATTACAGGCAG |
| 3502 | GAGTAGCTGGAATTACAGGCAGG |
| 3503 | AGTAGCTGGAATTACAGGCAGGT |
| 3504 | GTAGCTGGAATTACAGGCAGGTG |

| ID | SEQUENCE |
|---|---|
| 3505 | TAGCTGGAATTACAGGCAGGTGC |
| 3506 | AGCTGGAATTACAGGCAGGTGCC |
| 3507 | GCTGGAATTACAGGCAGGTGCCA |
| 3508 | CTGGAATTACAGGCAGGTGCCAC |
| 3509 | TGGAATTACAGGCAGGTGCCACC |
| 3510 | GGAATTACAGGCAGGTGCCACCA |
| 3511 | GAATTACAGGCAGGTGCCACCAT |
| 3512 | AATTACAGGCAGGTGCCACCATG |
| 3513 | ATTACAGGCAGGTGCCACCATGC |
| 3514 | TTACAGGCAGGTGCCACCATGCC |
| 3515 | TACAGGCAGGTGCCACCATGCCC |
| 3516 | ACAGGCAGGTGCCACCATGCCCG |
| 3517 | CAGGCAGGTGCCACCATGCCCGA |
| 3518 | AGGCAGGTGCCACCATGCCCGAC |
| 3519 | GGCAGGTGCCACCATGCCCGACT |
| 3520 | GCAGGTGCCACCATGCCCGACTA |
| 3521 | CAGGTGCCACCATGCCCGACTAA |
| 3522 | AGGTGCCACCATGCCCGACTAAT |
| 3523 | GGTGCCACCATGCCCGACTAATT |
| 3524 | GTGCCACCATGCCCGACTAATTT |
| 3525 | TGCCACCATGCCCGACTAATTTT |
| 3526 | GCCACCATGCCCGACTAATTTTT |
| 3527 | CCACCATGCCCGACTAATTTTTT |
| 3528 | CACCATGCCCGACTAATTTTTTT |
| 3529 | ACCATGCCCGACTAATTTTTTTT |
| 3530 | TTTTTTTATTTTTAGTAGAGAC |
| 3531 | TTTTTTATTTTTAGTAGAGACG |
| 3532 | TTTTTATTTTTAGTAGAGACGG |
| 3533 | TTTTTATTTTAGTAGAGACGGG |
| 3534 | TTTTATTTTAGTAGAGACGGGG |
| 3535 | TTTATTTTTAGTAGAGACGGGGT |
| 3536 | TTATTTTTAGTAGAGACGGGGTT |
| 3537 | TATTTTTAGTAGAGACGGGGTTT |
| 3538 | ATTTTTAGTAGAGACGGGGTTTC |
| 3539 | TTTTTAGTAGAGACGGGGTTTCA |
| 3540 | TTTTAGTAGAGACGGGGTTTCAC |
| 3541 | TTTAGTAGAGACGGGGTTTCACC |
| 3542 | TTAGTAGAGACGGGGTTTCACCA |
| 3543 | TAGTAGAGACGGGGTTTCACCAT |
| 3544 | AGTAGAGACGGGGTTTCACCATG |
| 3545 | GTAGAGACGGGGTTTCACCATGT |
| 3546 | TAGAGACGGGGTTTCACCATGTT |
| 3547 | AGAGACGGGGTTTCACCATGTTG |
| 3548 | GAGACGGGGTTTCACCATGTTGG |
| 3549 | AGACGGGGTTTCACCATGTTGGC |
| 3550 | GACGGGGTTTCACCATGTTGGCC |
| 3551 | ACGGGGTTTCACCATGTTGGCCA |
| 3552 | CGGGGTTTCACCATGTTGGCCAG |

| ID | SEQUENCE |
|---|---|
| 3553 | GGGGTTTCACCATGTTGGCCAGG |
| 3554 | GGGTTTCACCATGTTGGCCAGGC |
| 3555 | GGTTTCACCATGTTGGCCAGGCT |
| 3556 | GTTTCACCATGTTGGCCAGGCTG |
| 3557 | TTTCACCATGTTGGCCAGGCTGG |
| 3558 | TTCACCATGTTGGCCAGGCTGGT |
| 3559 | TCACCATGTTGGCCAGGCTGGTA |
| 3560 | CACCATGTTGGCCAGGCTGGTAT |
| 3561 | ACCATGTTGGCCAGGCTGGTATC |
| 3562 | CCATGTTGGCCAGGCTGGTATCA |
| 3563 | CATGTTGGCCAGGCTGGTATCAA |
| 3564 | ATGTTGGCCAGGCTGGTATCAAA |
| 3565 | TGTTGGCCAGGCTGGTATCAAAC |
| 3566 | GTTGGCCAGGCTGGTATCAAACT |
| 3567 | TTGGCCAGGCTGGTATCAAACTC |
| 3568 | TGGCCAGGCTGGTATCAAACTCC |
| 3569 | GGCCAGGCTGGTATCAAACTCCT |
| 3570 | GCCAGGCTGGTATCAAACTCCTG |
| 3571 | CCAGGCTGGTATCAAACTCCTGA |
| 3572 | CAGGCTGGTATCAAACTCCTGAC |
| 3573 | AGGCTGGTATCAAACTCCTGACC |
| 3574 | GGCTGGTATCAAACTCCTGACCT |
| 3575 | GCTGGTATCAAACTCCTGACCTC |
| 3576 | CTGGTATCAAACTCCTGACCTCA |
| 3577 | TGGTATCAAACTCCTGACCTCAA |
| 3578 | GGTATCAAACTCCTGACCTCAAG |
| 3579 | GTATCAAACTCCTGACCTCAAGA |
| 3580 | TATCAAACTCCTGACCTCAAGAG |
| 3581 | ATCAAACTCCTGACCTCAAGAGA |
| 3582 | TCAAACTCCTGACCTCAAGAGAT |
| 3583 | CAAACTCCTGACCTCAAGAGATC |
| 3584 | AAACTCCTGACCTCAAGAGATCC |
| 3585 | AACTCCTGACCTCAAGAGATCCA |
| 3586 | ACTCCTGACCTCAAGAGATCCAC |
| 3587 | CTCCTGACCTCAAGAGATCCACT |
| 3588 | TCCTGACCTCAAGAGATCCACTC |
| 3589 | CCTGACCTCAAGAGATCCACTCG |
| 3590 | CTGACCTCAAGAGATCCACTCGC |
| 3591 | TGACCTCAAGAGATCCACTCGCC |
| 3592 | GACCTCAAGAGATCCACTCGCCT |
| 3593 | ACCTCAAGAGATCCACTCGCCTT |
| 3594 | CCTCAAGAGATCCACTCGCCTTG |
| 3595 | CTCAAGAGATCCACTCGCCTTGC |
| 3596 | TCAAGAGATCCACTCGCCTTGCC |
| 3597 | CAAGAGATCCACTCGCCTTGCCC |
| 3598 | AAGAGATCCACTCGCCTTGCCCT |
| 3599 | AGAGATCCACTCGCCTTGCCCTC |
| 3600 | GAGATCCACTCGCCTTGCCCTCC |

| ID | SEQUENCE |
|---|---|
| 3601 | AGATCCACTCGCCTTGCCCTCCC |
| 3602 | GATCCACTCGCCTTGCCCTCCCA |
| 3603 | ATCCACTCGCCTTGCCCTCCCAA |
| 3604 | TCCACTCGCCTTGCCCTCCCAAA |
| 3605 | CCACTCGCCTTGCCCTCCCAAAG |
| 3606 | CACTCGCCTTGCCCTCCCAAAGT |
| 3607 | ACTCGCCTTGCCCTCCCAAAGTG |
| 3608 | CTCGCCTTGCCCTCCCAAAGTGC |
| 3609 | TCGCCTTGCCCTCCCAAAGTGCT |
| 3610 | CGCCTTGCCCTCCCAAAGTGCTG |
| 3611 | GCCTTGCCCTCCCAAAGTGCTGG |
| 3612 | CCTTGCCCTCCCAAAGTGCTGGG |
| 3613 | CTTGCCCTCCCAAAGTGCTGGGA |
| 3614 | TTGCCCTCCCAAAGTGCTGGGAT |
| 3615 | TGCCCTCCCAAAGTGCTGGGATT |
| 3616 | GCCCTCCCAAAGTGCTGGGATTA |
| 3617 | CCCTCCCAAAGTGCTGGGATTAC |
| 3618 | CCTCCCAAAGTGCTGGGATTACA |
| 3619 | CTCCCAAAGTGCTGGGATTACAG |
| 3620 | TCCCAAAGTGCTGGGATTACAGG |
| 3621 | CCCAAAGTGCTGGGATTACAGGC |
| 3622 | CCAAAGTGCTGGGATTACAGGCT |
| 3623 | CAAAGTGCTGGGATTACAGGCTT |
| 3624 | AAAGTGCTGGGATTACAGGCTTG |
| 3625 | AAGTGCTGGGATTACAGGCTTGA |
| 3626 | AGTGCTGGGATTACAGGCTTGAG |
| 3627 | GTGCTGGGATTACAGGCTTGAGC |
| 3628 | TGCTGGGATTACAGGCTTGAGCC |
| 3629 | GCTGGGATTACAGGCTTGAGCCA |
| 3630 | CTGGGATTACAGGCTTGAGCCAC |
| 3631 | TGGGATTACAGGCTTGAGCCACC |
| 3632 | GGGATTACAGGCTTGAGCCACCA |
| 3633 | GGATTACAGGCTTGAGCCACCAC |
| 3634 | GATTACAGGCTTGAGCCACCACG |
| 3635 | ATTACAGGCTTGAGCCACCACGC |
| 3636 | TTACAGGCTTGAGCCACCACGCC |
| 3637 | TACAGGCTTGAGCCACCACGCCC |
| 3638 | ACAGGCTTGAGCCACCACGCCCG |
| 3639 | CAGGCTTGAGCCACCACGCCCGG |
| 3640 | AGGCTTGAGCCACCACGCCCGGC |
| 3641 | GGCTTGAGCCACCACGCCCGGCT |
| 3642 | GCTTGAGCCACCACGCCCGGCTA |
| 3643 | CTTGAGCCACCACGCCCGGCTAA |
| 3644 | TTGAGCCACCACGCCCGGCTAAA |
| 3645 | TGAGCCACCACGCCCGGCTAAAA |
| 3646 | GAGCCACCACGCCCGGCTAAAAC |
| 3647 | AGCCACCACGCCCGGCTAAAACA |
| 3648 | GCCACCACGCCCGGCTAAAACAT |

| ID | SEQUENCE |
|---|---|
| 3649 | CCACCACGCCCGGCTAAAACATT |
| 3650 | CACCACGCCCGGCTAAAACATTG |
| 3651 | ACCACGCCCGGCTAAAACATTGC |
| 3652 | CCACGCCCGGCTAAAACATTGCA |
| 3653 | CACGCCCGGCTAAAACATTGCAA |
| 3654 | ACGCCCGGCTAAAACATTGCAAA |
| 3655 | CGCCCGGCTAAAACATTGCAAAT |
| 3656 | GCCCGGCTAAAACATTGCAAATT |
| 3657 | CCCGGCTAAAACATTGCAAATTT |
| 3658 | CCGGCTAAAACATTGCAAATTTA |
| 3659 | CGGCTAAAACATTGCAAATTTAA |
| 3660 | GGCTAAAACATTGCAAATTTAAA |
| 3661 | GCTAAAACATTGCAAATTTAAAT |
| 3662 | CTAAAACATTGCAAATTTAAATG |
| 3663 | TAAAACATTGCAAATTTAAATGA |
| 3664 | AAAACATTGCAAATTTAAATGAG |
| 3665 | AAACATTGCAAATTTAAATGAGA |
| 3666 | AACATTGCAAATTTAAATGAGAG |
| 3667 | ACATTGCAAATTTAAATGAGAGT |
| 3668 | CATTGCAAATTTAAATGAGAGTT |
| 3669 | ATTGCAAATTTAAATGAGAGTTT |
| 3670 | TTGCAAATTTAAATGAGAGTTTT |
| 3671 | TGCAAATTTAAATGAGAGTTTTA |
| 3672 | GCAAATTTAAATGAGAGTTTTAA |
| 3673 | CAAATTTAAATGAGAGTTTTAAA |
| 3674 | AAATTTAAATGAGAGTTTTAAAA |
| 3675 | AATTTAAATGAGAGTTTTAAAAA |
| 3676 | ATTTAAATGAGAGTTTTAAAAAT |
| 3677 | TTTAAATGAGAGTTTTAAAAATT |
| 3678 | TTAAATGAGAGTTTTAAAAATTA |
| 3679 | TAAATGAGAGTTTTAAAAATTAA |
| 3680 | AAATGAGAGTTTTAAAAATTAAA |
| 3681 | AATGAGAGTTTTAAAAATTAAAT |
| 3682 | ATGAGAGTTTTAAAAATTAAATA |
| 3683 | TGAGAGTTTTAAAAATTAAATAA |
| 3684 | GAGAGTTTTAAAAATTAAATAAT |
| 3685 | AGAGTTTTAAAAATTAAATAATG |
| 3686 | GAGTTTTAAAAATTAAATAATGA |
| 3687 | AGTTTTAAAAATTAAATAATGAC |
| 3688 | GTTTTAAAAATTAAATAATGACT |
| 3689 | TTTTAAAAATTAAATAATGACTG |
| 3690 | TTTAAAAATTAAATAATGACTGC |
| 3691 | TTAAAAATTAAATAATGACTGCC |
| 3692 | TAAAAATTAAATAATGACTGCCC |
| 3693 | AAAAATTAAATAATGACTGCCCT |
| 3694 | AAAATTAAATAATGACTGCCCTG |
| 3695 | AAATTAAATAATGACTGCCCTGT |
| 3696 | AATTAAATAATGACTGCCCTGTT |

| ID | SEQUENCE |
|---|---|
| 3697 | ATTAAATAATGACTGCCCTGTTT |
| 3698 | TTAAATAATGACTGCCCTGTTTC |
| 3699 | TAAATAATGACTGCCCTGTTTCT |
| 3700 | AAATAATGACTGCCCTGTTTCTG |
| 3701 | AATAATGACTGCCCTGTTTCTGT |
| 3702 | ATAATGACTGCCCTGTTTCTGTT |
| 3703 | TAATGACTGCCCTGTTTCTGTTT |
| 3704 | AATGACTGCCCTGTTTCTGTTTT |
| 3705 | ATGACTGCCCTGTTTCTGTTTTA |
| 3706 | TGACTGCCCTGTTTCTGTTTTAG |
| 3707 | GACTGCCCTGTTTCTGTTTTAGT |
| 3708 | ACTGCCCTGTTTCTGTTTTAGTA |
| 3709 | CTGCCCTGTTTCTGTTTTAGTAT |
| 3710 | TGCCCTGTTTCTGTTTTAGTATG |
| 3711 | GCCCTGTTTCTGTTTTAGTATGT |
| 3712 | CCCTGTTTCTGTTTTAGTATGTA |
| 3713 | CCTGTTTCTGTTTTAGTATGTAA |
| 3714 | CTGTTTCTGTTTTAGTATGTAAA |
| 3715 | TGTTTCTGTTTTAGTATGTAAAT |
| 3716 | GTTTCTGTTTTAGTATGTAAATC |
| 3717 | TTTCTGTTTTAGTATGTAAATCC |
| 3718 | TTCTGTTTTAGTATGTAAATCCT |
| 3719 | TCTGTTTTAGTATGTAAATCCTC |
| 3720 | CTGTTTTAGTATGTAAATCCTCA |
| 3721 | TGTTTTAGTATGTAAATCCTCAG |
| 3722 | GTTTTAGTATGTAAATCCTCAGT |
| 3723 | TTTTAGTATGTAAATCCTCAGTT |
| 3724 | TTTAGTATGTAAATCCTCAGTTC |
| 3725 | TTAGTATGTAAATCCTCAGTTCT |
| 3726 | TAGTATGTAAATCCTCAGTTCTT |
| 3727 | AGTATGTAAATCCTCAGTTCTTC |
| 3728 | GTATGTAAATCCTCAGTTCTTCA |
| 3729 | TATGTAAATCCTCAGTTCTTCAC |
| 3730 | ATGTAAATCCTCAGTTCTTCACC |
| 3731 | TGTAAATCCTCAGTTCTTCACCT |
| 3732 | GTAAATCCTCAGTTCTTCACCTT |
| 3733 | TAAATCCTCAGTTCTTCACCTTT |
| 3734 | AAATCCTCAGTTCTTCACCTTTG |
| 3735 | AATCCTCAGTTCTTCACCTTTGC |
| 3736 | ATCCTCAGTTCTTCACCTTTGCA |
| 3737 | TCCTCAGTTCTTCACCTTTGCAC |
| 3738 | CCTCAGTTCTTCACCTTTGCACT |
| 3739 | CTCAGTTCTTCACCTTTGCACTG |
| 3740 | TCAGTTCTTCACCTTTGCACTGT |
| 3741 | CAGTTCTTCACCTTTGCACTGTC |
| 3742 | AGTTCTTCACCTTTGCACTGTCT |
| 3743 | GTTCTTCACCTTTGCACTGTCTG |
| 3744 | TTCTTCACCTTTGCACTGTCTGC |

| ID | SEQUENCE |
|---|---|
| 3745 | TCTTCACCTTTGCACTGTCTGCC |
| 3746 | CTTCACCTTTGCACTGTCTGCCA |
| 3747 | TTCACCTTTGCACTGTCTGCCAC |
| 3748 | TCACCTTTGCACTGTCTGCCACT |
| 3749 | CACCTTTGCACTGTCTGCCACTT |
| 3750 | ACCTTTGCACTGTCTGCCACTTA |
| 3751 | CCTTTGCACTGTCTGCCACTTAG |
| 3752 | CTTTGCACTGTCTGCCACTTAGT |
| 3753 | TTTGCACTGTCTGCCACTTAGTT |
| 3754 | TTGCACTGTCTGCCACTTAGTTT |
| 3755 | TGCACTGTCTGCCACTTAGTTTG |
| 3756 | GCACTGTCTGCCACTTAGTTTGG |
| 3757 | CACTGTCTGCCACTTAGTTTGGT |
| 3758 | ACTGTCTGCCACTTAGTTTGGTT |
| 3759 | CTGTCTGCCACTTAGTTTGGTTA |
| 3760 | TGTCTGCCACTTAGTTTGGTTAT |
| 3761 | GTCTGCCACTTAGTTTGGTTATA |
| 3762 | TCTGCCACTTAGTTTGGTTATAT |
| 3763 | CTGCCACTTAGTTTGGTTATATA |
| 3764 | TGCCACTTAGTTTGGTTATATAG |
| 3765 | GCCACTTAGTTTGGTTATATAGT |
| 3766 | CCACTTAGTTTGGTTATATAGTC |
| 3767 | CACTTAGTTTGGTTATATAGTCA |
| 3768 | ACTTAGTTTGGTTATATAGTCAT |
| 3769 | CTTAGTTTGGTTATATAGTCATT |
| 3770 | TTAGTTTGGTTATATAGTCATTA |
| 3771 | TAGTTTGGTTATATAGTCATTAA |
| 3772 | AGTTTGGTTATATAGTCATTAAC |
| 3773 | GTTTGGTTATATAGTCATTAACT |
| 3774 | TTTGGTTATATAGTCATTAACTT |
| 3775 | TTGGTTATATAGTCATTAACTTG |
| 3776 | TGGTTATATAGTCATTAACTTGA |
| 3777 | GGTTATATAGTCATTAACTTGAA |
| 3778 | GTTATATAGTCATTAACTTGAAT |
| 3779 | TTATATAGTCATTAACTTGAATT |
| 3780 | TATATAGTCATTAACTTGAATTT |
| 3781 | ATATAGTCATTAACTTGAATTTG |
| 3782 | TATAGTCATTAACTTGAATTTGG |
| 3783 | ATAGTCATTAACTTGAATTTGGT |
| 3784 | TAGTCATTAACTTGAATTTGGTC |
| 3785 | AGTCATTAACTTGAATTTGGTCT |
| 3786 | GTCATTAACTTGAATTTGGTCTG |
| 3787 | TCATTAACTTGAATTTGGTCTGT |
| 3788 | CATTAACTTGAATTTGGTCTGTA |
| 3789 | ATTAACTTGAATTTGGTCTGTAT |
| 3790 | TTAACTTGAATTTGGTCTGTATA |
| 3791 | TAACTTGAATTTGGTCTGTATAG |
| 3792 | AACTTGAATTTGGTCTGTATAGT |

| ID | SEQUENCE |
|---|---|
| 3793 | ACTTGAATTTGGTCTGTATAGTC |
| 3794 | CTTGAATTTGGTCTGTATAGTCT |
| 3795 | TTGAATTTGGTCTGTATAGTCTA |
| 3796 | TGAATTTGGTCTGTATAGTCTAG |
| 3797 | GAATTTGGTCTGTATAGTCTAGA |
| 3798 | AATTTGGTCTGTATAGTCTAGAC |
| 3799 | ATTTGGTCTGTATAGTCTAGACT |
| 3800 | TTTGGTCTGTATAGTCTAGACTT |
| 3801 | TTGGTCTGTATAGTCTAGACTTT |
| 3802 | TGGTCTGTATAGTCTAGACTTTA |
| 3803 | GGTCTGTATAGTCTAGACTTTAA |
| 3804 | GTCTGTATAGTCTAGACTTTAAA |
| 3805 | TCTGTATAGTCTAGACTTTAAAT |
| 3806 | CTGTATAGTCTAGACTTTAAATT |
| 3807 | TGTATAGTCTAGACTTTAAATTT |
| 3808 | GTATAGTCTAGACTTTAAATTTA |
| 3809 | TATAGTCTAGACTTTAAATTTAA |
| 3810 | ATAGTCTAGACTTTAAATTTAAA |
| 3811 | TAGTCTAGACTTTAAATTTAAAG |
| 3812 | AGTCTAGACTTTAAATTTAAAGT |
| 3813 | GTCTAGACTTTAAATTTAAAGTT |
| 3814 | TCTAGACTTTAAATTTAAAGTTT |
| 3815 | CTAGACTTTAAATTTAAAGTTTT |
| 3816 | TAGACTTTAAATTTAAAGTTTTC |
| 3817 | AGACTTTAAATTTAAAGTTTTCT |
| 3818 | GACTTTAAATTTAAAGTTTTCTA |
| 3819 | ACTTTAAATTTAAAGTTTTCTAC |
| 3820 | CTTTAAATTTAAAGTTTTCTACA |
| 3821 | TTTAAATTTAAAGTTTTCTACAA |
| 3822 | TTAAATTTAAAGTTTTCTACAAG |
| 3823 | TAAATTTAAAGTTTTCTACAAGG |
| 3824 | AAATTTAAAGTTTTCTACAAGGG |
| 3825 | AATTTAAAGTTTTCTACAAGGGG |
| 3826 | ATTTAAAGTTTTCTACAAGGGGA |
| 3827 | TTTAAAGTTTTCTACAAGGGGAG |
| 3828 | TTAAAGTTTTCTACAAGGGGAGA |
| 3829 | TAAAGTTTTCTACAAGGGGAGAA |
| 3830 | AAAGTTTTCTACAAGGGGAGAAA |
| 3831 | AAGTTTTCTACAAGGGGAGAAAA |
| 3832 | AGTTTTCTACAAGGGGAGAAAAG |
| 3833 | GTTTTCTACAAGGGGAGAAAAGT |
| 3834 | TTTTCTACAAGGGGAGAAAAGTG |
| 3835 | TTTCTACAAGGGGAGAAAAGTGT |
| 3836 | TTCTACAAGGGGAGAAAAGTGTT |
| 3837 | TCTACAAGGGGAGAAAAGTGTTA |
| 3838 | CTACAAGGGGAGAAAAGTGTTAA |
| 3839 | TACAAGGGGAGAAAAGTGTTAAA |
| 3840 | ACAAGGGGAGAAAAGTGTTAAAA |

| ID | SEQUENCE |
|---|---|
| 3841 | CAAGGGGAGAAAAGTGTTAAAAT |
| 3842 | AAGGGGAGAAAAGTGTTAAAATT |
| 3843 | AGGGGAGAAAAGTGTTAAAATTT |
| 3844 | GGGGAGAAAAGTGTTAAAATTTT |
| 3845 | GGGAGAAAAGTGTTAAAATTTTT |
| 3846 | GGAGAAAAGTGTTAAAATTTTTA |
| 3847 | GAGAAAAGTGTTAAAATTTTTAA |
| 3848 | AGAAAAGTGTTAAAATTTTTAAA |
| 3849 | GAAAAGTGTTAAAATTTTTAAAA |
| 3850 | AAAAGTGTTAAAATTTTTAAAAT |
| 3851 | AAAGTGTTAAAATTTTTAAAATA |
| 3852 | AAGTGTTAAAATTTTTAAAATAT |
| 3853 | AGTGTTAAAATTTTTAAAATATG |
| 3854 | GTGTTAAAATTTTTAAAATATGT |
| 3855 | TGTTAAAATTTTTAAAATATGTT |
| 3856 | GTTAAAATTTTTAAAATATGTTT |
| 3857 | TTAAAATTTTTAAAATATGTTTT |
| 3858 | TAAAATTTTTAAAATATGTTTTC |
| 3859 | AAAATTTTTAAAATATGTTTTCC |
| 3860 | AAATTTTTAAAATATGTTTTCCA |
| 3861 | AATTTTTAAAATATGTTTTCCAG |
| 3862 | ATTTTTAAAATATGTTTTCCAGG |
| 3863 | TTTTTAAAATATGTTTTCCAGGA |
| 3864 | TTTTAAAATATGTTTTCCAGGAC |
| 3865 | TTTAAAATATGTTTTCCAGGACA |
| 3866 | TTAAAATATGTTTTCCAGGACAC |
| 3867 | TAAAATATGTTTTCCAGGACACT |
| 3868 | AAAATATGTTTTCCAGGACACTT |
| 3869 | AAATATGTTTTCCAGGACACTTC |
| 3870 | AATATGTTTTCCAGGACACTTCA |
| 3871 | ATATGTTTTCCAGGACACTTCAC |
| 3872 | TATGTTTTCCAGGACACTTCACT |
| 3873 | ATGTTTTCCAGGACACTTCACTT |
| 3874 | TGTTTTCCAGGACACTTCACTTC |
| 3875 | GTTTTCCAGGACACTTCACTTCC |
| 3876 | TTTTCCAGGACACTTCACTTCCA |
| 3877 | TTTCCAGGACACTTCACTTCCAA |
| 3878 | TTCCAGGACACTTCACTTCCAAG |
| 3879 | TCCAGGACACTTCACTTCCAAGT |
| 3880 | CCAGGACACTTCACTTCCAAGTC |
| 3881 | CAGGACACTTCACTTCCAAGTCA |
| 3882 | AGGACACTTCACTTCCAAGTCAG |
| 3883 | GGACACTTCACTTCCAAGTCAGG |
| 3884 | GACACTTCACTTCCAAGTCAGGT |
| 3885 | ACACTTCACTTCCAAGTCAGGTA |
| 3886 | CACTTCACTTCCAAGTCAGGTAG |
| 3887 | ACTTCACTTCCAAGTCAGGTAGG |
| 3888 | CTTCACTTCCAAGTCAGGTAGGT |

| ID | SEQUENCE |
|---|---|
| 3889 | TTCACTTCCAAGTCAGGTAGGTA |
| 3890 | TCACTTCCAAGTCAGGTAGGTAG |
| 3891 | CACTTCCAAGTCAGGTAGGTAGT |
| 3892 | ACTTCCAAGTCAGGTAGGTAGTT |
| 3893 | CTTCCAAGTCAGGTAGGTAGTTC |
| 3894 | TTCCAAGTCAGGTAGGTAGTTCA |
| 3895 | TCCAAGTCAGGTAGGTAGTTCAA |
| 3896 | CCAAGTCAGGTAGGTAGTTCAAT |
| 3897 | CAAGTCAGGTAGGTAGTTCAATC |
| 3898 | AAGTCAGGTAGGTAGTTCAATCT |
| 3899 | AGTCAGGTAGGTAGTTCAATCTA |
| 3900 | GTCAGGTAGGTAGTTCAATCTAG |
| 3901 | TCAGGTAGGTAGTTCAATCTAGT |
| 3902 | CAGGTAGGTAGTTCAATCTAGTT |
| 3903 | AGGTAGGTAGTTCAATCTAGTTG |
| 3904 | GGTAGGTAGTTCAATCTAGTTGT |
| 3905 | GTAGGTAGTTCAATCTAGTTGTT |
| 3906 | TAGGTAGTTCAATCTAGTTGTTA |
| 3907 | AGGTAGTTCAATCTAGTTGTTAG |
| 3908 | GGTAGTTCAATCTAGTTGTTAGC |
| 3909 | GTAGTTCAATCTAGTTGTTAGCC |
| 3910 | TAGTTCAATCTAGTTGTTAGCCA |
| 3911 | AGTTCAATCTAGTTGTTAGCCAA |
| 3912 | GTTCAATCTAGTTGTTAGCCAAG |
| 3913 | TTCAATCTAGTTGTTAGCCAAGG |
| 3914 | TCAATCTAGTTGTTAGCCAAGGA |
| 3915 | CAATCTAGTTGTTAGCCAAGGAC |
| 3916 | AATCTAGTTGTTAGCCAAGGACT |
| 3917 | ATCTAGTTGTTAGCCAAGGACTC |
| 3918 | TCTAGTTGTTAGCCAAGGACTCA |
| 3919 | CTAGTTGTTAGCCAAGGACTCAA |
| 3920 | TAGTTGTTAGCCAAGGACTCAAG |
| 3921 | AGTTGTTAGCCAAGGACTCAAGG |
| 3922 | GTTGTTAGCCAAGGACTCAAGGA |
| 3923 | TTGTTAGCCAAGGACTCAAGGAC |
| 3924 | TGTTAGCCAAGGACTCAAGGACT |
| 3925 | GTTAGCCAAGGACTCAAGGACTG |
| 3926 | TTAGCCAAGGACTCAAGGACTGA |
| 3927 | TAGCCAAGGACTCAAGGACTGAA |
| 3928 | AGCCAAGGACTCAAGGACTGAAT |
| 3929 | GCCAAGGACTCAAGGACTGAATT |
| 3930 | CCAAGGACTCAAGGACTGAATTG |
| 3931 | CAAGGACTCAAGGACTGAATTGT |
| 3932 | AAGGACTCAAGGACTGAATTGTT |
| 3933 | AGGACTCAAGGACTGAATTGTTT |
| 3934 | GGACTCAAGGACTGAATTGTTTT |
| 3935 | GACTCAAGGACTGAATTGTTTTA |
| 3936 | ACTCAAGGACTGAATTGTTTTAA |

| ID | SEQUENCE |
|---|---|
| 3937 | CTCAAGGACTGAATTGTTTTAAC |
| 3938 | TCAAGGACTGAATTGTTTTAACA |
| 3939 | CAAGGACTGAATTGTTTTAACAT |
| 3940 | AAGGACTGAATTGTTTTAACATA |
| 3941 | AGGACTGAATTGTTTTAACATAA |
| 3942 | GGACTGAATTGTTTTAACATAAG |
| 3943 | GACTGAATTGTTTTAACATAAGG |
| 3944 | ACTGAATTGTTTTAACATAAGGC |
| 3945 | CTGAATTGTTTTAACATAAGGCT |
| 3946 | TGAATTGTTTTAACATAAGGCTT |
| 3947 | GAATTGTTTTAACATAAGGCTTT |
| 3948 | AATTGTTTTAACATAAGGCTTTT |
| 3949 | ATTGTTTTAACATAAGGCTTTTC |
| 3950 | TTGTTTTAACATAAGGCTTTTCC |
| 3951 | TGTTTTAACATAAGGCTTTTCCT |
| 3952 | GTTTTAACATAAGGCTTTTCCTG |
| 3953 | TTTTAACATAAGGCTTTTCCTGT |
| 3954 | TTTAACATAAGGCTTTTCCTGTT |
| 3955 | TTAACATAAGGCTTTTCCTGTTC |
| 3956 | TAACATAAGGCTTTTCCTGTTCT |
| 3957 | AACATAAGGCTTTTCCTGTTCTG |
| 3958 | ACATAAGGCTTTTCCTGTTCTGG |
| 3959 | CATAAGGCTTTTCCTGTTCTGGG |
| 3960 | ATAAGGCTTTTCCTGTTCTGGGA |
| 3961 | TAAGGCTTTTCCTGTTCTGGGAG |
| 3962 | AAGGCTTTTCCTGTTCTGGGAGC |
| 3963 | AGGCTTTTCCTGTTCTGGGAGCC |
| 3964 | GGCTTTTCCTGTTCTGGGAGCCG |
| 3965 | GCTTTTCCTGTTCTGGGAGCCGC |
| 3966 | CTTTTCCTGTTCTGGGAGCCGCA |
| 3967 | TTTTCCTGTTCTGGGAGCCGCAC |
| 3968 | TTTCCTGTTCTGGGAGCCGCACT |
| 3969 | TTCCTGTTCTGGGAGCCGCACTT |
| 3970 | TCCTGTTCTGGGAGCCGCACTTC |
| 3971 | CCTGTTCTGGGAGCCGCACTTCA |
| 3972 | CTGTTCTGGGAGCCGCACTTCAT |
| 3973 | TGTTCTGGGAGCCGCACTTCATT |
| 3974 | GTTCTGGGAGCCGCACTTCATTA |
| 3975 | TTCTGGGAGCCGCACTTCATTAA |
| 3976 | TCTGGGAGCCGCACTTCATTAAA |
| 3977 | CTGGGAGCCGCACTTCATTAAAA |
| 3978 | TGGGAGCCGCACTTCATTAAAAT |
| 3979 | GGGAGCCGCACTTCATTAAAATT |
| 3980 | GGAGCCGCACTTCATTAAAATTC |
| 3981 | GAGCCGCACTTCATTAAAATTCT |
| 3982 | AGCCGCACTTCATTAAAATTCTT |
| 3983 | GCCGCACTTCATTAAAATTCTTC |
| 3984 | CCGCACTTCATTAAAATTCTTCT |

| ID | SEQUENCE |
|---|---|
| 3985 | CGCACTTCATTAAAATTCTTCTA |
| 3986 | GCACTTCATTAAAATTCTTCTAA |
| 3987 | CACTTCATTAAAATTCTTCTAAA |
| 3988 | ACTTCATTAAAATTCTTCTAAAA |
| 3989 | CTTCATTAAAATTCTTCTAAAAC |
| 3990 | TTCATTAAAATTCTTCTAAAACT |
| 3991 | TCATTAAAATTCTTCTAAAACTT |
| 3992 | CATTAAAATTCTTCTAAAACTTG |
| 3993 | ATTAAAATTCTTCTAAAACTTGT |
| 3994 | TTAAAATTCTTCTAAAACTTGTA |
| 3995 | TAAAATTCTTCTAAAACTTGTAT |
| 3996 | AAAATTCTTCTAAAACTTGTATG |
| 3997 | AAATTCTTCTAAAACTTGTATGT |
| 3998 | AATTCTTCTAAAACTTGTATGTT |
| 3999 | ATTCTTCTAAAACTTGTATGTTT |
| 4000 | TTCTTCTAAAACTTGTATGTTTA |
| 4001 | TCTTCTAAAACTTGTATGTTTAG |
| 4002 | CTTCTAAAACTTGTATGTTTAGA |
| 4003 | TTCTAAAACTTGTATGTTTAGAG |
| 4004 | TCTAAAACTTGTATGTTTAGAGT |
| 4005 | CTAAAACTTGTATGTTTAGAGTT |
| 4006 | TAAAACTTGTATGTTTAGAGTTA |
| 4007 | AAAACTTGTATGTTTAGAGTTAA |
| 4008 | AAACTTGTATGTTTAGAGTTAAG |
| 4009 | AACTTGTATGTTTAGAGTTAAGC |
| 4010 | ACTTGTATGTTTAGAGTTAAGCA |
| 4011 | CTTGTATGTTTAGAGTTAAGCAA |
| 4012 | TTGTATGTTTAGAGTTAAGCAAG |
| 4013 | TGTATGTTTAGAGTTAAGCAAGA |
| 4014 | GTATGTTTAGAGTTAAGCAAGAC |
| 4015 | TATGTTTAGAGTTAAGCAAGACT |
| 4016 | ATGTTTAGAGTTAAGCAAGACTT |
| 4017 | TGTTTAGAGTTAAGCAAGACTTT |
| 4018 | GTTTAGAGTTAAGCAAGACTTTT |
| 4019 | TTTAGAGTTAAGCAAGACTTTTT |
| 4020 | TTAGAGTTAAGCAAGACTTTTTT |
| 4021 | TAGAGTTAAGCAAGACTTTTTTT |
| 4022 | AGAGTTAAGCAAGACTTTTTTTC |
| 4023 | GAGTTAAGCAAGACTTTTTTTCT |
| 4024 | AGTTAAGCAAGACTTTTTTCTT |
| 4025 | GTTAAGCAAGACTTTTTTCTTC |
| 4026 | TTAAGCAAGACTTTTTTCTTCC |
| 4027 | TAAGCAAGACTTTTTTCTTCCT |
| 4028 | AAGCAAGACTTTTTTCTTCCTC |
| 4029 | AGCAAGACTTTTTTCTTCCTCT |
| 4030 | GCAAGACTTTTTTCTTCCTCTC |
| 4031 | CAAGACTTTTTTCTTCCTCTCC |
| 4032 | AAGACTTTTTTCTTCCTCTCCA |

| ID | SEQUENCE |
|---|---|
| 4033 | AGACTTTTTTCTTCCTCTCCAT |
| 4034 | GACTTTTTTCTTCCTCTCCATG |
| 4035 | ACTTTTTTCTTCCTCTCCATGA |
| 4036 | CTTTTTTCTTCCTCTCCATGAG |
| 4037 | TTTTTTCTTCCTCTCCATGAGT |
| 4038 | TTTTTCTTCCTCTCCATGAGTT |
| 4039 | TTTTCTTCCTCTCCATGAGTTG |
| 4040 | TTTCTTCCTCTCCATGAGTTGT |
| 4041 | TTCTTCCTCTCCATGAGTTGTG |
| 4042 | TCTTCCTCTCCATGAGTTGTGA |
| 4043 | TCTTCCTCTCCATGAGTTGTGAA |
| 4044 | CTTCCTCTCCATGAGTTGTGAAA |
| 4045 | TTCCTCTCCATGAGTTGTGAAAT |
| 4046 | TCCTCTCCATGAGTTGTGAAATT |
| 4047 | CCTCTCCATGAGTTGTGAAATTT |
| 4048 | CTCTCCATGAGTTGTGAAATTTA |
| 4049 | TCTCCATGAGTTGTGAAATTTAA |
| 4050 | CTCCATGAGTTGTGAAATTTAAT |
| 4051 | TCCATGAGTTGTGAAATTTAATG |
| 4052 | CCATGAGTTGTGAAATTTAATGC |
| 4053 | CATGAGTTGTGAAATTTAATGCA |
| 4054 | ATGAGTTGTGAAATTTAATGCAC |
| 4055 | TGAGTTGTGAAATTTAATGCACA |
| 4056 | GAGTTGTGAAATTTAATGCACAA |
| 4057 | AGTTGTGAAATTTAATGCACAAC |
| 4058 | GTTGTGAAATTTAATGCACAACG |
| 4059 | TTGTGAAATTTAATGCACAACGC |
| 4060 | TGTGAAATTTAATGCACAACGCT |
| 4061 | GTGAAATTTAATGCACAACGCTG |
| 4062 | TGAAATTTAATGCACAACGCTGA |
| 4063 | GAAATTTAATGCACAACGCTGAT |
| 4064 | AAATTTAATGCACAACGCTGATG |
| 4065 | AATTTAATGCACAACGCTGATGT |
| 4066 | ATTTAATGCACAACGCTGATGTG |
| 4067 | TTTAATGCACAACGCTGATGTGG |
| 4068 | TTAATGCACAACGCTGATGTGGC |
| 4069 | TAATGCACAACGCTGATGTGGCT |
| 4070 | AATGCACAACGCTGATGTGGCTA |
| 4071 | ATGCACAACGCTGATGTGGCTAA |
| 4072 | TGCACAACGCTGATGTGGCTAAC |
| 4073 | GCACAACGCTGATGTGGCTAACA |
| 4074 | CACAACGCTGATGTGGCTAACAA |
| 4075 | ACAACGCTGATGTGGCTAACAAG |
| 4076 | CAACGCTGATGTGGCTAACAAGT |
| 4077 | AACGCTGATGTGGCTAACAAGTT |
| 4078 | ACGCTGATGTGGCTAACAAGTTT |
| 4079 | CGCTGATGTGGCTAACAAGTTTA |
| 4080 | GCTGATGTGGCTAACAAGTTTAT |

| ID | SEQUENCE |
|---|---|
| 4081 | CTGATGTGGCTAACAAGTTTATT |
| 4082 | TGATGTGGCTAACAAGTTTATTT |
| 4083 | GATGTGGCTAACAAGTTTATTTT |
| 4084 | ATGTGGCTAACAAGTTTATTTTA |
| 4085 | TGTGGCTAACAAGTTTATTTTAA |
| 4086 | GTGGCTAACAAGTTTATTTTAAG |
| 4087 | TGGCTAACAAGTTTATTTTAAGA |
| 4088 | GGCTAACAAGTTTATTTTAAGAA |
| 4089 | GCTAACAAGTTTATTTTAAGAAT |
| 4090 | CTAACAAGTTTATTTTAAGAATT |
| 4091 | TAACAAGTTTATTTTAAGAATTG |
| 4092 | AACAAGTTTATTTTAAGAATTGT |
| 4093 | ACAAGTTTATTTTAAGAATTGTT |
| 4094 | CAAGTTTATTTTAAGAATTGTTT |
| 4095 | AAGTTTATTTTAAGAATTGTTTA |
| 4096 | AGTTTATTTTAAGAATTGTTTAG |
| 4097 | GTTTATTTTAAGAATTGTTTAGA |
| 4098 | TTTATTTTAAGAATTGTTTAGAA |
| 4099 | TTATTTTAAGAATTGTTTAGAAA |
| 4100 | TATTTTAAGAATTGTTTAGAAAT |
| 4101 | ATTTTAAGAATTGTTTAGAAATG |
| 4102 | TTTTAAGAATTGTTTAGAAATGC |
| 4103 | TTTAAGAATTGTTTAGAAATGCT |
| 4104 | TTAAGAATTGTTTAGAAATGCTG |
| 4105 | TAAGAATTGTTTAGAAATGCTGT |
| 4106 | AAGAATTGTTTAGAAATGCTGTT |
| 4107 | AGAATTGTTTAGAAATGCTGTTG |
| 4108 | GAATTGTTTAGAAATGCTGTTGC |
| 4109 | AATTGTTTAGAAATGCTGTTGCT |
| 4110 | ATTGTTTAGAAATGCTGTTGCTT |
| 4111 | TTGTTTAGAAATGCTGTTGCTTC |
| 4112 | TGTTTAGAAATGCTGTTGCTTCA |
| 4113 | GTTTAGAAATGCTGTTGCTTCAG |
| 4114 | TTTAGAAATGCTGTTGCTTCAGG |
| 4115 | TTAGAAATGCTGTTGCTTCAGGT |
| 4116 | TAGAAATGCTGTTGCTTCAGGTT |
| 4117 | AGAAATGCTGTTGCTTCAGGTTC |
| 4118 | GAAATGCTGTTGCTTCAGGTTCT |
| 4119 | AAATGCTGTTGCTTCAGGTTCTT |
| 4120 | AATGCTGTTGCTTCAGGTTCTTA |
| 4121 | ATGCTGTTGCTTCAGGTTCTTAA |
| 4122 | TGCTGTTGCTTCAGGTTCTTAAA |
| 4123 | GCTGTTGCTTCAGGTTCTTAAAA |
| 4124 | CTGTTGCTTCAGGTTCTTAAAAT |
| 4125 | TGTTGCTTCAGGTTCTTAAAATC |
| 4126 | GTTGCTTCAGGTTCTTAAAATCA |
| 4127 | TTGCTTCAGGTTCTTAAAATCAC |
| 4128 | TGCTTCAGGTTCTTAAAATCACT |

| ID | SEQUENCE |
|---|---|
| 4129 | GCTTCAGGTTCTTAAAATCACTC |
| 4130 | CTTCAGGTTCTTAAAATCACTCA |
| 4131 | TTCAGGTTCTTAAAATCACTCAG |
| 4132 | TCAGGTTCTTAAAATCACTCAGC |
| 4133 | CAGGTTCTTAAAATCACTCAGCA |
| 4134 | AGGTTCTTAAAATCACTCAGCAC |
| 4135 | GGTTCTTAAAATCACTCAGCACT |
| 4136 | GTTCTTAAAATCACTCAGCACTC |
| 4137 | TTCTTAAAATCACTCAGCACTCC |
| 4138 | TCTTAAAATCACTCAGCACTCCA |
| 4139 | CTTAAAATCACTCAGCACTCCAA |
| 4140 | TTAAAATCACTCAGCACTCCAAC |
| 4141 | TAAAATCACTCAGCACTCCAACT |
| 4142 | AAAATCACTCAGCACTCCAACTT |
| 4143 | AAATCACTCAGCACTCCAACTTC |
| 4144 | AATCACTCAGCACTCCAACTTCT |
| 4145 | ATCACTCAGCACTCCAACTTCTA |
| 4146 | TCACTCAGCACTCCAACTTCTAA |
| 4147 | CACTCAGCACTCCAACTTCTAAT |
| 4148 | ACTCAGCACTCCAACTTCTAATC |
| 4149 | CTCAGCACTCCAACTTCTAATCA |
| 4150 | TCAGCACTCCAACTTCTAATCAA |
| 4151 | CAGCACTCCAACTTCTAATCAAA |
| 4152 | AGCACTCCAACTTCTAATCAAAT |
| 4153 | GCACTCCAACTTCTAATCAAATT |
| 4154 | CACTCCAACTTCTAATCAAATTT |
| 4155 | ACTCCAACTTCTAATCAAATTTT |
| 4156 | CTCCAACTTCTAATCAAATTTTT |
| 4157 | TCCAACTTCTAATCAAATTTTTG |
| 4158 | CCAACTTCTAATCAAATTTTTGG |
| 4159 | CAACTTCTAATCAAATTTTTGGA |
| 4160 | AACTTCTAATCAAATTTTTGGAG |
| 4161 | ACTTCTAATCAAATTTTTGGAGA |
| 4162 | CTTCTAATCAAATTTTTGGAGAC |
| 4163 | TTCTAATCAAATTTTTGGAGACT |
| 4164 | TCTAATCAAATTTTTGGAGACTT |
| 4165 | CTAATCAAATTTTTGGAGACTTA |
| 4166 | TAATCAAATTTTTGGAGACTTAA |
| 4167 | AATCAAATTTTTGGAGACTTAAC |
| 4168 | ATCAAATTTTTGGAGACTTAACA |
| 4169 | TCAAATTTTTGGAGACTTAACAG |
| 4170 | CAAATTTTTGGAGACTTAACAGC |
| 4171 | AAATTTTTGGAGACTTAACAGCA |
| 4172 | AATTTTTGGAGACTTAACAGCAT |
| 4173 | ATTTTTGGAGACTTAACAGCATT |
| 4174 | TTTTTGGAGACTTAACAGCATTT |
| 4175 | TTTTGGAGACTTAACAGCATTTG |
| 4176 | TTTGGAGACTTAACAGCATTTGT |

| ID | SEQUENCE |
|---|---|
| 4177 | TTGGAGACTTAACAGCATTTGTC |
| 4178 | TGGAGACTTAACAGCATTTGTCT |
| 4179 | GGAGACTTAACAGCATTTGTCTG |
| 4180 | GAGACTTAACAGCATTTGTCTGT |
| 4181 | AGACTTAACAGCATTTGTCTGTG |
| 4182 | GACTTAACAGCATTTGTCTGTGT |
| 4183 | ACTTAACAGCATTTGTCTGTGTT |
| 4184 | CTTAACAGCATTTGTCTGTGTTT |
| 4185 | TTAACAGCATTTGTCTGTGTTTG |
| 4186 | TAACAGCATTTGTCTGTGTTTGA |
| 4187 | AACAGCATTTGTCTGTGTTTGAA |
| 4188 | ACAGCATTTGTCTGTGTTTGAAC |
| 4189 | CAGCATTTGTCTGTGTTTGAACT |
| 4190 | AGCATTTGTCTGTGTTTGAACTA |
| 4191 | GCATTTGTCTGTGTTTGAACTAT |
| 4192 | CATTTGTCTGTGTTTGAACTATA |
| 4193 | ATTTGTCTGTGTTTGAACTATAA |
| 4194 | TTTGTCTGTGTTTGAACTATAAA |
| 4195 | TTGTCTGTGTTTGAACTATAAAA |
| 4196 | TGTCTGTGTTTGAACTATAAAAA |
| 4197 | GTCTGTGTTTGAACTATAAAAAG |
| 4198 | TCTGTGTTTGAACTATAAAAAGC |
| 4199 | CTGTGTTTGAACTATAAAAAGCA |
| 4200 | TGTGTTTGAACTATAAAAAGCAC |
| 4201 | GTGTTTGAACTATAAAAAGCACC |
| 4202 | TGTTTGAACTATAAAAAGCACCG |
| 4203 | GTTTGAACTATAAAAAGCACCGG |
| 4204 | TTTGAACTATAAAAAGCACCGGA |
| 4205 | TTGAACTATAAAAAGCACCGGAT |
| 4206 | TGAACTATAAAAAGCACCGGATC |
| 4207 | GAACTATAAAAAGCACCGGATCT |
| 4208 | AACTATAAAAAGCACCGGATCTT |
| 4209 | ACTATAAAAAGCACCGGATCTTT |
| 4210 | CTATAAAAAGCACCGGATCTTTT |
| 4211 | TATAAAAAGCACCGGATCTTTTC |
| 4212 | ATAAAAAGCACCGGATCTTTTCC |
| 4213 | TAAAAAGCACCGGATCTTTTCCA |
| 4214 | AAAAAGCACCGGATCTTTTCCAT |
| 4215 | AAAAGCACCGGATCTTTTCCATC |
| 4216 | AAAGCACCGGATCTTTTCCATCT |
| 4217 | AAGCACCGGATCTTTTCCATCTA |
| 4218 | AGCACCGGATCTTTTCCATCTAA |
| 4219 | GCACCGGATCTTTTCCATCTAAT |
| 4220 | CACCGGATCTTTTCCATCTAATT |
| 4221 | ACCGGATCTTTTCCATCTAATTC |
| 4222 | CCGGATCTTTTCCATCTAATTCC |
| 4223 | CGGATCTTTTCCATCTAATTCCG |
| 4224 | GGATCTTTTCCATCTAATTCCGC |

| ID | SEQUENCE |
|---|---|
| 4225 | GATCTTTTCCATCTAATTCCGCA |
| 4226 | ATCTTTTCCATCTAATTCCGCAA |
| 4227 | TCTTTTCCATCTAATTCCGCAAA |
| 4228 | CTTTTCCATCTAATTCCGCAAAA |
| 4229 | TTTTCCATCTAATTCCGCAAAAA |
| 4230 | TTTCCATCTAATTCCGCAAAAAT |
| 4231 | TTCCATCTAATTCCGCAAAAATT |
| 4232 | TCCATCTAATTCCGCAAAAATTG |
| 4233 | CCATCTAATTCCGCAAAAATTGA |
| 4234 | CATCTAATTCCGCAAAAATTGAT |
| 4235 | ATCTAATTCCGCAAAAATTGATC |
| 4236 | TCTAATTCCGCAAAAATTGATCA |
| 4237 | CTAATTCCGCAAAAATTGATCAT |
| 4238 | TAATTCCGCAAAAATTGATCATT |
| 4239 | AATTCCGCAAAAATTGATCATTT |
| 4240 | ATTCCGCAAAAATTGATCATTTG |
| 4241 | TTCCGCAAAAATTGATCATTTGC |
| 4242 | TCCGCAAAAATTGATCATTTGCA |
| 4243 | CCGCAAAAATTGATCATTTGCAA |
| 4244 | CGCAAAAATTGATCATTTGCAAA |
| 4245 | GCAAAAATTGATCATTTGCAAAG |
| 4246 | CAAAAATTGATCATTTGCAAAGT |
| 4247 | AAAAATTGATCATTTGCAAAGTC |
| 4248 | AAAATTGATCATTTGCAAAGTCA |
| 4249 | AAATTGATCATTTGCAAAGTCAA |
| 4250 | AATTGATCATTTGCAAAGTCAAA |
| 4251 | ATTGATCATTTGCAAAGTCAAAA |
| 4252 | TTGATCATTTGCAAAGTCAAAAC |
| 4253 | TGATCATTTGCAAAGTCAAAACT |
| 4254 | GATCATTTGCAAAGTCAAAACTA |
| 4255 | ATCATTTGCAAAGTCAAAACTAT |
| 4256 | TCATTTGCAAAGTCAAAACTATA |
| 4257 | CATTTGCAAAGTCAAAACTATAG |
| 4258 | ATTTGCAAAGTCAAAACTATAGC |
| 4259 | TTTGCAAAGTCAAAACTATAGCC |
| 4260 | TTGCAAAGTCAAAACTATAGCCA |
| 4261 | TGCAAAGTCAAAACTATAGCCAT |
| 4262 | GCAAAGTCAAAACTATAGCCATA |
| 4263 | CAAAGTCAAAACTATAGCCATAT |
| 4264 | AAAGTCAAAACTATAGCCATATC |
| 4265 | AAGTCAAAACTATAGCCATATCC |
| 4266 | AGTCAAAACTATAGCCATATCCA |
| 4267 | GTCAAAACTATAGCCATATCCAA |
| 4268 | TCAAAACTATAGCCATATCCAAA |
| 4269 | CAAAACTATAGCCATATCCAAAT |
| 4270 | AAAACTATAGCCATATCCAAATC |
| 4271 | AAACTATAGCCATATCCAAATCT |
| 4272 | AACTATAGCCATATCCAAATCTT |

| ID | SEQUENCE |
|---|---|
| 4273 | ACTATAGCCATATCCAAATCTTT |
| 4274 | CTATAGCCATATCCAAATCTTTT |
| 4275 | TATAGCCATATCCAAATCTTTTC |
| 4276 | ATAGCCATATCCAAATCTTTTCC |
| 4277 | TAGCCATATCCAAATCTTTTCCC |
| 4278 | AGCCATATCCAAATCTTTTCCCC |
| 4279 | GCCATATCCAAATCTTTTCCCCC |
| 4280 | CCATATCCAAATCTTTTCCCCCT |
| 4281 | CATATCCAAATCTTTTCCCCCTC |
| 4282 | ATATCCAAATCTTTTCCCCCTCC |
| 4283 | TATCCAAATCTTTTCCCCCTCCC |
| 4284 | ATCCAAATCTTTTCCCCCTCCCA |
| 4285 | TCCAAATCTTTTCCCCCTCCCAA |
| 4286 | CCAAATCTTTTCCCCCTCCCAAG |
| 4287 | CAAATCTTTTCCCCCTCCCAAGA |
| 4288 | AAATCTTTTCCCCCTCCCAAGAG |
| 4289 | AATCTTTTCCCCCTCCCAAGAGT |
| 4290 | ATCTTTTCCCCCTCCCAAGAGTT |
| 4291 | TCTTTTCCCCCTCCCAAGAGTTC |
| 4292 | CTTTTCCCCCTCCCAAGAGTTCT |
| 4293 | TTTTCCCCCTCCCAAGAGTTCTC |
| 4294 | TTTCCCCCTCCCAAGAGTTCTCA |
| 4295 | TTCCCCCTCCCAAGAGTTCTCAG |
| 4296 | TCCCCCTCCCAAGAGTTCTCAGT |
| 4297 | CCCCCTCCCAAGAGTTCTCAGTG |
| 4298 | CCCCTCCCAAGAGTTCTCAGTGT |
| 4299 | CCCTCCCAAGAGTTCTCAGTGTC |
| 4300 | CCTCCCAAGAGTTCTCAGTGTCT |
| 4301 | CTCCCAAGAGTTCTCAGTGTCTA |
| 4302 | TCCCAAGAGTTCTCAGTGTCTAC |
| 4303 | CCCAAGAGTTCTCAGTGTCTACA |
| 4304 | CCAAGAGTTCTCAGTGTCTACAT |
| 4305 | CAAGAGTTCTCAGTGTCTACATG |
| 4306 | AAGAGTTCTCAGTGTCTACATGT |
| 4307 | AGAGTTCTCAGTGTCTACATGTA |
| 4308 | GAGTTCTCAGTGTCTACATGTAG |
| 4309 | AGTTCTCAGTGTCTACATGTAGA |
| 4310 | GTTCTCAGTGTCTACATGTAGAC |
| 4311 | TTCTCAGTGTCTACATGTAGACT |
| 4312 | TCTCAGTGTCTACATGTAGACTA |
| 4313 | CTCAGTGTCTACATGTAGACTAT |
| 4314 | TCAGTGTCTACATGTAGACTATT |
| 4315 | CAGTGTCTACATGTAGACTATTC |
| 4316 | AGTGTCTACATGTAGACTATTCC |
| 4317 | GTGTCTACATGTAGACTATTCCT |
| 4318 | TGTCTACATGTAGACTATTCCTT |
| 4319 | GTCTACATGTAGACTATTCCTTT |
| 4320 | TCTACATGTAGACTATTCCTTTT |

| ID | SEQUENCE |
|---|---|
| 4321 | CTACATGTAGACTATTCCTTTTC |
| 4322 | TACATGTAGACTATTCCTTTTCT |
| 4323 | ACATGTAGACTATTCCTTTTCTG |
| 4324 | CATGTAGACTATTCCTTTTCTGT |
| 4325 | ATGTAGACTATTCCTTTTCTGTA |
| 4326 | TGTAGACTATTCCTTTTCTGTAT |
| 4327 | GTAGACTATTCCTTTTCTGTATA |
| 4328 | TAGACTATTCCTTTTCTGTATAA |
| 4329 | AGACTATTCCTTTTCTGTATAAA |
| 4330 | GACTATTCCTTTTCTGTATAAAG |
| 4331 | ACTATTCCTTTTCTGTATAAAGT |
| 4332 | CTATTCCTTTTCTGTATAAAGTT |
| 4333 | TATTCCTTTTCTGTATAAAGTTC |
| 4334 | ATTCCTTTTCTGTATAAAGTTCA |
| 4335 | TTCCTTTTCTGTATAAAGTTCAC |
| 4336 | TCCTTTTCTGTATAAAGTTCACT |
| 4337 | CCTTTTCTGTATAAAGTTCACTC |
| 4338 | CTTTTCTGTATAAAGTTCACTCT |
| 4339 | TTTTCTGTATAAAGTTCACTCTA |
| 4340 | TTTCTGTATAAAGTTCACTCTAG |
| 4341 | TTCTGTATAAAGTTCACTCTAGG |
| 4342 | TCTGTATAAAGTTCACTCTAGGA |
| 4343 | CTGTATAAAGTTCACTCTAGGAT |
| 4344 | TGTATAAAGTTCACTCTAGGATT |
| 4345 | GTATAAAGTTCACTCTAGGATTT |
| 4346 | TATAAAGTTCACTCTAGGATTTC |
| 4347 | ATAAAGTTCACTCTAGGATTTCA |
| 4348 | TAAAGTTCACTCTAGGATTTCAA |
| 4349 | AAAGTTCACTCTAGGATTTCAAG |
| 4350 | AAGTTCACTCTAGGATTTCAAGT |
| 4351 | AGTTCACTCTAGGATTTCAAGTC |
| 4352 | GTTCACTCTAGGATTTCAAGTCA |
| 4353 | TTCACTCTAGGATTTCAAGTCAC |
| 4354 | TCACTCTAGGATTTCAAGTCACC |
| 4355 | CACTCTAGGATTTCAAGTCACCA |
| 4356 | ACTCTAGGATTTCAAGTCACCAC |
| 4357 | CTCTAGGATTTCAAGTCACCACT |
| 4358 | TCTAGGATTTCAAGTCACCACTT |
| 4359 | CTAGGATTTCAAGTCACCACTTA |
| 4360 | TAGGATTTCAAGTCACCACTTAT |
| 4361 | AGGATTTCAAGTCACCACTTATT |
| 4362 | GGATTTCAAGTCACCACTTATTT |
| 4363 | GATTTCAAGTCACCACTTATTTT |
| 4364 | ATTTCAAGTCACCACTTATTTTA |
| 4365 | TTTCAAGTCACCACTTATTTTAC |
| 4366 | TTCAAGTCACCACTTATTTTACA |
| 4367 | TCAAGTCACCACTTATTTTACAT |
| 4368 | CAAGTCACCACTTATTTTACATT |

| ID | SEQUENCE |
|---|---|
| 4369 | AAGTCACCACTTATTTTACATTT |
| 4370 | AGTCACCACTTATTTTACATTTT |
| 4371 | GTCACCACTTATTTTACATTTTA |
| 4372 | TCACCACTTATTTTACATTTTAG |
| 4373 | CACCACTTATTTTACATTTTAGT |
| 4374 | ACCACTTATTTTACATTTTAGTC |
| 4375 | CCACTTATTTTACATTTTAGTCA |
| 4376 | CACTTATTTTACATTTTAGTCAT |
| 4377 | ACTTATTTTACATTTTAGTCATG |
| 4378 | CTTATTTTACATTTTAGTCATGC |
| 4379 | TTATTTTACATTTTAGTCATGCA |
| 4380 | TATTTTACATTTTAGTCATGCAA |
| 4381 | ATTTTACATTTTAGTCATGCAAA |
| 4382 | TTTTACATTTTAGTCATGCAAAG |
| 4383 | TTTACATTTTAGTCATGCAAAGA |
| 4384 | TTACATTTTAGTCATGCAAAGAT |
| 4385 | TACATTTTAGTCATGCAAAGATT |
| 4386 | ACATTTTAGTCATGCAAAGATTC |
| 4387 | CATTTTAGTCATGCAAAGATTCA |
| 4388 | ATTTTAGTCATGCAAAGATTCAA |
| 4389 | TTTTAGTCATGCAAAGATTCAAG |
| 4390 | TTTAGTCATGCAAAGATTCAAGT |
| 4391 | TTAGTCATGCAAAGATTCAAGTA |
| 4392 | TAGTCATGCAAAGATTCAAGTAG |
| 4393 | AGTCATGCAAAGATTCAAGTAGT |
| 4394 | GTCATGCAAAGATTCAAGTAGTT |
| 4395 | TCATGCAAAGATTCAAGTAGTTT |
| 4396 | CATGCAAAGATTCAAGTAGTTTT |
| 4397 | ATGCAAAGATTCAAGTAGTTTTG |
| 4398 | TGCAAAGATTCAAGTAGTTTTGC |
| 4399 | GCAAAGATTCAAGTAGTTTTGCA |
| 4400 | CAAAGATTCAAGTAGTTTTGCAA |
| 4401 | AAAGATTCAAGTAGTTTTGCAAT |
| 4402 | AAGATTCAAGTAGTTTTGCAATA |
| 4403 | AGATTCAAGTAGTTTTGCAATAA |
| 4404 | GATTCAAGTAGTTTTGCAATAAG |
| 4405 | ATTCAAGTAGTTTTGCAATAAGT |
| 4406 | TTCAAGTAGTTTTGCAATAAGTA |
| 4407 | TCAAGTAGTTTTGCAATAAGTAC |
| 4408 | CAAGTAGTTTTGCAATAAGTACT |
| 4409 | AAGTAGTTTTGCAATAAGTACTT |
| 4410 | AGTAGTTTTGCAATAAGTACTTA |
| 4411 | GTAGTTTTGCAATAAGTACTTAT |
| 4412 | TAGTTTTGCAATAAGTACTTATC |
| 4413 | AGTTTTGCAATAAGTACTTATCT |
| 4414 | GTTTTGCAATAAGTACTTATCTT |
| 4415 | TTTTGCAATAAGTACTTATCTTT |
| 4416 | TTTGCAATAAGTACTTATCTTTA |

| ID | SEQUENCE |
|---|---|
| 4417 | TTGCAATAAGTACTTATCTTTAT |
| 4418 | TGCAATAAGTACTTATCTTTATT |
| 4419 | GCAATAAGTACTTATCTTTATTT |
| 4420 | CAATAAGTACTTATCTTTATTTG |
| 4421 | AATAAGTACTTATCTTTATTTGT |
| 4422 | ATAAGTACTTATCTTTATTTGTA |
| 4423 | TAAGTACTTATCTTTATTTGTAA |
| 4424 | AAGTACTTATCTTTATTTGTAAT |
| 4425 | AGTACTTATCTTTATTTGTAATA |
| 4426 | GTACTTATCTTTATTTGTAATAA |
| 4427 | TACTTATCTTTATTTGTAATAAT |
| 4428 | ACTTATCTTTATTTGTAATAATT |
| 4429 | CTTATCTTTATTTGTAATAATTT |
| 4430 | TTATCTTTATTTGTAATAATTTA |
| 4431 | TATCTTTATTTGTAATAATTTAG |
| 4432 | ATCTTTATTTGTAATAATTTAGT |
| 4433 | TCTTTATTTGTAATAATTTAGTC |
| 4434 | CTTTATTTGTAATAATTTAGTCT |
| 4435 | TTTATTTGTAATAATTTAGTCTG |
| 4436 | TTATTTGTAATAATTTAGTCTGC |
| 4437 | TATTTGTAATAATTTAGTCTGCT |
| 4438 | ATTTGTAATAATTTAGTCTGCTG |
| 4439 | TTTGTAATAATTTAGTCTGCTGA |
| 4440 | TTGTAATAATTTAGTCTGCTGAT |
| 4441 | TGTAATAATTTAGTCTGCTGATC |
| 4442 | GTAATAATTTAGTCTGCTGATCA |
| 4443 | TAATAATTTAGTCTGCTGATCAA |
| 4444 | AATAATTTAGTCTGCTGATCAAA |
| 4445 | ATAATTTAGTCTGCTGATCAAAA |
| 4446 | TAATTTAGTCTGCTGATCAAAAG |
| 4447 | AATTTAGTCTGCTGATCAAAAGC |
| 4448 | ATTTAGTCTGCTGATCAAAAGCA |
| 4449 | TTTAGTCTGCTGATCAAAAGCAT |
| 4450 | TTAGTCTGCTGATCAAAAGCATT |
| 4451 | TAGTCTGCTGATCAAAAGCATTG |
| 4452 | AGTCTGCTGATCAAAAGCATTGT |
| 4453 | GTCTGCTGATCAAAAGCATTGTC |
| 4454 | TCTGCTGATCAAAAGCATTGTCT |
| 4455 | CTGCTGATCAAAAGCATTGTCTT |
| 4456 | TGCTGATCAAAAGCATTGTCTTA |
| 4457 | GCTGATCAAAAGCATTGTCTTAA |
| 4458 | CTGATCAAAAGCATTGTCTTAAT |
| 4459 | TGATCAAAAGCATTGTCTTAATT |
| 4460 | GATCAAAAGCATTGTCTTAATTT |
| 4461 | ATCAAAAGCATTGTCTTAATTTT |
| 4462 | TCAAAAGCATTGTCTTAATTTTT |
| 4463 | CAAAAGCATTGTCTTAATTTTTG |
| 4464 | AAAAGCATTGTCTTAATTTTTGA |

| ID | SEQUENCE |
|---|---|
| 4465 | AAAGCATTGTCTTAATTTTGAG |
| 4466 | AAGCATTGTCTTAATTTTGAGA |
| 4467 | AGCATTGTCTTAATTTTGAGAA |
| 4468 | GCATTGTCTTAATTTTGAGAAC |
| 4469 | CATTGTCTTAATTTTGAGAACT |
| 4470 | ATTGTCTTAATTTTGAGAACTG |
| 4471 | TTGTCTTAATTTTGAGAACTGG |
| 4472 | TGTCTTAATTTTGAGAACTGGT |
| 4473 | GTCTTAATTTTGAGAACTGGTT |
| 4474 | TCTTAATTTTGAGAACTGGTTT |
| 4475 | CTTAATTTTGAGAACTGGTTTT |
| 4476 | TTAATTTTGAGAACTGGTTTTA |
| 4477 | TAATTTTGAGAACTGGTTTTAG |
| 4478 | AATTTTGAGAACTGGTTTTAGC |
| 4479 | ATTTTGAGAACTGGTTTTAGCA |
| 4480 | TTTTGAGAACTGGTTTTAGCAT |
| 4481 | TTTGAGAACTGGTTTTAGCATT |
| 4482 | TTGAGAACTGGTTTTAGCATTT |
| 4483 | TGAGAACTGGTTTTAGCATTTA |
| 4484 | GAGAACTGGTTTTAGCATTTAC |
| 4485 | AGAACTGGTTTTAGCATTTACA |
| 4486 | GAACTGGTTTTAGCATTTACAA |
| 4487 | AACTGGTTTTAGCATTTACAAA |
| 4488 | ACTGGTTTTAGCATTTACAAAC |
| 4489 | CTGGTTTTAGCATTTACAAACT |
| 4490 | TGGTTTTAGCATTTACAAACTA |
| 4491 | GGTTTTAGCATTTACAAACTAA |
| 4492 | GTTTTAGCATTTACAAACTAAA |
| 4493 | TTTTAGCATTTACAAACTAAAT |
| 4494 | TTTAGCATTTACAAACTAAATT |
| 4495 | TTAGCATTTACAAACTAAATTC |
| 4496 | TAGCATTTACAAACTAAATTCC |
| 4497 | AGCATTTACAAACTAAATTCCA |
| 4498 | GCATTTACAAACTAAATTCCAG |
| 4499 | CATTTACAAACTAAATTCCAGT |
| 4500 | ATTTACAAACTAAATTCCAGTT |
| 4501 | TTTACAAACTAAATTCCAGTTA |
| 4502 | TTACAAACTAAATTCCAGTTAA |
| 4503 | TACAAACTAAATTCCAGTTAAT |
| 4504 | ACAAACTAAATTCCAGTTAATT |
| 4505 | CAAACTAAATTCCAGTTAATTA |
| 4506 | AAACTAAATTCCAGTTAATTAA |
| 4507 | AACTAAATTCCAGTTAATTAAT |
| 4508 | ACTAAATTCCAGTTAATTAATT |
| 4509 | CTAAATTCCAGTTAATTAATTA |
| 4510 | TAAATTCCAGTTAATTAATTAA |
| 4511 | AAATTCCAGTTAATTAATTAAT |
| 4512 | AATTCCAGTTAATTAATTAATA |

| ID | SEQUENCE |
|---|---|
| 4513 | AATTCCAGTTAATTAATTAATAG |
| 4514 | ATTCCAGTTAATTAATTAATAGC |
| 4515 | TTCCAGTTAATTAATTAATAGCT |
| 4516 | TCCAGTTAATTAATTAATAGCTT |
| 4517 | CCAGTTAATTAATTAATAGCTTT |
| 4518 | CAGTTAATTAATTAATAGCTTTA |
| 4519 | AGTTAATTAATTAATAGCTTTAT |
| 4520 | GTTAATTAATTAATAGCTTTATA |
| 4521 | TTAATTAATTAATAGCTTTATAT |
| 4522 | TAATTAATTAATAGCTTTATATT |
| 4523 | AATTAATTAATAGCTTTATATTG |
| 4524 | ATTAATTAATAGCTTTATATTGC |
| 4525 | TTAATTAATAGCTTTATATTGCC |
| 4526 | TAATTAATAGCTTTATATTGCCT |
| 4527 | AATTAATAGCTTTATATTGCCTT |
| 4528 | ATTAATAGCTTTATATTGCCTTT |
| 4529 | TTAATAGCTTTATATTGCCTTTC |
| 4530 | TAATAGCTTTATATTGCCTTTCC |
| 4531 | AATAGCTTTATATTGCCTTTCCT |
| 4532 | ATAGCTTTATATTGCCTTTCCTG |
| 4533 | TAGCTTTATATTGCCTTTCCTGC |
| 4534 | AGCTTTATATTGCCTTTCCTGCT |
| 4535 | GCTTTATATTGCCTTTCCTGCTA |
| 4536 | CTTTATATTGCCTTTCCTGCTAC |
| 4537 | TTTATATTGCCTTTCCTGCTACA |
| 4538 | TTATATTGCCTTTCCTGCTACAT |
| 4539 | TATATTGCCTTTCCTGCTACATT |
| 4540 | ATATTGCCTTTCCTGCTACATTT |
| 4541 | TATTGCCTTTCCTGCTACATTTG |
| 4542 | ATTGCCTTTCCTGCTACATTTGG |
| 4543 | TTGCCTTTCCTGCTACATTTGGT |
| 4544 | TGCCTTTCCTGCTACATTTGGTT |
| 4545 | GCCTTTCCTGCTACATTTGGTTT |
| 4546 | CCTTTCCTGCTACATTTGGTTTT |
| 4547 | CTTTCCTGCTACATTTGGTTTTT |
| 4548 | TTTCCTGCTACATTTGGTTTTTT |
| 4549 | TTCCTGCTACATTTGGTTTTTTC |
| 4550 | TCCTGCTACATTTGGTTTTTTCC |
| 4551 | CCTGCTACATTTGGTTTTTTCCC |
| 4552 | CTGCTACATTTGGTTTTTTCCCC |
| 4553 | TGCTACATTTGGTTTTTTCCCCT |
| 4554 | GCTACATTTGGTTTTTTCCCCTG |
| 4555 | CTACATTTGGTTTTTTCCCCTGT |
| 4556 | TACATTTGGTTTTTTCCCCTGTC |
| 4557 | ACATTTGGTTTTTTCCCCTGTCC |
| 4558 | CATTTGGTTTTTTCCCCTGTCCC |
| 4559 | ATTTGGTTTTTTCCCCTGTCCCT |
| 4560 | TTTGGTTTTTTCCCCTGTCCCTT |

| ID | SEQUENCE |
|---|---|
| 4561 | TTGGTTTTTCCCCTGTCCCTTT |
| 4562 | TGGTTTTTTCCCCTGTCCCTTTG |
| 4563 | GGTTTTTTCCCCTGTCCCTTTGA |
| 4564 | GTTTTTTCCCCTGTCCCTTTGAT |
| 4565 | TTTTTTCCCCTGTCCCTTTGATT |
| 4566 | TTTTTCCCCTGTCCCTTTGATTA |
| 4567 | TTTTCCCCTGTCCCTTTGATTAC |
| 4568 | TTTCCCCTGTCCCTTTGATTACG |
| 4569 | TTCCCCTGTCCCTTTGATTACGG |
| 4570 | TCCCCTGTCCCTTTGATTACGGG |
| 4571 | CCCCTGTCCCTTTGATTACGGGC |
| 4572 | CCCTGTCCCTTTGATTACGGGCT |
| 4573 | CCTGTCCCTTTGATTACGGGCTA |
| 4574 | CTGTCCCTTTGATTACGGGCTAA |
| 4575 | TGTCCCTTTGATTACGGGCTAAG |
| 4576 | GTCCCTTTGATTACGGGCTAAGG |
| 4577 | TCCCTTTGATTACGGGCTAAGGT |
| 4578 | CCCTTTGATTACGGGCTAAGGTA |
| 4579 | CCTTTGATTACGGGCTAAGGTAG |
| 4580 | CTTTGATTACGGGCTAAGGTAGG |
| 4581 | TTTGATTACGGGCTAAGGTAGGG |
| 4582 | TTGATTACGGGCTAAGGTAGGGT |
| 4583 | TGATTACGGGCTAAGGTAGGGTA |
| 4584 | GATTACGGGCTAAGGTAGGGTAG |
| 4585 | ATTACGGGCTAAGGTAGGGTAGA |
| 4586 | TTACGGGCTAAGGTAGGGTAGAG |
| 4587 | TACGGGCTAAGGTAGGGTAGAGT |
| 4588 | ACGGGCTAAGGTAGGGTAGAGTG |
| 4589 | CGGGCTAAGGTAGGGTAGAGTGG |
| 4590 | GGGCTAAGGTAGGGTAGAGTGGG |
| 4591 | GGCTAAGGTAGGGTAGAGTGGGT |
| 4592 | GCTAAGGTAGGGTAGAGTGGGTG |
| 4593 | CTAAGGTAGGGTAGAGTGGGTGT |
| 4594 | TAAGGTAGGGTAGAGTGGGTGTA |
| 4595 | AAGGTAGGGTAGAGTGGGTGTAG |
| 4596 | AGGTAGGGTAGAGTGGGTGTAGT |
| 4597 | GGTAGGGTAGAGTGGGTGTAGTG |
| 4598 | GTAGGGTAGAGTGGGTGTAGTGA |
| 4599 | TAGGGTAGAGTGGGTGTAGTGAG |
| 4600 | AGGGTAGAGTGGGTGTAGTGAGT |
| 4601 | GGGTAGAGTGGGTGTAGTGAGTG |
| 4602 | GGTAGAGTGGGTGTAGTGAGTGT |
| 4603 | GTAGAGTGGGTGTAGTGAGTGTA |
| 4604 | TAGAGTGGGTGTAGTGAGTGTAT |
| 4605 | AGAGTGGGTGTAGTGAGTGTATA |
| 4606 | GAGTGGGTGTAGTGAGTGTATAT |
| 4607 | AGTGGGTGTAGTGAGTGTATATA |
| 4608 | GTGGGTGTAGTGAGTGTATATAA |

| ID | SEQUENCE |
|---|---|
| 4609 | TGGGTGTAGTGAGTGTATATAAT |
| 4610 | GGGTGTAGTGAGTGTATATAATG |
| 4611 | GGTGTAGTGAGTGTATATAATGT |
| 4612 | GTGTAGTGAGTGTATATAATGTG |
| 4613 | TGTAGTGAGTGTATATAATGTGA |
| 4614 | GTAGTGAGTGTATATAATGTGAT |
| 4615 | TAGTGAGTGTATATAATGTGATT |
| 4616 | AGTGAGTGTATATAATGTGATTT |
| 4617 | GTGAGTGTATATAATGTGATTTG |
| 4618 | TGAGTGTATATAATGTGATTTGG |
| 4619 | GAGTGTATATAATGTGATTTGGC |
| 4620 | AGTGTATATAATGTGATTTGGCC |
| 4621 | GTGTATATAATGTGATTTGGCCC |
| 4622 | TGTATATAATGTGATTTGGCCCT |
| 4623 | GTATATAATGTGATTTGGCCCTG |
| 4624 | TATATAATGTGATTTGGCCCTGT |
| 4625 | ATATAATGTGATTTGGCCCTGTG |
| 4626 | TATAATGTGATTTGGCCCTGTGT |
| 4627 | ATAATGTGATTTGGCCCTGTGTA |
| 4628 | TAATGTGATTTGGCCCTGTGTAT |
| 4629 | AATGTGATTTGGCCCTGTGTATT |
| 4630 | ATGTGATTTGGCCCTGTGTATTA |
| 4631 | TGTGATTTGGCCCTGTGTATTAT |
| 4632 | GTGATTTGGCCCTGTGTATTATG |
| 4633 | TGATTTGGCCCTGTGTATTATGA |
| 4634 | GATTTGGCCCTGTGTATTATGAT |
| 4635 | ATTTGGCCCTGTGTATTATGATA |
| 4636 | TTTGGCCCTGTGTATTATGATAT |
| 4637 | TTGGCCCTGTGTATTATGATATT |
| 4638 | TGGCCCTGTGTATTATGATATTT |
| 4639 | GGCCCTGTGTATTATGATATTTT |
| 4640 | GCCCTGTGTATTATGATATTTTG |
| 4641 | CCCTGTGTATTATGATATTTTGT |
| 4642 | CCTGTGTATTATGATATTTTGTT |
| 4643 | CTGTGTATTATGATATTTTGTTA |
| 4644 | TGTGTATTATGATATTTTGTTAT |
| 4645 | GTGTATTATGATATTTTGTTATT |
| 4646 | TGTATTATGATATTTTGTTATTT |
| 4647 | GTATTATGATATTTTGTTATTTT |
| 4648 | TATTATGATATTTTGTTATTTTT |
| 4649 | ATTATGATATTTTGTTATTTTTG |
| 4650 | TTATGATATTTTGTTATTTTTGT |
| 4651 | TATGATATTTTGTTATTTTTGTT |
| 4652 | ATGATATTTTGTTATTTTTGTTG |
| 4653 | TGATATTTTGTTATTTTTGTTGT |
| 4654 | GATATTTTGTTATTTTTGTTGTT |
| 4655 | ATATTTTGTTATTTTTGTTGTTA |
| 4656 | TATTTTGTTATTTTTGTTGTTAT |

| ID | SEQUENCE |
|---|---|
| 4657 | ATTTTGTTATTTTTGTTGTTATA |
| 4658 | TTTTGTTATTTTTGTTGTTATAT |
| 4659 | TTTGTTATTTTTGTTGTTATATT |
| 4660 | TTGTTATTTTTGTTGTTATATTA |
| 4661 | TGTTATTTTTGTTGTTATATTAT |
| 4662 | GTTATTTTTGTTGTTATATTATT |
| 4663 | TTATTTTTGTTGTTATATTATTT |
| 4664 | TATTTTTGTTGTTATATTATTTA |
| 4665 | ATTTTTGTTGTTATATTATTTAC |
| 4666 | TTTTTGTTGTTATATTATTTACA |
| 4667 | TTTTGTTGTTATATTATTTACAT |
| 4668 | TTTGTTGTTATATTATTTACATT |
| 4669 | TTGTTGTTATATTATTTACATTT |
| 4670 | TGTTGTTATATTATTTACATTTC |
| 4671 | GTTGTTATATTATTTACATTTCA |
| 4672 | TTGTTATATTATTTACATTTCAG |
| 4673 | TGTTATATTATTTACATTTCAGT |
| 4674 | GTTATATTATTTACATTTCAGTA |
| 4675 | TTATATTATTTACATTTCAGTAG |
| 4676 | TATATTATTTACATTTCAGTAGT |
| 4677 | ATATTATTTACATTTCAGTAGTT |
| 4678 | TATTATTTACATTTCAGTAGTTG |
| 4679 | ATTATTTACATTTCAGTAGTTGT |
| 4680 | TTATTTACATTTCAGTAGTTGTT |
| 4681 | TATTTACATTTCAGTAGTTGTTT |
| 4682 | ATTTACATTTCAGTAGTTGTTTT |
| 4683 | TTTACATTTCAGTAGTTGTTTTT |
| 4684 | TTACATTTCAGTAGTTGTTTTTT |
| 4685 | TACATTTCAGTAGTTGTTTTTTG |
| 4686 | ACATTTCAGTAGTTGTTTTTTGT |
| 4687 | CATTTCAGTAGTTGTTTTTTGTG |
| 4688 | ATTTCAGTAGTTGTTTTTTGTGT |
| 4689 | TTTCAGTAGTTGTTTTTTGTGTT |
| 4690 | TTCAGTAGTTGTTTTTTGTGTTT |
| 4691 | TCAGTAGTTGTTTTTTGTGTTTC |
| 4692 | CAGTAGTTGTTTTTTGTGTTTCC |
| 4693 | AGTAGTTGTTTTTTGTGTTTCCA |
| 4694 | GTAGTTGTTTTTTGTGTTTCCAT |
| 4695 | TAGTTGTTTTTTGTGTTTCCATT |
| 4696 | AGTTGTTTTTTGTGTTTCCATTT |
| 4697 | GTTGTTTTTTGTGTTTCCATTTT |
| 4698 | TTGTTTTTTGTGTTTCCATTTTA |
| 4699 | TGTTTTTTGTGTTTCCATTTTAG |
| 4700 | GTTTTTTGTGTTTCCATTTTAGT |
| 4701 | TTTTTTGTGTTTCCATTTTAGTG |
| 4702 | TTTTTGTGTTTCCATTTTAGTGG |
| 4703 | TTTTGTGTTTCCATTTTAGTGGA |
| 4704 | TTTGTGTTTCCATTTTAGTGGAT |

| ID | SEQUENCE |
|---|---|
| 4705 | TTGTGTTTCCATTTTAGTGGATA |
| 4706 | TGTGTTTCCATTTTAGTGGATAA |
| 4707 | GTGTTTCCATTTTAGTGGATAAA |
| 4708 | TGTTTCCATTTTAGTGGATAAAA |
| 4709 | GTTTCCATTTTAGTGGATAAAAT |
| 4710 | TTTCCATTTTAGTGGATAAAATT |
| 4711 | TTCCATTTTAGTGGATAAAATTT |
| 4712 | TCCATTTTAGTGGATAAAATTTG |
| 4713 | CCATTTTAGTGGATAAAATTTGT |
| 4714 | CATTTTAGTGGATAAAATTTGTA |
| 4715 | ATTTTAGTGGATAAAATTTGTAT |
| 4716 | TTTTAGTGGATAAAATTTGTATT |
| 4717 | TTTAGTGGATAAAATTTGTATTT |
| 4718 | TTAGTGGATAAAATTTGTATTTT |
| 4719 | TAGTGGATAAAATTTGTATTTTG |
| 4720 | AGTGGATAAAATTTGTATTTTGA |
| 4721 | GTGGATAAAATTTGTATTTTGAA |
| 4722 | TGGATAAAATTTGTATTTTGAAC |
| 4723 | GGATAAAATTTGTATTTTGAACT |
| 4724 | GATAAAATTTGTATTTTGAACTA |
| 4725 | ATAAAATTTGTATTTTGAACTAT |
| 4726 | TAAAATTTGTATTTTGAACTATG |
| 4727 | AAAATTTGTATTTTGAACTATGA |
| 4728 | AAATTTGTATTTTGAACTATGAA |
| 4729 | AATTTGTATTTTGAACTATGAAT |
| 4730 | ATTTGTATTTTGAACTATGAATG |
| 4731 | TTTGTATTTTGAACTATGAATGG |
| 4732 | TTGTATTTTGAACTATGAATGGA |
| 4733 | TGTATTTTGAACTATGAATGGAG |
| 4734 | GTATTTTGAACTATGAATGGAGA |
| 4735 | TATTTTGAACTATGAATGGAGAC |
| 4736 | ATTTTGAACTATGAATGGAGACT |
| 4737 | TTTTGAACTATGAATGGAGACTA |
| 4738 | TTTGAACTATGAATGGAGACTAC |
| 4739 | TTGAACTATGAATGGAGACTACC |
| 4740 | TGAACTATGAATGGAGACTACCG |
| 4741 | GAACTATGAATGGAGACTACCGC |
| 4742 | AACTATGAATGGAGACTACCGCC |
| 4743 | ACTATGAATGGAGACTACCGCCC |
| 4744 | CTATGAATGGAGACTACCGCCCC |
| 4745 | TATGAATGGAGACTACCGCCCCA |
| 4746 | ATGAATGGAGACTACCGCCCCAG |
| 4747 | TGAATGGAGACTACCGCCCCAGC |
| 4748 | GAATGGAGACTACCGCCCCAGCA |
| 4749 | AATGGAGACTACCGCCCCAGCAT |
| 4750 | ATGGAGACTACCGCCCCAGCATT |
| 4751 | TGGAGACTACCGCCCCAGCATTA |
| 4752 | GGAGACTACCGCCCCAGCATTAG |

| ID | SEQUENCE |
|---|---|
| 4753 | GAGACTACCGCCCCAGCATTAGT |
| 4754 | AGACTACCGCCCCAGCATTAGTT |
| 4755 | GACTACCGCCCCAGCATTAGTTT |
| 4756 | ACTACCGCCCCAGCATTAGTTTC |
| 4757 | CTACCGCCCCAGCATTAGTTTCA |
| 4758 | TACCGCCCCAGCATTAGTTTCAC |
| 4759 | ACCGCCCCAGCATTAGTTTCACA |
| 4760 | CCGCCCCAGCATTAGTTTCACAT |
| 4761 | CGCCCCAGCATTAGTTTCACATG |
| 4762 | GCCCCAGCATTAGTTTCACATGA |
| 4763 | CCCCAGCATTAGTTTCACATGAT |
| 4764 | CCCAGCATTAGTTTCACATGATA |
| 4765 | CCAGCATTAGTTTCACATGATAT |
| 4766 | CAGCATTAGTTTCACATGATATA |
| 4767 | AGCATTAGTTTCACATGATATAC |
| 4768 | GCATTAGTTTCACATGATATACC |
| 4769 | CATTAGTTTCACATGATATACCC |
| 4770 | ATTAGTTTCACATGATATACCCT |
| 4771 | TTAGTTTCACATGATATACCCTT |
| 4772 | TAGTTTCACATGATATACCCTTT |
| 4773 | AGTTTCACATGATATACCCTTTA |
| 4774 | GTTTCACATGATATACCCTTTAA |
| 4775 | TTTCACATGATATACCCTTTAAA |
| 4776 | TTCACATGATATACCCTTTAAAC |
| 4777 | TCACATGATATACCCTTTAAACC |
| 4778 | CACATGATATACCCTTTAAACCC |
| 4779 | ACATGATATACCCTTTAAACCCG |
| 4780 | CATGATATACCCTTTAAACCCGA |
| 4781 | ATGATATACCCTTTAAACCCGAA |
| 4782 | TGATATACCCTTTAAACCCGAAT |
| 4783 | GATATACCCTTTAAACCCGAATC |
| 4784 | ATATACCCTTTAAACCCGAATCA |
| 4785 | TATACCCTTTAAACCCGAATCAT |
| 4786 | ATACCCTTTAAACCCGAATCATT |
| 4787 | TACCCTTTAAACCCGAATCATTG |
| 4788 | ACCCTTTAAACCCGAATCATTGT |
| 4789 | CCCTTTAAACCCGAATCATTGTT |
| 4790 | CCTTTAAACCCGAATCATTGTTT |
| 4791 | CTTTAAACCCGAATCATTGTTTT |
| 4792 | TTTAAACCCGAATCATTGTTTTA |
| 4793 | TTAAACCCGAATCATTGTTTTAT |
| 4794 | TAAACCCGAATCATTGTTTTATT |
| 4795 | AAACCCGAATCATTGTTTTATTT |
| 4796 | AACCCGAATCATTGTTTTATTTC |
| 4797 | ACCCGAATCATTGTTTTATTTCC |
| 4798 | CCCGAATCATTGTTTTATTTCCT |
| 4799 | CCGAATCATTGTTTTATTTCCTG |
| 4800 | CGAATCATTGTTTTATTTCCTGA |

| ID | SEQUENCE |
|---|---|
| 4801 | GAATCATTGTTTTATTTCCTGAT |
| 4802 | AATCATTGTTTTATTTCCTGATT |
| 4803 | ATCATTGTTTTATTTCCTGATTA |
| 4804 | TCATTGTTTTATTTCCTGATTAC |
| 4805 | CATTGTTTTATTTCCTGATTACA |
| 4806 | ATTGTTTTATTTCCTGATTACAC |
| 4807 | TTGTTTTATTTCCTGATTACACA |
| 4808 | TGTTTTATTTCCTGATTACACAG |
| 4809 | GTTTTATTTCCTGATTACACAGG |
| 4810 | TTTTATTTCCTGATTACACAGGT |
| 4811 | TTTATTTCCTGATTACACAGGTG |
| 4812 | TTATTTCCTGATTACACAGGTGT |
| 4813 | TATTTCCTGATTACACAGGTGTT |
| 4814 | ATTTCCTGATTACACAGGTGTTG |
| 4815 | TTTCCTGATTACACAGGTGTTGA |
| 4816 | TTCCTGATTACACAGGTGTTGAA |
| 4817 | TCCTGATTACACAGGTGTTGAAT |
| 4818 | CCTGATTACACAGGTGTTGAATG |
| 4819 | CTGATTACACAGGTGTTGAATGG |
| 4820 | TGATTACACAGGTGTTGAATGGG |
| 4821 | GATTACACAGGTGTTGAATGGGG |
| 4822 | ATTACACAGGTGTTGAATGGGGA |
| 4823 | TTACACAGGTGTTGAATGGGGAA |
| 4824 | TACACAGGTGTTGAATGGGGAAA |
| 4825 | ACACAGGTGTTGAATGGGGAAAG |
| 4826 | CACAGGTGTTGAATGGGGAAAGG |
| 4827 | ACAGGTGTTGAATGGGGAAAGGG |
| 4828 | CAGGTGTTGAATGGGGAAAGGGG |
| 4829 | AGGTGTTGAATGGGGAAAGGGGC |
| 4830 | GGTGTTGAATGGGGAAAGGGGCT |
| 4831 | GTGTTGAATGGGGAAAGGGGCTA |
| 4832 | TGTTGAATGGGGAAAGGGGCTAG |
| 4833 | GTTGAATGGGGAAAGGGGCTAGT |
| 4834 | TTGAATGGGGAAAGGGGCTAGTA |
| 4835 | TGAATGGGGAAAGGGGCTAGTAT |
| 4836 | GAATGGGGAAAGGGGCTAGTATA |
| 4837 | AATGGGGAAAGGGGCTAGTATAT |
| 4838 | ATGGGGAAAGGGGCTAGTATATC |
| 4839 | TGGGGAAAGGGGCTAGTATATCA |
| 4840 | GGGGAAAGGGGCTAGTATATCAG |
| 4841 | GGGAAAGGGGCTAGTATATCAGT |
| 4842 | GGAAAGGGGCTAGTATATCAGTA |
| 4843 | GAAAGGGGCTAGTATATCAGTAG |
| 4844 | AAAGGGGCTAGTATATCAGTAGG |
| 4845 | AAGGGGCTAGTATATCAGTAGGA |
| 4846 | AGGGGCTAGTATATCAGTAGGAT |
| 4847 | GGGGCTAGTATATCAGTAGGATA |
| 4848 | GGGCTAGTATATCAGTAGGATAT |

| ID | SEQUENCE |
|---|---|
| 4849 | GGCTAGTATATCAGTAGGATATA |
| 4850 | GCTAGTATATCAGTAGGATATAC |
| 4851 | CTAGTATATCAGTAGGATATACT |
| 4852 | TAGTATATCAGTAGGATATACTA |
| 4853 | AGTATATCAGTAGGATATACTAT |
| 4854 | GTATATCAGTAGGATATACTATG |
| 4855 | TATATCAGTAGGATATACTATGG |
| 4856 | ATATCAGTAGGATATACTATGGG |
| 4857 | TATCAGTAGGATATACTATGGGA |
| 4858 | ATCAGTAGGATATACTATGGGAT |
| 4859 | TCAGTAGGATATACTATGGGATG |
| 4860 | CAGTAGGATATACTATGGGATGT |
| 4861 | AGTAGGATATACTATGGGATGTA |
| 4862 | GTAGGATATACTATGGGATGTAT |
| 4863 | TAGGATATACTATGGGATGTATA |
| 4864 | AGGATATACTATGGGATGTATAT |
| 4865 | GGATATACTATGGGATGTATATA |
| 4866 | GATATACTATGGGATGTATATAT |
| 4867 | ATATACTATGGGATGTATATATA |
| 4868 | TATACTATGGGATGTATATATAT |
| 4869 | ATACTATGGGATGTATATATATC |
| 4870 | TACTATGGGATGTATATATATCA |
| 4871 | ACTATGGGATGTATATATATCAT |
| 4872 | CTATGGGATGTATATATATCATT |
| 4873 | TATGGGATGTATATATATCATTG |
| 4874 | ATGGGATGTATATATATCATTGC |
| 4875 | TGGGATGTATATATATCATTGCT |
| 4876 | GGGATGTATATATATCATTGCTG |
| 4877 | GGATGTATATATATCATTGCTGT |
| 4878 | GATGTATATATATCATTGCTGTT |
| 4879 | ATGTATATATATCATTGCTGTTA |
| 4880 | TGTATATATATCATTGCTGTTAG |
| 4881 | GTATATATATCATTGCTGTTAGA |
| 4882 | TATATATATCATTGCTGTTAGAG |
| 4883 | ATATATATCATTGCTGTTAGAGA |
| 4884 | TATATATCATTGCTGTTAGAGAA |
| 4885 | ATATATCATTGCTGTTAGAGAAA |
| 4886 | TATATCATTGCTGTTAGAGAAAT |
| 4887 | ATATCATTGCTGTTAGAGAAATG |
| 4888 | TATCATTGCTGTTAGAGAAATGA |
| 4889 | ATCATTGCTGTTAGAGAAATGAA |
| 4890 | TCATTGCTGTTAGAGAAATGAAA |
| 4891 | CATTGCTGTTAGAGAAATGAAAT |
| 4892 | ATTGCTGTTAGAGAAATGAAATA |
| 4893 | TTGCTGTTAGAGAAATGAAATAA |
| 4894 | TGCTGTTAGAGAAATGAAATAAA |
| 4895 | GCTGTTAGAGAAATGAAATAAAA |
| 4896 | CTGTTAGAGAAATGAAATAAAAT |

| ID | SEQUENCE |
|---|---|
| 4897 | TGTTAGAGAAATGAAATAAAATG |
| 4898 | GTTAGAGAAATGAAATAAAATGG |
| 4899 | TTAGAGAAATGAAATAAAATGGG |
| 4900 | TAGAGAAATGAAATAAAATGGGG |
| 4901 | AGAGAAATGAAATAAAATGGGGC |
| 4902 | GAGAAATGAAATAAAATGGGGCT |
| 4903 | AGAAATGAAATAAAATGGGGCTG |
| 4904 | GAAATGAAATAAAATGGGGCTGG |
| 4905 | AAATGAAATAAAATGGGGCTGGG |
| 4906 | AATGAAATAAAATGGGGCTGGGC |
| 4907 | ATGAAATAAAATGGGGCTGGGCT |
| 4908 | TGAAATAAAATGGGGCTGGGCTC |
| 4909 | GAAATAAAATGGGGCTGGGCTCA |
| 4910 | AAATAAAATGGGGCTGGGCTCAG |
| 4911 | AATAAAATGGGGCTGGGCTCAGT |
| 4912 | ATAAAATGGGGCTGGGCTCAGTG |
| 4913 | TAAAATGGGGCTGGGCTCAGTGG |
| 4914 | AAAATGGGGCTGGGCTCAGTGGC |
| 4915 | AAATGGGGCTGGGCTCAGTGGCT |
| 4916 | AATGGGGCTGGGCTCAGTGGCTC |
| 4917 | ATGGGGCTGGGCTCAGTGGCTCA |
| 4918 | TGGGGCTGGGCTCAGTGGCTCAC |
| 4919 | GGGGCTGGGCTCAGTGGCTCACG |
| 4920 | GGGCTGGGCTCAGTGGCTCACGC |
| 4921 | GGCTGGGCTCAGTGGCTCACGCC |
| 4922 | GCTGGGCTCAGTGGCTCACGCCT |
| 4923 | CTGGGCTCAGTGGCTCACGCCTG |
| 4924 | TGGGCTCAGTGGCTCACGCCTGT |
| 4925 | GGGCTCAGTGGCTCACGCCTGTA |
| 4926 | GGCTCAGTGGCTCACGCCTGTAA |
| 4927 | GCTCAGTGGCTCACGCCTGTAAT |
| 4928 | CTCAGTGGCTCACGCCTGTAATC |
| 4929 | TCAGTGGCTCACGCCTGTAATCC |
| 4930 | CAGTGGCTCACGCCTGTAATCCC |
| 4931 | AGTGGCTCACGCCTGTAATCCCA |
| 4932 | GTGGCTCACGCCTGTAATCCCAG |
| 4933 | TGGCTCACGCCTGTAATCCCAGC |
| 4934 | GGCTCACGCCTGTAATCCCAGCA |
| 4935 | GCTCACGCCTGTAATCCCAGCAC |
| 4936 | CTCACGCCTGTAATCCCAGCACT |
| 4937 | TCACGCCTGTAATCCCAGCACTT |
| 4938 | CACGCCTGTAATCCCAGCACTTT |
| 4939 | ACGCCTGTAATCCCAGCACTTTG |
| 4940 | CGCCTGTAATCCCAGCACTTTGG |
| 4941 | GCCTGTAATCCCAGCACTTTGGG |
| 4942 | CCTGTAATCCCAGCACTTTGGGA |
| 4943 | CTGTAATCCCAGCACTTTGGGAG |
| 4944 | TGTAATCCCAGCACTTTGGGAGG |

| ID | SEQUENCE |
|---|---|
| 4945 | GTAATCCCAGCACTTTGGGAGGC |
| 4946 | TAATCCCAGCACTTTGGGAGGCT |
| 4947 | AATCCCAGCACTTTGGGAGGCTG |
| 4948 | ATCCCAGCACTTTGGGAGGCTGA |
| 4949 | TCCCAGCACTTTGGGAGGCTGAG |
| 4950 | CCCAGCACTTTGGGAGGCTGAGG |
| 4951 | CCAGCACTTTGGGAGGCTGAGGC |
| 4952 | CAGCACTTTGGGAGGCTGAGGCA |
| 4953 | AGCACTTTGGGAGGCTGAGGCAG |
| 4954 | GCACTTTGGGAGGCTGAGGCAGG |
| 4955 | CACTTTGGGAGGCTGAGGCAGGT |
| 4956 | ACTTTGGGAGGCTGAGGCAGGTG |
| 4957 | CTTTGGGAGGCTGAGGCAGGTGG |
| 4958 | TTTGGGAGGCTGAGGCAGGTGGA |
| 4959 | TTGGGAGGCTGAGGCAGGTGGAT |
| 4960 | TGGGAGGCTGAGGCAGGTGGATC |
| 4961 | GGGAGGCTGAGGCAGGTGGATCA |
| 4962 | GGAGGCTGAGGCAGGTGGATCAC |
| 4963 | GAGGCTGAGGCAGGTGGATCACG |
| 4964 | AGGCTGAGGCAGGTGGATCACGA |
| 4965 | GGCTGAGGCAGGTGGATCACGAG |
| 4966 | GCTGAGGCAGGTGGATCACGAGG |
| 4967 | CTGAGGCAGGTGGATCACGAGGT |
| 4968 | TGAGGCAGGTGGATCACGAGGTC |
| 4969 | GAGGCAGGTGGATCACGAGGTCA |
| 4970 | AGGCAGGTGGATCACGAGGTCAG |
| 4971 | GGCAGGTGGATCACGAGGTCAGG |
| 4972 | GCAGGTGGATCACGAGGTCAGGA |
| 4973 | CAGGTGGATCACGAGGTCAGGAG |
| 4974 | AGGTGGATCACGAGGTCAGGAGA |
| 4975 | GGTGGATCACGAGGTCAGGAGAT |
| 4976 | GTGGATCACGAGGTCAGGAGATC |
| 4977 | TGGATCACGAGGTCAGGAGATCG |
| 4978 | GGATCACGAGGTCAGGAGATCGA |
| 4979 | GATCACGAGGTCAGGAGATCGAG |
| 4980 | ATCACGAGGTCAGGAGATCGAGA |
| 4981 | TCACGAGGTCAGGAGATCGAGAC |
| 4982 | CACGAGGTCAGGAGATCGAGACC |
| 4983 | ACGAGGTCAGGAGATCGAGACCA |
| 4984 | CGAGGTCAGGAGATCGAGACCAT |
| 4985 | GAGGTCAGGAGATCGAGACCATC |
| 4986 | AGGTCAGGAGATCGAGACCATCC |
| 4987 | GGTCAGGAGATCGAGACCATCCT |
| 4988 | GTCAGGAGATCGAGACCATCCTG |
| 4989 | TCAGGAGATCGAGACCATCCTGG |
| 4990 | CAGGAGATCGAGACCATCCTGGC |
| 4991 | AGGAGATCGAGACCATCCTGGCT |
| 4992 | GGAGATCGAGACCATCCTGGCTA |

| ID | SEQUENCE |
|---|---|
| 4993 | GAGATCGAGACCATCCTGGCTAA |
| 4994 | AGATCGAGACCATCCTGGCTAAC |
| 4995 | GATCGAGACCATCCTGGCTAACA |
| 4996 | ATCGAGACCATCCTGGCTAACAC |
| 4997 | TCGAGACCATCCTGGCTAACACG |
| 4998 | CGAGACCATCCTGGCTAACACGG |
| 4999 | GAGACCATCCTGGCTAACACGGT |
| 5000 | AGACCATCCTGGCTAACACGGTG |
| 5001 | GACCATCCTGGCTAACACGGTGA |
| 5002 | ACCATCCTGGCTAACACGGTGAA |
| 5003 | CCATCCTGGCTAACACGGTGAAA |
| 5004 | CATCCTGGCTAACACGGTGAAAC |
| 5005 | ATCCTGGCTAACACGGTGAAACC |
| 5006 | TCCTGGCTAACACGGTGAAACCC |
| 5007 | CCTGGCTAACACGGTGAAACCCC |
| 5008 | CTGGCTAACACGGTGAAACCCCG |
| 5009 | TGGCTAACACGGTGAAACCCCGT |
| 5010 | GGCTAACACGGTGAAACCCCGTC |
| 5011 | GCTAACACGGTGAAACCCCGTCT |
| 5012 | CTAACACGGTGAAACCCCGTCTC |
| 5013 | TAACACGGTGAAACCCCGTCTCT |
| 5014 | AACACGGTGAAACCCCGTCTCTA |
| 5015 | ACACGGTGAAACCCCGTCTCTAC |
| 5016 | CACGGTGAAACCCCGTCTCTACT |
| 5017 | ACGGTGAAACCCCGTCTCTACTA |
| 5018 | CGGTGAAACCCCGTCTCTACTAA |
| 5019 | GGTGAAACCCCGTCTCTACTAAA |
| 5020 | GTGAAACCCCGTCTCTACTAAAA |
| 5021 | TGAAACCCCGTCTCTACTAAAAA |
| 5022 | GAAACCCCGTCTCTACTAAAAAA |
| 5023 | AAACCCCGTCTCTACTAAAAAAC |
| 5024 | AACCCCGTCTCTACTAAAAAACA |
| 5025 | ACCCCGTCTCTACTAAAAAACAG |
| 5026 | CCCCGTCTCTACTAAAAAACAGA |
| 5027 | CCCGTCTCTACTAAAAAACAGAA |
| 5028 | CCGTCTCTACTAAAAAACAGAAA |
| 5029 | CGTCTCTACTAAAAAACAGAAAA |
| 5030 | GTCTCTACTAAAAAACAGAAAAT |
| 5031 | TCTCTACTAAAAAACAGAAAATT |
| 5032 | CTCTACTAAAAAACAGAAAATTA |
| 5033 | TCTACTAAAAAACAGAAAATTAG |
| 5034 | CTACTAAAAAACAGAAAATTAGC |
| 5035 | TACTAAAAAACAGAAAATTAGCC |
| 5036 | ACTAAAAAACAGAAAATTAGCCG |
| 5037 | CTAAAAAACAGAAAATTAGCCGG |
| 5038 | TAAAAAACAGAAAATTAGCCGGG |
| 5039 | AAAAAACAGAAAATTAGCCGGGC |
| 5040 | AAAAACAGAAAATTAGCCGGGCG |

| ID | SEQUENCE |
|---|---|
| 5041 | AAAACAGAAAATTAGCCGGGCGT |
| 5042 | AAACAGAAAATTAGCCGGGCGTG |
| 5043 | AACAGAAAATTAGCCGGGCGTGG |
| 5044 | ACAGAAAATTAGCCGGGCGTGGT |
| 5045 | CAGAAAATTAGCCGGGCGTGGTG |
| 5046 | AGAAAATTAGCCGGGCGTGGTGG |
| 5047 | GAAAATTAGCCGGGCGTGGTGGC |
| 5048 | AAAATTAGCCGGGCGTGGTGGCG |
| 5049 | AAATTAGCCGGGCGTGGTGGCGG |
| 5050 | AATTAGCCGGGCGTGGTGGCGGG |
| 5051 | ATTAGCCGGGCGTGGTGGCGGGC |
| 5052 | TTAGCCGGGCGTGGTGGCGGGCG |
| 5053 | CGGGCGCCTGTAGTCCCAGCTAC |
| 5054 | GGGCGCCTGTAGTCCCAGCTACT |
| 5055 | GGCGCCTGTAGTCCCAGCTACTC |
| 5056 | GCGCCTGTAGTCCCAGCTACTCG |
| 5057 | CGCCTGTAGTCCCAGCTACTCGG |
| 5058 | GCCTGTAGTCCCAGCTACTCGGG |
| 5059 | CCTGTAGTCCCAGCTACTCGGGA |
| 5060 | CTGTAGTCCCAGCTACTCGGGAG |
| 5061 | TGTAGTCCCAGCTACTCGGGAGG |
| 5062 | GTAGTCCCAGCTACTCGGGAGGC |
| 5063 | TAGTCCCAGCTACTCGGGAGGCT |
| 5064 | AGTCCCAGCTACTCGGGAGGCTG |
| 5065 | GTCCCAGCTACTCGGGAGGCTGA |
| 5066 | TCCCAGCTACTCGGGAGGCTGAG |
| 5067 | CCCAGCTACTCGGGAGGCTGAGG |
| 5068 | CCAGCTACTCGGGAGGCTGAGGC |
| 5069 | CAGCTACTCGGGAGGCTGAGGCA |
| 5070 | AGCTACTCGGGAGGCTGAGGCAG |
| 5071 | GCTACTCGGGAGGCTGAGGCAGG |
| 5072 | CTACTCGGGAGGCTGAGGCAGGA |
| 5073 | TACTCGGGAGGCTGAGGCAGGAG |
| 5074 | ACTCGGGAGGCTGAGGCAGGAGA |
| 5075 | CTCGGGAGGCTGAGGCAGGAGAA |
| 5076 | TCGGGAGGCTGAGGCAGGAGAAT |
| 5077 | CGGGAGGCTGAGGCAGGAGAATG |
| 5078 | GGGAGGCTGAGGCAGGAGAATGG |
| 5079 | GGAGGCTGAGGCAGGAGAATGGT |
| 5080 | GAGGCTGAGGCAGGAGAATGGTG |
| 5081 | AGGCTGAGGCAGGAGAATGGTGT |
| 5082 | GGCTGAGGCAGGAGAATGGTGTG |
| 5083 | GCTGAGGCAGGAGAATGGTGTGA |
| 5084 | CTGAGGCAGGAGAATGGTGTGAA |
| 5085 | TGAGGCAGGAGAATGGTGTGAAC |
| 5086 | GAGGCAGGAGAATGGTGTGAACC |
| 5087 | AGGCAGGAGAATGGTGTGAACCC |
| 5088 | GGCAGGAGAATGGTGTGAACCCG |

| ID | SEQUENCE |
|---|---|
| 5089 | GCAGGAGAATGGTGTGAACCCGG |
| 5090 | CAGGAGAATGGTGTGAACCCGGG |
| 5091 | AGGAGAATGGTGTGAACCCGGGA |
| 5092 | GGAGAATGGTGTGAACCCGGGAG |
| 5093 | GAGAATGGTGTGAACCCGGGAGG |
| 5094 | AGAATGGTGTGAACCCGGGAGGC |
| 5095 | GAATGGTGTGAACCCGGGAGGCA |
| 5096 | AATGGTGTGAACCCGGGAGGCAG |
| 5097 | ATGGTGTGAACCCGGGAGGCAGA |
| 5098 | TGGTGTGAACCCGGGAGGCAGAG |
| 5099 | GGTGTGAACCCGGGAGGCAGAGC |
| 5100 | GTGTGAACCCGGGAGGCAGAGCT |
| 5101 | TGTGAACCCGGGAGGCAGAGCTT |
| 5102 | GTGAACCCGGGAGGCAGAGCTTG |
| 5103 | TGAACCCGGGAGGCAGAGCTTGC |
| 5104 | GAACCCGGGAGGCAGAGCTTGCA |
| 5105 | AACCCGGGAGGCAGAGCTTGCAG |
| 5106 | ACCCGGGAGGCAGAGCTTGCAGT |
| 5107 | CCCGGGAGGCAGAGCTTGCAGTG |
| 5108 | CCGGGAGGCAGAGCTTGCAGTGA |
| 5109 | CGGGAGGCAGAGCTTGCAGTGAG |
| 5110 | GGGAGGCAGAGCTTGCAGTGAGC |
| 5111 | GGAGGCAGAGCTTGCAGTGAGCC |
| 5112 | GAGGCAGAGCTTGCAGTGAGCCG |
| 5113 | AGGCAGAGCTTGCAGTGAGCCGA |
| 5114 | GGCAGAGCTTGCAGTGAGCCGAG |
| 5115 | GCAGAGCTTGCAGTGAGCCGAGA |
| 5116 | CAGAGCTTGCAGTGAGCCGAGAT |
| 5117 | AGAGCTTGCAGTGAGCCGAGATC |
| 5118 | GAGCTTGCAGTGAGCCGAGATCT |
| 5119 | AGCTTGCAGTGAGCCGAGATCTC |
| 5120 | GCTTGCAGTGAGCCGAGATCTCG |
| 5121 | CTTGCAGTGAGCCGAGATCTCGC |
| 5122 | TTGCAGTGAGCCGAGATCTCGCC |
| 5123 | TGCAGTGAGCCGAGATCTCGCCA |
| 5124 | GCAGTGAGCCGAGATCTCGCCAC |
| 5125 | CAGTGAGCCGAGATCTCGCCACT |
| 5126 | AGTGAGCCGAGATCTCGCCACTG |
| 5127 | GTGAGCCGAGATCTCGCCACTGC |
| 5128 | TGAGCCGAGATCTCGCCACTGCA |
| 5129 | GAGCCGAGATCTCGCCACTGCAC |
| 5130 | AGCCGAGATCTCGCCACTGCACT |
| 5131 | GCCGAGATCTCGCCACTGCACTC |
| 5132 | CCGAGATCTCGCCACTGCACTCC |
| 5133 | CGAGATCTCGCCACTGCACTCCA |
| 5134 | GAGATCTCGCCACTGCACTCCAG |
| 5135 | AGATCTCGCCACTGCACTCCAGC |
| 5136 | GATCTCGCCACTGCACTCCAGCC |

| ID | SEQUENCE |
|---|---|
| 5137 | ATCTCGCCACTGCACTCCAGCCT |
| 5138 | TCTCGCCACTGCACTCCAGCCTG |
| 5139 | CTCGCCACTGCACTCCAGCCTGG |
| 5140 | TCGCCACTGCACTCCAGCCTGGG |
| 5141 | CGCCACTGCACTCCAGCCTGGGC |
| 5142 | GCCACTGCACTCCAGCCTGGGCA |
| 5143 | CCACTGCACTCCAGCCTGGGCAA |
| 5144 | CACTGCACTCCAGCCTGGGCAAC |
| 5145 | ACTGCACTCCAGCCTGGGCAACA |
| 5146 | CTGCACTCCAGCCTGGGCAACAG |
| 5147 | TGCACTCCAGCCTGGGCAACAGA |
| 5148 | GCACTCCAGCCTGGGCAACAGAG |
| 5149 | CACTCCAGCCTGGGCAACAGAGC |
| 5150 | ACTCCAGCCTGGGCAACAGAGCA |
| 5151 | CTCCAGCCTGGGCAACAGAGCAA |
| 5152 | TCCAGCCTGGGCAACAGAGCAAG |
| 5153 | CCAGCCTGGGCAACAGAGCAAGA |
| 5154 | CAGCCTGGGCAACAGAGCAAGAC |
| 5155 | AGCCTGGGCAACAGAGCAAGACT |
| 5156 | GCCTGGGCAACAGAGCAAGACTC |
| 5157 | CCTGGGCAACAGAGCAAGACTCT |
| 5158 | CTGGGCAACAGAGCAAGACTCTG |
| 5159 | TGGGCAACAGAGCAAGACTCTGT |
| 5160 | GGGCAACAGAGCAAGACTCTGTC |
| 5161 | GGCAACAGAGCAAGACTCTGTCT |
| 5162 | GCAACAGAGCAAGACTCTGTCTC |
| 5163 | CAACAGAGCAAGACTCTGTCTCA |
| 5164 | AACAGAGCAAGACTCTGTCTCAA |
| 5165 | ACAGAGCAAGACTCTGTCTCAAA |
| 5166 | CAGAGCAAGACTCTGTCTCAAAA |
| 5167 | AGAGCAAGACTCTGTCTCAAAAA |
| 5168 | GAGCAAGACTCTGTCTCAAAAAA |
| 5169 | AGCAAGACTCTGTCTCAAAAAAA |
| 5170 | GCAAGACTCTGTCTCAAAAAAAA |
| 5171 | AAAAAAAGAAATAAGAAAATGG |
| 5172 | AAAAAAGAAATAAGAAAATGGG |
| 5173 | AAAAAGAAATAAGAAAATGGGA |
| 5174 | AAAAGAAATAAGAAAATGGGAA |
| 5175 | AAAGAAATAAGAAAATGGGAAG |
| 5176 | AAGAAATAAGAAAATGGGAAGC |
| 5177 | AGAAATAAGAAAATGGGAAGCA |
| 5178 | AGAAATAAGAAAATGGGAAGCAA |
| 5179 | GAAATAAGAAAATGGGAAGCAAT |
| 5180 | AAATAAGAAAATGGGAAGCAATA |
| 5181 | AATAAGAAAATGGGAAGCAATAT |
| 5182 | ATAAGAAAATGGGAAGCAATATT |
| 5183 | TAAGAAAATGGGAAGCAATATTT |
| 5184 | AAGAAAATGGGAAGCAATATTTG |

| ID | SEQUENCE |
|---|---|
| 5185 | AGAAAATGGGAAGCAATATTTGA |
| 5186 | GAAAATGGGAAGCAATATTTGAC |
| 5187 | AAAATGGGAAGCAATATTTGACA |
| 5188 | AAATGGGAAGCAATATTTGACAT |
| 5189 | AATGGGAAGCAATATTTGACATA |
| 5190 | ATGGGAAGCAATATTTGACATAG |
| 5191 | TGGGAAGCAATATTTGACATAGT |
| 5192 | GGGAAGCAATATTTGACATAGTT |
| 5193 | GGAAGCAATATTTGACATAGTTC |
| 5194 | GAAGCAATATTTGACATAGTTCT |
| 5195 | AAGCAATATTTGACATAGTTCTT |
| 5196 | AGCAATATTTGACATAGTTCTTT |
| 5197 | GCAATATTTGACATAGTTCTTTT |
| 5198 | CAATATTTGACATAGTTCTTTTT |
| 5199 | AATATTTGACATAGTTCTTTTTA |
| 5200 | ATATTTGACATAGTTCTTTTTAG |
| 5201 | TATTTGACATAGTTCTTTTTAGT |
| 5202 | ATTTGACATAGTTCTTTTTAGTC |
| 5203 | TTTGACATAGTTCTTTTTAGTCA |
| 5204 | TTGACATAGTTCTTTTTAGTCAA |
| 5205 | TGACATAGTTCTTTTTAGTCAAA |
| 5206 | GACATAGTTCTTTTTAGTCAAAT |
| 5207 | ACATAGTTCTTTTTAGTCAAATC |
| 5208 | CATAGTTCTTTTTAGTCAAATCT |
| 5209 | ATAGTTCTTTTTAGTCAAATCTA |
| 5210 | TAGTTCTTTTTAGTCAAATCTAC |
| 5211 | AGTTCTTTTTAGTCAAATCTACT |
| 5212 | GTTCTTTTTAGTCAAATCTACTT |
| 5213 | TTCTTTTTAGTCAAATCTACTTG |
| 5214 | TCTTTTTAGTCAAATCTACTTGT |
| 5215 | CTTTTTAGTCAAATCTACTTGTT |
| 5216 | TTTTTAGTCAAATCTACTTGTTA |
| 5217 | TTTTAGTCAAATCTACTTGTTAA |
| 5218 | TTTAGTCAAATCTACTTGTTAAA |
| 5219 | TTAGTCAAATCTACTTGTTAAAA |
| 5220 | TAGTCAAATCTACTTGTTAAAAA |
| 5221 | AGTCAAATCTACTTGTTAAAAAA |
| 5222 | GTCAAATCTACTTGTTAAAAAAA |
| 5223 | TCAAATCTACTTGTTAAAAAAAG |
| 5224 | CAAATCTACTTGTTAAAAAAGG |
| 5225 | AAATCTACTTGTTAAAAAAGGG |
| 5226 | AATCTACTTGTTAAAAAAGGGT |
| 5227 | ATCTACTTGTTAAAAAAGGGTA |
| 5228 | TCTACTTGTTAAAAAAGGGTAG |
| 5229 | CTACTTGTTAAAAAAGGGTAGC |
| 5230 | TACTTGTTAAAAAAGGGTAGCA |
| 5231 | ACTTGTTAAAAAAGGGTAGCAG |
| 5232 | CTTGTTAAAAAAGGGTAGCAGT |

| ID | SEQUENCE |
|---|---|
| 5233 | TTGTTAAAAAAGGGTAGCAGTT |
| 5234 | TGTTAAAAAAGGGTAGCAGTTT |
| 5235 | GTTAAAAAAGGGTAGCAGTTTA |
| 5236 | TTAAAAAAGGGTAGCAGTTTAT |
| 5237 | TAAAAAAGGGTAGCAGTTTATT |
| 5238 | AAAAAAGGGTAGCAGTTTATTC |
| 5239 | AAAAAGGGTAGCAGTTTATTCA |
| 5240 | AAAAGGGTAGCAGTTTATTCAT |
| 5241 | AAAGGGTAGCAGTTTATTCATC |
| 5242 | AAGGGTAGCAGTTTATTCATCT |
| 5243 | AGGGTAGCAGTTTATTCATCTG |
| 5244 | GGGTAGCAGTTTATTCATCTGT |
| 5245 | GGTAGCAGTTTATTCATCTGTG |
| 5246 | GTAGCAGTTTATTCATCTGTGA |
| 5247 | TAGCAGTTTATTCATCTGTGAA |
| 5248 | AGCAGTTTATTCATCTGTGAAA |
| 5249 | GCAGTTTATTCATCTGTGAAAG |
| 5250 | CAGTTTATTCATCTGTGAAAGG |
| 5251 | AGTTTATTCATCTGTGAAAGGA |
| 5252 | GTTTATTCATCTGTGAAAGGAA |
| 5253 | TTTATTCATCTGTGAAAGGAAA |
| 5254 | TTATTCATCTGTGAAAGGAAAA |
| 5255 | TATTCATCTGTGAAAGGAAAAT |
| 5256 | ATTCATCTGTGAAAGGAAAATA |
| 5257 | TTCATCTGTGAAAGGAAAATAA |
| 5258 | TCATCTGTGAAAGGAAAATAAT |
| 5259 | CATCTGTGAAAGGAAAATAATA |
| 5260 | ATCTGTGAAAGGAAAATAATAC |
| 5261 | TCTGTGAAAGGAAAATAATACT |
| 5262 | CTGTGAAAGGAAAATAATACTT |
| 5263 | TGTGAAAGGAAAATAATACTTA |
| 5264 | GTGAAAGGAAAATAATACTTAT |
| 5265 | TGAAAGGAAAATAATACTTATC |
| 5266 | GAAAGGAAAATAATACTTATCT |
| 5267 | AAAGGAAAATAATACTTATCTT |
| 5268 | AAGGAAAATAATACTTATCTTA |
| 5269 | AGGAAAATAATACTTATCTTAC |
| 5270 | GGAAAATAATACTTATCTTACA |
| 5271 | GAAAATAATACTTATCTTACAA |
| 5272 | AAAATAATACTTATCTTACAAG |
| 5273 | AAATAATACTTATCTTACAAGG |
| 5274 | AATAATACTTATCTTACAAGGT |
| 5275 | ATAATACTTATCTTACAAGGTT |
| 5276 | TAATACTTATCTTACAAGGTTG |
| 5277 | AATACTTATCTTACAAGGTTGC |
| 5278 | ATACTTATCTTACAAGGTTGCA |
| 5279 | TACTTATCTTACAAGGTTGCAA |
| 5280 | ACTTATCTTACAAGGTTGCAAG |

| ID | SEQUENCE |
|---|---|
| 5281 | ACTTATCTTACAAGGTTGCAAGA |
| 5282 | CTTATCTTACAAGGTTGCAAGAG |
| 5283 | TTATCTTACAAGGTTGCAAGAGC |
| 5284 | TATCTTACAAGGTTGCAAGAGCT |
| 5285 | ATCTTACAAGGTTGCAAGAGCTC |
| 5286 | TCTTACAAGGTTGCAAGAGCTCA |
| 5287 | CTTACAAGGTTGCAAGAGCTCAA |
| 5288 | TTACAAGGTTGCAAGAGCTCAAG |
| 5289 | TACAAGGTTGCAAGAGCTCAAGG |
| 5290 | ACAAGGTTGCAAGAGCTCAAGGA |
| 5291 | CAAGGTTGCAAGAGCTCAAGGAG |
| 5292 | AAGGTTGCAAGAGCTCAAGGAGA |
| 5293 | AGGTTGCAAGAGCTCAAGGAGAC |
| 5294 | GGTTGCAAGAGCTCAAGGAGACC |
| 5295 | GTTGCAAGAGCTCAAGGAGACCA |
| 5296 | TTGCAAGAGCTCAAGGAGACCAT |
| 5297 | TGCAAGAGCTCAAGGAGACCATG |
| 5298 | GCAAGAGCTCAAGGAGACCATGT |
| 5299 | CAAGAGCTCAAGGAGACCATGTA |
| 5300 | AAGAGCTCAAGGAGACCATGTAT |
| 5301 | AGAGCTCAAGGAGACCATGTATG |
| 5302 | GAGCTCAAGGAGACCATGTATGT |
| 5303 | AGCTCAAGGAGACCATGTATGTA |
| 5304 | GCTCAAGGAGACCATGTATGTAA |
| 5305 | CTCAAGGAGACCATGTATGTAAA |
| 5306 | TCAAGGAGACCATGTATGTAAAG |
| 5307 | CAAGGAGACCATGTATGTAAAGT |
| 5308 | AAGGAGACCATGTATGTAAAGTT |
| 5309 | AGGAGACCATGTATGTAAAGTTC |
| 5310 | GGAGACCATGTATGTAAAGTTCC |
| 5311 | GAGACCATGTATGTAAAGTTCCT |
| 5312 | AGACCATGTATGTAAAGTTCCTG |
| 5313 | GACCATGTATGTAAAGTTCCTGC |
| 5314 | ACCATGTATGTAAAGTTCCTGCT |
| 5315 | CCATGTATGTAAAGTTCCTGCTG |
| 5316 | CATGTATGTAAAGTTCCTGCTGT |
| 5317 | ATGTATGTAAAGTTCCTGCTGTA |
| 5318 | TGTATGTAAAGTTCCTGCTGTAA |
| 5319 | GTATGTAAAGTTCCTGCTGTAAA |
| 5320 | TATGTAAAGTTCCTGCTGTAAAT |
| 5321 | ATGTAAAGTTCCTGCTGTAAATA |
| 5322 | TGTAAAGTTCCTGCTGTAAATAT |
| 5323 | GTAAAGTTCCTGCTGTAAATATG |
| 5324 | TAAAGTTCCTGCTGTAAATATGA |
| 5325 | AAAGTTCCTGCTGTAAATATGAA |
| 5326 | AAGTTCCTGCTGTAAATATGAAC |
| 5327 | AGTTCCTGCTGTAAATATGAACT |
| 5328 | GTTCCTGCTGTAAATATGAACTC |

| ID | SEQUENCE |
|---|---|
| 5329 | TTCCTGCTGTAAATATGAACTCC |
| 5330 | TCCTGCTGTAAATATGAACTCCC |
| 5331 | CCTGCTGTAAATATGAACTCCCA |
| 5332 | CTGCTGTAAATATGAACTCCCAT |
| 5333 | TGCTGTAAATATGAACTCCCATC |
| 5334 | GCTGTAAATATGAACTCCCATCC |
| 5335 | CTGTAAATATGAACTCCCATCCT |
| 5336 | TGTAAATATGAACTCCCATCCTA |
| 5337 | GTAAATATGAACTCCCATCCTAA |
| 5338 | TAAATATGAACTCCCATCCTAAT |
| 5339 | AAATATGAACTCCCATCCTAATA |
| 5340 | AATATGAACTCCCATCCTAATAC |
| 5341 | ATATGAACTCCCATCCTAATACC |
| 5342 | TATGAACTCCCATCCTAATACCC |
| 5343 | ATGAACTCCCATCCTAATACCCT |
| 5344 | TGAACTCCCATCCTAATACCCTT |
| 5345 | GAACTCCCATCCTAATACCCTTT |
| 5346 | AACTCCCATCCTAATACCCTTTT |
| 5347 | ACTCCCATCCTAATACCCTTTTA |
| 5348 | CTCCCATCCTAATACCCTTTTAC |
| 5349 | TCCCATCCTAATACCCTTTTACC |
| 5350 | CCCATCCTAATACCCTTTTACCT |
| 5351 | CCATCCTAATACCCTTTTACCTC |
| 5352 | CATCCTAATACCCTTTTACCTCT |
| 5353 | ATCCTAATACCCTTTTACCTCTC |
| 5354 | TCCTAATACCCTTTTACCTCTCT |
| 5355 | CCTAATACCCTTTTACCTCTCTG |
| 5356 | CTAATACCCTTTTACCTCTCTGT |
| 5357 | TAATACCCTTTTACCTCTCTGTG |
| 5358 | AATACCCTTTTACCTCTCTGTGG |
| 5359 | ATACCCTTTTACCTCTCTGTGGG |
| 5360 | TACCCTTTTACCTCTCTGTGGGT |
| 5361 | ACCCTTTTACCTCTCTGTGGGTT |
| 5362 | CCCTTTTACCTCTCTGTGGGTTT |
| 5363 | CCTTTTACCTCTCTGTGGGTTTG |
| 5364 | CTTTTACCTCTCTGTGGGTTTGT |
| 5365 | TTTTACCTCTCTGTGGGTTTGTC |
| 5366 | TTTACCTCTCTGTGGGTTTGTCT |
| 5367 | TTACCTCTCTGTGGGTTTGTCTT |
| 5368 | TACCTCTCTGTGGGTTTGTCTTG |
| 5369 | ACCTCTCTGTGGGTTTGTCTTGA |
| 5370 | CCTCTCTGTGGGTTTGTCTTGAC |
| 5371 | CTCTCTGTGGGTTTGTCTTGACC |
| 5372 | TCTCTGTGGGTTTGTCTTGACCT |
| 5373 | CTCTGTGGGTTTGTCTTGACCTG |
| 5374 | TCTGTGGGTTTGTCTTGACCTGG |
| 5375 | CTGTGGGTTTGTCTTGACCTGGA |
| 5376 | TGTGGGTTTGTCTTGACCTGGAA |

| ID | SEQUENCE |
|---|---|
| 5377 | GTGGGTTTGTCTTGACCTGGAAA |
| 5378 | TGGGTTTGTCTTGACCTGGAAAT |
| 5379 | GGGTTTGTCTTGACCTGGAAATT |
| 5380 | GGTTTGTCTTGACCTGGAAATTT |
| 5381 | GTTTGTCTTGACCTGGAAATTTG |
| 5382 | TTTGTCTTGACCTGGAAATTTGG |
| 5383 | TTGTCTTGACCTGGAAATTTGGG |
| 5384 | TGTCTTGACCTGGAAATTTGGGC |
| 5385 | GTCTTGACCTGGAAATTTGGGCT |
| 5386 | TCTTGACCTGGAAATTTGGGCTA |
| 5387 | CTTGACCTGGAAATTTGGGCTAA |
| 5388 | TTGACCTGGAAATTTGGGCTAAA |
| 5389 | TGACCTGGAAATTTGGGCTAAAA |
| 5390 | GACCTGGAAATTTGGGCTAAAAC |
| 5391 | ACCTGGAAATTTGGGCTAAAACT |
| 5392 | CCTGGAAATTTGGGCTAAAACTT |
| 5393 | CTGGAAATTTGGGCTAAAACTTA |
| 5394 | TGGAAATTTGGGCTAAAACTTAG |
| 5395 | GGAAATTTGGGCTAAAACTTAGA |
| 5396 | GAAATTTGGGCTAAAACTTAGAA |
| 5397 | AAATTTGGGCTAAAACTTAGAAA |
| 5398 | AATTTGGGCTAAAACTTAGAAAA |
| 5399 | ATTTGGGCTAAAACTTAGAAAAA |
| 5400 | TTTGGGCTAAAACTTAGAAAAAA |
| 5401 | TTGGGCTAAAACTTAGAAAAAAT |
| 5402 | TGGGCTAAAACTTAGAAAAAATT |
| 5403 | GGGCTAAAACTTAGAAAAAATTC |
| 5404 | GGCTAAAACTTAGAAAAAATTCT |
| 5405 | GCTAAAACTTAGAAAAAATTCTT |
| 5406 | CTAAAACTTAGAAAAAATTCTTA |
| 5407 | TAAAACTTAGAAAAAATTCTTAC |
| 5408 | AAAACTTAGAAAAAATTCTTACA |
| 5409 | AAACTTAGAAAAAATTCTTACAT |
| 5410 | AACTTAGAAAAAATTCTTACATG |
| 5411 | ACTTAGAAAAAATTCTTACATGA |
| 5412 | CTTAGAAAAAATTCTTACATGAT |
| 5413 | TTAGAAAAAATTCTTACATGATA |
| 5414 | TAGAAAAAATTCTTACATGATAA |
| 5415 | AGAAAAAATTCTTACATGATAAC |
| 5416 | GAAAAAATTCTTACATGATAACT |
| 5417 | AAAAAATTCTTACATGATAACTC |
| 5418 | AAAAATTCTTACATGATAACTCA |
| 5419 | AAAATTCTTACATGATAACTCAG |
| 5420 | AAATTCTTACATGATAACTCAGT |
| 5421 | AATTCTTACATGATAACTCAGTG |
| 5422 | ATTCTTACATGATAACTCAGTGA |
| 5423 | TTCTTACATGATAACTCAGTGAT |
| 5424 | TCTTACATGATAACTCAGTGATG |

| ID | SEQUENCE |
|---|---|
| 5425 | CTTACATGATAACTCAGTGATGC |
| 5426 | TTACATGATAACTCAGTGATGCT |
| 5427 | TACATGATAACTCAGTGATGCTT |
| 5428 | ACATGATAACTCAGTGATGCTTA |
| 5429 | CATGATAACTCAGTGATGCTTAC |
| 5430 | ATGATAACTCAGTGATGCTTACT |
| 5431 | TGATAACTCAGTGATGCTTACTC |
| 5432 | GATAACTCAGTGATGCTTACTCA |
| 5433 | ATAACTCAGTGATGCTTACTCAT |
| 5434 | TAACTCAGTGATGCTTACTCATA |
| 5435 | AACTCAGTGATGCTTACTCATAG |
| 5436 | ACTCAGTGATGCTTACTCATAGT |
| 5437 | CTCAGTGATGCTTACTCATAGTT |
| 5438 | TCAGTGATGCTTACTCATAGTTT |
| 5439 | CAGTGATGCTTACTCATAGTTTT |
| 5440 | AGTGATGCTTACTCATAGTTTTT |
| 5441 | GTGATGCTTACTCATAGTTTTTG |
| 5442 | TGATGCTTACTCATAGTTTTTGG |
| 5443 | GATGCTTACTCATAGTTTTTGGT |
| 5444 | ATGCTTACTCATAGTTTTTGGTG |
| 5445 | TGCTTACTCATAGTTTTTGGTGT |
| 5446 | GCTTACTCATAGTTTTTGGTGTT |
| 5447 | CTTACTCATAGTTTTTGGTGTTT |
| 5448 | TTACTCATAGTTTTTGGTGTTTC |
| 5449 | TACTCATAGTTTTTGGTGTTTCT |
| 5450 | ACTCATAGTTTTTGGTGTTTCTC |
| 5451 | CTCATAGTTTTTGGTGTTTCTCA |
| 5452 | TCATAGTTTTTGGTGTTTCTCAT |
| 5453 | CATAGTTTTTGGTGTTTCTCATA |
| 5454 | ATAGTTTTTGGTGTTTCTCATAG |
| 5455 | TAGTTTTTGGTGTTTCTCATAGA |
| 5456 | AGTTTTTGGTGTTTCTCATAGAT |
| 5457 | GTTTTTGGTGTTTCTCATAGATA |
| 5458 | TTTTTGGTGTTTCTCATAGATAA |
| 5459 | TTTTGGTGTTTCTCATAGATAAG |
| 5460 | TTTGGTGTTTCTCATAGATAAGA |
| 5461 | TTGGTGTTTCTCATAGATAAGAT |
| 5462 | TGGTGTTTCTCATAGATAAGATA |
| 5463 | GGTGTTTCTCATAGATAAGATAT |
| 5464 | GTGTTTCTCATAGATAAGATATA |
| 5465 | TGTTTCTCATAGATAAGATATAA |
| 5466 | GTTTCTCATAGATAAGATATAAA |
| 5467 | TTTCTCATAGATAAGATATAAAT |
| 5468 | TTCTCATAGATAAGATATAAATC |
| 5469 | TCTCATAGATAAGATATAAATCA |
| 5470 | CTCATAGATAAGATATAAATCAG |
| 5471 | TCATAGATAAGATATAAATCAGC |
| 5472 | CATAGATAAGATATAAATCAGCT |

| ID | SEQUENCE |
|---|---|
| 5473 | ATAGATAAGATATAAATCAGCTG |
| 5474 | TAGATAAGATATAAATCAGCTGG |
| 5475 | AGATAAGATATAAATCAGCTGGG |
| 5476 | GATAAGATATAAATCAGCTGGGC |
| 5477 | ATAAGATATAAATCAGCTGGGCG |
| 5478 | TAAGATATAAATCAGCTGGGCGC |
| 5479 | AAGATATAAATCAGCTGGGCGCG |
| 5480 | AGATATAAATCAGCTGGGCGCGG |
| 5481 | GATATAAATCAGCTGGGCGCGGT |
| 5482 | ATATAAATCAGCTGGGCGCGGTG |
| 5483 | TATAAATCAGCTGGGCGCGGTGG |
| 5484 | ATAAATCAGCTGGGCGCGGTGGC |
| 5485 | TAAATCAGCTGGGCGCGGTGGCT |
| 5486 | AAATCAGCTGGGCGCGGTGGCTC |
| 5487 | AATCAGCTGGGCGCGGTGGCTCA |
| 5488 | ATCAGCTGGGCGCGGTGGCTCAT |
| 5489 | TCAGCTGGGCGCGGTGGCTCATG |
| 5490 | CAGCTGGGCGCGGTGGCTCATGC |
| 5491 | AGCTGGGCGCGGTGGCTCATGCC |
| 5492 | GCTGGGCGCGGTGGCTCATGCCT |
| 5493 | CTGGGCGCGGTGGCTCATGCCTG |
| 5494 | TGGGCGCGGTGGCTCATGCCTGT |
| 5495 | GGGCGCGGTGGCTCATGCCTGTA |
| 5496 | GGCGCGGTGGCTCATGCCTGTAA |
| 5497 | GCGCGGTGGCTCATGCCTGTAAT |
| 5498 | CGCGGTGGCTCATGCCTGTAATC |
| 5499 | GCGGTGGCTCATGCCTGTAATCC |
| 5500 | CGGTGGCTCATGCCTGTAATCCC |
| 5501 | GGTGGCTCATGCCTGTAATCCCA |
| 5502 | GTGGCTCATGCCTGTAATCCCAG |
| 5503 | TGGCTCATGCCTGTAATCCCAGC |
| 5504 | GGCTCATGCCTGTAATCCCAGCA |
| 5505 | GCTCATGCCTGTAATCCCAGCAC |
| 5506 | CTCATGCCTGTAATCCCAGCACT |
| 5507 | TCATGCCTGTAATCCCAGCACTT |
| 5508 | CATGCCTGTAATCCCAGCACTTT |
| 5509 | ATGCCTGTAATCCCAGCACTTTG |
| 5510 | TGCCTGTAATCCCAGCACTTTGG |
| 5511 | GCCTGTAATCCCAGCACTTTGGG |
| 5512 | CCTGTAATCCCAGCACTTTGGGA |
| 5513 | CTGTAATCCCAGCACTTTGGGAG |
| 5514 | TGTAATCCCAGCACTTTGGGAGG |
| 5515 | GTAATCCCAGCACTTTGGGAGGC |
| 5516 | TAATCCCAGCACTTTGGGAGGCC |
| 5517 | AATCCCAGCACTTTGGGAGGCCG |
| 5518 | ATCCCAGCACTTTGGGAGGCCGA |
| 5519 | TCCCAGCACTTTGGGAGGCCGAG |
| 5520 | CCCAGCACTTTGGGAGGCCGAGG |

| ID | SEQUENCE |
|---|---|
| 5521 | CCAGCACTTTGGGAGGCCGAGGC |
| 5522 | CAGCACTTTGGGAGGCCGAGGCG |
| 5523 | AGCACTTTGGGAGGCCGAGGCGG |
| 5524 | GCACTTTGGGAGGCCGAGGCGGG |
| 5525 | CACTTTGGGAGGCCGAGGCGGGC |
| 5526 | ACTTTGGGAGGCCGAGGCGGGCA |
| 5527 | CTTTGGGAGGCCGAGGCGGGCAG |
| 5528 | TTTGGGAGGCCGAGGCGGGCAGA |
| 5529 | TTGGGAGGCCGAGGCGGGCAGAT |
| 5530 | TGGGAGGCCGAGGCGGGCAGATC |
| 5531 | GGGAGGCCGAGGCGGGCAGATCA |
| 5532 | GGAGGCCGAGGCGGGCAGATCAC |
| 5533 | GAGGCCGAGGCGGGCAGATCACC |
| 5534 | AGGCCGAGGCGGGCAGATCACCT |
| 5535 | GGCCGAGGCGGGCAGATCACCTG |
| 5536 | GCCGAGGCGGGCAGATCACCTGA |
| 5537 | CCGAGGCGGGCAGATCACCTGAG |
| 5538 | CGAGGCGGGCAGATCACCTGAGG |
| 5539 | GAGGCGGGCAGATCACCTGAGGT |
| 5540 | AGGCGGGCAGATCACCTGAGGTC |
| 5541 | GGCGGGCAGATCACCTGAGGTCG |
| 5542 | GCGGGCAGATCACCTGAGGTCGG |
| 5543 | CGGGCAGATCACCTGAGGTCGGG |
| 5544 | GGGCAGATCACCTGAGGTCGGGA |
| 5545 | GGCAGATCACCTGAGGTCGGGAG |
| 5546 | GCAGATCACCTGAGGTCGGGAGG |
| 5547 | CAGATCACCTGAGGTCGGGAGGT |
| 5548 | AGATCACCTGAGGTCGGGAGGTC |
| 5549 | GATCACCTGAGGTCGGGAGGTCG |
| 5550 | ATCACCTGAGGTCGGGAGGTCGA |
| 5551 | TCACCTGAGGTCGGGAGGTCGAG |
| 5552 | CACCTGAGGTCGGGAGGTCGAGA |
| 5553 | ACCTGAGGTCGGGAGGTCGAGAC |
| 5554 | CCTGAGGTCGGGAGGTCGAGACC |
| 5555 | CTGAGGTCGGGAGGTCGAGACCA |
| 5556 | TGAGGTCGGGAGGTCGAGACCAG |
| 5557 | GAGGTCGGGAGGTCGAGACCAGC |
| 5558 | AGGTCGGGAGGTCGAGACCAGCC |
| 5559 | GGTCGGGAGGTCGAGACCAGCCT |
| 5560 | GTCGGGAGGTCGAGACCAGCCTG |
| 5561 | TCGGGAGGTCGAGACCAGCCTGA |
| 5562 | CGGGAGGTCGAGACCAGCCTGAC |
| 5563 | GGGAGGTCGAGACCAGCCTGACC |
| 5564 | GGAGGTCGAGACCAGCCTGACCA |
| 5565 | GAGGTCGAGACCAGCCTGACCAA |
| 5566 | AGGTCGAGACCAGCCTGACCAAC |
| 5567 | GGTCGAGACCAGCCTGACCAACA |
| 5568 | GTCGAGACCAGCCTGACCAACAT |

| ID | SEQUENCE |
|---|---|
| 5569 | TCGAGACCAGCCTGACCAACATG |
| 5570 | CGAGACCAGCCTGACCAACATGG |
| 5571 | GAGACCAGCCTGACCAACATGGA |
| 5572 | AGACCAGCCTGACCAACATGGAG |
| 5573 | GACCAGCCTGACCAACATGGAGA |
| 5574 | ACCAGCCTGACCAACATGGAGAA |
| 5575 | CCAGCCTGACCAACATGGAGAAA |
| 5576 | CAGCCTGACCAACATGGAGAAAC |
| 5577 | AGCCTGACCAACATGGAGAAACC |
| 5578 | GCCTGACCAACATGGAGAAACCC |
| 5579 | CCTGACCAACATGGAGAAACCCC |
| 5580 | CTGACCAACATGGAGAAACCCCG |
| 5581 | TGACCAACATGGAGAAACCCCGT |
| 5582 | GACCAACATGGAGAAACCCCGTC |
| 5583 | ACCAACATGGAGAAACCCCGTCT |
| 5584 | CCAACATGGAGAAACCCCGTCTC |
| 5585 | CAACATGGAGAAACCCCGTCTCT |
| 5586 | AACATGGAGAAACCCCGTCTCTA |
| 5587 | ACATGGAGAAACCCCGTCTCTAC |
| 5588 | CATGGAGAAACCCCGTCTCTACT |
| 5589 | ATGGAGAAACCCCGTCTCTACTA |
| 5590 | TGGAGAAACCCCGTCTCTACTAA |
| 5591 | GGAGAAACCCCGTCTCTACTAAA |
| 5592 | GAGAAACCCCGTCTCTACTAAAA |
| 5593 | AGAAACCCCGTCTCTACTAAAAA |
| 5594 | GAAACCCCGTCTCTACTAAAAAT |
| 5595 | AAACCCCGTCTCTACTAAAAATA |
| 5596 | AACCCCGTCTCTACTAAAAATAC |
| 5597 | ACCCCGTCTCTACTAAAAATACA |
| 5598 | CCCCGTCTCTACTAAAAATACAA |
| 5599 | CCCGTCTCTACTAAAAATACAAA |
| 5600 | CCGTCTCTACTAAAAATACAAAA |
| 5601 | CGTCTCTACTAAAAATACAAAAT |
| 5602 | GTCTCTACTAAAAATACAAAATT |
| 5603 | TCTCTACTAAAAATACAAAATTA |
| 5604 | CTCTACTAAAAATACAAAATTAG |
| 5605 | TCTACTAAAAATACAAAATTAGC |
| 5606 | CTACTAAAAATACAAAATTAGCT |
| 5607 | TACTAAAAATACAAAATTAGCTG |
| 5608 | ACTAAAAATACAAAATTAGCTGG |
| 5609 | CTAAAAATACAAAATTAGCTGGG |
| 5610 | TAAAAATACAAAATTAGCTGGGC |
| 5611 | AAAAATACAAAATTAGCTGGGCG |
| 5612 | AAAATACAAAATTAGCTGGGCGT |
| 5613 | AAATACAAAATTAGCTGGGCGTG |
| 5614 | AATACAAAATTAGCTGGGCGTGG |
| 5615 | ATACAAAATTAGCTGGGCGTGGT |
| 5616 | TACAAAATTAGCTGGGCGTGGTG |

| ID | SEQUENCE |
|---|---|
| 5617 | ACAAAATTAGCTGGGCGTGGTGG |
| 5618 | CAAAATTAGCTGGGCGTGGTGGC |
| 5619 | AAAATTAGCTGGGCGTGGTGGCT |
| 5620 | AAATTAGCTGGGCGTGGTGGCTC |
| 5621 | AATTAGCTGGGCGTGGTGGCTCA |
| 5622 | ATTAGCTGGGCGTGGTGGCTCAT |
| 5623 | TTAGCTGGGCGTGGTGGCTCATG |
| 5624 | TAGCTGGGCGTGGTGGCTCATGC |
| 5625 | AGCTGGGCGTGGTGGCTCATGCC |
| 5626 | GCTGGGCGTGGTGGCTCATGCCT |
| 5627 | CTGGGCGTGGTGGCTCATGCCTG |
| 5628 | TGGGCGTGGTGGCTCATGCCTGT |
| 5629 | GGGCGTGGTGGCTCATGCCTGTA |
| 5630 | GGCGTGGTGGCTCATGCCTGTAA |
| 5631 | GCGTGGTGGCTCATGCCTGTAAT |
| 5632 | CGTGGTGGCTCATGCCTGTAATC |
| 5633 | GTGGTGGCTCATGCCTGTAATCC |
| 5634 | TGGTGGCTCATGCCTGTAATCCC |
| 5635 | GGTGGCTCATGCCTGTAATCCCA |
| 5636 | GTGGCTCATGCCTGTAATCCCAG |
| 5637 | TGGCTCATGCCTGTAATCCCAGC |
| 5638 | GGCTCATGCCTGTAATCCCAGCT |
| 5639 | GCTCATGCCTGTAATCCCAGCTA |
| 5640 | CTCATGCCTGTAATCCCAGCTAC |
| 5641 | TCATGCCTGTAATCCCAGCTACT |
| 5642 | CATGCCTGTAATCCCAGCTACTT |
| 5643 | ATGCCTGTAATCCCAGCTACTTG |
| 5644 | TGCCTGTAATCCCAGCTACTTGG |
| 5645 | GCCTGTAATCCCAGCTACTTGGG |
| 5646 | CCTGTAATCCCAGCTACTTGGGA |
| 5647 | CTGTAATCCCAGCTACTTGGGAG |
| 5648 | TGTAATCCCAGCTACTTGGGAGG |
| 5649 | GTAATCCCAGCTACTTGGGAGGC |
| 5650 | TAATCCCAGCTACTTGGGAGGCT |
| 5651 | AATCCCAGCTACTTGGGAGGCTG |
| 5652 | ATCCCAGCTACTTGGGAGGCTGA |
| 5653 | TCCCAGCTACTTGGGAGGCTGAG |
| 5654 | CCCAGCTACTTGGGAGGCTGAGG |
| 5655 | CCAGCTACTTGGGAGGCTGAGGC |
| 5656 | CAGCTACTTGGGAGGCTGAGGCA |
| 5657 | AGCTACTTGGGAGGCTGAGGCAG |
| 5658 | GCTACTTGGGAGGCTGAGGCAGG |
| 5659 | CTACTTGGGAGGCTGAGGCAGGA |
| 5660 | TACTTGGGAGGCTGAGGCAGGAG |
| 5661 | ACTTGGGAGGCTGAGGCAGGAGA |
| 5662 | CTTGGGAGGCTGAGGCAGGAGAA |
| 5663 | TTGGGAGGCTGAGGCAGGAGAAT |
| 5664 | TGGGAGGCTGAGGCAGGAGAATC |

| ID | SEQUENCE |
|---|---|
| 5665 | GGGAGGCTGAGGCAGGAGAATCG |
| 5666 | GGAGGCTGAGGCAGGAGAATCGC |
| 5667 | GAGGCTGAGGCAGGAGAATCGCT |
| 5668 | AGGCTGAGGCAGGAGAATCGCTT |
| 5669 | GGCTGAGGCAGGAGAATCGCTTG |
| 5670 | GCTGAGGCAGGAGAATCGCTTGA |
| 5671 | CTGAGGCAGGAGAATCGCTTGAA |
| 5672 | TGAGGCAGGAGAATCGCTTGAAC |
| 5673 | GAGGCAGGAGAATCGCTTGAACC |
| 5674 | AGGCAGGAGAATCGCTTGAACCC |
| 5675 | GGCAGGAGAATCGCTTGAACCCA |
| 5676 | GCAGGAGAATCGCTTGAACCCAG |
| 5677 | CAGGAGAATCGCTTGAACCCAGG |
| 5678 | AGGAGAATCGCTTGAACCCAGGA |
| 5679 | GGAGAATCGCTTGAACCCAGGAG |
| 5680 | GAGAATCGCTTGAACCCAGGAGG |
| 5681 | AGAATCGCTTGAACCCAGGAGGC |
| 5682 | GAATCGCTTGAACCCAGGAGGCG |
| 5683 | AATCGCTTGAACCCAGGAGGCGG |
| 5684 | ATCGCTTGAACCCAGGAGGCGGA |
| 5685 | TCGCTTGAACCCAGGAGGCGGAG |
| 5686 | CGCTTGAACCCAGGAGGCGGAGG |
| 5687 | GCTTGAACCCAGGAGGCGGAGGT |
| 5688 | CTTGAACCCAGGAGGCGGAGGTT |
| 5689 | TTGAACCCAGGAGGCGGAGGTTG |
| 5690 | TGAACCCAGGAGGCGGAGGTTGT |
| 5691 | GAACCCAGGAGGCGGAGGTTGTG |
| 5692 | AACCCAGGAGGCGGAGGTTGTGG |
| 5693 | ACCCAGGAGGCGGAGGTTGTGGT |
| 5694 | CCCAGGAGGCGGAGGTTGTGGTG |
| 5695 | CCAGGAGGCGGAGGTTGTGGTGA |
| 5696 | CAGGAGGCGGAGGTTGTGGTGAG |
| 5697 | AGGAGGCGGAGGTTGTGGTGAGC |
| 5698 | GGAGGCGGAGGTTGTGGTGAGCG |
| 5699 | GAGGCGGAGGTTGTGGTGAGCGA |
| 5700 | AGGCGGAGGTTGTGGTGAGCGAA |
| 5701 | GGCGGAGGTTGTGGTGAGCGAAG |
| 5702 | GCGGAGGTTGTGGTGAGCGAAGA |
| 5703 | CGGAGGTTGTGGTGAGCGAAGAT |
| 5704 | GGAGGTTGTGGTGAGCGAAGATC |
| 5705 | GAGGTTGTGGTGAGCGAAGATCG |
| 5706 | AGGTTGTGGTGAGCGAAGATCGT |
| 5707 | GGTTGTGGTGAGCGAAGATCGTG |
| 5708 | GTTGTGGTGAGCGAAGATCGTGC |
| 5709 | TTGTGGTGAGCGAAGATCGTGCC |
| 5710 | TGTGGTGAGCGAAGATCGTGCCA |
| 5711 | GTGGTGAGCGAAGATCGTGCCAT |
| 5712 | TGGTGAGCGAAGATCGTGCCATT |

| ID | SEQUENCE |
|---|---|
| 5713 | GGTGAGCGAAGATCGTGCCATTG |
| 5714 | GTGAGCGAAGATCGTGCCATTGC |
| 5715 | TGAGCGAAGATCGTGCCATTGCA |
| 5716 | GAGCGAAGATCGTGCCATTGCAC |
| 5717 | AGCGAAGATCGTGCCATTGCACT |
| 5718 | GCGAAGATCGTGCCATTGCACTC |
| 5719 | CGAAGATCGTGCCATTGCACTCC |
| 5720 | GAAGATCGTGCCATTGCACTCCA |
| 5721 | AAGATCGTGCCATTGCACTCCAG |
| 5722 | AGATCGTGCCATTGCACTCCAGC |
| 5723 | GATCGTGCCATTGCACTCCAGCC |
| 5724 | ATCGTGCCATTGCACTCCAGCCT |
| 5725 | TCGTGCCATTGCACTCCAGCCTG |
| 5726 | CGTGCCATTGCACTCCAGCCTGG |
| 5727 | GTGCCATTGCACTCCAGCCTGGG |
| 5728 | TGCCATTGCACTCCAGCCTGGGC |
| 5729 | GCCATTGCACTCCAGCCTGGGCA |
| 5730 | CCATTGCACTCCAGCCTGGGCAA |
| 5731 | CATTGCACTCCAGCCTGGGCAAC |
| 5732 | ATTGCACTCCAGCCTGGGCAACA |
| 5733 | TTGCACTCCAGCCTGGGCAACAA |
| 5734 | TGCACTCCAGCCTGGGCAACAAG |
| 5735 | GCACTCCAGCCTGGGCAACAAGA |
| 5736 | CACTCCAGCCTGGGCAACAAGAG |
| 5737 | ACTCCAGCCTGGGCAACAAGAGC |
| 5738 | CTCCAGCCTGGGCAACAAGAGCA |
| 5739 | TCCAGCCTGGGCAACAAGAGCAA |
| 5740 | CCAGCCTGGGCAACAAGAGCAAA |
| 5741 | CAGCCTGGGCAACAAGAGCAAAA |
| 5742 | AGCCTGGGCAACAAGAGCAAAAC |
| 5743 | GCCTGGGCAACAAGAGCAAAACT |
| 5744 | CCTGGGCAACAAGAGCAAAACTC |
| 5745 | CTGGGCAACAAGAGCAAAACTCT |
| 5746 | TGGGCAACAAGAGCAAAACTCTG |
| 5747 | GGGCAACAAGAGCAAAACTCTGT |
| 5748 | GGCAACAAGAGCAAAACTCTGTC |
| 5749 | GCAACAAGAGCAAAACTCTGTCT |
| 5750 | CAACAAGAGCAAAACTCTGTCTC |
| 5751 | AACAAGAGCAAAACTCTGTCTCA |
| 5752 | ACAAGAGCAAAACTCTGTCTCAA |
| 5753 | CAAGAGCAAAACTCTGTCTCAAA |
| 5754 | AAGAGCAAAACTCTGTCTCAAAA |
| 5755 | AGAGCAAAACTCTGTCTCAAAAA |
| 5756 | GAGCAAAACTCTGTCTCAAAAAA |
| 5757 | AGCAAAACTCTGTCTCAAAAAAA |
| 5758 | GCAAAACTCTGTCTCAAAAAAAA |
| 5759 | AAAAAAAGATATAAATCACAAT |
| 5760 | AAAAAAAGATATAAATCACAATA |

| ID | SEQUENCE |
|---|---|
| 5761 | AAAAAAGATATAAATCACAATAA |
| 5762 | AAAAAGATATAAATCACAATAAA |
| 5763 | AAAAGATATAAATCACAATAAAT |
| 5764 | AAAGATATAAATCACAATAAATA |
| 5765 | AAGATATAAATCACAATAAATAA |
| 5766 | AGATATAAATCACAATAAATAAA |
| 5767 | GATATAAATCACAATAAATAAAT |
| 5768 | ATATAAATCACAATAAATAAATA |
| 5769 | TATAAATCACAATAAATAAATAG |
| 5770 | ATAAATCACAATAAATAAATAGG |
| 5771 | TAAATCACAATAAATAAATAGGT |
| 5772 | AAATCACAATAAATAAATAGGTC |
| 5773 | AATCACAATAAATAAATAGGTCA |
| 5774 | ATCACAATAAATAAATAGGTCAA |
| 5775 | TCACAATAAATAAATAGGTCAAT |
| 5776 | CACAATAAATAAATAGGTCAATA |
| 5777 | ACAATAAATAAATAGGTCAATAC |
| 5778 | CAATAAATAAATAGGTCAATACA |
| 5779 | AATAAATAAATAGGTCAATACAA |
| 5780 | ATAAATAAATAGGTCAATACAAA |
| 5781 | TAAATAAATAGGTCAATACAAAT |
| 5782 | AAATAAATAGGTCAATACAAATG |
| 5783 | AATAAATAGGTCAATACAAATGT |
| 5784 | ATAAATAGGTCAATACAAATGTT |
| 5785 | TAAATAGGTCAATACAAATGTTA |
| 5786 | AAATAGGTCAATACAAATGTTAG |
| 5787 | AATAGGTCAATACAAATGTTAGC |
| 5788 | ATAGGTCAATACAAATGTTAGCC |
| 5789 | TAGGTCAATACAAATGTTAGCCA |
| 5790 | AGGTCAATACAAATGTTAGCCAG |
| 5791 | GGTCAATACAAATGTTAGCCAGG |
| 5792 | GTCAATACAAATGTTAGCCAGGC |
| 5793 | TCAATACAAATGTTAGCCAGGCG |
| 5794 | CAATACAAATGTTAGCCAGGCGT |
| 5795 | AATACAAATGTTAGCCAGGCGTG |
| 5796 | ATACAAATGTTAGCCAGGCGTGG |
| 5797 | TACAAATGTTAGCCAGGCGTGGT |
| 5798 | ACAAATGTTAGCCAGGCGTGGTG |
| 5799 | CAAATGTTAGCCAGGCGTGGTGG |
| 5800 | AAATGTTAGCCAGGCGTGGTGGC |
| 5801 | AATGTTAGCCAGGCGTGGTGGCA |
| 5802 | ATGTTAGCCAGGCGTGGTGGCAC |
| 5803 | TGTTAGCCAGGCGTGGTGGCACA |
| 5804 | GTTAGCCAGGCGTGGTGGCACAT |
| 5805 | TTAGCCAGGCGTGGTGGCACATG |
| 5806 | TAGCCAGGCGTGGTGGCACATGC |
| 5807 | AGCCAGGCGTGGTGGCACATGCC |
| 5808 | GCCAGGCGTGGTGGCACATGCCC |

| ID | SEQUENCE |
|---|---|
| 5809 | CCAGGCGTGGTGGCACATGCCCA |
| 5810 | CAGGCGTGGTGGCACATGCCCAT |
| 5811 | AGGCGTGGTGGCACATGCCCATA |
| 5812 | GGCGTGGTGGCACATGCCCATAG |
| 5813 | GCGTGGTGGCACATGCCCATAGT |
| 5814 | CGTGGTGGCACATGCCCATAGTC |
| 5815 | GTGGTGGCACATGCCCATAGTCG |
| 5816 | TGGTGGCACATGCCCATAGTCGC |
| 5817 | GGTGGCACATGCCCATAGTCGCA |
| 5818 | GTGGCACATGCCCATAGTCGCAG |
| 5819 | TGGCACATGCCCATAGTCGCAGC |
| 5820 | GGCACATGCCCATAGTCGCAGCT |
| 5821 | GCACATGCCCATAGTCGCAGCTA |
| 5822 | CACATGCCCATAGTCGCAGCTAC |
| 5823 | ACATGCCCATAGTCGCAGCTACT |
| 5824 | CATGCCCATAGTCGCAGCTACTC |
| 5825 | ATGCCCATAGTCGCAGCTACTCT |
| 5826 | TGCCCATAGTCGCAGCTACTCTG |
| 5827 | GCCCATAGTCGCAGCTACTCTGG |
| 5828 | CCCATAGTCGCAGCTACTCTGGA |
| 5829 | CCATAGTCGCAGCTACTCTGGAG |
| 5830 | CATAGTCGCAGCTACTCTGGAGG |
| 5831 | ATAGTCGCAGCTACTCTGGAGGC |
| 5832 | TAGTCGCAGCTACTCTGGAGGCA |
| 5833 | AGTCGCAGCTACTCTGGAGGCAG |
| 5834 | GTCGCAGCTACTCTGGAGGCAGA |
| 5835 | TCGCAGCTACTCTGGAGGCAGAG |
| 5836 | CGCAGCTACTCTGGAGGCAGAGG |
| 5837 | GCAGCTACTCTGGAGGCAGAGGC |
| 5838 | CAGCTACTCTGGAGGCAGAGGCA |
| 5839 | AGCTACTCTGGAGGCAGAGGCAG |
| 5840 | GCTACTCTGGAGGCAGAGGCAGG |
| 5841 | CTACTCTGGAGGCAGAGGCAGGA |
| 5842 | TACTCTGGAGGCAGAGGCAGGAG |
| 5843 | ACTCTGGAGGCAGAGGCAGGAGG |
| 5844 | CTCTGGAGGCAGAGGCAGGAGGA |
| 5845 | TCTGGAGGCAGAGGCAGGAGGAT |
| 5846 | CTGGAGGCAGAGGCAGGAGGATC |
| 5847 | TGGAGGCAGAGGCAGGAGGATCA |
| 5848 | GGAGGCAGAGGCAGGAGGATCAC |
| 5849 | GAGGCAGAGGCAGGAGGATCACT |
| 5850 | AGGCAGAGGCAGGAGGATCACTT |
| 5851 | GGCAGAGGCAGGAGGATCACTTG |
| 5852 | GCAGAGGCAGGAGGATCACTTGA |
| 5853 | CAGAGGCAGGAGGATCACTTGAG |
| 5854 | AGAGGCAGGAGGATCACTTGAGC |
| 5855 | GAGGCAGGAGGATCACTTGAGCC |
| 5856 | AGGCAGGAGGATCACTTGAGCCC |

| ID | SEQUENCE |
|---|---|
| 5857 | GGCAGGAGGATCACTTGAGCCCA |
| 5858 | GCAGGAGGATCACTTGAGCCCAT |
| 5859 | CAGGAGGATCACTTGAGCCCATG |
| 5860 | AGGAGGATCACTTGAGCCCATGA |
| 5861 | GGAGGATCACTTGAGCCCATGAA |
| 5862 | GAGGATCACTTGAGCCCATGAAT |
| 5863 | AGGATCACTTGAGCCCATGAATT |
| 5864 | GGATCACTTGAGCCCATGAATTT |
| 5865 | GATCACTTGAGCCCATGAATTTG |
| 5866 | ATCACTTGAGCCCATGAATTTGA |
| 5867 | TCACTTGAGCCCATGAATTTGAG |
| 5868 | CACTTGAGCCCATGAATTTGAGG |
| 5869 | ACTTGAGCCCATGAATTTGAGGC |
| 5870 | CTTGAGCCCATGAATTTGAGGCA |
| 5871 | TTGAGCCCATGAATTTGAGGCAG |
| 5872 | TGAGCCCATGAATTTGAGGCAGC |
| 5873 | GAGCCCATGAATTTGAGGCAGCA |
| 5874 | AGCCCATGAATTTGAGGCAGCAG |
| 5875 | GCCCATGAATTTGAGGCAGCAGT |
| 5876 | CCCATGAATTTGAGGCAGCAGTG |
| 5877 | CCATGAATTTGAGGCAGCAGTGA |
| 5878 | CATGAATTTGAGGCAGCAGTGAG |
| 5879 | ATGAATTTGAGGCAGCAGTGAGC |
| 5880 | TGAATTTGAGGCAGCAGTGAGCT |
| 5881 | GAATTTGAGGCAGCAGTGAGCTA |
| 5882 | AATTTGAGGCAGCAGTGAGCTAT |
| 5883 | ATTTGAGGCAGCAGTGAGCTATG |
| 5884 | TTTGAGGCAGCAGTGAGCTATGA |
| 5885 | TTGAGGCAGCAGTGAGCTATGAT |
| 5886 | TGAGGCAGCAGTGAGCTATGATT |
| 5887 | GAGGCAGCAGTGAGCTATGATTG |
| 5888 | AGGCAGCAGTGAGCTATGATTGT |
| 5889 | GGCAGCAGTGAGCTATGATTGTG |
| 5890 | GCAGCAGTGAGCTATGATTGTGC |
| 5891 | CAGCAGTGAGCTATGATTGTGCC |
| 5892 | AGCAGTGAGCTATGATTGTGCCA |
| 5893 | GCAGTGAGCTATGATTGTGCCAC |
| 5894 | CAGTGAGCTATGATTGTGCCACT |
| 5895 | AGTGAGCTATGATTGTGCCACTG |
| 5896 | GTGAGCTATGATTGTGCCACTGT |
| 5897 | TGAGCTATGATTGTGCCACTGTA |
| 5898 | GAGCTATGATTGTGCCACTGTAC |
| 5899 | AGCTATGATTGTGCCACTGTACT |
| 5900 | GCTATGATTGTGCCACTGTACTC |
| 5901 | CTATGATTGTGCCACTGTACTCC |
| 5902 | TATGATTGTGCCACTGTACTCCA |
| 5903 | ATGATTGTGCCACTGTACTCCAG |
| 5904 | TGATTGTGCCACTGTACTCCAGT |

| ID | SEQUENCE |
|---|---|
| 5905 | GATTGTGCCACTGTACTCCAGTC |
| 5906 | ATTGTGCCACTGTACTCCAGTCT |
| 5907 | TTGTGCCACTGTACTCCAGTCTG |
| 5908 | TGTGCCACTGTACTCCAGTCTGG |
| 5909 | GTGCCACTGTACTCCAGTCTGGG |
| 5910 | TGCCACTGTACTCCAGTCTGGGT |
| 5911 | GCCACTGTACTCCAGTCTGGGTG |
| 5912 | CCACTGTACTCCAGTCTGGGTGA |
| 5913 | CACTGTACTCCAGTCTGGGTGAC |
| 5914 | ACTGTACTCCAGTCTGGGTGACA |
| 5915 | CTGTACTCCAGTCTGGGTGACAG |
| 5916 | TGTACTCCAGTCTGGGTGACAGA |
| 5917 | GTACTCCAGTCTGGGTGACAGAG |
| 5918 | TACTCCAGTCTGGGTGACAGAGT |
| 5919 | ACTCCAGTCTGGGTGACAGAGTG |
| 5920 | CTCCAGTCTGGGTGACAGAGTGA |
| 5921 | TCCAGTCTGGGTGACAGAGTGAG |
| 5922 | CCAGTCTGGGTGACAGAGTGAGA |
| 5923 | CAGTCTGGGTGACAGAGTGAGAC |
| 5924 | AGTCTGGGTGACAGAGTGAGACC |
| 5925 | GTCTGGGTGACAGAGTGAGACCC |
| 5926 | TCTGGGTGACAGAGTGAGACCCC |
| 5927 | CTGGGTGACAGAGTGAGACCCCA |
| 5928 | TGGGTGACAGAGTGAGACCCCAT |
| 5929 | GGGTGACAGAGTGAGACCCCATC |
| 5930 | GGTGACAGAGTGAGACCCCATCT |
| 5931 | GTGACAGAGTGAGACCCCATCTC |
| 5932 | TGACAGAGTGAGACCCCATCTCT |
| 5933 | GACAGAGTGAGACCCCATCTCTA |
| 5934 | ACAGAGTGAGACCCCATCTCTAA |
| 5935 | CAGAGTGAGACCCCATCTCTAAA |
| 5936 | AGAGTGAGACCCCATCTCTAAAT |
| 5937 | GAGTGAGACCCCATCTCTAAATA |
| 5938 | AGTGAGACCCCATCTCTAAATAA |
| 5939 | GTGAGACCCCATCTCTAAATAAA |
| 5940 | TGAGACCCCATCTCTAAATAAAT |
| 5941 | GAGACCCCATCTCTAAATAAATA |
| 5942 | AGACCCCATCTCTAAATAAATAG |
| 5943 | GACCCCATCTCTAAATAAATAGG |
| 5944 | ACCCCATCTCTAAATAAATAGGT |
| 5945 | CCCCATCTCTAAATAAATAGGTC |
| 5946 | CCCATCTCTAAATAAATAGGTCA |
| 5947 | CCATCTCTAAATAAATAGGTCAA |
| 5948 | CATCTCTAAATAAATAGGTCAAA |
| 5949 | ATCTCTAAATAAATAGGTCAAAC |
| 5950 | TCTCTAAATAAATAGGTCAAACC |
| 5951 | CTCTAAATAAATAGGTCAAACCC |
| 5952 | TCTAAATAAATAGGTCAAACCCT |

| ID | SEQUENCE |
|---|---|
| 5953 | CTAAATAAATAGGTCAAACCCTT |
| 5954 | TAAATAAATAGGTCAAACCCTTA |
| 5955 | AAATAAATAGGTCAAACCCTTAA |
| 5956 | AATAAATAGGTCAAACCCTTAAA |
| 5957 | ATAAATAGGTCAAACCCTTAAAA |
| 5958 | TAAATAGGTCAAACCCTTAAAAA |
| 5959 | AAATAGGTCAAACCCTTAAAAAT |
| 5960 | AATAGGTCAAACCCTTAAAAATA |
| 5961 | ATAGGTCAAACCCTTAAAAATAT |
| 5962 | TAGGTCAAACCCTTAAAAATATT |
| 5963 | AGGTCAAACCCTTAAAAATATTT |
| 5964 | GGTCAAACCCTTAAAAATATTTA |
| 5965 | GTCAAACCCTTAAAAATATTTAA |
| 5966 | TCAAACCCTTAAAAATATTTAAA |
| 5967 | CAAACCCTTAAAAATATTTAAAT |
| 5968 | AAACCCTTAAAAATATTTAAATT |
| 5969 | AACCCTTAAAAATATTTAAATTC |
| 5970 | ACCCTTAAAAATATTTAAATTCT |
| 5971 | CCCTTAAAAATATTTAAATTCTT |
| 5972 | CCTTAAAAATATTTAAATTCTTA |
| 5973 | CTTAAAAATATTTAAATTCTTAA |
| 5974 | TTAAAAATATTTAAATTCTTAAA |
| 5975 | TAAAAATATTTAAATTCTTAAAA |
| 5976 | AAAAATATTTAAATTCTTAAAAA |
| 5977 | AAAATATTTAAATTCTTAAAAAA |
| 5978 | AAATATTTAAATTCTTAAAAAAT |
| 5979 | AATATTTAAATTCTTAAAAAATT |
| 5980 | ATATTTAAATTCTTAAAAAATTG |
| 5981 | TATTTAAATTCTTAAAAAATTGA |
| 5982 | ATTTAAATTCTTAAAAAATTGAA |
| 5983 | TTTAAATTCTTAAAAAATTGAAA |
| 5984 | TTAAATTCTTAAAAAATTGAAAA |
| 5985 | TAAATTCTTAAAAAATTGAAAAG |
| 5986 | AAATTCTTAAAAAATTGAAAAGA |
| 5987 | AATTCTTAAAAAATTGAAAAGAT |
| 5988 | ATTCTTAAAAAATTGAAAAGATT |
| 5989 | TTCTTAAAAAATTGAAAAGATTA |
| 5990 | TCTTAAAAAATTGAAAAGATTAT |
| 5991 | CTTAAAAAATTGAAAAGATTATT |
| 5992 | TTAAAAAATTGAAAAGATTATTC |
| 5993 | TAAAAAATTGAAAAGATTATTCT |
| 5994 | AAAAAATTGAAAAGATTATTCTT |
| 5995 | AAAAATTGAAAAGATTATTCTTC |
| 5996 | AAAATTGAAAAGATTATTCTTCT |
| 5997 | AAATTGAAAAGATTATTCTTCTC |
| 5998 | AATTGAAAAGATTATTCTTCTCA |
| 5999 | ATTGAAAAGATTATTCTTCTCAA |
| 6000 | TTGAAAAGATTATTCTTCTCAAA |

| ID | SEQUENCE |
|---|---|
| 6001 | TGAAAAGATTATTCTTCTCAAAT |
| 6002 | GAAAAGATTATTCTTCTCAAATT |
| 6003 | AAAAGATTATTCTTCTCAAATTT |
| 6004 | AAAGATTATTCTTCTCAAATTTA |
| 6005 | AAGATTATTCTTCTCAAATTTAG |
| 6006 | AGATTATTCTTCTCAAATTTAGT |
| 6007 | GATTATTCTTCTCAAATTTAGTT |
| 6008 | ATTATTCTTCTCAAATTTAGTTG |
| 6009 | TTATTCTTCTCAAATTTAGTTGA |
| 6010 | TATTCTTCTCAAATTTAGTTGAG |
| 6011 | ATTCTTCTCAAATTTAGTTGAGC |
| 6012 | TTCTTCTCAAATTTAGTTGAGCT |
| 6013 | TCTTCTCAAATTTAGTTGAGCTT |
| 6014 | CTTCTCAAATTTAGTTGAGCTTT |
| 6015 | TTCTCAAATTTAGTTGAGCTTTC |
| 6016 | TCTCAAATTTAGTTGAGCTTTCT |
| 6017 | CTCAAATTTAGTTGAGCTTTCTA |
| 6018 | TCAAATTTAGTTGAGCTTTCTAA |
| 6019 | CAAATTTAGTTGAGCTTTCTAAG |
| 6020 | AAATTTAGTTGAGCTTTCTAAGA |
| 6021 | AATTTAGTTGAGCTTTCTAAGAG |
| 6022 | ATTTAGTTGAGCTTTCTAAGAGA |
| 6023 | TTTAGTTGAGCTTTCTAAGAGAA |
| 6024 | TTAGTTGAGCTTTCTAAGAGAAG |
| 6025 | TAGTTGAGCTTTCTAAGAGAAGC |
| 6026 | AGTTGAGCTTTCTAAGAGAAGCA |
| 6027 | GTTGAGCTTTCTAAGAGAAGCAA |
| 6028 | TTGAGCTTTCTAAGAGAAGCAAT |
| 6029 | TGAGCTTTCTAAGAGAAGCAATT |
| 6030 | GAGCTTTCTAAGAGAAGCAATTG |
| 6031 | AGCTTTCTAAGAGAAGCAATTGG |
| 6032 | GCTTTCTAAGAGAAGCAATTGGC |
| 6033 | CTTTCTAAGAGAAGCAATTGGCT |
| 6034 | TTTCTAAGAGAAGCAATTGGCTT |
| 6035 | TTCTAAGAGAAGCAATTGGCTTT |
| 6036 | TCTAAGAGAAGCAATTGGCTTTT |
| 6037 | CTAAGAGAAGCAATTGGCTTTTT |
| 6038 | TAAGAGAAGCAATTGGCTTTTTC |
| 6039 | AAGAGAAGCAATTGGCTTTTTCC |
| 6040 | AGAGAAGCAATTGGCTTTTTCCC |
| 6041 | GAGAAGCAATTGGCTTTTTCCCA |
| 6042 | AGAAGCAATTGGCTTTTTCCCAC |
| 6043 | GAAGCAATTGGCTTTTTCCCACT |
| 6044 | AAGCAATTGGCTTTTTCCCACTT |
| 6045 | AGCAATTGGCTTTTTCCCACTTC |
| 6046 | GCAATTGGCTTTTTCCCACTTCA |
| 6047 | CAATTGGCTTTTTCCCACTTCAA |
| 6048 | AATTGGCTTTTTCCCACTTCAAT |

| ID | SEQUENCE |
|---|---|
| 6049 | ATTGGCTTTTCCCACTTCAATA |
| 6050 | TTGGCTTTTCCCACTTCAATAA |
| 6051 | TGGCTTTTCCCACTTCAATAAT |
| 6052 | GGCTTTTCCCACTTCAATAATC |
| 6053 | GCTTTTCCCACTTCAATAATCA |
| 6054 | CTTTTCCCACTTCAATAATCAT |
| 6055 | TTTTCCCACTTCAATAATCATT |
| 6056 | TTTCCCACTTCAATAATCATTT |
| 6057 | TTCCCACTTCAATAATCATTTT |
| 6058 | TCCCACTTCAATAATCATTTTC |
| 6059 | CCCACTTCAATAATCATTTTCA |
| 6060 | CCACTTCAATAATCATTTTCAG |
| 6061 | CACTTCAATAATCATTTTCAGT |
| 6062 | ACTTCAATAATCATTTTCAGTT |
| 6063 | CTTCAATAATCATTTTCAGTTT |
| 6064 | TTCAATAATCATTTTCAGTTTG |
| 6065 | TCAATAATCATTTTCAGTTTGA |
| 6066 | CAATAATCATTTTCAGTTTGAC |
| 6067 | AATAATCATTTTCAGTTTGACT |
| 6068 | ATAATCATTTTCAGTTTGACTC |
| 6069 | TAATCATTTTCAGTTTGACTCA |
| 6070 | AATCATTTTCAGTTTGACTCAT |
| 6071 | ATCATTTTCAGTTTGACTCATA |
| 6072 | TCATTTTCAGTTTGACTCATAC |
| 6073 | CATTTTCAGTTTGACTCATACA |
| 6074 | ATTTTCAGTTTGACTCATACAG |
| 6075 | TTTTCAGTTTGACTCATACAGT |
| 6076 | TTTCAGTTTGACTCATACAGTT |
| 6077 | TTCAGTTTGACTCATACAGTTA |
| 6078 | TCAGTTTGACTCATACAGTTAA |
| 6079 | CAGTTTGACTCATACAGTTAAC |
| 6080 | AGTTTGACTCATACAGTTAACA |
| 6081 | GTTTGACTCATACAGTTAACAC |
| 6082 | TTTGACTCATACAGTTAACACA |
| 6083 | TTGACTCATACAGTTAACACAA |
| 6084 | TGACTCATACAGTTAACACAAT |
| 6085 | GACTCATACAGTTAACACAATG |
| 6086 | ACTCATACAGTTAACACAATGT |
| 6087 | CTCATACAGTTAACACAATGTG |
| 6088 | TCATACAGTTAACACAATGTGA |
| 6089 | CATACAGTTAACACAATGTGAA |
| 6090 | ATACAGTTAACACAATGTGAAT |
| 6091 | TACAGTTAACACAATGTGAATT |
| 6092 | ACAGTTAACACAATGTGAATTT |
| 6093 | CAGTTAACACAATGTGAATTTC |
| 6094 | AGTTAACACAATGTGAATTTCT |
| 6095 | GTTAACACAATGTGAATTTCTT |
| 6096 | TTAACACAATGTGAATTTCTTC |

| ID | SEQUENCE |
|---|---|
| 6097 | TTAACACAATGTGAATTTCTTCC |
| 6098 | TAACACAATGTGAATTTCTTCCT |
| 6099 | AACACAATGTGAATTTCTTCCTC |
| 6100 | ACACAATGTGAATTTCTTCCTCA |
| 6101 | CACAATGTGAATTTCTTCCTCAG |
| 6102 | ACAATGTGAATTTCTTCCTCAGC |
| 6103 | CAATGTGAATTTCTTCCTCAGCA |
| 6104 | AATGTGAATTTCTTCCTCAGCAT |
| 6105 | ATGTGAATTTCTTCCTCAGCATA |
| 6106 | TGTGAATTTCTTCCTCAGCATAA |
| 6107 | GTGAATTTCTTCCTCAGCATAAC |
| 6108 | TGAATTTCTTCCTCAGCATAACA |
| 6109 | GAATTTCTTCCTCAGCATAACAG |
| 6110 | AATTTCTTCCTCAGCATAACAGA |
| 6111 | ATTTCTTCCTCAGCATAACAGAG |
| 6112 | TTTCTTCCTCAGCATAACAGAGT |
| 6113 | TTCTTCCTCAGCATAACAGAGTT |
| 6114 | TCTTCCTCAGCATAACAGAGTTA |
| 6115 | CTTCCTCAGCATAACAGAGTTAT |
| 6116 | TTCCTCAGCATAACAGAGTTATA |
| 6117 | TCCTCAGCATAACAGAGTTATAG |
| 6118 | CCTCAGCATAACAGAGTTATAGA |
| 6119 | CTCAGCATAACAGAGTTATAGAA |
| 6120 | TCAGCATAACAGAGTTATAGAAT |
| 6121 | CAGCATAACAGAGTTATAGAATG |
| 6122 | AGCATAACAGAGTTATAGAATGA |
| 6123 | GCATAACAGAGTTATAGAATGAC |
| 6124 | CATAACAGAGTTATAGAATGACA |
| 6125 | ATAACAGAGTTATAGAATGACAG |
| 6126 | TAACAGAGTTATAGAATGACAGG |
| 6127 | AACAGAGTTATAGAATGACAGGG |
| 6128 | ACAGAGTTATAGAATGACAGGGC |
| 6129 | CAGAGTTATAGAATGACAGGGCT |
| 6130 | AGAGTTATAGAATGACAGGGCTG |
| 6131 | GAGTTATAGAATGACAGGGCTGG |
| 6132 | AGTTATAGAATGACAGGGCTGGA |
| 6133 | GTTATAGAATGACAGGGCTGGAA |
| 6134 | TTATAGAATGACAGGGCTGGAAG |
| 6135 | TATAGAATGACAGGGCTGGAAGT |
| 6136 | ATAGAATGACAGGGCTGGAAGTG |
| 6137 | TAGAATGACAGGGCTGGAAGTGA |
| 6138 | AGAATGACAGGGCTGGAAGTGAC |
| 6139 | GAATGACAGGGCTGGAAGTGACC |
| 6140 | AATGACAGGGCTGGAAGTGACCT |
| 6141 | ATGACAGGGCTGGAAGTGACCTT |
| 6142 | TGACAGGGCTGGAAGTGACCTTA |
| 6143 | GACAGGGCTGGAAGTGACCTTAG |
| 6144 | ACAGGGCTGGAAGTGACCTTAGA |

| ID | SEQUENCE |
|---|---|
| 6145 | CAGGGCTGGAAGTGACCTTAGAG |
| 6146 | AGGGCTGGAAGTGACCTTAGAGA |
| 6147 | GGGCTGGAAGTGACCTTAGAGAG |
| 6148 | GGCTGGAAGTGACCTTAGAGAGT |
| 6149 | GCTGGAAGTGACCTTAGAGAGTA |
| 6150 | CTGGAAGTGACCTTAGAGAGTAT |
| 6151 | TGGAAGTGACCTTAGAGAGTATC |
| 6152 | GGAAGTGACCTTAGAGAGTATCC |
| 6153 | GAAGTGACCTTAGAGAGTATCCA |
| 6154 | AAGTGACCTTAGAGAGTATCCAG |
| 6155 | AGTGACCTTAGAGAGTATCCAGT |
| 6156 | GTGACCTTAGAGAGTATCCAGTT |
| 6157 | TGACCTTAGAGAGTATCCAGTTC |
| 6158 | GACCTTAGAGAGTATCCAGTTCT |
| 6159 | ACCTTAGAGAGTATCCAGTTCTT |
| 6160 | CCTTAGAGAGTATCCAGTTCTTT |
| 6161 | CTTAGAGAGTATCCAGTTCTTTC |
| 6162 | TTAGAGAGTATCCAGTTCTTTCA |
| 6163 | TAGAGAGTATCCAGTTCTTTCAT |
| 6164 | AGAGAGTATCCAGTTCTTTCATT |
| 6165 | GAGAGTATCCAGTTCTTTCATTT |
| 6166 | AGAGTATCCAGTTCTTTCATTTT |
| 6167 | GAGTATCCAGTTCTTTCATTTTA |
| 6168 | AGTATCCAGTTCTTTCATTTTAC |
| 6169 | GTATCCAGTTCTTTCATTTTACA |
| 6170 | TATCCAGTTCTTTCATTTTACAG |
| 6171 | ATCCAGTTCTTTCATTTTACAGG |
| 6172 | TCCAGTTCTTTCATTTTACAGGT |
| 6173 | CCAGTTCTTTCATTTTACAGGTG |
| 6174 | CAGTTCTTTCATTTTACAGGTGA |
| 6175 | AGTTCTTTCATTTTACAGGTGAG |
| 6176 | GTTCTTTCATTTTACAGGTGAGG |
| 6177 | TTCTTTCATTTTACAGGTGAGGC |
| 6178 | TCTTTCATTTTACAGGTGAGGCA |
| 6179 | CTTTCATTTTACAGGTGAGGCAA |
| 6180 | TTTCATTTTACAGGTGAGGCAAC |
| 6181 | TTCATTTTACAGGTGAGGCAACT |
| 6182 | TCATTTTACAGGTGAGGCAACTG |
| 6183 | CATTTTACAGGTGAGGCAACTGA |
| 6184 | ATTTTACAGGTGAGGCAACTGAG |
| 6185 | TTTTACAGGTGAGGCAACTGAGA |
| 6186 | TTTACAGGTGAGGCAACTGAGAC |
| 6187 | TTACAGGTGAGGCAACTGAGACT |
| 6188 | TACAGGTGAGGCAACTGAGACTC |
| 6189 | ACAGGTGAGGCAACTGAGACTCA |
| 6190 | CAGGTGAGGCAACTGAGACTCAA |
| 6191 | AGGTGAGGCAACTGAGACTCAAA |
| 6192 | GGTGAGGCAACTGAGACTCAAAG |

| ID | SEQUENCE |
|---|---|
| 6193 | GTGAGGCAACTGAGACTCAAAGG |
| 6194 | TGAGGCAACTGAGACTCAAAGGT |
| 6195 | GAGGCAACTGAGACTCAAAGGTG |
| 6196 | AGGCAACTGAGACTCAAAGGTGA |
| 6197 | GGCAACTGAGACTCAAAGGTGAT |
| 6198 | GCAACTGAGACTCAAAGGTGATG |
| 6199 | CAACTGAGACTCAAAGGTGATGT |
| 6200 | AACTGAGACTCAAAGGTGATGTA |
| 6201 | ACTGAGACTCAAAGGTGATGTAA |
| 6202 | CTGAGACTCAAAGGTGATGTAAT |
| 6203 | TGAGACTCAAAGGTGATGTAATT |
| 6204 | GAGACTCAAAGGTGATGTAATTT |
| 6205 | AGACTCAAAGGTGATGTAATTTG |
| 6206 | GACTCAAAGGTGATGTAATTTGT |
| 6207 | ACTCAAAGGTGATGTAATTTGTG |
| 6208 | CTCAAAGGTGATGTAATTTGTGC |
| 6209 | TCAAAGGTGATGTAATTTGTGCA |
| 6210 | CAAAGGTGATGTAATTTGTGCAA |
| 6211 | AAAGGTGATGTAATTTGTGCAAA |
| 6212 | AAGGTGATGTAATTTGTGCAAAG |
| 6213 | AGGTGATGTAATTTGTGCAAAGA |
| 6214 | GGTGATGTAATTTGTGCAAAGAT |
| 6215 | GTGATGTAATTTGTGCAAAGATT |
| 6216 | TGATGTAATTTGTGCAAAGATTA |
| 6217 | GATGTAATTTGTGCAAAGATTAT |
| 6218 | ATGTAATTTGTGCAAAGATTATA |
| 6219 | TGTAATTTGTGCAAAGATTATAG |
| 6220 | GTAATTTGTGCAAAGATTATAGC |
| 6221 | TAATTTGTGCAAAGATTATAGCT |
| 6222 | AATTTGTGCAAAGATTATAGCTA |
| 6223 | ATTTGTGCAAAGATTATAGCTAA |
| 6224 | TTTGTGCAAAGATTATAGCTAAT |
| 6225 | TTGTGCAAAGATTATAGCTAATT |
| 6226 | TGTGCAAAGATTATAGCTAATTA |
| 6227 | GTGCAAAGATTATAGCTAATTAG |
| 6228 | TGCAAAGATTATAGCTAATTAGT |
| 6229 | GCAAAGATTATAGCTAATTAGTA |
| 6230 | CAAAGATTATAGCTAATTAGTAG |
| 6231 | AAAGATTATAGCTAATTAGTAGC |
| 6232 | AAGATTATAGCTAATTAGTAGCA |
| 6233 | AGATTATAGCTAATTAGTAGCAG |
| 6234 | GATTATAGCTAATTAGTAGCAGA |
| 6235 | ATTATAGCTAATTAGTAGCAGAG |
| 6236 | TTATAGCTAATTAGTAGCAGAGC |
| 6237 | TATAGCTAATTAGTAGCAGAGCC |
| 6238 | ATAGCTAATTAGTAGCAGAGCCC |
| 6239 | TAGCTAATTAGTAGCAGAGCCCT |
| 6240 | AGCTAATTAGTAGCAGAGCCCTG |

| ID | SEQUENCE |
|---|---|
| 6241 | GCTAATTAGTAGCAGAGCCCTGA |
| 6242 | CTAATTAGTAGCAGAGCCCTGAC |
| 6243 | TAATTAGTAGCAGAGCCCTGACT |
| 6244 | AATTAGTAGCAGAGCCCTGACTG |
| 6245 | ATTAGTAGCAGAGCCCTGACTGG |
| 6246 | TTAGTAGCAGAGCCCTGACTGGG |
| 6247 | TAGTAGCAGAGCCCTGACTGGGA |
| 6248 | AGTAGCAGAGCCCTGACTGGGAC |
| 6249 | GTAGCAGAGCCCTGACTGGGACA |
| 6250 | TAGCAGAGCCCTGACTGGGACAT |
| 6251 | AGCAGAGCCCTGACTGGGACATA |
| 6252 | GCAGAGCCCTGACTGGGACATAG |
| 6253 | CAGAGCCCTGACTGGGACATAGT |
| 6254 | AGAGCCCTGACTGGGACATAGTT |
| 6255 | GAGCCCTGACTGGGACATAGTTT |
| 6256 | AGCCCTGACTGGGACATAGTTTG |
| 6257 | GCCCTGACTGGGACATAGTTTGA |
| 6258 | CCCTGACTGGGACATAGTTTGAA |
| 6259 | CCTGACTGGGACATAGTTTGAAG |
| 6260 | CTGACTGGGACATAGTTTGAAGG |
| 6261 | TGACTGGGACATAGTTTGAAGGT |
| 6262 | GACTGGGACATAGTTTGAAGGTG |
| 6263 | ACTGGGACATAGTTTGAAGGTGA |
| 6264 | CTGGGACATAGTTTGAAGGTGAA |
| 6265 | TGGGACATAGTTTGAAGGTGAAA |
| 6266 | GGGACATAGTTTGAAGGTGAAAA |
| 6267 | GGACATAGTTTGAAGGTGAAAAA |
| 6268 | GACATAGTTTGAAGGTGAAAAAC |
| 6269 | ACATAGTTTGAAGGTGAAAAACT |
| 6270 | CATAGTTTGAAGGTGAAAAACTT |
| 6271 | ATAGTTTGAAGGTGAAAAACTTC |
| 6272 | TAGTTTGAAGGTGAAAAACTTCA |
| 6273 | AGTTTGAAGGTGAAAAACTTCAC |
| 6274 | GTTTGAAGGTGAAAAACTTCACC |
| 6275 | TTTGAAGGTGAAAAACTTCACCA |
| 6276 | TTGAAGGTGAAAAACTTCACCAA |
| 6277 | TGAAGGTGAAAAACTTCACCAAG |
| 6278 | GAAGGTGAAAAACTTCACCAAGC |
| 6279 | AAGGTGAAAAACTTCACCAAGCT |
| 6280 | AGGTGAAAAACTTCACCAAGCTA |
| 6281 | GGTGAAAAACTTCACCAAGCTAC |
| 6282 | GTGAAAAACTTCACCAAGCTACC |
| 6283 | TGAAAAACTTCACCAAGCTACCT |
| 6284 | GAAAAACTTCACCAAGCTACCTT |
| 6285 | AAAAACTTCACCAAGCTACCTTT |
| 6286 | AAAACTTCACCAAGCTACCTTTC |
| 6287 | AAACTTCACCAAGCTACCTTTCT |
| 6288 | AACTTCACCAAGCTACCTTTCTT |

| ID | SEQUENCE |
|---|---|
| 6289 | ACTTCACCAAGCTACCTTTCTTG |
| 6290 | CTTCACCAAGCTACCTTTCTTGA |
| 6291 | TTCACCAAGCTACCTTTCTTGAA |
| 6292 | TCACCAAGCTACCTTTCTTGAAA |
| 6293 | CACCAAGCTACCTTTCTTGAAAG |
| 6294 | ACCAAGCTACCTTTCTTGAAAGG |
| 6295 | CCAAGCTACCTTTCTTGAAAGGT |
| 6296 | CAAGCTACCTTTCTTGAAAGGTC |
| 6297 | AAGCTACCTTTCTTGAAAGGTCC |
| 6298 | AGCTACCTTTCTTGAAAGGTCCA |
| 6299 | GCTACCTTTCTTGAAAGGTCCAA |
| 6300 | CTACCTTTCTTGAAAGGTCCAAA |
| 6301 | TACCTTTCTTGAAAGGTCCAAAT |
| 6302 | ACCTTTCTTGAAAGGTCCAAATG |
| 6303 | CCTTTCTTGAAAGGTCCAAATGT |
| 6304 | CTTTCTTGAAAGGTCCAAATGTT |
| 6305 | TTTCTTGAAAGGTCCAAATGTTT |
| 6306 | TTCTTGAAAGGTCCAAATGTTTA |
| 6307 | TCTTGAAAGGTCCAAATGTTTAT |
| 6308 | CTTGAAAGGTCCAAATGTTTATG |
| 6309 | TTGAAAGGTCCAAATGTTTATGT |
| 6310 | TGAAAGGTCCAAATGTTTATGTT |
| 6311 | GAAAGGTCCAAATGTTTATGTTT |
| 6312 | AAAGGTCCAAATGTTTATGTTTT |
| 6313 | AAGGTCCAAATGTTTATGTTTTC |
| 6314 | AGGTCCAAATGTTTATGTTTTCA |
| 6315 | GGTCCAAATGTTTATGTTTTCAA |
| 6316 | GTCCAAATGTTTATGTTTTCAAC |
| 6317 | TCCAAATGTTTATGTTTTCAACT |
| 6318 | CCAAATGTTTATGTTTTCAACTA |
| 6319 | CAAATGTTTATGTTTTCAACTAC |
| 6320 | AAATGTTTATGTTTTCAACTACT |
| 6321 | AATGTTTATGTTTTCAACTACTC |
| 6322 | ATGTTTATGTTTTCAACTACTCT |
| 6323 | TGTTTATGTTTTCAACTACTCTT |
| 6324 | GTTTATGTTTTCAACTACTCTTT |
| 6325 | TTTATGTTTTCAACTACTCTTTC |
| 6326 | TTATGTTTTCAACTACTCTTTCC |
| 6327 | TATGTTTTCAACTACTCTTTCCA |
| 6328 | ATGTTTTCAACTACTCTTTCCAC |
| 6329 | TGTTTTCAACTACTCTTTCCACT |
| 6330 | GTTTTCAACTACTCTTTCCACTG |
| 6331 | TTTTCAACTACTCTTTCCACTGT |
| 6332 | TTTCAACTACTCTTTCCACTGTA |
| 6333 | TTCAACTACTCTTTCCACTGTAC |
| 6334 | TCAACTACTCTTTCCACTGTACC |
| 6335 | CAACTACTCTTTCCACTGTACCA |
| 6336 | AACTACTCTTTCCACTGTACCAT |

| ID | SEQUENCE |
|---|---|
| 6337 | ACTACTCTTTCCACTGTACCATA |
| 6338 | CTACTCTTTCCACTGTACCATAA |
| 6339 | TACTCTTTCCACTGTACCATAAC |
| 6340 | ACTCTTTCCACTGTACCATAACT |
| 6341 | CTCTTTCCACTGTACCATAACTT |
| 6342 | TCTTTCCACTGTACCATAACTTT |
| 6343 | CTTTCCACTGTACCATAACTTTC |
| 6344 | TTTCCACTGTACCATAACTTTCA |
| 6345 | TTCCACTGTACCATAACTTTCAC |
| 6346 | TCCACTGTACCATAACTTTCACT |
| 6347 | CCACTGTACCATAACTTTCACTA |
| 6348 | CACTGTACCATAACTTTCACTAC |
| 6349 | ACTGTACCATAACTTTCACTACA |
| 6350 | CTGTACCATAACTTTCACTACAT |
| 6351 | TGTACCATAACTTTCACTACATA |
| 6352 | GTACCATAACTTTCACTACATAT |
| 6353 | TACCATAACTTTCACTACATATT |
| 6354 | ACCATAACTTTCACTACATATTA |
| 6355 | CCATAACTTTCACTACATATTAA |
| 6356 | CATAACTTTCACTACATATTAAA |
| 6357 | ATAACTTTCACTACATATTAAAT |
| 6358 | TAACTTTCACTACATATTAAATG |
| 6359 | AACTTTCACTACATATTAAATGA |
| 6360 | ACTTTCACTACATATTAAATGAC |
| 6361 | CTTTCACTACATATTAAATGACA |
| 6362 | TTTCACTACATATTAAATGACAC |
| 6363 | TTCACTACATATTAAATGACACT |
| 6364 | TCACTACATATTAAATGACACTT |
| 6365 | CACTACATATTAAATGACACTTT |
| 6366 | ACTACATATTAAATGACACTTTA |
| 6367 | CTACATATTAAATGACACTTTAT |
| 6368 | TACATATTAAATGACACTTTATA |
| 6369 | ACATATTAAATGACACTTTATAA |
| 6370 | CATATTAAATGACACTTTATAAC |
| 6371 | ATATTAAATGACACTTTATAACT |
| 6372 | TATTAAATGACACTTTATAACTA |
| 6373 | ATTAAATGACACTTTATAACTAA |
| 6374 | TTAAATGACACTTTATAACTAAT |
| 6375 | TAAATGACACTTTATAACTAATA |
| 6376 | AAATGACACTTTATAACTAATAT |
| 6377 | AATGACACTTTATAACTAATATA |
| 6378 | ATGACACTTTATAACTAATATAA |
| 6379 | TGACACTTTATAACTAATATAAT |
| 6380 | GACACTTTATAACTAATATAATA |
| 6381 | ACACTTTATAACTAATATAATAG |
| 6382 | CACTTTATAACTAATATAATAGG |
| 6383 | ACTTTATAACTAATATAATAGGA |
| 6384 | CTTTATAACTAATATAATAGGAC |

| ID | SEQUENCE |
| --- | --- |
| 6385 | TTTATAACTAATATAATAGGACA |
| 6386 | TTATAACTAATATAATAGGACAA |
| 6387 | TATAACTAATATAATAGGACAAT |
| 6388 | ATAACTAATATAATAGGACAATC |
| 6389 | TAACTAATATAATAGGACAATCA |
| 6390 | AACTAATATAATAGGACAATCAT |
| 6391 | ACTAATATAATAGGACAATCATC |
| 6392 | CTAATATAATAGGACAATCATCA |
| 6393 | TAATATAATAGGACAATCATCAA |
| 6394 | AATATAATAGGACAATCATCAAT |
| 6395 | ATATAATAGGACAATCATCAATG |
| 6396 | TATAATAGGACAATCATCAATGC |
| 6397 | ATAATAGGACAATCATCAATGCA |
| 6398 | TAATAGGACAATCATCAATGCAT |
| 6399 | AATAGGACAATCATCAATGCATA |
| 6400 | ATAGGACAATCATCAATGCATAT |
| 6401 | TAGGACAATCATCAATGCATATA |
| 6402 | AGGACAATCATCAATGCATATAT |
| 6403 | GGACAATCATCAATGCATATATA |
| 6404 | GACAATCATCAATGCATATATAG |
| 6405 | ACAATCATCAATGCATATATAGC |
| 6406 | CAATCATCAATGCATATATAGCC |
| 6407 | AATCATCAATGCATATATAGCCA |
| 6408 | ATCATCAATGCATATATAGCCAG |
| 6409 | TCATCAATGCATATATAGCCAGC |
| 6410 | CATCAATGCATATATAGCCAGCC |
| 6411 | ATCAATGCATATATAGCCAGCCC |
| 6412 | TCAATGCATATATAGCCAGCCCT |
| 6413 | CAATGCATATATAGCCAGCCCTT |
| 6414 | AATGCATATATAGCCAGCCCTTC |
| 6415 | ATGCATATATAGCCAGCCCTTCA |
| 6416 | TGCATATATAGCCAGCCCTTCAT |
| 6417 | GCATATATAGCCAGCCCTTCATA |
| 6418 | CATATATAGCCAGCCCTTCATAT |
| 6419 | ATATATAGCCAGCCCTTCATATC |
| 6420 | TATATAGCCAGCCCTTCATATCT |
| 6421 | ATATAGCCAGCCCTTCATATCTG |
| 6422 | TATAGCCAGCCCTTCATATCTGT |
| 6423 | ATAGCCAGCCCTTCATATCTGTG |
| 6424 | TAGCCAGCCCTTCATATCTGTGG |
| 6425 | AGCCAGCCCTTCATATCTGTGGG |
| 6426 | GCCAGCCCTTCATATCTGTGGGT |
| 6427 | CCAGCCCTTCATATCTGTGGGTT |
| 6428 | CAGCCCTTCATATCTGTGGGTTT |
| 6429 | AGCCCTTCATATCTGTGGGTTTT |
| 6430 | GCCCTTCATATCTGTGGGTTTTG |
| 6431 | CCCTTCATATCTGTGGGTTTTGC |
| 6432 | CCTTCATATCTGTGGGTTTTGCA |

| ID | SEQUENCE |
|---|---|
| 6433 | CTTCATATCTGTGGGTTTTGCAT |
| 6434 | TTCATATCTGTGGGTTTTGCATC |
| 6435 | TCATATCTGTGGGTTTTGCATCC |
| 6436 | CATATCTGTGGGTTTTGCATCCA |
| 6437 | ATATCTGTGGGTTTTGCATCCAT |
| 6438 | TATCTGTGGGTTTTGCATCCATG |
| 6439 | ATCTGTGGGTTTTGCATCCATGG |
| 6440 | TCTGTGGGTTTTGCATCCATGGA |
| 6441 | CTGTGGGTTTTGCATCCATGGAT |
| 6442 | TGTGGGTTTTGCATCCATGGATT |
| 6443 | GTGGGTTTTGCATCCATGGATTC |
| 6444 | TGGGTTTTGCATCCATGGATTCA |
| 6445 | GGGTTTTGCATCCATGGATTCAA |
| 6446 | GGTTTTGCATCCATGGATTCAAC |
| 6447 | GTTTTGCATCCATGGATTCAACC |
| 6448 | TTTTGCATCCATGGATTCAACCA |
| 6449 | TTTGCATCCATGGATTCAACCAA |
| 6450 | TTGCATCCATGGATTCAACCAAG |
| 6451 | TGCATCCATGGATTCAACCAAGG |
| 6452 | GCATCCATGGATTCAACCAAGGA |
| 6453 | CATCCATGGATTCAACCAAGGAG |
| 6454 | ATCCATGGATTCAACCAAGGAGG |
| 6455 | TCCATGGATTCAACCAAGGAGGA |
| 6456 | CCATGGATTCAACCAAGGAGGAA |
| 6457 | CATGGATTCAACCAAGGAGGAAT |
| 6458 | ATGGATTCAACCAAGGAGGAATT |
| 6459 | TGGATTCAACCAAGGAGGAATTG |
| 6460 | GGATTCAACCAAGGAGGAATTGA |
| 6461 | GATTCAACCAAGGAGGAATTGAA |
| 6462 | ATTCAACCAAGGAGGAATTGAAA |
| 6463 | TTCAACCAAGGAGGAATTGAAAA |
| 6464 | TCAACCAAGGAGGAATTGAAAAC |
| 6465 | CAACCAAGGAGGAATTGAAAACA |
| 6466 | AACCAAGGAGGAATTGAAAACAC |
| 6467 | ACCAAGGAGGAATTGAAAACACT |
| 6468 | CCAAGGAGGAATTGAAAACACTG |
| 6469 | CAAGGAGGAATTGAAAACACTGA |
| 6470 | AAGGAGGAATTGAAAACACTGAG |
| 6471 | AGGAGGAATTGAAAACACTGAGA |
| 6472 | GGAGGAATTGAAAACACTGAGAA |
| 6473 | GAGGAATTGAAAACACTGAGAAA |
| 6474 | AGGAATTGAAAACACTGAGAAAA |
| 6475 | GGAATTGAAAACACTGAGAAAAA |
| 6476 | GAATTGAAAACACTGAGAAAAAA |
| 6477 | AATTGAAAACACTGAGAAAAAAA |
| 6478 | ATTGAAAACACTGAGAAAAAAAA |
| 6479 | AAAAAAAGACCACACAATAAAAA |
| 6480 | AAAAAAAGACCACACAATAAAAA |

| ID | SEQUENCE |
|---|---|
| 6481 | AAAAAAGACCACACAATAAAAAA |
| 6482 | AAAAAGACCACACAATAAAAAAA |
| 6483 | AAAAGACCACACAATAAAAAAAA |
| 6484 | AAAAAAATACAAAATAATACAA |
| 6485 | AAAAAAATACAAAATAATACAAA |
| 6486 | AAAAAATACAAAATAATACAAAG |
| 6487 | AAAAATACAAAATAATACAAAGA |
| 6488 | AAAATACAAAATAATACAAAGAA |
| 6489 | AAATACAAAATAATACAAAGAAA |
| 6490 | AATACAAAATAATACAAAGAAAA |
| 6491 | ATACAAAATAATACAAAGAAAAA |
| 6492 | TACAAAATAATACAAAGAAAAAG |
| 6493 | ACAAAATAATACAAAGAAAAAGC |
| 6494 | CAAAATAATACAAAGAAAAAGCC |
| 6495 | AAAATAATACAAAGAAAAAGCCA |
| 6496 | AAATAATACAAAGAAAAAGCCAA |
| 6497 | AATAATACAAAGAAAAAGCCAAA |
| 6498 | ATAATACAAAGAAAAAGCCAAAA |
| 6499 | TAATACAAAGAAAAAGCCAAAAT |
| 6500 | AATACAAAGAAAAAGCCAAAATT |
| 6501 | ATACAAAGAAAAAGCCAAAATTG |
| 6502 | TACAAAGAAAAAGCCAAAATTGT |
| 6503 | ACAAAGAAAAAGCCAAAATTGTC |
| 6504 | CAAAGAAAAAGCCAAAATTGTCA |
| 6505 | AAAGAAAAAGCCAAAATTGTCAT |
| 6506 | AAGAAAAAGCCAAAATTGTCATA |
| 6507 | AGAAAAAGCCAAAATTGTCATAC |
| 6508 | GAAAAAGCCAAAATTGTCATACT |
| 6509 | AAAAAGCCAAAATTGTCATACTG |
| 6510 | AAAAGCCAAAATTGTCATACTGT |
| 6511 | AAAGCCAAAATTGTCATACTGTT |
| 6512 | AAGCCAAAATTGTCATACTGTTG |
| 6513 | AGCCAAAATTGTCATACTGTTGT |
| 6514 | GCCAAAATTGTCATACTGTTGTT |
| 6515 | CCAAAATTGTCATACTGTTGTTA |
| 6516 | CAAAATTGTCATACTGTTGTTAA |
| 6517 | AAAATTGTCATACTGTTGTTAAG |
| 6518 | AAATTGTCATACTGTTGTTAAGC |
| 6519 | AATTGTCATACTGTTGTTAAGCA |
| 6520 | ATTGTCATACTGTTGTTAAGCAA |
| 6521 | TTGTCATACTGTTGTTAAGCAAC |
| 6522 | TGTCATACTGTTGTTAAGCAACA |
| 6523 | GTCATACTGTTGTTAAGCAACAG |
| 6524 | TCATACTGTTGTTAAGCAACAGT |
| 6525 | CATACTGTTGTTAAGCAACAGTA |
| 6526 | ATACTGTTGTTAAGCAACAGTAT |
| 6527 | TACTGTTGTTAAGCAACAGTATA |
| 6528 | ACTGTTGTTAAGCAACAGTATAA |

| ID | SEQUENCE |
|---|---|
| 6529 | CTGTTGTTAAGCAACAGTATAAC |
| 6530 | TGTTGTTAAGCAACAGTATAACA |
| 6531 | GTTGTTAAGCAACAGTATAACAA |
| 6532 | TTGTTAAGCAACAGTATAACAAC |
| 6533 | TGTTAAGCAACAGTATAACAACT |
| 6534 | GTTAAGCAACAGTATAACAACTA |
| 6535 | TTAAGCAACAGTATAACAACTAT |
| 6536 | TAAGCAACAGTATAACAACTATT |
| 6537 | AAGCAACAGTATAACAACTATTT |
| 6538 | AGCAACAGTATAACAACTATTTA |
| 6539 | GCAACAGTATAACAACTATTTAC |
| 6540 | CAACAGTATAACAACTATTTACA |
| 6541 | AACAGTATAACAACTATTTACAT |
| 6542 | ACAGTATAACAACTATTTACATA |
| 6543 | CAGTATAACAACTATTTACATAG |
| 6544 | AGTATAACAACTATTTACATAGC |
| 6545 | GTATAACAACTATTTACATAGCA |
| 6546 | TATAACAACTATTTACATAGCAT |
| 6547 | ATAACAACTATTTACATAGCATT |
| 6548 | TAACAACTATTTACATAGCATTA |
| 6549 | AACAACTATTTACATAGCATTAA |
| 6550 | ACAACTATTTACATAGCATTAAG |
| 6551 | CAACTATTTACATAGCATTAAGG |
| 6552 | AACTATTTACATAGCATTAAGGT |
| 6553 | ACTATTTACATAGCATTAAGGTT |
| 6554 | CTATTTACATAGCATTAAGGTTG |
| 6555 | TATTTACATAGCATTAAGGTTGG |
| 6556 | ATTTACATAGCATTAAGGTTGGT |
| 6557 | TTTACATAGCATTAAGGTTGGTG |
| 6558 | TTACATAGCATTAAGGTTGGTGC |
| 6559 | TACATAGCATTAAGGTTGGTGCA |
| 6560 | ACATAGCATTAAGGTTGGTGCAA |
| 6561 | CATAGCATTAAGGTTGGTGCAAA |
| 6562 | ATAGCATTAAGGTTGGTGCAAAA |
| 6563 | TAGCATTAAGGTTGGTGCAAAAA |
| 6564 | AGCATTAAGGTTGGTGCAAAAAT |
| 6565 | GCATTAAGGTTGGTGCAAAAATG |
| 6566 | CATTAAGGTTGGTGCAAAAATGC |
| 6567 | ATTAAGGTTGGTGCAAAAATGCA |
| 6568 | TTAAGGTTGGTGCAAAAATGCAA |
| 6569 | TAAGGTTGGTGCAAAAATGCAAA |
| 6570 | AAGGTTGGTGCAAAAATGCAAAA |
| 6571 | AGGTTGGTGCAAAAATGCAAAAA |
| 6572 | GGTTGGTGCAAAAATGCAAAAAA |
| 6573 | GTTGGTGCAAAAATGCAAAAAAA |
| 6574 | TTGGTGCAAAAATGCAAAAAAAA |
| 6575 | AAAAAAAGCAATTATTTTAAA |
| 6576 | AAAAAAAGCAATTATTTTAAAC |

| ID | SEQUENCE |
|---|---|
| 6577 | AAAAAAGCAATTATTTTAAACC |
| 6578 | AAAAAGCAATTATTTTAAACCA |
| 6579 | AAAAGCAATTATTTTAAACCAA |
| 6580 | AAAGCAATTATTTTAAACCAAC |
| 6581 | AAGCAATTATTTTAAACCAACC |
| 6582 | AGCAATTATTTTAAACCAACCT |
| 6583 | GCAATTATTTTAAACCAACCTA |
| 6584 | CAATTATTTTAAACCAACCTAA |
| 6585 | AATTATTTTAAACCAACCTAAT |
| 6586 | ATTATTTTAAACCAACCTAATA |
| 6587 | TTATTTTAAACCAACCTAATAT |
| 6588 | TATTTTAAACCAACCTAATATA |
| 6589 | ATTTTAAACCAACCTAATATAT |
| 6590 | TTTTAAACCAACCTAATATATT |
| 6591 | TTTAAACCAACCTAATATATTG |
| 6592 | TTAAACCAACCTAATATATTGT |
| 6593 | TAAACCAACCTAATATATTGTA |
| 6594 | AAACCAACCTAATATATTGTAT |
| 6595 | AACCAACCTAATATATTGTATT |
| 6596 | ACCAACCTAATATATTGTATTA |
| 6597 | CCAACCTAATATATTGTATTAG |
| 6598 | CAACCTAATATATTGTATTAGG |
| 6599 | AACCTAATATATTGTATTAGGT |
| 6600 | ACCTAATATATTGTATTAGGTA |
| 6601 | CCTAATATATTGTATTAGGTAT |
| 6602 | CTAATATATTGTATTAGGTATT |
| 6603 | TAATATATTGTATTAGGTATTA |
| 6604 | AATATATTGTATTAGGTATTAA |
| 6605 | ATATATTGTATTAGGTATTAAA |
| 6606 | TATATTGTATTAGGTATTAAAG |
| 6607 | ATATTGTATTAGGTATTAAAGT |
| 6608 | TATTGTATTAGGTATTAAAGTC |
| 6609 | ATTGTATTAGGTATTAAAGTCA |
| 6610 | TTGTATTAGGTATTAAAGTCAT |
| 6611 | TGTATTAGGTATTAAAGTCATC |
| 6612 | GTATTAGGTATTAAAGTCATCT |
| 6613 | TATTAGGTATTAAAGTCATCTG |
| 6614 | ATTAGGTATTAAAGTCATCTGG |
| 6615 | TTAGGTATTAAAGTCATCTGGA |
| 6616 | TAGGTATTAAAGTCATCTGGAC |
| 6617 | AGGTATTAAAGTCATCTGGACA |
| 6618 | GGTATTAAAGTCATCTGGACAT |
| 6619 | GTATTAAAGTCATCTGGACATG |
| 6620 | TATTAAAGTCATCTGGACATGA |
| 6621 | ATTAAAGTCATCTGGACATGAA |
| 6622 | TTAAAGTCATCTGGACATGAAT |
| 6623 | TAAAGTCATCTGGACATGAATT |
| 6624 | AAAGTCATCTGGACATGAATTA |

| ID | SEQUENCE |
|---|---|
| 6625 | AAAGTCATCTGGACATGAATTAA |
| 6626 | AAGTCATCTGGACATGAATTAAA |
| 6627 | AGTCATCTGGACATGAATTAAAG |
| 6628 | GTCATCTGGACATGAATTAAAGT |
| 6629 | TCATCTGGACATGAATTAAAGTA |
| 6630 | CATCTGGACATGAATTAAAGTAT |
| 6631 | ATCTGGACATGAATTAAAGTATA |
| 6632 | TCTGGACATGAATTAAAGTATAT |
| 6633 | CTGGACATGAATTAAAGTATATG |
| 6634 | TGGACATGAATTAAAGTATATGA |
| 6635 | GGACATGAATTAAAGTATATGAT |
| 6636 | GACATGAATTAAAGTATATGATG |
| 6637 | ACATGAATTAAAGTATATGATGC |
| 6638 | CATGAATTAAAGTATATGATGCC |
| 6639 | ATGAATTAAAGTATATGATGCCA |
| 6640 | TGAATTAAAGTATATGATGCCAG |
| 6641 | GAATTAAAGTATATGATGCCAGC |
| 6642 | AATTAAAGTATATGATGCCAGCC |
| 6643 | ATTAAAGTATATGATGCCAGCCT |
| 6644 | TTAAAGTATATGATGCCAGCCTG |
| 6645 | TAAAGTATATGATGCCAGCCTGG |
| 6646 | AAAGTATATGATGCCAGCCTGGA |
| 6647 | AAGTATATGATGCCAGCCTGGAC |
| 6648 | AGTATATGATGCCAGCCTGGACA |
| 6649 | GTATATGATGCCAGCCTGGACAA |
| 6650 | TATATGATGCCAGCCTGGACAAA |
| 6651 | ATATGATGCCAGCCTGGACAAAA |
| 6652 | TATGATGCCAGCCTGGACAAAAG |
| 6653 | ATGATGCCAGCCTGGACAAAAGG |
| 6654 | TGATGCCAGCCTGGACAAAAGGC |
| 6655 | GATGCCAGCCTGGACAAAAGGCA |
| 6656 | ATGCCAGCCTGGACAAAAGGCAA |
| 6657 | TGCCAGCCTGGACAAAAGGCAAA |
| 6658 | GCCAGCCTGGACAAAAGGCAAAA |
| 6659 | CCAGCCTGGACAAAAGGCAAAAC |
| 6660 | CAGCCTGGACAAAAGGCAAAACC |
| 6661 | AGCCTGGACAAAAGGCAAAACCC |
| 6662 | GCCTGGACAAAAGGCAAAACCCT |
| 6663 | CCTGGACAAAAGGCAAAACCCTG |
| 6664 | CTGGACAAAAGGCAAAACCCTGT |
| 6665 | TGGACAAAAGGCAAAACCCTGTC |
| 6666 | GGACAAAAGGCAAAACCCTGTCT |
| 6667 | GACAAAAGGCAAAACCCTGTCTC |
| 6668 | ACAAAAGGCAAAACCCTGTCTCT |
| 6669 | CAAAAGGCAAAACCCTGTCTCTA |
| 6670 | AAAAGGCAAAACCCTGTCTCTAC |
| 6671 | AAAGGCAAAACCCTGTCTCTACA |
| 6672 | AAGGCAAAACCCTGTCTCTACAA |

| ID | SEQUENCE |
|---|---|
| 6673 | AGGCAAAACCCTGTCTCTACAAA |
| 6674 | GGCAAAACCCTGTCTCTACAAAA |
| 6675 | GCAAAACCCTGTCTCTACAAAAA |
| 6676 | CAAAACCCTGTCTCTACAAAAAA |
| 6677 | AAAACCCTGTCTCTACAAAAAAT |
| 6678 | AAACCCTGTCTCTACAAAAAATA |
| 6679 | AACCCTGTCTCTACAAAAAATAC |
| 6680 | ACCCTGTCTCTACAAAAAATACA |
| 6681 | CCCTGTCTCTACAAAAAATACAA |
| 6682 | CCTGTCTCTACAAAAAATACAAA |
| 6683 | CTGTCTCTACAAAAAATACAAAA |
| 6684 | TGTCTCTACAAAAAATACAAAAA |
| 6685 | GTCTCTACAAAAAATACAAAAAT |
| 6686 | TCTCTACAAAAAATACAAAAATT |
| 6687 | CTCTACAAAAAATACAAAAATTA |
| 6688 | TCTACAAAAAATACAAAAATTAG |
| 6689 | CTACAAAAAATACAAAAATTAGC |
| 6690 | TACAAAAAATACAAAAATTAGCT |
| 6691 | ACAAAAAATACAAAAATTAGCTG |
| 6692 | CAAAAAATACAAAAATTAGCTGG |
| 6693 | AAAAAATACAAAAATTAGCTGGG |
| 6694 | AAAAATACAAAAATTAGCTGGGC |
| 6695 | AAAATACAAAAATTAGCTGGGCA |
| 6696 | AAATACAAAAATTAGCTGGGCAT |
| 6697 | AATACAAAAATTAGCTGGGCATG |
| 6698 | ATACAAAAATTAGCTGGGCATGG |
| 6699 | TACAAAAATTAGCTGGGCATGGT |
| 6700 | ACAAAAATTAGCTGGGCATGGTG |
| 6701 | CAAAAATTAGCTGGGCATGGTGG |
| 6702 | AAAAATTAGCTGGGCATGGTGGT |
| 6703 | AAAATTAGCTGGGCATGGTGGTG |
| 6704 | AAATTAGCTGGGCATGGTGGTGT |
| 6705 | AATTAGCTGGGCATGGTGGTGTG |
| 6706 | ATTAGCTGGGCATGGTGGTGTGT |
| 6707 | TTAGCTGGGCATGGTGGTGTGTG |
| 6708 | TAGCTGGGCATGGTGGTGTGTGC |
| 6709 | AGCTGGGCATGGTGGTGTGTGCC |
| 6710 | GCTGGGCATGGTGGTGTGTGCCT |
| 6711 | CTGGGCATGGTGGTGTGTGCCTG |
| 6712 | TGGGCATGGTGGTGTGTGCCTGT |
| 6713 | GGGCATGGTGGTGTGTGCCTGTA |
| 6714 | GGCATGGTGGTGTGTGCCTGTAG |
| 6715 | GCATGGTGGTGTGTGCCTGTAGT |
| 6716 | CATGGTGGTGTGTGCCTGTAGTC |
| 6717 | ATGGTGGTGTGTGCCTGTAGTCC |
| 6718 | TGGTGGTGTGTGCCTGTAGTCCT |
| 6719 | GGTGGTGTGTGCCTGTAGTCCTG |
| 6720 | GTGGTGTGTGCCTGTAGTCCTGG |

| ID | SEQUENCE |
|---|---|
| 6721 | TGGTGTGTGCCTGTAGTCCTGGC |
| 6722 | GGTGTGTGCCTGTAGTCCTGGCT |
| 6723 | GTGTGTGCCTGTAGTCCTGGCTA |
| 6724 | TGTGTGCCTGTAGTCCTGGCTAC |
| 6725 | GTGTGCCTGTAGTCCTGGCTACT |
| 6726 | TGTGCCTGTAGTCCTGGCTACTC |
| 6727 | GTGCCTGTAGTCCTGGCTACTCC |
| 6728 | TGCCTGTAGTCCTGGCTACTCCG |
| 6729 | GCCTGTAGTCCTGGCTACTCCGG |
| 6730 | CCTGTAGTCCTGGCTACTCCGGA |
| 6731 | CTGTAGTCCTGGCTACTCCGGAG |
| 6732 | TGTAGTCCTGGCTACTCCGGAGC |
| 6733 | GTAGTCCTGGCTACTCCGGAGCC |
| 6734 | TAGTCCTGGCTACTCCGGAGCCT |
| 6735 | AGTCCTGGCTACTCCGGAGCCTG |
| 6736 | GTCCTGGCTACTCCGGAGCCTGA |
| 6737 | TCCTGGCTACTCCGGAGCCTGAG |
| 6738 | CCTGGCTACTCCGGAGCCTGAGG |
| 6739 | CTGGCTACTCCGGAGCCTGAGGT |
| 6740 | TGGCTACTCCGGAGCCTGAGGTG |
| 6741 | GGCTACTCCGGAGCCTGAGGTGG |
| 6742 | GCTACTCCGGAGCCTGAGGTGGG |
| 6743 | CTACTCCGGAGCCTGAGGTGGGA |
| 6744 | TACTCCGGAGCCTGAGGTGGGAG |
| 6745 | ACTCCGGAGCCTGAGGTGGGAGG |
| 6746 | CTCCGGAGCCTGAGGTGGGAGGA |
| 6747 | TCCGGAGCCTGAGGTGGGAGGAT |
| 6748 | CCGGAGCCTGAGGTGGGAGGATC |
| 6749 | CGGAGCCTGAGGTGGGAGGATCG |
| 6750 | GGAGCCTGAGGTGGGAGGATCGC |
| 6751 | GAGCCTGAGGTGGGAGGATCGCT |
| 6752 | AGCCTGAGGTGGGAGGATCGCTT |
| 6753 | GCCTGAGGTGGGAGGATCGCTTG |
| 6754 | CCTGAGGTGGGAGGATCGCTTGA |
| 6755 | CTGAGGTGGGAGGATCGCTTGAG |
| 6756 | TGAGGTGGGAGGATCGCTTGAGT |
| 6757 | GAGGTGGGAGGATCGCTTGAGTC |
| 6758 | AGGTGGGAGGATCGCTTGAGTCT |
| 6759 | GGTGGGAGGATCGCTTGAGTCTG |
| 6760 | GTGGGAGGATCGCTTGAGTCTGG |
| 6761 | TGGGAGGATCGCTTGAGTCTGGG |
| 6762 | GGGAGGATCGCTTGAGTCTGGGA |
| 6763 | GGAGGATCGCTTGAGTCTGGGAG |
| 6764 | GAGGATCGCTTGAGTCTGGGAGG |
| 6765 | AGGATCGCTTGAGTCTGGGAGGC |
| 6766 | GGATCGCTTGAGTCTGGGAGGCA |
| 6767 | GATCGCTTGAGTCTGGGAGGCAG |
| 6768 | ATCGCTTGAGTCTGGGAGGCAGA |

| ID | SEQUENCE |
|---|---|
| 6769 | TCGCTTGAGTCTGGGAGGCAGAG |
| 6770 | CGCTTGAGTCTGGGAGGCAGAGG |
| 6771 | GCTTGAGTCTGGGAGGCAGAGGC |
| 6772 | CTTGAGTCTGGGAGGCAGAGGCT |
| 6773 | TTGAGTCTGGGAGGCAGAGGCTG |
| 6774 | TGAGTCTGGGAGGCAGAGGCTGC |
| 6775 | GAGTCTGGGAGGCAGAGGCTGCA |
| 6776 | AGTCTGGGAGGCAGAGGCTGCAT |
| 6777 | GTCTGGGAGGCAGAGGCTGCATT |
| 6778 | TCTGGGAGGCAGAGGCTGCATTG |
| 6779 | CTGGGAGGCAGAGGCTGCATTGA |
| 6780 | TGGGAGGCAGAGGCTGCATTGAG |
| 6781 | GGGAGGCAGAGGCTGCATTGAGC |
| 6782 | GGAGGCAGAGGCTGCATTGAGCT |
| 6783 | GAGGCAGAGGCTGCATTGAGCTA |
| 6784 | AGGCAGAGGCTGCATTGAGCTAT |
| 6785 | GGCAGAGGCTGCATTGAGCTATG |
| 6786 | GCAGAGGCTGCATTGAGCTATGA |
| 6787 | CAGAGGCTGCATTGAGCTATGAT |
| 6788 | AGAGGCTGCATTGAGCTATGATC |
| 6789 | GAGGCTGCATTGAGCTATGATCA |
| 6790 | AGGCTGCATTGAGCTATGATCAT |
| 6791 | GGCTGCATTGAGCTATGATCATG |
| 6792 | GCTGCATTGAGCTATGATCATGG |
| 6793 | CTGCATTGAGCTATGATCATGGC |
| 6794 | TGCATTGAGCTATGATCATGGCA |
| 6795 | GCATTGAGCTATGATCATGGCAC |
| 6796 | CATTGAGCTATGATCATGGCACT |
| 6797 | ATTGAGCTATGATCATGGCACTG |
| 6798 | TTGAGCTATGATCATGGCACTGC |
| 6799 | TGAGCTATGATCATGGCACTGCA |
| 6800 | GAGCTATGATCATGGCACTGCAT |
| 6801 | AGCTATGATCATGGCACTGCATT |
| 6802 | GCTATGATCATGGCACTGCATTC |
| 6803 | CTATGATCATGGCACTGCATTCC |
| 6804 | TATGATCATGGCACTGCATTCCA |
| 6805 | ATGATCATGGCACTGCATTCCAG |
| 6806 | TGATCATGGCACTGCATTCCAGC |
| 6807 | GATCATGGCACTGCATTCCAGCC |
| 6808 | ATCATGGCACTGCATTCCAGCCT |
| 6809 | TCATGGCACTGCATTCCAGCCTG |
| 6810 | CATGGCACTGCATTCCAGCCTGG |
| 6811 | ATGGCACTGCATTCCAGCCTGGG |
| 6812 | TGGCACTGCATTCCAGCCTGGGT |
| 6813 | GGCACTGCATTCCAGCCTGGGTG |
| 6814 | GCACTGCATTCCAGCCTGGGTGA |
| 6815 | CACTGCATTCCAGCCTGGGTGAC |
| 6816 | ACTGCATTCCAGCCTGGGTGACA |

| ID | SEQUENCE |
|---|---|
| 6817 | CTGCATTCCAGCCTGGGTGACAG |
| 6818 | TGCATTCCAGCCTGGGTGACAGT |
| 6819 | GCATTCCAGCCTGGGTGACAGTG |
| 6820 | CATTCCAGCCTGGGTGACAGTGC |
| 6821 | ATTCCAGCCTGGGTGACAGTGCA |
| 6822 | TTCCAGCCTGGGTGACAGTGCAA |
| 6823 | TCCAGCCTGGGTGACAGTGCAAG |
| 6824 | CCAGCCTGGGTGACAGTGCAAGA |
| 6825 | CAGCCTGGGTGACAGTGCAAGAC |
| 6826 | AGCCTGGGTGACAGTGCAAGACC |
| 6827 | GCCTGGGTGACAGTGCAAGACCT |
| 6828 | CCTGGGTGACAGTGCAAGACCTT |
| 6829 | CTGGGTGACAGTGCAAGACCTTG |
| 6830 | TGGGTGACAGTGCAAGACCTTGT |
| 6831 | GGGTGACAGTGCAAGACCTTGTC |
| 6832 | GGTGACAGTGCAAGACCTTGTCT |
| 6833 | GTGACAGTGCAAGACCTTGTCTC |
| 6834 | TGACAGTGCAAGACCTTGTCTCA |
| 6835 | GACAGTGCAAGACCTTGTCTCAG |
| 6836 | ACAGTGCAAGACCTTGTCTCAGA |
| 6837 | CAGTGCAAGACCTTGTCTCAGAA |
| 6838 | AGTGCAAGACCTTGTCTCAGAAT |
| 6839 | GTGCAAGACCTTGTCTCAGAATA |
| 6840 | TGCAAGACCTTGTCTCAGAATAA |
| 6841 | GCAAGACCTTGTCTCAGAATAAA |
| 6842 | CAAGACCTTGTCTCAGAATAAAT |
| 6843 | AAGACCTTGTCTCAGAATAAATA |
| 6844 | AGACCTTGTCTCAGAATAAATAA |
| 6845 | GACCTTGTCTCAGAATAAATAAA |
| 6846 | ACCTTGTCTCAGAATAAATAAAG |
| 6847 | CCTTGTCTCAGAATAAATAAAGT |
| 6848 | CTTGTCTCAGAATAAATAAAGTA |
| 6849 | TTGTCTCAGAATAAATAAAGTAT |
| 6850 | TGTCTCAGAATAAATAAAGTATG |
| 6851 | GTCTCAGAATAAATAAAGTATGT |
| 6852 | TCTCAGAATAAATAAAGTATGTG |
| 6853 | CTCAGAATAAATAAAGTATGTGA |
| 6854 | TCAGAATAAATAAAGTATGTGAT |
| 6855 | CAGAATAAATAAAGTATGTGATG |
| 6856 | AGAATAAATAAAGTATGTGATGA |
| 6857 | GAATAAATAAAGTATGTGATGAA |
| 6858 | AATAAATAAAGTATGTGATGAAG |
| 6859 | ATAAATAAAGTATGTGATGAAGA |
| 6860 | TAAATAAAGTATGTGATGAAGAT |
| 6861 | AAATAAAGTATGTGATGAAGATG |
| 6862 | AATAAAGTATGTGATGAAGATGT |
| 6863 | ATAAAGTATGTGATGAAGATGTG |
| 6864 | TAAAGTATGTGATGAAGATGTGC |

| ID | SEQUENCE |
|---|---|
| 6865 | AAAGTATGTGATGAAGATGTGCA |
| 6866 | AAGTATGTGATGAAGATGTGCAT |
| 6867 | AGTATGTGATGAAGATGTGCATA |
| 6868 | GTATGTGATGAAGATGTGCATAC |
| 6869 | TATGTGATGAAGATGTGCATACA |
| 6870 | ATGTGATGAAGATGTGCATACAT |
| 6871 | TGTGATGAAGATGTGCATACATT |
| 6872 | GTGATGAAGATGTGCATACATTA |
| 6873 | TGATGAAGATGTGCATACATTAT |
| 6874 | GATGAAGATGTGCATACATTATA |
| 6875 | ATGAAGATGTGCATACATTATAT |
| 6876 | TGAAGATGTGCATACATTATATG |
| 6877 | GAAGATGTGCATACATTATATGC |
| 6878 | AAGATGTGCATACATTATATGCA |
| 6879 | AGATGTGCATACATTATATGCAA |
| 6880 | GATGTGCATACATTATATGCAAA |
| 6881 | ATGTGCATACATTATATGCAAAT |
| 6882 | TGTGCATACATTATATGCAAATA |
| 6883 | GTGCATACATTATATGCAAATAC |
| 6884 | TGCATACATTATATGCAAATACT |
| 6885 | GCATACATTATATGCAAATACTG |
| 6886 | CATACATTATATGCAAATACTGT |
| 6887 | ATACATTATATGCAAATACTGTT |
| 6888 | TACATTATATGCAAATACTGTTT |
| 6889 | ACATTATATGCAAATACTGTTTT |
| 6890 | CATTATATGCAAATACTGTTTTT |
| 6891 | ATTATATGCAAATACTGTTTTTT |
| 6892 | TTATATGCAAATACTGTTTTTTT |
| 6893 | TATATGCAAATACTGTTTTTTTT |
| 6894 | TTTTTTTAATTTAAACAGTCTC |
| 6895 | TTTTTTTAATTTAAACAGTCTCA |
| 6896 | TTTTTTAATTTAAACAGTCTCAC |
| 6897 | TTTTTAATTTAAACAGTCTCACT |
| 6898 | TTTTAATTTAAACAGTCTCACTG |
| 6899 | TTTAATTTAAACAGTCTCACTGT |
| 6900 | TTAATTTAAACAGTCTCACTGTG |
| 6901 | TAATTTAAACAGTCTCACTGTGT |
| 6902 | AATTTAAACAGTCTCACTGTGTT |
| 6903 | ATTTAAACAGTCTCACTGTGTTG |
| 6904 | TTTAAACAGTCTCACTGTGTTGC |
| 6905 | TTAAACAGTCTCACTGTGTTGCC |
| 6906 | TAAACAGTCTCACTGTGTTGCCC |
| 6907 | AAACAGTCTCACTGTGTTGCCCA |
| 6908 | AACAGTCTCACTGTGTTGCCCAG |
| 6909 | ACAGTCTCACTGTGTTGCCCAGG |
| 6910 | CAGTCTCACTGTGTTGCCCAGGA |
| 6911 | AGTCTCACTGTGTTGCCCAGGAT |
| 6912 | GTCTCACTGTGTTGCCCAGGATG |

| ID | SEQUENCE |
|---|---|
| 6913 | TCTCACTGTGTTGCCCAGGATGG |
| 6914 | CTCACTGTGTTGCCCAGGATGGA |
| 6915 | TCACTGTGTTGCCCAGGATGGAG |
| 6916 | CACTGTGTTGCCCAGGATGGAGT |
| 6917 | ACTGTGTTGCCCAGGATGGAGTG |
| 6918 | CTGTGTTGCCCAGGATGGAGTGC |
| 6919 | TGTGTTGCCCAGGATGGAGTGCA |
| 6920 | GTGTTGCCCAGGATGGAGTGCAA |
| 6921 | TGTTGCCCAGGATGGAGTGCAAT |
| 6922 | GTTGCCCAGGATGGAGTGCAATG |
| 6923 | TTGCCCAGGATGGAGTGCAATGG |
| 6924 | TGCCCAGGATGGAGTGCAATGGC |
| 6925 | GCCCAGGATGGAGTGCAATGGCA |
| 6926 | CCCAGGATGGAGTGCAATGGCAC |
| 6927 | CCAGGATGGAGTGCAATGGCACA |
| 6928 | CAGGATGGAGTGCAATGGCACAA |
| 6929 | AGGATGGAGTGCAATGGCACAAT |
| 6930 | GGATGGAGTGCAATGGCACAATC |
| 6931 | GATGGAGTGCAATGGCACAATCT |
| 6932 | ATGGAGTGCAATGGCACAATCTT |
| 6933 | TGGAGTGCAATGGCACAATCTTG |
| 6934 | GGAGTGCAATGGCACAATCTTGG |
| 6935 | GAGTGCAATGGCACAATCTTGGC |
| 6936 | AGTGCAATGGCACAATCTTGGCT |
| 6937 | GTGCAATGGCACAATCTTGGCTC |
| 6938 | TGCAATGGCACAATCTTGGCTCA |
| 6939 | GCAATGGCACAATCTTGGCTCAT |
| 6940 | CAATGGCACAATCTTGGCTCATG |
| 6941 | AATGGCACAATCTTGGCTCATGG |
| 6942 | ATGGCACAATCTTGGCTCATGGC |
| 6943 | TGGCACAATCTTGGCTCATGGCA |
| 6944 | GGCACAATCTTGGCTCATGGCAA |
| 6945 | GCACAATCTTGGCTCATGGCAAA |
| 6946 | CACAATCTTGGCTCATGGCAAAC |
| 6947 | ACAATCTTGGCTCATGGCAAACT |
| 6948 | CAATCTTGGCTCATGGCAAACTC |
| 6949 | AATCTTGGCTCATGGCAAACTCT |
| 6950 | ATCTTGGCTCATGGCAAACTCTG |
| 6951 | TCTTGGCTCATGGCAAACTCTGC |
| 6952 | CTTGGCTCATGGCAAACTCTGCC |
| 6953 | TTGGCTCATGGCAAACTCTGCCT |
| 6954 | TGGCTCATGGCAAACTCTGCCTC |
| 6955 | GGCTCATGGCAAACTCTGCCTCG |
| 6956 | GCTCATGGCAAACTCTGCCTCGC |
| 6957 | CTCATGGCAAACTCTGCCTCGCA |
| 6958 | TCATGGCAAACTCTGCCTCGCAA |
| 6959 | CATGGCAAACTCTGCCTCGCAAG |
| 6960 | ATGGCAAACTCTGCCTCGCAAGC |

| ID | SEQUENCE |
|---|---|
| 6961 | TGGCAAACTCTGCCTCGCAAGCA |
| 6962 | GGCAAACTCTGCCTCGCAAGCAG |
| 6963 | GCAAACTCTGCCTCGCAAGCAGC |
| 6964 | CAAACTCTGCCTCGCAAGCAGCT |
| 6965 | AAACTCTGCCTCGCAAGCAGCTG |
| 6966 | AACTCTGCCTCGCAAGCAGCTGG |
| 6967 | ACTCTGCCTCGCAAGCAGCTGGG |
| 6968 | CTCTGCCTCGCAAGCAGCTGGGA |
| 6969 | TCTGCCTCGCAAGCAGCTGGGAC |
| 6970 | CTGCCTCGCAAGCAGCTGGGACT |
| 6971 | TGCCTCGCAAGCAGCTGGGACTA |
| 6972 | GCCTCGCAAGCAGCTGGGACTAC |
| 6973 | CCTCGCAAGCAGCTGGGACTACA |
| 6974 | CTCGCAAGCAGCTGGGACTACAG |
| 6975 | TCGCAAGCAGCTGGGACTACAGG |
| 6976 | CGCAAGCAGCTGGGACTACAGGC |
| 6977 | GCAAGCAGCTGGGACTACAGGCA |
| 6978 | CAAGCAGCTGGGACTACAGGCAT |
| 6979 | AAGCAGCTGGGACTACAGGCATG |
| 6980 | AGCAGCTGGGACTACAGGCATGC |
| 6981 | GCAGCTGGGACTACAGGCATGCT |
| 6982 | CAGCTGGGACTACAGGCATGCTC |
| 6983 | AGCTGGGACTACAGGCATGCTCC |
| 6984 | GCTGGGACTACAGGCATGCTCCA |
| 6985 | CTGGGACTACAGGCATGCTCCAC |
| 6986 | TGGGACTACAGGCATGCTCCACG |
| 6987 | GGGACTACAGGCATGCTCCACGG |
| 6988 | GGACTACAGGCATGCTCCACGGT |
| 6989 | GACTACAGGCATGCTCCACGGTG |
| 6990 | ACTACAGGCATGCTCCACGGTGC |
| 6991 | CTACAGGCATGCTCCACGGTGCC |
| 6992 | TACAGGCATGCTCCACGGTGCCC |
| 6993 | ACAGGCATGCTCCACGGTGCCCA |
| 6994 | CAGGCATGCTCCACGGTGCCCAG |
| 6995 | AGGCATGCTCCACGGTGCCCAGT |
| 6996 | GGCATGCTCCACGGTGCCCAGTT |
| 6997 | GCATGCTCCACGGTGCCCAGTTA |
| 6998 | CATGCTCCACGGTGCCCAGTTAA |
| 6999 | ATGCTCCACGGTGCCCAGTTAAT |
| 7000 | TGCTCCACGGTGCCCAGTTAATT |
| 7001 | GCTCCACGGTGCCCAGTTAATTT |
| 7002 | CTCCACGGTGCCCAGTTAATTTT |
| 7003 | TCCACGGTGCCCAGTTAATTTTT |
| 7004 | CCACGGTGCCCAGTTAATTTTTT |
| 7005 | CACGGTGCCCAGTTAATTTTTTT |
| 7006 | ACGGTGCCCAGTTAATTTTTTTT |
| 7007 | CGGTGCCCAGTTAATTTTTTTTG |
| 7008 | GGTGCCCAGTTAATTTTTTTGT |

| ID | SEQUENCE |
|---|---|
| 7009 | GTGCCCAGTTAATTTTTTTGTA |
| 7010 | TGCCCAGTTAATTTTTTTGTAT |
| 7011 | GCCCAGTTAATTTTTTTGTATT |
| 7012 | CCCAGTTAATTTTTTTGTATTC |
| 7013 | CCAGTTAATTTTTTTGTATTCT |
| 7014 | CAGTTAATTTTTTTGTATTCTT |
| 7015 | AGTTAATTTTTTTGTATTCTTA |
| 7016 | GTTAATTTTTTTGTATTCTTAG |
| 7017 | TTAATTTTTTTGTATTCTTAGT |
| 7018 | TAATTTTTTTGTATTCTTAGTA |
| 7019 | AATTTTTTTGTATTCTTAGTAG |
| 7020 | ATTTTTTTGTATTCTTAGTAGA |
| 7021 | TTTTTTTGTATTCTTAGTAGAG |
| 7022 | TTTTTTGTATTCTTAGTAGAGA |
| 7023 | TTTTTGTATTCTTAGTAGAGAC |
| 7024 | TTTTGTATTCTTAGTAGAGACA |
| 7025 | TTTGTATTCTTAGTAGAGACAG |
| 7026 | TTGTATTCTTAGTAGAGACAGG |
| 7027 | TGTATTCTTAGTAGAGACAGGG |
| 7028 | GTATTCTTAGTAGAGACAGGGT |
| 7029 | TATTCTTAGTAGAGACAGGGTT |
| 7030 | ATTCTTAGTAGAGACAGGGTTT |
| 7031 | TTCTTAGTAGAGACAGGGTTTC |
| 7032 | TCTTAGTAGAGACAGGGTTTCA |
| 7033 | CTTAGTAGAGACAGGGTTTCAC |
| 7034 | TTAGTAGAGACAGGGTTTCACC |
| 7035 | TAGTAGAGACAGGGTTTCACCA |
| 7036 | AGTAGAGACAGGGTTTCACCAT |
| 7037 | GTAGAGACAGGGTTTCACCATG |
| 7038 | TAGAGACAGGGTTTCACCATGT |
| 7039 | AGAGACAGGGTTTCACCATGTT |
| 7040 | GAGACAGGGTTTCACCATGTTG |
| 7041 | AGACAGGGTTTCACCATGTTGG |
| 7042 | GACAGGGTTTCACCATGTTGGC |
| 7043 | ACAGGGTTTCACCATGTTGGCC |
| 7044 | CAGGGTTTCACCATGTTGGCCA |
| 7045 | AGGGTTTCACCATGTTGGCCAG |
| 7046 | GGGTTTCACCATGTTGGCCAGG |
| 7047 | GGTTTCACCATGTTGGCCAGGC |
| 7048 | GTTTCACCATGTTGGCCAGGCT |
| 7049 | TTTCACCATGTTGGCCAGGCTA |
| 7050 | TTCACCATGTTGGCCAGGCTAG |
| 7051 | TCACCATGTTGGCCAGGCTAGT |
| 7052 | CACCATGTTGGCCAGGCTAGTC |
| 7053 | ACCATGTTGGCCAGGCTAGTCT |
| 7054 | CCATGTTGGCCAGGCTAGTCTT |
| 7055 | CATGTTGGCCAGGCTAGTCTTG |
| 7056 | ATGTTGGCCAGGCTAGTCTTGA |

| ID | SEQUENCE |
|---|---|
| 7057 | ATGTTGGCCAGGCTAGTCTTGAA |
| 7058 | TGTTGGCCAGGCTAGTCTTGAAT |
| 7059 | GTTGGCCAGGCTAGTCTTGAATT |
| 7060 | TTGGCCAGGCTAGTCTTGAATTT |
| 7061 | TGGCCAGGCTAGTCTTGAATTTC |
| 7062 | GGCCAGGCTAGTCTTGAATTTCT |
| 7063 | GCCAGGCTAGTCTTGAATTTCTG |
| 7064 | CCAGGCTAGTCTTGAATTTCTGA |
| 7065 | CAGGCTAGTCTTGAATTTCTGAC |
| 7066 | AGGCTAGTCTTGAATTTCTGACC |
| 7067 | GGCTAGTCTTGAATTTCTGACCT |
| 7068 | GCTAGTCTTGAATTTCTGACCTC |
| 7069 | CTAGTCTTGAATTTCTGACCTCA |
| 7070 | TAGTCTTGAATTTCTGACCTCAA |
| 7071 | AGTCTTGAATTTCTGACCTCAAG |
| 7072 | GTCTTGAATTTCTGACCTCAAGT |
| 7073 | TCTTGAATTTCTGACCTCAAGTG |
| 7074 | CTTGAATTTCTGACCTCAAGTGA |
| 7075 | TTGAATTTCTGACCTCAAGTGAT |
| 7076 | TGAATTTCTGACCTCAAGTGATT |
| 7077 | GAATTTCTGACCTCAAGTGATTC |
| 7078 | AATTTCTGACCTCAAGTGATTCA |
| 7079 | ATTTCTGACCTCAAGTGATTCAT |
| 7080 | TTTCTGACCTCAAGTGATTCATC |
| 7081 | TTCTGACCTCAAGTGATTCATCT |
| 7082 | TCTGACCTCAAGTGATTCATCTC |
| 7083 | CTGACCTCAAGTGATTCATCTCC |
| 7084 | TGACCTCAAGTGATTCATCTCCC |
| 7085 | GACCTCAAGTGATTCATCTCCCA |
| 7086 | ACCTCAAGTGATTCATCTCCCAA |
| 7087 | CCTCAAGTGATTCATCTCCCAAA |
| 7088 | CTCAAGTGATTCATCTCCCAAAG |
| 7089 | TCAAGTGATTCATCTCCCAAAGT |
| 7090 | CAAGTGATTCATCTCCCAAAGTG |
| 7091 | AAGTGATTCATCTCCCAAAGTGC |
| 7092 | AGTGATTCATCTCCCAAAGTGCT |
| 7093 | GTGATTCATCTCCCAAAGTGCTG |
| 7094 | TGATTCATCTCCCAAAGTGCTGG |
| 7095 | GATTCATCTCCCAAAGTGCTGGG |
| 7096 | ATTCATCTCCCAAAGTGCTGGGA |
| 7097 | TTCATCTCCCAAAGTGCTGGGAT |
| 7098 | TCATCTCCCAAAGTGCTGGGATT |
| 7099 | CATCTCCCAAAGTGCTGGGATTA |
| 7100 | ATCTCCCAAAGTGCTGGGATTAC |
| 7101 | TCTCCCAAAGTGCTGGGATTACA |
| 7102 | CTCCCAAAGTGCTGGGATTACAG |
| 7103 | TCCCAAAGTGCTGGGATTACAGG |
| 7104 | CCCAAAGTGCTGGGATTACAGGC |

| ID | SEQUENCE |
|---|---|
| 7105 | CCAAAGTGCTGGGATTACAGGCG |
| 7106 | CAAAGTGCTGGGATTACAGGCGT |
| 7107 | AAAGTGCTGGGATTACAGGCGTG |
| 7108 | AAGTGCTGGGATTACAGGCGTGA |
| 7109 | AGTGCTGGGATTACAGGCGTGAG |
| 7110 | GTGCTGGGATTACAGGCGTGAGC |
| 7111 | TGCTGGGATTACAGGCGTGAGCC |
| 7112 | GCTGGGATTACAGGCGTGAGCCA |
| 7113 | CTGGGATTACAGGCGTGAGCCAC |
| 7114 | TGGGATTACAGGCGTGAGCCACC |
| 7115 | GGGATTACAGGCGTGAGCCACCA |
| 7116 | GGATTACAGGCGTGAGCCACCAC |
| 7117 | GATTACAGGCGTGAGCCACCACG |
| 7118 | ATTACAGGCGTGAGCCACCACGG |
| 7119 | TTACAGGCGTGAGCCACCACGGC |
| 7120 | TACAGGCGTGAGCCACCACGGCC |
| 7121 | ACAGGCGTGAGCCACCACGGCCG |
| 7122 | CAGGCGTGAGCCACCACGGCCGG |
| 7123 | AGGCGTGAGCCACCACGGCCGGC |
| 7124 | GGCGTGAGCCACCACGGCCGGCT |
| 7125 | GCGTGAGCCACCACGGCCGGCTA |
| 7126 | CGTGAGCCACCACGGCCGGCTAA |
| 7127 | GTGAGCCACCACGGCCGGCTAAT |
| 7128 | TGAGCCACCACGGCCGGCTAATT |
| 7129 | GAGCCACCACGGCCGGCTAATTT |
| 7130 | AGCCACCACGGCCGGCTAATTTT |
| 7131 | GCCACCACGGCCGGCTAATTTTT |
| 7132 | CCACCACGGCCGGCTAATTTTTG |
| 7133 | CACCACGGCCGGCTAATTTTTGT |
| 7134 | ACCACGGCCGGCTAATTTTTGTA |
| 7135 | CCACGGCCGGCTAATTTTTGTAT |
| 7136 | CACGGCCGGCTAATTTTTGTATT |
| 7137 | ACGGCCGGCTAATTTTTGTATTT |
| 7138 | CGGCCGGCTAATTTTTGTATTTT |
| 7139 | GGCCGGCTAATTTTTGTATTTTT |
| 7140 | GCCGGCTAATTTTTGTATTTTTT |
| 7141 | CCGGCTAATTTTTGTATTTTTTA |
| 7142 | CGGCTAATTTTTGTATTTTTTAG |
| 7143 | GGCTAATTTTTGTATTTTTTAGT |
| 7144 | GCTAATTTTTGTATTTTTTAGTA |
| 7145 | CTAATTTTTGTATTTTTTAGTAG |
| 7146 | TAATTTTTGTATTTTTTAGTAGT |
| 7147 | AATTTTTGTATTTTTTAGTAGTG |
| 7148 | ATTTTTGTATTTTTTAGTAGTGA |
| 7149 | TTTTTGTATTTTTTAGTAGTGAC |
| 7150 | TTTTGTATTTTTTAGTAGTGACT |
| 7151 | TTTGTATTTTTTAGTAGTGACTG |
| 7152 | TTGTATTTTTTAGTAGTGACTGG |

| ID | SEQUENCE |
|---|---|
| 7153 | TGTATTTTTAGTAGTGACTGGT |
| 7154 | GTATTTTTAGTAGTGACTGGTT |
| 7155 | TATTTTTAGTAGTGACTGGTTT |
| 7156 | ATTTTTAGTAGTGACTGGTTTC |
| 7157 | TTTTTAGTAGTGACTGGTTTCG |
| 7158 | TTTTAGTAGTGACTGGTTTCGC |
| 7159 | TTTAGTAGTGACTGGTTTCGCG |
| 7160 | TTAGTAGTGACTGGTTTCGCGG |
| 7161 | TAGTAGTGACTGGTTTCGCGGT |
| 7162 | AGTAGTGACTGGTTTCGCGGTG |
| 7163 | GTAGTGACTGGTTTCGCGGTGT |
| 7164 | TAGTGACTGGTTTCGCGGTGTT |
| 7165 | AGTGACTGGTTTCGCGGTGTTG |
| 7166 | GTGACTGGTTTCGCGGTGTTGA |
| 7167 | TGACTGGTTTCGCGGTGTTGAC |
| 7168 | GACTGGTTTCGCGGTGTTGACC |
| 7169 | ACTGGTTTCGCGGTGTTGACCA |
| 7170 | CTGGTTTCGCGGTGTTGACCAG |
| 7171 | TGGTTTCGCGGTGTTGACCAGG |
| 7172 | GGTTTCGCGGTGTTGACCAGGC |
| 7173 | GTTTCGCGGTGTTGACCAGGCT |
| 7174 | TTTCGCGGTGTTGACCAGGCTG |
| 7175 | TTCGCGGTGTTGACCAGGCTGG |
| 7176 | TCGCGGTGTTGACCAGGCTGGT |
| 7177 | CGCGGTGTTGACCAGGCTGGTC |
| 7178 | GCGGTGTTGACCAGGCTGGTCT |
| 7179 | CGGTGTTGACCAGGCTGGTCTC |
| 7180 | GGTGTTGACCAGGCTGGTCTCG |
| 7181 | GTGTTGACCAGGCTGGTCTCGA |
| 7182 | TGTTGACCAGGCTGGTCTCGAA |
| 7183 | GTTGACCAGGCTGGTCTCGAAC |
| 7184 | TTGACCAGGCTGGTCTCGAACT |
| 7185 | TGACCAGGCTGGTCTCGAACTC |
| 7186 | GACCAGGCTGGTCTCGAACTCC |
| 7187 | ACCAGGCTGGTCTCGAACTCCT |
| 7188 | CCAGGCTGGTCTCGAACTCCTG |
| 7189 | CAGGCTGGTCTCGAACTCCTGA |
| 7190 | AGGCTGGTCTCGAACTCCTGAT |
| 7191 | GGCTGGTCTCGAACTCCTGATC |
| 7192 | GCTGGTCTCGAACTCCTGATCT |
| 7193 | CTGGTCTCGAACTCCTGATCTC |
| 7194 | TGGTCTCGAACTCCTGATCTCA |
| 7195 | GGTCTCGAACTCCTGATCTCAG |
| 7196 | GTCTCGAACTCCTGATCTCAGG |
| 7197 | TCTCGAACTCCTGATCTCAGGT |
| 7198 | CTCGAACTCCTGATCTCAGGTG |
| 7199 | TCGAACTCCTGATCTCAGGTGA |
| 7200 | CGAACTCCTGATCTCAGGTGAT |

| ID | SEQUENCE |
|---|---|
| 7201 | CGAACTCCTGATCTCAGGTGATC |
| 7202 | GAACTCCTGATCTCAGGTGATCT |
| 7203 | AACTCCTGATCTCAGGTGATCTG |
| 7204 | ACTCCTGATCTCAGGTGATCTGC |
| 7205 | CTCCTGATCTCAGGTGATCTGCC |
| 7206 | TCCTGATCTCAGGTGATCTGCCT |
| 7207 | CCTGATCTCAGGTGATCTGCCTG |
| 7208 | CTGATCTCAGGTGATCTGCCTGC |
| 7209 | TGATCTCAGGTGATCTGCCTGCC |
| 7210 | GATCTCAGGTGATCTGCCTGCCT |
| 7211 | ATCTCAGGTGATCTGCCTGCCTC |
| 7212 | TCTCAGGTGATCTGCCTGCCTCG |
| 7213 | CTCAGGTGATCTGCCTGCCTCGG |
| 7214 | TCAGGTGATCTGCCTGCCTCGGC |
| 7215 | CAGGTGATCTGCCTGCCTCGGCC |
| 7216 | AGGTGATCTGCCTGCCTCGGCCT |
| 7217 | GGTGATCTGCCTGCCTCGGCCTC |
| 7218 | GTGATCTGCCTGCCTCGGCCTCA |
| 7219 | TGATCTGCCTGCCTCGGCCTCAC |
| 7220 | GATCTGCCTGCCTCGGCCTCACA |
| 7221 | ATCTGCCTGCCTCGGCCTCACAA |
| 7222 | TCTGCCTGCCTCGGCCTCACAAA |
| 7223 | CTGCCTGCCTCGGCCTCACAAAG |
| 7224 | TGCCTGCCTCGGCCTCACAAAGT |
| 7225 | GCCTGCCTCGGCCTCACAAAGTG |
| 7226 | CCTGCCTCGGCCTCACAAAGTGC |
| 7227 | CTGCCTCGGCCTCACAAAGTGCT |
| 7228 | TGCCTCGGCCTCACAAAGTGCTG |
| 7229 | GCCTCGGCCTCACAAAGTGCTGG |
| 7230 | CCTCGGCCTCACAAAGTGCTGGG |
| 7231 | CTCGGCCTCACAAAGTGCTGGGA |
| 7232 | TCGGCCTCACAAAGTGCTGGGAT |
| 7233 | CGGCCTCACAAAGTGCTGGGATT |
| 7234 | GGCCTCACAAAGTGCTGGGATTA |
| 7235 | GCCTCACAAAGTGCTGGGATTAC |
| 7236 | CCTCACAAAGTGCTGGGATTACA |
| 7237 | CTCACAAAGTGCTGGGATTACAG |
| 7238 | TCACAAAGTGCTGGGATTACAGG |
| 7239 | CACAAAGTGCTGGGATTACAGGT |
| 7240 | ACAAAGTGCTGGGATTACAGGTG |
| 7241 | CAAAGTGCTGGGATTACAGGTGT |
| 7242 | AAAGTGCTGGGATTACAGGTGTG |
| 7243 | AAGTGCTGGGATTACAGGTGTGA |
| 7244 | AGTGCTGGGATTACAGGTGTGAA |
| 7245 | GTGCTGGGATTACAGGTGTGAAC |
| 7246 | TGCTGGGATTACAGGTGTGAACC |
| 7247 | GCTGGGATTACAGGTGTGAACCA |
| 7248 | CTGGGATTACAGGTGTGAACCAC |

| ID | SEQUENCE |
|---|---|
| 7249 | TGGGATTACAGGTGTGAACCACT |
| 7250 | GGGATTACAGGTGTGAACCACTG |
| 7251 | GGATTACAGGTGTGAACCACTGC |
| 7252 | GATTACAGGTGTGAACCACTGCT |
| 7253 | ATTACAGGTGTGAACCACTGCTC |
| 7254 | TTACAGGTGTGAACCACTGCTCC |
| 7255 | TACAGGTGTGAACCACTGCTCCC |
| 7256 | ACAGGTGTGAACCACTGCTCCCG |
| 7257 | CAGGTGTGAACCACTGCTCCCGG |
| 7258 | AGGTGTGAACCACTGCTCCCGGC |
| 7259 | GGTGTGAACCACTGCTCCCGGCC |
| 7260 | GTGTGAACCACTGCTCCCGGCCT |
| 7261 | TGTGAACCACTGCTCCCGGCCTT |
| 7262 | GTGAACCACTGCTCCCGGCCTTG |
| 7263 | TGAACCACTGCTCCCGGCCTTGT |
| 7264 | GAACCACTGCTCCCGGCCTTGTG |
| 7265 | AACCACTGCTCCCGGCCTTGTGT |
| 7266 | ACCACTGCTCCCGGCCTTGTGTG |
| 7267 | CCACTGCTCCCGGCCTTGTGTGA |
| 7268 | CACTGCTCCCGGCCTTGTGTGAT |
| 7269 | ACTGCTCCCGGCCTTGTGTGATT |
| 7270 | CTGCTCCCGGCCTTGTGTGATTT |
| 7271 | TGCTCCCGGCCTTGTGTGATTTT |
| 7272 | GCTCCCGGCCTTGTGTGATTTTA |
| 7273 | CTCCCGGCCTTGTGTGATTTTAT |
| 7274 | TCCCGGCCTTGTGTGATTTTATC |
| 7275 | CCCGGCCTTGTGTGATTTTATCT |
| 7276 | CCGGCCTTGTGTGATTTTATCTA |
| 7277 | CGGCCTTGTGTGATTTTATCTAA |
| 7278 | GGCCTTGTGTGATTTTATCTAAG |
| 7279 | GCCTTGTGTGATTTTATCTAAGG |
| 7280 | CCTTGTGTGATTTTATCTAAGGG |
| 7281 | CTTGTGTGATTTTATCTAAGGGA |
| 7282 | TTGTGTGATTTTATCTAAGGGAC |
| 7283 | TGTGTGATTTTATCTAAGGGACT |
| 7284 | GTGTGATTTTATCTAAGGGACTT |
| 7285 | TGTGATTTTATCTAAGGGACTTA |
| 7286 | GTGATTTTATCTAAGGGACTTAA |
| 7287 | TGATTTTATCTAAGGGACTTAAG |
| 7288 | GATTTTATCTAAGGGACTTAAGC |
| 7289 | ATTTTATCTAAGGGACTTAAGCG |
| 7290 | TTTTATCTAAGGGACTTAAGCGT |
| 7291 | TTTATCTAAGGGACTTAAGCGTC |
| 7292 | TTATCTAAGGGACTTAAGCGTCC |
| 7293 | TATCTAAGGGACTTAAGCGTCCT |
| 7294 | ATCTAAGGGACTTAAGCGTCCTC |
| 7295 | TCTAAGGGACTTAAGCGTCCTCA |
| 7296 | CTAAGGGACTTAAGCGTCCTCAG |

| ID | SEQUENCE |
|---|---|
| 7297 | TAAGGGACTTAAGCGTCCTCAGG |
| 7298 | AAGGGACTTAAGCGTCCTCAGGT |
| 7299 | AGGGACTTAAGCGTCCTCAGGTC |
| 7300 | GGGACTTAAGCGTCCTCAGGTCC |
| 7301 | GGACTTAAGCGTCCTCAGGTCCT |
| 7302 | GACTTAAGCGTCCTCAGGTCCTA |
| 7303 | ACTTAAGCGTCCTCAGGTCCTAG |
| 7304 | CTTAAGCGTCCTCAGGTCCTAGG |
| 7305 | TTAAGCGTCCTCAGGTCCTAGGG |
| 7306 | TAAGCGTCCTCAGGTCCTAGGGG |
| 7307 | AAGCGTCCTCAGGTCCTAGGGGG |
| 7308 | AGCGTCCTCAGGTCCTAGGGGGT |
| 7309 | GCGTCCTCAGGTCCTAGGGGGTC |
| 7310 | CGTCCTCAGGTCCTAGGGGGTCG |
| 7311 | GTCCTCAGGTCCTAGGGGGTCGT |
| 7312 | TCCTCAGGTCCTAGGGGGTCGTG |
| 7313 | CCTCAGGTCCTAGGGGGTCGTGA |
| 7314 | CTCAGGTCCTAGGGGGTCGTGAA |
| 7315 | TCAGGTCCTAGGGGGTCGTGAAA |
| 7316 | CAGGTCCTAGGGGGTCGTGAAAC |
| 7317 | AGGTCCTAGGGGGTCGTGAAACC |
| 7318 | GGTCCTAGGGGGTCGTGAAACCA |
| 7319 | GTCCTAGGGGGTCGTGAAACCAA |
| 7320 | TCCTAGGGGGTCGTGAAACCAAA |
| 7321 | CCTAGGGGGTCGTGAAACCAAAA |
| 7322 | CTAGGGGGTCGTGAAACCAAAAC |
| 7323 | TAGGGGGTCGTGAAACCAAAACC |
| 7324 | AGGGGGTCGTGAAACCAAAACCC |
| 7325 | GGGGGTCGTGAAACCAAAACCCC |
| 7326 | GGGGTCGTGAAACCAAAACCCCA |
| 7327 | GGGTCGTGAAACCAAAACCCCAG |
| 7328 | GGTCGTGAAACCAAAACCCCAGG |
| 7329 | GTCGTGAAACCAAAACCCCAGGG |
| 7330 | TCGTGAAACCAAAACCCCAGGGA |
| 7331 | CGTGAAACCAAAACCCCAGGGAT |
| 7332 | GTGAAACCAAAACCCCAGGGATA |
| 7333 | TGAAACCAAAACCCCAGGGATAG |
| 7334 | GAAACCAAAACCCCAGGGATAGC |
| 7335 | AAACCAAAACCCCAGGGATAGCA |
| 7336 | AACCAAAACCCCAGGGATAGCAA |
| 7337 | ACCAAAACCCCAGGGATAGCAAG |
| 7338 | CCAAAACCCCAGGGATAGCAAGG |
| 7339 | CAAAACCCCAGGGATAGCAAGGG |
| 7340 | AAAACCCCAGGGATAGCAAGGGA |
| 7341 | AAACCCCAGGGATAGCAAGGGAC |
| 7342 | AACCCCAGGGATAGCAAGGGACA |
| 7343 | ACCCCAGGGATAGCAAGGGACAA |
| 7344 | CCCCAGGGATAGCAAGGGACAAT |

| ID | SEQUENCE |
|---|---|
| 7345 | CCCAGGGATAGCAAGGGACAATT |
| 7346 | CCAGGGATAGCAAGGGACAATTG |
| 7347 | CAGGGATAGCAAGGGACAATTGT |
| 7348 | AGGGATAGCAAGGGACAATTGTA |
| 7349 | GGGATAGCAAGGGACAATTGTAT |
| 7350 | GGATAGCAAGGGACAATTGTATC |
| 7351 | GATAGCAAGGGACAATTGTATCT |
| 7352 | ATAGCAAGGGACAATTGTATCTT |
| 7353 | TAGCAAGGGACAATTGTATCTTC |
| 7354 | AGCAAGGGACAATTGTATCTTCA |
| 7355 | GCAAGGGACAATTGTATCTTCAA |
| 7356 | CAAGGGACAATTGTATCTTCAAA |
| 7357 | AAGGGACAATTGTATCTTCAAAG |
| 7358 | AGGGACAATTGTATCTTCAAAGT |
| 7359 | GGGACAATTGTATCTTCAAAGTA |
| 7360 | GGACAATTGTATCTTCAAAGTAG |
| 7361 | GACAATTGTATCTTCAAAGTAGA |
| 7362 | ACAATTGTATCTTCAAAGTAGAC |
| 7363 | CAATTGTATCTTCAAAGTAGACA |
| 7364 | AATTGTATCTTCAAAGTAGACAA |
| 7365 | ATTGTATCTTCAAAGTAGACAAA |
| 7366 | TTGTATCTTCAAAGTAGACAAAT |
| 7367 | TGTATCTTCAAAGTAGACAAATG |
| 7368 | GTATCTTCAAAGTAGACAAATGG |
| 7369 | TATCTTCAAAGTAGACAAATGGC |
| 7370 | ATCTTCAAAGTAGACAAATGGCG |
| 7371 | TCTTCAAAGTAGACAAATGGCGC |
| 7372 | CTTCAAAGTAGACAAATGGCGCC |
| 7373 | TTCAAAGTAGACAAATGGCGCCG |
| 7374 | TCAAAGTAGACAAATGGCGCCGG |
| 7375 | CGCCGGGCACGGTGGCTCACGCC |
| 7376 | GCCGGGCACGGTGGCTCACGCCT |
| 7377 | CCGGGCACGGTGGCTCACGCCTG |
| 7378 | CGGGCACGGTGGCTCACGCCTGT |
| 7379 | GGGCACGGTGGCTCACGCCTGTA |
| 7380 | GGCACGGTGGCTCACGCCTGTAA |
| 7381 | GCACGGTGGCTCACGCCTGTAAT |
| 7382 | CACGGTGGCTCACGCCTGTAATC |
| 7383 | ACGGTGGCTCACGCCTGTAATCC |
| 7384 | CGGTGGCTCACGCCTGTAATCCC |
| 7385 | GGTGGCTCACGCCTGTAATCCCA |
| 7386 | GTGGCTCACGCCTGTAATCCCAG |
| 7387 | TGGCTCACGCCTGTAATCCCAGC |
| 7388 | GGCTCACGCCTGTAATCCCAGCA |
| 7389 | GCTCACGCCTGTAATCCCAGCAG |
| 7390 | CTCACGCCTGTAATCCCAGCAGT |
| 7391 | TCACGCCTGTAATCCCAGCAGTT |
| 7392 | CACGCCTGTAATCCCAGCAGTTT |

| ID | SEQUENCE |
|---|---|
| 7393 | ACGCCTGTAATCCCAGCAGTTTC |
| 7394 | CGCCTGTAATCCCAGCAGTTTCC |
| 7395 | GCCTGTAATCCCAGCAGTTTCCG |
| 7396 | CCTGTAATCCCAGCAGTTTCCGA |
| 7397 | CTGTAATCCCAGCAGTTTCCGAG |
| 7398 | TGTAATCCCAGCAGTTTCCGAGG |
| 7399 | GTAATCCCAGCAGTTTCCGAGGC |
| 7400 | TAATCCCAGCAGTTTCCGAGGCT |
| 7401 | AATCCCAGCAGTTTCCGAGGCTG |
| 7402 | ATCCCAGCAGTTTCCGAGGCTGA |
| 7403 | TCCCAGCAGTTTCCGAGGCTGAG |
| 7404 | CCCAGCAGTTTCCGAGGCTGAGG |
| 7405 | CCAGCAGTTTCCGAGGCTGAGGC |
| 7406 | CAGCAGTTTCCGAGGCTGAGGCA |
| 7407 | AGCAGTTTCCGAGGCTGAGGCAG |
| 7408 | GCAGTTTCCGAGGCTGAGGCAGG |
| 7409 | CAGTTTCCGAGGCTGAGGCAGGC |
| 7410 | AGTTTCCGAGGCTGAGGCAGGCG |
| 7411 | GTTTCCGAGGCTGAGGCAGGCGG |
| 7412 | TTTCCGAGGCTGAGGCAGGCGGC |
| 7413 | TTCCGAGGCTGAGGCAGGCGGCT |
| 7414 | TCCGAGGCTGAGGCAGGCGGCTC |
| 7415 | CCGAGGCTGAGGCAGGCGGCTCA |
| 7416 | CGAGGCTGAGGCAGGCGGCTCAC |
| 7417 | GAGGCTGAGGCAGGCGGCTCACC |
| 7418 | AGGCTGAGGCAGGCGGCTCACCT |
| 7419 | GGCTGAGGCAGGCGGCTCACCTG |
| 7420 | GCTGAGGCAGGCGGCTCACCTGA |
| 7421 | CTGAGGCAGGCGGCTCACCTGAG |
| 7422 | TGAGGCAGGCGGCTCACCTGAGG |
| 7423 | GAGGCAGGCGGCTCACCTGAGGT |
| 7424 | AGGCAGGCGGCTCACCTGAGGTC |
| 7425 | GGCAGGCGGCTCACCTGAGGTCA |
| 7426 | GCAGGCGGCTCACCTGAGGTCAG |
| 7427 | CAGGCGGCTCACCTGAGGTCAGG |
| 7428 | AGGCGGCTCACCTGAGGTCAGGA |
| 7429 | GGCGGCTCACCTGAGGTCAGGAG |
| 7430 | GCGGCTCACCTGAGGTCAGGAGT |
| 7431 | CGGCTCACCTGAGGTCAGGAGTT |
| 7432 | GGCTCACCTGAGGTCAGGAGTTG |
| 7433 | GCTCACCTGAGGTCAGGAGTTGG |
| 7434 | CTCACCTGAGGTCAGGAGTTGGA |
| 7435 | TCACCTGAGGTCAGGAGTTGGAG |
| 7436 | CACCTGAGGTCAGGAGTTGGAGA |
| 7437 | ACCTGAGGTCAGGAGTTGGAGAC |
| 7438 | CCTGAGGTCAGGAGTTGGAGACC |
| 7439 | CTGAGGTCAGGAGTTGGAGACCA |
| 7440 | TGAGGTCAGGAGTTGGAGACCAG |

| ID | SEQUENCE |
|---|---|
| 7441 | GAGGTCAGGAGTTGGAGACCAGC |
| 7442 | AGGTCAGGAGTTGGAGACCAGCC |
| 7443 | GGTCAGGAGTTGGAGACCAGCCT |
| 7444 | GTCAGGAGTTGGAGACCAGCCTG |
| 7445 | TCAGGAGTTGGAGACCAGCCTGG |
| 7446 | CAGGAGTTGGAGACCAGCCTGGC |
| 7447 | AGGAGTTGGAGACCAGCCTGGCC |
| 7448 | GGAGTTGGAGACCAGCCTGGCCA |
| 7449 | GAGTTGGAGACCAGCCTGGCCAA |
| 7450 | AGTTGGAGACCAGCCTGGCCAAC |
| 7451 | GTTGGAGACCAGCCTGGCCAACA |
| 7452 | TTGGAGACCAGCCTGGCCAACAT |
| 7453 | TGGAGACCAGCCTGGCCAACATG |
| 7454 | GGAGACCAGCCTGGCCAACATGC |
| 7455 | GAGACCAGCCTGGCCAACATGCT |
| 7456 | AGACCAGCCTGGCCAACATGCTG |
| 7457 | GACCAGCCTGGCCAACATGCTGA |
| 7458 | ACCAGCCTGGCCAACATGCTGAA |
| 7459 | CCAGCCTGGCCAACATGCTGAAA |
| 7460 | CAGCCTGGCCAACATGCTGAAAC |
| 7461 | AGCCTGGCCAACATGCTGAAACC |
| 7462 | GCCTGGCCAACATGCTGAAACCC |
| 7463 | CCTGGCCAACATGCTGAAACCCT |
| 7464 | CTGGCCAACATGCTGAAACCCTG |
| 7465 | TGGCCAACATGCTGAAACCCTGT |
| 7466 | GGCCAACATGCTGAAACCCTGTC |
| 7467 | GCCAACATGCTGAAACCCTGTCT |
| 7468 | CCAACATGCTGAAACCCTGTCTG |
| 7469 | CAACATGCTGAAACCCTGTCTGT |
| 7470 | AACATGCTGAAACCCTGTCTGTA |
| 7471 | ACATGCTGAAACCCTGTCTGTAC |
| 7472 | CATGCTGAAACCCTGTCTGTACA |
| 7473 | ATGCTGAAACCCTGTCTGTACAA |
| 7474 | TGCTGAAACCCTGTCTGTACAAA |
| 7475 | GCTGAAACCCTGTCTGTACAAAA |
| 7476 | CTGAAACCCTGTCTGTACAAAAA |
| 7477 | TGAAACCCTGTCTGTACAAAAAT |
| 7478 | GAAACCCTGTCTGTACAAAAATA |
| 7479 | AAACCCTGTCTGTACAAAAATAC |
| 7480 | AACCCTGTCTGTACAAAAATACA |
| 7481 | ACCCTGTCTGTACAAAAATACAA |
| 7482 | CCCTGTCTGTACAAAAATACAAA |
| 7483 | CCTGTCTGTACAAAAATACAAAA |
| 7484 | CTGTCTGTACAAAAATACAAAAA |
| 7485 | TGTCTGTACAAAAATACAAAAAT |
| 7486 | GTCTGTACAAAAATACAAAAATA |
| 7487 | TCTGTACAAAAATACAAAAATAG |
| 7488 | CTGTACAAAAATACAAAAATAGC |

| ID | SEQUENCE |
|---|---|
| 7489 | TGTACAAAAATACAAAAATAGCT |
| 7490 | GTACAAAAATACAAAAATAGCTG |
| 7491 | TACAAAAATACAAAAATAGCTGG |
| 7492 | ACAAAAATACAAAAATAGCTGGG |
| 7493 | CAAAAATACAAAAATAGCTGGGC |
| 7494 | AAAAATACAAAAATAGCTGGGCA |
| 7495 | AAAATACAAAAATAGCTGGGCAT |
| 7496 | AAATACAAAAATAGCTGGGCATG |
| 7497 | AATACAAAAATAGCTGGGCATGG |
| 7498 | ATACAAAAATAGCTGGGCATGGT |
| 7499 | TACAAAAATAGCTGGGCATGGTG |
| 7500 | ACAAAAATAGCTGGGCATGGTGG |
| 7501 | CAAAAATAGCTGGGCATGGTGGC |
| 7502 | AAAAATAGCTGGGCATGGTGGCG |
| 7503 | AAAATAGCTGGGCATGGTGGCGC |
| 7504 | AAATAGCTGGGCATGGTGGCGCA |
| 7505 | AATAGCTGGGCATGGTGGCGCAT |
| 7506 | ATAGCTGGGCATGGTGGCGCATG |
| 7507 | TAGCTGGGCATGGTGGCGCATGC |
| 7508 | AGCTGGGCATGGTGGCGCATGCC |
| 7509 | GCTGGGCATGGTGGCGCATGCCT |
| 7510 | CTGGGCATGGTGGCGCATGCCTG |
| 7511 | TGGGCATGGTGGCGCATGCCTGT |
| 7512 | GGGCATGGTGGCGCATGCCTGTA |
| 7513 | GGCATGGTGGCGCATGCCTGTAG |
| 7514 | GCATGGTGGCGCATGCCTGTAGT |
| 7515 | CATGGTGGCGCATGCCTGTAGTC |
| 7516 | ATGGTGGCGCATGCCTGTAGTCC |
| 7517 | TGGTGGCGCATGCCTGTAGTCCC |
| 7518 | GGTGGCGCATGCCTGTAGTCCCA |
| 7519 | GTGGCGCATGCCTGTAGTCCCAG |
| 7520 | TGGCGCATGCCTGTAGTCCCAGC |
| 7521 | GGCGCATGCCTGTAGTCCCAGCT |
| 7522 | GCGCATGCCTGTAGTCCCAGCTA |
| 7523 | CGCATGCCTGTAGTCCCAGCTAC |
| 7524 | GCATGCCTGTAGTCCCAGCTACT |
| 7525 | CATGCCTGTAGTCCCAGCTACTA |
| 7526 | ATGCCTGTAGTCCCAGCTACTAG |
| 7527 | TGCCTGTAGTCCCAGCTACTAGA |
| 7528 | GCCTGTAGTCCCAGCTACTAGAG |
| 7529 | CCTGTAGTCCCAGCTACTAGAGC |
| 7530 | CTGTAGTCCCAGCTACTAGAGCG |
| 7531 | TGTAGTCCCAGCTACTAGAGCGA |
| 7532 | GTAGTCCCAGCTACTAGAGCGAC |
| 7533 | TAGTCCCAGCTACTAGAGCGACT |
| 7534 | AGTCCCAGCTACTAGAGCGACTG |
| 7535 | GTCCCAGCTACTAGAGCGACTGA |
| 7536 | TCCCAGCTACTAGAGCGACTGAG |

| ID | SEQUENCE |
|---|---|
| 7537 | CCCAGCTACTAGAGCGACTGAGG |
| 7538 | CCAGCTACTAGAGCGACTGAGGC |
| 7539 | CAGCTACTAGAGCGACTGAGGCA |
| 7540 | AGCTACTAGAGCGACTGAGGCAG |
| 7541 | GCTACTAGAGCGACTGAGGCAGG |
| 7542 | CTACTAGAGCGACTGAGGCAGGA |
| 7543 | TACTAGAGCGACTGAGGCAGGAG |
| 7544 | ACTAGAGCGACTGAGGCAGGAGA |
| 7545 | CTAGAGCGACTGAGGCAGGAGAA |
| 7546 | TAGAGCGACTGAGGCAGGAGAAT |
| 7547 | AGAGCGACTGAGGCAGGAGAATT |
| 7548 | GAGCGACTGAGGCAGGAGAATTG |
| 7549 | AGCGACTGAGGCAGGAGAATTGC |
| 7550 | GCGACTGAGGCAGGAGAATTGCT |
| 7551 | CGACTGAGGCAGGAGAATTGCTT |
| 7552 | GACTGAGGCAGGAGAATTGCTTG |
| 7553 | ACTGAGGCAGGAGAATTGCTTGA |
| 7554 | CTGAGGCAGGAGAATTGCTTGAA |
| 7555 | TGAGGCAGGAGAATTGCTTGAAC |
| 7556 | GAGGCAGGAGAATTGCTTGAACC |
| 7557 | AGGCAGGAGAATTGCTTGAACCT |
| 7558 | GGCAGGAGAATTGCTTGAACCTG |
| 7559 | GCAGGAGAATTGCTTGAACCTGG |
| 7560 | CAGGAGAATTGCTTGAACCTGGG |
| 7561 | AGGAGAATTGCTTGAACCTGGGA |
| 7562 | GGAGAATTGCTTGAACCTGGGAG |
| 7563 | GAGAATTGCTTGAACCTGGGAGG |
| 7564 | AGAATTGCTTGAACCTGGGAGGC |
| 7565 | GAATTGCTTGAACCTGGGAGGCG |
| 7566 | AATTGCTTGAACCTGGGAGGCGG |
| 7567 | ATTGCTTGAACCTGGGAGGCGGA |
| 7568 | TTGCTTGAACCTGGGAGGCGGAG |
| 7569 | TGCTTGAACCTGGGAGGCGGAGG |
| 7570 | GCTTGAACCTGGGAGGCGGAGGT |
| 7571 | CTTGAACCTGGGAGGCGGAGGTT |
| 7572 | TTGAACCTGGGAGGCGGAGGTTG |
| 7573 | TGAACCTGGGAGGCGGAGGTTGC |
| 7574 | GAACCTGGGAGGCGGAGGTTGCA |
| 7575 | AACCTGGGAGGCGGAGGTTGCAG |
| 7576 | ACCTGGGAGGCGGAGGTTGCAGG |
| 7577 | CCTGGGAGGCGGAGGTTGCAGGG |
| 7578 | CTGGGAGGCGGAGGTTGCAGGGA |
| 7579 | TGGGAGGCGGAGGTTGCAGGGAG |
| 7580 | GGGAGGCGGAGGTTGCAGGGAGC |
| 7581 | GGAGGCGGAGGTTGCAGGGAGCC |
| 7582 | GAGGCGGAGGTTGCAGGGAGCCA |
| 7583 | AGGCGGAGGTTGCAGGGAGCCAA |
| 7584 | GGCGGAGGTTGCAGGGAGCCAAG |

| ID | SEQUENCE |
|---|---|
| 7585 | GCGGAGGTTGCAGGGAGCCAAGA |
| 7586 | CGGAGGTTGCAGGGAGCCAAGAT |
| 7587 | GGAGGTTGCAGGGAGCCAAGATG |
| 7588 | GAGGTTGCAGGGAGCCAAGATGG |
| 7589 | AGGTTGCAGGGAGCCAAGATGGC |
| 7590 | GGTTGCAGGGAGCCAAGATGGCG |
| 7591 | GTTGCAGGGAGCCAAGATGGCGC |
| 7592 | TTGCAGGGAGCCAAGATGGCGCC |
| 7593 | TGCAGGGAGCCAAGATGGCGCCA |
| 7594 | GCAGGGAGCCAAGATGGCGCCAC |
| 7595 | CAGGGAGCCAAGATGGCGCCACC |
| 7596 | AGGGAGCCAAGATGGCGCCACCG |
| 7597 | GGGAGCCAAGATGGCGCCACCGC |
| 7598 | GGAGCCAAGATGGCGCCACCGCA |
| 7599 | GAGCCAAGATGGCGCCACCGCAC |
| 7600 | AGCCAAGATGGCGCCACCGCACT |
| 7601 | GCCAAGATGGCGCCACCGCACTC |
| 7602 | CCAAGATGGCGCCACCGCACTCC |
| 7603 | CAAGATGGCGCCACCGCACTCCA |
| 7604 | AAGATGGCGCCACCGCACTCCAG |
| 7605 | AGATGGCGCCACCGCACTCCAGC |
| 7606 | GATGGCGCCACCGCACTCCAGCC |
| 7607 | ATGGCGCCACCGCACTCCAGCCT |
| 7608 | TGGCGCCACCGCACTCCAGCCTA |
| 7609 | GGCGCCACCGCACTCCAGCCTAG |
| 7610 | GCGCCACCGCACTCCAGCCTAGG |
| 7611 | CGCCACCGCACTCCAGCCTAGGT |
| 7612 | GCCACCGCACTCCAGCCTAGGTG |
| 7613 | CCACCGCACTCCAGCCTAGGTGA |
| 7614 | CACCGCACTCCAGCCTAGGTGAT |
| 7615 | ACCGCACTCCAGCCTAGGTGATA |
| 7616 | CCGCACTCCAGCCTAGGTGATAG |
| 7617 | CGCACTCCAGCCTAGGTGATAGA |
| 7618 | GCACTCCAGCCTAGGTGATAGAG |
| 7619 | CACTCCAGCCTAGGTGATAGAGT |
| 7620 | ACTCCAGCCTAGGTGATAGAGTG |
| 7621 | CTCCAGCCTAGGTGATAGAGTGA |
| 7622 | TCCAGCCTAGGTGATAGAGTGAG |
| 7623 | CCAGCCTAGGTGATAGAGTGAGA |
| 7624 | CAGCCTAGGTGATAGAGTGAGAC |
| 7625 | AGCCTAGGTGATAGAGTGAGACT |
| 7626 | GCCTAGGTGATAGAGTGAGACTC |
| 7627 | CCTAGGTGATAGAGTGAGACTCC |
| 7628 | CTAGGTGATAGAGTGAGACTCCC |
| 7629 | TAGGTGATAGAGTGAGACTCCCT |
| 7630 | AGGTGATAGAGTGAGACTCCCTC |
| 7631 | GGTGATAGAGTGAGACTCCCTCT |
| 7632 | GTGATAGAGTGAGACTCCCTCTC |

| ID | SEQUENCE |
|---|---|
| 7633 | TGATAGAGTGAGACTCCCTCTCA |
| 7634 | GATAGAGTGAGACTCCCTCTCAA |
| 7635 | ATAGAGTGAGACTCCCTCTCAAA |
| 7636 | TAGAGTGAGACTCCCTCTCAAAA |
| 7637 | AGAGTGAGACTCCCTCTCAAAAA |
| 7638 | GAGTGAGACTCCCTCTCAAAAAC |
| 7639 | AGTGAGACTCCCTCTCAAAAACA |
| 7640 | GTGAGACTCCCTCTCAAAAACAA |
| 7641 | TGAGACTCCCTCTCAAAAACAAA |
| 7642 | GAGACTCCCTCTCAAAAACAAAA |
| 7643 | AGACTCCCTCTCAAAAACAAAAC |
| 7644 | GACTCCCTCTCAAAAACAAAACA |
| 7645 | ACTCCCTCTCAAAAACAAAACAA |
| 7646 | CTCCCTCTCAAAAACAAAACAAA |
| 7647 | TCCCTCTCAAAAACAAAACAAAA |
| 7648 | CCCTCTCAAAAACAAAACAAAAC |
| 7649 | CCTCTCAAAAACAAAACAAAACA |
| 7650 | CTCTCAAAAACAAAACAAAACAA |
| 7651 | TCTCAAAAACAAAACAAAACAAA |
| 7652 | CTCAAAAACAAAACAAAACAAAA |
| 7653 | TCAAAAACAAAACAAAACAAAAA |
| 7654 | CAAAAACAAAACAAAACAAAAAA |
| 7655 | AAAAACAAAACAAAACAAAAAAA |
| 7656 | AAAACAAAACAAAACAAAAAAAT |
| 7657 | AAACAAAACAAAACAAAAAAATT |
| 7658 | AACAAAACAAAACAAAAAAATTA |
| 7659 | ACAAAACAAAACAAAAAAATTAG |
| 7660 | CAAAACAAAACAAAAAAATTAGA |
| 7661 | AAAACAAAACAAAAAAATTAGAC |
| 7662 | AAACAAAACAAAAAAATTAGACA |
| 7663 | AACAAAACAAAAAAATTAGACAA |
| 7664 | ACAAAACAAAAAAATTAGACAAA |
| 7665 | CAAAACAAAAAAATTAGACAAAT |
| 7666 | AAAACAAAAAAATTAGACAAATG |
| 7667 | AAACAAAAAAATTAGACAAATGC |
| 7668 | AACAAAAAAATTAGACAAATGCT |
| 7669 | ACAAAAAAATTAGACAAATGCTA |
| 7670 | CAAAAAAATTAGACAAATGCTAC |
| 7671 | AAAAAAATTAGACAAATGCTACA |
| 7672 | AAAAAATTAGACAAATGCTACAT |
| 7673 | AAAAATTAGACAAATGCTACATT |
| 7674 | AAAATTAGACAAATGCTACATTA |
| 7675 | AAATTAGACAAATGCTACATTAA |
| 7676 | AATTAGACAAATGCTACATTAAT |
| 7677 | ATTAGACAAATGCTACATTAATG |
| 7678 | TTAGACAAATGCTACATTAATGT |
| 7679 | TAGACAAATGCTACATTAATGTT |
| 7680 | AGACAAATGCTACATTAATGTTT |

| ID | SEQUENCE |
|---|---|
| 7681 | GACAAATGCTACATTAATGTTTG |
| 7682 | ACAAATGCTACATTAATGTTTGG |
| 7683 | CAAATGCTACATTAATGTTTGGG |
| 7684 | AAATGCTACATTAATGTTTGGGT |
| 7685 | AATGCTACATTAATGTTTGGGTG |
| 7686 | ATGCTACATTAATGTTTGGGTGG |
| 7687 | TGCTACATTAATGTTTGGGTGGT |
| 7688 | GCTACATTAATGTTTGGGTGGTC |
| 7689 | CTACATTAATGTTTGGGTGGTCA |
| 7690 | TACATTAATGTTTGGGTGGTCAG |
| 7691 | ACATTAATGTTTGGGTGGTCAGA |
| 7692 | CATTAATGTTTGGGTGGTCAGAT |
| 7693 | ATTAATGTTTGGGTGGTCAGATT |
| 7694 | TTAATGTTTGGGTGGTCAGATTC |
| 7695 | TAATGTTTGGGTGGTCAGATTCT |
| 7696 | AATGTTTGGGTGGTCAGATTCTA |
| 7697 | ATGTTTGGGTGGTCAGATTCTAC |
| 7698 | TGTTTGGGTGGTCAGATTCTACT |
| 7699 | GTTTGGGTGGTCAGATTCTACTT |
| 7700 | TTTGGGTGGTCAGATTCTACTTT |
| 7701 | TTGGGTGGTCAGATTCTACTTTG |
| 7702 | TGGGTGGTCAGATTCTACTTTGA |
| 7703 | GGGTGGTCAGATTCTACTTTGAA |
| 7704 | GGTGGTCAGATTCTACTTTGAAT |
| 7705 | GTGGTCAGATTCTACTTTGAATC |
| 7706 | TGGTCAGATTCTACTTTGAATCT |
| 7707 | GGTCAGATTCTACTTTGAATCTG |
| 7708 | GTCAGATTCTACTTTGAATCTGA |
| 7709 | TCAGATTCTACTTTGAATCTGAA |
| 7710 | CAGATTCTACTTTGAATCTGAAG |
| 7711 | AGATTCTACTTTGAATCTGAAGT |
| 7712 | GATTCTACTTTGAATCTGAAGTT |
| 7713 | ATTCTACTTTGAATCTGAAGTTT |
| 7714 | TTCTACTTTGAATCTGAAGTTTG |
| 7715 | TCTACTTTGAATCTGAAGTTTGC |
| 7716 | CTACTTTGAATCTGAAGTTTGCA |
| 7717 | TACTTTGAATCTGAAGTTTGCAG |
| 7718 | ACTTTGAATCTGAAGTTTGCAGA |
| 7719 | CTTTGAATCTGAAGTTTGCAGAT |
| 7720 | TTTGAATCTGAAGTTTGCAGATA |
| 7721 | TTGAATCTGAAGTTTGCAGATAT |
| 7722 | TGAATCTGAAGTTTGCAGATATG |
| 7723 | GAATCTGAAGTTTGCAGATATGC |
| 7724 | AATCTGAAGTTTGCAGATATGCC |
| 7725 | ATCTGAAGTTTGCAGATATGCCT |
| 7726 | TCTGAAGTTTGCAGATATGCCTA |
| 7727 | CTGAAGTTTGCAGATATGCCTAT |
| 7728 | TGAAGTTTGCAGATATGCCTATA |

| ID | SEQUENCE |
|---|---|
| 7729 | GAAGTTTGCAGATATGCCTATAG |
| 7730 | AAGTTTGCAGATATGCCTATAGA |
| 7731 | AGTTTGCAGATATGCCTATAGAT |
| 7732 | GTTTGCAGATATGCCTATAGATT |
| 7733 | TTTGCAGATATGCCTATAGATTT |
| 7734 | TTGCAGATATGCCTATAGATTTT |
| 7735 | TGCAGATATGCCTATAGATTTTT |
| 7736 | GCAGATATGCCTATAGATTTTTG |
| 7737 | CAGATATGCCTATAGATTTTTGG |
| 7738 | AGATATGCCTATAGATTTTTGGA |
| 7739 | GATATGCCTATAGATTTTTGGAG |
| 7740 | ATATGCCTATAGATTTTTGGAGT |
| 7741 | TATGCCTATAGATTTTTGGAGTT |
| 7742 | ATGCCTATAGATTTTTGGAGTTT |
| 7743 | TGCCTATAGATTTTTGGAGTTTA |
| 7744 | GCCTATAGATTTTTGGAGTTTAC |
| 7745 | CCTATAGATTTTTGGAGTTTACC |
| 7746 | CTATAGATTTTTGGAGTTTACCA |
| 7747 | TATAGATTTTTGGAGTTTACCAC |
| 7748 | ATAGATTTTTGGAGTTTACCACT |
| 7749 | TAGATTTTTGGAGTTTACCACTT |
| 7750 | AGATTTTTGGAGTTTACCACTTT |
| 7751 | GATTTTTGGAGTTTACCACTTTC |
| 7752 | ATTTTTGGAGTTTACCACTTTCT |
| 7753 | TTTTTGGAGTTTACCACTTTCTT |
| 7754 | TTTTGGAGTTTACCACTTTCTTA |
| 7755 | TTTGGAGTTTACCACTTTCTTAT |
| 7756 | TTGGAGTTTACCACTTTCTTATT |
| 7757 | TGGAGTTTACCACTTTCTTATTC |
| 7758 | GGAGTTTACCACTTTCTTATTCT |
| 7759 | GAGTTTACCACTTTCTTATTCTG |
| 7760 | AGTTTACCACTTTCTTATTCTGT |
| 7761 | GTTTACCACTTTCTTATTCTGTA |
| 7762 | TTTACCACTTTCTTATTCTGTAT |
| 7763 | TTACCACTTTCTTATTCTGTATC |
| 7764 | TACCACTTTCTTATTCTGTATCA |
| 7765 | ACCACTTTCTTATTCTGTATCAT |
| 7766 | CCACTTTCTTATTCTGTATCATT |
| 7767 | CACTTTCTTATTCTGTATCATTA |
| 7768 | ACTTTCTTATTCTGTATCATTAA |
| 7769 | CTTTCTTATTCTGTATCATTAAT |
| 7770 | TTTCTTATTCTGTATCATTAATG |
| 7771 | TTCTTATTCTGTATCATTAATGT |
| 7772 | TCTTATTCTGTATCATTAATGTA |
| 7773 | CTTATTCTGTATCATTAATGTAA |
| 7774 | TTATTCTGTATCATTAATGTAAT |
| 7775 | TATTCTGTATCATTAATGTAATA |
| 7776 | ATTCTGTATCATTAATGTAATAT |

| ID | SEQUENCE |
|---|---|
| 7777 | TTCTGTATCATTAATGTAATATT |
| 7778 | TCTGTATCATTAATGTAATATTT |
| 7779 | CTGTATCATTAATGTAATATTTT |
| 7780 | TGTATCATTAATGTAATATTTTA |
| 7781 | GTATCATTAATGTAATATTTTAA |
| 7782 | TATCATTAATGTAATATTTTAAA |
| 7783 | ATCATTAATGTAATATTTTAAAT |
| 7784 | TCATTAATGTAATATTTTAAATT |
| 7785 | CATTAATGTAATATTTTAAATTA |
| 7786 | ATTAATGTAATATTTTAAATTAC |
| 7787 | TTAATGTAATATTTTAAATTACT |
| 7788 | TAATGTAATATTTTAAATTACTA |
| 7789 | AATGTAATATTTTAAATTACTAT |
| 7790 | ATGTAATATTTTAAATTACTATA |
| 7791 | TGTAATATTTTAAATTACTATAT |
| 7792 | GTAATATTTTAAATTACTATATA |
| 7793 | TAATATTTTAAATTACTATATAT |
| 7794 | AATATTTTAAATTACTATATATG |
| 7795 | ATATTTTAAATTACTATATATGT |
| 7796 | TATTTTAAATTACTATATATGTT |
| 7797 | ATTTTAAATTACTATATATGTTA |
| 7798 | TTTTAAATTACTATATATGTTAC |
| 7799 | TTTAAATTACTATATATGTTACC |
| 7800 | TTAAATTACTATATATGTTACCA |
| 7801 | TAAATTACTATATATGTTACCAT |
| 7802 | AAATTACTATATATGTTACCATT |
| 7803 | AATTACTATATATGTTACCATTT |
| 7804 | ATTACTATATATGTTACCATTTT |
| 7805 | TTACTATATATGTTACCATTTTT |
| 7806 | TACTATATATGTTACCATTTTTC |
| 7807 | ACTATATATGTTACCATTTTTCT |
| 7808 | CTATATATGTTACCATTTTTCTG |
| 7809 | TATATATGTTACCATTTTTCTGG |
| 7810 | ATATATGTTACCATTTTTCTGGA |
| 7811 | TATATGTTACCATTTTTCTGGAT |
| 7812 | ATATGTTACCATTTTTCTGGATT |
| 7813 | TATGTTACCATTTTTCTGGATTT |
| 7814 | ATGTTACCATTTTTCTGGATTTA |
| 7815 | TGTTACCATTTTTCTGGATTTAG |
| 7816 | GTTACCATTTTTCTGGATTTAGT |
| 7817 | TTACCATTTTTCTGGATTTAGTA |
| 7818 | TACCATTTTTCTGGATTTAGTAA |
| 7819 | ACCATTTTTCTGGATTTAGTAAG |
| 7820 | CCATTTTTCTGGATTTAGTAAGA |
| 7821 | CATTTTTCTGGATTTAGTAAGAA |
| 7822 | ATTTTTCTGGATTTAGTAAGAAA |
| 7823 | TTTTTCTGGATTTAGTAAGAAAT |
| 7824 | TTTTCTGGATTTAGTAAGAAATT |

| ID | SEQUENCE |
|---|---|
| 7825 | TTTCTGGATTTAGTAAGAAATTT |
| 7826 | TTCTGGATTTAGTAAGAAATTTG |
| 7827 | TCTGGATTTAGTAAGAAATTTGC |
| 7828 | CTGGATTTAGTAAGAAATTTGCA |
| 7829 | TGGATTTAGTAAGAAATTTGCAG |
| 7830 | GGATTTAGTAAGAAATTTGCAGT |
| 7831 | GATTTAGTAAGAAATTTGCAGTT |
| 7832 | ATTTAGTAAGAAATTTGCAGTTT |
| 7833 | TTTAGTAAGAAATTTGCAGTTTT |
| 7834 | TTAGTAAGAAATTTGCAGTTTTG |
| 7835 | TAGTAAGAAATTTGCAGTTTTGG |
| 7836 | AGTAAGAAATTTGCAGTTTTGGT |
| 7837 | GTAAGAAATTTGCAGTTTTGGTT |
| 7838 | TAAGAAATTTGCAGTTTTGGTTT |
| 7839 | AAGAAATTTGCAGTTTTGGTTTG |
| 7840 | AGAAATTTGCAGTTTTGGTTTGA |
| 7841 | GAAATTTGCAGTTTTGGTTTGAT |
| 7842 | AAATTTGCAGTTTTGGTTTGATG |
| 7843 | AATTTGCAGTTTTGGTTTGATGT |
| 7844 | ATTTGCAGTTTTGGTTTGATGTA |
| 7845 | TTTGCAGTTTTGGTTTGATGTAA |
| 7846 | TTGCAGTTTTGGTTTGATGTAAC |
| 7847 | TGCAGTTTTGGTTTGATGTAACA |
| 7848 | GCAGTTTTGGTTTGATGTAACAA |
| 7849 | CAGTTTTGGTTTGATGTAACAAG |
| 7850 | AGTTTTGGTTTGATGTAACAAGG |
| 7851 | GTTTTGGTTTGATGTAACAAGGG |
| 7852 | TTTTGGTTTGATGTAACAAGGGT |
| 7853 | TTTGGTTTGATGTAACAAGGGTT |
| 7854 | TTGGTTTGATGTAACAAGGGTTT |
| 7855 | TGGTTTGATGTAACAAGGGTTTT |
| 7856 | GGTTTGATGTAACAAGGGTTTTA |
| 7857 | GTTTGATGTAACAAGGGTTTTAA |
| 7858 | TTTGATGTAACAAGGGTTTTAAT |
| 7859 | TTGATGTAACAAGGGTTTTAATG |
| 7860 | TGATGTAACAAGGGTTTTAATGT |
| 7861 | GATGTAACAAGGGTTTTAATGTA |
| 7862 | ATGTAACAAGGGTTTTAATGTAA |
| 7863 | TGTAACAAGGGTTTTAATGTAAT |
| 7864 | GTAACAAGGGTTTTAATGTAATT |
| 7865 | TAACAAGGGTTTTAATGTAATTT |
| 7866 | AACAAGGGTTTTAATGTAATTTA |
| 7867 | ACAAGGGTTTTAATGTAATTTAT |
| 7868 | CAAGGGTTTTAATGTAATTTATG |
| 7869 | AAGGGTTTTAATGTAATTTATGT |
| 7870 | AGGGTTTTAATGTAATTTATGTT |
| 7871 | GGGTTTTAATGTAATTTATGTTA |
| 7872 | GGTTTTAATGTAATTTATGTTAG |

| ID | SEQUENCE |
|---|---|
| 7873 | GTTTTAATGTAATTTATGTTAGA |
| 7874 | TTTTAATGTAATTTATGTTAGAT |
| 7875 | TTTAATGTAATTTATGTTAGATT |
| 7876 | TTAATGTAATTTATGTTAGATTT |
| 7877 | TAATGTAATTTATGTTAGATTTT |
| 7878 | AATGTAATTTATGTTAGATTTTG |
| 7879 | ATGTAATTTATGTTAGATTTTGC |
| 7880 | TGTAATTTATGTTAGATTTTGCA |
| 7881 | GTAATTTATGTTAGATTTTGCAT |
| 7882 | TAATTTATGTTAGATTTTGCATT |
| 7883 | AATTTATGTTAGATTTTGCATTT |
| 7884 | ATTTATGTTAGATTTTGCATTTT |
| 7885 | TTTATGTTAGATTTTGCATTTTT |
| 7886 | TTATGTTAGATTTTGCATTTTTT |
| 7887 | TATGTTAGATTTTGCATTTTTTT |
| 7888 | ATGTTAGATTTTGCATTTTTTTC |
| 7889 | TGTTAGATTTTGCATTTTTTTCA |
| 7890 | GTTAGATTTTGCATTTTTTTCAT |
| 7891 | TTAGATTTTGCATTTTTTTCATT |
| 7892 | TAGATTTTGCATTTTTTTCATTA |
| 7893 | AGATTTTGCATTTTTTTCATTAC |
| 7894 | GATTTTGCATTTTTTTCATTACT |
| 7895 | ATTTTGCATTTTTTTCATTACTG |
| 7896 | TTTTGCATTTTTTTCATTACTGT |
| 7897 | TTTGCATTTTTTTCATTACTGTT |
| 7898 | TTGCATTTTTTTCATTACTGTTA |
| 7899 | TGCATTTTTTTCATTACTGTTAT |
| 7900 | GCATTTTTTTCATTACTGTTATA |
| 7901 | CATTTTTTTCATTACTGTTATAT |
| 7902 | ATTTTTTTCATTACTGTTATATT |
| 7903 | TTTTTTTCATTACTGTTATATTT |
| 7904 | TTTTTTCATTACTGTTATATTTT |
| 7905 | TTTTTCATTACTGTTATATTTTA |
| 7906 | TTTTCATTACTGTTATATTTTAA |
| 7907 | TTTCATTACTGTTATATTTTAAC |
| 7908 | TTCATTACTGTTATATTTTAACC |
| 7909 | TCATTACTGTTATATTTTAACCT |
| 7910 | CATTACTGTTATATTTTAACCTG |
| 7911 | ATTACTGTTATATTTTAACCTGA |
| 7912 | TTACTGTTATATTTTAACCTGAC |
| 7913 | TACTGTTATATTTTAACCTGACT |
| 7914 | ACTGTTATATTTTAACCTGACTG |
| 7915 | CTGTTATATTTTAACCTGACTGA |
| 7916 | TGTTATATTTTAACCTGACTGAC |
| 7917 | GTTATATTTTAACCTGACTGACT |
| 7918 | TTATATTTTAACCTGACTGACTG |
| 7919 | TATATTTTAACCTGACTGACTGA |
| 7920 | ATATTTTAACCTGACTGACTGAT |

| ID | SEQUENCE |
|---|---|
| 7921 | TATTTTAACCTGACTGACTGATC |
| 7922 | ATTTTAACCTGACTGACTGATCT |
| 7923 | TTTTAACCTGACTGACTGATCTA |
| 7924 | TTTAACCTGACTGACTGATCTAA |
| 7925 | TTAACCTGACTGACTGATCTAAT |
| 7926 | TAACCTGACTGACTGATCTAATT |
| 7927 | AACCTGACTGACTGATCTAATTG |
| 7928 | ACCTGACTGACTGATCTAATTGT |
| 7929 | CCTGACTGACTGATCTAATTGTA |
| 7930 | CTGACTGACTGATCTAATTGTAT |
| 7931 | TGACTGACTGATCTAATTGTATT |
| 7932 | GACTGACTGATCTAATTGTATTA |
| 7933 | ACTGACTGATCTAATTGTATTAG |
| 7934 | CTGACTGATCTAATTGTATTAGT |
| 7935 | TGACTGATCTAATTGTATTAGTA |
| 7936 | GACTGATCTAATTGTATTAGTAT |
| 7937 | ACTGATCTAATTGTATTAGTATT |
| 7938 | CTGATCTAATTGTATTAGTATTG |
| 7939 | TGATCTAATTGTATTAGTATTGT |
| 7940 | GATCTAATTGTATTAGTATTGTG |
| 7941 | ATCTAATTGTATTAGTATTGTGA |
| 7942 | TCTAATTGTATTAGTATTGTGAA |
| 7943 | CTAATTGTATTAGTATTGTGAAT |
| 7944 | TAATTGTATTAGTATTGTGAATA |
| 7945 | AATTGTATTAGTATTGTGAATAA |
| 7946 | ATTGTATTAGTATTGTGAATAAT |
| 7947 | TTGTATTAGTATTGTGAATAATC |
| 7948 | TGTATTAGTATTGTGAATAATCA |
| 7949 | GTATTAGTATTGTGAATAATCAT |
| 7950 | TATTAGTATTGTGAATAATCATG |
| 7951 | ATTAGTATTGTGAATAATCATGT |
| 7952 | TTAGTATTGTGAATAATCATGTG |
| 7953 | TAGTATTGTGAATAATCATGTGA |
| 7954 | AGTATTGTGAATAATCATGTGAA |
| 7955 | GTATTGTGAATAATCATGTGAAA |
| 7956 | TATTGTGAATAATCATGTGAAAT |
| 7957 | ATTGTGAATAATCATGTGAAATG |
| 7958 | TTGTGAATAATCATGTGAAATGT |
| 7959 | TGTGAATAATCATGTGAAATGTT |
| 7960 | GTGAATAATCATGTGAAATGTTT |
| 7961 | TGAATAATCATGTGAAATGTTTT |
| 7962 | GAATAATCATGTGAAATGTTTTG |
| 7963 | AATAATCATGTGAAATGTTTTGA |
| 7964 | ATAATCATGTGAAATGTTTTGAG |
| 7965 | TAATCATGTGAAATGTTTTGAGA |
| 7966 | AATCATGTGAAATGTTTTGAGAC |
| 7967 | ATCATGTGAAATGTTTTGAGACA |
| 7968 | TCATGTGAAATGTTTTGAGACAG |

| ID | SEQUENCE |
|---|---|
| 7969 | CATGTGAAATGTTTTGAGACAGA |
| 7970 | ATGTGAAATGTTTTGAGACAGAG |
| 7971 | TGTGAAATGTTTTGAGACAGAGT |
| 7972 | GTGAAATGTTTTGAGACAGAGTA |
| 7973 | TGAAATGTTTTGAGACAGAGTAC |
| 7974 | GAAATGTTTTGAGACAGAGTACT |
| 7975 | AAATGTTTTGAGACAGAGTACTA |
| 7976 | AATGTTTTGAGACAGAGTACTAT |
| 7977 | ATGTTTTGAGACAGAGTACTATA |
| 7978 | TGTTTTGAGACAGAGTACTATAT |
| 7979 | GTTTTGAGACAGAGTACTATATT |
| 7980 | TTTTGAGACAGAGTACTATATTT |
| 7981 | TTTGAGACAGAGTACTATATTTG |
| 7982 | TTGAGACAGAGTACTATATTTGT |
| 7983 | TGAGACAGAGTACTATATTTGTG |
| 7984 | GAGACAGAGTACTATATTTGTGA |
| 7985 | AGACAGAGTACTATATTTGTGAA |
| 7986 | GACAGAGTACTATATTTGTGAAT |
| 7987 | ACAGAGTACTATATTTGTGAATA |
| 7988 | CAGAGTACTATATTTGTGAATAT |
| 7989 | AGAGTACTATATTTGTGAATATA |
| 7990 | GAGTACTATATTTGTGAATATAA |
| 7991 | AGTACTATATTTGTGAATATAAT |
| 7992 | GTACTATATTTGTGAATATAATT |
| 7993 | TACTATATTTGTGAATATAATTT |
| 7994 | ACTATATTTGTGAATATAATTTT |
| 7995 | CTATATTTGTGAATATAATTTTA |
| 7996 | TATATTTGTGAATATAATTTTAT |
| 7997 | ATATTTGTGAATATAATTTTATG |
| 7998 | TATTTGTGAATATAATTTTATGG |
| 7999 | ATTTGTGAATATAATTTTATGGT |
| 8000 | TTTGTGAATATAATTTTATGGTT |
| 8001 | TTGTGAATATAATTTTATGGTTT |
| 8002 | TGTGAATATAATTTTATGGTTTT |
| 8003 | GTGAATATAATTTTATGGTTTTT |
| 8004 | TGAATATAATTTTATGGTTTTTT |
| 8005 | GAATATAATTTTATGGTTTTTTT |
| 8006 | AATATAATTTTATGGTTTTTTTC |
| 8007 | ATATAATTTTATGGTTTTTTTCA |
| 8008 | TATAATTTTATGGTTTTTTTCAC |
| 8009 | ATAATTTTATGGTTTTTTTCACT |
| 8010 | TAATTTTATGGTTTTTTTCACTT |
| 8011 | AATTTTATGGTTTTTTTCACTTA |
| 8012 | ATTTTATGGTTTTTTTCACTTAG |
| 8013 | TTTTATGGTTTTTTTCACTTAGA |
| 8014 | TTTATGGTTTTTTTCACTTAGAA |
| 8015 | TTATGGTTTTTTTCACTTAGAAC |
| 8016 | TATGGTTTTTTTCACTTAGAACC |

| ID | SEQUENCE |
|---|---|
| 8017 | ATGGTTTTTTCACTTAGAACCT |
| 8018 | TGGTTTTTTCACTTAGAACCTT |
| 8019 | GGTTTTTTCACTTAGAACCTTT |
| 8020 | GTTTTTTCACTTAGAACCTTTC |
| 8021 | TTTTTTCACTTAGAACCTTTCT |
| 8022 | TTTTTCACTTAGAACCTTTCTG |
| 8023 | TTTTCACTTAGAACCTTTCTGT |
| 8024 | TTTCACTTAGAACCTTTCTGTG |
| 8025 | TTCACTTAGAACCTTTCTGTGT |
| 8026 | TCACTTAGAACCTTTCTGTGTG |
| 8027 | CACTTAGAACCTTTCTGTGTGG |
| 8028 | ACTTAGAACCTTTCTGTGTGGA |
| 8029 | CTTAGAACCTTTCTGTGTGGAA |
| 8030 | TTAGAACCTTTCTGTGTGGAAA |
| 8031 | TAGAACCTTTCTGTGTGGAAAA |
| 8032 | AGAACCTTTCTGTGTGGAAAAC |
| 8033 | GAACCTTTCTGTGTGGAAAACT |
| 8034 | AACCTTTCTGTGTGGAAAACTA |
| 8035 | ACCTTTCTGTGTGGAAAACTAA |
| 8036 | CCTTTCTGTGTGGAAAACTAAG |
| 8037 | CTTTCTGTGTGGAAAACTAAGA |
| 8038 | TTTCTGTGTGGAAAACTAAGAA |
| 8039 | TTCTGTGTGGAAAACTAAGAAA |
| 8040 | TCTGTGTGGAAAACTAAGAAAA |
| 8041 | CTGTGTGGAAAACTAAGAAAAT |
| 8042 | TGTGTGGAAAACTAAGAAAATT |
| 8043 | GTGTGGAAAACTAAGAAAATTG |
| 8044 | TGTGGAAAACTAAGAAAATTGC |
| 8045 | GTGGAAAACTAAGAAAATTGCT |
| 8046 | TGGAAAACTAAGAAAATTGCTT |
| 8047 | GGAAAACTAAGAAAATTGCTTT |
| 8048 | GAAAACTAAGAAAATTGCTTTC |
| 8049 | AAAACTAAGAAAATTGCTTTCT |
| 8050 | AAACTAAGAAAATTGCTTTCTG |
| 8051 | AACTAAGAAAATTGCTTTCTGC |
| 8052 | ACTAAGAAAATTGCTTTCTGCT |
| 8053 | CTAAGAAAATTGCTTTCTGCTG |
| 8054 | TAAGAAAATTGCTTTCTGCTGT |
| 8055 | AAGAAAATTGCTTTCTGCTGTA |
| 8056 | AGAAAATTGCTTTCTGCTGTAT |
| 8057 | GAAAATTGCTTTCTGCTGTATA |
| 8058 | AAAATTGCTTTCTGCTGTATAA |
| 8059 | AAATTGCTTTCTGCTGTATAAT |
| 8060 | AATTGCTTTCTGCTGTATAATC |
| 8061 | ATTGCTTTCTGCTGTATAATCT |
| 8062 | TTGCTTTCTGCTGTATAATCTG |
| 8063 | TGCTTTCTGCTGTATAATCTGG |
| 8064 | GCTTTCTGCTGTATAATCTGGC |

| ID | SEQUENCE |
|---|---|
| 8065 | GCTTTCTGCTGTATAATCTGGCA |
| 8066 | CTTTCTGCTGTATAATCTGGCAT |
| 8067 | TTTCTGCTGTATAATCTGGCATT |
| 8068 | TTCTGCTGTATAATCTGGCATTC |
| 8069 | TCTGCTGTATAATCTGGCATTCA |
| 8070 | CTGCTGTATAATCTGGCATTCAT |
| 8071 | TGCTGTATAATCTGGCATTCATT |
| 8072 | GCTGTATAATCTGGCATTCATTG |
| 8073 | CTGTATAATCTGGCATTCATTGT |
| 8074 | TGTATAATCTGGCATTCATTGTA |
| 8075 | GTATAATCTGGCATTCATTGTAG |
| 8076 | TATAATCTGGCATTCATTGTAGA |
| 8077 | ATAATCTGGCATTCATTGTAGAT |
| 8078 | TAATCTGGCATTCATTGTAGATT |
| 8079 | AATCTGGCATTCATTGTAGATTA |
| 8080 | ATCTGGCATTCATTGTAGATTAA |
| 8081 | TCTGGCATTCATTGTAGATTAAA |
| 8082 | CTGGCATTCATTGTAGATTAAAG |
| 8083 | TGGCATTCATTGTAGATTAAAGC |
| 8084 | GGCATTCATTGTAGATTAAAGCT |
| 8085 | GCATTCATTGTAGATTAAAGCTT |
| 8086 | CATTCATTGTAGATTAAAGCTTA |
| 8087 | ATTCATTGTAGATTAAAGCTTAT |
| 8088 | TTCATTGTAGATTAAAGCTTATT |
| 8089 | TCATTGTAGATTAAAGCTTATTT |
| 8090 | CATTGTAGATTAAAGCTTATTTT |
| 8091 | ATTGTAGATTAAAGCTTATTTTT |
| 8092 | TTGTAGATTAAAGCTTATTTTTC |
| 8093 | TGTAGATTAAAGCTTATTTTTCT |
| 8094 | GTAGATTAAAGCTTATTTTTCTG |
| 8095 | TAGATTAAAGCTTATTTTTCTGT |
| 8096 | AGATTAAAGCTTATTTTTCTGTG |
| 8097 | GATTAAAGCTTATTTTTCTGTGA |
| 8098 | ATTAAAGCTTATTTTTCTGTGAA |
| 8099 | TTAAAGCTTATTTTTCTGTGAAT |
| 8100 | TAAAGCTTATTTTTCTGTGAATA |
| 8101 | AAAGCTTATTTTTCTGTGAATAA |
| 8102 | AAGCTTATTTTTCTGTGAATAAA |
| 8103 | AGCTTATTTTTCTGTGAATAAAA |
| 8104 | GCTTATTTTTCTGTGAATAAAAC |
| 8105 | CTTATTTTTCTGTGAATAAAACG |
| 8106 | TTATTTTTCTGTGAATAAAACGT |
| 8107 | TATTTTTCTGTGAATAAAACGTA |
| 8108 | ATTTTTCTGTGAATAAAACGTAT |
| 8109 | TTTTTCTGTGAATAAAACGTATT |
| 8110 | TTTTCTGTGAATAAAACGTATTC |
| 8111 | TTTCTGTGAATAAAACGTATTCA |
| 8112 | TTCTGTGAATAAAACGTATTCAA |

| ID | SEQUENCE |
|---|---|
| 8113 | TCTGTGAATAAAACGTATTCAAT |
| 8114 | CTGTGAATAAAACGTATTCAATA |
| 8115 | TGTGAATAAAACGTATTCAATAA |
| 8116 | GTGAATAAAACGTATTCAATAAA |
| 8117 | TGAATAAAACGTATTCAATAAAA |
| 8118 | GAATAAAACGTATTCAATAAAAT |
| 8119 | AATAAAACGTATTCAATAAAATA |
| 8120 | ATAAAACGTATTCAATAAAATAC |
| 8121 | TAAAACGTATTCAATAAAATACT |
| 8122 | AAAACGTATTCAATAAAATACTA |
| 8123 | AAACGTATTCAATAAAATACTAT |
| 8124 | AACGTATTCAATAAAATACTATT |
| 8125 | ACGTATTCAATAAAATACTATTC |
| 8126 | CGTATTCAATAAAATACTATTCT |
| 8127 | GTATTCAATAAAATACTATTCTT |
| 8128 | TATTCAATAAAATACTATTCTTT |
| 8129 | ATTCAATAAAATACTATTCTTTA |
| 8130 | TTCAATAAAATACTATTCTTTAA |
| 8131 | TCAATAAAATACTATTCTTTAAA |
| 8132 | CAATAAAATACTATTCTTTAAAA |
| 8133 | AATAAAATACTATTCTTTAAAAT |
| 8134 | ATAAAATACTATTCTTTAAAATT |
| 8135 | TAAAATACTATTCTTTAAAATTA |

SIRNA SILENCING OF GENES EXPRESSED IN CANCER

CROSS-REFERENCES TO RELATED APPLICATIONS

This application claims the benefit of U.S. Provisional Patent Application Nos. 60/808,859, filed May 26, 2006, and 60/817,556 filed Jun. 28, 2006, the disclosures of which are hereby incorporated by reference in their entirety for all purposes.

REFERENCE TO A "SEQUENCE LISTING," A TABLE, OR A COMPUTER PROGRAM LISTING APPENDIX SUBMITTED ON A COMPACT DISK

The Sequence Listing written in file -69-2.APP, 4,222,976 bytes, machine format IBM-PC, MS-Windows operating system, created on Oct. 7, 2008 on duplicate copies of compact disc of the written form of the Sequence Listing, i.e., "Copy 1 of 3" and "Copy 2 of 3", and the sequence information recorded in computer readable form on compact disc, i.e., "Copy 3 of 3" for application Ser. No. 11/807,872, MacLachlan et al., siRNA SILENCING OF GENES EXPRESSED IN CANCER, is hereby incorporated by reference.

BACKGROUND OF THE INVENTION

Cell proliferation and programmed cell death play important roles in the growth and development of an organism. In proliferative diseases such as cancer, the processes of cell proliferation and/or programmed cell death are often perturbed. For example, a cancer cell may have unregulated cell division through either the overexpression of a positive regulator of the cell cycle or the loss of a negative regulator of the cell cycle, perhaps by mutation. Alternatively, a cancer cell may have lost the ability to undergo programmed cell death through the overexpression of a negative regulator of apoptosis. Therefore, there is a need to develop new therapeutic agents that will restore the processes of checkpoint control and programmed cell death to cancerous cells.

RNA interference (RNAi) is an evolutionarily conserved process in which recognition of double-stranded RNA (dsRNA) ultimately leads to posttranscriptional suppression of gene expression. This suppression is mediated by short double stranded RNA (dsRNA), also called small interfering RNA (siRNA), which induces specific degradation of mRNA through complementary base pairing. In several model systems, i.e., mostly lower order animals, this natural response has been developed into a powerful tool for the investigation of gene function (Elbashir S M, et al., *Genes Dev,* 2001, 15:188-200; Hammond S M, et al., *Nat Rev Genet.,* 2001, 2:110-119). More recently it was discovered that introducing synthetic 21-nucleotide dsRNA duplexes into mammalian cells could efficiently silence gene expression. Although the precise mechanism is still unclear, RNAi offers a new way to inactivate genes of interest. In particular, for the treatment of neoplastic disorders (cancer), RNAi provides a potential new approach to modulate (e.g., reduce) the expression of certain genes, e.g., an anti-apoptotic molecule, a growth factor, a growth factor receptor, a mitotic spindle protein, a cell cycle protein, an angiogenic factor, an oncogene, an intracellular signal transducer, a molecular chaperone, and combinations thereof.

One such target is the Eg5 gene which produces the microtubule-associated protein, Eg5 (Kapoor, T. M., et al., *J. Cell Biol.,* 2001, 154, 1125-1133; Garrett, S. et al., *Curr Biol.,* 2003, 13, R810-812; Cassimeris, L., et al., *Curr Issues Mol. Biol.,* 2003, 5, 99-112; Houliston, E., et al., *Dev. Biol.* 1994, 164, 147-159). Generally, due to the clinical success seen with antimitotics in cancer therapy (e.g. taxanes), other proteins that that are also involved in the mitotic machinery, such as Eg5, have become desirable targets as next generation anti-cancer therapeutics. The mitotic kinesin, Eg5, contains an N-terminal motor domain which generates force along the microtubule, moving Eg5 to the microtubule plus end. During interphase in most epithelial cells, the plus ends of microtubules are oriented toward the plasma membrane while the minus ends are facing toward the nucleus. Upon entry into mitosis, microtubule plus ends reorient toward the chromosomes, while the minus ends are anchored at the spindle poles, forming a bipolar spindle. The homotetrameric structure of Eg5 has its motor domains arranged at two ends of a dumbbell such that it can bind and push apart spindle microtubules and generate and outward-directed force pushing spindle poles apart (Sawin, K. E., et al., *Prod Natl. Acad. Sci. USA,* 1995, 92, 4289-4293; Kapoor, T. M., et al., *J Cell Biol.,* 2000, 150, 975-988; Gaglio, T., et al., *J Cell Biol.,* 1996, 135, 399-414). Thus, Eg5 is critical for proper spindle formation during the mitotic process. Disruption of the process leads to activation of spindle assembly checkpoint, the major cell cycle control mechanism which prevents the cell undergoing mitosis to progress to anaphase and leads to cell cycle arrest. Inhibition of the production of the Eg5 protein, which is only expressed during mitosis, results in the induction of cancer cell apoptosis through a unique mechanism. In view of the important role of Eg5 has in the mitotic process, Eg5 has become an attractive therapeutic target for rapidly dividing cells, in particular, in cancer therapy.

The first small molecule inhibitors of Eg5 was identified in a phenotype-based screen and has been termed Monastrol, because of the formation of monoastral spindles due to Eg5 inhibition seen in cells treated with Monastrol (Mayer, T. U., et al., Science, 1999, 286, 971-974). Other small molecule inhibitors of Eg5 have been discovered since and are currently under development (Sakowicz, R., et al., *Cancer Res.,* 2004, 64, 3276-3280; Hotha, S. et al., Angew Chem. Intl. Ed. Engl., 2003, 42, 2379-2382). However, recent literature publications suggest that certain cancer cell lines, e.g., HT-29 colorectal cancer cells, are resistant toward small molecule Eg5 inhibitors, and thus suggest that small molecule Eg5 inhibitors may have be of more limited clinical use than previously thought.

A second target is the EGFR gene that encodes for the epidermal growth factor receptor (EGFR), a glycoprotein with a molecular weight of 170,000 to 180,000. EGFR is an intrinsic tyrosine-specific protein kinase, which is stimulated upon epidermal growth factor (EGF) binding. The known downstream effectors of EGFR include PI3-K, RAS-RAF-MAPK P44/P42, and protein kinase C signaling pathways. EGFR signaling involved in cell growth, angiogenesis, DNA repair, and autocrine growth regulation in a wide spectrum of human cancer cells (Wakeling A E., *Curr Opin Pharmacol* 2002, 2:382-387). Therefore, it has recently emerged as an innovative target for the development of new cancer therapy. Recently, a monoclonal antibody against EGFR called cetuximab has been developed. It has shown excellent clinical effects for the treatment of lung and head and neck cancer in a clinical trial in humans (Shin et al., *Clin Cancer Res,* 2001, 7:1204-1213). Other small chemical inhibitors, such as ZD-1839 have also been developed and demonstrated antitumor effects in in vitro and in vivo (Shawver L K, et al., *Cancer Cell* 2002, 1:117-123). However, clinical use of ZD-1839 in humans has not been very successful. (Baselga *Eur J Cancer* 2001, 37:S16-22).

A third target is the XIAP (X-linked inhibitor of apoptosis protein) which is a member of the mammalian IAP gene family and encodes for the X-linked IAP (XIAP) protein. The anti-apoptotic function of XIAP is executed, at least in part, by inhibition of caspase-3 and caspase-7, two principal effectors of apoptosis. XIAP protein plays a critical role in regulating programmed cell death by suppressing activation of downstream caspase-3 and caspase-7. Interestingly, in pre-cancerous and cancerous cells, it is believed that expression or overexpression of XIAPs makes it difficult for cancer cells to eliminate themselves, instead allowing them to proliferate, metastasize and accumulate additional oncogenic mutations. Inhibition of XIAP activity using anti-sense oligonucleotides has demonstrates anti-tumor activity in human tumor xenograft animal model.

In view of the above, there is a need for compositions and methods for modulating the expression of genes involved in cancer. The present invention addresses these and other needs.

SUMMARY OF THE INVENTION

The present invention provides compositions comprising siRNA molecules that target genes expressed in cancer and methods of using such compositions to silence expression of such genes.

One embodiment of the invention provides a nucleic acid-lipid particle comprising an siRNA molecule that targets a gene expressed in cancer. In some embodiments, the gene is selected from an anti-apoptotic molecule, a growth factor, a growth factor receptor, a mitotic spindle protein, a cell cycle protein, an angiogenic factor, an oncogene, an intracellular signal transducer, a molecular chaperone, and combinations thereof. In some embodiments, the lipid portion of the particle comprises a cationic lipid and a non-cationic lipid. In some embodiments, the nucleic acid-lipid particle further comprises a conjugated lipid that prevents aggregation of the particles and/or a sterol (e.g., cholesterol).

Another embodiment of the invention provides a nucleic acid-lipid particle that targets expression of the Eg5, EGFR or XIAP gene. The nucleic acid-lipid particle comprises an siRNA molecule that silences expression of the Eg5, EGFR or XIAP gene; a cationic lipid; a non-cationic lipid; and a conjugated lipid that inhibits aggregation of particles. The siRNA molecules may comprise at least one sequence set forth in Tables 1-9 (i.e., Tables 1-2 and 7 for Eg5; Tables 3-4 and 8 for EGFR; or Tables 5-6 and 9 for XIAP). In some embodiments, nucleic acid-lipid particles comprise at least 2, 3, 4, 5, or 6 of the sequences set forth in Tables 1-2 and 7 for Eg5; Tables 3-4 and 8 for EGFR; or Tables 5-6 and 9 for XIAP. In some embodiments, The cationic lipid may be, e.g., N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), and N,N-dimethyl-2,3-dioleyloxy)propylamine (DODMA), 1,2-DiLinoleyloxy-N,N-dimethylaminopropane (DLinDMA), and 1,2-Dilinolenyloxy-N,N-dimethylaminopropane (DLendMA), or mixtures thereof. The cationic lipid may comprise from about 2 mol % to about 60 mol %, about 5 mol % to about 45 mol %, about 5 mol % to about 15 mol %, about 30 mol % to about 50 mol % or about 40 mol % to about 50 mol % of the total lipid present in the particle.

The non-cationic lipid may be an anionic lipid or a neutral lipid including, but not limited to, a non-cationic lipid is a member selected from the group consisting of dioleoylphosphatidylethanolamine (DOPE), palmitoyloleoylphosphatidylcholine (POPC), egg phosphatidylcholine (EPC), distearoylphosphatidylcholine (DSPC), palmitoyloleoylphosphatidylglycerol (POPG), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, palmitoyloleoyl-phosphatidylethanolamine (POPE), 1-stearoyl-2-oleoyl-phosphatidyethanolamine (SOPE), 1,2-dielaidoyl-sn-glycero-3-phophoethanolamine (transDOPE), cholesterol, or mixtures thereof. The non-cationic lipid comprises from about 5 mol % to about 90 mol % or about 20 mol % to about 85 mol % of the total lipid present in the particle.

The conjugated lipid that inhibits aggregation of particles may be a polyethyleneglycol (PEG)-lipid conjugate, a polyamide (ATTA)-lipid conjugate, a cationic-polymer-lipid conjugates (CPLs), or mixtures thereof. In one preferred embodiment, the nucleic acid-lipid particles comprise either a PEG-lipid conjugate or an ATTA-lipid conjugate together with a CPL. The conjugated lipid that inhibits aggregation of particles may comprise a polyethyleneglycol-lipid including, e.g., a PEG-diacylglycerol (DAG), a PEG dialkyloxypropyl (DAA), a PEG-phospholipid, a PEG-ceramide (Cer), or mixtures thereof. The PEG-DAA conjugate may be PEG-dilauryloxypropyl (C12), a PEG-dimyristyloxypropyl (C14), a PEG-dipalmityloxypropyl (C16), and a PEG-distearyloxypropyl (C18). In some embodiments, the conjugated lipid that inhibits aggregation of particles has the formula: A-W-Y, wherein: A is a lipid moiety; W is a hydrophilic polymer; and Y is a polycationic moiety. W may be a polymer selected from the group consisting of polyethyleneglycol (PEG), polyamide, polylactic acid, polyglycolic acid, polylactic acid/polyglycolic acid copolymers or combinations thereof, said polymer having a molecular weight of about 250 to about 7000 daltons. In some embodiments, Y has at least 4 positive charges at a selected pH. In some embodiments, Y may be lysine, arginine, asparagine, glutamine, derivatives thereof and combinations thereof. The conjugated lipid that prevents aggregation of particles may be about 0 mol % to about 20 mol %, about 1 mol % to about 15 mol %, about 4 mol % to about 10 mol %, or about 2 mol % of the total lipid present in said particle.

In some embodiments, the nucleic acid-lipid particle further comprises cholesterol at, e.g., about 0 mol % to about 10 mol %, about 2 mol % to about 10 mol %, about 10 mol % to about 60 mol % or about 20 mol % to about 45 mol % of the total lipid present in the particle.

In a specific embodiment of the invention, the nucleic acid-lipid particle comprises 48% cholesterol; 10% DSPC; 2% PEG-cDMA; and 40% DLinDMA.

In some embodiments, the siRNA in the nucleic acid-lipid particle is not substantially degraded after exposure of the particle to a nuclease at 37° C. for at least 20, 30, 45, or 60 minutes; or after incubation of the particle in serum at 37° C. for at least 30, 45, or 60 minutes, 2, 3, 4, 5, 6, 7, 8, 9, 10, 12, 14, 16, 18, 20, 22, 24, 26, 28, 30, 32, 34, or 36 hours. In some embodiments, the siRNA is fully encapsulated in the nucleic acid-lipid particle. In some embodiments, the siRNA is complexed to the lipid portion of the particle.

The present invention further provides pharmaceutical compositions comprising the nucleic acid-lipid particles described herein and a pharmaceutically acceptable carrier.

The nucleic acid-lipid particles of the present invention are useful for the therapeutic delivery of nucleic acids comprising an interfering RNA sequence (i.e., an siRNA sequence that targets expression of an Eg5, EGFR or XIAP gene. In particular, it is an object of this invention to provide in vitro and in vivo methods for treatment of a disease in a mammal by downregulating or silencing the transcription and translation of a target nucleic acid sequence of interest. In these methods, an interfering RNA is formulated into a nucleic acid-lipid particle, and the particles are administered to patients requiring such treatment. Alternatively, cells are removed from a patient, the interfering RNA delivered in vitro, and reinjected into the patient. In one embodiment, the present invention provides for a method of introducing a nucleic acid into a cell by contacting a cell with a nucleic acid-lipid particle comprised of a cationic lipid, a non-cationic lipid, a conjugated lipid that inhibits aggregation, and an interfering RNA.

In one embodiment, at least 1%, 2%, 4%, 6%, 8%, 10%, 12%. 14%. 16% or 18% of the total injected dose of the nucleic acid-lipid particles is present in plasma 1, 2, 4, 6, 8, 12, 16, 18, or 24 hours after injection. In other embodiments, more than 20%, 30%, 40% and as much as 60%, 70% or 80% of the total injected dose of the nucleic acid-lipid particles is present in plasma 1, 4, 6, 8, 10, 12, 20, or 24 hours after injection. In one embodiment, the effect of an interfering RNA (e.g., downregulation of the target sequence) at a site proximal or distal to the site of administration is detectable at 12, 24, 48, 72, or 96 hours, 6, 8, 10, 12, 14, 16, 18, 19, 20, 22, 24, 26, or 28 days after administration of the nucleic acid-lipid particles. In one embodiment, downregulation of expression of the target sequence is detectable at 12, 24, 48, 72, or 96 hours, 6, 8, 10, 12, 14, 16, 18, 19, 20, 22, 24, 26, or 28 days after administration. In some embodiments, downregulation of Eg5, EGFR or XIAP gene is detected by detecting mRNA or protein levels in a biological sample from the mammal. In some embodiments, downregulation of expression of a Eg5, EGFR or XIAP sequence is detected by measuring the cell viability or the induction of apoptosis of cells in a biological sample from the mammal.

The particles are suitable for use in intravenous nucleic acid transfer as they are stable in circulation, of a size required for pharmacodynamic behavior resulting in access to extravascular sites and target cell populations. The invention also provides for pharmaceutically acceptable compositions comprising a nucleic acid-lipid particle.

Another embodiment of the present invention provides methods for in vivo delivery of interfering RNA (e.g., interfering RNA that silences expression of an Eg5, EGFR or XIAP gene). A nucleic acid-lipid particle comprising a cationic lipid, a non-cationic lipid, a conjugated lipid that inhibits aggregation of particles, and interfering RNA is administered (e.g., intravenously, intramuscularly, or subcutaneously) to a subject (e.g., a mammal such as a human or a rodent).

A further embodiment of the present invention provides a method of treating a disease or disorder in a mammalian subject. A therapeutically effective amount of a nucleic acid-lipid particle comprising a cationic lipid, a non-cationic lipid, a conjugated lipid that inhibits aggregation of particles, and interfering RNA (e.g., interfering RNA that silences expression of a Eg5, EGFR or XIAP gene) is administered to the mammalian subject (e.g., a rodent such as a mouse, a primate such as a human, a chimpanzee, or a monkey). In some embodiments, the mammalian subject has a cell proliferative disorder. In certain aspects of this embodiment, the mammalian subject has a said cell proliferative disorder is selected from the group consisting of neoplasia (cancer), hyperplasias, restenosis, cardiac hypertrophy, immune disorders and inflammation. Preferably, said cell proliferative disorder is a neoplastic disorder, i.e., cancer. In some embodiments, the cancer includes, but is not limited to papilloma, blastoglioma, Kaposi's sarcoma, melanoma, lung cancer, ovarian cancer, prostate cancer, squamous cell carcinoma, astrocytoma, head cancer, neck cancer, bladder cancer, breast cancer, lung cancer, colorectal cancer, thyroid cancer, pancreatic cancer, gastric cancer, hepatocellular carcinoma, leukemia, lymphoma, Hodgkin's disease, osteosarcoma, testicular cancer, and Burkitt's disease.

The invention further provides siRNA molecules having the sequences set forth in any one of Tables 1-9. In some embodiments, the siRNA molecules comprise modified nucleotides. The siRNA molecules comprising modified nucleotides are capable of silencing expression of a target sequence and are less immunostimulatory than a corresponding unmodified siRNA sequence. In some embodiments, less than about 20%, 15%, 10%, 5%, or 2% of the nucleotides in the siRNA comprise modified nucleotides. In some embodiments, the modified nucleotide is selected from a 2'-O-methyl (2'OMe) pyrimidine and a 2'OMe purine (e.g., a 2'OMe-guanosine, a 2'OMe-uridine, and a 2'OMe-adenosine). In some embodiments, the modified nucleotide is not 2'OMe-cytosine. In some embodiments, the modified nucleotides are present in one strand of the siRNA (e.g., in the sense strand). In some embodiments the corresponding unmodified siRNA sequence comprises at least one 5'-GU-3' motif. In some embodiments, the at least one 5'-GU-3' motif is in the sense strand of the unmodified siRNA sequence. In some embodiments, the double-stranded sequence comprises a hairpin loop structure.

The invention also provides compositions comprising the siRNA molecules described herein and a pharmaceutically acceptable carrier.

These and other embodiments of the invention are further described in the detailed description that follows.

BRIEF DESCRIPTION OF THE DRAWINGS

FIG. 5 illustrates data demonstrating certain characteristic changes seen in cell phenotype following treatment with Eg5 O/O siRNA.

FIG. 6 illustrates a list showing the sequences of various 2'-OMe modified Eg5 2263 siRNAs (SEQ ID NOS:1-3, 2, 3, 4, 2, 1, 5, 1, 6, 3, 5, 3, 6, 4, 6, 4 and 5, respectively).

FIG. 21 is Table 1 which sets forth a list of Eg5 siRNA (SEQ ID NOS:7-32).

FIG. 22 is Table 2 which sets forth an additional list of Eg5 siRNA (SEQ ID NOS:33-62).

FIG. 23 is Table 3 which sets forth a list of EGFR siRNA (SEQ ID NOS:63-92).

FIG. 24 is Table 4 which sets forth an additional list of EGFR siRNA (SEQ ID NOS:93-118).

FIG. 25 is Table 5 which sets forth a list of XIAP siRNA (SEQ ID NOS:119-145).

FIG. 26 is Table 6 which sets forth an additional list of XIAP siRNA (SEQ ID NOS:146-173).

FIG. 27 is Table 7 which sets forth an additional list of Eg5 siRNA (SEQ ID NOS:174-4977).

FIG. 28 is Table 8 which sets forth an additional list of EGFR siRNA (SEQ ID NOS:4978-10362).

FIG. 29 is Table 9 which sets forth an additional list of XIAP siRNA (SEQ ID NOS:10363-18497).

DETAILED DESCRIPTION OF THE INVENTION

I. Introduction

Figure 1:
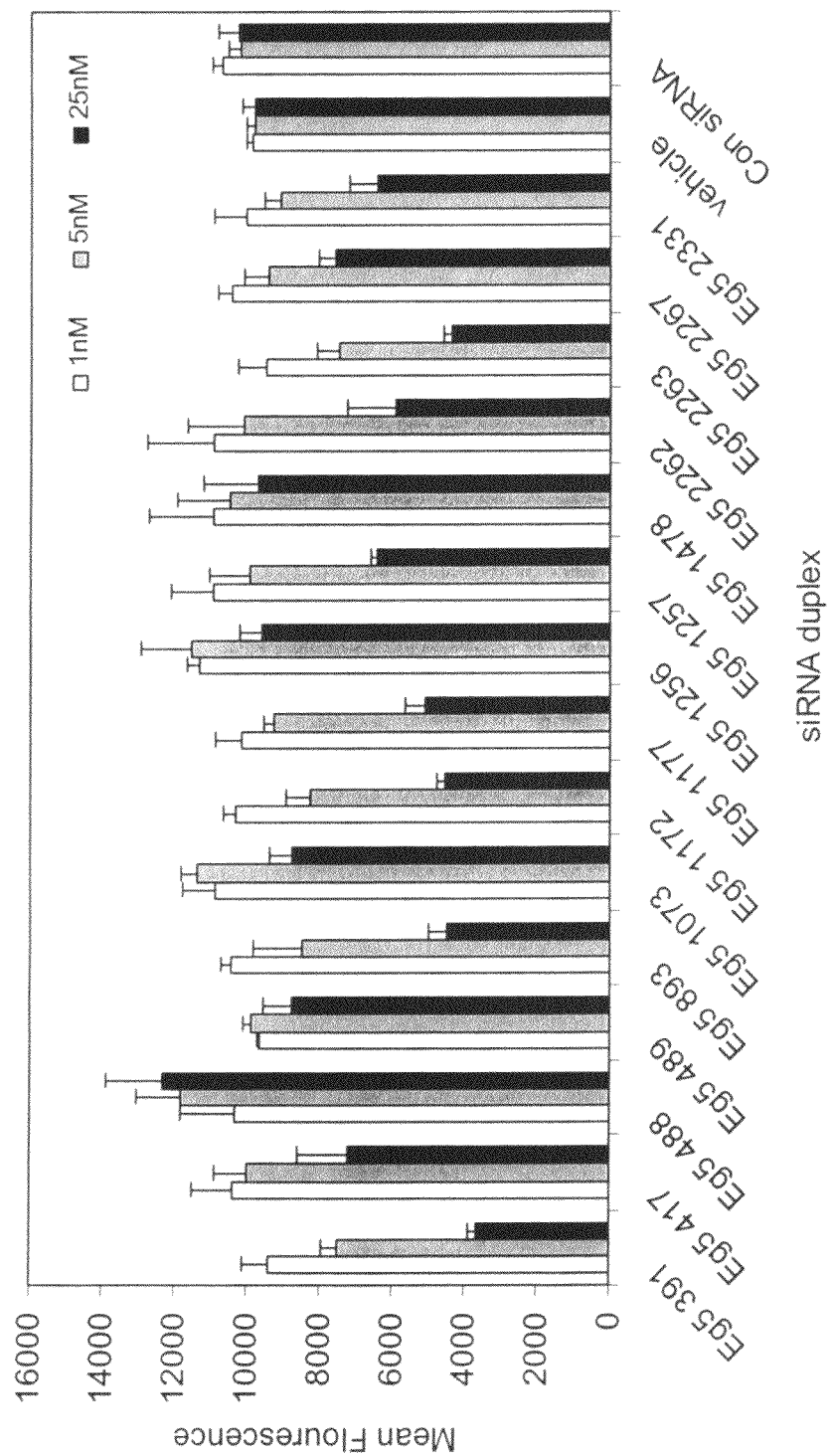
FIG. 1 illustrates data demonstrating RNAi activity of a Eg5 siRNA panel (at 1, 5, and 25 nM concentration) complexed with lipofectamine in HeLa cells (human).

The invention provides compositions and methods for treating cancer. In particular, the invention provides nucleic acid-lipid particles comprising siRNA molecules that silence genes expressed in cancer including, e.g., growth factors (e.g. epidermal growth factor ("EGF") and insulin growth factor-1 ("IGF-1")), growth factor receptors (e.g., epidermal growth factor receptor ("EGFR") and hepatocyte growth factor receptor (i.e. c-Met)), mitotic spindle proteins (e.g., kinesins such as kinesin family member 11 ("Eg5" or "KIF11"), anti-apoptotic molecules (e.g., caspase inhibitors such as XIAP and CrmA, survivin, bcl-2), cell cycle proteins (e.g., cyclin E and aurora kinase), angiogenic factors (e.g., vascular endothelial growth factor ("VEGF") and vascular endothelial growth factor receptor ("VEGFR")); oncogenes (e.g., src, fyn, ras and myc), intracellular signal transducers (e.g., mammalian target of rapamycin ("mTOR"), MAP kinase kinases ("MEK") and nuclear factor kappa-B ("NFkB")), and molecular chaperones (e.g., HSP90). The lipid portion of the nucleic acid-lipid particles comprise a cationic lipid, a non-cationic lipid, optionally a lipid that prevents aggregation of particles. It is a discovery of the invention that the nucleic acid-lipid particles described herein are particularly effective for encapsulating and delivering siRNA molecules that target cancer cells.

This invention is based in part on the discovery that silencing Eg5, EGFR and/or XIAP gene expression is an effective means to halt proliferation of rapidly dividing cells, e.g., cancer cells. Accordingly, the present invention also provides nucleic acid-lipid particles that target Eg5, EGFR and/or XIAP gene expression comprising an siRNA that silences Eg5, EGFR and/or XIAP gene expression; a cationic lipid; a non-cationic lipid; and a conjugated lipid that inhibits aggregation of particles. The invention further provides methods of silencing Eg5, EGFR or XIAP gene expression by administering the nucleic acid-lipid particles described herein to a mammalian subject. In addition, the invention provides methods of treating a subject who suffers from a cell proliferative disorder, e.g., cancer, by administering the nucleic acid-lipid particles described herein.

II. Definitions

The term "Eg5" refers to the kif11 gene product, a member in a class of kinesin-related proteins that are involved in functions related to movements of organelles, microtubules, or chromosomes along microtubules. These functions include axonal transport, microtubule sliding during nuclear fusion or division, and chromosome disjunction during meiosis and early mitosis. Eg5 appears to play a critical role in mitosis of mammalian cells. Sequences for Eg5 are set forth in, e.g., Genbank Accession Nos. NM_004523 (human) and NM_010615 (mouse).

The term "EGFR" refers to the cell surface receptor, epidermal growth factor receptor, also known as ERBB1, that is a member of the ERBB tyrosine kinase family. EGF has 3 regions: one projects outside the cell and contains the site for binding epidermal growth factor (EGF) and related growth factors; the second is embedded in the membrane; the third projects into the cytoplasm of the cell's interior. EGFR is a phosphotyrosinekinase. Binding of EGFR by EGF has a profound effect on the differentiation of specific cells in vivo and is a potent mitogenic factor for a variety of cultured cells of both ectodermal and mesodermal origin. Sequences for the EGF gene are set forth in Genbank Accession Nos. NM_005228 (human) and NM_207655 (mouse).

The term "XIAP" or "X-linked inhibitor of apoptosis" is a potent member of the inhibitor of apoptosis (IAP) family. All members of this family possess baculoviral IAP (BIR) repeats, cysteine-rich domains of approximately 80 amino acids that bind and inhibit caspases. XIAP has 3 BIR domains and a C-terminal RING zinc finger that possesses E3 ubiquitin ligase activity. The anticaspase activity of XIAP and is important in mediating apoptosis resistance in cancer cells. Sequences for XIAP are set forth in Genbank Accession Nos. NM_001167 (human) and NM_009688 (mouse).

The term "interfering RNA" or "RNAi" or "interfering RNA sequence" refers to double-stranded RNA (i.e., duplex RNA) that targets (i.e., silences, reduces, or inhibits) expression of a target gene (i.e., by mediating the degradation of mRNAs which are complementary to the sequence of the interfering RNA) when the interfering RNA is in the same cell as the target gene. Interfering RNA thus refers to the double stranded RNA formed by two complementary strands or by a single, self-complementary strand. Interfering RNA typically has substantial or complete identity to the target gene. The sequence of the interfering RNA can correspond to the full length target gene, or a subsequence thereof. Interfering RNA includes small-interfering RNA" or "siRNA," i.e., interfering RNA of about 15-60, 15-50, 15-50, or 15-40 (duplex) nucleotides in length, more typically about, 15-30, 15-25 or 19-25 (duplex) nucleotides in length, and is preferably about 20-24 or about 21-22 or 21-23 (duplex) nucleotides in length (e.g., each complementary sequence of the double stranded siRNA is 15-60, 15-50, 15-50, 15-40, 15-30, 15-25 or 19-25 nucleotides in length, preferably about 20-24 or about 21-22 or 21-23 nucleotides in length, and the double stranded siRNA is about 15-60, 15-50, 15-50, 15-40, 15-30, 15-25 or 19-25 preferably about 20-24 or about 21-22 or 21-23 base pairs in length). siRNA duplexes may comprise 3' overhangs of about 1 to about 4 nucleotides, preferably of about 2 to about 3 nucleotides and 5' phosphate termini. The siRNA can be chemically synthesized or maybe encoded by a plasmid (e.g., transcribed as sequences that automatically fold into duplexes with hairpin loops). siRNA can also be generated by cleavage of longer dsRNA (e.g., dsRNA greater than about 25 nucleotides in length) with the *E. coli* RNase III or Dicer. These enzymes process the dsRNA into biologically active siRNA (see, e.g., Yang et al., *PNAS USA* 99: 9942-7 (2002); Calegari et al., *PNAS USA* 99: 14236 (2002); Byrom et al., *Ambion TechNotes* 10(1): 4-6 (2003); Kawasaki et al., *Nucleic Acids Res.* 31: 981-7 (2003); Knight and Bass, *Science* 293: 2269-71 (2001); and Robertson et al., *J. Biol. Chem.* 243: 82 (1968)). Preferably, dsRNA are at least 50 nucleotides to about 100, 200, 300, 400 or 500 nucleotides in length. A dsRNA may be as long as 1000, 1500, 2000, 5000 nucleotides in length, or longer. The dsRNA can encode for an entire gene transcript or a partial gene transcript.

"Substantial identity" refers to a sequence that hybridizes to a reference sequence under stringent conditions, or to a sequence that has a specified percent identity over a specified region of a reference sequence.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization.

Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and Current Protocols in Molecular Biology, ed. Ausubel, et al.

The terms "substantially identical" or "substantial identity," in the context of two or more nucleic acids, refer to two or more sequences or subsequences that are the same or have a specified percentage of nucleotides that are the same (i.e., at least about 60%, preferably 65%, 70%, 75%, preferably 80%, 85%, 90%, or 95% identity over a specified region), when compared and aligned for maximum correspondence over a comparison window, or designated region as measured using one of the following sequence comparison algorithms or by manual alignment and visual inspection. This definition, when the context indicates, also refers analogously to the complement of a sequence. Preferably, the substantial identity exists over a region that is at least about 5, 10, 15, 20, 25, 30, 35, 40, 45, 50, 75, or 100 nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The phrase "inhibiting expression of a target gene" refers to the ability of a siRNA of the invention to silence, reduce, or inhibit expression of a target gene (e.g., an Eg5, EGFR or XIAP gene). To examine the extent of gene silencing, a test sample (e.g., a biological sample from organism of interest expressing the target gene or a sample of cells in culture expressing the target gene) is contacted with an siRNA that silences, reduces, or inhibits expression of the target gene. Expression of the target gene in the test sample is compared to expression of the target gene in a control sample (e.g., a biological sample from organism of interest expressing the target gene or a sample of cells in culture expressing the target gene) that is not contacted with the siRNA. Control samples (i.e., samples expressing the target gene) are assigned a value of 100%. Silencing, inhibition, or reduction of expression of a target gene is achieved when the value of the test sample relative to the control sample is about 95%, 90%, 85%, 80%, 75%, 70%, 65%, 60%, 55%, 50%, 45%, 40%, 35%, 30%, 25%, 20%, or 10%. Suitable assays include, e.g., examination of protein or mRNA levels using techniques known to those of skill in the art such as dot blots, northern blots, in situ hybridization, ELISA, immunoprecipitation, enzyme function, as well as phenotypic assays known to those of skill in the art.

"Nucleic acid" refers to deoxyribonucleotides or ribonucleotides and polymers thereof in single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

An "effective amount" or "therapeutically effective amount" of a siRNA is an amount sufficient to produce the desired effect, e.g., a decrease in the expression of a target sequence in comparison to the normal expression level detected in the absence of the siRNA.

The term "lipid" refers to a group of organic compounds that include, but are not limited to, esters of fatty acids and are characterized by being insoluble in water, but soluble in many organic solvents. They are usually divided into at least three classes: (1) "simple lipids' which include fats and oils as well as waxes; (2) "compound lipids" which include phospholipids and glycolipids; (3) "derived lipids" such as steroids.

"Lipid vesicle" refers to any lipid composition that can be used to deliver a compound including, but not limited to, liposomes, wherein an aqueous volume is encapsulated by an amphipathic lipid bilayer; or wherein the lipids coat an interior comprising a large molecular component, such as a plasmid comprising an interfering RNA sequence, with a reduced aqueous interior; or lipid aggregates or micelles, wherein the encapsulated component is contained within a relatively disordered lipid mixture.

As used herein, "lipid encapsulated" can refer to a lipid formulation that provides a compound with full encapsulation, partial encapsulation, or both. In some embodiments, the nucleic acid is fully encapsulated in the lipid formulation (e.g., to form an SPLP, pSPLP, SNALP, or other nucleic acid-lipid particle).

As used herein, the term "cell proliferative disorder" includes disorders involving the undesired proliferation of a cell. Non-limiting examples of such disorders include neoplasias (i.e., cancer), hyperplasias, restenosis, cardiac hypertrophy, immune disorders and inflammation.

The nucleic acid-lipid particles of the present invention typically have a mean diameter of less than about 150 nm and are substantially nontoxic. In addition, the nucleic acids when present in the nucleic acid-lipid particles of the present invention are resistant in aqueous solution to degradation with a nuclease. Nucleic acid-lipid particles and their method of preparation are disclosed in U.S. Pat. No. 5,976,567, U.S. Pat. No. 5,981,501 and PCT Patent Publication No. WO 96/40964.

Various suitable cationic lipids may be used in the present invention, either alone or in combination with one or more other cationic lipid species or non-cationic lipid species.

The cationic lipids of Formula I and Formula II described herein typically carry a net positive charge at a selected pH, such as physiological pH. It has been surprisingly found that cationic lipids comprising alkyl chains with multiple sites of unsaturation, e.g., at least two or three sites of unsaturation, are particularly useful for forming lipid-nucleic acid particles with increased membrane fluidity. A number of cationic lipids and related analogs, which are also useful in the present invention, have been described in U.S. Pat. Nos. 5,208,036, 5,264,618, 5,279,833 and 5,283,185, and WO 96/10390, the disclosures of which are incorporated herein by reference.

The noncationic lipids used in the present invention can be any of a variety of neutral uncharged, zwitterionic or anionic lipids capable of producing a stable complex. They are preferably neutral, although they can alternatively be negatively charged. Examples of noncationic lipids useful in the present invention include: phospholipid-related materials, such as lecithin, phosphatidylethanolamine, lysolecithin, lysophosphatidylethanolamine, phosphatidylserine, phosphatidylinositol, sphingomyelin, cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal). Noncationic lipids or sterols such as cholesterol may be present. Additional nonphosphorous containing lipids are, e.g., stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyloxylated fatty acid amides, dioctadecyldimethyl ammonium bromide and the like, diacylphosphatidylcholine, diacylphosphatidylethanolamine, ceramide, sphingomyelin, cephalin, and cerebrosides. Other lipids such as lysophosphatidylcholine and lysophosphatidylethanolamine may be present. Noncationic lipids also include polyethylene glycol-based polymers such as PEG 2000, PEG 5000 and polyethylene glycol conjugated to phospholipids or to ceramides (referred to as PEG-Cer).

In preferred embodiments, the noncationic lipids are diacylphosphatidylcholine (e.g., distearoylphosphatidylcholine, dioleoylphosphatidylcholine, dipalmitoylphosphatidylcholine and dilinoleoylphosphatidylcholine), diacylphosphatidylethanolamine (e.g. dioleoylphosphatidylethanolamine and palmitoyloleoylphosphatidylethanolamine), ceramide or sphingomyelin. The acyl groups in these lipids are preferably acyl groups derived from fatty acids having $C_{10}$-$C_{24}$ carbon chains. More preferably the acyl groups are lauroyl, myristoyl, palmitoyl, stearoyl or oleoyl. In particularly preferred embodiments, the noncationic lipid will be cholesterol, 1,2-sn-dioleoylphosphatidylethanolamine, or egg sphingomyelin (ESM).

In addition to cationic and non-cationic lipids, the nucleic acid-lipid particles (e.g., SPLPs and SNALPs of the present invention comprise bilayer stabilizing component (BSC) such as an ATTA-lipid or a PEG-lipid, such as PEG coupled to dialkyloxypropyls (PEG-DAA) (see, copending U.S. Patent Application No. 60/503,239), PEG coupled to diacylglycerol (PEG-DAG) (see, copending U.S. patent application Ser. No. 10/136,707), PEG coupled to phosphatidylethanolamine (PE) (PEG-PE), or PEG conjugated to ceramides, or a mixture thereof (see, U.S. Pat. No. 5,885,613, which is incorporated herein by reference). In one preferred embodiment, the BSC is a conjugated lipid that inhibits aggregation of the nucleic acid-lipid particles. Suitable conjugated lipids include, but are not limited to PEG-lipid conjugates, ATTA-lipid conjugates, cationic-polymer-lipid conjugates (CPLs) or mixtures thereof. In one preferred embodiment, the nucleic acid-lipid particles comprise either a PEG-lipid conjugate or an ATTA-lipid conjugate together with a CPL.

PEG is a polyethylene glycol, a linear, water-soluble polymer of ethylene PEG repeating units with two terminal hydroxyl groups. PEGs are classified by their molecular weights; for example, PEG 2000 has an average molecular weight of about 2,000 daltons, and PEG 5000 has an average molecular weight of about 5,000 daltons. PEGs are commercially available from Sigma Chemical Co. and other companies and include, for example, the following: monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH$_2$), monomethoxypolyethylene glycol-tresylate (MePEG-TRES), and monomethoxypolyethylene glycol-imidazolyl-carbonyl (MePEG-IM). In addition, monomethoxypolyethyleneglycol-acetic acid (MePEG-CH$_2$COOH), is particularly useful for preparing the PEG-lipid conjugates including, e.g., PEG-DAA conjugates.

In some embodiments, the PEG has an average molecular weight of from about 1000 to about 5000 daltons, more preferably, from about 1,000 to about 3,000 daltons and, even more preferably, of about 2,000 daltons. The PEG can be optionally substituted by an alkyl, alkoxy, acyl or aryl group. PEG can be conjugated directly to the lipid or may be linked to the lipid via a linker moiety. Any linker moiety suitable for coupling the PEG to a lipid can be used including, e.g., non-ester containing linker moieties and ester-containing linker moieties.

As used herein, the term "non-ester containing linker moiety" refers to a linker moiety that does not contain a carboxylic ester bond (—OC(O)—). Suitable non-ester containing linker moieties include, but are not limited to, amido (—C(O) NH—), amino (—NR—), carbonyl (—C(O)—), carbamate (—NHC(O)O—), urea (—NHC(O)NH—), disulphide (—S—S—), ether (—O—), succinyl (—(O)CCH$_2$CH$_2$C(O)—), succinamidyl (—NHC(O)CH$_2$CH$_2$C(O)NH—), ether, disulphide, etc. as well as combinations thereof (such as a linker containing both a carbamate linker moiety and an amido linker moiety). In some embodiments, a carbamate linker is used to couple the PEG to the lipid.

In other embodiments, an ester containing linker moiety is used to couple the PEG to the lipid. Suitable ester containing linker moieties include, e.g., carbonate (—OC(O)O—), succinoyl, phosphate esters (—O—(O)POH—O—), sulfonate esters, and combinations thereof.

As used herein, the term "SNALP" refers to a stable nucleic acid-lipid particle, including SPLP. A SNALP represents a vesicle of lipids coating a reduced aqueous interior comprising a nucleic acid (e.g., ssDNA, dsDNA, ssRNA, dsRNA, siRNA, or a plasmid, including plasmids from which an interfering RNA is transcribed). As used herein, the term "SPLP" refers to a nucleic acid-lipid particle comprising a nucleic acid (e.g., a plasmid) encapsulated within a lipid vesicle. SNALPs and SPLPs typically contain a cationic lipid, a noncationic lipid, and a lipid that prevents aggregation of the particle (e.g., a PEG-lipid conjugate). SNALPs and SPLPs have systemic application as they exhibit extended circulation lifetimes following intravenous (i.v.) injection, accumulate at distal sites (e.g., sites physically separated from the administration site) and can mediate gene silencing or gene expression of a transfected nucleic acid at these distal sites. SPLPs include "pSPLP" which comprise an encapsulated condensing agent-nucleic acid complex as set forth in WO 00/03683.

The term "vesicle-forming lipid" is intended to include any amphipathic lipid having a hydrophobic moiety and a polar head group, and which by itself can form spontaneously into bilayer vesicles in water, as exemplified by most phospholipids.

The term "vesicle-adopting lipid" is intended to include any amphipathic lipid that is stably incorporated into lipid bilayers in combination with other amphipathic lipids, with its hydrophobic moiety in contact with the interior, hydrophobic region of the bilayer membrane, and its polar head group moiety oriented toward the exterior, polar surface of the membrane. Vesicle-adopting lipids include lipids that on their own tend to adopt a nonlamellar phase, yet which are capable of assuming a bilayer structure in the presence of a bilayer-stabilizing component. A typical example is DOPE (dioleoylphosphatidylethanolamine). Bilayer stabilizing components include, but are not limited to, conjugated lipids that inhibit aggregation of the SNALPs, polyamide oligomers (e.g., ATTA-lipid derivatives), peptides, proteins, detergents, lipid-derivatives, PEG-lipid derivatives such as PEG coupled to dialkyloxypropyls, PEG coupled to diacylglycerols, PEG coupled to phosphatidyl-ethanolamines, and PEG conjugated to ceramides (see, U.S. Pat. No. 5,885,613, which is incorporated herein by reference).

The term "amphipathic lipid" refers, in part, to any suitable material wherein the hydrophobic portion of the lipid material orients into a hydrophobic phase, while the hydrophilic portion orients toward the aqueous phase. Amphipathic lipids are usually the major component of a lipid vesicle. Hydrophilic characteristics derive from the presence of polar or charged groups such as carbohydrates, phosphate, carboxylic, sulfato, amino, sulfhydryl, nitro, hydroxy and other like groups. Hydrophobicity can be conferred by the inclusion of apolar groups that include, but are not limited to, long chain saturated and unsaturated aliphatic hydrocarbon groups and such groups substituted by one or more aromatic, cycloaliphatic or heterocyclic group(s). Examples of amphipathic compounds include, but are not limited to, phospholipids, aminolipids and sphingolipids. Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine or dilinoleoylphosphatidylcholine. Other compounds lacking in phosphorus, such as sphingolipid, glycosphingolipid families, diacylglycerols and .beta.-acyloxyacids, are also within the group designated as amphipathic lipids. Additionally, the amphipathic lipid described above can be mixed with other lipids including triglycerides and sterols.

The term "neutral lipid" refers to any of a number of lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides and diacylglycerols.

The term "noncationic lipid" refers to any neutral lipid as described above as well as anionic lipids.

The term "anionic lipid" refers to any lipid that is negatively charged at physiological pH. These lipids include, but are not limited to, phosphatidylglycerol, cardiolipin, diacylphosphatidylserine, diacylphosphatidic acid, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids.

The term "cationic lipid" refers to any of a number of lipid species that carry a net positive charge at a selected pH, such as physiological pH (e.g., pH of about 7.0). As used herein, physiological pH refers to the pH of a biological fluid such as blood or lymph as well as the pH of a cellular compartment such as an endosome, an acidic endosome, or a lysosome). Such lipids include, but are not limited to, N,N-dioleyl-N,N-dimethylammonium chloride ("DODAC"); N-(2,3-dioleyloxy)propyl)-N,N,N-trimethylammonium chloride ("DOTMA"); N,N-distearyl-N,N-dimethylammonium bromide ("DDAB"); N-(2,3-dioleoyloxy)propyl)-N,N,N-trimethylammonium chloride ("DOTAP"); 3-(N—(N',N'-dimethylaminoethane)-carbamoyl)cholesterol ("DC-Chol"); N-(1,2-dimyristyloxyprop-3-yl)-N,N-dimethyl-N-hydroxyethyl ammonium bromide ("DMRIE"); 1,2-DiLinoleyloxy-N,N-dimethylaminopropane (DLinDMA); and 1,2-Dilinolenyloxy-N,N-dimethylaminopropane (DLenDMA). The following lipids are cationic and have a positive charge at below physiological pH or at physiological pH: DODAP, DODMA, DLinDMA and the like.

The term "hydrophobic lipid" refers to compounds having apolar groups that include, but are not limited to, long chain saturated and unsaturated aliphatic hydrocarbon groups and such groups optionally substituted by one or more aromatic, cycloaliphatic or heterocyclic group(s). Suitable examples include, but are not limited to, diacylglycerol, dialkylglycerol, N-N-dialkylamino, 1,2-diacyloxy-3-aminopropane and 1,2-dialkyl-3-aminopropane.

The term "fusogenic" refers to the ability of a liposome, an SNALP or other drug delivery system to fuse with membranes of a cell. The membranes can be either the plasma membrane or membranes surrounding organelles, e.g., endosome, nucleus, etc.

The term "diacylglycerol" refers to a compound having 2-fatty acyl chains, R$^1$ and R$^2$, both of which have independdently between 2 and 30 carbons bonded to the 1- and 2-position of glycerol by ester linkages. The acyl groups can be saturated or have varying degrees of unsaturation. Diacylglycerols have the following general formula:

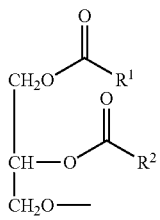
(III)

The term "dialkyloxypropyl" refers to a compound having 2-alkyl chains, $R^1$ and $R^2$, both of which have independently between 2 and 30 carbons. The alkyl groups can be saturated or have varying degrees of unsaturation. Dialkyloxypropyls have the following general formula:

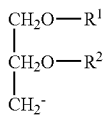
(IV)

The term "ATTA" or "polyamide" refers to, but is not limited to, compounds disclosed in U.S. Pat. Nos. 6,320,017 and 6,586,559, both of which are incorporated herein by reference. These compounds include a compound having the formula

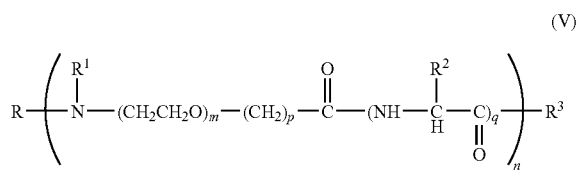
(V)

wherein: R is a member selected from the group consisting of hydrogen, alkyl and acyl; $R^1$ is a member selected from the group consisting of hydrogen and alkyl; or optionally, R and $R^1$ and the nitrogen to which they are bound form an azido moiety; $R^2$ is a member of the group selected from hydrogen, optionally substituted alkyl, optionally substituted aryl and a side chain of an amino acid; $R^3$ is a member selected from the group consisting of hydrogen, halogen, hydroxy, alkoxy, mercapto, hydrazino, amino and $NR^4R^5$, wherein $R^4$ and $R^5$ are independently hydrogen or alkyl; n is 4 to 80; m is 2 to 6; p is 1 to 4; and q is 0 or 1. It will be apparent to those of skill in the art that other polyamides can be used in the compounds of the present invention.

The term "nucleic acid" or "polynucleotide" refers to a polymer containing at least two ribonucleotides (e.g. deoxy or ribo) in either single- or double-stranded form. Unless specifically limited, the terms encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Cassol et al. (1992); Rossolini et al., *Mol. Cell. Probes* 8:91-98 (1994)). "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides. DNA may be in the form of antisense, plasmid DNA, parts of a plasmid DNA, pre-condensed DNA, product of a polymerase chain reaction (PCR), vectors (P1, PAC, BAC, YAC, artificial chromosomes), expression cassettes, chimeric sequences, chromosomal DNA, or derivatives of these groups. The term nucleic acid is used interchangeably with gene, cDNA, mRNA encoded by a gene, and an interfering RNA molecule.

The term "gene" refers to a nucleic acid (e.g., DNA or RNA) sequence that comprises partial length or entire length coding sequences necessary for the production of a polypeptide or precursor (e.g., Eg5, EGFR or XIAP).

"Gene product," as used herein, refers to a product of a gene such as an RNA transcript.

As used herein, the term "aqueous solution" refers to a composition comprising in whole, or in part, water.

As used herein, the term "organic lipid solution" refers to a composition comprising in whole, or in part, an organic solvent having a lipid.

"Distal site," as used herein, refers to a physically separated site, which is not limited to an adjacent capillary bed, but includes sites broadly distributed throughout an organism.

"Serum-stable" in relation to nucleic acid-lipid particles means that the particle is not significantly degraded after exposure to a serum or nuclease assay that would significantly degrade free DNA. Suitable assays include, for example, a standard serum assay or a DNAse assay such as those described in the Examples below.

"Fully encapsulated" in relation to nucleic acid-lipid particles means that the nucleic acid portion of the particle is serum stable and is not accessible to a fluorescent dye (e.g., such as RiboGreen™). In contrast to a nucleic acid that forms a complex with the lipid vehicle (e.g., a liposome or multilammelar vesicle), a nucleic acid fully encapsulated in the lipid portion of a particle does not fluoresce in the presence of a fluorescent dye.

"Systemic delivery," as used herein, refers to delivery that leads to a broad biodistribution of a compound within an organism. Some techniques of administration can lead to the systemic delivery of certain compounds, but not others. Systemic delivery means that a useful, preferably therapeutic, amount of a compound is exposed to most parts of the body. To obtain broad biodistribution generally requires a blood lifetime such that the compound is not rapidly degraded or cleared (such as by first pass organs (liver, lung, etc.) or by rapid, nonspecific cell binding) before reaching a disease site distal to the site of administration. Systemic delivery of nucleic acid-lipid particles can be by any means known in the art including, for example, intravenous, subcutaneous, intraperitoneal, In some embodiments, systemic delivery of nucleic acid-lipid particles is by intravenous delivery.

"Local delivery" as used herein refers to delivery of a compound directly to a target site within an organism. For example, a compound can be locally delivered by direct injection into a disease site such as a tumor or other target site such as a site of inflammation or a target organ such as the liver, heart, pancreas, kidney, and the like.

III. Carrier Systems Containing siRNA

In one aspect, the present invention provides carrier systems containing the siRNA molecules described herein. In some embodiments, the carrier system is a lipid-based carrier system such as a stabilized nucleic acid-lipid particle (e.g., SNALP or SPLP), cationic lipid or liposome nucleic acid complexes (i.e., lipoplexes), a liposome, a micelle, a virosome, or a mixture thereof. In other embodiments, the carrier system is a polymer-based carrier system such as a cationic polymer-nucleic acid complex (i.e., polyplex). In additional embodiments, the carrier system is a cyclodextrin-based carrier system such as a cyclodextrin polymer-nucleic acid complex. In further embodiments, the carrier system is a protein-based carrier system such as a cationic peptide-nucleic acid complex. Preferably, the carrier system is a stabilized nucleic acid-lipid particle such as a SNALP or SPLP. One skilled in the art will appreciate that the siRNA molecules of the present invention can also be delivered as naked siRNA.

IV. Stable Nucleic Acid-Lipid Particles (SNALPs) and Properties Thereof

The stable nucleic acid-lipid particles or, alternatively, SNALPs typically comprise an siRNA molecule that targets expression of a gene expressed in cancer (e.g., an Eg5, EGFR or XIAP gene), a cationic lipid (e.g., a cationic lipid of Formula I or II), a noncationic lipid and a bilayer stabilizing component (i.e., a conjugated lipid that inhibits aggregation of the SNALPs) The nucleic acid-lipid particles may comprise at least 1, 2, 3, 4, 5, or more of the sequences set forth in Tables 1-9.

The SNALPs of the present invention typically have a mean diameter of about 50 nm to about 150 nm, more typically about 60 nm to about 130 nm, more typically about 70 nm to about 110 nm, most typically about 70 to about 90 nm and are substantially nontoxic. In addition, the nucleic acids present in the SNALPs of the present invention are resistant in aqueous solution to degradation with a nuclease.

In one embodiment, the present invention provides stabilized nucleic acid-lipid particles (SPLPs or SNALPs) and other lipid-based carrier systems (e.g., a liposome, a micelle, a virosome, a lipid-nucleic acid particle, a nucleic acid complex and mixtures thereof) containing cationic lipids. The lipid-nucleic acid particles of the present invention typically comprise a nucleic acid, a cationic lipid, a non-cationic lipid and a PEG-lipid conjugate. The cationic lipid typically comprises from about 2 mol % to about 60 mol %, from about 5 mol % to about 50 mol %, from about 10 mol % to about 45 mol %, from about 20 mol % to about 40 mol %, or from about 30 mol % to about 40 mol % of the total lipid present in said particle. The non-cationic lipid typically comprises from about 5 mol % to about 90 mol %, from about 10 mol % to about 85 mol %, from about 20 mol % to about 80 mol %, from about 30 mol % to about 70 mol %, from about 40 mol % to about 60 mol % or about 48 mol % of the total lipid present in said particle. The PEG-lipid conjugate typically comprises from about 0.5 mol % to about 20 mol %, from about 1.5 mol % to about 18 mol %, from about 4 mol % to about 15 mol %, from about 5 mol % to about 12 mol %, or about 2 mol % of the total lipid present in said particle. The nucleic acid-lipid particles of the present invention may further comprise cholesterol. If present, the cholesterol typically comprises from about 0 mol % to about 10 mol %, about 2 mol % to about 10 mol %, about 10 mol % to about 60 mol %, from about 12 mol % to about 58 mol %, from about 20 mol % to about 55 mol %, or about 48 mol % of the total lipid present in said particle. It will be readily apparent to one of skill in the art that the proportions of the components of the nucleic acid-lipid particles may be varied. In a specific formulation, the total lipid in the nucleic acid-lipid particle comprises 48 mol % cholesterol; 10 mol % DSPC; 2 mol % PEG-cDMA; and 40 mol % DLinDMA of the total lipid present in said particle.

A. Cationic Lipids

Various suitable cationic lipids may be used in the present invention, either alone or in combination with one or more other cationic lipid species or neutral lipid species.

Suitable cationic lipids include, for example, DLinDMA, DLenDMA, DODAC, DOTMA, DDAB, DOTAP, DOSPA, DOGS, DC-Chol and DMRIE, or combinations thereof. A number of these lipids and related analogs, which are also useful in the present invention, have been described in U.S. Pat. Nos. 5,208,036, 5,264,618, 5,279,833, 5,283,185, 5,753, 613 and 5,785,992. Additionally, a number of commercial preparations of cationic lipids are available and can be used in the present invention. These include, for example, LIPOFECTIN® (commercially available cationic liposomes comprising DOTMA and DOPE, from GIBCO/BRL, Grand Island, N.Y., USA); LIPOFECTAMINE® (commercially available cationic liposomes comprising DOSPA and DOPE, from GIBCO/BRL); and TRANSFECTAM® (commercially available cationic liposomes comprising DOGS from Promega Corp., Madison, Wis., USA). In addition, cationic lipids of Formula I and Formula II can be used in the present invention. Cationic lipids of Formula I and II have the following structures:

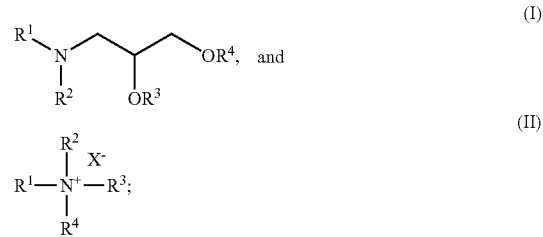

wherein $R^1$ and $R^2$ are independently selected and are H or $C_1$-$C_3$ alkyls. $R^3$ and $R^4$ are independently selected and are alkyl groups having from about 10 to about 20 carbon atoms; at least one of $R^3$ and $R^4$ comprises at least two sites of unsaturation. In one embodiment, $R^3$ and $R^4$ are both the same, i.e., $R^3$ and $R^4$ are both linoleyl (C18), etc. In another embodiment, $R^3$ and $R^4$ are different, i.e., $R^3$ is myristyl (C14) and $R^4$ is linoleyl (C18). In some embodiments, the cationic lipids of the present invention are symmetrical, i.e., $R^3$ and $R^4$ are both the same. In another preferred embodiment, both $R^3$ and $R^4$ comprise at least two sites of unsaturation. In some embodiments, $R^3$ and $R^4$ are independently selected from dodecadienyl, tetradecadienyl, hexadecadienyl, linoleyl, and icosadienyl. In some embodiments, $R^3$ and $R^4$ are both linoleyl. In some embodiments, $R^3$ and $R^4$ comprise at least three sites of unsaturation and are independently selected from, e.g., dodecatrienyl, tetradectrienyl, hexadecatrienyl, linolenyl, and icosatrienyl.

The cationic lipids of Formula I and Formula II described herein typically carry a net positive charge at a selected pH, such as physiological pH. It has been surprisingly found that cationic lipids comprising alkyl chains with multiple sites of unsaturation, e.g., at least two or three sites of unsaturation, are particularly useful for forming lipid-nucleic acid particles with increased membrane fluidity. A number of cationic lipids and related analogs, which are also useful in the present invention, have been described in U.S. Pat. Nos. 5,208,036, 5,264,618, 5,279,833 and 5,283,185, and WO 96/10390.

Additional suitable cationic lipids include, e.g., dioctadecyldimethylammonium ("DODMA"), Distearyldimethylammonium ("DSDMA"), N,N-dioleyl-N,N-dimethylammonium chloride ("DODAC"); N-(2,3-dioleyloxy)propyl)-N,N,N-trimethylammonium chloride ("DOTMA"); N,N-distearyl-N,N-dimethylammonium bromide ("DDAB"); N-(2,3-dioleoyloxy)propyl)-N,N,N-trimethylammonium chloride ("DOTAP"); 3-(N—(N',N'-dimethylaminoethane)-carbamoyl)cholesterol ("DC-Chol") and N-(1,2-dimyristyloxyprop-3-yl)-N,N-dimethyl-N-hydroxyethyl ammonium bromide ("DMRIE"). A number of these lipids and related analogs, which are also useful in the present invention, have been described in U.S. Pat. Nos. 5,208,036, 5,264,618, 5,279,833, 5,283,185, 5,753,613 and 5,785,992.

B. Non-Cationic Lipids

The noncationic lipids used in the present invention can be any of a variety of neutral uncharged, zwitterionic or anionic lipids capable of producing a stable complex. They are preferably neutral, although they can alternatively be negatively charged. Examples of noncationic lipids useful in the present invention include: phospholipid-related materials, such as lecithin, phosphatidylethanolamine, lysolecithin, lysophosphatidylethanolamine, phosphatidylserine, phosphatidylinositol, sphingomyelin, cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), and 1,2-dielaidoyl-sn-glycero-3-phophoethanolamine (trans-DOPE). Noncationic lipids or sterols such as cholesterol may be present. Additional nonphosphorous containing lipids are, e.g., stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyloxylated fatty acid amides, dioctadecyldimethyl ammonium bromide and the like, diacylphosphatidylcholine, diacylphosphatidylethanolamine, ceramide, sphingomyelin, cephalin, and cerebrosides. Other lipids such as lysophosphatidylcholine and lysophosphatidylethanolamine may be present. Noncationic lipids also include polyethylene glycol-based polymers such as PEG 2000, PEG 5000 and polyethylene glycol conjugated to phospholipids or to ceramides (referred to as PEG-Cer).

In preferred embodiments, the noncationic lipids are diacylphosphatidylcholine (e.g., distearoylphosphatidylcholine, dioleoylphosphatidylcholine, dipalmitoylphosphatidylcholine and dilinoleoylphosphatidylcholine), diacylphosphatidylethanolamine (e.g., dioleoylphosphatidylethanolamine and palmitoyloleoylphosphatidylethanolamine), ceramide or sphingomyelin. The acyl groups in these lipids are preferably acyl groups derived from fatty acids having $C_{10}$-$C_{24}$ carbon chains. More preferably the acyl groups are lauroyl, myristoyl, palmitoyl, stearoyl or oleoyl. In particularly preferred embodiments, the noncationic lipid will be cholesterol, 1,2-sn-dioleoylphosphatidylethanolamine, or egg sphingomyelin (ESM).

C. Bilayer Stabilizing Component

In addition to cationic and non-cationic lipids, the nucleic acid-lipid particles (e.g., SNALPs and SPLPs) of the present invention comprise bilayer stabilizing component (BSC) such as an ATTA-lipid or a PEG-lipid, such as PEG coupled to dialkyloxypropyls (PEG-DAA) as described in, e.g., WO 05/026372, PEG coupled to diacylglycerol (PEG-DAG) as described in, e.g., U.S. Patent Publication Nos. 20030077829 and 2005008689), PEG coupled to phosphatidylethanolamine (PE) (PEG-PE), or PEG conjugated to ceramides, or a mixture thereof (see, U.S. Pat. No. 5,885,613). In one preferred embodiment, the BSC is a conjugated lipid that inhibits aggregation of the nucleic acid-lipid particles. Suitable conjugated lipids include, but are not limited to PEG-lipid conjugates, ATTA-lipid conjugates, cationic-polymer-lipid conjugates (CPLs) or mixtures thereof. In one preferred embodiment, the nucleic acid-lipid particles comprise either a PEG-lipid conjugate or an ATTA-lipid conjugate together with a CPL.

PEG is a polyethylene glycol, a linear, water-soluble polymer of ethylene PEG repeating units with two terminal hydroxyl groups. PEGs are classified by their molecular weights; for example, PEG 2000 has an average molecular weight of about 2,000 daltons, and PEG 5000 has an average molecular weight of about 5,000 daltons. PEGs are commercially available from Sigma Chemical Co. and other companies and include, for example, the following: monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH$_2$), monomethoxypolyethylene glycol-tresylate (MePEG-TRES), and monomethoxypolyethylene glycol-imidazolyl-carbonyl (MePEG-IM). In addition, monomethoxypolyethyleneglycol-acetic acid (MePEG-CH$_2$COOH), is particularly useful for preparing the PEG-lipid conjugates including, e.g., PEG-DAA conjugates.

In some embodiments, the PEG has an average molecular weight of from about 550 daltons to about 10,000 daltons, more preferably of about 750 daltons to about 5,000 daltons, more preferably of about 1,000 daltons to about 5,000 daltons, more preferably of about 1,500 daltons to about 3,000 daltons and, even more preferably, of about 2,000 daltons, or about 750 daltons. The PEG can be optionally substituted by an alkyl, alkoxy, acyl or aryl group. PEG can be conjugated directly to the lipid or may be linked to the lipid via a linker moiety. Any linker moiety suitable for coupling the PEG to a lipid can be used including, e.g., non-ester containing linker moieties and ester-containing linker moieties. In some embodiments, the linker moiety is a non-ester containing linker moiety. As used herein, the term "non-ester containing linker moiety" refers to a linker moiety that does not contain a carboxylic ester bond (—OC(O)—). Suitable non-ester containing linker moieties include, but are not limited to, amido (—C(O)NH—), amino (—NR—), carbonyl (—C(O)—), carbamate (—NHC(O)O—), urea (—NHC(O)NH—), disulphide (—S—S—), ether (—O—), succinyl (—(O)CCH₂CH₂C(O)—), succinamidyl (—NHC(O)CH₂CH₂C(O)NH—), ether, disulphide, etc. as well as combinations thereof (such as a linker containing both a carbamate linker moiety and an amido linker moiety). In some embodiments, a carbamate linker is used to couple the PEG to the lipid.

In other embodiments, an ester containing linker moiety is used to couple the PEG to the lipid. Suitable ester containing linker moieties include, e.g., carbonate (—OC(O)O—), succinoyl, phosphate esters (—O—(O)POH—O—), sulfonate esters, and combinations thereof.

Phosphatidylethanolamines having a variety of acyl chain groups of varying chain lengths and degrees of saturation can be conjugated to polyethyleneglycol to form the bilayer stabilizing component. Such phosphatidylethanolamines are commercially available, or can be isolated or synthesized using conventional techniques known to those of skilled in the art. Phosphatidylethanolamines containing saturated or unsaturated fatty acids with carbon chain lengths in the range of $C_{10}$ to $C_{20}$ are preferred. Phosphatidylethanolamines with mono- or diunsaturated fatty acids and mixtures of saturated and unsaturated fatty acids can also be used. Suitable phosphatidylethanolamines include, but are not limited to, the following: dimyristoylphosphatidylethanolamine (DMPE), dipalmitoylphosphatidylethanolamine (DPPE), dioleoylphosphatidylethanolamine (DOPE) and distearoylphosphatidylethanolamine (DSPE).

In some embodiments, the PEG-lipid is a PEG-DAA conjugate has the following formula:

(VI)

In Formula VI, $R^1$ and $R^2$ are independently selected and are alkyl groups having from about 10 to about 22 carbon atoms. The long-chain alkyl groups can be saturated or unsaturated. Suitable alkyl groups include, but are not limited to, lauryl (C12), myristyl (C14), palmityl (C16), stearyl (C18) and icosyl (C20). In some embodiments, $R^1$ and $R^2$ are the same, i.e., $R^1$ and $R^2$ are both myristyl (i.e., dimyristyl), $R^1$ and $R^2$ are both stearyl (i.e., distearyl), etc. In some embodiments, the alkyl groups are saturated.

In Formula VI above, "PEG" is a polyethylene glycol having an average molecular weight ranging of about 550 daltons to about 10,000 daltons, about 750 daltons to about 5,000 daltons, about 1,000 daltons to about 5,000 daltons, about 1,500 daltons to about 3,000 daltons, about 2,000 daltons, or about 750 daltons. The PEG can be optionally substituted with alkyl, alkoxy, acyl or aryl. In some embodiments, the terminal hydroxyl group is substituted with a methoxy or methyl group.

In Formula VI, above, "L" is a non-ester containing linker moiety or an ester containing linker moiety. In some embodiments, L is a non-ester containing linker moiety. Suitable non-ester containing linkers include, but not limited to, an amido linker moiety, an amino linker moiety, a carbonyl linker moiety, a carbamate linker moiety, a urea linker moiety, an ether linker moiety, a disulphide linker moiety, a succinamidyl linker moiety and combinations thereof. In some embodiments, the non-ester containing linker moiety is a carbamate linker moiety (i.e., a PEG-C-DAA conjugate), an amido linker moiety (i.e., a PEG-A-DAA conjugate), or a succinamidyl linker moiety (i.e., a PEG-S-DAA conjugate).

The PEG-DAA conjugates are synthesized using standard techniques and reagents known to those of skill in the art. It will be recognized that the PEG-DAA conjugates will contain various amide, amine, ether, thio, carbamate and urea linkages. Those of skill in the art will recognize that methods and reagents for forming these bonds are well known and readily available. See, e.g., March, ADVANCED ORGANIC CHEMISTRY (Wiley 1992), Larock, COMPREHENSIVE ORGANIC TRANSFORMATIONS (VCH 1989); and Fumiss, VOGEL'S TEXTBOOK OF PRACTICAL ORGANIC CHEMISTRY 5th ed. (Longman 1989). It will also be appreciated that any functional groups present may require protection and deprotection at different points in the synthesis of the PEG-DAA conjugates. Those of skill in the art will recognize that such techniques are well known. See, e.g., Green and Wuts, PROTECTIVE GROUPS IN ORGANIC SYNTHESIS (Wiley 1991).

In some embodiments, the PEG-DAA conjugate is a dilauryloxypropyl (C12)-PEG conjugate, dimyristyloxypropyl (C14)-PEG conjugate, a dipalmitoyloxypropyl (C16)-PEG conjugate or a disteryloxypropyl (C18)-PEG conjugate. Those of skill in the art will readily appreciate that other dialkyloxypropyls can be used in the PEG-DAA conjugates of the present invention.

In addition to the foregoing, it will be readily apparent to those of skill in the art that other hydrophilic polymers can be used in place of PEG. Examples of suitable polymers that can be used in place of PEG include, but are not limited to, polyvinylpyrrolidone, polymethyloxazoline, polyethyloxazoline, polyhydroxypropyl methacrylamide, polymethacrylamide and polydimethylacrylamide, polylactic acid, polyglycolic acid, and derivatized celluloses, such as hydroxymethylcellulose or hydroxyethylcellulose.

In addition to the foregoing components, the SNALPs and SPLPs of the present invention can further comprise cationic poly(ethylene glycol) (PEG) lipids, or CPLs, that have been designed for insertion into lipid bilayers to impart a positive charge(see, Chen, et al., *Bioconj. Chem.* 11:433-437 (2000)). Suitable SPLPs and SPLP-CPLs for use in the present invention, and methods of making and using SPLPs and SPLP-CPLs, are disclosed, e.g., in U.S. Pat. No. 6,852,334 and WO 00/62813. Cationic polymer lipids (CPLs) useful in the present invention have the following architectural features: (1) a lipid anchor, such as a hydrophobic lipid, for incorporating the CPLs into the lipid bilayer; (2) a hydrophilic spacer, such as a polyethylene glycol, for linking the lipid anchor to a cationic head group; and (3) a polycationic moiety, such as a naturally occurring amino acid, to produce a protonizable cationic head group.

Suitable CPL include compounds of Formula VII:

(VII)

wherein A, W and Y are as described below.

With reference to Formula VII, "A" is a lipid moiety such as an amphipathic lipid, a neutral lipid or a hydrophobic lipid that acts as a lipid anchor. Suitable lipid examples include vesicle-forming lipids or vesicle adopting lipids and include, but are not limited to, diacylglycerolyls, dialkylglycerolyls, N-N-dialkylaminos, 1,2-diacyloxy-3-aminopropanes and 1,2-dialkyl-3-aminopropanes.

"W" is a polymer or an oligomer, such as a hydrophilic polymer or oligomer. Typically, the hydrophilic polymer is a biocompatable polymer that is nonimmunogenic or possesses low inherent immunogenicity. Alternatively, the hydrophilic polymer can be weakly antigenic if used with appropriate adjuvants. Suitable nonimmunogenic polymers include, but are not limited to, PEG, polyamides, polylactic acid, polyglycolic acid, polylactic acid/polyglycolic acid copolymers and combinations thereof. In some embodiments, the polymer has a molecular weight of about 250 to about 7000 daltons.

"Y" is a polycationic moiety. The term polycationic moiety refers to a compound, derivative, or functional group having a positive charge, typically at least 2 positive charges at a selected pH, typically physiological pH. Suitable polycationic moieties include basic amino acids and their derivatives such as arginine, asparagine, glutamine, lysine and histidine; spermine; spermidine; cationic dendrimers; polyamines; polyamine sugars; and amino polysaccharides. The polycationic moieties can be linear, such as linear tetralysine, branched or dendrimeric in structure. Polycationic moieties have between about 2 to about 15 positive charges, between about 2 to about 12 positive charges, or between about 2 to about 8 positive charges at selected pH values. The selection of which polycationic moiety to employ may be determined by the type of liposome application which is desired.

The charges on the polycationic moieties can be either distributed around the entire liposome moiety, or alternatively, they can be a discrete concentration of charge density in one particular area of the liposome moiety e.g., a charge spike. If the charge density is distributed on the liposome, the charge density can be equally distributed or unequally distributed. All variations of charge distribution of the polycationic moiety are encompassed by the present invention.

The lipid "A," and the nonimmunogenic polymer "W," can be attached by various methods and preferably, by covalent attachment. Methods known to those of skill in the art can be used for the covalent attachment of "A" and "W." Suitable linkages include, but are not limited to, amide, amine, carboxyl, carbonate, carbamate, ester and hydrazone linkages. It will be apparent to those skilled in the art that "A" and "W" must have complementary functional groups to effectuate the linkage. The reaction of these two groups, one on the lipid and the other on the polymer, will provide the desired linkage. For example, when the lipid is a diacylglycerol and the terminal hydroxyl is activated, for instance with NHS and DCC, to form an active ester, and is then reacted with a polymer which contains an amino group, such as with a polyamide (see, U.S. Pat. Nos. 6,320,017 and 6,586,559), an amide bond will form between the two groups.

In certain instances, the polycationic moiety can have a ligand attached, such as a targeting ligand or a chelating moiety for complexing calcium. Preferably, after the ligand is attached, the cationic moiety maintains a positive charge. In certain instances, the ligand that is attached has a positive charge. Suitable ligands include, but are not limited to, a compound or device with a reactive functional group and include lipids, amphipathic lipids, carrier compounds, bioaffinity compounds, biomaterials, biopolymers, biomedical devices, analytically detectable compounds, therapeutically active compounds, enzymes, peptides, proteins, antibodies, immune stimulators, radiolabels, fluorogens, biotin, drugs, haptens, DNA, RNA, polysaccharides, liposomes, virosomes, micelles, immunoglobulins, functional groups, other targeting moieties, or toxins.

D. Nucleic Acid Component

The nucleic acid component of the present invention comprises an interfering RNA that silences (e.g., partially or completely inhibits) expression of a gene of interest (e.g., an Eg5, EGFR and/or XIAP gene). An interfering RNA can be provided in several forms. For example an interfering RNA can be provided as one or more isolated small-interfering RNA (siRNA) duplexes, longer double-stranded RNA (dsRNA) or as siRNA or dsRNA transcribed from a transcriptional cassette in a DNA plasmid. The interfering RNA can be administered alone or in combination with the administration of conventional agents used to treat the disease or disorder associated with the gene of interest including, e.g., cancer. Genes of interest include, but are not limited to, genes associated with viral infection and survival, genes associated with liver and kidney diseases and disorders, genes associated with tumorigenesis and cell transformation, angiogenic genes, immunomodulator genes, such as those associated with inflammatory and autoimmune responses, ligand receptor genes, and genes associated with neurodegenerative disorders.

E. siRNAs

The siRNAs of the invention are capable of silencing expression of a target sequence such as, e.g., Eg5, EGFR or XIAP mRNA. Suitable siRNA sequences are set forth in, e.g., Tables 1-2 and 7 for Eg5; Tables 3-4 and 9 for EGFR; or Tables 5-6 and 9 for XIAP. For any of the sequences set forth in the Tables above, thymines (i.e., T) can substituted with uracil ("U") and uracil can be substituted with ("T"). In some embodiments, the siRNA are about 15 to 30 nucleotides in length.

1. Selecting siRNA Sequences

Suitable siRNA sequences can be identified using any means known in the art. Typically, the methods described in Elbashir et al., *Nature,* 411:494-498 (2001) and Elbashir et al., *EMBO J,* 20:6877-6888 (2001) are combined with rational design rules set forth in Reynolds et al., *Nature Biotech.,* 22:326-330 (2004).

Generally, the nucleotide sequence 3' of the AUG start codon of a transcript from the target gene of interest is scanned for dinucleotide sequences (e.g., AA, NA, CC, GG, or UU, wherein N=C, G, or U) (see, e.g., Elbashir et al., *EMBO J,* 20:6877-6888 (2001)). The nucleotides immediately 3' to the dinucleotide sequences are identified as potential siRNA sequences (i.e., a target sequence or a sense strand sequence). Typically, the 19, 21, 23, 25, 27, 29, 31, 33, 35, or more nucleotides immediately 3' to the dinucleotide sequences are identified as potential siRNA sequences. In some embodiments, the dinucleotide sequence is an AA or NA sequence and the 19 nucleotides immediately 3' to the AA or NA dinucleotide are identified as a potential siRNA sequences. siRNA sequences are usually spaced at different positions along the length of the target gene. To further enhance silencing efficiency of the siRNA sequences, potential siRNA sequences may be analyzed to identify sites that do not contain regions of homology to other coding sequences, e.g., in the target cell or organism. For example, a suitable siRNA sequence of about 21 base pairs typically will not have more than 16-17 contiguous base pairs of homology to coding sequences in the target cell or organism. If the siRNA sequences are to be expressed from an RNA Pol III promoter, siRNA sequences lacking more than 4 contiguous A's or T's are selected.

Once a potential siRNA sequence has been identified, the sequence can be analyzed using a variety of criteria known in the art. For example, to enhance their silencing efficiency, the siRNA sequences may be analyzed by a rational design algorithm to identify sequences that have one or more of the following features: (1) G/C content of about 25% to about 60% G/C; (2) at least 3 A/Us at positions 15-19 of the sense strand; (3) no internal repeats; (4) an A at position 19 of the sense strand; (5) an A at position 3 of the sense strand; (6) a U at position 10 of the sense strand; (7) no G/C at position 19 of the sense strand; and (8) no G at position 13 of the sense strand. siRNA design tools that incorporate algorithms that assign suitable values of each of these features are useful for selection of siRNA. One of skill in the art will appreciate that sequences with one or more of the foregoing characteristics may be selected for further analysis and testing as potential siRNA sequences.

Additionally, potential siRNA target sequences with one or more of the following criteria can often be eliminated as siRNA: (1) sequences comprising a stretch of 4 or more of the same base in a row; (2) sequences comprising homopolymers of Gs (i.e., to reduce possible non-specific effects due to structural characteristics of these polymers; (3) sequences comprising triple base motifs (e.g., GGG, CCC, AAA, or TTT); (4) sequences comprising stretches of 7 or more G/Cs in a row; and (5) sequences comprising direct repeats of 4 or more bases within the candidates resulting in internal foldback structures. However, one of skill in the art will appreciate that sequences with one or more of the foregoing characteristics may still be selected for further analysis and testing as potential siRNA sequences.

In some embodiments, potential siRNA target sequences may be further analyzed based on siRNA duplex asymmetry as described in, e.g., Khvorova et al., *Cell*, 115:209-216 (2003); and Schwarz et al., *Cell*, 115:199-208 (2003). In other embodiments, potential siRNA target sequences may be further analyzed based on secondary structure at the mRNA target site as described in, e.g., Luo et al., *Biophys. Res. Commun.*, 318:303-310 (2004). For example, mRNA secondary structure can be modeled using the Mfold algorithm to select siRNA sequences which favor accessibility at the mRNA target site where less secondary structure in the form of base-pairing and stem-loops is present.

Once a potential siRNA sequence has been identified, the sequence can be analyzed for the presence of any immunostimulatory properties, e.g., using an in vitro cytokine assay or an in vivo animal model. Motifs in the sense and/or antisense strand of the siRNA sequence such as GU-rich motifs (e.g., 5'-GU-3',5'-UGU-3',5'-GUGU-3',5'-UGUGU-3', etc.) can also provide an indication of whether the sequence may be immunostimulatory. Once an siRNA molecule is found to be immunostimulatory, it can then be modified to decrease its immunostimulatory properties as described herein. As a non-limiting example, an siRNA sequence can be contacted with a mammalian responder cell under conditions such that the cell produces a detectable immune response to determine whether the siRNA is an immunostimulatory or a non-immunostimulatory siRNA. The mammalian responder cell may be from a naïve mammal (i.e., a mammal that has not previously been in contact with the siRNA sequence). The mammalian responder cell may be, e.g., a peripheral blood mononuclear cell (PBMC), a macrophage, and the like. The detectable immune response may comprise production of a cytokine or growth factor such as, e.g., TNF-α, IFN-α, IFN-β, IFN-γ, IL-6, IL-12, or a combination thereof. An siRNA molecule identified as being immunostimulatory can then be modified to decrease its immunostimulatory properties by replacing at least one of the nucleotides on the sense and/or antisense strand with modified nucleotides. For example, less than about 30% (e.g., less than about 30%, 25%, 20%, 15%, 10%, or 5%) of the nucleotides in the double-stranded region of the siRNA duplex can be replaced with modified nucleotides such as 2'OMe nucleotides. The modified siRNA can then be contacted with a mammalian responder cell as described above to confirm that its immunostimulatory properties have been reduced or abrogated.

Suitable in vitro assays for detecting an immune response include, but are not limited to, the double monoclonal antibody sandwich immunoassay technique of David et al. (U.S. Pat. No. 4,376,110); monoclonal-polyclonal antibody sandwich assays (Wide et al., in Kirkham and Hunter, eds., *Radioimmunoassay Methods*, E. and S. Livingstone, Edinburgh (1970)); the "Western blot" method of Gordon et al. (U.S. Pat. No. 4,452,901); immunoprecipitation of labeled ligand (Brown et al., *J. Biol. Chem.*, 255:4980-4983 (1980)); enzyme-linked immunosorbent assays (ELISA) as described, for example, by Raines et al., *J. Biol. Chem.*, 257:5154-5160 (1982); immunocytochemical techniques, including the use of fluorochromes (Brooks et al., *Clin. Exp. Immunol.*, 39:477 (1980)); and neutralization of activity (Bowen-Pope et al., *Proc. Natl. Acad. Sci. USA*, 81:2396-2400 (1984)). In addition to the immunoassays described above, a number of other immunoassays are available, including those described in U.S. Pat. Nos. 3,817,827; 3,850,752; 3,901,654; 3,935,074; 3,984,533; 3,996,345; 4,034,074; and 4,098,876.

A non-limiting example of an in vivo model for detecting an immune response includes an in vivo mouse cytokine induction assay that can be performed as follows: (1) siRNA can be administered by standard intravenous injection in the lateral tail vein; (2) blood can be collected by cardiac puncture about 6 hours after administration and processed as plasma for cytokine analysis; and (3) cytokines can be quantified using sandwich ELISA kits according to the manufacturer's instructions (e.g., mouse and human IFN-α (PBL Biomedical; Piscataway, N.J.); human IL-6 and TNF-α (eBioscience; San Diego, Calif.); and mouse IL-6, TNF-α, and IFN-γ (BD Biosciences; San Diego, Calif.)).

Monoclonal antibodies that specifically bind cytokines and growth factors are commercially available from multiple sources and can be generated using methods known in the art (see, e.g., Kohler and Milstein, *Nature*, 256: 495-497 (1975); and Harlow and Lane, ANTIBODIES, A LABORATORY MANUAL, Cold Spring Harbor Publication, New York (1999)). Generation of monoclonal antibodies has been previously described and can be accomplished by any means known in the art (see, e.g., Buhring et al. in Hybridoma, Vol. 10, No. 1, pp. 77-78 (1991)). In some methods, the monoclonal antibody is labeled (e.g., with any composition detectable by spectroscopic, photochemical, biochemical, electrical, optical, chemical means, and the like) to facilitate detection.

F. Generating siRNA Molecules siRNA molecules can be provided in several forms including, e.g., as one or more isolated small-interfering RNA (siRNA) duplexes, as longer double-stranded RNA (dsRNA), or as siRNA or dsRNA transcribed from a transcriptional cassette in a DNA plasmid. The siRNA sequences may have overhangs (e.g., 3' or 5' overhangs as described in Elbashir et al., *Genes Dev.*, 15:188 (2001) or Nykänen et al., *Cell*, 107: 309 (2001)), or may lack overhangs (i.e., have blunt ends).

An RNA population can be used to provide long precursor RNAs, or long precursor RNAs that have substantial or complete identity to a selected target sequence can be used to make the siRNA. The RNAs can be isolated from cells or tissue, synthesized, and/or cloned according to methods well known to those of skill in the art. The RNA can be a mixed population (obtained from cells or tissue, transcribed from cDNA, subtracted, selected, etc.), or can represent a single target sequence. RNA can be naturally occurring (e.g., isolated from tissue or cell samples), synthesized in vitro (e.g., using T7 or SP6 polymerase and PCR products or a cloned cDNA), or chemically synthesized.

To form a long dsRNA, for synthetic RNAs, the complement is also transcribed in vitro and hybridized to form a dsRNA. If a naturally occurring RNA population is used, the RNA complements are also provided (e.g., to form dsRNA for digestion by *E. coli* RNAse III or Dicer), e.g., by transcribing cDNAs corresponding to the RNA population, or by using RNA polymerases. The precursor RNAs are then hybridized to form double stranded RNAs for digestion. The dsRNAs can be directly administered to a subject or can be digested in vitro prior to administration.

Alternatively, one or more DNA plasmids encoding one or more siRNA templates are used to provide siRNA. siRNA can be transcribed as sequences that automatically fold into duplexes with hairpin loops from DNA templates in plasmids having RNA polymerase III transcriptional units, for example, based on the naturally occurring transcription units for small nuclear RNA U6 or human RNase P RNA H1 (see, Brummelkamp et al., *Science*, 296:550 (2002); Donzé et al., *Nucleic Acids Res.*, 30:e46 (2002); Paddison et al., *Genes Dev.*, 16:948 (2002); Yu et al., *Proc. Natl. Acad. Sci. USA*, 99:6047 (2002); Lee et al., *Nat. Biotech.*, 20:500 (2002); Miyagishi et al., *Nat. Biotech.*, 20:497 (2002); Paul et al., *Nat. Biotech.*, 20:505 (2002); and Sui et al., *Proc. Natl. Acad. Sci. USA*, 99:5515 (2002)). Typically, a transcriptional unit or cassette will contain an RNA transcript promoter sequence, such as an H1-RNA or a U6 promoter, operably linked to a template for transcription of a desired siRNA sequence and a termination sequence, comprised of 2-3 uridine residues and a polythymidine (T5) sequence (polyadenylation signal) (Brummelkamp et al., supra). The selected promoter can provide for constitutive or inducible transcription. Compositions and methods for DNA-directed transcription of RNA interference molecules is described in detail in U.S. Pat. No. 6,573,099. The transcriptional unit is incorporated into a plasmid or DNA vector from which the interfering RNA is transcribed. Plasmids suitable for in vivo delivery of genetic material for therapeutic purposes are described in detail in U.S. Pat. Nos. 5,962,428 and 5,910,488. The selected plasmid can provide for transient or stable delivery of a target cell. It will be apparent to those of skill in the art that plasmids originally designed to express desired gene sequences can be modified to contain a transcriptional unit cassette for transcription of siRNA.

Methods for isolating RNA, synthesizing RNA, hybridizing nucleic acids, making and screening cDNA libraries, and performing PCR are well known in the art (see, e.g., Gubler and Hoffman, *Gene* 25:263-269 (1983); Sambrook et al., supra; Ausubel et al., supra), as are PCR methods (see, U.S. Pat. Nos. 4,683,195 and 4,683,202; *PCR Protocols: A Guide to Methods and Applications* (Innis et al., eds, 1990)). Expression libraries are also well known to those of skill in the art. Additional basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994).

Preferably, siRNA molecules are chemically synthesized. The single-stranded molecules that comprise the siRNA molecule can be synthesized using any of a variety of techniques known in the art, such as those described in Usman et al., *J. Am. Chem. Soc.*, 109:7845 (1987); Scaringe et al., *Nuc. Acids Res.*, 18:5433 (1990); Wincott et al., *Nucl. Acids Res.*, 23:2677-2684 (1995); and Wincott et al., *Methods Mol. Bio.*, 74:59 (1997). The synthesis of the single-stranded molecules makes use of common nucleic acid protecting and coupling groups, such as dimethoxytrityl at the 5'-end and phosphoramidites at the 3'-end. As a non-limiting example, small scale syntheses can be conducted on an Applied Biosystems synthesizer using a 0.2 µmol scale protocol with a 2.5 min coupling step for 2'-O-methylated nucleotides. Alternatively, syntheses at the 0.2 µmol scale can be performed on a 96-well plate synthesizer from Protogene (Palo Alto, Calif.). However, a larger or smaller scale of synthesis is also within the scope of the present invention. Suitable reagents for synthesis of the siRNA single-stranded molecules, methods for RNA deprotection, and methods for RNA purification are known to those of skill in the art.

The siRNA molecules can also be synthesized via a tandem synthesis technique, wherein both strands are synthesized as a single continuous fragment or strand separated by a cleavable linker that is subsequently cleaved to provide separate fragments or strands that hybridize to form the siRNA duplex. The linker can be a polynucleotide linker or a non-nucleotide linker. The tandem synthesis of siRNA can be readily adapted to both multiwell/multiplate synthesis platforms as well as large scale synthesis platforms employing batch reactors, synthesis columns, and the like. Alternatively, the siRNA molecules can be assembled from two distinct single-stranded molecules, wherein one strand comprises the sense strand and the other comprises the antisense strand of the siRNA. For example, each strand can be synthesized separately and joined together by hybridization or ligation following synthesis and/or deprotection. In certain other instances, the siRNA molecules can be synthesized as a single continuous fragment, where the self-complementary sense and antisense regions hybridize to form an siRNA duplex having hairpin secondary structure.

C. Modifying siRNA Sequences

In certain aspects, the siRNA molecules of the present invention comprise a duplex having two strands and at least one modified nucleotide in the double-stranded region, wherein each strand is about 15 to about 60 nucleotides in length. Advantageously, the modified siRNA is less immunostimulatory than a corresponding unmodified siRNA sequence, but retains the capability of silencing the expression of a target sequence.

Examples of modified nucleotides suitable for use in the present invention include, but are not limited to, ribonucleotides having a 2'-O-methyl (2'OMe), 2'-deoxy-2'-fluoro (2° F.), 2'-deoxy, 5-C-methyl, 2'-O-(2-methoxyethyl) (MOE), 4'-thio, 2'-amino, or 2'-C-allyl group. Modified nucleotides having a Northern conformation such as those described in, e.g., Saenger, *Principles of Nucleic Acid Structure*, Springer-Verlag Ed. (1984), are also suitable for use in the siRNA molecules of the present invention. Such modified nucleotides include, without limitation, locked nucleic acid (LNA) nucleotides (e.g., 2'-O, 4'-C-methylene-(D-ribofuranosyl) nucleotides), 2'-O-(2-methoxyethyl) (MOE) nucleotides, 2'-methyl-thio-ethyl nucleotides, 2'-deoxy-2'-fluoro (2° F.) nucleotides, 2'-deoxy-2'-chloro (2'Cl) nucleotides, and 2'-azido nucleotides. In certain instances, the siRNA molecules of the present invention include one or more G-clamp nucleotides. A G-clamp nucleotide refers to a modified cytosine analog wherein the modifications confer the ability to hydrogen bond both Watson-Crick and Hoogsteen faces of a complementary guanine nucleotide within a duplex (see, e.g., Lin et al., *J. Am. Chem. Soc.*, 120:8531-8532 (1998)). In addition, nucleotides having a nucleotide base analog such as, for example, C-phenyl, C-naphthyl, other aromatic derivatives, inosine, azole carboxamides, and nitroazole derivatives such as 3-nitropyrrole, 4-nitroindole, 5-nitroindole, and 6-nitroindole (see, e.g., Loakes, *Nucl. Acids Res.,* 29:2437-2447 (2001)) can be incorporated into the siRNA molecules of the present invention.

In certain embodiments, the siRNA molecules of the present invention further comprise one or more chemical modifications such as terminal cap moieties, phosphate backbone modifications, and the like. Examples of terminal cap moieties include, without limitation, inverted deoxy abasic residues, glyceryl modifications, 4',5'-methylene nucleotides, 1-(β-D-erythrofuranosyl) nucleotides, 4'-thio nucleotides, carbocyclic nucleotides, 1,5-anhydrohexitol nucleotides, L-nucleotides, α-nucleotides, modified base nucleotides, threo-pentofuranosyl nucleotides, acyclic 3',4'-seco nucleotides, acyclic 3,4-dihydroxybutyl nucleotides, acyclic 3,5-dihydroxypentyl nucleotides, 3'-3'-inverted nucleotide moieties, 3'-3'-inverted abasic moieties, 3'-2'-inverted nucleotide moieties, 3'-2'-inverted abasic moieties, 5'-5'-inverted nucleotide moieties, 5'-5'-inverted abasic moieties, 3'-5'-inverted deoxy abasic moieties, 5'-amino-alkyl phosphate, 1,3-diamino-2-propyl phosphate, 3-aminopropyl phosphate, 6-aminohexyl phosphate, 1,2-aminododecyl phosphate, hydroxypropyl phosphate, 1,4-butanediol phosphate, 3'-phosphoramidate, 5'-phosphoramidate, hexylphosphate, aminohexyl phosphate, 3'-phosphate, 5'-amino, 3'-phosphorothioate, 5'-phosphorothioate, phosphorodithioate, and bridging or non-bridging methylphosphonate or 5'-mercapto moieties (see, e.g., U.S. Pat. No. 5,998,203; Beaucage et al., *Tetrahedron* 49:1925 (1993)). Non-limiting examples of phosphate backbone modifications (i.e., resulting in modified internucleotide linkages) include phosphorothioate, phosphorodithioate, methylphosphonate, phosphotriester, morpholino, amidate, carbamate, carboxymethyl, acetamidate, polyamide, sulfonate, sulfonamide, sulfamate, formacetal, thioformacetal, and alkylsilyl substitutions (see, e.g., Hunziker et al., *Nucleic Acid Analogues: Synthesis and Properties, in Modern Synthetic Methods,* VCH, 331-417 (1995); Mesmaeker et al., *Novel Backbone Replacements for Oligonucleotides, in Carbohydrate Modifications in Antisense Research,* ACS, 24-39 (1994)). Such chemical modifications can occur at the 5'-end and/or 3'-end of the sense strand, antisense strand, or both strands of the siRNA.

In some embodiments, the sense and/or antisense strand can further comprise a 3'-terminal overhang having about 1 to about 4 (e.g., 1, 2, 3, or 4) 2'-deoxy ribonucleotides and/or any combination of modified and unmodified nucleotides. Additional examples of modified nucleotides and types of chemical modifications that can be introduced into the modified siRNA molecules of the present invention are described, e.g., in UK Patent No. GB 2,397,818 B and U.S. Patent Publication Nos. 20040192626 and 20050282188.

The siRNA molecules of the present invention can optionally comprise one or more non-nucleotides in one or both strands of the siRNA. As used herein, the term "non-nucleotide" refers to any group or compound that can be incorporated into a nucleic acid chain in the place of one or more nucleotide units, including sugar and/or phosphate substitutions, and allows the remaining bases to exhibit their activity. The group or compound is abasic in that it does not contain a commonly recognized nucleotide base such as adenosine, guanine, cytosine, uracil, or thymine and therefore lacks a base at the 1'-position.

In other embodiments, chemical modification of the siRNA comprises attaching a conjugate to the siRNA molecule. The conjugate can be attached at the 5'- and/or 3'-end of the sense and/or antisense strand of the siRNA via a covalent attachment such as, e.g., a biodegradable linker. The conjugate can also be attached to the siRNA, e.g., through a carbamate group or other linking group (see, e.g., U.S. Patent Publication Nos. 20050074771, 20050043219, and 20050158727). In certain instances, the conjugate is a molecule that facilitates the delivery of the siRNA into a cell. Examples of conjugate molecules suitable for attachment to the siRNA of the present invention include, without limitation, steroids such as cholesterol, glycols such as polyethylene glycol (PEG), human serum albumin (HSA), fatty acids, carotenoids, terpenes, bile acids, folates (e.g., folic acid, folate analogs and derivatives thereof), sugars (e.g., galactose, galactosamine, N-acetyl galactosamine, glucose, mannose, fructose, fucose, etc.), phospholipids, peptides, ligands for cellular receptors capable of mediating cellular uptake, and combinations thereof (see, e.g., U.S. Patent Publication Nos. 20030130186, 20040110296, and 20040249178; U.S. Pat. No. 6,753,423). Other examples include the lipophilic moiety, vitamin, polymer, peptide, protein, nucleic acid, small molecule, oligosaccharide, carbohydrate cluster, intercalator, minor groove binder, cleaving agent, and cross-linking agent conjugate molecules described in U.S. Patent Publication Nos. 20050119470 and 20050107325. Yet other examples include the 2'-O-alkyl amine, 2'-O-alkoxyalkyl amine, polyamine, C5-cationic modified pyrimidine, cationic peptide, guanidinium group, amidininium group, cationic amino acid conjugate molecules described in U.S. Patent Publication No. 20050153337. Additional examples include the hydrophobic group, membrane active compound, cell penetrating compound, cell targeting signal, interaction modifier, and steric stabilizer conjugate molecules described in U.S. Patent Publication No. 20040167090. Further examples include the conjugate molecules described in U.S. Patent Publication No. 20050239739. The type of conjugate used and the extent of conjugation to the siRNA molecule can be evaluated for improved pharmacokinetic profiles, bioavailability, and/or stability of the siRNA while retaining RNAi activity. As such, one skilled in the art can screen siRNA molecules having various conjugates attached thereto to identify ones having improved properties and RNAi activity using any of a variety of well-known in vitro cell culture or in vivo animal models.

V. Additional Carrier Systems

Non-limiting examples of additional lipid-based carrier systems suitable for use in the present invention include lipoplexes (see, e.g., U.S. Patent Publication No. 20030203865; and Zhang et al., *J. Control Release,* 100:165-180 (2004)), pH-sensitive lipoplexes (see, e.g., U.S. Patent Publication No. 20020192275), reversibly masked lipoplexes (see, e.g., U.S. Patent Publication Nos. 20030180950), cationic lipid-based compositions (see, e.g., U.S. Pat. No. 6,756,054; and U.S. Patent Publication No. 20050234232), cationic liposomes (see, e.g., U.S. Patent Publication Nos. 20030229040, 20020160038, and 20020012998; U.S. Pat. No. 5,908,635; and PCT Publication No. WO 01/72283), anionic liposomes (see, e.g., U.S. Patent Publication No. 20030026831), pH-sensitive liposomes (see, e.g., U.S. Patent Publication No. 20020192274; and AU 2003210303), antibody-coated liposomes (see, e.g., U.S. Patent Publication No. 20030108597; and PCT Publication No. WO 00/50008), cell-type specific liposomes (see, e.g., U.S. Patent Publication No. 20030198664), liposomes containing nucleic acid and peptides (see, e.g., U.S. Pat. No. 6,207,456), liposomes containing lipids derivatized with releasable hydrophilic polymers (see, e.g., U.S. Patent Publication No. 20030031704), lipid-entrapped nucleic acid (see, e.g., PCT Publication Nos. WO 03/057190 and WO 03/059322), lipid-encapsulated nucleic acid (see, e.g., U.S. Patent Publication No. 20030129221; and U.S. Pat. No. 5,756,122), other liposomal compositions (see, e.g., U.S. Patent Publication Nos. 20030035829 and 20030072794; and U.S. Pat. No. 6,200,599), stabilized mixtures of liposomes and emulsions (see, e.g., EP1304160), emulsion compositions (see, e.g., U.S. Pat. No. 6,747,014), and nucleic acid micro-emulsions (see, e.g., U.S. Patent Publication No. 20050037086).

Examples of polymer-based carrier systems suitable for use in the present invention include, but are not limited to, cationic polymer-nucleic acid complexes (i.e., polyplexes). To form a polyplex, a nucleic acid (e.g., siRNA) is typically complexed with a cationic polymer having a linear, branched, star, or dendritic polymeric structure that condenses the nucleic acid into positively charged particles capable of interacting with anionic proteoglycans at the cell surface and entering cells by endocytosis. In some embodiments, the polyplex comprises nucleic acid (e.g., siRNA) complexed with a cationic polymer such as polyethylenimine (PEI) (see, e.g., U.S. Pat. No. 6,013,240; commercially available from Qbiogene, Inc. (Carlsbad, Calif.) as In vivo jetPEI™, a linear form of PEI), polypropylenimine (PPI), polyvinylpyrrolidone (PVP), poly-L-lysine (PLL), diethylaminoethyl (DEAE)-dextran, poly(β-amino ester) (PAE) polymers (see, e.g., Lynn et al., *J. Am. Chem. Soc.*, 123:8155-8156 (2001)), chitosan, polyamidoamine (PAMAM) dendrimers (see, e.g., Kukowska-Latallo et al., *Proc. Natl. Acad. Sci. USA*, 93:4897-4902 (1996)), porphyrin (see, e.g., U.S. Pat. No. 6,620,805), polyvinylether (see, e.g., U.S. Patent Publication No. 20040156909), polycyclic amidinium (see, e.g., U.S. Patent Publication No. 20030220289), other polymers comprising primary amine, imine, guanidine, and/or imidazole groups (see, e.g., U.S. Pat. No. 6,013,240; PCT Publication No. WO/9602655; PCT Publication No. WO95/21931; Zhang et al., *J. Control Release*, 100:165-180 (2004); and Tiera et al., *Curr. Gene Ther.*, 6:59-71 (2006)), and a mixture thereof. In other embodiments, the polyplex comprises cationic polymer-nucleic acid complexes as described in U.S. Patent Publication Nos. 20060211643, 20050222064, 20030125281, and 20030185890, and PCT Publication No. WO 03/066069; biodegradable poly(β-amino ester) polymer-nucleic acid complexes as described in U.S. Patent Publication No. 20040071654; microparticles containing polymeric matrices as described in U.S. Patent Publication No. 20040142475; other microparticle compositions as described in U.S. Patent Publication No. 20030157030; condensed nucleic acid complexes as described in U.S. Patent Publication No. 20050123600; and nanocapsule and microcapsule compositions as described in AU 2002358514 and PCT Publication No. WO 02/096551.

In certain instances, the nucleic acid (e.g., siRNA) may be complexed with cyclodextrin or a polymer thereof. Non-limiting examples of cyclodextrin-based carrier systems include the cyclodextrin-modified polymer-nucleic acid complexes described in U.S. Patent Publication No. 20040087024; the linear cyclodextrin copolymer-nucleic acid complexes described in U.S. Pat. Nos. 6,509,323, 6,884,789, and 7,091,192; and the cyclodextrin polymer-complexing agent-nucleic acid complexes described in U.S. Pat. No. 7,018,609. In certain other instances, the nucleic acid (e.g., siRNA) may be complexed with a peptide or polypeptide. An example of a protein-based carrier system includes, but is not limited to, the cationic oligopeptide-nucleic acid complex described in PCT Publication No. WO95/21931.

VI. Preparation of SNALPs

The present invention provides a method of preparing serum-stable nucleic acid-lipid particles in which the siRNA, plasmid or other nucleic acid is encapsulated in a lipid bilayer and is protected from degradation. The particles made by the methods of this invention typically have a size of about 50 nm to about 150 nm, about 60 nm to about 130 nm, about 70 nm to about 110 nm, or about 70 to about 90 nm. The particles can be formed by any method known in the art including, but not limited to: a continuous mixing method, a detergent dialysis method, or a modification of a reverse-phase method which utilizes organic solvents to provide a single phase during mixing of the components.

In preferred embodiments, the cationic lipids are lipids of Formula I and II or combinations thereof. In other preferred embodiments, the noncationic lipids are ESM, DOPE, DOPC, DPPE, DMPE, 16:0 Monomethyl Phosphatidylethanolamine, 16:0 Dimethyl Phosphatidylethanolamine, 18:1 Trans Phosphatidylethanolamine, 18:0 18:1 Phosphatidylethanolamine (SOPE), 1,2-dielaidoyl-sn-glycero-3-phophoethanolamine (transDOPE), 16:0 18:1 Phosphatidylethanolamine, DSPE, polyethylene glycol-based polymers (e.g., PEG 2000, PEG 5000, PEG-modified diacylglycerols, or PEG-modified dialkyloxypropyls), distearoylphosphatidylcholine (DSPC), cholesterol, or combinations thereof. In still other preferred embodiments, the organic solvents are methanol, chloroform, methylene chloride, ethanol, diethyl ether or combinations thereof.

In a particularly preferred embodiment, the nucleic acid is an siRNA molecule; the cationic lipid is a lipid of Formula I or II or combinations thereof; the noncationic lipid is ESM, DOPE, PEG-DAAs, distearoylphosphatidylcholine (DSPC), cholesterol, or combinations thereof (e.g. DSPC and PEG-DAAs); and the organic solvent is methanol, chloroform, methylene chloride, ethanol, diethyl ether or combinations thereof.

In a particularly preferred embodiment, the present invention provides for nucleic acid-lipid particles produced via a continuous mixing method, e.g., process that includes providing an aqueous solution comprising a nucleic acid such as an siRNA or a plasmid, in a first reservoir, and providing an organic lipid solution in a second reservoir, and mixing the aqueous solution with the organic lipid solution such that the organic lipid solution mixes with the aqueous solution so as to substantially instantaneously produce a liposome encapsulating the nucleic acid (e.g., siRNA). This process and the apparatus for carrying this process is described in detail in U.S. Patent Publication No. 20040142025.

The action of continuously introducing lipid and buffer solutions into a mixing environment, such as in a mixing chamber, causes a continuous dilution of the lipid solution with the buffer solution, thereby producing a liposome substantially instantaneously upon mixing. As used herein, the phrase "continuously diluting a lipid solution with a buffer solution" (and variations) generally means that the lipid solution is diluted sufficiently rapidly in a hydration process with sufficient force to effectuate vesicle generation. By mixing the aqueous solution comprising a nucleic acid with the organic lipid solution, the organic lipid solution undergoes a continuous stepwise dilution in the presence of the buffer solution (i.e., aqueous solution) to produce a nucleic acid-lipid particle.

In another embodiment, the present invention provides for nucleic acid-lipid particles produced via a direct dilution process that includes forming a liposome solution and immediately and directly introducing the liposome solution into a collection vessel containing a controlled amount of dilution buffer. In preferred aspects, the collection vessel includes one or more elements configured to stir the contents of the collection vessel to facilitate dilution. In one aspect, the amount of dilution buffer present in the collection vessel is substantially equal to the volume of liposome solution introduced thereto. As an example, liposome solution in 45% ethanol when introduced into the collection vessel containing an equal volume of aqueous solution will advantageously yield smaller particles in about 22.5%, about 20%, or about 15% ethanol.

In even another embodiment, the present invention provides for nucleic acid-lipid particles produced via a direct dilution process in which a third reservoir containing dilution buffer is fluidly coupled to a second mixing region. In this embodiment, the liposome solution formed in a first mixing region is immediately and directly mixed with dilution buffer in the second mixing region. In preferred aspects, the second mixing region includes a T-connector arranged so that the liposome solution and the dilution buffer flows meet as opposing 180° flows, however, connectors providing shallower angles can be used, e.g., 27° to about 180°. A pump mechanism delivers a controllable flow of buffer to the second mixing region. In one aspect, the flow rate of dilution buffer provided to the second mixing region is controlled to be substantially equal to the flow rate of liposome solution introduced thereto from the first mixing region. This embodiment advantageously allows for more control of the flow of dilution buffer mixing with the liposome solution in the second mixing region, and therefore also the concentration of liposome solution in buffer throughout the second mixing process. Such control of the dilution buffer flow rate advantageously allows for small particle size formation at reduced concentrations.

These processes and the apparati for carrying these direct dilution processes is described in detail in U.S. Provisional Patent Application No. 60/703,380 filed Jul. 27, 2005 (Systems and Methods for Manufacturing Liposomes, which is incorporated herein by reference.

The serum-stable nucleic acid-lipid particles formed using the continuous mixing method typically have a size of from about 50 nm to about 150 nm, about 100 nm to about 130 nm, about 110 nm to about 115 nm, about 65 nm to about 95 nm, or about 50 nm to about 75 nm. The particles thus formed do not aggregate and are optionally sized to achieve a uniform particle size.

In some embodiments, the particles are formed using detergent dialysis. Without intending to be bound by any particular mechanism of formation, a plasmid or other nucleic acid (e.g., siRNA) is contacted with a detergent solution of cationic lipids to form a coated nucleic acid complex. These coated nucleic acids can aggregate and precipitate. However, the presence of a detergent reduces this aggregation and allows the coated nucleic acids to react with excess lipids (typically, non-cationic lipids) to form particles in which the plasmid or other nucleic acid is encapsulated in a lipid bilayer. Thus, the present invention provides a method for the preparation of serum-stable nucleic acid-lipid particles, comprising:

(a) combining a nucleic acid with cationic lipids in a detergent solution to form a coated nucleic acid-lipid complex;
(b) contacting non-cationic lipids with the coated nucleic acid-lipid complex to form a detergent solution comprising a nucleic acid-lipid complex and non-cationic lipids; and
(c) dialyzing the detergent solution of step (b) to provide a solution of serum-stable nucleic acid-lipid particles, wherein the nucleic acid is encapsulated in a lipid bilayer and the particles are serum-stable and have a size of from about 50 to about 150 nm.

An initial solution of coated nucleic acid-lipid complexes is formed by combining the nucleic acid with the cationic lipids in a detergent solution.

In these embodiments, the detergent solution is preferably an aqueous solution of a neutral detergent having a critical micelle concentration of 15-300 mM, more preferably 20-50 mM. Examples of suitable detergents include, for example, N,N'-((octanoylimino)-bis-(trimethylene))-bis-(D-gluconamide) (BIGCHAP); BRIJ 35; Deoxy-BIGCHAP; dodecylpoly(ethylene glycol) ether; Tween 20; Tween 40; Tween 60; Tween 80; Tween 85; Mega 8; Mega 9; Zwittergent® 3-08; Zwittergent® 3-10; Triton X-405; hexyl-, heptyl-, octyl- and nonyl-β-D-glucopyranoside; and heptylthioglucopyranoside; with octyl β-D-glucopyranoside and Tween-20 being the most preferred. The concentration of detergent in the detergent solution is typically about 100 mM to about 2 M, preferably from about 200 mM to about 1.5 M.

The cationic lipids and nucleic acids will typically be combined to produce a charge ratio (+/−) of about 1:1 to about 20:1, in a ratio of about 1:1 to about 12:1, or in a ratio of about 2:1 to about 6:1. Additionally, the overall concentration of nucleic acid in solution will typically be from about 25 µg/mL to about 1 mg/mL, from about 25 µg/mL to about 200 µg/mL, or from about 50 µg/mL to about 100 µg/mL. The combination of nucleic acids and cationic lipids in detergent solution is kept, typically at room temperature, for a period of time which is sufficient for the coated complexes to form. Alternatively, the nucleic acids and cationic lipids can be combined in the detergent solution and warmed to temperatures of up to about 37° C., about 50° C., about 60° C., or about 70° C. For nucleic acids which are particularly sensitive to temperature, the coated complexes can be formed at lower temperatures, typically down to about 4° C.

In some embodiments, the nucleic acid to lipid ratios (mass/mass ratios) in a formed nucleic acid-lipid particle will range from about 0.01 to about 0.2, from about 0.03 to about 0.01 or about 0.01 to about 0.08. The ratio of the starting materials also falls within this range. In another preferred embodiment, the nucleic acid-lipid particle preparation uses about 400 µg nucleic acid per 10 mg total lipid or a nucleic acid to lipid ratio of about 0.01 to about 0.08 or about 0.04, which corresponds to 1.25 mg of total lipid per 50 µg of nucleic acid.

The detergent solution of the coated nucleic acid-lipid complexes is then contacted with non-cationic lipids to provide a detergent solution of nucleic acid-lipid complexes and non-cationic lipids. The non-cationic lipids which are useful in this step include, diacylphosphatidylcholine, diacylphosphatidylethanolamine, ceramide, sphingomyelin, cephalin, cardiolipin, and cerebrosides. In preferred embodiments, the non-cationic lipids are diacylphosphatidylcholine, diacylphosphatidylethanolamine, ceramide or sphingomyelin. The acyl groups in these lipids are preferably acyl groups derived from fatty acids having $C_{10}$-$C_{24}$ carbon chains. More preferably the acyl groups are lauroyl, myristoyl, palmitoyl, stearoyl or oleoyl. In particularly preferred embodiments, the non-cationic lipid will be 1,2-sn-dioleoylphosphatidylethanolamine (DOPE), palmitoyl oleoyl phosphatidylcholine (POPC), egg phosphatidylcholine (EPC), distearoylphosphatidylcholine (DSPC), cholesterol, or a mixture thereof. In the most preferred embodiments, the nucleic acid-lipid particles will be fusogenic particles with enhanced properties in vivo and the non-cationic lipid will be DSPC or DOPE. In addition, the nucleic acid-lipid particles of the present invention may further comprise cholesterol. In other preferred embodiments, the non-cationic lipids will further comprise polyethylene glycol-based polymers such as PEG 2000, PEG 5000 and polyethylene glycol conjugated to a diacylglycerol, a ceramide or a phospholipid, as described in U.S. Pat. No. 5,820,873 and U.S. Patent Publication No. 20030077829. In further preferred embodiments, the non-cationic lipids will further comprise polyethylene glycol-based polymers such as PEG 2000, PEG 5000 and polyethylene glycol conjugated to a dialkyloxypropyl.

Following formation of the detergent solution of nucleic acid-lipid complexes and non-cationic lipids, the detergent is removed, preferably by dialysis. The removal of the detergent results in the formation of a lipid-bilayer which surrounds the nucleic acid providing serum-stable nucleic acid-lipid particles which have a size of from about 50 nm to about 150 nm, more typically about 60 nm to about 130 nm, more typically about 70 nm to about 110 nm, most typically about 70 to about 90 nm. The particles thus formed do not aggregate and are optionally sized to achieve a uniform particle size.

The serum-stable nucleic acid-lipid particles can be sized by any of the methods available for sizing liposomes. The sizing may be conducted in order to achieve a desired size range and relatively narrow distribution of particle sizes.

Several techniques are available for sizing the particles to a desired size. One sizing method, used for liposomes and equally applicable to the present particles is described in U.S. Pat. No. 4,737,323. Sonicating a particle suspension either by bath or probe sonication produces a progressive size reduction down to particles of less than about 50 nm in size. Homogenization is another method which relies on shearing energy to fragment larger particles into smaller ones. In a typical homogenization procedure, particles are recirculated through a standard emulsion homogenizer until selected particle sizes, typically between about 60 and 80 nm, are observed. In both methods, the particle size distribution can be monitored by conventional laser-beam particle size discrimination, or QELS.

Extrusion of the particles through a small-pore polycarbonate membrane or an asymmetric ceramic membrane is also an effective method for reducing particle sizes to a relatively well-defined size distribution. Typically, the suspension is cycled through the membrane one or more times until the desired particle size distribution is achieved. The particles may be extruded through successively smaller-pore membranes, to achieve a gradual reduction in size.

In another group of embodiments, the present invention provides a method for the preparation of serum-stable nucleic acid-lipid particles, comprising:
(a) preparing a mixture comprising cationic lipids and non-cationic lipids in an organic solvent;
(b) contacting an aqueous solution of nucleic acid with said mixture in step (a) to provide a clear single phase; and
(c) removing said organic solvent to provide a suspension of nucleic acid-lipid particles, wherein said nucleic acid is encapsulated in a lipid bilayer, and said particles are stable in serum and have a size of from about 50 to about 150 nm.

The nucleic acids (or plasmids), cationic lipids and non-cationic lipids which are useful in this group of embodiments are as described for the detergent dialysis methods above.

The selection of an organic solvent will typically involve consideration of solvent polarity and the ease with which the solvent can be removed at the later stages of particle formation. The organic solvent, which is also used as a solubilizing agent, is in an amount sufficient to provide a clear single phase mixture of nucleic acid and lipids. Suitable solvents include, but are not limited to, chloroform, dichloromethane, diethylether, cyclohexane, cyclopentane, benzene, toluene, methanol, or other aliphatic alcohols such as propanol, isopropanol, butanol, tert-butanol, iso-butanol, pentanol and hexanol. Combinations of two or more solvents may also be used in the present invention.

Contacting the nucleic acid with the organic solution of cationic and non-cationic lipids is accomplished by mixing together a first solution of nucleic acid, which is typically an aqueous solution, and a second organic solution of the lipids. One of skill in the art will understand that this mixing can take place by any number of methods, for example by mechanical means such as by using vortex mixers.

After the nucleic acid has been contacted with the organic solution of lipids, the organic solvent is removed, thus forming an aqueous suspension of serum-stable nucleic acid-lipid particles. The methods used to remove the organic solvent will typically involve evaporation at reduced pressures or blowing a stream of inert gas (e.g., nitrogen or argon) across the mixture.

The serum-stable nucleic acid-lipid particles thus formed will typically be sized from about 50 nm to about 150 nm, more typically about 60 nm to about 130 nm, more typically about 70 nm to about 100 nm, most typically about 70 to about 90 nm. To achieve further size reduction or homogeneity of size in the particles, sizing can be conducted as described above.

In other embodiments, the methods will further comprise adding nonlipid polycations which are useful to effect the delivery to cells using the present compositions. Examples of suitable nonlipid polycations include, but are limited to, hexadimethrine bromide (sold under the brandname POLYBRENE®, from Aldrich Chemical Co., Milwaukee, Wis., USA) or other salts of heaxadimethrine. Other suitable polycations include, for example, salts of poly-L-ornithine, poly-L-arginine, poly-L-lysine, poly-D-lysine, polyallylamine and polyethyleneimine.

In certain embodiments, the formation of the nucleic acid-lipid particles can be carried out either in a mono-phase system (e.g., a Bligh and Dyer monophase or similar mixture of aqueous and organic solvents) or in a two-phase system with suitable mixing.

When formation of the complexes is carried out in a mono-phase system, the cationic lipids and nucleic acids are each dissolved in a volume of the mono-phase mixture. Combination of the two solutions provides a single mixture in which the complexes form. Alternatively, the complexes can form in two-phase mixtures in which the cationic lipids bind to the nucleic acid (which is present in the aqueous phase), and "pull" it into the organic phase.

In another embodiment, the present invention provides a method for the preparation of nucleic acid-lipid particles, comprising:
(a) contacting nucleic acids with a solution comprising non-cationic lipids and a detergent to form a nucleic acid-lipid mixture;
(b) contacting cationic lipids with the nucleic acid-lipid mixture to neutralize a portion of the negative charge of the nucleic acids and form a charge-neutralized mixture of nucleic acids and lipids; and
(c) removing the detergent from the charge-neutralized mixture to provide the nucleic acid-lipid particles in which the nucleic acids are protected from degradation.

In one group of embodiments, the solution of non-cationic lipids and detergent is an aqueous solution. Contacting the nucleic acids with the solution of non-cationic lipids and detergent is typically accomplished by mixing together a first solution of nucleic acids and a second solution of the lipids and detergent. One of skill in the art will understand that this mixing can take place by any number of methods, for example, by mechanical means such as by using vortex mixers. Preferably, the nucleic acid solution is also a detergent solution. The amount of non-cationic lipid which is used in the present method is typically determined based on the amount of cationic lipid used, and is typically of from about 0.2 to 5 times the amount of cationic lipid, preferably from about 0.5 to about 2 times the amount of cationic lipid used.

In some embodiments, the nucleic acids are precondensed as described in, e.g., U.S. patent application Ser. No. 09/744,103.

The nucleic acid-lipid mixture thus formed is contacted with cationic lipids to neutralize a portion of the negative charge which is associated with the nucleic acids (or other polyanionic materials) present. The amount of cationic lipids used will typically be sufficient to neutralize at least 50% of the negative charge of the nucleic acid. Preferably, the negative charge will be at least 70% neutralized, more preferably at least 90% neutralized. Cationic lipids which are useful in the present invention, include, for example, DLinDMA and, DLenDMA. These lipids and related analogs have been described in U.S. patent application Ser. No. 11/148,430, filed Jun. 7, 2005.

Contacting the cationic lipids with the nucleic acid-lipid mixture can be accomplished by any of a number of techniques, preferably by mixing together a solution of the cationic lipid and a solution containing the nucleic acid-lipid mixture. Upon mixing the two solutions (or contacting in any other manner), a portion of the negative charge associated with the nucleic acid is neutralized. Nevertheless, the nucleic acid remains in an uncondensed state and acquires hydrophilic characteristics.

After the cationic lipids have been contacted with the nucleic acid-lipid mixture, the detergent (or combination of detergent and organic solvent) is removed, thus forming the nucleic acid-lipid particles. The methods used to remove the detergent will typically involve dialysis. When organic solvents are present, removal is typically accomplished by evaporation at reduced pressures or by blowing a stream of inert gas (e.g., nitrogen or argon) across the mixture.

The particles thus formed will typically be sized from about 50 nm to several microns, more typically about 50 nm to about 150 nm, more typically about 60 nm to about 130 nm, more typically about 70 nm to about 110 nm, most typically about 70 to about 90 nm. To achieve further size reduction or homogeneity of size in the particles, the nucleic acid-lipid particles can be sonicated, filtered or subjected to other sizing techniques which are used in liposomal formulations and are known to those of skill in the art.

In other embodiments, the methods will further comprise adding nonlipid polycations which are useful to effect the lipofection of cells using the present compositions. Examples of suitable nonlipid polycations include, hexadimethrine bromide (sold under the brandname POLYBRENE®, from Aldrich Chemical Co., Milwaukee, Wis., USA) or other salts of hexadimethrine. Other suitable polycations include, for example, salts of poly-L-ornithine, poly-L-arginine, poly-L-lysine, poly-D-lysine, polyallylamine and polyethyleneimine. Addition of these salts is preferably after the particles have been formed.

In another aspect, the present invention provides methods for the preparation of nucleic acid-lipid particles, comprising:
  (a) contacting an amount of cationic lipids with nucleic acids in a solution; the solution comprising from about 15-35% water and about 65-85% organic solvent and the amount of cationic lipids being sufficient to produce a +/−charge ratio of from about 0.85 to about 2.0, to provide a hydrophobic nucleic acid-lipid complex;
  (b) contacting the hydrophobic, nucleic acid-lipid complex in solution with non-cationic lipids, to provide a nucleic acid-lipid mixture; and
  (c) removing the organic solvents from the nucleic acid-lipid mixture to provide nucleic acid-lipid particles in which the nucleic acids are protected from degradation.

The nucleic acids, non-cationic lipids, cationic lipids and organic solvents which are useful in this aspect of the invention are the same as those described for the methods above which used detergents. In one group of embodiments, the solution of step (a) is a mono-phase. In another group of embodiments, the solution of step (a) is two-phase.

In preferred embodiments, the non-cationic lipids are ESM, DOPE, DOPC, polyethylene glycol-based polymers (e.g., PEG 2000, PEG 5000, PEG-modified diacylglycerols, or PEG-modified dialkyloxypropyls), distearoylphosphatidylcholine (DSPC), DPPE, DMPE, 16:0 Monomethyl Phosphatidylethanolamine, 16:0 Dimethyl Phosphatidylethanolamine, 18:1 Trans Phosphatidylethanolamine, 18:0 18:1 Phosphatidylethanolamine (SOPE), 1,2-dielaidoyl-sn-glycero-3-phophoethanolamine (transDOPE), 16:0 18:1 Phosphatidylethanolamine, DSPE, cholesterol, or combinations thereof. In still other preferred embodiments, the organic solvents are methanol, chloroform, methylene chloride, ethanol, diethyl ether or combinations thereof.

In one embodiment, the nucleic acid is a plasmid from which an interfering RNA is transcribed; the cationic lipid is DLinDMA, DLenDMA, DODAC, DDAB, DOTMA, DOSPA, DMRIE, DOGS or combinations thereof; the non-cationic lipid is ESM, DOPE, DAG-PEGs, distearoylphosphatidylcholine (DSPC), DPPE, DMPE, 16:0 Monomethyl Phosphatidylethanolamine, 16:0 Dimethyl Phosphatidylethanolamine, 18:1 Trans Phosphatidylethanolamine, 18:0 18:1 Phosphatidylethanolamine (SOPE), 1,2-dielaidoyl-sn-glycero-3-phophoethanolamine (transDOPE), 16:0 18:1 Phosphatidylethanolamine DSPE, cholesterol, or combinations thereof (e.g. DSPC and PEG-DAA); and the organic solvent is methanol, chloroform, methylene chloride, ethanol, diethyl ether or combinations thereof.

As above, contacting the nucleic acids with the cationic lipids is typically accomplished by mixing together a first solution of nucleic acids and a second solution of the lipids, preferably by mechanical means such as by using vortex mixers. The resulting mixture contains complexes as described above. These complexes are then converted to particles by the addition of non-cationic lipids and the removal of the organic solvent. The addition of the non-cationic lipids is typically accomplished by simply adding a solution of the non-cationic lipids to the mixture containing the complexes. A reverse addition can also be used. Subsequent removal of organic solvents can be accomplished by methods known to those of skill in the art and also described above.

The amount of non-cationic lipids which is used in this aspect of the invention is typically an amount of from about 0.2 to about 15 times the amount (on a mole basis) of cationic lipids which was used to provide the charge-neutralized nucleic acid-lipid complex. Preferably, the amount is from about 0.5 to about 9 times the amount of cationic lipids used.

In yet another aspect, the present invention provides nucleic acid-lipid particles which are prepared by the methods described above. In these embodiments, the nucleic acid-lipid particles are either net charge neutral or carry an overall charge which provides the particles with greater gene lipofection activity. Preferably, the nucleic acid component of the particles is a nucleic acid which interferes with the production of an undesired protein. In some embodiments, the nucleic acid comprises an interfering RNA, the non-cationic lipid is egg sphingomyelin and the cationic lipid is DLinDMA or DLenDMA. In some embodiments, the nucleic acid comprises an interfering RNA, the non-cationic lipid is a mixture of DSPC and cholesterol, and the cationic lipid is DLinDMA or DLenDMA. In other preferred embodiments, the non-cationic lipid may further comprise cholesterol.

A variety of general methods for making SNALP-CPLs (CPL-containing SNALPs) are discussed herein. Two general techniques include "post-insertion" technique, that is, insertion of a CPL into for example, a pre-formed SNALP, and the "standard" technique, wherein the CPL is included in the lipid mixture during for example, the SNALP formation steps. The post-insertion technique results in SNALPs having CPLs mainly in the external face of the SNALP bilayer membrane, whereas standard techniques provide SNALPs having CPLs on both internal and external faces. The method is especially useful for vesicles made from phospholipids (which can contain cholesterol) and also for vesicles containing PEG-lipids (such as PEG-DAAs and PEG-DAGs). Methods of making SNALP-CPL, are taught, for example, in U.S. Pat. Nos. 5,705,385, 6,586,410, 5,981,501 6,534,484; 6,852,334; U.S. Patent Publication No. 20020072121; and WO 00/62813.

VII. Kits

The present invention also provides nucleic acid-lipid particles in kit form. The kit will typically be comprised of a container which is compartmentalized for holding the various elements of the nucleic acid-lipid particles. The kit will contain the compositions of the present inventions, preferably in dehydrated form, with instructions for their rehydration and administration. In still other embodiments, the particles and/or compositions comprising the particles will have a targeting moiety attached to the surface of the particle. Methods of attaching targeting moieties (e.g., antibodies, proteins) to lipids (such as those used in the present particles) are known to those of skill in the art.

VIII. Administration of Nucleic Acid-Lipid Particles

Once formed, the serum-stable nucleic acid-lipid particles of the present invention are useful for the introduction of nucleic acids (i.e., siRNA that silences expression of gene expressed in cancer such as an Eg5, EGFR and/or XIAP gene) into cells. Accordingly, the present invention also provides methods for introducing a nucleic acids (e.g., a plasmid or and siRNA) into a cell. The methods are carried out in vitro or in vivo by first forming the particles as described above and then contacting the particles with the cells for a period of time sufficient for delivery of the nucleic acid to the cell to occur.

The nucleic acid-lipid particles of the present invention can be adsorbed to almost any cell type with which they are mixed or contacted. Once adsorbed, the particles can either be endocytosed by a portion of the cells, exchange lipids with cell membranes, or fuse with the cells. Transfer or incorporation of the nucleic acid portion of the particle can take place via any one of these pathways. In particular, when fusion takes place, the particle membrane is integrated into the cell membrane and the contents of the particle combine with the intracellular fluid.

The nucleic acid-lipid particles of the present invention can be administered either alone or in mixture with a physiologically-acceptable carrier (such as physiological saline or phosphate buffer) selected in accordance with the route of administration and standard pharmaceutical practice. Generally, normal saline will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc.

The pharmaceutical carrier is generally added following particle formation. Thus, after the particle is formed, the particle can be diluted into pharmaceutically acceptable carriers such as normal saline.

The concentration of particles in the pharmaceutical formulations can vary widely, i.e., from less than about 0.05%, usually at or at least about 2-5% to as much as 10 to 30% by weight and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, particles composed of irritating lipids may be diluted to low concentrations to lessen inflammation at the site of administration.

The pharmaceutical compositions of the present invention may be sterilized by conventional, well known sterilization techniques. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, and calcium chloride. Additionally, the particle suspension may include lipid-protective agents which protect lipids against free-radical and lipid-peroxidative damages on storage. Lipophilic free-radical quenchers, such as alphatocopherol and water-soluble iron-specific chelators, such as ferrioxamine, are suitable.

The nucleic acid-lipid particles can be incorporated into a broad range of topical dosage forms including, but not limited to, gels, oils, emulsions, topical creams, pastes, ointments, lotions and the like.

A. In Vivo Administration

Systemic delivery for in vivo therapy, i.e., delivery of a therapeutic nucleic acid to a distal target cell via body systems such as the circulation, has been achieved using nucleic acid-lipid particles such as those disclosed in WO 96/40964 and U.S. Pat. Nos. 5,705,385, 5,976,567, 5,981,501 and 6,410,328. This latter format provides a fully encapsulated nucleic acid-lipid particle that protects the nucleic acid from nuclease degradation in serum, is nonimmunogenic, is small in size and is suitable for repeat dosing.

For in vivo administration, administration can be in any manner known in the art, e.g., by injection, oral administration, inhalation (e.g., intransal or intratracheal), transdermal application, or rectal administration. Administration can be accomplished via single or divided doses. The pharmaceutical compositions can be administered parenterally, i.e., intraarticularly, intravenously, intraperitoneally, subcutaneously, intramuscularly, or intratumorally. In some embodiments, the pharmaceutical compositions are administered intravenously or intraperitoneally by a bolus injection (see, e.g., Stadler, et al., U.S. Pat. No. 5,286,634) or by pump infusion. Intracellular nucleic acid delivery has also been discussed in Straubringer, et al., *Methods Enzymol*, Academic Press, New York. 101:512 (1983); Mannino, et al., *Biotechniques* 6:682 (1988); Nicolau, et al., *Crit. Rev. Ther. Drug Carrier Syst.* 6:239 (1989), and Behr, *Acc. Chem. Res.* 26:274 (1993). Still other methods of administering lipid based therapeutics are described in, for example, Rahman et al., U.S. Pat.

No. 3,993,754; Sears, U.S. Pat. No. 4,145,410; Papahadjopoulos et al., U.S. Pat. No. 4,235,871; Schneider, U.S. Pat. No. 4,224,179; Lenk et al., U.S. Pat. No. 4,522,803; and Fountain et al., U.S. Pat. No. 4,588,578. The lipid nucleic acid particles can be administered by direct injection at the site of disease or by injection at a site distal from the site of disease (see, e.g., Culver, HUMAN GENE THERAPY, MaryAnn Liebert, Inc., Publishers, New York. pp. 70-71 (1994)).

The compositions of the present invention, either alone or in combination with other suitable components, can be made into aerosol formulations (i.e., they can be "nebulized") to be administered via inhalation (e.g., intranasally or intratracheally) (see, Brigham, et al., *Am. J. Sci.* 298(4):278 (1989)). Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

Generally, when administered intravenously, the nucleic acid-lipid formulations are formulated with a suitable pharmaceutical carrier. Many pharmaceutically acceptable carriers may be employed in the compositions and methods of the present invention. Suitable formulations for use in the present invention are found, for example, in REMINGTON'S PHARMACEUTICAL SCIENCES, Mack Publishing Company, Philadelphia, Pa., 17th ed. (1985). A variety of aqueous carriers may be used, for example, water, buffered water, 0.4% saline, 0.3% glycine, and the like, and may include glycoproteins for enhanced stability, such as albumin, lipoprotein, globulin, etc. Generally, normal buffered saline (135-150 mM NaCl) will be employed as the pharmaceutically acceptable carrier, but other suitable carriers will suffice. These compositions can be sterilized by conventional liposomal sterilization techniques, such as filtration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc. These compositions can be sterilized using the techniques referred to above or, alternatively, they can be produced under sterile conditions. The resulting aqueous solutions may be packaged for use or filtered under aseptic conditions and lyophilized, the lyophilized preparation being combined with a sterile aqueous solution prior to administration.

The methods of the present invention may be practiced in a variety of hosts. Preferred hosts include mammalian species, such as primates (e.g., humans and chimpanzees as well as other nonhuman primates), canines, felines, equines, bovines, ovines, caprines, rodents (e.g., rats and mice), lagomorphs, and swine.

The amount of particles administered will depend upon the ratio of nucleic acid to lipid; the particular nucleic acid used, the disease state being diagnosed; the age, weight, and condition of the patient and the judgment of the clinician; but will generally be between about 0.01 and about 50 mg per kilogram of body weight; preferably between about 0.1 and about 5 mg/kg of body weight or about $10^8$-$10^{10}$ particles per injection.

B. Combination Therapy

In some embodiments, the nucleic acid-lipid particles described herein are administered in combination with a second therapeutic agent for treating or preventing cancer. For example, the nucleic acid-lipid particles may be administered in conjunction with any of the standard treatments for cancer including, but not limited to, chemotherapeutic agents including, e.g., alitretinoin, altretamine, anastrozole, azathioprine, bicalutamide, busulfan, capecitabine, carboplatin, cisplatin, cyclophosphamide, cytarabine, doxorubicin, epirubicin, etoposide, exemestane, finasteride, fluorouracil, fulvestrant, gemtuzumab, ozogamicin, hydroxyurea, ibritumomab, idarubicin, ifosfamide, imatinib, letrozole, megestrol acetate, methotrexate, mifepristone, paclitaxel, rituximab, tamoxifen, temozolomide, tretinoin, triptorelin, vincristine, or vinorelbine, and radiation treatment.

The nucleic acid-lipid particles and the second therapeutic agent may be administered simultaneously or sequentially. For example, the nucleic acid-lipid particles may be administered first, followed by the second therapeutic agent. Alternatively, the second therapeutic agent may be administered first, followed by the nucleic acid-lipid particles. In some cases, the nucleic acid-lipid particles and the second therapeutic agent are administered in the same formulation. In other cases the nucleic acid-lipid particles and nucleic acids and the second therapeutic agent are administered in different formulations.

C. Cells for Delivery of Interfering RNA

The compositions and methods of the present invention are used to treat a wide variety of cell types, in vivo and in vitro. Suitable cells include, e.g., hematopoietic precursor (stem) cells, fibroblasts, keratinocytes, hepatocytes, endothelial cells, skeletal and smooth muscle cells, osteoblasts, neurons, quiescent lymphocytes, terminally differentiated cells, slow or noncycling primary cells, parenchymal cells, lymphoid cells, epithelial cells, bone cells, and the like.

In vivo delivery of nucleic acid-lipid particles encapsulating an interfering RNA is particularly suited for targeting tumor cells of any cell type. In vivo studies show that SNALP's accumulate at tumor sites and predominantly transfect tumor cells. See, Fenske, et al., *Methods Enzymol*, Academic Press, New York 346:36 (2002). The methods and compositions can be employed with cells of a wide variety of vertebrates, including mammals, and especially those of veterinary importance, e.g., canine, feline, equine, bovine, ovine, caprine, rodent, lagomorph, swine, etc., in addition to human cell populations.

To the extent that tissue culture of cells may be required, it is well known in the art. Freshney (1994) (Culture of Animal Cells, a Manual of Basic Technique, third edition Wiley-Liss, New York), Kuchler et al. (1977) Biochemical Methods in Cell Culture and Virology, Kuchler, R. J., Dowden, Hutchinson and Ross, Inc., and the references cited therein provides a general guide to the culture of cells. Cultured cell systems often will be in the form of monolayers of cells, although cell suspensions are also used.

D. Detection of SNALPs

In some embodiments, the nucleic acid-lipid particles are detectable in the subject 8, 12, 24, 48, 60, 72, or 96 hours, 6, 8, 10, 12, 14, 16, 18, 19, 22, 24, 25, or 28 days after administration of the particles. The presence of the particles can be detected in the cells, tissues, or other biological samples from the subject. The particles may be detected, e.g., by direct detection of the particles, detection of the interfering RNA sequence, detection of the target sequence of interest (i.e., by detecting expression or reduced expression of the Eg5, EGFR and/or XIAP sequence of interest), detection of a target protein of interest (e.g., by detecting expression or reduced expression of Eg5, EGFR and/or XIAP protein), detection of a compound modulated directly or indirectly by the Eg5, EGFR and/or XIAP (e.g., tubulin, phosphor-histones, P13 kinase-AKT, STATS, caspases) or by detection of apoptosis and cell viability in the subject or a combination thereof.

1. Detection of Particles

Nucleic acid-lipid particles can be detected using any methods known in the art. For example, a label can be coupled directly or indirectly to a component of the SNALP or other lipid-based carrier system using methods well known in the art. A wide variety of labels can be used, with the choice of label depending on sensitivity required, ease of conjugation with the SNALP component, stability requirements, and available instrumentation and disposal provisions. Suitable labels include, but are not limited to, spectral labels, such as fluorescent dyes (e.g., fluorescein and derivatives, such as fluorescein isothiocyanate (FITC) and Oregon Green™; rhodamine and derivatives, such Texas red, tetrarhodimine isothiocynate (TRITC), etc., digoxigenin, biotin, phycoerythrin, AMCA, CyDyes™, and the like; radiolabels, such as $^3$H, $^{125}$I, $^{35}$S, $^{14}$C, $^{32}$P, $^{33}$P, etc.; enzymes, such as horse radish peroxidase, alkaline phosphatase, etc.; spectral colorimetric labels, such as colloidal gold or colored glass or plastic beads, such as polystyrene, polypropylene, latex, etc. The label can be detected using any means known in the art.

2. Detection of Nucleic Acids

Nucleic acids (i.e., siRNA that silence expression of an Eg5, EGFR and/or XIAP gene) are detected and quantified herein by any of a number of means well known to those of skill in the art. The detection of nucleic acids proceeds by well known methods such as Southern analysis, northern analysis, gel electrophoresis, PCR, radiolabeling, scintillation counting, and affinity chromatography. Additional analytic biochemical methods such as spectrophotometry, radiography, electrophoresis, capillary electrophoresis, high performance liquid chromatography (HPLC), thin layer chromatography (TLC), hyperdiffusion chromatography, may also be employed The selection of a nucleic acid hybridization format is not critical. A variety of nucleic acid hybridization formats are known to those skilled in the art. For example, common formats include sandwich assays and competition or displacement assays. Hybridization techniques are generally described in "Nucleic Acid Hybridization, A Practical Approach," Ed. Hames, B. D. and Higgins, S. J., IRL Press, 1985.

The sensitivity of the hybridization assays may be enhanced through use of a nucleic acid amplification system which multiplies the target nucleic acid being detected. In vitro amplification techniques suitable for amplifying sequences for use as molecular probes or for generating nucleic acid fragments for subsequent subcloning are known. Examples of techniques sufficient to direct persons of skill through such in vitro amplification methods, including the polymerase chain reaction (PCR) the ligase chain reaction (LCR), Qβ-replicase amplification and other RNA polymerase mediated techniques (e.g., NASBA™) are found in Sambrook, et al., In *Molecular Cloning. A Laboratory Manual*, Cold Spring Harbor Laboratory Press, 2000, and Ausubel et al., SHORT PROTOCOLS IN MOLECULAR BIOLOGY, eds., Current Protocols, a joint venture between Greene Publishing Associates, Inc. and John Wiley & Sons, Inc., (2002), as well as Mullis et al. (1987), U.S. Pat. No. 4,683,202; PCR Protocols A Guide to Methods and Applications (Innis et al. eds) Academic Press Inc. San Diego, Calif. (1990) (Innis); Arnheim & Levinson (Oct. 1, 1990), *C&EN* 36; The *Journal Of NIH Research*, 3:81 (1991); (Kwoh et al., *Proc. Natl. Acad. Sci. USA*, 86:1173 (1989); Guatelli et al., *Proc. Natl. Acad. Sci. USA*, 87:1874 (1990); Lomell et al., *J. Clin. Chem.*, 35:1826 (1989); Landegren et al., *Science*, 241:1077 (1988); Van Brunt, *Biotechnology*, 8:291 (1990); Wu and Wallace, *Gene*, 4:560 (1989); Barringer et al., *Gene*, 89:117 (1990), and Sooknanan and Malek, *Biotechnology*, 13:563 (1995). Improved methods of cloning in vitro amplified nucleic acids are described in Wallace et al., U.S. Pat. No. 5,426,039. Other methods described in the art are the nucleic acid sequence based amplification (NASBA™, Cangene, Mississauga, Ontario) and Q Beta Replicase systems. These systems can be used to directly identify mutants where the PCR or LCR primers are designed to be extended or ligated only when a select sequence is present. Alternatively, the select sequences can be generally amplified using, for example, nonspecific PCR primers and the amplified target region later probed for a specific sequence indicative of a mutation.

Oligonucleotides for use as probes, e.g., in in vitro amplification methods, for use as gene probes, or as inhibitor components are typically synthesized chemically according to the solid phase phosphoramidite triester method described by Beaucage and Caruthers, *Tetrahedron Letts.*, 22(20):1859 1862 (1981), e.g., using an automated synthesizer, as described in Needham VanDevanter et al., *Nucleic Acids Res.*, 12:6159 (1984). Purification of oligonucleotides, where necessary, is typically performed by either native acrylamide gel electrophoresis or by anion exchange HPLC as described in Pearson and Regnier, *J. Chrom.*, 255:137 149 (1983). The sequence of the synthetic oligonucleotides can be verified using the chemical degradation method of Maxam and Gilbert (1980) in Grossman and Moldave (eds.) Academic Press, New York, *Methods in Enzymology*, 65:499.

An alternative means for determining the level of transcription is in situ hybridization. In situ hybridization assays are well known and are generally described in Angerer et al., *Methods Enzymol.*, 152:649 (1987). In an in situ hybridization assay cells are fixed to a solid support, typically a glass slide. If DNA is to be probed, the cells are denatured with heat or alkali. The cells are then contacted with a hybridization solution at a moderate temperature to permit annealing of specific probes that are labeled. The probes are preferably labeled with radioisotopes or fluorescent reporters.

E. Detection of an Immune Response

An immune response to induced by the siRNA (i.e., siRNA that silence expression of an Eg5, EGFR and/or XIAP gene) described herein can be long-lived and can be detected long after administration of the siRNA or nucleic acid-lipid particles containing the siRNA. An immune response to the siRNA can be detected by using immunoassays that detect the presence or absence of cytokines and growth factors e.g., produced by responder cells.

Suitable immunoassays include the double monoclonal antibody sandwich immunoassay technique of David et al. (U.S. Pat. No. 4,376,110); monoclonal-polyclonal antibody sandwich assays (Wide et al., in Kirkham and Hunter, eds., *Radioimmunoassay Methods*, E. and S. Livingstone, Edinburgh (1970)); the "western blot" method of Gordon et al. (U.S. Pat. No. 4,452,901); immunoprecipitation of labeled ligand (Brown et al. (1980) *J. Biol. Chem.* 255:4980-4983); enzyme-linked immunosorbent assays (ELISA) as described, for example, by Raines et al. (1982) *J. Biol. Chem.* 257:5154-5160; immunocytochemical techniques, including the use of fluorochromes (Brooks et al. (1980) *Clin. Exp. Immunol.* 39:477); and neutralization of activity (Bowen-Pope et al. (1984) *Proc. Natl. Acad. Sci. USA* 81:2396-2400). In addition to the immunoassays described above, a number of other immunoassays are available, including those described in U.S. Pat. Nos. 3,817,827; 3,850,752; 3,901,654; 3,935,074; 3,984,533; 3,996,345; 4,034,074; and 4,098,876. Monoclonal antibodies that specifically bind cytokines and growth factors (e.g., II-6, IL-12, TNF-α, IFN-α, and IFN-γ can be generated using methods known in the art (see, e.g., Kohler and Milstein, *Nature* 256: 495-497 (1975) and Harlow and Lane, ANTIBODIES, A LABORATORY MANUAL, Cold Spring Harbor Publication, New York (1999)). Generation of monoclonal antibodies has been previously described and can be accomplished by any means known in the art. (Buhring et al. in Hybridoma 1991, Vol. 10, No. 1, pp. 77-78). For example, an animal such as a guinea pig or rat, preferably a mouse is immunized with an immunogenic polypeptide, the antibody-producing cells, preferably splenic lymphocytes, are collected and fused to a stable, immortalized cell line, preferably a myeloma cell line, to produce hybridoma cells which are then isolated and cloned. (U.S. Pat. No. 6,156,882). In some methods, the monoclonal antibody is labeled to facilitate detection.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

The following examples are provided to illustrate, but not to limit the claimed invention.

Example 1

Materials and Methods siRNA:

All siRNA used in these studies were chemically synthesized by Protiva Biotherapeutics (Burnaby, BC), University of Calgary (Calgary, AB) or Dharmacon Inc. (Lafayette, Colo.). siRNA were desalted and annealed using standard procedures.

Lipid Encapsulation of siRNA:

Unless otherwise indicated, siRNAs were encapsulated into liposomes composed of the following lipids: synthetic cholesterol (Sigma, St. Louis, Mo.), the phospholipid DSPC (1,2-distearoyl-sn-glycero-3-phosphocholine; Avanti Polar Lipids, Alabaster, Ala.), the PEG-lipid PEG-cDMA (3-N-[(-Methoxy poly(ethylene glycol)2000)carbamoyl]-1,2-dimyrestyloxy-propylamine), and the cationic lipid DLinDMA (1,2-Dilinoleyloxy-3-(N,N-dimethyl)aminopropane) in the molar ratios 48:10:2:40 respectively. In other words, unless otherwise indicated, siRNA's were encapsulated in to liposomes of the following SNALP formulation: 2% PEG-cDMA, 40% DLinDMA, 10% DSPC, 48% cholesterol. For vehicle controls, empty liposomes with identical lipid composition were formed in the absence of siRNA.

Serum Nuclease Protection Assay:

Unmodified naked or lipid encapsulated siRNA (0.25 mg/ml) were incubated in 50% mouse serum at 37° C. At the times indicated, aliquots were taken directly into gel loading buffer containing 0.1% SDS and frozen in liquid nitrogen. After the final timepoint, siRNA samples were run on a non-denaturing 20% polyacrylamide TBE gel and visualized by ethidium bromide staining. To confirm that nuclease protection of siRNA was conferred by lipid encapsulation, 0.1% Triton-X100 was added to disrupt lipid bilayer integrity immediately prior to incubation with serum.

RiboGreen™ Assay:

Equal volumes of diluted RiboGreen™ and SNALP are combined so that the final concentration of siRNA is ~167 ng/mL. 30 µl of a 10% Triton X-100 solution is added to the RiboGreen™/SNALP mixture and the resulting solution is incubated at room temperature for at least 2 minutes. Fluorescence measurements are taken at an appropriate wavelength before and after the addition of triton X-100 to determine the amount of encapsulated siRNA (see, e.g., Muriaux et al., *PNAS USA* 98(9): 5246-5251 (2001)).

In Vivo Cytokine Induction:

Animal studies were completed in accordance with the Canadian Council on Animal Care guidelines following approval by the local Animal Care and Use Committee at Protiva Biotherapeutics. 6-8 week old CD1 ICR mice (Harlan; Indianapolis, Ind.) were subjected to a three week quarantine and acclimation period prior to use. Encapsulated siRNA formulations were administered by standard intravenous injection in the lateral tail vein in 0.2 ml PBS. Blood was collected by cardiac puncture 6 h after administration and processed as plasma for cytokine analysis. In RNAi efficacy experiments, plasma was collected from 50 µl test bleeds 6 h after initial siRNA administration.

Cytokine ELISA:

All cytokines were quantified using sandwich ELISA kits according to manufacturers instructions. These were mouse and human IFN-α (PBL Biomedical; Piscataway, N.J.), human IL-6 and TNF-α (eBioscience; San Diego, Calif.), and mouse IL-6, TNF-α, and IFN-γ (BD Biosciences; San Diego, Calif.); and Mouse IFN-α and IFN-β (BD Biosciences, San Diego, Calif.).

Cell Viability Assay:

Cell viability of in vitro cell cultures was assessed using the commercial reagent CellTiter Blue (Promega Corp. Madison, Wis.), a resazurin dye that is reduced by metabolically active cells to the fluorogenic product resorufin. Various cancer cell lines were cultured in vitro using standard tissue culture techniques. 48-72 hours after treatment with siRNA formulations or small molecule drugs, CellTiter Blue reagent was added to the culture to quantify the metabolic activity of the cells—a measure of cell viability.

Target mRNA Quantitation:

The QuantiGene branched DNA assay (Genospectra) was used to quantify the reduction of target mRNA in cell cultures treated with SNALP. Cell lysates were prepared according to the manufacturer's instructions and used directly for Eg5 (kif11) and GAPDH mRNA quantification. The ratio of Eg5 to GAPDH mRNA was calculated for each cell culture and data expressed relative to the vehicle treated control cells. Specific probe sets used for detection of mRNA were designed by Genospectra to target the following regions: for the Eg5 mRNA, positions 4188-4882 of accession NM_004523; for GAPDH mRNA, positions 1-1303 of accession NM-002046.

Antibody Assay:

An ELISA was developed to detect IgM and IgG antibodies against the PEG-lipid and other lipid components of SNALP using a method described in Judge et al in Molecular Therapy (2006). 13(2) pp. 328-337.10 µg of PEG-cDSA was added in 20 µL 100% ethanol to 96 well plates containing PVDF membranes (Millipore Corp. Bedford, Mass.). PEG-cDSA coated membranes were allowed to completely air dry for 2 hours before blocking for 1 h with 10% FBS in PBS. 100 uL of serially diluted serum samples in blocking buffer were then applied in duplicate wells for 1 h and washed 4 times with 1% FBS in PBS. Plate bound antibodies were detected with HRP-conjugated goat anti-IgM Fcµ, or IgG Fcγ. Bound enzyme was developed with TMB substrate, stopped with 2N sulphuric acid, then read in a spectrophotometer at 450 nm (minus 570 nm).

Apoptosis/Caspase 3/7 Assay

The level of Caspase 3 and 7 enzyme activity in siRNA treated cells was assessed using the commercial reagent Apo-ONE (Promega Corp. Madison, Wis.). This assay is based on the specific enzymatic cleavage of the Caspase 3/7 substrate (Z-DEVD)2-Rhodamine 110 to a fluorogenic product and is used to quantify the level of apoptosis in cultured cells. The relative level of Caspase 3/7 activity was assessed in a number of cancer cell lines at 24-48 hours after treatment with siRNA formulations.

Example 2

Selection of Candidate Eg5, EGFR or XIAP siRNA with Specificity to Mouse and Human Targets Candidate Eg5, EGFR or XIAP sequences were identified by scanning Eg5 (Genbank Accession Nos. NM_004523 and NM_010615), EGFR (Genbank Accession Nos. NM_005228 and NM_207655), and XIAP (Genbank Accession Nos. NM_001167 and NM_009688) sequences to identify AA dinucleotide motifs and the 19 nucleotides 3' of the motif. The following candidate sequences were eliminated: (1) sequences comprising a stretch of 4 or more of the same base in a row; (2) sequences comprising homopolymers of Gs; (3) sequences comprising triple base motifs (GGG, CCC, AAA, or TTT); and (4) sequences comprising stretches of 7 or more G/Cs in a row.

Reynold's Rational Design criteria was then applied to the remaining candidate sequences to identify sequences with 5 or more of the following criteria:
1. 30%-52% GC content;
2. At least 3 A/Us at positions 15-19 (sense);
3. Absence of internal repeats;
4. A at position 19 (sense);
5. A at position 3 (sense);
6. U at position 10 (sense);
7. No G/C at position 19 (sense); and
8. No G at position 13 (sense).

Only results with a score of 6 or more in the Stockholm rules (see, Chalk, Wahlestedt, and Sonnhammer method described in Chalk et al., *Biochem. Biophys. Res. Commun.*, 319:264-274 (2004)) were retained.

Next, sequences with a high score from, e.g., Classification tree method or Chalk, Wahlestedt, and Sonnhammer method, were retained.

Next, sequences with a score of 3 or more based on the rules of Amarzguioui and Prydz, *Biochem. Biophys. Res. Commun.*, 316:1050-1058 (2004), were retained.

Next, sequences with thermodynamics >0 were eliminated.

Finally, BLASTn was used to compare the sequences with the mouse and human databases and sequences with homology to 15-16 contiguous bp from the center of the target sequence (bp 3-18) against any relevant gene were eliminated. The candidate sequences are shown in Tables 1-9.

The candidate sequences are shown in Tables 1-9.

Example 3 siRNA Targeting the Kinesin Eg5 can Inhibit the Growth of Cancer Cells

Figure 2:
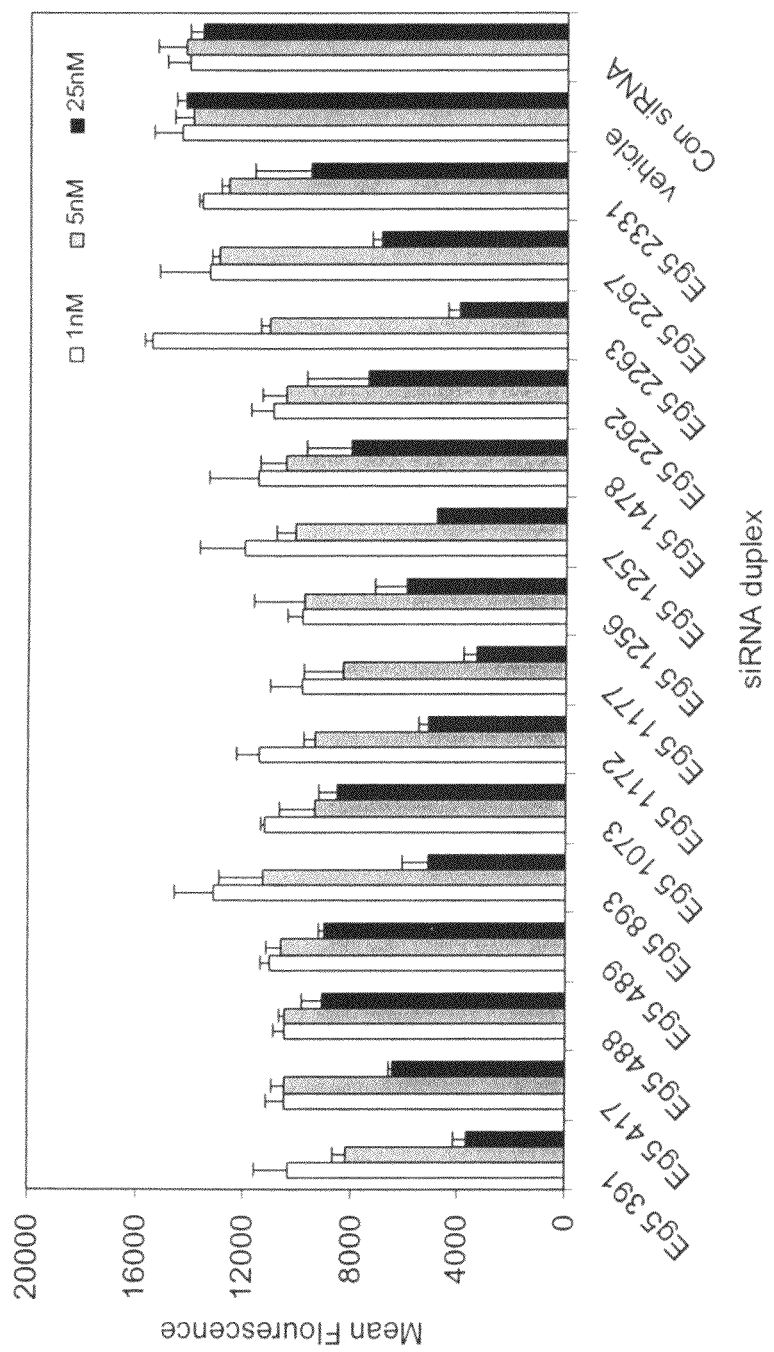
FIG. 2 illustrates data demonstrating RNAi activity of a Eg5 siRNA panel (at 1, 5, and 25 nM concentration) complexed with lipofectamine in Neuro2A cells (mouse).

A panel of siRNA sequences, including Eg5 2263, were evaluated for their antiproliferative effects against cancer cells. Eg5 2263 was previously described in the literature (see, Weil et al. 2002, *BioTechniques* 33:1244-1248) but the authors do not describe its use as a therapeutic or anti-cancer agent. The RNAi activity of the Eg5 siRNA panel were screened in vitro with HeLa cells (human; FIG. 1) and Neuro2A cells (mouse; FIG. 2) using a cell viability assay. The cells were treated with 1, 5, or 25 nM siRNA complexed with lipofectamine. Viability of the cell cultures were measured 48 h after treatment and expressed as mean fluorescence units as shown in FIGS. 1 and 2.

Example 4 siRNA Formulated as SNALP are Potent Inhibitors of Cell Growth In Vitro

Figure 3:
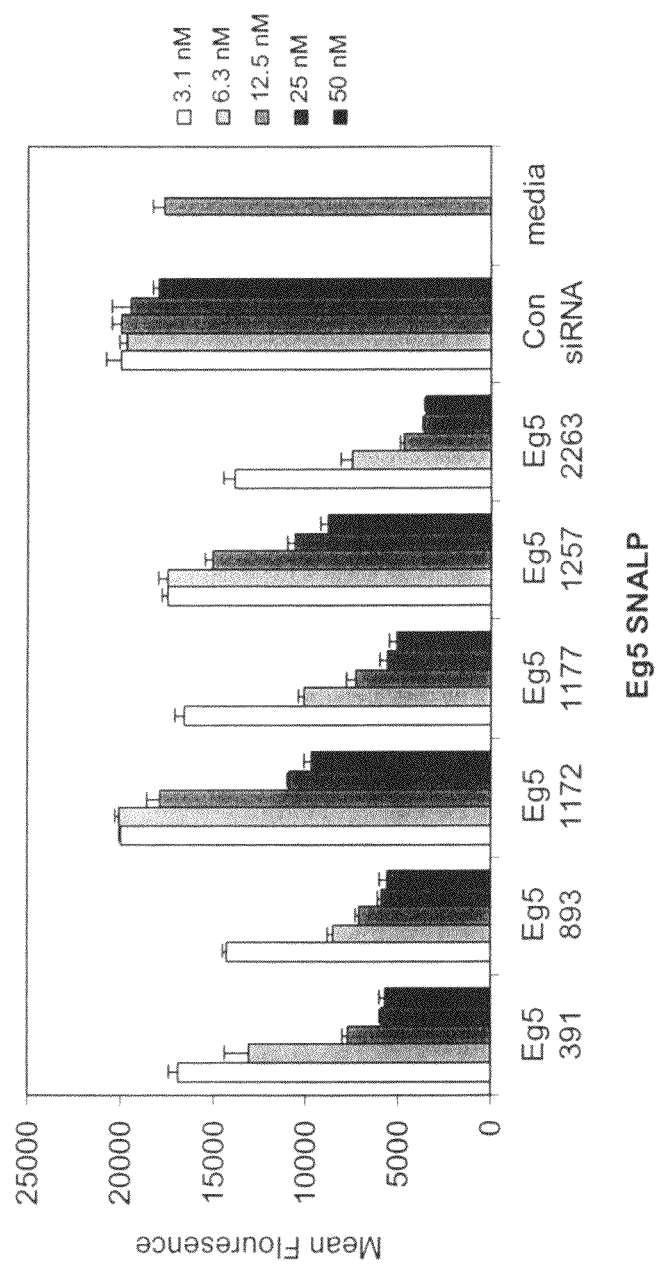
FIG. 3 illustrates data demonstrating RNAi activity of selected SNALP formulated Eg5 siRNA sequences in Neuro2A cells.

Various Eg5 siRNAs were formulated as SNALP (SNALP formulation: 2% PEG-cDMA, 40% DLinDMA, 10% DSPC, 48% cholesterol) and evaluated for their inhibitory effects on cell growth in vitro. The cells (i.e., Neuro2A cells) were treated with various SNALP formulated Eg5 siRNAs, at different concentrations i.e. 3.1 nM, 6.3 nM, 12.5 nM, 25 nM and 50 nM, and their effect on cell viability was evaluated (FIG. 3). Viability of cell cultures is expressed as mean fluorescence units.

Example 5

Dose Dependent Silencing of Eg5 mRNA in Human HepG2 Cell by Eg5 SNALP

Figure 4:
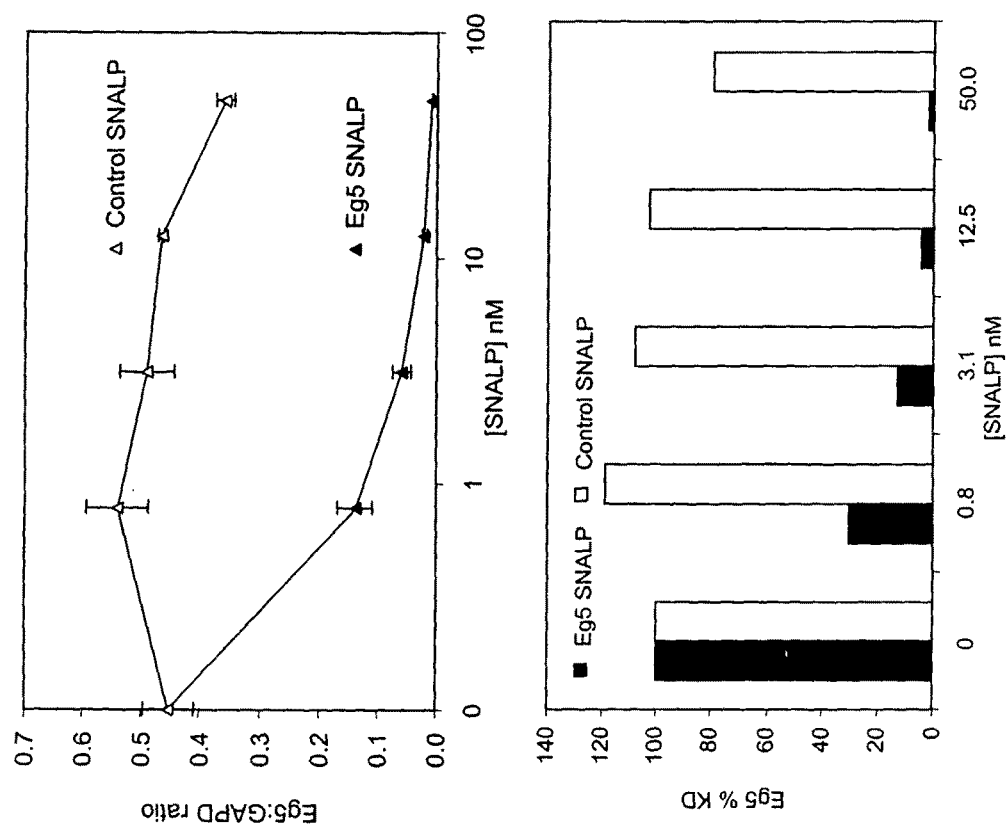
FIG. 4 illustrates data demonstrating that that the potent effects of Eg5 2263 U/U SNALP on cell viability is due to the silencing of Eg5 protein. Top panel: Eg5:GAPD mRNA ratios, bottom panel: Percent knockdown of Eg5 mRNA versus non-treated cells.

Human hepatocellular HepG2 cells were treated with either Eg5 2263 SNALP (SNALP formulation: 2% PEG-cDMA, 40% DLinDMA, 10% DSPC, 48% cholesterol) or control (i.e., a non-targeting siRNA) SNALP. Eg5 mRNA levels were measured after 48 h by a branched DNA assay. The results are shown in FIG. 4: Top Panel—Eg5:GAPD mRNA ratios; Bottom panel—% knockdown of Eg5 mRNA versus non-treated cells. The results confirm that the potent effects of Eg5 SNALP on cell viability is due to the silencing of Eg5 RNA.

Example 6

Cell Phenotype Changes Following Treatment with Eg5 siRNA

Control siRNA treated HeLa cells and Eg5 siRNA treated HeLa cells were analyzed by immunohistological staining (DAPI (DNA), blue; tubulin, green). The staining results showed that the control cells demonstrated typical mitotic phenotypes, while the Eg5 siRNA treated HeLa cells induced aberrant cell mitosis characterized by monoastral spindle formation due to Eg5 inhibition (FIG. 5).

Example 7

Anti-Proliferative Activity of Chemically Modified Eg5 2273 siRNA's

Figure 7:
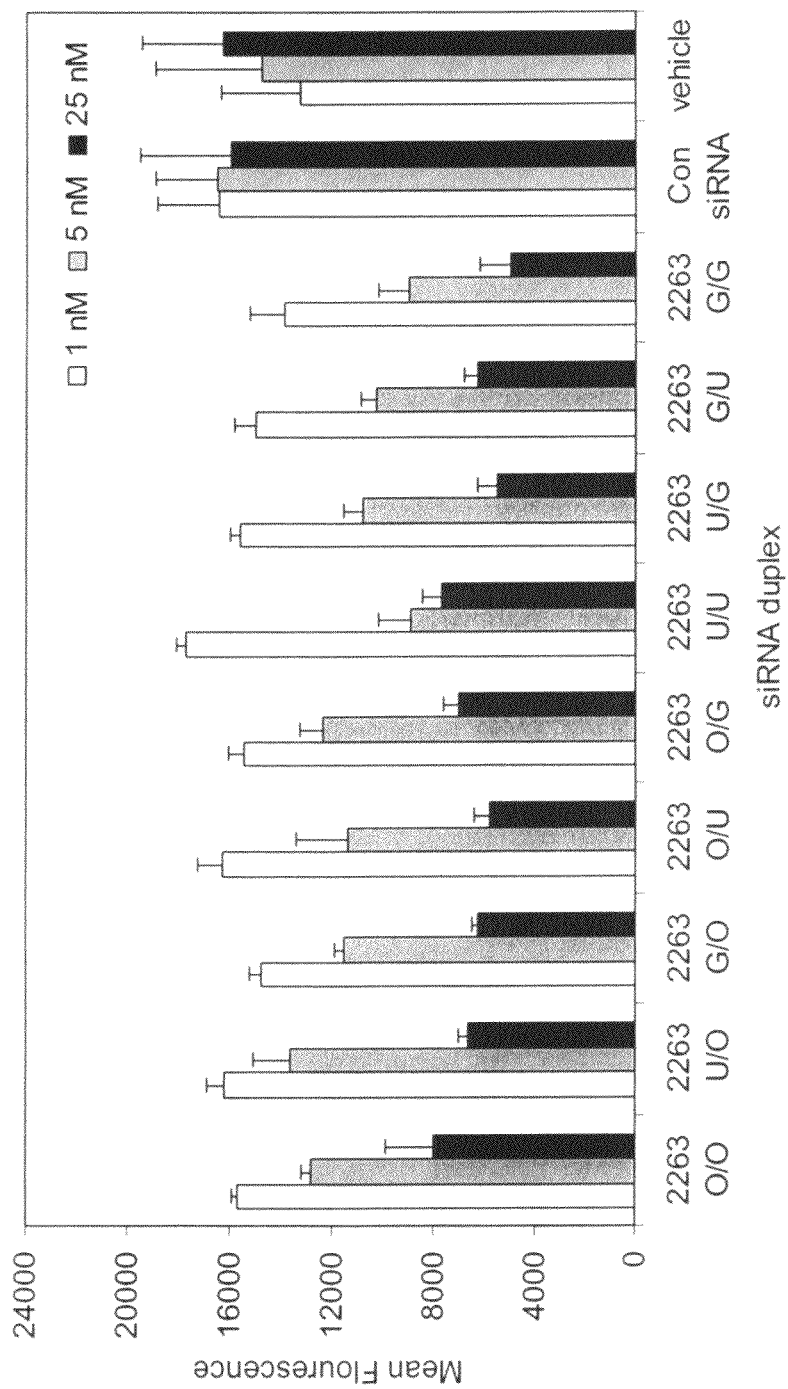
FIG. 7 illustrates data demonstrating the activity of 2'-OMe modified Eg5 2263 siRNAs in HeLa cells (human).
Figure 8:
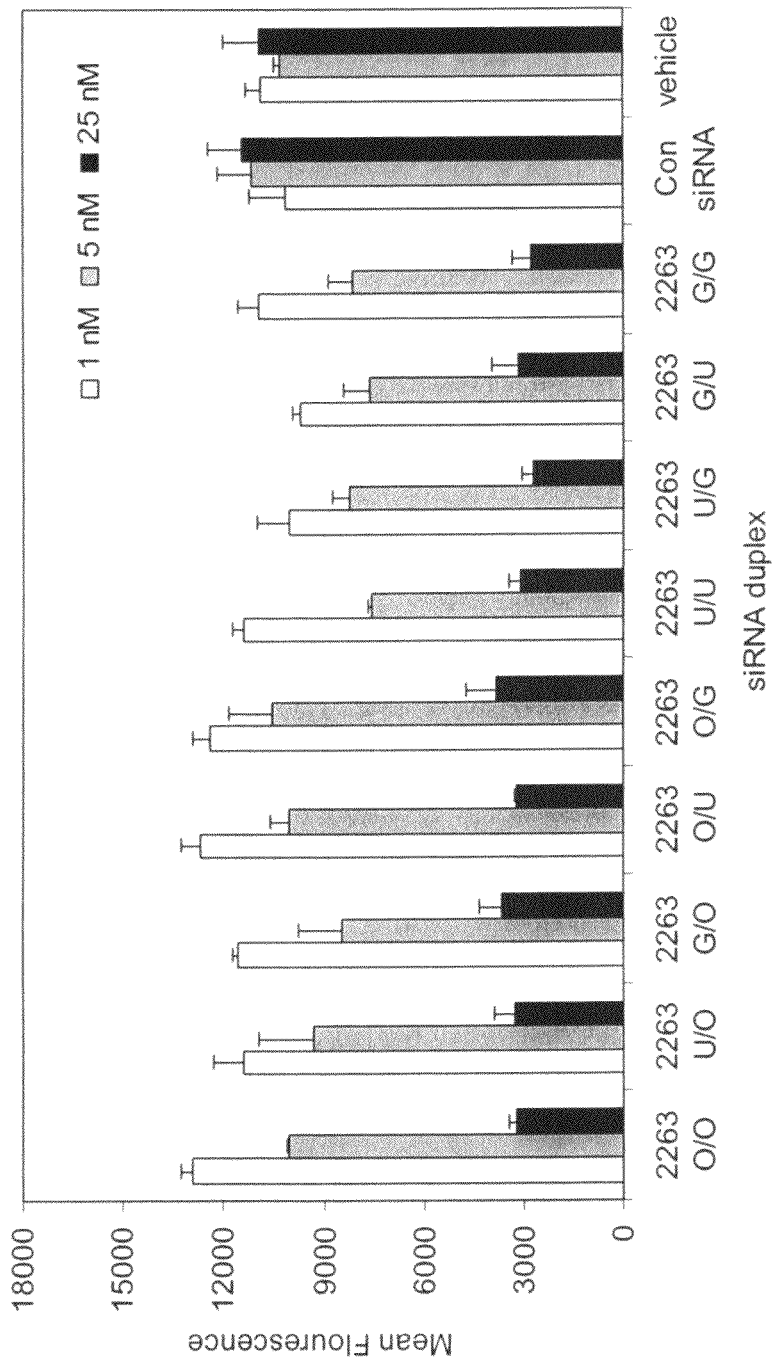
FIG. 8 illustrates data demonstrating the activity of 2'-OMe modified Eg5 2263 siRNAs in Neuro2A cells (mouse).

A panel (8 total) of 2'-OMe modified siRNAs of Eg5 2263 siRNA sequence was prepared and their RNAi activity was evaluated in HeLa human cells or Neuro2A mouse cells. The modifications involved introducing 2'-OMe guanosine or 2'-OMe uridine at selected positions in the sense or antisense strand the sequence modification are shown in (FIG. 6). The modified Eg5 2263 siRNAs incorporated less than 20% of chemically modified nucleosides. Anti-proliferative activity was evaluated in a cell viability bioassay (FIGS. 7, HeLa human cells; and FIG. 8 Neuro2A mouse cells). Cell viability of cell cultures was measured 48 hours after treatment and expressed as mean fluorescence units.

Example 8

In Vivo Cytokine Induction by Chemically Modified Eg5 2263 SNALP

Figure 9:
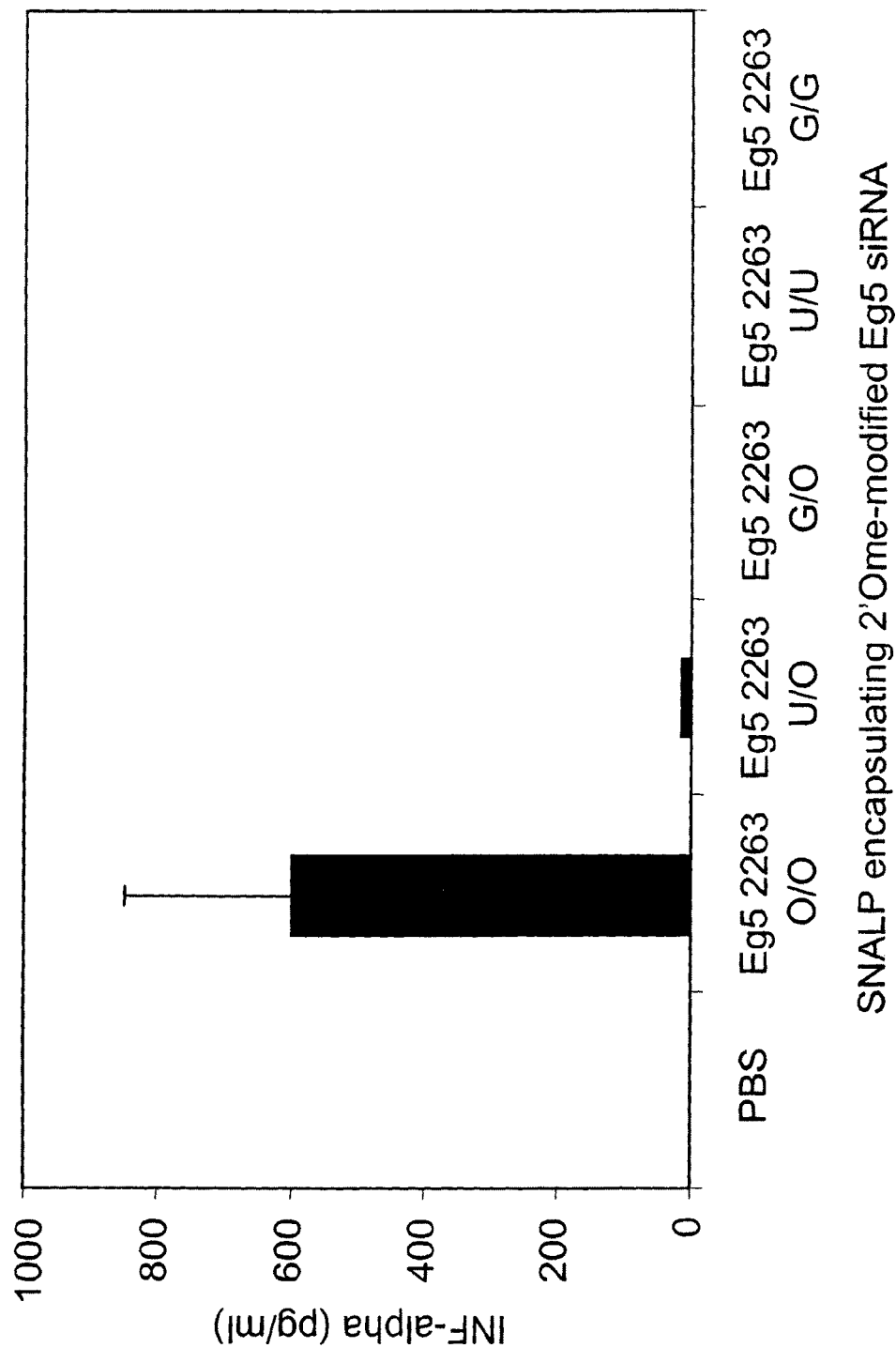
FIG. 9 illustrates data demonstrating the Interferon induction activity for various 2'-OMe modified Eg5 2263 siRNAs, (i.e., U/O, G/O, U/U, G/G) in a SNALP formulation.

Unmodified Eg5 2263 siRNA and certain 2'-OMe modified variants thereof (i.e., U/O, G/O, U/U and G/G) were formulated into SNALP (SNALP formulation: 2% PEG-cDMA, 40% DLinDMA, 10% DSPC, 48% cholesterol). These SNALP formulations were tested in vivo in to look for the induction of an immune response, e.g., cytokine induction. Balb/c mice (n=3/treatment group) were injected with 40 ug of the SNALP formulation and samples were collected 6 h post treatment with SNALP and tested for Interferon-alpha by ELISA assay. The results show that 2'-OMe modifications to Eg5 2263 siRNA abrogate Interferon induction associated with systemic administration of the native (unmodified) duplex (FIG. 9).

Example 9

Antibody Response Against the Delivery Vehicle for siRNA with Selectively 2'-OMe Modified Eg5 2263

Figure 10:
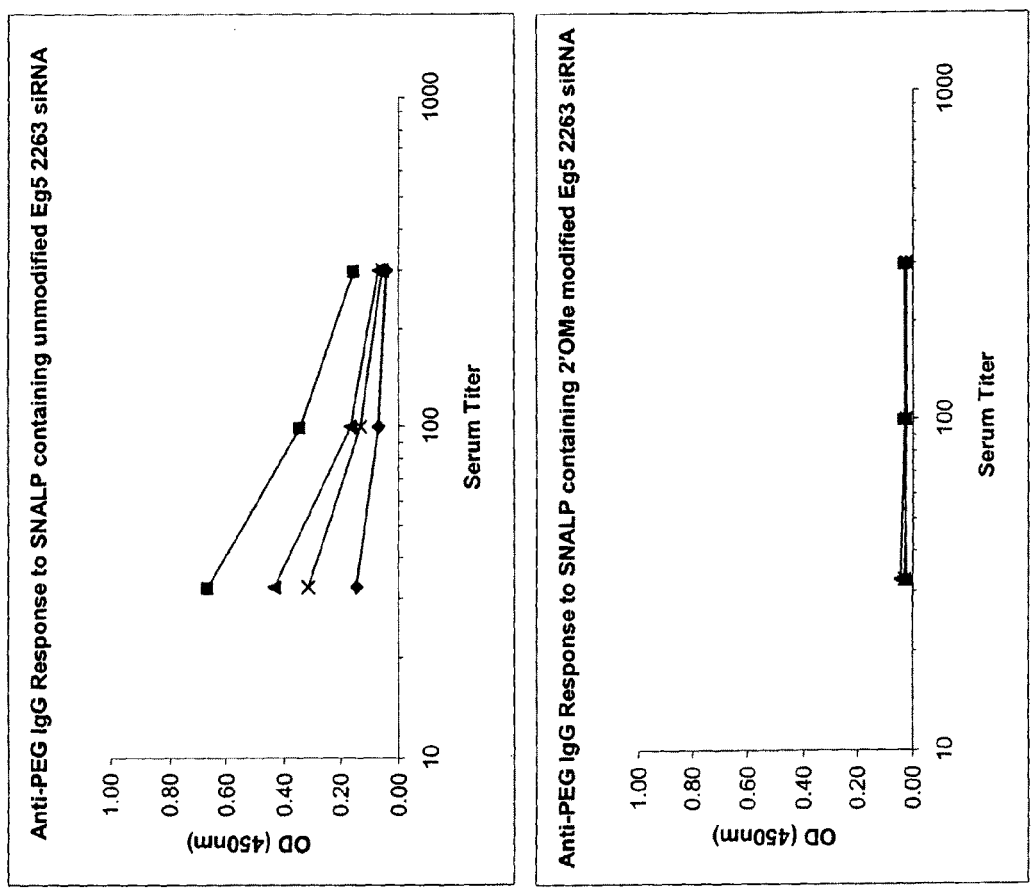
FIG. 10 illustrates data demonstrating the antibody response against the delivery vehicle for 2'-OMe modified Eg5 2663 U/U SNALP as compared to an unmodified Eg5 siRNA.

Unmodified Eg5 2263 siRNA and a 2'-OMe modified variant thereof (i.e., Eg5 2263 U/U siRNA) were formulated into SNALP (SNALP formulation: 2% PEG-cDMA, 40% DLinDMA, 10% DSPC, 48% cholesterol) and tested in vivo in mice (protocol: 3×2 mg/kg daily; serum assayed on day 10) to look for the induction of an immune response against the delivery vehicle (PEG). The results show that selective 2'-OMe modification to Eg5 2263 siRNA (e.g. U/U modified) abrogates the antibody response against the delivery vehicle that is associated with systemic administration of the native (unmodified) duplex. (FIG. 10). In FIG. 10, the top panel show PEG antibody levels in individual mice treated with unmodified Eg5 SNALP or with U/U modified Eg5 SNALP.

Example 10

The Anti-Cancer Activity of Eg5 U/U SNALP in a Range of Cancer Cell Lines

Figure 11:
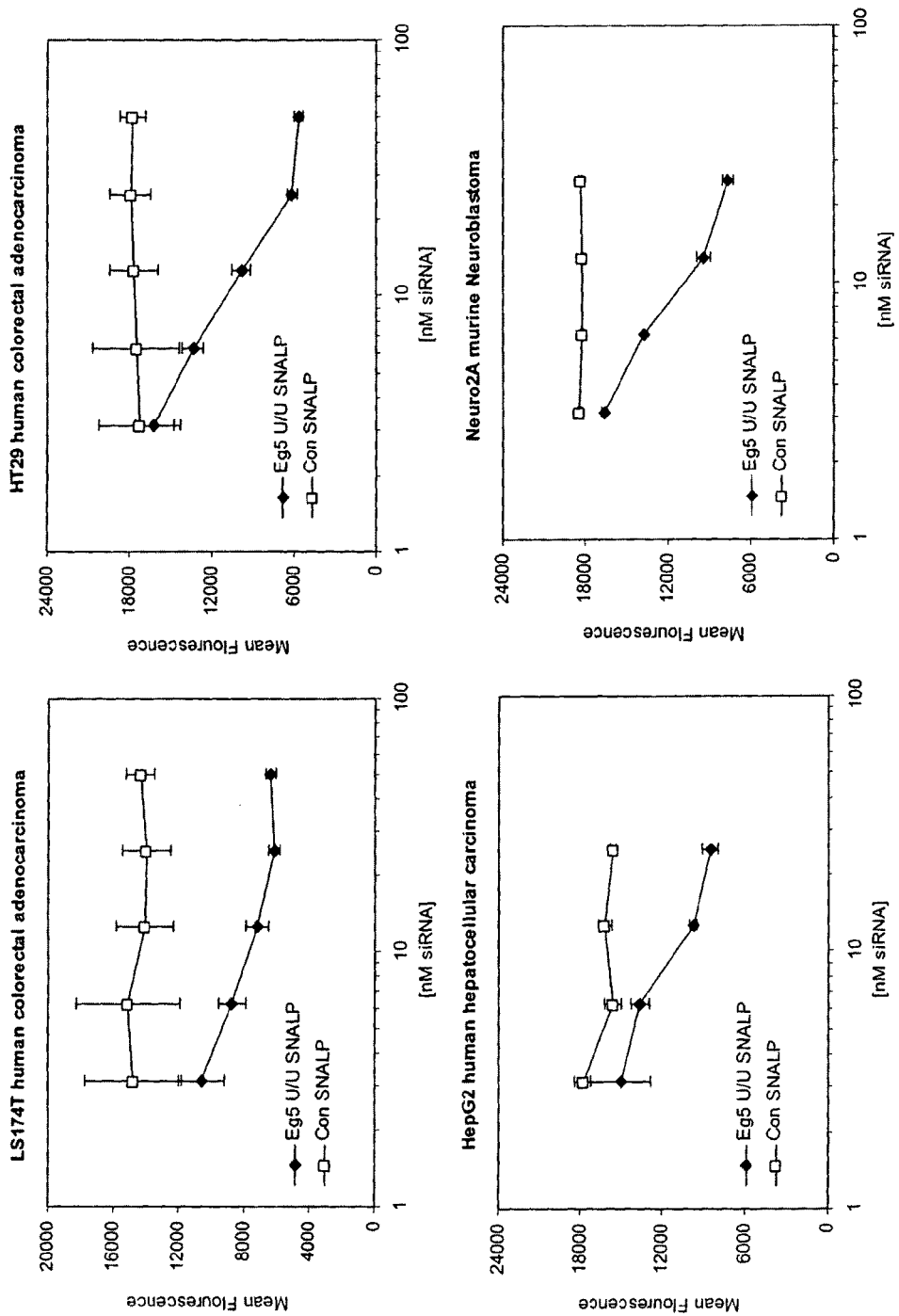
FIG. 11 illustrates data demonstrating the RNAi activity of 2'-OMe modified Eg5 2263 U/U SNALP against a range of tumor cells.
Figure 12:
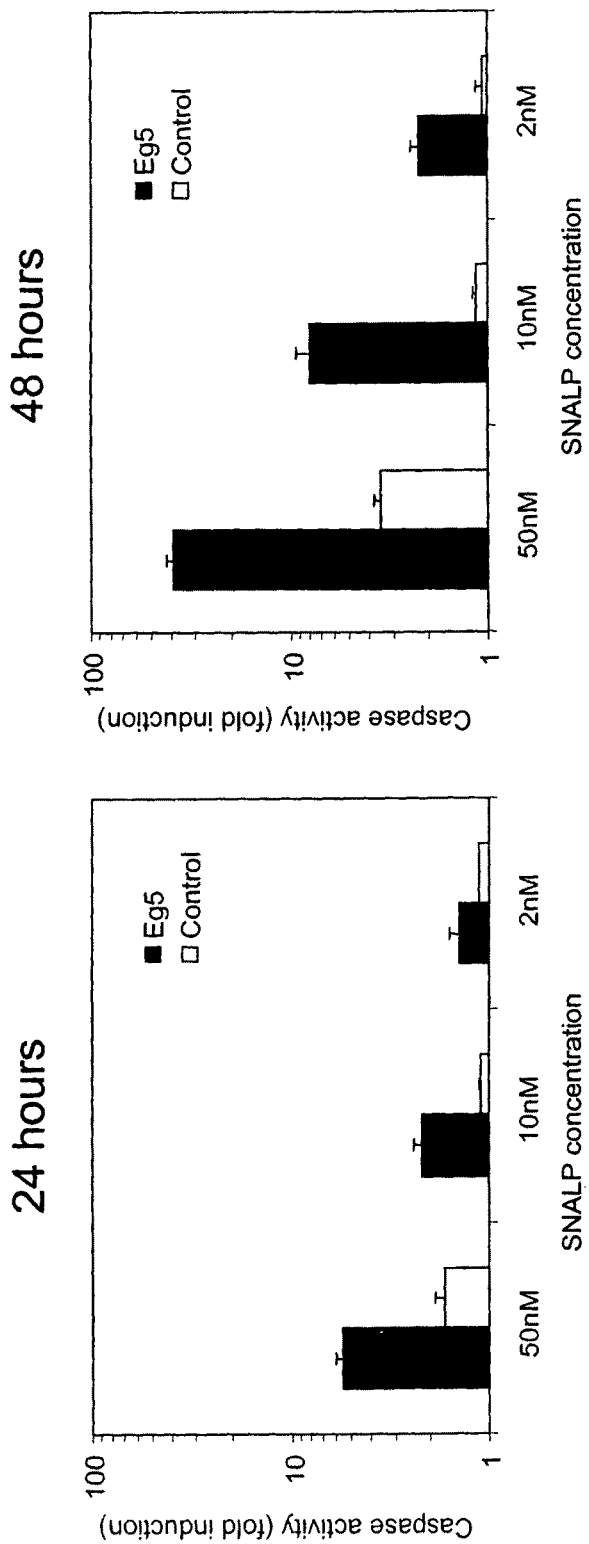
FIG. 12 illustrates data demonstrating the induction of apoptosis by Eg5 2263 U/U SNALP in human hepatocellular carcinoma cells.
Figure 13:
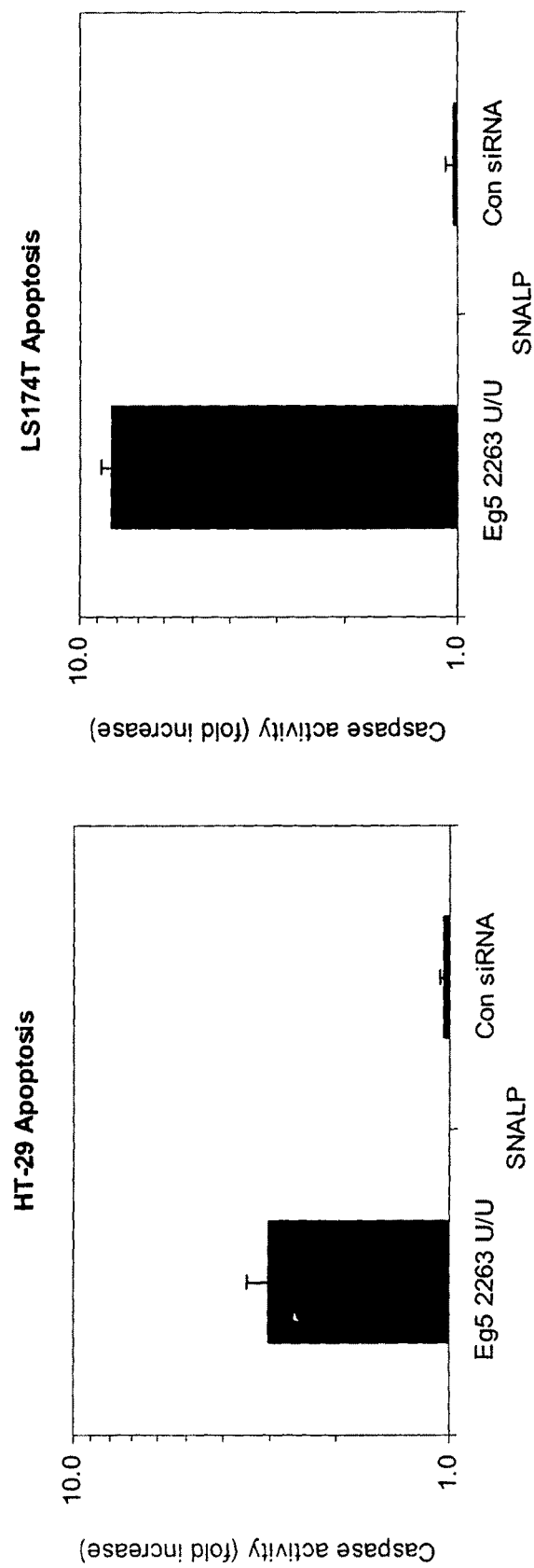
FIG. 13 illustrates data demonstrating the induction of apoptosis by Eg5 2263 U/U SNALP in human colorectal cancer cells.

The anti-cancer activity of Eg5 U/U SNALP was demonstrated against a range of cancer cell lines. Activity against the cell lines was monitored by a cell viability assay, and by an apoptosis assay as measured by Caspase 3/7 activation. Eg5 U/U SNALP specificity is confirmed by comparison with control SNALP containing non-targeting siRNA. FIG. 11 illustrates a decrease in cell viability in all cell lines tested after treatment with Eg5 U/U SNALP as compared to control. Upper left panel: LS174T human colorectal adenocarcinoma; Upper right panel: HT29 human colorectal adenocarcinoma; lower left panel: HepG2 human hepatocellular carcinoma; Lower right panel; Neuro2A murine Neuroblastoma. The induction of apoptosis by Eg5 SNALP U/U modified siRNA, as measured by Caspase 3/7 activity, was measured in human hepatocellular carcinoma cells and human colorectal cancer cells after 24 hours and after 48 hours. The Caspase 3/7 activity is expressed as fold induction over media only treated cells. FIG. 12 illustrates that apoptosis induction in human hepatocarcinoma cells is increased in Eg5 2263 U/U SNALP as compared to control siRNA. FIG. 13 illustrates that apoptosis induction is increased in Eg5 2263 U/U SNALP in human colorectal cancer cells (HT-29 and LS 174T) as compared to control.

Example 11

Comparison Between Eg5 2263 U/U SNALP Vs. Small Molecule Eg5 Inhibitor Drug

Figure 14:
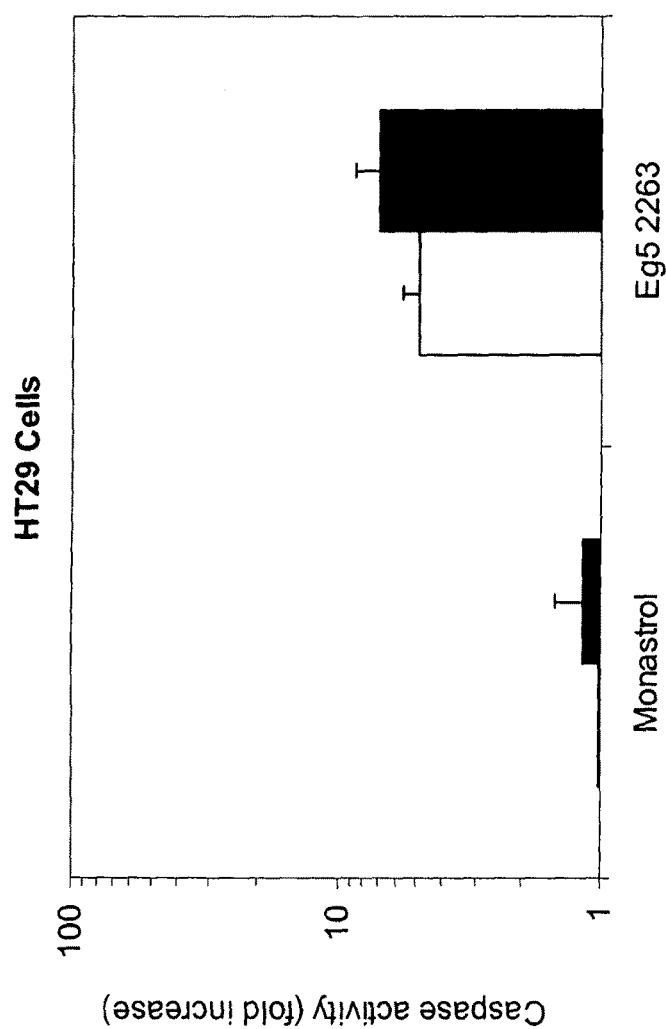
FIG. 14 illustrates data comparing the induction of apoptosis by Eg5 2263 U/U SNALP with a small molecule Eg5 inhibitor in human colorectal cells.
Figure 15:
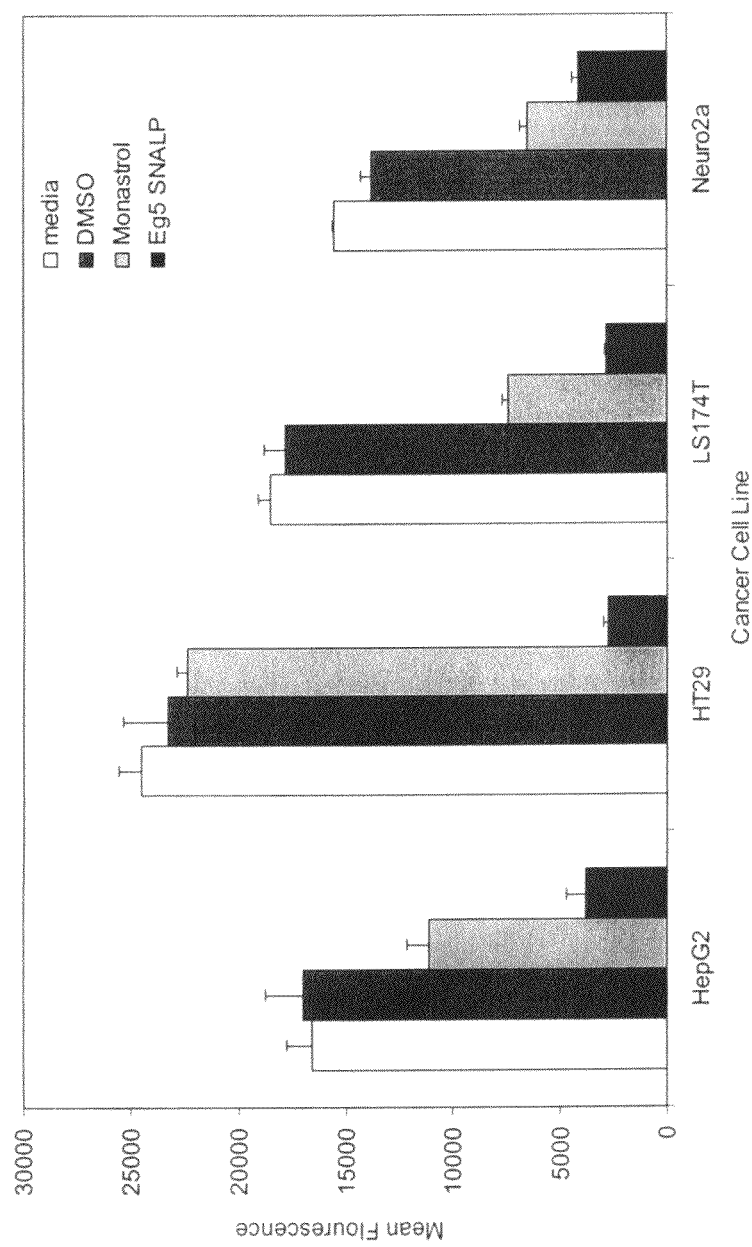
FIG. 15 illustrates data comparing the RNAi activity of Eg5 2263 U/U SNALP vs. a small molecule Eg5 inhibitor in a variety of cancer cells.

There are currently several small molecule Eg5 inhibitors under clinical evaluation. Recent publications indicate that certain cancer cell lines (e.g., HT-29 colorectal adenocarcinoma cells) are resistant to apoptosis induction by small molecule Eg5 inhibitors. A comparison of apoptosis activity, via a comparison of Caspase 3/7 induction activity, in HT-29 colorectal adenocarcinoma cells (a small molecule Eg5 inhibitor resistant cell type) after treatment with a small molecule Eg5 inhibitor (i.e, Monastrol at 50 or 100 uM concentration), or with Eg5 2263 U/U SNALP (at 25 or 50 nM concentration) demonstrates that cells lines that are resistant to small molecule Eg5 inhibitors are highly sensitive to Eg5 SNALP (FIG. 14). A comparison of Eg5 2263 U/U SNALP with the small molecule Eg5 inhibitor, monastrol, in the inhibition of various cancer cell lines, as measure by cell viability assays, demonstrates that Eg5 2263 U/U SNALP is superior at inhibiting cell growth in these cancer cell lines than monastrol (FIG. 15). The results of these experiments shows that SNALP can confer advantages over conventional small molecule drugs as anti-cancer agents.

Example 12

Serum Nuclease Protection Assay

Figure 16:
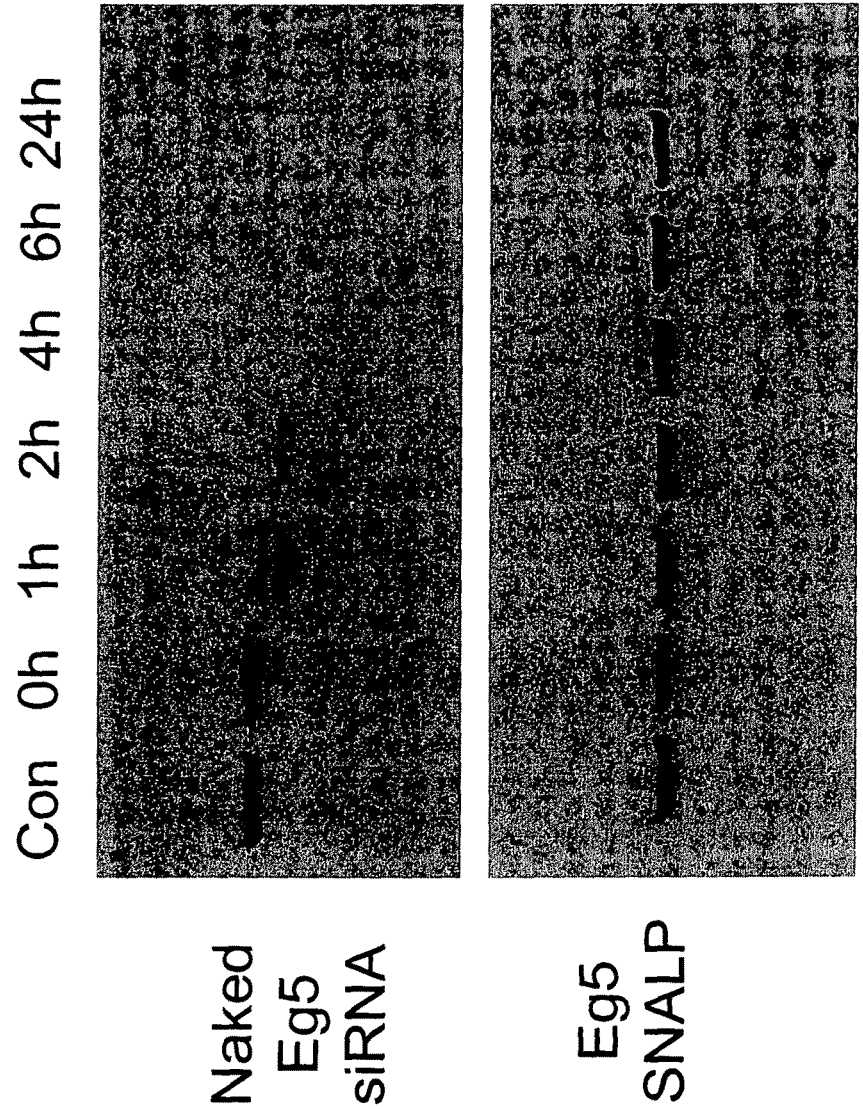
FIG. 16 illustrates data demonstrating the stability of naked Eg5 siRNA and SNALP encapsulated Eg5 O/O siRNA toward serum nuclease degradation.

Naked Eg5 siRNA and SNALP encapsulated Eg5 siRNA were subjected to serum nuclease degradation. The result in the serum nuclease protection assay (presented in FIG. 16) shows that SNALP encapsulation provide the protection from serum nuclease required for in vivo use of siRNA.

Example 13

In Vivo Activity of Eg5 SNALP in Tumor Bearing Mice

Figure 17:
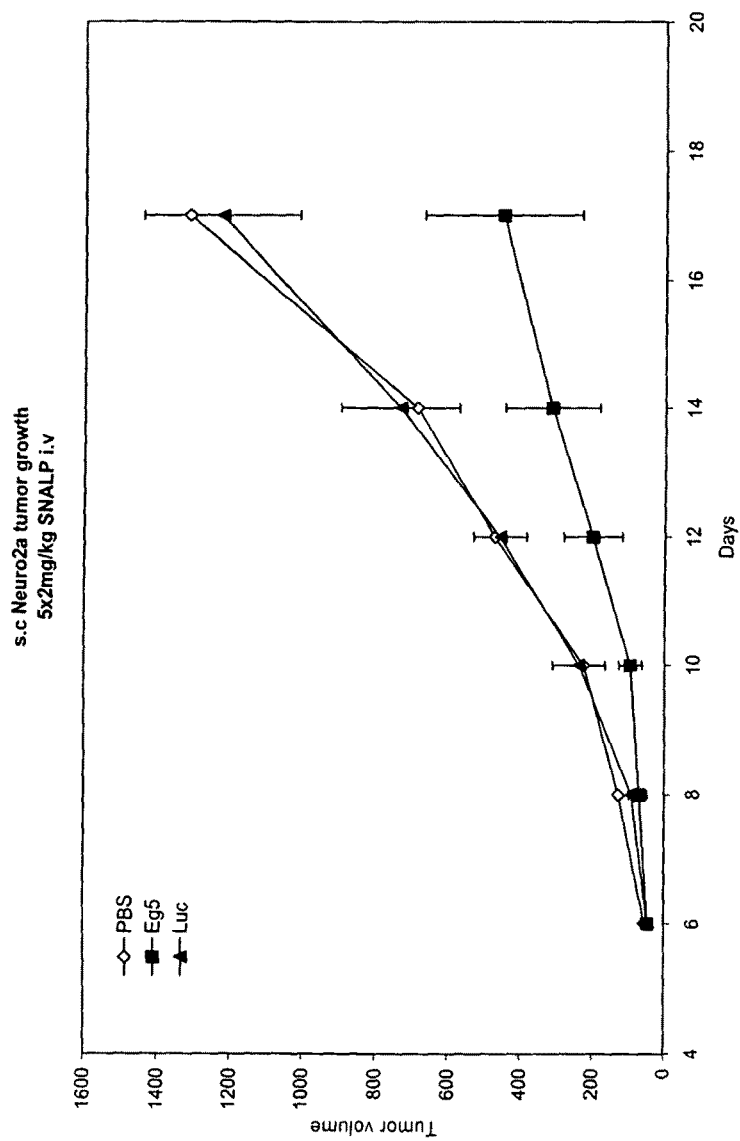
FIG. 17 illustrates data demonstrating in vivo s.c. tumor growth of Neuro2A after treatment with Eg5 2263 U/U SNALP.
Figure 18:
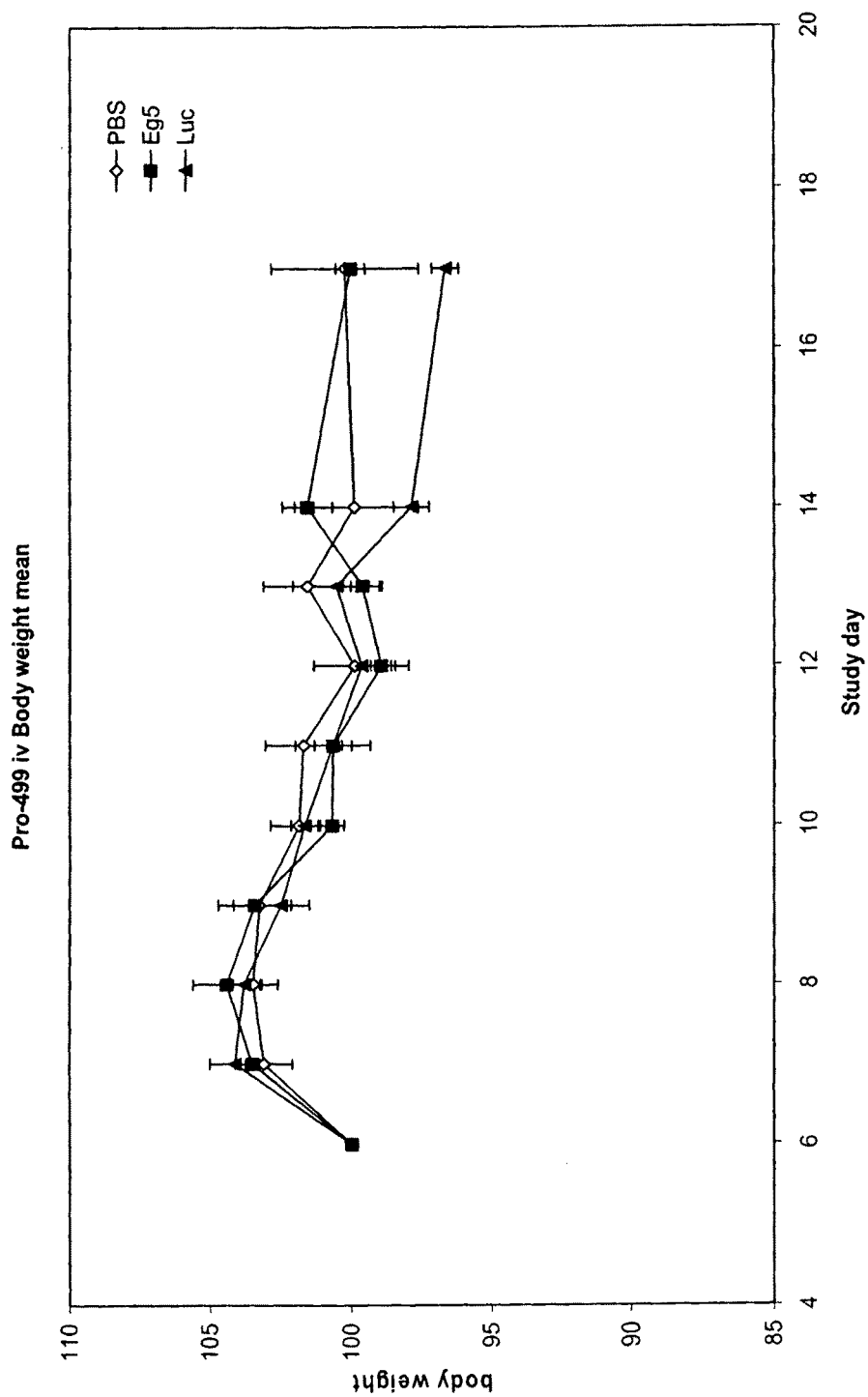
FIG. 18 illustrates data demonstrating that in vivo dosing with Eg5 2263 U/U SNALP in mice bearing s.c. Neuro2A tumors is well tolerated.

Anti-tumor effects of Eg5 2263 U/U SNALP (2% PEG-cDSA, 40% DLinDMA, 10% DSPC, 48% cholesterol), as compared to SNALP containing control siRNA (Luc), was evaluated in a subcutaneous model in mice. A/J mice bearing s.c. Neuro2A tumors were treated with SNALP at 5×2 mg/kg daily (d6-10) by i.v. administration. Tumors were measured by calipers and recorded as tumor volume. The results of this study demonstrates that Eg5 2263 U/U SNALP exerts a specific anti-tumor effect in a s.c. tumor model (FIG. 17). Additionally, therapeutic dosing is well tolerated in tumor-bearing mice (FIG. 18).

Example 14

In Vivo Activity of Eg5 SNALP in Tumor Bearing Mice

Figure 19:
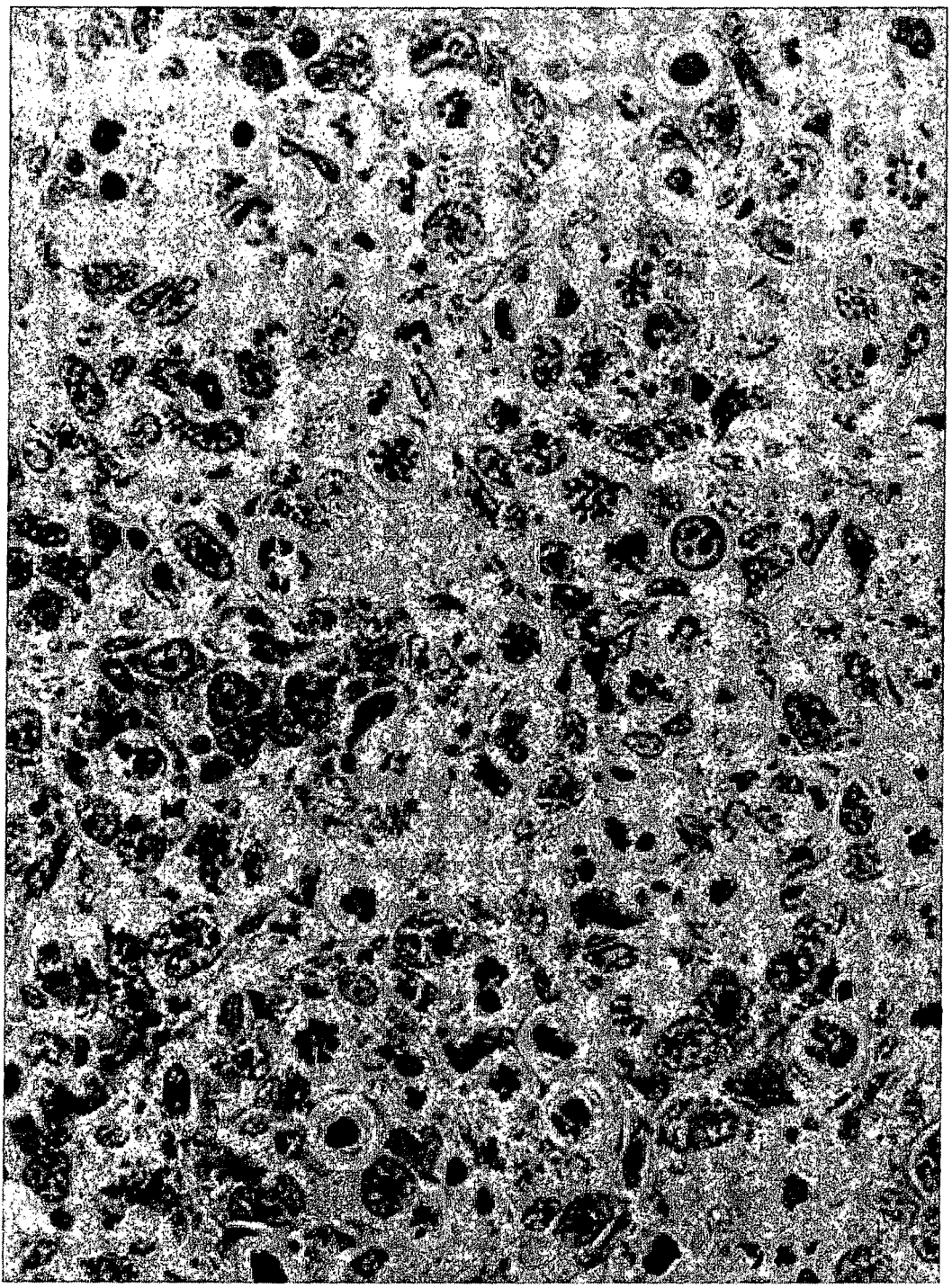
FIG. 19 illustrates data showing that the tumor histopathology of the intrahepatic Neuro2A tumor that was treated with Eg5 2263 U/U SNALP.
Figure 20:
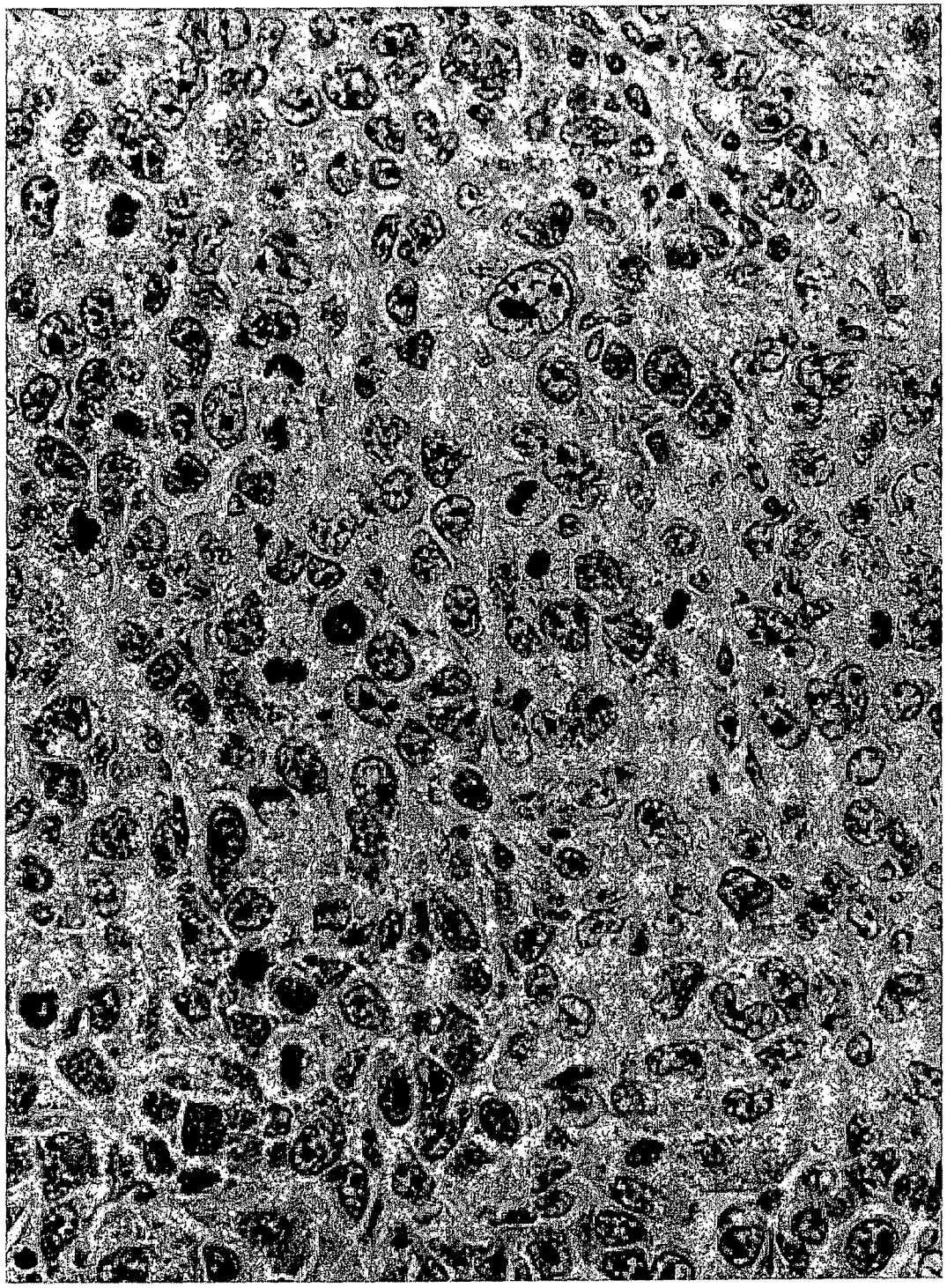
FIG. 20 illustrates data showing the tumor histopathology of the intrahepatic Neuro2A tumor that was treated with control SNALP

Anti-tumor effects of Eg5 2263 U/U SNALP (2% PEG-cDMA, 40% DLinDMA, 10% DSPC, 48% cholesterol), as compared to SNALP containing control siRNA (Luc), was evaluated in an intrahepatic tumor model in mice. In this study, A/J mice were seeded with 100,000 Neuro2A cells by intrahepatic injection. On day 12, the mice were treated with Eg5 2263 U/U SNALP (n=6) or control siRNA (Luc SNALP; n=5). The mice were dosed at 3 mg/kg at t=0 h and at t=6 h, for a cumulative dosage of 6 mg/kg. The livers were collected 30 h after the first dose (d13), and formalin-fixed for conventional histology. The tissues were processed and stained with H&E. Tumor histology showed that Eg5 2263 U/U SNALP treated mice induced extensive phenotypic changes (e.g., aberrant mitosis and apoptosis) in the intrahepatic tumor cells, which is characteristic of Eg5 inhibition, as compared to control treated subjects. FIG. 19 shows the tumor histopathology of the intrahepatic Neuro2A tumor that was treated with Eg5 2263 U/U SNALP. Histology shows numerous tumor cells with atypical mitotic figures and apoptotic bodies characteristic of Eg5 inhibition. FIG. 20 shows the tumor histopathology of the intrahepatic Neuro2A tumor that was treated with control SNALP. Histology results shows numerous tumor cells with normal mitotic figures.

Example 15

In Vitro Activity of EGFr siRNA

Figure 30:
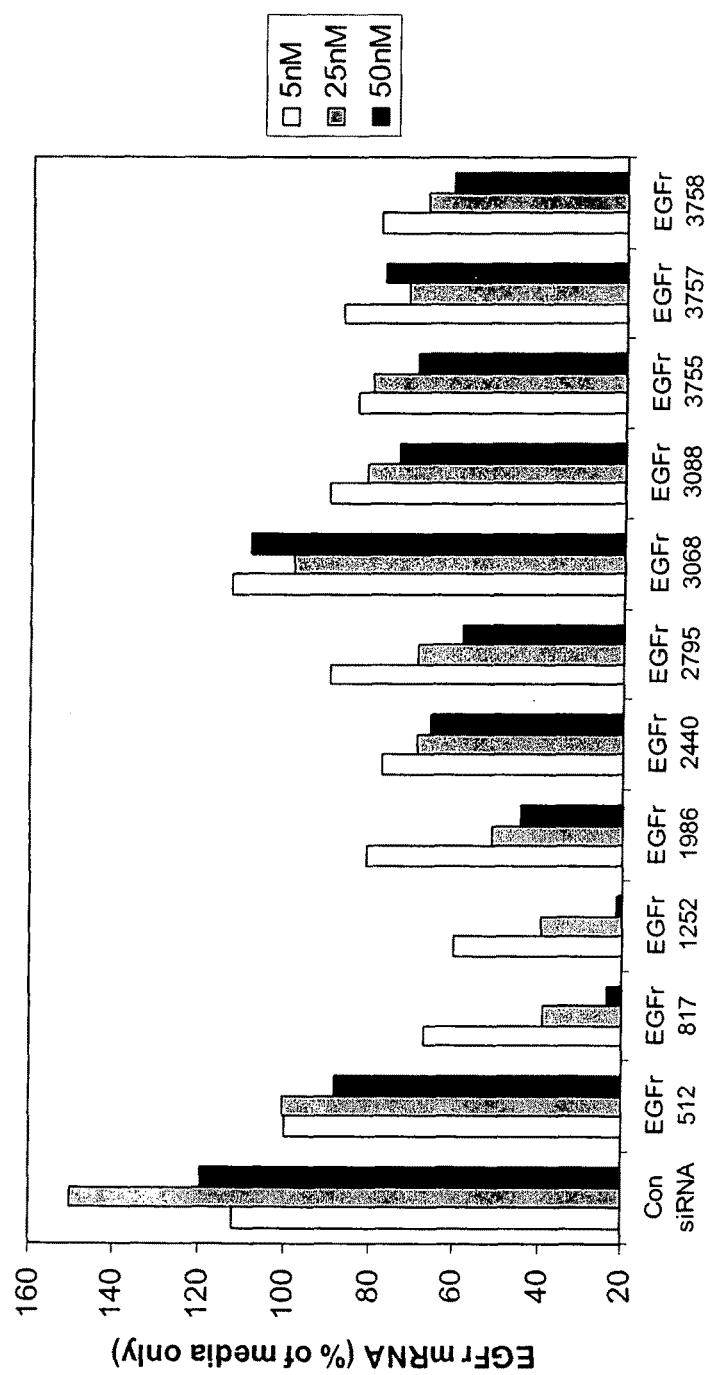
FIG. 30 illustrates data showing in vitro silencing of EGFR mRNA by the panels of EGFR siRNA sequences set forth in Tables 3 and 4.

A431 carcinoma cells were treated with increasing concentrations of lipofectamine complexed EGFr or non-targeting control siRNA. EGFr mRNA levels were quantitated by branched DNA assay after 48 h culture. EGFr mRNA values are expressed as % of media treated cells. As shown in FIG. 30, EGFr sequences 817 and 1252 and 1986 displayed the greatest levels of mRNA silencing.

Figure 31:
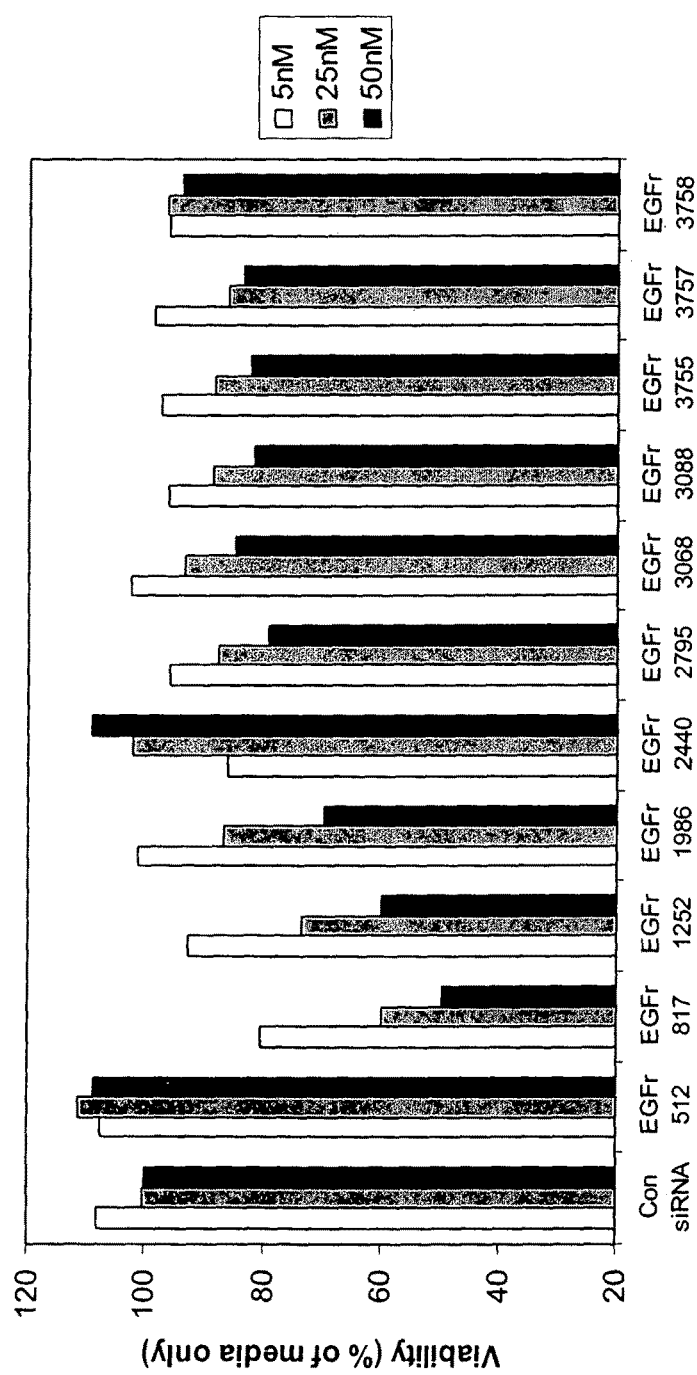
FIG. 31 illustrates data showing the silencing of EGFR mRNA correlates with a decrease in tumor cell viability.

Cell viability was also quantitated by CellTiter Blue fluorescence assay after 48 h culture. inability scores are expressed as % of media treated cells. As shown in FIG. 31, EGFr sequences 817 and 1252 and 1986 that displayed the greatest levels of mRNA silencing also show the most significant effects on cell viability.

Example 16

In Vitro Activity of EGFr siRNA

Figure 32:
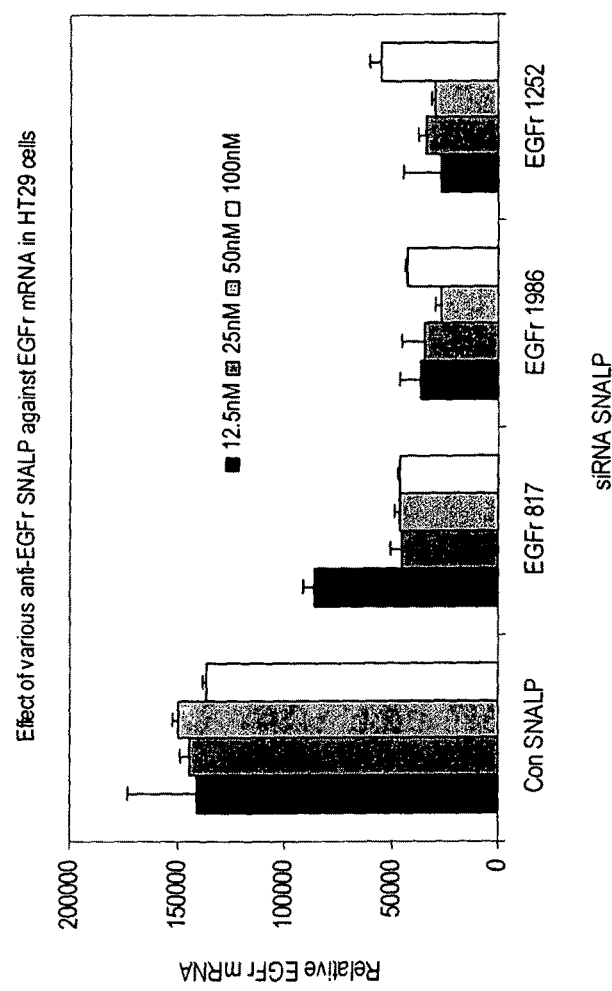
FIG. 32 illustrates data showing in vitro silencing of EGFR mRNA by EGFR SNALP.

HT-29 tumor cells were treated with increasing concentrations of EGFr sequences 817 and 1252 and 1986 siRNA sequences or a non-targeting control siRNA formulated in SNALP. EGFr mRNA levels were measured 48 h after SNALP treatment by bDNA assay. As shown in FIG. 32, EGFr sequences 817 and 1252 and 1986 siRNA formulated in SNALP silence EGFR siRNA.

Example 17

In Vitro Activity of XIAP SNALP

Figure 33:
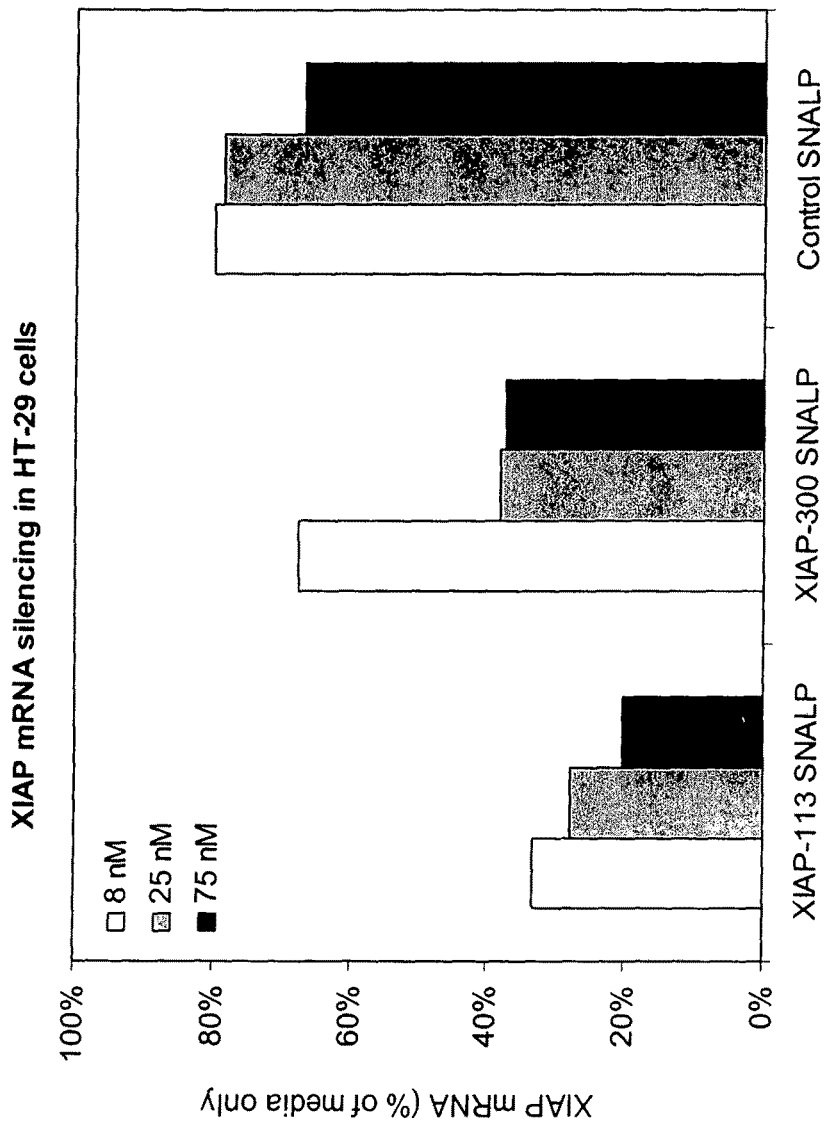
FIG. 33 illustrates data showing in vitro silencing of XIAP mRNA by XIAP SNALP.

SNALP containing XIAP-113, XIAP-300 or non-targeting control siRNA were applied to HT-29 cells in vitro at various concentrations. 48 h later, XIAP mRNA levels were measured by bDNA assay and expressed as % of media treated cells. As shown in FIG. 33, XIAP-113 SNALP causes significant, dose-dependent decreases in XIAP mRNA levels

Example 18

In Vitro Activity of XIAP SNALP

Figure 34:
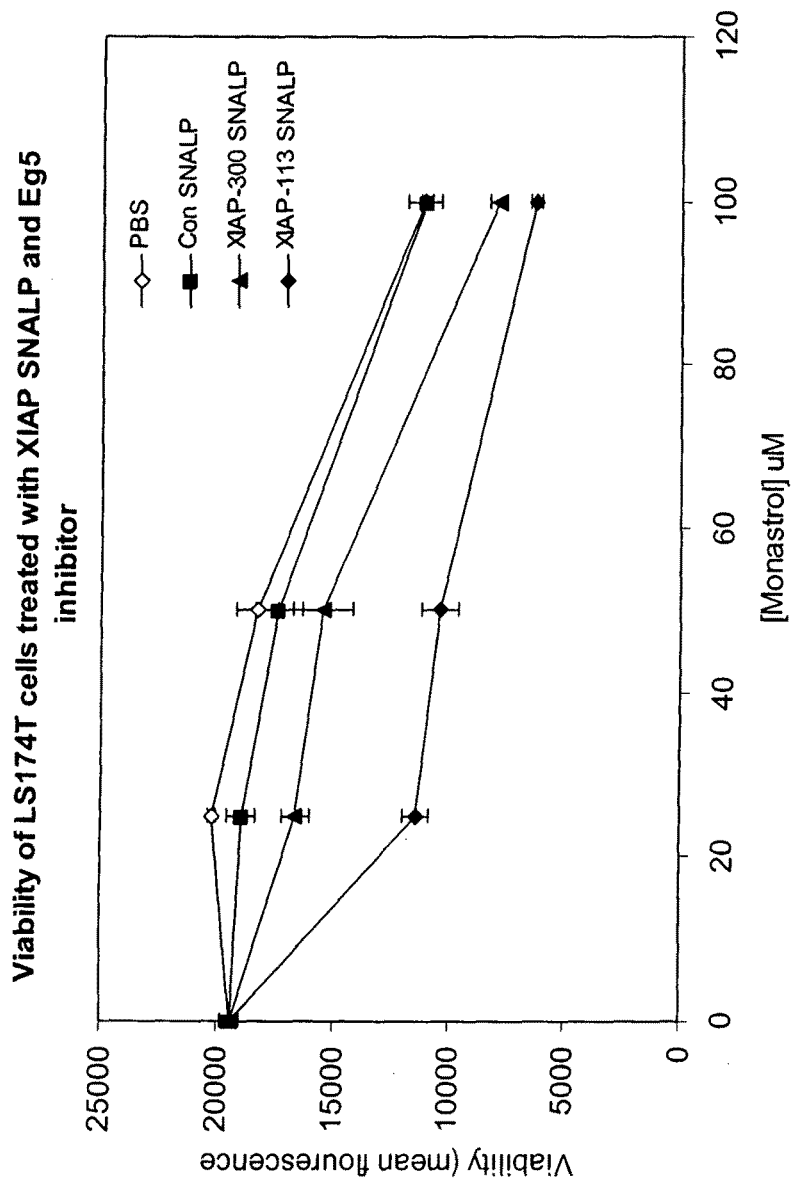
FIG. 34 illustrates data showing the cells treated with XIAP SNALP are sensitized to Eg5 inhibitors.

SNALP containing XIAP-113, XIAP-300 or non-targeting control siRNA were applied to LS174T colon adenocarcinoma cells in vitro at 35 nM siRNA. Cells were then treated with monastrol, a small molecule inhibitor of Eg5. Viability of cell cultures was assessed after 48 h. As shown in FIG. 34, XIAP-113 and -300 SNALP sensitize human colon cancer cells to the cytotoxic effects of the Eg5 inhibitor. Degree of sensitization correlates with the relative potency of mRNA silencing by these SNALP

Example 19

In Vitro Activity of Eg5 SNALP in in Combination with XIAP SNALP

Figure 35:
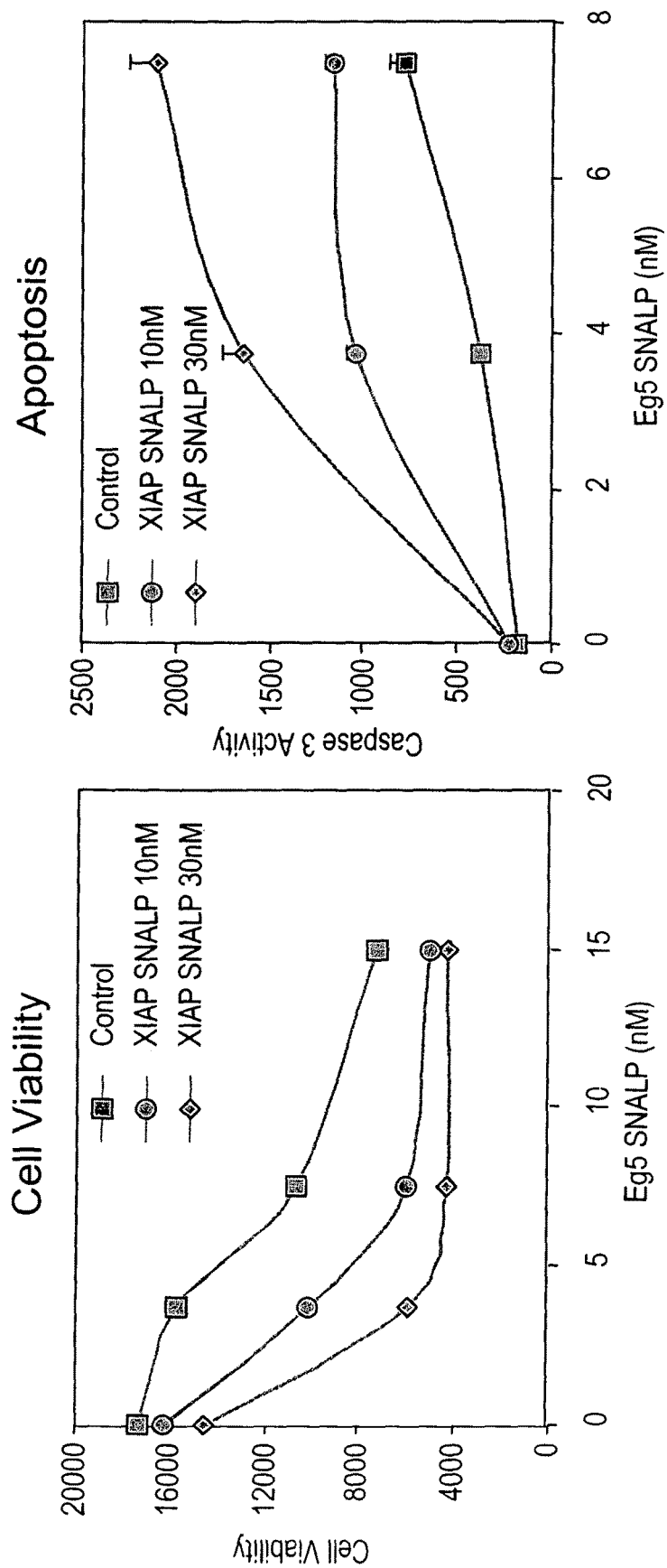
FIG. 35 illustrates data showing that silencing of XIAP mRNA with XIAP SNALP sensitizes tumor cells to killing by Eg5 SNALP.

HT29 colon cancer cells were co-cultured with 10 nM or 30 nM XIAP-113 SNALP plus increasing concentrations of Eg5 2263 SNALP. Cell viability and caspase 3/7 activity were assayed after 48 h culture. As shown in FIG. 35, co-administration of XIAP SNALP sensitizes HT29 cells to killing by Eg5 SNALP, as demonstrated by significant increases in the level of apoptosis and corresponding decrease in cell viability in the cultures.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications, patents, PCT publications, and Accession Nos. are incorporated herein by reference for all purposes.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08598333B2). An electronic copy of the "Sequence Listing" will also be available from the USPTO upon request and payment of the fee set forth in 37 CFR 1.19(b)(3).

What is claimed is:

1. An siRNA molecule that silences Eg5 expression comprising a sense strand and a complementary antisense strand, wherein the antisense strand consists of the nucleic acid sequence of SEQ ID NO:44.

2. The siRNA molecule of claim 1, wherein the siRNA molecule is chemically synthesized.

3. The siRNA molecule of claim 1, wherein the sense strand comprises the nucleic acid sequence of SEQ ID NO:20.

4. The siRNA molecule of claim 1, wherein the sense strand consists of the nucleic acid sequence of SEQ ID NO:43.

5. The siRNA molecule of claim 1, wherein the siRNA molecule comprises at least one modified nucleotide.

6. The siRNA molecule of claim 5, wherein the modified nucleotide is a 2'-O-methyl (2'OMe) nucleotide.

7. A composition comprising the siRNA molecule of claim 1 and a pharmaceutically acceptable carrier.

8. A nucleic acid-lipid particle comprising:
(a) the siRNA molecule of claim 1;
(b) a cationic lipid; and
(c) a non-cationic lipid.

* * * * *

UNITED STATES PATENT AND TRADEMARK OFFICE
CERTIFICATE OF CORRECTION

| | | |
|---|---|---|
| PATENT NO. | : 8,598,333 B2 | Page 1 of 1 |
| APPLICATION NO. | : 11/807872 | |
| DATED | : December 3, 2013 | |
| INVENTOR(S) | : MacLachlan et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1404 days.

Signed and Sealed this
Seventh Day of July, 2015

Michelle K. Lee
*Director of the United States Patent and Trademark Office*